United States Patent
Dominguez et al.

(10) Patent No.: US 10,479,802 B2
(45) Date of Patent: Nov. 19, 2019

(54) PROBES FOR IMAGING HUNTINGTIN PROTEIN

(71) Applicant: CHDI Foundation, Inc., New York, NY (US)

(72) Inventors: Celia Dominguez, Los Angeles, CA (US); Samuel Coe, Tommy Taylors Lane (GB); Jonathan Bard, New York, NY (US); Peter David Johnson, Abingdon (GB); Michael Edward Prime, Swindon (GB); Christopher John Brown, Abingdon (GB); Sébastien René Gabriel Galan, Abingdon (GB); Paul Richard Giles, Abingdon (GB); Elise Luciennen Paulette Gadouleau, Didcot (GB); Thomas Martin Krülle, Oxford (GB); Daniel Clark-Frew, Wantage (GB); John Wityak, Carlsbad, CA (US); Alex Kiselyov, New York, NY (US); Sarah Hayes, Abingdon (GB)

(73) Assignee: CHDI Foundation, Inc., New York, NY (US)

( * ) Notice: Subject to any disclaimer, the term of this patent is extended or adjusted under 35 U.S.C. 154(b) by 53 days.

(21) Appl. No.: 15/507,208

(22) PCT Filed: Aug. 28, 2015

(86) PCT No.: PCT/US2015/047407
§ 371 (c)(1),
(2) Date: Feb. 27, 2017

(87) PCT Pub. No.: WO2016/033445
PCT Pub. Date: Mar. 3, 2016

(65) Prior Publication Data
US 2017/0283436 A1    Oct. 5, 2017

Related U.S. Application Data

(60) Provisional application No. 62/043,603, filed on Aug. 29, 2014.

(51) Int. Cl.
| | | |
|---|---|---|
| C07D 513/04 | (2006.01) | |
| C07D 413/14 | (2006.01) | |
| C07D 471/04 | (2006.01) | |
| A61K 51/04 | (2006.01) | |
| C07D 413/12 | (2006.01) | |
| C07D 263/57 | (2006.01) | |
| C07D 498/04 | (2006.01) | |
| C07D 405/14 | (2006.01) | |
| C07D 413/04 | (2006.01) | |

(52) U.S. Cl.
CPC ........ *C07D 513/04* (2013.01); *A61K 51/0455* (2013.01); *A61K 51/0459* (2013.01); *A61K 51/0463* (2013.01); *C07D 263/57* (2013.01); *C07D 405/14* (2013.01); *C07D 413/04* (2013.01); *C07D 413/12* (2013.01); *C07D 413/14* (2013.01); *C07D 471/04* (2013.01); *C07D 498/04* (2013.01)

(58) Field of Classification Search
CPC .. C07D 471/04; C07D 513/04; C07D 413/14; A61K 51/04
See application file for complete search history.

(56) References Cited

U.S. PATENT DOCUMENTS

| | | |
|---|---|---|
| 3,985,755 A | 10/1976 | Narayanan et al. |
| 6,770,642 B2 | 8/2004 | Cole et al. |
| 2006/0018825 A1 | 1/2006 | Kudo et al. |
| 2008/0267879 A1 | 10/2008 | Elmaleh et al. |
| 2009/0123373 A1 | 5/2009 | Wang et al. |
| 2009/0163464 A1 | 6/2009 | Black et al. |
| 2010/0209345 A1 | 8/2010 | Katsifis et al. |
| 2011/0085985 A1* | 4/2011 | Barrow ............... C07D 498/04 424/9.3 |
| 2011/0160543 A1 | 6/2011 | Parsey et al. |
| 2011/0182812 A1 | 7/2011 | Szardenings et al. |
| 2012/0094996 A1 | 4/2012 | Fernandez et al. |
| 2012/0263646 A1 | 10/2012 | Catoen et al. |
| 2017/0056535 A1 | 3/2017 | Dominguez et al. |
| 2017/0281804 A1 | 10/2017 | Dominguez et al. |

(Continued)

FOREIGN PATENT DOCUMENTS

| | | |
|---|---|---|
| WO | WO 2010/051196 | 5/2010 |
| WO | WO 2010/112093 | * 10/2010 |

OTHER PUBLICATIONS

Extended European Search Report and Opinion dated May 2, 2018 for EP Application No. 15836321.8. 11 pages.

(Continued)

*Primary Examiner* — Michael G. Hartley
*Assistant Examiner* — Jagadishwar R Samala
(74) *Attorney, Agent, or Firm* — Sheppard Mullin Richter & Hampton LLP

(57) ABSTRACT

Provided are imaging agents comprising a compound of Formula (I), or a pharmaceutically acceptable salt thereof, and methods of their use.

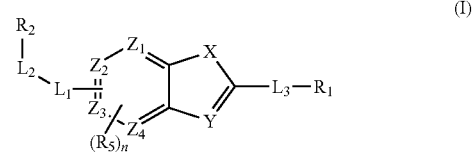

25 Claims, 1 Drawing Sheet

(56) References Cited

U.S. PATENT DOCUMENTS

2017/0283439 A1 10/2017 Dominguez et al.
2017/0292150 A1 10/2017 Dominguez et al.

OTHER PUBLICATIONS

International Preliminary Report on Patentability dated Mar. 7, 2017 for PCT/US2015/047407. 6 pages.
International Search Report and Written Opinion dated Dec. 7, 2015 for PCT/US2015/047407. 8 pages.
Zhang, et al. 11C-AC-5216: A Novel PET Ligand for Peripheral Benzodiazepine Receptors in the Primate Brain. J. Nucl. Med. 2007; 48:1853-1861.
Extended European Search Report and Opinion dated Apr. 9, 2018 for EP Application No. 15836157.6. 15 pages.
International Preliminary Report on Patentability dated Feb. 28, 2017 for PCT/US2015/047427. 6 pages.
International Search Report and Written Opinion dated Dec. 7, 2015 for PCT/US2015/047427. 13 pages.
Mathis, et al. Synthesis and evaluation of 11C-labeled 6-substituted 2-arylbenzothiazoles as amyloid imaging agents. J Med Chem. Jun. 19, 2003;46(13):2740-54.
Serdons, et al. Synthesis and evaluation of three 18F-labeled aminophenylbenzothiazoles as amyloid imaging agents. J Med Chem. Nov. 26, 2009;52(22):7090-102.
Zeng, et al. 9Fluorine-18 radiolabeled heterocycles as PET tracers for imaging β-amyloid plaques in Alzheimer's disease. Curr Top Med Chem. 2013;13(8):909-19.

\* cited by examiner

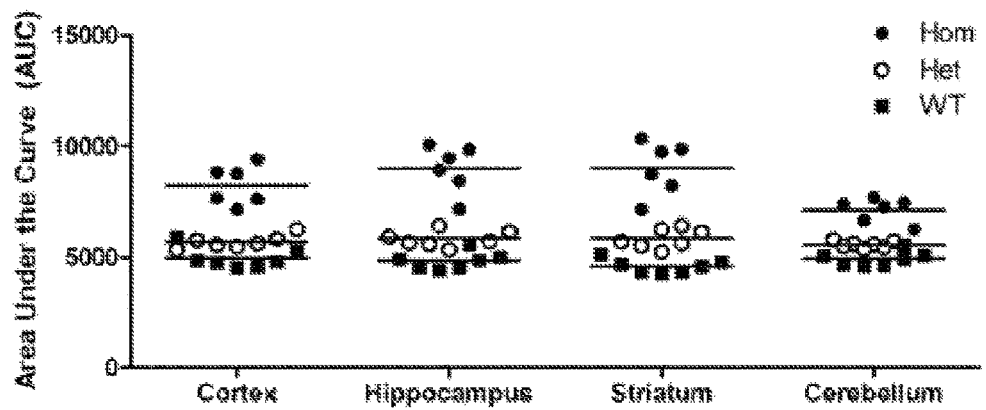

PROBES FOR IMAGING HUNTINGTIN PROTEIN

CROSS REFERENCE TO RELATED APPLICATIONS

This application is a U.S. National Stage Application under 35 U.S.C. § 371 of PCT Application No. PCT/US2015/047407, filed Aug. 28, 2015, which claims priority to U.S. Provisional Application No. 62/043,603, filed Aug. 29, 2014, which is incorporated herein by reference for all purposes.

The advent of molecular imaging approaches such as positron emission tomography (PET) and single photon emission computed tomography (SPECT) has enabled measurements of molecular and cellular mechanisms throughout the body in preclinical and clinical settings. Such measurements have widespread diagnostic utility and their use for evaluation of treatment responses and to assist drug development is expanding rapidly. The recent introduction of high-resolution molecular imaging technology is considered by many experts as a major breakthrough that will potentially lead to a revolutionary paradigm shift in health care and revolutionize clinical practice.

PET involves the administration to a subject of a positron-emitting radionuclide tracer followed by detection of the positron emission (annihilation) events in the body. The radionuclide tracer is typically composed of a targeting molecule having incorporated therein one or more types of positron-emitting radionuclides.

Many new molecular probes labeled with positron-emitting radionuclides and associated PET imaging assays are under development to target, detect, visualize, and quantify various extracellular and intracellular molecules and processes associated with diseases such as cancer, heart disease, and neurological disorders. For instance, several types of agents have been synthesized and evaluated for imaging amyloid β (Aβ) plaques in patients with Alzheimer's disease (AD) including, arylbenzothiazoles, stilbenes, imidazopyridines, pyridylbenzothiazoles, pyridylbenzoxazoles and pyridylbenzofurans (Swahn et al., *Bioorganic & Medicinal Chemistry Letters*, 20 (2010) 1976-1980). Furthermore, styrylbenzimidazole (SBIM) derivatives have been developed as agents for imaging neurofibrillary tangles (NFT), composed of hyperphosphorylated tau protein, in patients with AD. In binding experiments using recombinant tau and amyloid $β_{1-42}$ ($Aβ_{1-42}$) aggregates, 4-[(E)-2-(6-iodo-1H-benzimidazol-2-yl)ethenyl]-N,N-dimethylaniline (SBIM-3) showed higher affinity for the tau aggregates than $Aβ_{1-42}$ aggregates (ratio of $K_d$ values was 2.73). In in vitro autoradiography and fluorescent staining, [$^{125}$I]SBIM-3 (or SBIM-3) bound NFT in sections of AD brain tissue. In biodistribution experiments using normal mice, all [$^{125}$I] SBIM derivatives showed high initial uptake into (3.20-4.11% ID/g at 2 min after the injection) and rapid clearance from (0.12-0.33% ID/g at 60 min after the injection) the brain (Matsumura et al., *Bioorganic & Medicinal Chemistry*, 21 (2013) 3356-3362).

Huntington's disease (HD) is an inherited progressive neurodegenerative disorder, characterized by motor, cognitive, and psychiatric deficits as well as neurodegeneration and brain atrophy beginning in the striatum and the cortex and extending to other subcortical brain regions. It belongs to a family of neurodegenerative diseases caused by mutations in which an expanded CAG repeat tract results in long stretches of polyglutamine (polyQ) in the encoded protein. This family also includes dentatorubral-pallidoluysian atrophy (DRPLA), spinal and bulbar muscular atrophy (SBMA) and the spinocerebellar ataxias (SCAs). Apart from their polyQ repeats, the proteins involved are unrelated, and although they are all widely expressed in the central nervous system and peripheral tissues, they lead to characteristic patterns of neurodegeneration. In HD, the selective neurodegeneration of the γ-aminobutyric acid-releasing spiny-projection neurons of the striatum is predominant, although loss of neurons in many other brain regions has also been reported. In the unaffected population, the number of CAG repeats in the $IT_{15}$ gene that encodes the HD protein huntingtin (HTT protein) varies from 6 to 35; repeats of 36 or more define an HD allele. The length of the CAG expansion is inversely correlated with age of disease onset, with cases of juvenile onset characterized by expansions of more than 60 repeats. HD has a prevalence of 5-10 cases per 100,000 worldwide, which makes it the most common inherited neurodegenerative disorder. HTT protein is a 348-kDa multidomain protein that contains a polymorphic glutamine/proline-rich domain at its amino-terminus. The longer polyQ domain seems to induce conformational changes in the protein, which causes it to form intracellular aggregates that, in most cases, manifest as nuclear inclusions. However, aggregates can also form outside the nucleus. HTT protein is present in the nucleus, cell body, dendrites and nerve terminals of neurons, and is also associated with a number of organelles including the Golgi apparatus, endoplasmic reticulum and mitochondria.

Several clinical trials are investigating means to alleviate or reduce symptoms and slow progression in clinically diagnosed HD. Consistent with other medical conditions, treatments might be ideally initiated at or before the earliest signs of disease. There are at least two primary challenges to the design of clinical trials for pre-HD: selection of participants who are most likely to show measurable change over the course of a clinical trial, and development of outcome measures that are sensitive to interventions and can demonstrate variation over the natural history of pre-HD. In order to meet these and other challenges to preventive clinical trials, indicators of very early disease are required.

In view of the central role of the accumulation of aggregated forms of HTT protein in the pathogenesis of HD, there is a need for molecular probes that bind to such abnormalities with high sensitivity and specificity, for molecular imaging in the living subject using PET. The compounds described herein meet this and other needs.

Provided is an imaging agent comprising a compound of Formula I, or a pharmaceutically acceptable salt thereof,

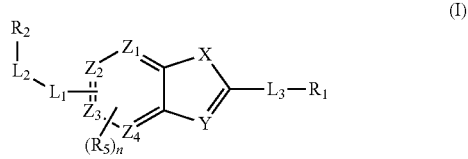

wherein
X is chosen from $NR_4$, O and S;
Y is chosen from $CR_4$ and N;
$Z_1$, $Z_2$, $Z_3$, and $Z_4$ are independently chosen from CH and N, provided that at least two of $Z_1$, $Z_2$, $Z_3$, and $Z_4$ are CH;
$R_1$ is chosen from heteroaryl, heterocycloalkenyl, and heterocycloalkyl, each of which is optionally substituted with one or two groups independently chosen from cyano, halo, lower alkyl optionally substituted with amino, alkylamino, or di(alkyl)amino, lower alkoxy optionally substituted with lower alkoxy, optionally substituted amino, haloalkyl, di(alkyl)aminocarbonyl, alkylaminocarbonyl, and aminocarbonyl, or $R_1$ is phenyl optionally substituted with one or two groups independently chosen from cyano, heteroaryl, halo, phenoxy, benzyloxy, heteroaryl, lower alkyl optionally substituted with amino, (alkyl)amino, or di(alkyl)amino, lower alkoxy, optionally substituted amino, di(alkyl)aminocarbonyl, alkylaminocarbonyl, and aminocarbonyl;

$L_1$ is —O— and $L_2$ is —$(CR_7R_8)_m$— or —$(CR_7R_8)_m$—O—; or $L_1$ is —$NR_3$— and $L_2$ is —C(O)— or —$(R_7R_8)_m$—; or $L_1$ is —$NR_3$— and $L_2$ is —C(O)(O)$(R_7R_8)_m$—; or $L_1$ is —$NR_3$— and $L_2$ is —C(O)$(R_7R_8)_m$(O)—; or $L_1$ is —$NR_3$— and $L_2$ is —C(O)$(R_7R_8)_m$—; or $L_1$ is —$NR_3$— and $L_2$ is —C(O)$CR_7$=$CR_8$—; or $L_1$ is —C(O)— and $L_2$ is —$NR_3$; or $L_1$ is —$(R_7R_8)_m$— and $L_2$ is —$NR_3$—, —C(O)— or —O—; or $L_1$ is absent and $L_2$ is absent; or $L_1$ taken together with $L_2$ is —CH=CH—, —C≡C—, or heterocyclylene;

$L_3$ is —CH=CH—, or $L_3$ is absent;

$R_2$ is chosen from heterocycloalkyl, aryl and heteroaryl, each of which is optionally substituted with one or two groups chosen from
  —OC(O)—$R_6$,
  —C(O)O—$R_6$,
  amino,
  halo,
  haloalkyl,
  phenyl,
  heteroaryl,
  cyano,
  (lower alkyl)thio,
  phenoxy,
  phenoxymethyl,
  heteroaryloxy,
  heteroaryloxy substituted with lower alkyl,
  hydroxyl,
  lower alkenyloxy,
  lower alkoxy,
  lower alkoxy substituted with lower alkoxy, amino, (alkyl)amino, (dialkyl)amino, heterocycloalkyl, heteroaryl, or halo,
  lower alkyl, and
  lower alkyl substituted with amino, (alkyl)amino, (dialkyl)amino, hydroxyl or lower alkoxy;

$R_3$ is chosen from hydrogen and lower alkyl;

$R_4$ is chosen from hydrogen, halo, cyano, and lower alkyl;

$R_5$ is chosen from lower alkyl, lower alkoxy, and halo;

$R_6$ is lower alkyl;

$R_7$ is chosen from hydrogen, hydroxyl, trifluoromethyl, and lower alkyl;

$R_8$ is chosen from hydrogen and lower alkyl;

n is 0 or 1; and m is 0, 1, or 2;

wherein the compound of Formula I, or a pharmaceutically acceptable salt thereof, is labeled with one or more positron-emitting radionuclides.

Also provided is a method of generating diagnostic images in an individual comprising administering an effective amount of an imaging agent described herein to an individual, and generating an image of at least a part of said individual.

BRIEF DESCRIPTION OF THE DRAWINGS

FIG. 1 shows AUC values for the binding of $^{11}$C-labeled Compound 3 of Method 14 in four regions of the brain in mice which are wild type, or heterozygous or homozygous for the zQ175 knock-in allele.

As used in the present specification, the following words, phrases and symbols are generally intended to have the meanings as set forth below, except to the extent that the context in which they are used indicates otherwise. The following abbreviations and terms have the indicated meanings throughout:

A dash ("-") that is not between two letters or symbols is used to indicate a point of attachment for a substituent. For example, —CONH$_2$ is attached through the carbon atom.

As used herein the terms "group", "radical" or "fragment" refer to a functional group or fragment of a molecule attachable to a bond or other fragments of molecules.

When a range of values is given (e.g., $C_{1-6}$ alkyl), each value within the range as well as all intervening ranges are included. For example, "$C_{1-6}$ alkyl" includes $C_1$, $C_2$, $C_3$, $C_4$, $C_5$, $C_6$, $C_{1-6}$, $C_{2-6}$, $C_{3-6}$, $C_{4-6}$, $C_{5-6}$, $C_{1-5}$, $C_{2-5}$, $C_{3-5}$, $C_{4-5}$, $C_{1-4}$, $C_{2-4}$, $C_{3-4}$, $C_{1-3}$, $C_{2-3}$, and $C_{1-2}$ alkyl.

When a moiety is defined as being optionally substituted, it may be substituted as itself or as part of another moiety. For example, if $R^x$ is defined as "$C_{1-6}$ alkyl or $OC_{1-6}$ alkyl, wherein $C_{1-6}$ alkyl is optionally substituted with halogen", then both the $C_{1-6}$ alkyl group alone and the $C_{1-6}$ alkyl that makes up part of the $OC_{1-6}$ alkyl group may be substituted with halogen.

The term "alkyl" encompasses straight chain and branched chain having the indicated number of carbon atoms, usually from 1 to 20 carbon atoms, for example 1 to 8 carbon atoms, such as 1 to 6 carbon atoms. For example $C_1$-$C_6$ alkyl encompasses both straight and branched chain alkyl of 1 to 6 carbon atoms. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. When an alkyl residue having a specific number of carbons is named, all geometric isomers having that number of carbons are intended to be encompassed; thus, for example, "butyl" is meant to include n-butyl, sec-butyl, isobutyl and tert-butyl; "propyl" includes n-propyl and isopropyl. "Lower alkyl" refers to alkyl groups having 1 to 6 carbons.

By "alkoxy" is meant an alkyl group of the indicated number of carbon atoms attached through an oxygen bridge such as, for example, methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. Alkoxy groups will usually have from 1 to 6 carbon atoms attached through the oxygen bridge. "Lower alkoxy" refers to alkoxy groups having 1 to 6 carbons. By "cycloalkoxy" is meant a cycloalkyl group that is likewise attached through an oxygen bridge.

"Alkenyl" refers to an unsaturated branched or straight-chain alkyl group having the indicated number of carbon atoms (e.g., 2 to 8 or 2 to 6 carbon atoms) and at least one carbon-carbon double bond derived by the removal of a molecule of hydrogen from adjacent carbon atoms of the corresponding alkyl. Alkenyl groups include, but are not limited to, ethenyl, propenyl and butenyl. "Lower alkenyl" refers to alkenyl groups having 2 to 6 carbons.

"Alkynyl" refers to an unsaturated branched or straight-chain alkyl group having the indicated number of carbon atoms (e.g., 2 to 8 or 2 to 6 carbon atoms) and at least one carbon-carbon triple bond derived by the removal of two molecules of hydrogen from adjacent carbon atoms of the corresponding alkyl. Alkynyl groups include, but are not limited to, ethynyl, propynyl (e.g., prop-1-yn-1-yl, prop-2-yn-1-yl) and butynyl (e.g., but-1-yn-1-yl, but-1-yn-3-yl, but-3-yn-1-yl). "Lower alkynyl" refers to alkynyl groups having 2 to 6 carbons.

"Aryl" indicates an aromatic carbon ring having the indicated number of carbon atoms, for example, 6 to 12 or 6 to 10 carbon atoms. Aryl groups may be monocyclic or polycyclic (e.g., bicyclic, tricyclic). In some instances, both rings of a polycyclic aryl group are aromatic (e.g., naphthyl). In other instances, polycyclic aryl groups may include a non-aromatic ring (e.g., cycloalkyl, cycloalkenyl, heterocycloalkyl, heterocycloalkenyl) fused to an aromatic ring, provided the polycyclic aryl group is bound to the parent structure via an atom in the aromatic ring. Thus, a 1,2,3,4-tetrahydronaphthalen-5-yl group (wherein the moiety is bound to the parent structure via an aromatic carbon atom) is considered an aryl group, while 1,2,3,4-tetrahydronaphthalen-1-yl (wherein the moiety is bound to the parent structure via a non-aromatic carbon atom) is not considered an aryl group. Similarly, a 1,2,3,4-tetrahydroquinolin-8-yl group (wherein the moiety is bound to the parent structure via an aromatic carbon atom) is considered an aryl group, while 1,2,3,4-tetrahydroquinolin-1-yl group (wherein the moiety is bound to the parent structure via a non-aromatic nitrogen atom) is not considered an aryl group. However, the term "aryl" does not encompass or overlap with "heteroaryl" regardless of the point of attachment (e.g., both quinolin-5-yl and quinolin-2-yl are heteroaryl groups). In some instances, aryl is phenyl or naphthyl. In certain instances, aryl is phenyl.

Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene.

"Cycloalkyl" indicates a non-aromatic, fully saturated carbocyclic ring having the indicated number of carbon atoms, for example, 3 to 10, or 3 to 8, or 3 to 6 ring carbon atoms. Cycloalkyl groups may be monocyclic or polycyclic (e.g., bicyclic, tricyclic). Examples of cycloalkyl groups include cyclopropyl, cyclobutyl, cyclopentyl and cyclohexyl, as well as bridged and caged ring groups (e.g., norbornane, bicyclo[2.2.2]octane). In addition, one ring of a polycyclic cycloalkyl group may be aromatic, provided the polycyclic cycloalkyl group is bound to the parent structure via a non-aromatic carbon. For example, a 1,2,3,4-tetrahydronaphthalen-1-yl group (wherein the moiety is bound to the parent structure via a non-aromatic carbon atom) is a cycloalkyl group, while 1,2,3,4-tetrahydronaphthalen-5-yl (wherein the moiety is bound to the parent structure via an aromatic carbon atom) is not considered a cycloalkyl group.

"Cycloalkenyl" indicates a non-aromatic carbocyclic ring, containing the indicated number of carbon atoms (e.g., 3 to 10, or 3 to 8, or 3 to 6 ring carbon atoms) and at least one carbon-carbon double bond derived by the removal of one molecule of hydrogen from adjacent carbon atoms of the corresponding cycloalkyl. Cycloalkenyl groups may be monocyclic or polycyclic (e.g., bicyclic, tricyclic). Examples of cycloalkenyl groups include cyclopropenyl, cyclobutenyl, cyclopentenyl, cyclopentadienyl, and cyclohexenyl, as well as bridged and caged ring groups (e.g., bicyclo[2.2.2]octene). In addition, one ring of a polycyclic cycloalkenyl group may be aromatic, provided the polycyclic alkenyl group is bound to the parent structure via a non-aromatic carbon atom. For example, inden-1-yl (wherein the moiety is bound to the parent structure via a non-aromatic carbon atom) is considered a cycloalkenyl group, while inden-4-yl (wherein the moiety is bound to the parent structure via an aromatic carbon atom) is not considered a cycloalkenyl group.

The term "halo" includes fluoro, chloro, bromo, and iodo, and the term "halogen" includes fluorine, chlorine, bromine, and iodine.

"Haloalkyl" includes straight and branched carbon chains having the indicated number of carbon atoms (e.g., 1 to 6 carbon atoms) substituted with at least one halogen atom. In instances wherein the haloalkyl group contains more than one halogen atom, the halogens may be the same (e.g., dichloromethyl) or different (e.g., chlorofluoromethyl). Examples of haloalkyl groups include, but are not limited to, chloromethyl, dichloromethyl, trichloromethyl, fluoromethyl, difluoromethyl, trifluoromethyl, chlorofluoromethyl, 2-fluoroethyl, 2,2-difluoroethyl, 2,2,2-trifluoroethyl, 1,2-difluoroethyl, 2-chloroethyl, 2,2-dichloroethyl, 2,2,2-trichloroethyl, 1,2-dichloroethyl, pentachloroethyl, and pentafluoroethyl.

"Heteroaryl" indicates an aromatic ring containing the indicated number of atoms (e.g., 5 to 12, or 5 to 10 membered heteroaryl) made up of one or more heteroatoms (e.g., 1, 2, 3 or 4 heteroatoms) selected from N, O and S and with the remaining ring atoms being carbon. Heteroaryl groups do not contain adjacent S and O atoms. In some embodiments, the total number of S and O atoms in the heteroaryl group is not more than 2. In some embodiments, the total number of S and O atoms in the heteroaryl group is not more than 1. Unless otherwise indicated, heteroaryl groups may be bound to the parent structure by a carbon or nitrogen atom, as valency permits. For example, "pyridyl" includes 2-pyridyl, 3-pyridyl and 4-pyridyl groups, and "pyrrolyl" includes 1-pyrrolyl, 2-pyrrolyl and 3-pyrrolyl groups. When nitrogen is present in a heteroaryl ring, it may, where the nature of the adjacent atoms and groups permits, exist in an oxidized state (i.e., $N^+$—$O^-$). Additionally, when sulfur is present in a heteroaryl ring, it may, where the nature of the adjacent atoms and groups permits, exist in an oxidized state (i.e., $S^+$—$O^-$ or $SO_2$). Heteroaryl groups may be monocyclic or polycyclic (e.g., bicyclic, tricyclic).

In some instances, a heteroaryl group is monocyclic. Examples include pyrrole, pyrazole, imidazole, triazole (e.g., 1,2,3-triazole, 1,2,4-triazole, 1,3,4-triazole), tetrazole, furan, isoxazole, oxazole, oxadiazole (e.g., 1,2,3-oxadiazole, 1,2,4-oxadiazole, 1,3,4-oxadiazole), thiophene, isothiazole, thiazole, thiadiazole (e.g., 1,2,3-thiadiazole, 1,2,4-thiadiazole, 1,3,4-thiadiazole), pyridine, pyridazine, pyrimidine, pyrazine, triazine (e.g., 1,2,4-triazine, 1,3,5-triazine) and tetrazine.

In some instances, both rings of a polycyclic heteroaryl group are aromatic. Examples include indole, isoindole, indazole, benzimidazole, benzotriazole, benzofuran, benzoxazole, benzisoxazole, benzoxadiazole, benzothiophene, benzothiazole, benzoisothiazole, benzothiadiazole, 1H-pyrrolo[2,3-b]pyridine, 1H-pyrazolo[3,4-b]pyridine, 3H-imidazo[4,5-b]pyridine, 3H-[1,2,3]triazolo[4,5-b]pyridine, 1H-pyrrolo[3,2-b]pyridine, 1H-pyrazolo[4,3-b]pyridine, 1H-imidazo[4,5-b]pyridine, 1H-[1,2,3]triazolo[4,5-b]pyridine, 1H-pyrrolo[2,3-c]pyridine, 1H-pyrazolo[3,4-c]pyridine, 3H-imidazo[4,5-c]pyridine, 3H-[1,2,3]triazolo[4,5-c]pyridine, 1H-pyrrolo[3,2-c]pyridine, 1H-pyrazolo[4,3-c]pyridine, 1H-imidazo[4,5-c]pyridine, 1H-[1,2,3]triazolo[4,5-c]pyridine, furo[2,3-b]pyridine, oxazolo[5,4-b]pyridine, isoxazolo[5,4-b]pyridine, [1,2,3]oxadiazolo[5,4-b]pyridine, furo[3,2-b]pyridine, oxazolo[4,5-b]pyridine, isoxazolo[4,5-b]pyridine, [1,2,3]oxadiazolo[4,5-b]pyridine, furo[2,3-c]pyridine, oxazolo[5,4-c]pyridine, isoxazolo[5,4-c]pyridine, [1,2,3]oxadiazolo[5,4-c]pyridine, furo[3,2-c]pyridine, oxazolo[4,5-c]pyridine, isoxazolo[4,5-c]pyridine, [1,2,3]oxadiazolo[4,5-c]pyridine, thieno[2,3-b]pyridine, thiazolo[5,4-b]pyridine, isothiazolo[5,4-b]pyridine, [1,2,3]thiadiazolo[5,4-b]pyridine, thieno[3,2-b]pyridine, thiazolo[4,5-b]pyridine, isothiazolo[4,5-b]pyridine, [1,2,3]thiadiazolo[4,5-b]pyridine, thieno[2,3-c]pyridine, thiazolo[5,4-c]pyridine, isothiazolo[5,4-c]pyridine, [1,2,3]thiadiazol o[5,4-c]pyridine, thieno[3,2-c]pyridine, thiazolo[4,5-c]pyridine, isothiazolo[4,5-c]pyridine, [1,2,3]thiadiazolo[4,5-c]pyridine, quinoline, isoquinoline, cinnoline, quinazoline, quinoxaline, phthalazine, naphthyridine (e.g., 1,8-naphthyridine, 1,7-naphthyridine, 1,6-naphthyridine, 1,5-naphthyridine, 2,7-naphthyridine, 2,6-naphthyridine), imidazo[1,2-a]pyridine, 1H-pyrazolo[3,4-d]thiazole, 1H-pyrazolo[4,3-d]thiazole and imidazo[2,1-b]thiazole.

In other instances, polycyclic heteroaryl groups may include a non-aromatic ring (e.g., cycloalkyl, cycloalkenyl, heterocycloalkyl, heterocycloalkenyl) fused to a heteroaryl ring, provided the polycyclic heteroaryl group is bound to the parent structure via an atom in the aromatic ring. For example, a 4,5,6,7-tetrahydrobenzo[d]thiazol-2-yl group (wherein the moiety is bound to the parent structure via an aromatic carbon atom) is considered a heteroaryl group, while 4,5,6,7-tetrahydrobenzo[d]thiazol-5-yl (wherein the moiety is bound to the parent structure via a non-aromatic carbon atom) is not considered a heteroaryl group.

"Heterocycloalkyl" indicates a non-aromatic, fully saturated ring having the indicated number of atoms (e.g., 3 to 10, or 3 to 7, membered heterocycloalkyl) made up of one or more heteroatoms (e.g., 1, 2, 3 or 4 heteroatoms) selected from N, O and S and with the remaining ring atoms being carbon. Heterocycloalkyl groups may be monocyclic or polycyclic (e.g., bicyclic, tricyclic).

Examples of monocyclic heterocycloalkyl groups include oxiranyl, aziridinyl, azetidinyl, pyrrolidinyl, imidazolidinyl, pyrazolidinyl, piperidinyl, piperazinyl, morpholinyl and thiomorpholinyl.

When nitrogen is present in a heterocycloalkyl ring, it may, where the nature of the adjacent atoms and groups permits, exist in an oxidized state (i.e., $N^+$—$O^-$). Examples include piperidinyl N-oxide and morpholinyl-N-oxide. Additionally, when sulfur is present in a heterocycloalkyl ring, it may, where the nature of the adjacent atoms and groups permits, exist in an oxidized state (i.e., $S^+$—$O^-$ or —$SO_2$—). Examples include thiomorpholine S-oxide and thiomorpholine S,S-dioxide.

In addition, one ring of a polycyclic heterocycloalkyl group may be aromatic (e.g., aryl or heteroaryl), provided the polycyclic heterocycloalkyl group is bound to the parent structure via a non-aromatic carbon or nitrogen atom. For example, a 1,2,3,4-tetrahydroquinolin-1-yl group (wherein the moiety is bound to the parent structure via a non-aromatic nitrogen atom) is considered a heterocycloalkyl group, while 1,2,3,4-tetrahydroquinolin-8-yl group (wherein the moiety is bound to the parent structure via an aromatic carbon atom) is not considered a heterocycloalkyl group.

"Heterocycloalkenyl" indicates a non-aromatic ring having the indicated number of atoms (e.g., 3 to 10, or 3 to 7, membered heterocycloalkyl) made up of one or more heteroatoms (e.g., 1, 2, 3 or 4 heteroatoms) selected from N, O and S and with the remaining ring atoms being carbon, and at least one double bond derived by the removal of one molecule of hydrogen from adjacent carbon atoms, adjacent nitrogen atoms, or adjacent carbon and nitrogen atoms of the corresponding heterocycloalkyl. Heterocycloalkenyl groups may be monocyclic or polycyclic (e.g., bicyclic, tricyclic). When nitrogen is present in a heterocycloalkenyl ring, it may, where the nature of the adjacent atoms and groups permits, exist in an oxidized state (i.e., $N^+$—$O^-$). Additionally, when sulfur is present in a heterocycloalkenyl ring, it may, where the nature of the adjacent atoms and groups permits, exist in an oxidized state (i.e., $S^+$—$O^-$ or —$SO_2$—). Examples of heterocycloalkenyl groups include dihydrofuranyl (e.g., 2,3-dihydrofuranyl, 2,5-dihydrofuranyl), dihydrothiophenyl (e.g., 2,3-dihydrothiophenyl, 2,5-dihydrothiophenyl), dihydropyrrolyl (e.g., 2,3-dihydro-1H-pyrrolyl, 2,5-dihydro-1H-pyrrolyl), dihydroimidazolyl (e.g., 2,3-dihydro-1H-imidazolyl, 4,5-dihydro-1H-imidazolyl), pyranyl, dihydropyranyl (e.g., 3,4-dihydro-2H-pyranyl, 3,6-dihydro-2H-pyranyl), tetrahydropyridinyl (e.g., 1,2,3,4-tetrahydropyridinyl, 1,2,3,6-tetrahydropyridinyl) and dihydropyridine (e.g., 1,2-dihydropyridine, 1,4-dihydropyridine). In addition, one ring of a polycyclic heterocycloalkenyl group may be aromatic (e.g., aryl or heteroaryl), provided the polycyclic heterocycloalkenyl group is bound to the parent structure via a non-aromatic carbon or nitrogen atom. For example, a 1,2-dihydroquinolin-1-yl group (wherein the moiety is bound to the parent structure via a non-aromatic nitrogen atom) is considered a heterocycloalkenyl group, while 1,2-dihydroquinolin-8-yl group (wherein the moiety is bound to the parent structure via an aromatic carbon atom) is not considered a heterocycloalkenyl group.

The term "heterocyclylene" as used herein refers to a non-aromatic monocyclic di-radical having 3- to 5-ring atoms. Examples of heterocyclylene include 1,2-oxiranylene, 2,2-oxiranylene, 1,2-aziridinylene, 2,2-aziridinylene, 2,2-oxetanylene, 2,3-oxetanylene, 2,4-oxetanylene, 3,3-oxetanylene, 2,2-azetindinylene, 2,3-azetindinylene, 2,3-azetindinylene, 3,3-azetindinylene, 2,3-tetrahydrofuranylene, and 3,4-tetrahydrofuranylene.

By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined herein. It will be understood by those skilled in the art, with respect to any group containing one or more substituents, that such groups are not intended to introduce any substitution or substitution patterns that are sterically impractical, synthetically non-feasible, and/or inherently unstable.

The term "substituted", as used herein, means that any one or more hydrogens on the designated atom or group is replaced with a selection from the indicated group, provided that the designated atom's normal valence is not exceeded. When a substituent is oxo (i.e., =O) then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility. Unless otherwise specified, substituents are named into the core structure. For example, it is to be understood that when (cycloalkyl)alkyl is listed as a possible substituent, the point of attachment of this substituent to the core structure is in the alkyl portion.

The terms "substituted" alkyl (including without limitation $C_1$-$C_4$ alkyl), cycloalkyl, cycloalkenyl, aryl, heterocycloalkyl, heterocycloalkenyl, and heteroaryl, unless otherwise expressly defined, refer respectively to alkyl, cycloalkyl, cycloalkenyl, aryl, heterocycloalkyl, heterocycloalkenyl, and heteroaryl, herein one or more (such as up to 5, for example, up to 3) hydrogen atoms are replaced by a substituent independently chosen from: —$R^a$, —$OR^b$, —$O(C_1$-$C_2$ alkyl)O— (e.g., methylenedioxy-), —$SR^b$, guanidine (—NHC(=NH)NH$_2$), guanidine wherein one or more of the guanidine hydrogens are replaced with a $C_1$-$C_4$alkyl group, —$NR^bR^c$, halo, cyano, oxo (as a substituent for heterocycloalkyl), nitro, —$COR^b$, —$CO_2R^b$, —$CONR^bR^c$, —$OCOR^b$, —$OCO_2R^a$, —$OCONR^bR^c$, —$NR^cCOR^b$, —$NR^cCO_2R^a$, —$NR^cCONR^bR^c$, —$SOR^a$, —$SO_2R^a$, —$SO_2NR^bR^c$, and —$NR^cSO_2R^a$, where $R^a$ is chosen from $C_1$-$C_6$ alkyl, cycloalkyl, aryl, heterocycloalkyl, and heteroaryl;

$R^b$ is chosen from H, $C_1$-$C_6$ alkyl, aryl, and heteroaryl; and $R^c$ is chosen from hydrogen and $C_1$-$C_4$ alkyl; or $R^b$ and $R^c$, and the nitrogen to which they are attached, form a heterocycloalkyl group; and where each $C_1$-$C_6$ alkyl, cycloalkyl, aryl, heterocycloalkyl, and heteroaryl is optionally substituted with one or more, such as one, two, or three, substituents independently selected from $C_1$-$C_4$ alkyl, $C_3$-$C_6$ cycloalkyl, aryl, heteroaryl, aryl-$C_1$-$C_4$ alkyl-, heteroaryl-$C_1$-$C_4$ alkyl-, $C_1$-$C_4$ haloalkyl-, —$OC_1$-$C_4$ alkyl, —$OC_1$-$C_4$ alkylphenyl, —$C_1$-$C_4$ alkyl-OH, —$C_1$-$C_4$ alkyl-O—$C_1$-$C_4$ alkyl, —$OC_1$-$C_4$ haloalkyl, halo, —OH, —NH$_2$, —$C_1$-$C_4$ alkyl-NH$_2$, —N($C_1$-$C_4$ alkyl)($C_1$-$C_4$ alkyl), —N($C_1$-$C_4$ alkyl)($C_1$-$C_4$ alkylheteroaryl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for heteroaryl), —$CO_2H$, —C(O)O$C_1$-$C_4$ alkyl, —CON($C_1$-$C_4$ alkyl)($C_1$-$C_4$ alkyl), —CONH($C_1$-$C_4$ alkyl), —CONH$_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —$SO_2(C_1$-$C_4$ alkyl), —$SO_2$(phenyl), —$SO_2(C_1$-$C_4$ haloalkyl), —$SO_2NH_2$, —$SO_2NH(C_1$-$C_4$ alkyl), —$SO_2NH$(phenyl), —$NHSO_2(C_1$-$C_4$ alkyl), —$NHSO_2$(phenyl), and —$NHSO_2(C_1$-$C_4$ haloalkyl).

The term "substituted amino" refers to the group —$NHR^d$ or —$NR^dR^d$ where each $R_d$ is independently chosen from: optionally substituted alkyl, optionally substituted cycloalkyl, optionally substituted acyl, optionally substituted aryl, optionally substituted heteroaryl, optionally substituted heterocycloalkyl, alkoxycarbonyl, sulfinyl and sulfonyl, wherein substituted alkyl, cycloalkyl, aryl, heterocycloalkyl, and heteroaryl refer respectively to alkyl, cycloalkyl, aryl, heterocycloalkyl, and heteroaryl wherein one or more (such as up to 5, for example, up to 3) hydrogen atoms are replaced by a substituent independently chosen from:

—$R^a$, —$OR^b$, —$O(C_1$-$C_2$ alkyl)O— (e.g., methylenedioxy-), —$SR^b$, guanidine, guanidine wherein one or more of the guanidine hydrogens are replaced with a lower-alkyl group, —$NR^bR^c$, halo, cyano, nitro, —$COR^b$, —$CO_2R^b$, —$CONR^bR^c$, —$OCOR^b$, —$OCO_2R^a$, —$OCONR^bR^c$, —$NR^cCOR^b$, —$NR^cCO_2R^a$, —$NR^cCONR^bR^c$, —$CO_2R^b$, —$CONR^bR^c$, —$NR^cCOR^b$, —$SOR^a$, —$SO_2R^a$, —$SO_2NR^bR^c$, and —$NR^cSO_2R^a$, where $R^a$ is chosen from optionally substituted $C_1$-$C_6$ alkyl, optionally substituted aryl, and optionally substituted heteroaryl;

$R^b$ is chosen from H, optionally substituted $C_1$-$C_6$ alkyl, optionally substituted aryl, and optionally substituted heteroaryl; and $R^c$ is chosen from hydrogen and optionally substituted $C_1$-$C_4$ alkyl;

where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl-, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —NH$_2$, —$C_1$-$C_4$ alkyl-NH$_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —N($C_1$-$C_4$ alkyl)($C_1$-$C_4$ alkylheteroaryl), —NH($C_1$-$C_4$ alkylphenyl), cyano, nitro, oxo (as a substitutent for heteroaryl), —$CO_2H$, —C(O)O$C_1$-$C_4$ alkyl, —CON($C_1$-$C_4$ alkyl)($C_1$-$C_4$ alkyl), —CONH($C_1$-$C_4$ alkyl), —CONH$_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —$SO_2(C_1$-$C_4$ alkyl), —$SO_2$(phenyl), —$SO_2(C_1$-$C_4$ haloalkyl), —$SO_2NH_2$, —$SO_2NH(C_1$-$C_4$ alkyl), —$SO_2NH$(phenyl), —$NHSO_2(C_1$-$C_4$ alkyl), —$NHSO_2$(phenyl), and —$NHSO_2(C_1$-$C_4$ haloalkyl).

The term "substituted amino" also refers to the group —$NR^eR^f$ wherein $R^e$ and $R^f$, together with the nitrogen to which they are bound, form an optionally substituted 5- to 7-membered nitrogen-containing, non-aromatic, heterocycle which optionally contains 1 or 2 additional heteroatoms chosen from nitrogen, oxygen, and sulfur.

"Aminocarbonyl" encompasses a group of the formula —(C=O)(optionally substituted amino) wherein substituted amino is as described herein.

Compounds described herein include, but are not limited to, their optical isomers, racemates, and other mixtures thereof. In those situations, the single enantiomers or diastereoisomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. The term "isomers" refers to different compounds that have the same molecular formula. The term "stereoisomers" refers to isomers that differ only in the way the atoms are arranged in space. The term "enantiomers" refers to stereoisomers that are non-superimposable mirror images of each other. A 1:1 mixture of a pair of enantiomers is a "racemic" mixture. The symbol "(±)" may be used to designate a racemic mixture where appropriate. The term "diastereoisomers" refers to stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. The absolute stereochemistry of substituted double bonds may be designated E or Z according to the priority rules of the Cahn-Ingold-Prelog system.

Where compounds described herein exist in various tautomeric forms, the term "compound" includes all tautomeric forms of the compound. Such compounds also include crystal forms including polymorphs and clathrates. Similarly, the term "salt" includes all tautomeric forms and crystal forms of the compound. The term "tautomers" refers to structurally distinct isomers that interconvert by tautomerization. Tautomerization is a form of isomerization and includes prototropic or proton-shift tautomerization, which is considered a subset of acid-base chemistry. Prototropic tautomerization or proton-shift tautomerization involves the migration of a proton accompanied by changes in bond order, often the interchange of a single bond with an adjacent double bond. Where tautomerization is possible (e.g. in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

Pharmaceutically acceptable forms of the compounds recited herein include pharmaceutically acceptable salts, and mixtures thereof. In some embodiments, the compounds described herein are in the form of pharmaceutically acceptable salts.

"Pharmaceutically acceptable salts" include, but are not limited to salts with inorganic acids, such as hydrochlorate, phosphate, diphosphate, hydrobromate, sulfate, sulfinate, nitrate, and like salts; as well as salts with an organic acid, such as malate, maleate, fumarate, tartrate, succinate, citrate, lactate, methanesulfonate, p-toluenesulfonate, 2-hydroxyethylsulfonate, benzoate, salicylate, stearate, haloalkanoate such as trifluoroacetate, and alkanoate such as acetate, $HOOC-(CH_2)_n-COOH$ where n is 0-4, and like salts. Similarly, pharmaceutically acceptable cations include, but are not limited to sodium, potassium, calcium, aluminum, lithium, and ammonium. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

The term "administering", as used herein in conjunction with a diagnostic agent, such as, for example, a positron-emitter labeled compound described herein, means administering directly into or onto a target tissue or to administer the diagnostic agent systemically to a patient whereby the diagnostic agent is used to image the tissue or a pathology associated with the tissue to which it is targeted. "Administering" a composition may be accomplished by injection, infusion, or by either method in combination with other known techniques.

The term "Curie" (Ci) is a unit of measurement of radioactivity. One Ci refers to that amount of any radioactive material that will decay at a rate of $3.7 \times 10^{10}$ disintegrations per second. The term "milliCurie" (mCi) refers to $10^{-3}$ Curie. It is understood that the International System (SI) unit of radioactivity, the Becquerel, is equal to one disintegration/second. Thus one Becquerel=$2.7 \times 10^{-11}$ Curie.

The term "diagnostic imaging", as used herein, refers to the use of electromagnetic radiation to produce images of internal structures of the human or animal body for the purpose of diagnosis.

The term "effective amount" of a compound, as used herein, is a predetermined amount calculated to achieve a desired effect such as an amount sufficient to enable the acquisition of a desired image of the target organ of an individual. In some instances the target organ is the brain.

The term "huntingtin protein" or "HTT protein", as used herein, refers to the protein encoded by the human huntingtin gene (HTT gene) located on the short (p) arm of chromosome 4 at position 16.3. More precisely, the $IT_{15}$ gene coding for the HTT protein is located from base pair 3,076,407 to base pair 3,245,686 on chromosome 4.

The term "HTT protein aggregate", as used herein refers to an insoluble fibrous amyloid comprising mis-folded HTT protein molecules.

The term "β-amyloid aggregate", as used herein refers to an insoluble fibrous amyloid comprising mis-folded β-amyloid protein molecules.

The term "imaging agent", as used herein, refers to a compound as described herein labeled with one or more positron-emitting isotopes or radionuclides. A positron-emitter labeled compound need only be enriched with a detectable isotope to a degree that permits detection with a technique suitable for the particular application.

The term "pathologic process", as used herein, refers to an altered endogenous biological process that may be associated with the aberrant production and/or functioning of proteins, peptides, RNA and other substances associated with such biological process.

The term "PET imaging", as used herein, refers to the use of a positron-emitter labeled compound to produce images of internal structures of the human or animal body.

The term "pharmaceutical composition" refers to a composition comprising at least one imaging agent described herein, whereby the composition is amenable to investigation for a specified, efficacious outcome in a mammal (for example, without limitation, a human). Those of ordinary skill in the art will understand and appreciate the techniques appropriate for determining whether a composition has a desired efficacious outcome based upon the needs of the artisan.

The term "positron-emitting radionuclide", as used herein, refers to a radio-active isotope that exhibits particular type of radioactive decay referred to as β+ decay, in which a proton inside a radionuclide nucleus is converted into a neutron while releasing a positron and an electron neutrino ($v_e$). Some examples of positron-emitting radionuclides include $^{15}O$, $^{13}N$, $^{11}C$, $^{18}F$, $^{76}Br$, and $^{124}I$. These radionuclides have half-lives of about 2, 10, 20, 110 minutes, 16 hours, and 4.2 days respectively.

The term "tomography", as used herein, refers to a process of imaging by sections. The images may be looked at individually, as a series of two-dimensional slices or together, as a computer-generated three-dimensional representation.

Provided is an imaging agent comprising a compound of Formula I, or a pharmaceutically acceptable salt thereof,

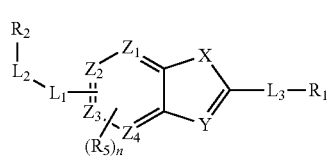

(I)

wherein

X is chosen from $NR_4$, O and S;

Y is chosen from $CR_4$ and N;

$Z_1$, $Z_2$, $Z_3$, and $Z_4$ are independently chosen from CH and N, provided that at least two of $Z_1$, $Z_2$, $Z_3$, and $Z_4$ are CH;

$R_1$ is chosen from heteroaryl, heterocycloalkenyl, and heterocycloalkyl, each of which is optionally substituted with one or two groups independently chosen from cyano, halo, lower alkyl optionally substituted with amino, alkylamino, or di(alkyl)amino, lower alkoxy optionally substituted with lower alkoxy, optionally substituted amino, haloalkyl, di(alkyl)aminocarbonyl, alkylaminocarbonyl, and aminocarbonyl, or $R_1$ is phenyl optionally substituted with one or two groups independently chosen from cyano, heteroaryl, halo, phenoxy, benzyloxy, heteroaryl, lower alkyl optionally substituted with amino, (alkyl)amino, or di(alkyl)amino, lower alkoxy, optionally substituted amino, di(alkyl)aminocarbonyl, alkylaminocarbonyl, and aminocarbonyl;

$L_1$ is —O— and $L_2$ is —$(CR_7R_8)_m$— or —$(CR_7R_8)_m$—O—; or $L_1$ is —$NR_3$— and $L_2$ is —C(O)— or —$(R_7R_8)_m$—; or $L_1$ is —$NR_3$— and $L_2$ is —C(O)(O)$(R_7R_8)_m$—; or $L_1$ is —$NR_3$— and $L_2$ is —C(O)$(R_7R_8)_m$(O)—; or $L_1$ is —$NR_3$— and $L_2$ is —C(O)$(R_7R_8)_m$—; or $L_1$ is —$NR_3$— and $L_2$ is —C(O)$CR_7$=$CR_8$—; or $L_1$ is —C(O)— and $L_2$ is —$NR_3$; or $L_1$ is —$(R_7R_8)_m$— and $L_2$ is —$NR_3$—, —C(O)— or —O—; or $L_1$ is absent and $L_2$ is absent; or $L_1$ taken together with $L_2$ is —CH=CH—, —C≡C—, or heterocyclylene;

$L_3$ is —CH=CH—, or $L_3$ is absent;

$R_2$ is chosen from heterocycloalkyl, aryl and heteroaryl, each of which is optionally substituted with one or two groups chosen from
—OC(O)—$R_6$,
—C(O)O—$R_6$,
amino,
halo,
haloalkyl,
phenyl,
heteroaryl,
cyano,
(lower alkyl)thio,
phenoxy,
phenoxymethyl,
heteroaryloxy,
heteroaryloxy substituted with lower alkyl,
hydroxyl,
lower alkenyloxy,
lower alkoxy,
lower alkoxy substituted with lower alkoxy, amino, (alkyl)amino, (dialkyl)amino, heterocycloalkyl, heteroaryl, or halo,
lower alkyl, and
lower alkyl substituted with amino, (alkyl)amino, (dialkyl)amino, hydroxyl or lower alkoxy;

$R_3$ is chosen from hydrogen and lower alkyl;

$R_4$ is chosen from hydrogen, halo, cyano, and lower alkyl;

$R_5$ is chosen from lower alkyl, lower alkoxy, and halo;

$R_6$ is lower alkyl;

$R_7$ is chosen from hydrogen, hydroxyl, trifluoromethyl, and lower alkyl;

$R_8$ is chosen from hydrogen and lower alkyl;

n is 0 or 1; and m is 0, 1, or 2;

wherein the compound of Formula I, or a pharmaceutically acceptable salt thereof, is labeled with one or more positron-emitting radionuclides.

Provided is an imaging agent comprising a compound of Formula I, or a pharmaceutically acceptable salt thereof, (I)

wherein

X is chosen from $NR_4$, O and S;

Y is chosen from $CR_4$ and N;

$Z_1$, $Z_2$, $Z_3$, and $Z_4$ are independently chosen from CH and N, provided that at least two of $Z_1$, $Z_2$, $Z_3$, and $Z_4$ are CH;

$R_1$ is chosen from heteroaryl and heterocycloalkyl, each of which is optionally substituted with one or two groups independently chosen from cyano, halo, lower alkyl, lower alkoxy optionally substituted with lower alkoxy, optionally substituted amino, and aminocarbonyl, or $R_1$ is phenyl optionally substituted with one or two groups independently chosen from cyano, halo, lower alkyl optionally substituted with amino, (alkyl)amino, or di(alkyl)amino, lower alkoxy, optionally substituted amino, and aminocarbonyl;

$L_1$ is —O— and $L_2$ is —$(CR_7R_8)_m$— or —$(CR_7R_8)_m$—O—; or $L_1$ is —$NR_3$— and $L_2$ is —C(O)— or —$(R_7R_8)_m$—; or $L_1$ is —$(R_7R_8)_m$— and $L_2$ is —$NR_3$—, —C(O)— or —O—; or $L_1$ is absent and $L_2$ is absent; or $L_1$ taken together with $L_2$ is —CH=CH—, —C≡C—, or heterocyclylene;

$R_2$ is chosen from heterocycloalkyl, aryl and heteroaryl, each of which is optionally substituted with one or two groups chosen from
—OC(O)—$R_6$,
hydroxyl,
lower alkenyloxy,
lower alkoxy,
lower alkoxy substituted with lower alkoxy, amino, (alkyl)amino, (dialkyl)amino, heterocycloalkyl, or halo,
lower alkyl, and
lower alkyl substituted with amino, (alkyl)amino, (dialkyl)amino, hydroxyl or lower alkoxy;

$R_3$ is chosen from hydrogen and lower alkyl;

$R_4$ is chosen from hydrogen, halo, cyano, and lower alkyl;

$R_5$ is chosen from lower alkyl, lower alkoxy, and halo;

$R_6$ is lower alkyl;

$R_7$ is chosen from hydrogen, hydroxyl, trifluoromethyl, and lower alkyl;

$R_8$ is chosen from hydrogen and lower alkyl;

n is 0 or 1; and m is 0, 1, or 2;

wherein the compound of Formula I, or a pharmaceutically acceptable salt thereof, is labeled with one or more positron-emitting radionuclides.

In some embodiments, X is O.
In some embodiments, X is S.
In some embodiments, X is $NR_4$.
In some embodiments, Y is $CR_4$.
In some embodiments, $R_4$ is hydrogen. In some embodiments, $R_4$ is halo. In some embodiments, $R_4$ is bromo. In some embodiments, $R_4$ is cyano. In some embodiments, $R_4$ is lower alkyl. In some embodiments, $R_4$ is methyl.

In some embodiments, Y is N.

In some embodiments, $Z_1$, $Z_2$, $Z_3$, and $Z_4$ are CH.
In some embodiments, $Z_1$ is N and $Z_2$, $Z_3$, and $Z_4$ are CH.
In some embodiments, $Z_2$ is N and $Z_1$, $Z_3$, and $Z_4$ are CH.
In some embodiments, $Z_2$ and $Z_4$ are N and $Z_1$ and $Z_3$ are CH.

In some embodiments, $R_1$ is chosen from phenyl, pyridine-2-yl, pyridine-3-yl, pyridine-3-yl-1-oxide, pyridine-4-yl, 1H-pyrazol-4-yl, pyrazin-2-yl, pyridazin-3-yl, pyridazin-4-yl, pyrimidin-4-yl, pyrimidin-5-yl, 2,3-dihydropyridazin-3-one-6-yl, 1,2-dihydropyridin-2-one-5-yl, 1,2-dihydropyrazin-2-one-5-yl, 1,3-thiazol-5-yl, 5,6,7,8-tetrahydro-1,7-naphthyridine-7-yl, 1H-imidazol-1-yl, 1-benzofuran-2-yl, 1-benzofuran-5-yl, 2,3-dihydro-1-benzofuran-2-yl, quinolone-2-yl, and 5H,6H,7H,8H-imidazo[1,2-a]pyrazin-7-yl, each of which is optionally substituted with one or two groups independently chosen from halo, lower alkyl, lower alkoxy, and optionally substituted amino.

In some embodiments $R_1$ is

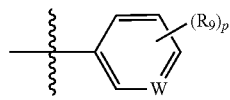

wherein W is chosen from CH, N, and N(O);
p is chosen from 0, 1, and 2;
for each occurrence, $R_9$ is independently chosen from cyano, halo, lower alkyl, lower haloalkyl, lower alkyl substituted with $-NR_{10}R_{11}$, lower alkoxy, $-C(O)NR_{10}R_{11}$, and $-NR_{10}R_{11}$;
$R_{10}$ is chosen from hydrogen and lower alkyl;
$R_{11}$ is chosen from hydrogen, lower alkyl, and $-C(O)R_{12}$; and
$R_{12}$ is chosen from hydrogen and lower alkyl.

In some embodiments,
W is chosen from CH and N;
p is chosen from 0, 1, and 2;
for each occurrence, $R_9$ is independently chosen from cyano, halo, lower alkyl, lower alkoxy, $-C(O)NR_{10}R_{11}$, and $-NR_{10}R_{11}$
$R_{10}$ is chosen from hydrogen and lower alkyl;
$R_{11}$ is chosen from hydrogen, lower alkyl, and $-C(O)R_{12}$; and
$R_{12}$ is chosen from hydrogen and lower alkyl.

In some embodiments, W is CH. In some embodiments, W is N. In some embodiments, W is N(O).
In some embodiments, p is 0.
In some embodiments, p is 1.
In some embodiments, $R_9$ is chosen from cyano, halo, methyl, and methoxy.

In some embodiments, $R_1$ is

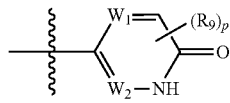

wherein
$W_1$ and $W_2$ are chosen from CH and N, provided that at least one of $W_1$ and $W_2$ is CH;
p is chosen from 0, 1, and 2; and
for each occurrence, $R_9$ is independently chosen from lower alkyl. In some embodiments, $R_1$ is 1H-pyrazol-4-yl optionally substituted with lower alkyl.

In some embodiments, $L_1$ is $-O-$ and $L_2$ is $-(CR_7R_8)_m-$ or $-(CR_7R_8)_m-O-$. In some embodiments, $L_1$ is $-O-$ and $L_2$ is $-(CR_7R_8)_m-$.

In some embodiments, $L_1$ is $-O-$, $L_2$ is $-(CR_7R_8)_m-$ or $-(CR_7R_8)_m-O-$ and $R_2$ is phenyl, pyridine-2-yl, pyridine-3-yl, pyrazin-2-yl, pyrimidine-5-yl, 1H-imidazol-4-yl, 1H-imidazol-2-yl, or 1H-pyrazol-4-yl, each of which is optionally substituted with one or two groups independent chosen from lower alkyl, hydroxyl, lower alkoxy, lower alkoxy substituted with amino, (alkyl)amino, (dialkyl)amino, or lower alkoxy, lower alkyl, and lower alkyl substituted with hydroxyl, lower alkoxy, amino, (alkyl)amino, or (dialkyl)amino.

In some embodiments, $L_1$ is $-O-$, $L_2$ is $-(CR_7R_8)_m-$ and $R_2$ is phenyl, pyridine-2-yl, pyridine-3-yl, pyrazin-2-yl, pyrimidine-5-yl, 1H-imidazol-4-yl, 1H-imidazol-2-yl, or 1H-pyrazol-4-yl, each of which is optionally substituted with one or two groups independent chosen from lower alkyl, hydroxyl, lower alkoxy, lower alkoxy substituted with amino, (alkyl)amino, (dialkyl)amino, or lower alkoxy, lower alkyl, and lower alkyl substituted with hydroxyl, lower alkoxy, amino, (alkyl)amino, or (dialkyl)amino.

In some embodiments, $L_1$ is $-NR_3-$ and $L_2$ is $-C(O)-$ or $-(CR_7R_8)_m-$. In some embodiments, $L_1$ is $-NR_3-$ and $L_2$ is $-C(O)-$. In some embodiments, $R_3$ is hydrogen.

In some embodiments, $L_1$ is $-NR_3-$, $L_2$ is $-C(O)-$ or $-(CR_7R_8)_m-$ and $R_2$ is phenyl, pyridine-3-yl, or pyrazin-2-yl, each of which is optionally substituted with lower alkyl, hydroxyl or lower alkoxy.

In some embodiments, $L_1$ is $-NR_3-$, $L_2$ is $-C(O)-$ or $-(CR_7R_8)_m-$ and $R_2$ is phenyl, pyridine-3-yl, or pyrazin-2-yl, each of which is optionally substituted with lower alkoxy.

In some embodiments, $L_1$ is $-NR_3-$, $L_2$ is $-C(O)-$ and $R_2$ is phenyl, pyridine-3-yl, or pyrazin-2-yl, each of which is optionally substituted with lower alkoxy.

In some embodiments, $L_1$ is $-NR_3-$ and $L_2$ is $-(CR_7R_8)_m$ where m is 1. In some embodiments, $R_3$ is hydrogen.

In some embodiments, $L_1$ is $-NR_3-$, $L_2$ is $-(CR_7R_8)_m$ where m is 1, and $R_2$ is phenyl or phenyl substituted with lower alkoxy.

In some embodiments, $L_1$ is $-NR_3-$ and $L_2$ is $-(CR_7R_8)_m$ where m is 0. In some embodiments, $R_3$ is hydrogen.

In some embodiments, $L_1$ is $-NR_3-$, $L_2$ is $-(CR_7R_8)_m$ where m is 0, and $R_2$ is phenyl, [1,2,4]triazolo[4,3-a]pyridin-3-yl, pyrimidin-4-yl, or pyrimidin-2-yl, each of which is optionally substituted with lower alkoxy.

In some embodiments, $L_1$ is absent and $L_2$ is absent.

In some embodiments, $L_1$ is absent, $L_2$ is absent, and $R_2$ is phenyl, pyrimidin-2-yl, pyridazin-3-yl, pyrazin-2-yl, piperazin-1-yl, 1H-pyrazol-4-yl, 1,2,3,4-tetrahydroisoquinolin-1-one-2-yl, 2,3-dihydro-1H-isoindol-1-one-2-yl, 1,2-dihydroisoquinolin-1-one-2-yl, or 5H,6H,7H-pyrrolo[3,4-b]pyridine-7-one-2-yl, each of which is optionally substituted with one or two groups independently chosen from 5-methoxypyrimidin-2-yl, hydroxyl and lower alkoxy.

In some embodiments, $L_1$ taken together with $L_2$ is $-CH=CH-$ or $-C\equiv C-$.

In some embodiments, L₁ taken together with L₂ is —CH=CH— or —C≡C—, and R₂ is phenyl or pyridine-3-yl, each of which is optionally substituted with one or two groups independently chosen from hydroxyl and lower alkoxy.

In some embodiments, L₁ taken together with L₂ is heterocyclylene. In some embodiments, L₁ taken together with L₂ is piperazin-1,4-diyl. In some embodiments, L₁ taken together with L₂ is heterocyclylene and R₂ is pyrimidin-2-yl, optionally substituted with one or two groups independently chosen from hydroxyl and lower alkoxy. In some embodiments, L₁ taken together with L₂ is piperazin-1,4-diyl and R₂ is pyrimidin-2-yl, optionally substituted with one or two groups independently chosen from hydroxyl and lower alkoxy In some embodiments, L₁ is —(CR₇R₈)ₘ— and L₂ is —NR₃—, —C(O)— or —O—.

In some embodiments, L₁ is —(CR₇R₈)ₘ—, L₂ is —NR₃—, —C(O)— or —O—, and R₂ is pyridin-2-yl or pyridin-2-yl substituted with lower alkoxy.

In some embodiments, m is 1 and each occurrence of R₇ and R₈ is hydrogen.

In some embodiments, m is 2 and each occurrence of R₇ and R₈ is hydrogen.

In some embodiments, m is 1, R₇ is hydroxyl, trifluoromethyl, or lower alkyl and R₈ is hydrogen.

In some embodiments, m is 2, one occurrence of R₇ is hydroxyl, trifluoromethyl, or lower alkyl, and the other occurrence of R₇ and each occurrence of R₈ is hydrogen.

Also provided is a compound of Formula I chosen from tert-butyl 4-[2-(pyridin-3-yl)-1,3-benzoxazol-5-yl]piperazine-1-carboxylate;
4-methoxy-N-[2-(pyridin-3-yl)-1,3-benzoxazol-5-yl]benzamide;
4-methoxy-N-[2-(pyridin-4-yl)-1,3-benzoxazol-5-yl]benzamide;
N-[(4-methoxyphenyl)methyl]-2-(pyridin-3-yl)-1,3-benzoxazol-5-amine;
2-(3-bromopyridin-4-yl)-6-[2-(morpholin-4-yl)ethoxy]-1,3-benzothiazole;
5-methoxy-N-[2-(3-methylphenyl)-1,3-benzoxazol-5-yl]pyridine-2-carboxamide;
6-methoxy-N-[2-(3-methylphenyl)-1,3-benzoxazol-5-yl]pyridine-3-carboxamide;
2-methoxy-N-[2-(3-methylphenyl)-1,3-benzoxazol-5-yl]pyrimidine-5-carboxamide;
5-methoxy-N-[2-(3-methylphenyl)-1,3-benzoxazol-5-yl]pyrazine-2-carboxamide;
4-methoxy-N-[2-(3-methylphenyl)-[1,3]oxazolo[5,4-b]pyridin-6-yl]benzamide;
5-(4-methoxyphenyl)-2-(pyridin-3-yl)-1,3-benzoxazole;
N-(4-methoxyphenyl)-2-(pyridin-3-yl)-1,3-benzoxazol-5-amine;
2-(pyridin-3-yl)-N-{[1,2,4]triazolo[4,3-a]pyridin-3-yl}-1,3-benzoxazol-5-amine;
2-(pyridin-3-yl)-N-(pyrimidin-4-yl)-1,3-benzoxazol-5-amine;
2-(pyridin-3-yl)-N-(pyrimidin-2-yl)-1,3-benzoxazol-5-amine;
5-(5-methoxypyridin-2-yl)-2-(pyridin-3-yl)-1,3-benzoxazole;
5-(2-methoxypyrimidin-5-yl)-2-(pyridin-3-yl)-1,3-benzoxazole;
5-(5-methoxypyrimidin-2-yl)-2-(pyridin-3-yl)-1,3-benzoxazole;
5-(6-methoxypyridazin-3-yl)-2-(pyridin-3-yl)-1,3-benzoxazole;
5-(5-methoxypyrazin-2-yl)-2-(pyridin-3-yl)-1,3-benzoxazole;
1-methyl-4-[5-(pyrimidin-5-ylmethoxy)-1-benzofuran-2-yl]-1H-pyrazole-3-carbonitrile;
4-[5-(pyrimidin-5-ylmethoxy)-1-benzofuran-2-yl]pyridine-3-carbonitrile;
4-{5-[(5-methoxypyridin-2-yl)methoxy]-1-benzofuran-2-yl}pyridine-3-carbonitrile;
4-{5-[(5-methoxypyridin-2-yl)methoxy]-1-benzofuran-2-yl}pyridine;
4-{5-[(1-methyl-1H-imidazol-4-yl)methoxy]-1-benzofuran-2-yl}pyridine-3-carbonitrile;
4-{5-[(1-methyl-1H-imidazol-2-yl)methoxy]-1-benzofuran-2-yl}pyridine-3-carbonitrile;
5-methoxy-2-[2-(pyridin-3-yl)-1,3-benzoxazol-5-yl]-2,3-dihydro-1H-isoindol-1-one;
3-{6-[(E)-2-(4-methoxyphenyl)ethenyl]-[1,3]oxazolo[5,4-b]pyridin-2-yl}pyridine;
4-[5-(pyridin-3-yloxy)-1-benzofuran-2-yl]pyridine-3-carbonitrile;
6-methoxy-2-[2-(pyridin-3-yl)-1,3-benzoxazol-5-yl]-1,2,3,4-tetrahydroisoquinolin-1-one;
dimethyl({3-[4-({[2-(pyridin-3-yl)-1,3-benzoxazol-5-yl]oxy}methyl)phenoxy]propyl})amine;
5-[(1-methyl-1H-pyrazol-4-yl)methoxy]-2-(pyridin-3-yl)-1,3-benzoxazole;
5-[(4-methoxyphenyl)methoxy]-2-(pyridin-3-yl)-1,3-benzoxazole;
5-[(3-methoxyphenyl)methoxy]-2-(pyridin-3-yl)-1,3-benzoxazole;
5-[(5-methoxypyridin-2-yl)methoxy]-2-(pyridin-3-yl)-1,3-benzoxazole;
2-(pyridin-3-yl)-5-(pyridin-3-ylmethoxy)-1,3-benzoxazole;
5-{5H,6H-imidazo[2,1-b][1,3]thiazol-3-ylmethoxy}-2-(pyridin-3-yl)-1,3-benzoxazole;
1-(pyridin-2-yl)-2-[2-(pyridin-3-yl)-1,3-benzoxazol-5-yl]ethan-1-ol;
1-(pyridin-2-yl)-2-[2-(pyridin-3-yl)-1,3-benzoxazol-5-yl]ethan-1-one;
6-methoxy-2-[2-(pyridin-3-yl)-1,3-benzoxazol-5-yl]-1,2-dihydroisoquinolin-1-one;
2-(pyridin-3-yl)-N-[2,2,2-trifluoro-1-(4-methoxyphenyl)ethyl]-[[1,3]oxazolo[5,4-b]pyridin-6-amine;
3-{6-[2-(4-methoxyphenyl)ethynyl]-[1,3]oxazolo[5,4-b]pyridin-2-yl}pyridine;
3-{6-[(Z)-2-(4-methoxyphenyl)ethenyl]-[1,3]oxazolo[5,4-b]pyridin-2-yl}pyridine;
5-methoxy-2-[2-(pyridin-3-yl)-[1,3]oxazolo[5,4-b]pyridin-6-yl]-2,3-dihydro-1H-isoindol-1-one;
5-[(5-methoxypyrazin-2-yl)methoxy]-2-(pyridin-3-yl)-1,3-benzoxazole;
3-methoxy-6-[2-(pyridin-3-yl)-1,3-benzoxazol-5-yl]-5H,6H,7H-pyrrolo[3,4-b]pyridin-7-one;
2-(pyridin-3-yl)-6-(pyridin-3-ylmethoxy)-1,3-benzoxazole;
3-{6-[2-(pyridin-3-yl)ethynyl]-[1,3]oxazolo[5,4-b]pyridin-2-yl}pyridine;
5-{[(5-methoxypyridin-2-yl)oxy]methyl}-2-(pyridin-3-yl)-1,3-benzoxazole;
4-[5-(pyridin-3-ylmethoxy)-1-benzofuran-2-yl]pyridine-3-carbonitrile;
4-{5-[(1-methyl-1H-pyrazol-4-yl)methoxy]-1-benzofuran-2-yl}pyridine-3-carbonitrile;
3-[5-(pyridin-3-ylmethoxy)-1-benzofuran-2-yl]pyridine-4-carbonitrile;
3-{5-[(1-methyl-1H-pyrazol-4-yl)methoxy]-1-benzofuran-2-yl}pyridine-4-carbonitrile;

3-{6-[1-(5-methoxypyridin-2-yl)ethoxy]-[1,3]oxazolo[5,4-b]pyridin-2-yl}pyridine;
4-{5-[(5-methoxypyrazin-2-yl)methoxy]-1-benzofuran-2-yl}pyridine-3-carbonitrile;
6-({[2-(pyridin-3-yl)-1,3-benzoxazol-5-yl]oxy}methyl)pyridin-3-ol;
5-{[5-(prop-2-en-1-yloxy)pyrazin-2-yl]methoxy}-2-(pyridin-3-yl)-1,3-benzoxazole;
5-({[2-(pyridin-3-yl)-1,3-benzoxazol-5-yl]oxy}methyl)-1,2-dihydropyrazin-2-one;
1-methyl-5-({[2-(pyridin-3-yl)-1,3-benzoxazol-5-yl]oxy}methyl)-1,2-dihydropyrazin-2-one;
5-[4-(5-methoxypyrimidin-2-yl)piperazin-1-yl]-2-(pyridin-3-yl)-1,3-benzoxazole;
3-{6-[(5-methoxypyridin-2-yl)methoxy]-[1,3]oxazolo[5,4-b]pyridin-2-yl}pyridine;
5-(1-methyl-1H-pyrazol-4-yl)-2-(pyridin-3-yl)-1,3-benzoxazole;
3-{6-[(6-methoxypyridin-3-yl)methoxy]-[1,3]oxazolo[5,4-b]pyridin-2-yl}pyridine;
5-[(5-methoxypyridin-2-yl)methoxy]-2-(pyridin-4-yl)-1,3-benzoxazole;
[(3-{5-[(5-methoxypyridin-2-yl)methoxy]-1,3-benzoxazol-2-yl}phenyl)methyl]dimethylamine;
5-[(5-methoxypyridin-2-yl)methoxy]-2-(1-methyl-1H-pyrazol-4-yl)-1,3-benzoxazole;
5-[(5-methoxypyridin-2-yl)methoxy]-2-(pyrazin-2-yl)-1,3-benzoxazole;
5-[(5-methoxypyridin-2-yl)methoxy]-2-(1-methylpiperidin-4-yl)-1,3-benzoxazole;
5-[(5-methoxypyridin-2-yl)methoxy]-2-(1,3-thiazol-5-yl)-1,3-benzoxazole;
5-[2-(pyridin-2-yloxy)ethoxy]-2-(pyridin-3-yl)-1,3-benzoxazole;
4-{5-(1H-pyrazol-4-ylmethoxy)-1-benzofuran-2-yl}pyridine-3-carbonitrile;
3-{[(2-{5H,6H-imidazo[2,1-b][1,3]thiazol-3-yl}-1-benzofuran-5-yl)oxy]methyl}pyridine;
2-(3-fluoroazetidin-1-yl)-5-[(5-methoxypyridin-2-yl)methoxy]-1,3-benzoxazole;
2-{3H,4H,5H,6H,7H-imidazo[4,5-c]pyridin-5-yl}-5-[(5-methoxypyridin-2-yl)methoxy]-1,3-benzoxazole;
5-[(5-methoxypyridin-2-yl)methoxy]-2-{2H,4H,5H,6H,7H-pyrazolo[4,3-c]pyridin-5-yl}-1,3-benzoxazole;
2-{5H,6H,7H,8H-imidazo[1,5-a]pyrazin-7-yl})-5-[(5-methoxypyridin-2-yl)methoxy]-1,3-benzoxazole;
5-[(5-methoxypyridin-2-yl)methoxy]-2-{5H,6H,7H-pyrrolo[3,4-b]pyridin-6-yl}-1,3-benzoxazole;
7-{5-[(5-methoxypyridin-2-yl)methoxy]-1,3-benzoxazol-2-yl}-5,6,7,8-tetrahydro-1,7-naphthyridine;
2-(1H-imidazol-1-yl)-5-[(5-methoxypyridin-2-yl)methoxy]-1,3-benzoxazole;
2-{5H,6H,7H,8H-imidazo[1,2-a]pyrazin-7-yl}-5-[(5-methoxypyridin-2-yl)methoxy]-1,3-benzoxazole;
4-(5-{[1-(2-methoxyethyl)-1H-pyrazol-4-yl]methoxy}-1-benzofuran-2-yl)pyridine-3-carbonitrile;
2-[5-(2-methoxyethoxy)pyridin-3-yl]-5-[(5-methoxypyridin-2-yl)methoxy]-1,3-benzoxazole;
N-(5-{5-[(5-methoxypyridin-2-yl)methoxy]-1,3-benzoxazol-2-yl}pyridin-2-yl)acetamide;
5-{5-[(5-methoxypyridin-2-yl)methoxy]-1,3-benzoxazol-2-yl}pyridin-2-amine;
methyl({[4-({[2-(pyridin-3-yl)-1,3-benzoxazol-5-yl]oxy}methyl)phenyl]methyl})amine;
4-(5-{[1-(2-hydroxyethyl)-1H-pyrazol-4-yl]methoxy}-1-benzofuran-2-yl)pyridine-3-carbonitrile;
dimethyl({2-[4-({[2-(pyridin-3-yl)-1,3-benzoxazol-5-yl]oxy}methyl)phenoxy]ethyl})amine;
5-{[5-(2-methoxyethoxy)pyridin-2-yl]methoxy}-2-(pyridin-3-yl)-1,3-benzoxazole;
4-[5-({1-[2-(dimethylamino)ethyl]-1H-pyrazol-4-yl}methoxy)-1-benzofuran-2-yl]pyridine-3-carbonitrile;
5-{5-[(5-methoxypyridin-2-yl)methoxy]-1,3-benzoxazol-2-yl}-N-methylpyridin-2-amine;
3-{[(2-{2-bromo-5H,6H-imidazo[2,1-b][1,3]thiazol-3-yl}-1-benzofuran-5-yl)oxy]methyl}pyridine;
5-[(5-methoxypyrazin-2-yl)methoxy]-1-methyl-2-(pyridin-3-yl)-1H-1,3-benzodiazole;
6-[(5-methoxypyrazin-2-yl)methoxy]-1-methyl-2-(pyridin-3-yl)-1H-1,3-benzodiazole;
5-[(5-methoxypyrazin-2-yl)methoxy]-2-(pyridin-3-yl)-1H-1,3-benzodiazole;
5-[(5-methoxypyridin-2-yl)methoxy]-2-(piperazin-1-yl)-1,3-benzoxazole;
N-methyl-6-({[2-(pyridin-3-yl)-1,3-benzoxazol-5-yl]oxy}methyl)pyridin-3-amine;
3-[5-(pyridin-3-ylmethoxy)-1-benzofuran-2-yl]-5H,6H-imidazo[2,1-b][1,3]thiazole-2-carbonitrile;
5-{5-[(5-methoxypyridin-2-yl)methoxy]-1,3-benzoxazol-2-yl}-N-methylpyridine-2-carboxamide;
5-[(5-methoxypyridin-2-yl)methoxy]-2-(1-methyl-1H-imidazol-4-yl)-1,3-benzoxazole;
5-methoxy-N-{[2-(pyridin-3-yl)-1,3-benzoxazol-5-yl]methyl}pyridin-2-amine;
4-(5-{5H,6H-imidazo[2,1-b][1,3]thiazol-3-ylmethoxy}-1-benzofuran-2-yl)pyridine-3-carbonitrile;
5-({5-[2-(morpholin-4-yl)ethoxy]pyridin-2-yl}methoxy)-2-(pyridin-3-yl)-1,3-benzoxazole;
2-bromo-6-{5-[(5-methoxypyridin-2-yl)methoxy]-1-benzofuran-2-yl}benzonitrile;
4-{[2-(4-chlorophenyl)-1,3-benzoxazol-5-yl]carbamoyl}phenyl acetate;
N-(2-phenyl-1,3-benzoxazol-5-yl)benzamide;
4-methoxy-N-[2-(3-methylphenyl)-1,3-benzoxazol-5-yl]benzamide;
2-methoxy-N-[2-(4-methoxyphenyl)-1,3-benzoxazol-5-yl]benzamide;
4-methoxy-N-[2-(4-methoxyphenyl)-1,3-benzoxazol-5-yl]benzamide;
3-methoxy-N-[2-(4-methoxyphenyl)-1,3-benzoxazol-5-yl]benzamide;
3-{5-[(5-methoxypyridin-2-yl)methoxy]-1,3-benzoxazol-2-yl}pyridin-1-ium-1-olate;
2-phenoxy-N-[2-(pyridin-3-yl)-1,3-benzoxazol-5-yl]acetamide;
N-[2-(pyridin-3-yl)-1,3-benzoxazol-5-yl]-1-benzofuran-2-carboxamide;
N-[2-(pyridin-3-yl)-1,3-benzoxazol-5-yl]-6-(trifluoromethyl)pyridine-3-carboxamide;
N-[2-(pyridin-3-yl)-1,3-benzoxazol-5-yl]quinoxaline-2-carboxamide;
6-phenoxy-N-[2-(pyridin-3-yl)-1,3-benzoxazol-5-yl]pyridine-3-carboxamide;
N-[2-(pyridin-3-yl)-1,3-benzoxazol-5-yl]-2H-1,3-benzodioxole-5-carboxamide;
3-(benzyloxy)-N-[2-(pyridin-3-yl)-1,3-benzoxazol-5-yl]benzamide;
3-phenoxy-N-[2-(pyridin-3-yl)-1,3-benzoxazol-5-yl]benzamide;
N-[2-(pyridin-3-yl)-1,3-benzoxazol-5-yl]quinoline-2-carboxamide;
N-[2-(pyridin-3-yl)-1,3-benzoxazol-5-yl]-2,3-dihydro-1-benzofuran-2-carboxamide;

5-methyl-N-[2-(pyridin-3-yl)-1,3-benzoxazol-5-yl]pyridine-3-carboxamide;
N-[2-(pyridin-3-yl)-1,3-benzoxazol-5-yl]quinoxaline-6-carboxamide;
(2E)-3-(4-methoxyphenyl)-N-[2-(pyridin-3-yl)-1,3-benzoxazol-5-yl]prop-2-enamide;
5-methoxy-N-[2-(pyridin-3-yl)-1,3-benzoxazol-5-yl]pyridine-2-carboxamide;
3-cyano-N-[2-(pyridin-3-yl)-1,3-benzoxazol-5-yl]benzamide;
4-(methylsulfanyl)-N-[2-(pyridin-3-yl)-1,3-benzoxazol-5-yl]benzamide;
benzyl N-[2-(pyridin-3-yl)-1,3-benzoxazol-5-yl]carbamate;
5-[2-(pyridin-3-yl)-1,3-benzoxazol-5-yl]pyrazin-2-ol;
5-[(5-methoxypyridin-2-yl)methoxy]-2-(pyrimidin-5-yl)-1,3-benzoxazole;
2-(2,3-dihydro-1-benzofuran-2-yl)-5-[(5-methoxypyridin-2-yl)methoxy]-1,3-benzoxazole;
2-[(2R)-2,3-dihydro-1-benzofuran-2-yl]-5-[(5-methoxypyridin-2-yl)methoxy]-1,3-benzoxazole;
2-[(2S)-2,3-dihydro-1-benzofuran-2-yl]-5-[(5-methoxypyridin-2-yl)methoxy]-1,3-benzoxazole;
5-[5-(2-methoxyethoxy)pyrimidin-2-yl]-2-(pyridin-3-yl)-1,3-benzoxazole;
5-[(5-methoxypyridin-2-yl)methoxy]-2-(5-methylpyridin-3-yl)-1,3-benzoxazole;
5-[(5-methoxypyridin-2-yl)methoxy]-2-(2-methylpyridin-4-yl)-1,3-benzoxazole;
5-[(5-methoxypyridin-2-yl)methoxy]-2-(3-phenoxyphenyl)-1,3-benzoxazole;
6-{5-[(5-methoxypyridin-2-yl)methoxy]-1,3-benzoxazol-2-yl}-2-methyl-2,3-dihydropyridazin-3-one;
5-[(5-methoxypyridin-2-yl)methoxy]-2-(pyridazin-3-yl)-1,3-benzoxazole;
5-[(5-methoxypyridin-2-yl)methoxy]-2-(pyridazin-4-yl)-1,3-benzoxazole;
5-{5-[(5-methoxypyridin-2-yl)methoxy]-1,3-benzoxazol-2-yl}-1,2-dihydropyridin-2-one;
5-{5-[(5-methoxypyridin-2-yl)methoxy]-1,3-benzoxazol-2-yl}-1-methyl-1,2-dihydropyridin-2-one;
5-phenyl-N-[2-(pyridin-3-yl)-1,3-benzoxazol-5-yl]-1,3,4-oxadiazole-2-carboxamide;
5-[(5-methoxypyridin-2-yl)methoxy]-2-(pyrimidin-4-yl)-1,3-benzoxazole;
5-[(5-bromopyridin-2-yl)methoxy]-2-(pyridin-3-yl)-1,3-benzoxazole;
5-(pyridin-2-ylmethoxy)-2-(pyridin-3-yl)-1,3-benzoxazole;
N-[2-(pyridin-3-yl)-1,3-benzoxazol-5-yl]-1-benzofuran-5-carboxamide;
2-phenyl-N-[2-(pyridin-3-yl)-1,3-benzoxazol-5-yl]pyrimidine-5-carboxamide;
N-[2-(pyridin-3-yl)-1,3-benzoxazol-5-yl]-4-(pyrimidin-2-yl)benzamide;
1-methyl-N-[2-(pyridin-3-yl)-1,3-benzoxazol-5-yl]-1H-pyrazole-4-carboxamide;
4-[(6-methylpyrazin-2-yl)oxy]-N-[2-(pyridin-3-yl)-1,3-benzoxazol-5-yl]benzamide;
4-(phenoxymethyl)-N-[2-(pyridin-3-yl)-1,3-benzoxazol-5-yl]benzamide;
2-phenoxy-N-[2-(pyridin-3-yl)-1,3-benzoxazol-5-yl]pyridine-3-carboxamide;
4-cyano-N-[2-(pyridin-3-yl)-1,3-benzoxazol-5-yl]benzamide;
6-methoxy-N-[2-(pyridin-3-yl)-1,3-benzoxazol-5-yl]pyridine-2-carboxamide;
2-methyl-N-[2-(pyridin-3-yl)-1,3-benzoxazol-5-yl]pyridine-4-carboxamide;
3-methoxy-N-[2-(pyridin-3-yl)-1,3-benzoxazol-5-yl]pyridine-2-carboxamide;
4-methoxy-N-[2-(pyridin-3-yl)-1,3-benzoxazol-5-yl]pyridine-2-carboxamide;
4-hydroxy-N-[2-(pyridin-3-yl)-1,3-benzoxazol-5-yl]pyridine-2-carboxamide;
3-methoxy-N-[2-(pyridin-3-yl)-1,3-benzoxazol-5-yl]-1,2-oxazole-5-carboxamide;
5-methoxy-N-[2-(pyridin-3-yl)-1,3-benzoxazol-5-yl]pyridine-3-carboxamide;
6-({[2-(1-methyl-1H-pyrazol-4-yl)-1,3-benzoxazol-5-yl]oxy}methyl)pyridin-3-ol;
5-[(5-methoxypyrazin-2-yl)methoxy]-2-(1-methyl-1H-pyrazol-4-yl)-1,3-benzoxazole;
2-methoxy-5-({[2-(1-methyl-1H-pyrazol-4-yl)-[1,3]oxazolo[5,4-b]pyridin-6-yl]oxy}methyl)pyrazine;
3-{6-[(5-bromopyridin-2-yl)methoxy]-[1,3]oxazolo[5,4-b]pyridin-2-yl}pyridine;
3-methoxy-6-({[2-(pyridin-3-yl)-[1,3]oxazolo[5,4-b]pyridin-6-yl]oxy}methyl)pyridazine;
3-{5-[(5-methoxypyridin-2-yl)methoxy]-1,3-benzoxazol-2-yl}benzonitrile;
4-{5-[(5-methoxypyridin-2-yl)methoxy]-1,3-benzoxazol-2-yl}benzonitrile;
5-(1-methyl-1H-pyrazol-4-yl)-2-({[2-(pyridin-3-yl)-[1,3]oxazolo[5,4-b]pyridin-6-yl]oxy}methyl)pyridine;
3-methoxy-5-({[2-(pyridin-3-yl)-[1,3]oxazolo[5,4-b]pyridin-6-yl]oxy}methyl)pyridine;
4-methoxy-2-({[2-(pyridin-3-yl)-[1,3]oxazolo[5,4-b]pyridin-6-yl]oxy}methyl)pyridine;
2-({[2-(1-methyl-1H-pyrazol-4-yl)-[1,3]oxazolo[5,4-b]pyridin-6-yl]oxy}methyl)pyrazine;
[(3-{5-[(5-methoxypyridin-2-yl)methoxy]-1,3-benzoxazol-2-yl}phenyl)methyl](methyl)amine;
(5-methoxypyridin-2-yl)methyl N-[2-(pyridin-3-yl)-1,3-benzoxazol-5-yl]carbamate;
2-(5-methoxypyridin-2-yl)-5-[(5-methoxypyridin-2-yl)methoxy]-1,3-benzoxazole;
2-(1-benzofuran-2-yl)-5-[(5-methoxypyridin-2-yl)methoxy]-1,3-benzoxazole;
5-[(5-methoxypyridin-2-yl)methoxy]-2-[6-(trifluoromethyl)pyridin-3-yl]-1,3-benzoxazole;
2-(1-benzofuran-5-yl)-5-[(5-methoxypyridin-2-yl)methoxy]-1,3-benzoxazole;
2-{5-[(5-methoxypyridin-2-yl)methoxy]-1,3-benzoxazol-2-yl}quinoline;
2-[3-(benzyloxy)phenyl]-5-[(5-methoxypyridin-2-yl)methoxy]-1,3-benzoxazole;
5-[(5-methoxypyridin-2-yl)methoxy]-2-[4-(pyrimidin-2-yl)phenyl]-1,3-benzoxazole;
2-[(E)-2-(4-Methoxyphenyl)ethenyl]-5-[(5-methoxypyridin-2-yl)methoxy]-1,3-benzoxazole;
5-methoxy-2-({[2-(pyridin-3-yl)-[1,3]oxazolo[5,4-b]pyridin-6-yl]oxy}methyl)pyrimidine;
6-({[2-(1-methyl-1H-pyrazol-4-yl)-[1,3]oxazolo[5,4-b]pyridin-6-yl]oxy}methyl)pyridin-3-amine;
5-{5-[(5-hydroxypyridin-2-yl)methoxy]-1,3-benzoxazol-2-yl}-N-methylpyridine-2-carboxamide;
6-{6-[(5-methoxypyridin-2-yl)methoxy]-[1,3]oxazolo[5,4-b]pyridin-2-yl}-2-methyl-2,3-dihydropyridazin-3-one;
2-methyl-6-({[2-(pyridin-3-yl)-[1,3]oxazolo[5,4-b]pyridin-6-yl]oxy}methyl)-2,3-dihydropyridazin-3-one;
2-{6-[(5-methoxypyridin-2-yl)methoxy]-[1,3]oxazolo[5,4-b]pyridin-2-yl}pyrazine;
5-{6-[(5-methoxypyridin-2-yl)methoxy]-[1,3]oxazolo[5,4-b]pyridin-2-yl}-N-methylpyridine-2-carboxamide;

5-{5-[(5-methoxypyridin-2-yl)methoxy]-1,3-benzoxazol-2-yl}-1-methyl-1,2-dihydropyrazin-2-one;
6-(6-{[5-(2-fluoroethoxy)pyridin-2-yl]methoxy}-[1,3]oxazolo[5,4-b]pyridin-2-yl)-2-methyl-2,3-dihydropyridazin-3-one;
5-methoxy-2-({[2-(pyridin-3-yl)-[1,3]oxazolo[5,4-b]pyridin-6-yl]oxy}methyl)pyridin-1-ium-1-olate;
3-{6-[(5-methoxy-1-oxidopyridin-1-ium-2-yl)methoxy]-[1,3]oxazolo[5,4-b]pyridin-2-yl}pyridin-1-ium-1-olate;
5-{5-[(5-methoxypyridin-2-yl)methoxy]-1,3-benzoxazol-2-yl}-2-(methylcarbamoyl)pyridin-1-ium-1-olate;
(5-hydroxypyridin-2-yl)methyl N-[2-(pyridin-3-yl)-1,3-benzoxazol-5-yl]carbamate;
5-methoxy-N-[2-(1-methyl-6-oxo-1,6-dihydropyridazin-3-yl)-1,3-benzoxazol-5-yl]pyridine-2-carboxamide;
5-methoxy-N-[2-(1-methyl-6-oxo-1,6-dihydropyridazin-3-yl)-1,3-benzoxazol-5-yl]pyridine-3-carboxamide;
4-methoxy-N-[2-(1-methyl-6-oxo-1,6-dihydropyridazin-3-yl)-1,3-benzoxazol-5-yl]pyridine-2-carboxamide;
1-methyl-N-[2-(1-methyl-6-oxo-1,6-dihydropyridazin-3-yl)-1,3-benzoxazol-5-yl]-6-oxo-1,6-dihydropyridazine-3-carboxamide;
[(5-{5-[(5-methoxypyridin-2-yl)methoxy]-1,3-benzoxazol-2-yl}pyridin-3-yl)methyl](methyl)amine;
6-{5-[(5-hydroxypyridin-2-yl)methoxy]-1,3-benzoxazol-2-yl}-2-methyl-2,3-dihydropyridazin-3-one; and
N-(5-Methoxypyridin-3-yl)-2-(pyridin-3-yl)-1,3-benzoxazole-5-carboxamide;
or a pharmaceutically acceptable salt thereof, wherein the compound of Formula I, or a pharmaceutically acceptable salt there of, is labeled with one or more positron-emitting radionuclides.

Also provided is a compound of Formula I chosen from tert-butyl 4-[2-(pyridin-3-yl)-1,3-benzoxazol-5-yl]piperazine-1-carboxylate;
4-methoxy-N-[2-(pyridin-3-yl)-1,3-benzoxazol-5-yl]benzamide;
4-methoxy-N-[2-(pyridin-4-yl)-1,3-benzoxazol-5-yl]benzamide;
N-[(4-methoxyphenyl)methyl]-2-(pyridin-3-yl)-1,3-benzoxazol-5-amine;
2-(3-bromopyridin-4-yl)-6-[2-(morpholin-4-yl)ethoxy]-1,3-benzothiazole;
5-methoxy-N-[2-(3-methylphenyl)-1,3-benzoxazol-5-yl]pyridine-2-carboxamide;
6-methoxy-N-[2-(3-methylphenyl)-1,3-benzoxazol-5-yl]pyridine-3-carboxamide;
2-methoxy-N-[2-(3-methylphenyl)-1,3-benzoxazol-5-yl]pyrimidine-5-carboxamide;
5-methoxy-N-[2-(3-methylphenyl)-1,3-benzoxazol-5-yl]pyrazine-2-carboxamide;
4-methoxy-N-[2-(3-methylphenyl)-[1,3]oxazolo[5,4-b]pyridin-6-yl]benzamide;
5-(4-methoxyphenyl)-2-(pyridin-3-yl)-1,3-benzoxazole;
N-(4-methoxyphenyl)-2-(pyridin-3-yl)-1,3-benzoxazol-5-amine;
2-(pyrridin-3-yl)-N-{[1,2,4]triazolo[4,3-a]pyridin-3-yl}-1,3-benzoxazol-5-amine;
2-(pyridin-3-yl)-N-(pyrimidin-4-yl)-1,3-benzoxazol-5-amine;
2-(pyridin-3-yl)-N-(pyrimidin-2-yl)-1,3-benzoxazol-5-amine;
5-(5-methoxypyridin-2-yl)-2-(pyridin-3-yl)-1,3-benzoxazole;
5-(2-methoxypyrimidin-5-yl)-2-(pyridin-3-yl)-1,3-benzoxazole;
5-(5-methoxypyrimidin-2-yl)-2-(pyridin-3-yl)-1,3-benzoxazole;
5-(6-methoxypyridazin-3-yl)-2-(pyridin-3-yl)-1,3-benzoxazole;
5-(5-methoxypyrazin-2-yl)-2-(pyridin-3-yl)-1,3-benzoxazole;
1-methyl-4-[5-(pyrimidin-5-ylmethoxy)-1-benzofuran-2-yl]-1H-pyrazole-3-carbonitrile;
4-[5-(pyrimidin-5-ylmethoxy)-1-benzofuran-2-yl]pyridine-3-carbonitrile;
4-{5-[(5-methoxypyridin-2-yl)methoxy]-1-benzofuran-2-yl}pyridine-3-carbonitrile;
4-{5-[(5-methoxypyridin-2-yl)methoxy]-1-benzofuran-2-yl}pyridine;
4-{5-[(1-methyl-1H-imidazol-4-yl)methoxy]-1-benzofuran-2-yl}pyridine-3-carbonitrile;
4-{5-[(1-methyl-1H-imidazol-2-yl)methoxy]-1-benzofuran-2-yl}pyridine-3-carbonitrile;
5-methoxy-2-[2-(pyridin-3-yl)-1,3-benzoxazol-5-yl]-2,3-dihydro-1H-isoindol-1-one;
3-{6-[(E)-2-(4-methoxyphenyl)ethenyl]-[1,3]oxazolo[5,4-b]pyridin-2-yl}pyridine;
4-[5-(pyridin-3-yloxy)-1-benzofuran-2-yl]pyridine-3-carbonitrile;
6-methoxy-2-[2-(pyridin-3-yl)-1,3-benzoxazol-5-yl]-1,2,3,4-tetrahydroisoquinolin-1-one;
dimethyl({3-[4-({[2-(pyridin-3-yl)-1,3-benzoxazol-5-yl]oxy}methyl)phenoxy]propyl})amine;
5-[(1-methyl-1H-pyrazol-4-yl)methoxy]-2-(pyridin-3-yl)-1,3-benzoxazole;
5-[(4-methoxyphenyl)methoxy]-2-(pyridin-3-yl)-1,3-benzoxazole;
5-[(3-methoxyphenyl)methoxy]-2-(pyridin-3-yl)-1,3-benzoxazole;
5-[(5-methoxypyridin-2-yl)methoxy]-2-(pyridin-3-yl)-1,3-benzoxazole;
2-(pyridin-3-yl)-5-(pyridin-3-ylmethoxy)-1,3-benzoxazole;
5-{5H,6H-imidazo[2,1-b][1,3]thiazol-3-ylmethoxy}-2-(pyridin-3-yl)-1,3-benzoxazole;
1-(pyridin-2-yl)-2-[2-(pyridin-3-yl)-1,3-benzoxazol-5-yl]ethan-1-ol;
1-(pyridin-2-yl)-2-[2-(pyridin-3-yl)-1,3-benzoxazol-5-yl]ethan-1-one;
6-methoxy-2-[2-(pyridin-3-yl)-1,3-benzoxazol-5-yl]-1,2-dihydroisoquinolin-1-one;
2-(pyridin-3-yl)-N-[2,2,2-trifluoro-1-(4-methoxyphenyl)ethyl]-[1,3]oxazolo[5,4-b]pyridin-6-amine;
3-{6-[2-(4-methoxyphenyl)ethynyl]-[1,3]oxazolo[5,4-b]pyridin-2-yl}pyridine;
3-{6-[(Z)-2-(4-methoxyphenyl)ethenyl]-[1,3]oxazolo[5,4-b]pyridin-2-yl}pyridine;
5-methoxy-2-[2-(pyridin-3-yl)-[1,3]oxazolo[5,4-b]pyridin-6-yl]-2,3-dihydro-1H-isoindol-1-one;
5-[(5-methoxypyrazin-2-yl)methoxy]-2-(pyridin-3-yl)-1,3-benzoxazole;
3-methoxy-6-[2-(pyridin-3-yl)-1,3-benzoxazol-5-yl]-5H,6H,7H-pyrrolo[3,4-b]pyridin-7-one;
2-(pyridin-3-yl)-6-(pyridin-3-ylmethoxy)-1,3-benzoxazole;
3-{6-[2-(pyridin-3-yl)ethynyl]-[1,3]oxazolo[5,4-b]pyridin-2-yl}pyridine;
5-{[(5-methoxypyridin-2-yl)oxy]methyl}-2-(pyridin-3-yl)-1,3-benzoxazole;
4-[5-(pyridin-3-ylmethoxy)-1-benzofuran-2-yl]pyridine-3-carbonitrile;
4-{5-[(1-methyl-1H-pyrazol-4-yl)methoxy]-1-benzofuran-2-yl}pyridine-3-carbonitrile;

3-[5-(pyridin-3-ylmethoxy)-1-benzofuran-2-yl]pyridine-4-carbonitrile;
3-{5-[(1-methyl-1H-pyrazol-4-yl)methoxy]-1-benzofuran-2-yl}pyridine-4-carbonitrile;
3-{6-[1-(5-methoxypyridin-2-yl)ethoxy]-[1,3]oxazolo[5,4-b]pyridin-2-yl}pyridine;
4-{5-[(5-methoxypyrazin-2-yl)methoxy]-1-benzofuran-2-yl}pyridine-3-carbonitrile;
6-({[2-(pyridin-3-yl)-1,3-benzoxazol-5-yl]oxy}methyl)pyridin-3-ol;
5-{[5-(prop-2-en-1-yloxy)pyrazin-2-yl]methoxy}-2-(pyridin-3-yl)-1,3-benzoxazole;
5-({[2-(pyridin-3-yl)-1,3-benzoxazol-5-yl]oxy}methyl)-1,2-dihydropyrazin-2-one;
1-methyl-5-({[2-(pyridin-3-yl)-1,3-benzoxazol-5-yl]oxy}methyl)-1,2-dihydropyrazin-2-one;
5-[4-(5-methoxypyrimidin-2-yl)piperazin-1-yl]-2-(pyridin-3-yl)-1,3-benzoxazole;
3-{6-[(5-methoxypyridin-2-yl)methoxy]-[1,3]oxazolo[5,4-b]pyridin-2-yl}pyridine;
5-(1-methyl-1H-pyrazol-4-yl)-2-(pyridin-3-yl)-1,3-benzoxazole;
3-{6-[(6-methoxypyridin-3-yl)methoxy]-[1,3]oxazolo[5,4-b]pyridin-2-yl}pyridine;
5-[(5-methoxypyridin-2-yl)methoxy]-2-(pyridin-4-yl)-1,3-benzoxazole;
[(3-{5-[(5-methoxypyridin-2-yl)methoxy]-1,3-benzoxazol-2-yl}phenyl)methyl]dimethylamine;
5-[(5-methoxypyridin-2-yl)methoxy]-2-(1-methyl-1H-pyrazol-4-yl)-1,3-benzoxazole;
5-[(5-methoxypyridin-2-yl)methoxy]-2-(pyrazin-2-yl)-1,3-benzoxazole;
5-[(5-methoxypyridin-2-yl)methoxy]-2-(1-methylpiperidin-4-yl)-1,3-benzoxazole;
5-[(5-methoxypyridin-2-yl)methoxy]-2-(1,3-thiazol-5-yl)-1,3-benzoxazole;
5-[2-(pyridin-2-yloxy)ethoxy]-2-(pyridin-3-yl)-1,3-benzoxazole;
4-[5-(1H-pyrazol-4-ylmethoxy)-1-benzofuran-2-yl]pyridine-3-carbonitrile;
3-{[(2-{5H,6H-imidazo[2,1-b][1,3]thiazol-3-yl}-1-benzofuran-5-yl)oxy]methyl}pyridine;
2-(3-fluoroazetidin-1-yl)-5-[(5-methoxypyridin-2-yl)methoxy]-1,3-benzoxazole;
2-{3H,4H, 5H,6H,7H-imidazo[4,5-c]pyridin-5-yl}-5-[(5-methoxypyridin-2-yl)methoxy]-1,3-benzoxazole;
5-[(5-methoxypyridin-2-yl)methoxy]-2-{2H,4H,5H,6H,7H-pyrazolo[4,3-c]pyridin-5-yl}-1,3-benzoxazole;
2-{(5H,6H, 7H,8H-imidazo[1,5-a]pyrazin-7-yl}-5-[(5-methoxypyridin-2-yl)methoxy]-1,3-benzoxazole;
5-[(5-methoxypyridin-2-yl)methoxy]-2-{5H,6H,7H-pyrrolo[3,4-b]pyridin-6-yl}-1,3-benzoxazole;
7-{5-[(5-methoxypyridin-2-yl)methoxy]-1,3-benzoxazol-2-yl}-5,6,7,8-tetrahydro-1,7-naphthyridine;
2-(1H-imidazol-1-yl)-5-[(5-methoxypyridin-2-yl)methoxy]-1,3-benzoxazole;
2-{5H,6H,7H,8H-imidazo[1,2-a]pyrazin-7-yl}-5-[(5-methoxypyridin-2-yl)methoxy]-1,3-benzoxazole;
4-(5-{[1-(2-methoxyethyl)-1H-pyrazol-4-yl]methoxy}-1-benzofuran-2-yl)pyridine-3-carbonitrile;
2-[5-(2-methoxyethoxy)pyridin-3-yl]-5-[(5-methoxypyridin-2-yl)methoxy]-1,3-benzoxazole;
N-(5-{5-[(5-methoxypyridin-2-yl)methoxy]-1,3-benzoxazol-2-yl}pyridin-2-yl)acetamide;
5-{5-[(5-methoxypyridin-2-yl)methoxy]-1,3-benzoxazol-2-yl}pyridin-2-amine;
methyl({[4-({[2-(pyridin-3-yl)-1,3-benzoxazol-5-yl]oxy}methyl)phenyl]methyl})amine;
4-(5-{[1-(2-hydroxyethyl)-1H-pyrazol-4-yl]methoxy}-1-benzofuran-2-yl)pyridine-3-carbonitrile;
dimethyl({2-[4-({[2-(pyridin-3-yl)-1,3-benzoxazol-5-yl]oxy}methyl)phenoxy]ethyl})amine;
5-{[5-(2-methoxyethoxy)pyridin-2-yl]methoxy}-2-(pyridin-3-yl)-1,3-benzoxazole;
4-[5-({1-[2-(dimethylamino)ethyl]-1H-pyrazol-4-yl}methoxy)-1-benzofuran-2-yl]pyridine-3-carbonitrile;
5-{5-[(5-methoxypyridin-2-yl)methoxy]-1,3-benzoxazol-2-yl}-N-methylpyridin-2-amine;
3-{[(2-{2-bromo-5H,6H-imidazo[2,1-b][1,3]thiazol-3-yl}-1-benzofuran-5-yl)oxy]methyl}pyridine;
5-[(5-methoxypyrazin-2-yl)methoxy]-1-methyl-2-(pyridin-3-yl)-1H-1,3-benzodiazole;
6-[(5-methoxypyrazin-2-yl)methoxy]-1-methyl-2-(pyridin-3-yl)-1H-1,3-benzodiazole;
5-[(5-methoxypyrazin-2-yl)methoxy]-2-(pyridin-3-yl)-1H-1,3-benzodiazole;
5-[(5-methoxypyridin-2-yl)methoxy]-2-(piperazin-1-yl)-1,3-benzoxazole;
N-methyl-6-({[2-(pyridin-3-yl)-1,3-benzoxazol-5-yl]oxy}methyl)pyridin-3-amine;
3-[5-(pyridin-3-ylmethoxy)-1-benzofuran-2-yl]-5H,6H-imidazo[2,1-b][1,3]thiazole-2-carbonitrile;
5-{5-[(5-methoxypyridin-2-yl)methoxy]-1,3-benzoxazol-2-yl}-N-methylpyridine-2-carboxamide;
5-[(5-methoxypyridin-2-yl)methoxy]-2-(1-methyl-1H-imidazol-4-yl)-1,3-benzoxazole;
5-methoxy-N-{[2-(pyridin-3-yl)-1,3-benzoxazol-5-yl]methyl}pyridin-2-amine;
4-(5-{5H,6H-imidazo[2,1-b][1,3]thiazol-3-ylmethoxy}-1-benzofuran-2-yl)pyridine-3-carbonitrile;
5-({5-[2-(morpholin-4-yl)ethoxy]pyridin-2-yl}methoxy)-2-(pyridin-3-yl)-1,3-benzoxazole;
2-bromo-6-{5-[(5-methoxypyridin-2-yl)methoxy]-1-benzofuran-2-yl}benzonitrile;
4-{[2-(4-chlorophenyl)-1,3-benzoxazol-5-yl]carbamoyl}phenyl acetate;
N-(2-phenyl-1,3-benzoxazol-5-yl)benzamide;
4-methoxy-N-[2-(3-methylphenyl)-1,3-benzoxazol-5-yl]benzamide;
2-methoxy-N-[2-(4-methoxyphenyl)-1,3-benzoxazol-5-yl]benzamide;
4-methoxy-N-[2-(4-methoxyphenyl)-1,3-benzoxazol-5-yl]benzamide; and
3-methoxy-N-[2-(4-methoxyphenyl)-1,3-benzoxazol-5-yl]benzamide, or a pharmaceutically acceptable salt thereof, wherein the compound of Formula I, or a pharmaceutically acceptable salt there of, is labeled with one or more positron-emitting radionuclides.

The compounds of Formula I, or a pharmaceutically acceptable salt thereof are labeled with one or more positron-emitting radionuclides. Suitable positron-emitting radionuclides that may be incorporated in the compounds of described herein, but are not limited to, $^{11}$C, $^{13}$N, $^{15}$O, $^{18}$F, $^{52}$Fe, $^{62}$Cu, $^{64}$Cu, $^{68}$Ga, $^{74}$As, $^{82}$Rb, $^{89}$Zr, $^{122}$I, and $^{124}$I. In some embodiments, the one or more positron-emitting radionuclides are selected from: $^{11}$C, $^{13}$N, $^{15}$O, $^{18}$F, $^{76}$Br, and $^{124}$I. In some embodiments the one or more positron-emitting radionuclides are selected from $^{11}$C, $^{13}$N, $^{15}$O, and $^{18}$F.

Non-metal radionuclides may be covalently linked to the compounds described herein by a reaction well known from the state of art. When the radionuclide is a metallic positron-emitter, it is understood that labeling may require the use of a chelating agent. Such chelating agents are well known from the state of the art.

A PET imaging agent may be labelled with the positron emitter $^{11}$C or $^{18}$F. Methods for the introduction of $^{11}$C may include, but are not limited to, alkylation with [$^{11}$C]iodomethane or [$^{11}$C]methyl triflate. Carbon-11 has a half-life of approximately 20 minutes, thus $^{11}$C needs to be generated in an on-site cyclotron, and is generally produced as [$^{11}$C]carbon dioxide. The [$^{11}$C]carbon dioxide is converted to the chemical species appropriate for the radiosynthesis (generally [$^{11}$C]iodomethane or the like), and the synthesis of the radiopharmaceutical is completed and used on-site in a PET imaging study after the appropriate radiochemical purity and specific activity have been determined. Typical methods of introducing $^{18}$F may include but are not limited to displacement of a halide, tosylate, or other leaving group with [$^{18}$F]tetrabutylamonium fluoride or [$^{18}$F]potassium fluoride kryptofix-222. Fluorine-18 has a half life of approximately 110 minutes, thus synthesis of [$^{18}$F] radiopharmaceuticals need not necessarily have to occur at the site of the cyclotron nor proximal to the PET imaging study center. General methods for the introduction of these positron emitters are described in the literature (Miller et al., *Angewandte Chemie International Edition*, 47 (2008), 8998-9033).

Provided are methods of generating diagnostic images in an individual comprising administering an effective amount of an imaging agent described herein to an individual, and generating an image of at least a part of the individual.

Also provided are methods of generating diagnostic images in a biological sample comprising contacting the biological sample with an effective amount of an imaging agent described herein and generating an image of the positron-emitter labeled compound associated with the biological sample. In this method both the contacting and the generating may be conducted in vitro, alternatively the contacting is in vivo and the generating in vitro.

Also provided are methods for detecting the presence or absence of a neurodegenerative pathologic process associated with huntingtin protein (HTT protein) in an individual comprising: administering an effective amount of a positron-emitter labeled compound described herein; generating an image to detect the presence or absence of HTT protein aggregates in the brain of the individual; and detecting the presence or absence of the pathologic process. In some embodiments, the HTT protein aggregates are present in the basal ganglia of the brain of the individual. In some embodiments, the pathologic process is Huntington's disease (HD). In some embodiments, the effective amount of the imaging agent comprises from about 0.1 to about 20 mCi. In some embodiments, the effective amount of the imaging agent comprises about 10 mCi. In some embodiments, generating an image comprises positron emission tomography (PET) imaging, PET with concurrent computed tomography imaging (PET/CT), PET with concurrent magnetic resonance imaging (PET/MRI), or a combination thereof. In some embodiments, generating an image comprises PET imaging.

Also provided are diagnostic methods of using the imaging agents to monitor disease progression in a patient by quantifying the change in levels of the target aggregates in the patient.

Also provided are methods for detecting the presence or absence of a neurodegenerative pathologic process associated with huntingtin protein (HTT protein) in an individual comprising: administering an effective amount of a positron-emitter labeled compound described herein; generating an image to detect the presence or absence of HTT protein aggregates in the individual; and detecting the presence or absence of the pathologic process. In some embodiments, the HTT protein monomers or aggegates are present in the brain, liver, heart, or muscle of said individual. In some embodiments, the HTT protein aggregates are present in the basal ganglia, cortex, hippocampus, or brain stem of the brain of the individual. In some embodiments, the pathologic process is Huntington's disease (HD). In some embodiments, the effective amount of the imaging agent comprises from about 0.1 to about 20 mCi. In some embodiments, the effective amount of the imaging agent comprises about 10 mCi. In some embodiments, generating an image comprises positron emission tomography (PET) imaging, PET with concurrent computed tomography imaging (PET/CT), PET with concurrent magnetic resonance imaging (PET/MRI), or a combination thereof. In some embodiments, generating an image comprises PET imaging.

Also provided are methods for detecting the presence or absence of a neurodegenerative pathologic process associated with β-amyloid protein in an individual comprising: administering an effective amount of a positron-emitter labeled compound described herein; generating an image to detect the presence or absence of β-amyloid protein aggregates in the individual; and detecting the presence or absence of the pathologic process. In some embodiments, the β-amyloid protein monomers or aggegates are present in the brain, liver, heart, or muscle of said individual. In some embodiments, the β-amyloid protein aggregates are present in the basal ganglia, cortex, hippocampus, or brain stem of the brain of the individual. In some embodiments, the pathologic process is Alzheimer's Disease (AD). In some embodiments, the effective amount of the imaging agent comprises from about 0.1 to about 20 mCi. In some embodiments, the effective amount of the imaging agent comprises about 10 mCi. In some embodiments, generating an image comprises positron emission tomography (PET) imaging, PET with concurrent computed tomography imaging (PET/CT), PET with concurrent magnetic resonance imaging (PET/MRI), or a combination thereof. In some embodiments, generating an image comprises PET imaging.

Provided herein are compounds having suitable HTT protein aggregate or β-amyloid protein aggregate binding kinetics to function as efficient imaging agents for HTT protein aggregates or β-amyloid protein aggregates. The requirements of the compounds of the invention to function as efficient imaging agents for HTT protein aggregates are: 1) a high affinity for HTT protein aggregates; 2) a low affinity for nearby structures; 3) slow dissociation kinetics from HTT protein aggregates, which may conveniently be expressed as the dissociation rate constant $k_{diss}$ as defined in the following equation, wherein A and B refer to the HTT protein aggregate and the imaging agent, and $k_{assn}$ is the association rate constant.

$$d[AB]/dt = k_{assn}[A][B] - k_{diss}[AB]$$

The part of the brain most affected by HD, and thus most likely to contain HTT protein abnormalities, is a group of nerve cells at the base of the brain known collectively as the basal ganglia. The basal ganglia organize muscle-driven movements of the body, or "motor movement." The major components of the basal ganglia are the caudate and the putamen (together known as the striatum) and the globus pallidus (external and internal regions). The substantia nigra and the subthalamic nucleus are often included as part of the basal ganglia as well.

The term basal ganglia, refers to a group of subcortical nuclei responsible primarily for motor control, as well as other roles such as motor learning, executive functions and behaviors, and emotions. Disruption of the basal ganglia network forms the basis for several movement disorders. Normal function of the basal ganglia requires fine tuning of neuronal excitability within each nucleus to determine the exact degree of movement facilitation or inhibition at any given moment. This is mediated by the complex organization of the striatum, where the excitability of medium spiny neurons is controlled by several pre- and postsynaptic mechanisms as well as interneuron activity, and secured by several recurrent or internal basal ganglia circuits. The motor circuit of the basal ganglia has two entry points, the striatum and the subthalamic nucleus, and an output, the globus pallidus pars interna, which connects to the cortex via the motor thalamus.

Provided are methods for imaging part of the brain of an individual involving administering a positron-emitter labeled compound described herein to the individual, e.g. into the individual's vascular system, from where it passes through the blood-brain barrier, and then generating an image of at least the part of the individual's brain to which the compound has distributed.

Also provided are pharmaceutical compositions comprising an effective amount of a positron-emitter labeled compound described herein, or a salt thereof, together with one or more pharmaceutically-acceptable adjuvants, excipients or diluents.

An imaging agent or pharmaceutical composition thereof may be administered to a patient in need of treatment via any suitable route. Routes of administration may include, for example, parenteral administration (including subcutaneous, intramuscular, intravenous, by means of, for example a drip patch). Further suitable routes of administration include (but are not limited to) oral, rectal, nasal, topical (including buccal and sublingual), infusion, vaginal, intradermal, intraperitoneally, intracranially, intrathecal and epidural administration or administration via oral or nasal inhalation, by means of, for example a nebulizer or inhaler, or by an implant.

An imaging agent or pharmaceutical composition thereof may also be administered via microspheres, liposomes, other microparticulate delivery systems or sustained release formulations placed in certain tissues including blood. Suitable examples of sustained release carriers include semi-permeable polymer matrices in the form of shared articles, e.g., suppositories or microcapsules. Examples of the techniques and protocols mentioned above and other techniques and protocols which may be used in accordance with the invention can be found in Remington's Pharmaceutical Sciences, 18th edition, Gennaro, A. R., Lippincott Williams & Wilkins; 20th edition (Dec. 15, 2000) ISBN 0-912734-04-3 and Pharmaceutical Dosage Forms and Drug Delivery Systems; Ansel, N. C. et al. 7th Edition ISBN 0-683305-72-7, the entire disclosures of which are herein incorporated by reference.

Also provided are uses of positron-emitter labeled compounds described herein for the manufacture of an imaging agent for use in a method of diagnosis of an individual.

Provided are methods of generating diagnostic images comprising proton emission tomography (PET). PET involves the administration of a positron-emitting radionuclide tracer to an individual. Once the tracer has had sufficient time to associate with the target of interest, the individual is placed within a scanning device comprising of a ring of scintillation detectors. An emitted positron travels through the individual's tissue for a short (isotope-dependent) distance, until it interacts with an electron. The interaction annihilates both the electron and the positron, producing a pair of photons moving in approximately opposite directions. These are detected when they reach a scintillator in the scanning device. Photons that do not arrive in pairs are ignored.

Also provided are methods of generating diagnostic images comprising PET with concurrent computed tomography imaging (PET/CT), or with concurrent magnetic resonance imaging (PET/MRI). Computed tomography uses X-rays to show the structure of the brain, while magnetic resonance imaging uses magnetic fields and radio waves.

Other uses of the disclosed imaging agents and methods will become apparent to those skilled in the art based upon, inter alia, a review of this disclosure.

As will be recognized, the steps of the methods described herein need not be performed any particular number of times or in any particular sequence. Additional objects, advantages and novel features of the disclosure will become apparent to those skilled in the art upon examination of the following examples thereof, which are intended to be illustrative and not intended to be limiting.

EXAMPLES

Commercially available reagents and solvents (HPLC grade) were used without further purification. $^1$H NMR spectra were recorded on a Bruker DRX 500 MHz spectrometer or a Bruker DPX 250 MHz spectrometer in deuterated solvents. Chemical shifts ($\delta$) are in parts per million. SCX chromatography was performed with Biotage Isolute Flash SCX-2 loading the sample in methanol and eluting with methanol then 5% ammonia in methanol.

Analytical HPLC-MS (METCR1278), was performed on Shimadzu LCMS-2010EV systems using reverse phase Atlantis dC18 columns (3 µm, 2.1×50 mm), gradient 5-100% B (A=water/0.1% formic acid, B=acetonitrile/0.1% formic acid) over 3 minutes injection volume 3 µL, flow=1.0 mL/minute. UV spectra were recorded at 215 nm using a SPD-M20A photo diode array detector. Mass spectra were obtained over the range m/z 150 to 850 at a sampling rate of 2 scans per second using a LCMS2010EV. Data were integrated and reported using Shimadzu LCMS-Solutions and PsiPort software.

Analytical HPLC-MS (METCR1673), was performed on Shimadzu LCMS-2010EV systems using reverse phase Supelco Ascentis Express (2.7 µm, 2.1×30 mm), gradient 5-100% B (A=water/0.1% formic acid, B=acetonitrile/0.1% formic acid) over 1.6 minutes injection volume 3 µL, flow=1.0 mL/minute. UV spectra were recorded at 215 nm using a SPD-M20A photo diode array detector. Mass spectra were obtained over the range m/z 100 to 100 at a sampling rate of 2 scans per second using a LCMS2010EV. Data were integrated and reported using Shimadzu LCMS-Solutions and PsiPort software.

Alternatively, (METCR1416) analytical HPLC-MS on Shimadzu LCMS-2010EV systems using reverse phase Water Atlantis dC18 columns (3 µm, 2.1×100 mm), gradient 5-100% B (A=water/0.1% formic acid, B=acetonitrile/0.1% formic acid) over 7 minutes, injection volume 3 µL, flow=0.6 mL/minute. UV spectra were recorded at 215 nm using a SPD-M20A photo diode array detector. Mass spectra were obtained over the range m/z 150 to 850 at a sampling rate of 2 scans per second using a LCMS2010EV. Data were integrated and reported using Shimadzu LCMS-Solutions and PsiPort software.

Alternatively, (MET-uHPLC-AB-101) analytical HPLC-MS were performed on a Waters Acquity UPLC system with Waters PDA and ELS detectors using a Phenomenex Kinetex-XB C-18 column, (1.7 μM, 2.1 mm×100 mm at a column temperature of 40° C., gradient 5-100% B (A=water/0.1% formic acid; B=acetonitrile/0.1% formic acid) over 5.3 minutes, then 100% B for 0.5 minute, flow=0.6 mL/minute. UV spectra were recorded at 215 nm using a Waters Acquity photo diode array. Mass spectra were obtained over the range m/z 150 to 850 at a sampling rate of 5 scans per second using a Waters SQD. Data were integrated and reported using Waters MassLynx and OpenLynx software.

All example compounds display an LC purity of >95% unless stated otherwise.

Commercial Compounds

TABLE 1

| Ex. | Structure | Mol. Weight | IUPAC Name | LCMS data |
| --- | --- | --- | --- | --- |
| 1 | 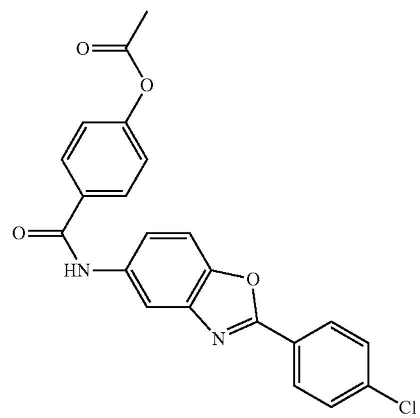 [SMILES: CC(=O)Oc1ccc(C(=O)Nc2ccc3oc(-c4ccc(Cl)cc4)nc3c2)cc1] | 406.82 | 4-{[2-(4-Chlorophenyl)-1,3-benzoxazol-5-yl]carbamoyl} phenyl acetate | Tr(MET-uHPLC-AB-101) = 3.89 min, (ES$^+$)(M + H)$^+$ 407 |
| 2 | 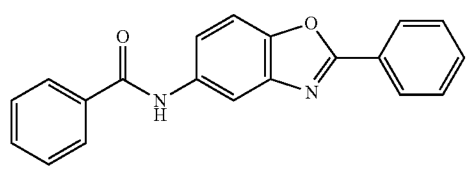 [SMILES: O=C(Nc1ccc2oc(-c3ccccc3)nc2c1)c1ccccc1] | 314.34 | N-(2-Phenyl-1,3-benzoxazol-5-yl)benzamide | Tr(MET-uHPLC-AB-101) = 3.55 min. (ES$^+$)(M + H)$^+$ 315 |
| 3 | 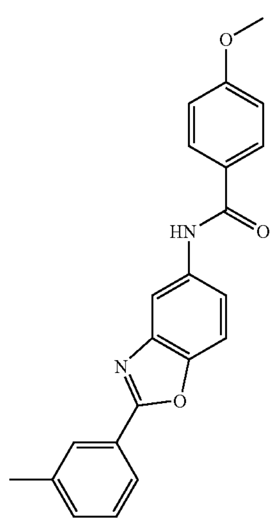 [SMILES: COc1ccc(C(=O)Nc2ccc3oc(-c4cccc(C)c4)nc3c2)cc1] | 358.39 | 4-Methoxy-N-[2-(3-methylphenyl)-1,3-benzoxazol-5-yl]benzamide | Tr(MET-uHPLC-AB-101) = 2.86 min, (ES$^+$)(M + H)$^+$ 359 |

TABLE 1-continued
| Ex. | Structure | Mol. Weight | IUPAC Name | LCMS data |
|---|---|---|---|---|
| 4 | 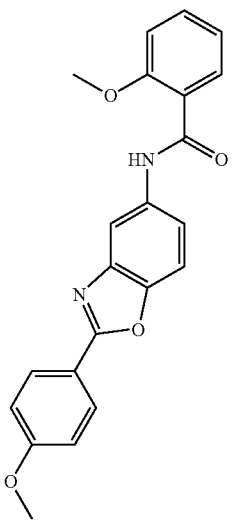 | 374.39 | 2-Methoxy-N-[2-(4-methoxyphenyl)-1,3-benzoxazol-5-yl]benzamide | Tr(MET-uHPLC-AB-101) = 3.85 min, (ES$^+$)(M + H)$^+$ 375 |
| 5 | 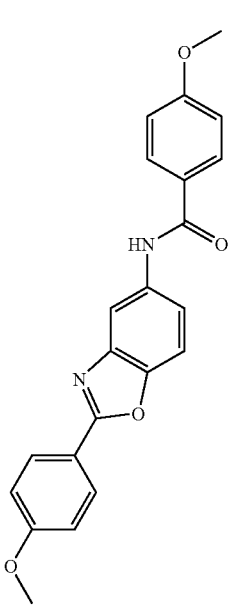 | 374.39 | 4-Methoxy-N-[2-(4-methoxyphenyl)-1,3-benzoxazol-5-yl]benzamide | Tr(MET-uHPLC-AB-101) = 3.56 min, (ES$^+$)(M + H)$^+$ 375 |

TABLE 1-continued

| Ex. | Structure | Mol. Weight | IUPAC Name | LCMS data |
|---|---|---|---|---|
| 6 | 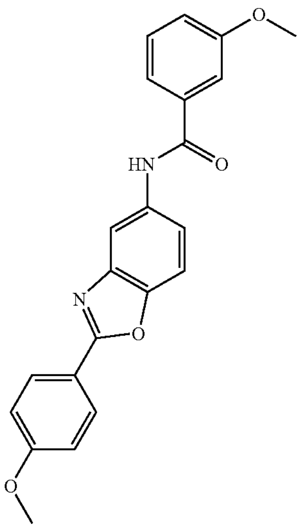 [SMILES: COc1ccc(-c2nc3cc(NC(=O)c4cccc(OC)c4)ccc3o2)cc1] | 374.39 | 3-Methoxy-N-[2-(4-methoxyphenyl)-1,3-benzoxazol-5-yl]benzamide | Tr(MET-uHPLC-AB-101) = 3.64 min, (ES$^+$)(M + H)$^+$ 375 |

Method 1
Scheme for Method 1

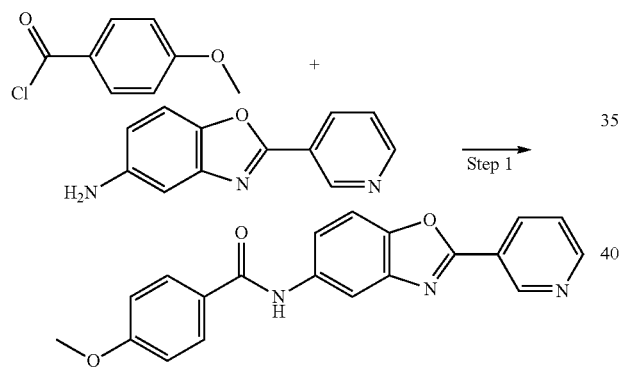

Step 1, Method 1: 4-Methoxy-N-[2-(pyridin-3-yl)-1,3-benzoxazol-5-yl]benzamide

To a stirred solution of 2-(pyridin-3-yl)-1,3-benzoxazol-5-amine (53 mg, 0.25 mmol) in pyridine (1 mL) was added 4-methoxybenzoyl chloride (41 µL, 0.293 mmol) and the mixture was stirred at room temperature for 16 hours. Water (10 mL) was added and the mixture stirred for 3 hours. The precipitate was filtered off and triturated, with sonication, in diethyl ether to give the title compound 63 mg (62% yield) as a beige power.

Example 1, Method 1:4-Methoxy-N-[2-(pyridin-3-yl)-1,3-benzoxazol-5-yl]benzamide $\delta_H$ NMR (500 MHz, DMSO) 10.29 (s, 1H), 9.36 (d, J=1.7 Hz, 1H), 8.81 (dd, J=4.8, 1.6 Hz, 1H), 8.54 (dt, J=8.0, 1.9 Hz, 1H), 8.32 (s, 1H), 8.00 (d, J=8.8 Hz, 2H), 7.82-7.77 (m, 2H), 7.66 (dd, J=7.9, 4.8 Hz, 1H), 7.09 (d, J=8.8 Hz, 2H), 3.85 (s, 3H). Tr(MET-uHPLC-AB-101)=2.73 min, (ES$^+$)(M+H)$^+$ 346.

The following examples were prepared using Method 1 described above:

TABLE 2

| Ex. | Structure | Mol. Weight | IUPAC Name | LCMS data |
|---|---|---|---|---|
| 1 | 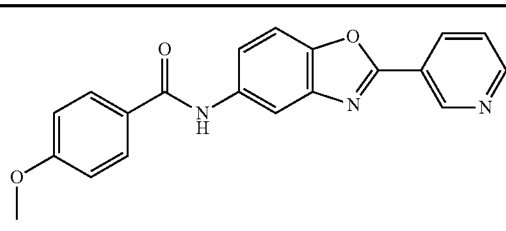 | 345.35 | 4-Methoxy-N-[2-(pyridin-3-yl)-1,3-benzoxazol-5-yl]benzamide | Tr(MET-uHPLC-AB-101) = 2.73 min, (ES$^+$)(M + H)$^+$ 346 |

TABLE 2-continued

| Ex. | Structure | Mol. Weight | IUPAC Name | LCMS data |
|---|---|---|---|---|
| 2 | 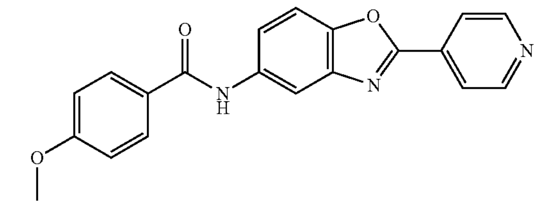 [SMILES: COc1ccc(C(=O)Nc2ccc3oc(-c4ccncc4)nc3c2)cc1] | 345.35 | 4-Methoxy-N-[2-(pyridin-4-yl)-1,3-benzoxazol-5-yl]benzamide | Tr(MET-uHPLC-AB-101) = 2.57 min, (ES$^+$)(M + H)$^+$ 346 |
| 3 | 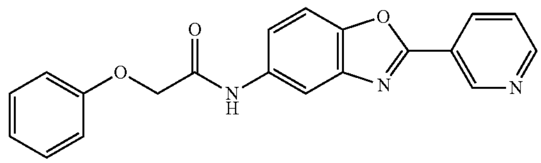 [SMILES: O=C(COc1ccccc1)Nc1ccc2oc(-c3cccnc3)nc2c1] | 345.36 | 2-Phenoxy-N-[2-(pyridin-3-yl)-1,3-benzoxazol-5-yl]acetamide | Tr(MET-uHPLC-AB-101) = 2.94 min, (ES$^+$)(M + H)$^+$ 346 |
| 4 | 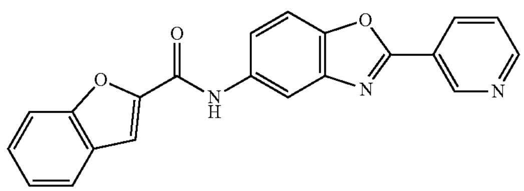 | 355.35 | N-[2-(Pyridin-3-yl)-1,3-benzoxazol-5-yl]-1-benzofuran-2-carboxamide | Tr(MET-uHPLC-AB-101) = 3.17 min, (ES$^+$)(M + H)$^+$ 356 |
| 5 | 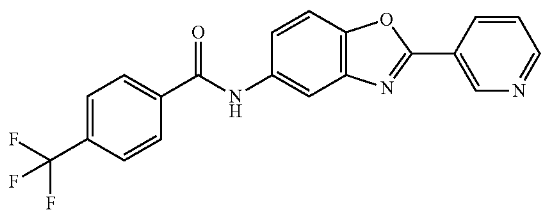 [SMILES: O=C(Nc1ccc2oc(-c3cccnc3)nc2c1)c1ccc(C(F)(F)F)cc1] | 384.32 | N-[2-(Pyridin-3-yl)-1,3-benzoxazol-5-yl]-6-(trifluoromethyl)pyridine-3-carboxamide | Tr(MET-uHPLC-AB-101) = 2.91 min, (ES$^+$)(M + H)$^+$ 385 |
| 6 | 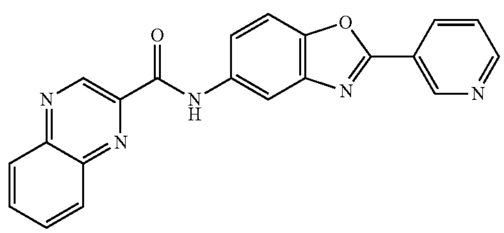 [SMILES: O=C(Nc1ccc2oc(-c3cccnc3)nc2c1)c1cnc2ccccc2n1] | 367.37 | N-[2-(Pyridin-3-yl)-1,3-benzoxazol-5-yl]quinoxaline-2-carboxamide | Tr(MET-uHPLC-AB-101) = 3.12 min, (ES$^+$)(M + H)$^+$ 368 |
| 7 | 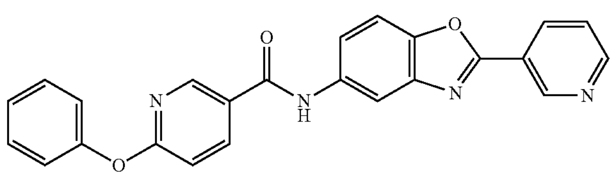 [SMILES: O=C(Nc1ccc2oc(-c3cccnc3)nc2c1)c1ccc(Oc2ccccc2)nc1] | 408.42 | 6-Phenoxy-N-[2-(pyridin-3-yl)-1,3-benzoxazol-5-yl]pyridine-3-carboxamide | Tr(MET-uHPLC-AB-101) = 3.23 min, (ES$^+$)(M + H)$^+$ 409 |
| 8 | 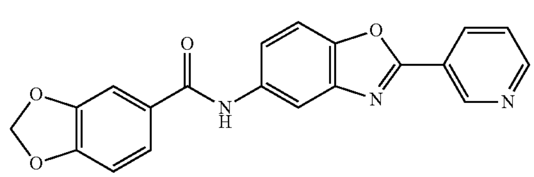 [SMILES: O=C(Nc1ccc2oc(-c3cccnc3)nc2c1)c1ccc2c(c1)OCO2] | 359.34 | N-[2-(Pyridin-3-yl)-1,3-benzoxazol-5-yl]-2H-1,3-benzodioxole-5-carboxamide | Tr(MET-uHPLC-AB-101) = 2.73 min, (ES$^+$)(M + H)$^+$ 360 |
| 9 | 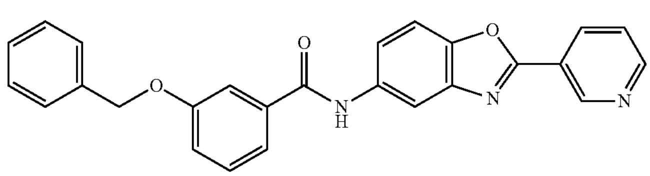 [SMILES: O=C(Nc1ccc2oc(-c3cccnc3)nc2c1)c1cccc(OCc2ccccc2)c1] | 421.46 | 3-(Benzyloxy)-N-[2-(pyridin-3-yl)-1,3-benzoxazol-5-yl]benzamide | Tr(MET-uHPLC-AB-101) = 3.67 min, (ES$^+$)(M + H)$^+$ 422 |

TABLE 2-continued

| Ex. | Structure | Mol. Weight | IUPAC Name | LCMS data |
|---|---|---|---|---|
| 10 | 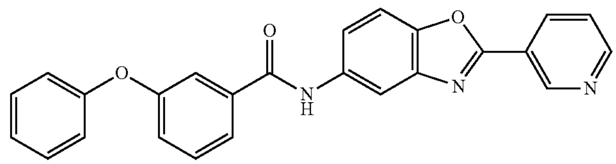 [SMILES: O=C(Nc1ccc2oc(-c3cccnc3)nc2c1)c1cccc(Oc2ccccc2)c1] | 407.43 | 3-Phenoxy-N-[2-(pyridin-3-yl)-1,3-benzoxazol-5-yl]benzamide | Tr(MET-uHPLC-AB-101) = 3.66 min, (ES$^+$)(M + H)$^+$ 408 |
| 11 | 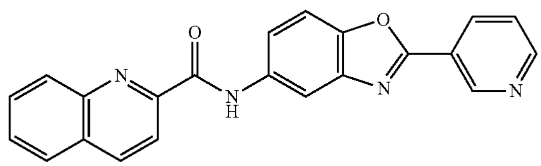 [SMILES: O=C(Nc1ccc2oc(-c3cccnc3)nc2c1)c1ccc2ccccc2n1] | 366.38 | N-[2-(Pyridin-3-yl)-1,3-benzoxazol-5-yl]quinoline-2-carboxamide | Tr(MET-uHPLC-AB-101) = 3.59 min, (ES$^+$)(M + H)$^+$ 367 |
| 12 | 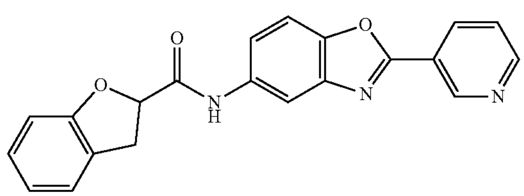 [SMILES: O=C(Nc1ccc2oc(-c3cccnc3)nc2c1)C1Cc2ccccc2O1] | 357.37 | N-[2-(Pyridin-3-yl)-1,3-benzoxazol-5-yl]-2,3-dihydro-1-benzofuran-2-carboxamide | Tr(MET-uHPLC-AB-101) = 3.01 min, (ES$^+$)(M + H)$^+$ 358 |
| 13 | 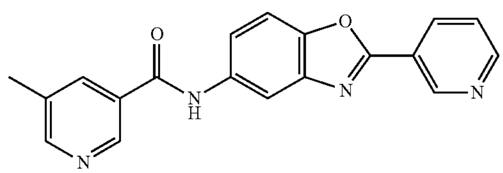 [SMILES: Cc1cncc(C(=O)Nc2ccc3oc(-c4cccnc4)nc3c2)c1] | 330.35 | 5-Methyl-N-[2-(pyridin-3-yl)-1,3-benzoxazol-5-yl]pyridine-3-carboxamide | Tr(MET-uHPLC-AB-101) = 2.01 min, (ES$^+$)(M + H)$^+$ 331 |
| 14 | 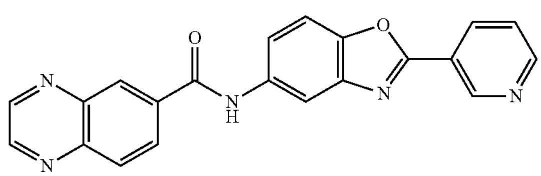 [SMILES: O=C(Nc1ccc2oc(-c3cccnc3)nc2c1)c1ccc2nccnc2c1] | 367.37 | N-[2-(Pyridin-3-yl)-1,3-benzoxazol-5-yl]quinoxaline-6-carboxamide | Tr(MET-uHPLC-AB-101) = 2.39 min, (ES$^+$)(M + H)$^+$ 368 |
| 15 | 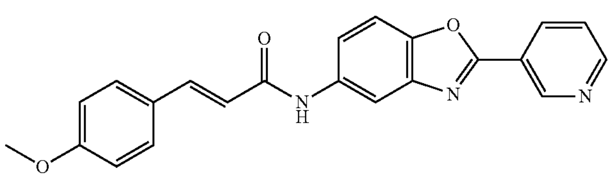 [SMILES: COc1ccc(/C=C/C(=O)Nc2ccc3oc(-c4cccnc4)nc3c2)cc1] | 371.40 | (2E)-3-(4-Methoxyphenyl)-N-[2-(pyridin-3-yl)-1,3-benzoxazol-5-yl]prop-2-enamide | Tr(METCR1600) = 4.11 min, (ES$^+$)(M + H)$^+$ 372 |
| 16 | 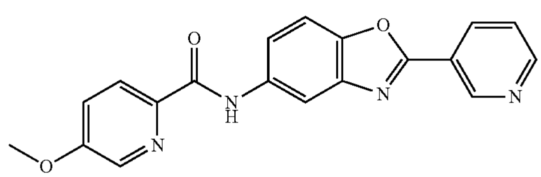 [SMILES: COc1ccc(C(=O)Nc2ccc3oc(-c4cccnc4)nc3c2)nc1] | 346.35 | 5-Methoxy-N-[2-(pyridin-3-yl)-1,3-benzoxazol-5-yl]pyridine-2-carboxamide | Tr(MET-uHPLC-AB-101) = 2.93 min, (ES$^+$)(M + H)$^+$ 347 |
| 17 | 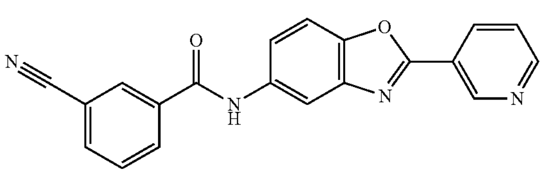 [SMILES: N#Cc1cccc(C(=O)Nc2ccc3oc(-c4cccnc4)nc3c2)c1] | 340.34 | 3-Cyano-N-[2-(pyridin-3-yl)-1,3-benzoxazol-5-yl]benzamide | Tr(MET-uHPLC-AB-101) = 2.72 min, (ES$^+$)(M + H)$^+$ 341 |

TABLE 2-continued

| Ex. | Structure | Mol. Weight | IUPAC Name | LCMS data |
|---|---|---|---|---|
| 18 | 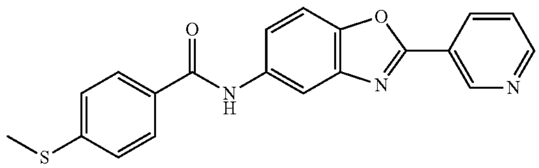 | 361.42 | 4-(Methylsulfanyl)-N-[2-(pyridin-3-yl)-1,3-benzoxazol-5-yl]benzamide | Tr(MET-uHPLC-AB-101) = 3.09 min, (ES+)(M + H)+ 362 |
| 19 | 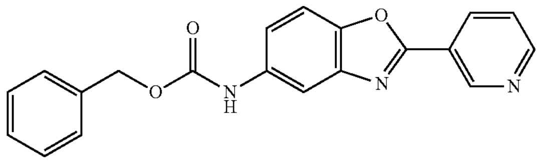 [SMILES: O=C(Nc1ccc2oc(-c3cccnc3)nc2c1)OCc1ccccc1] | 345.36 | Benzyl N-[2-(pyridin-3-yl)-1,3-benzoxazol-5-yl]carbamate | Tr(MET-uHPLC-AB-101) = 3.24 min, (ES+)(M + H)+ 346 |

Method 2
Scheme for Method 2

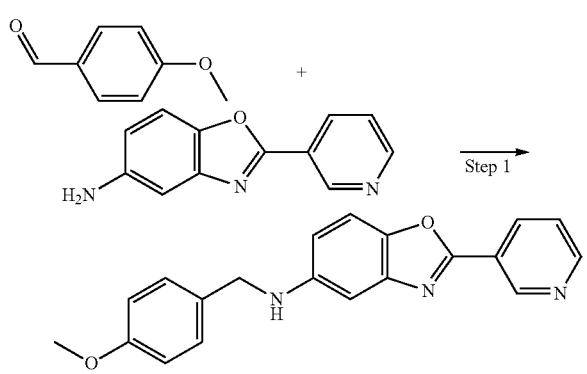

Step 1, Method 2: N-[(4-Methoxyphenyl)methyl]-2-(pyridin-3-yl)-1,3-benzoxazol-5-amine To a stirred suspension of 2-(pyridin-3-yl)-1,3-benzoxazol-5-amine (50 mg, 0.24 mmol) in 1,2-dichloroethane (1 mL), was added 4-methoxybenzaldehyde (32 mg, 0.24 mmol) followed by sodium triacetoxyborohydride (60 mg, 0.28 mmol) and the mixture was stirred at room temperature overnight. The mixture was treated with sodium triacetoxyborohydride (60 mg, 0.28 mmol) and acetic acid (0.026 mL, 0.47 mmol) and stirred at 40° C. for 48 hours. The mixture was then diluted with ethyl acetate (20 mL), washed with water (15 mL) and saturated sodium bicarbonate solution (15 mL). The organic extract was dried over sodium sulfate, filtered and concentrated. Purification by preparative HPLC (acetonitrile/water) gave the title compound (13.8 mg, 18% yield) as a white solid.

Example 1, Method 2: N-[(4-Methoxyphenyl)methyl]-2-(pyridin-3-yl)-1,3-benzoxazol-5-amine $\delta_H$ NMR (500 MHz, DMSO) 9.26 (dd, J=2.2, 0.6 Hz, 1H), 8.75 (dd, J=4.8, 1.6 Hz, 1H), 8.44 (dt, J=8.0, 1.9 Hz, 1H), 7.61 (ddd, J=8.0, 4.8, 0.7 Hz, 1H), 7.54-7.45 (m, 1H), 7.33 (d, J=8.6 Hz, 2H), 6.93-6.85 (m, 2H), 6.84-6.76 (m, 2H), 6.34 (t, J=5.9 Hz, 1H), 4.24 (d, J=5.9 Hz, 2H), 3.72 (s, 2H). Tr(MET-uHPLC-AB-101)=2.98 min, (ES+) (M+H)+ 332.

The following example was prepared using Method 2 described above:

TABLE 3

| Ex. | Structure | Mol. Weight | IUPAC Name | LCMS data |
|---|---|---|---|---|
| 1 | 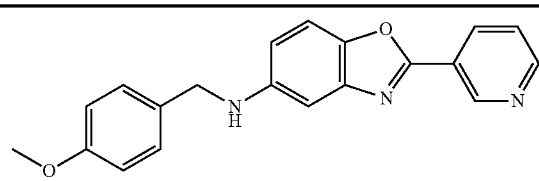 | 331.37 | N-[(4-Methoxyphenyl)methyl]-2-(pyridin-3-yl)-1,3-benzoxazol-5-amine | Tr(MET-uHPLC-AB-101) = 2.98 min, (ES+)(M + H)+ 332 |

Method 3
Scheme for Method 3

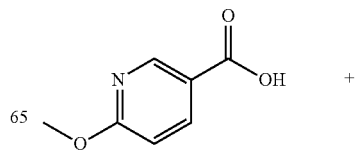

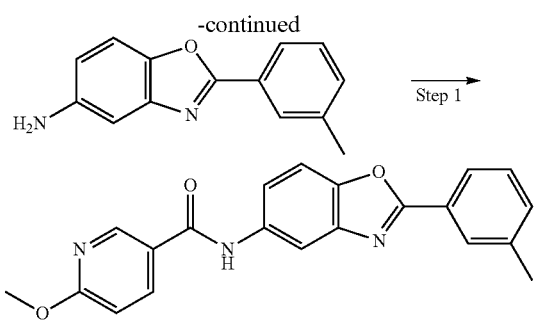

Step 1, Method 3: 6-Methoxy-N-[2-(3-methylphenyl)-1,3-benzoxazol-5-yl]pyridine-3-carboxamide To a stirred suspension of 6-methoxypyridine-3-carboxylic acid (75 mg, 0.49 mmol) in dichloromethane (1 mL) was added 1-chloro-N,N-2-trimethylprop-1-en-1-amine (71 µL, 0.54 mmol). The mixture was stirred at room temperature for 2 hours. 2-(3-Methylphenyl)-1,3-benzoxazol-5-amine (100 mg, 0.45 mmol) was then added followed by triethylamine (68 µL, 0.49 mmol). The mixture was stirred at room temperature for 60 hours. Water (5 mL) was added to the mixture and the organic layer was separated. The aqueous layer was extracted twice with dichloromethane (5 mL). The organic layers were combined and washed with saturated aqueous potassium carbonate (5 mL). Purification by FCC (silica, 0-20% ethyl acetate in dichloromethane) and trituration with a minimum of diethyl ether to give the title compound 24 mg (15% yield) as a white solid.

Example 1 Method 3: 6-Methoxy-N-[2-(3-methylphenyl)-1,3-benzoxazol-5-yl]pyridine-3-carboxamide $\delta_H$ NMR (500 MHz, DMSO) 10.42 (s, 1H), 8.82 (d, J=2.4 Hz, 1H), 8.27 (d, J=8.4 Hz, 2H), 8.04 (s, 1H), 8.01 (d, J=7.6 Hz, 1H), 7.77 (d, J=8.8 Hz, 1H), 7.73 (dd, J=8.8, 1.9 Hz, 1H), 7.51 (t, J=7.6 Hz, 1H), 7.46 (d, J=7.6 Hz, 1H), 6.98 (d, J=8.7 Hz, 1H), 3.95 (s, 3H), 2.44 (s, 3H). Tr(MET-uHPLC-AB-101)=3.68 min, (ES$^+$) (M+H)$^+$ 360.

The following examples were prepared using Method 3 described above:

TABLE 4

| Ex. | Structure | Mol. Weight | IUPAC Name | LCMS data |
|---|---|---|---|---|
| 1 | 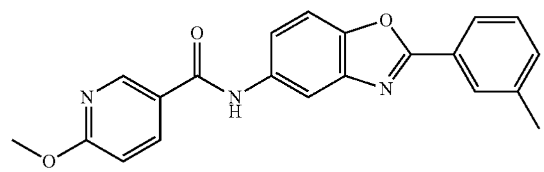 | 359.38 | 6-Methoxy-N-[2-(3-methylphenyl)-1,3-benzoxazol-5-yl]pyridine-3-carboxamide | Tr(MET-uHPLC-AB-101) = 3.68 min, (ES$^+$)(M + H)$^+$ 360 |
| 2 | 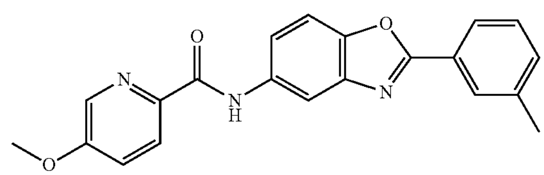 | 359.38 | 5-Methoxy-N-[2-(3-methylphenyl)-1,3-benzoxazol-5-yl]pyridine-2-carboxamide | Tr(MET-uHPLC-AB-101) = 4.09 min, (ES$^+$)(M + H)$^+$ 360 |
| 3 | 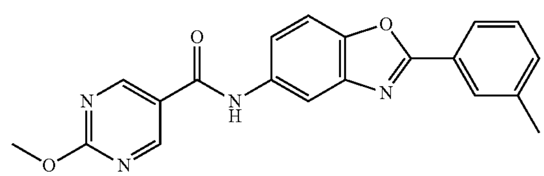 | 360.37 | 2-Methoxy-N-[2-(3-methylphenyl)-1,3-benzoxazol-5-yl]pyrimidine-5-carboxamide | Tr(MET-uHPLC-AB-101) = 3.36 min, (ES$^+$)(M + H)$^+$ 361 |
| 4 | 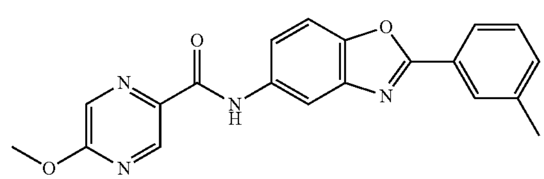 | 360.37 | 5-Methoxy-N-[2-(3-methylphenyl)-1,3-benzoxazol-5-yl]pyrazine-2-carboxamide | Tr(MET-uHPLC-AB-101) = 4.05 min, (ES$^+$)(M + H)$^+$ 361 |

Method 4
Scheme for Method 4

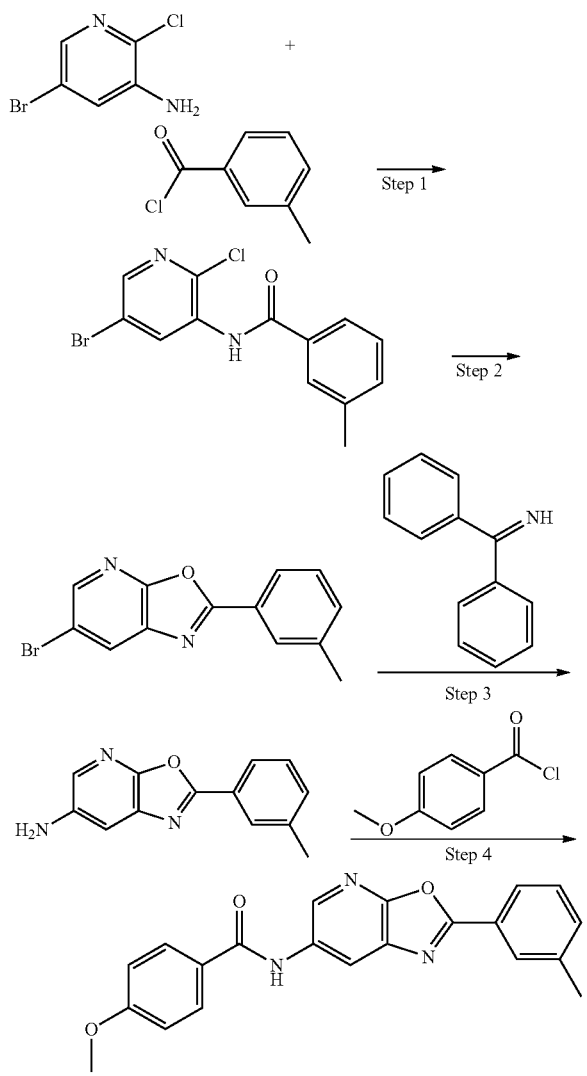

Step 1, Method 4: N-(5-Bromo-2-chloropyridin-3-yl)-3-methylbenzamide

To a stirred solution of 5-bromo-2-chloropyridin-3-amine (500 mg, 2.41 mmol) in pyridine (5 mL) at 0° C. was added 3-methylbenzoyl chloride (410 mg, 2.65 mmol). The mixture was stirred at room temperature for 1 hour. Water (50 mL) was added to the mixture. The precipitate was filtered and washed with water to give the title compound 653 mg (83% yield) as an off-white solid. $\delta_H$ NMR (250 MHz, DMSO) 10.28 (s, 1H), 8.49 (d, J=2.3 Hz, 1H), 8.39 (d, J=2.3 Hz, 1H), 7.85-7.70 (m, 2H), 7.45 (d, J=5.2 Hz, 2H), 2.41 (s, 3H). Tr (METCR1278)=2.25 min, (ES+) (M+H)+ 325/327.

Step 2, Method 4: 6-Bromo-2-(3-methylphenyl)-[1,3]oxazolo[5,4-b]pyridine

To a mixture of N-(5-bromo-2-chloropyridin-3-yl)-3-methylbenzamide (200 mg, 0.61 mmol), copper(I) iodide (6 mg, 0.03 mmol), N,N'-dimethylethane-1,2-diamine (7 μL, 0.06 mmol) and potassium carbonate (170 mg, 1.23 mmol) was added 1,4-dioxane (1 mL). The reaction was stirred at reflux for 24 hours. The mixture was added to a diluted aqueous solution of ammonia (100 mL). The aqueous layer was extracted with ethyl acetate (3×100 mL). The ethyl acetate layers were combined, dried over sodium sulfate and concentrated to give the title compound 120 mg (67% yield) as a beige solid. $\delta_H$ NMR (500 MHz, DMSO) 8.59 (d, J=2.1 Hz, 1H), 8.51 (d, J=2.1 Hz, 1H), 8.07-7.99 (m, 2H), 7.53 (q, J=7.7 Hz, 2H), 2.45 (s, 3H). Tr(METCR1278)=2.58 min, (ES+) (M+H)+ 289/291.

Step 3, Method 4: 2-(3-Methylphenyl)-[1,3]oxazolo[5,4-b]pyridin-6-amine

Under nitrogen, a mixture of 6-bromo-2-(3-methylphenyl)-[1,3]oxazolo[5,4-b]pyridine (230 mg, 0.8 mmol), diphenylmethanimine (217 mg, 1.19 mmol), tris(dibenzylideneacetone)dipalladium(0) (44 mg, 0.05 mmol), 9,9-dimethyl-9H-xanthene-4,5-diyl)bis(diphenylphosphane) (41 mg, 0.07 mmol) and caesium carbonate (415 mg, 1.27 mmol) in N,N-dimethylacetamide (2 mL) was stirred at 120° C. for 16 hours. The mixture was cooled to room temperature and water (50 mL) was added. The mixture was then extracted with ethyl acetate (3×25 mL). The combined organic layers were dried over sodium sulfate, filtered and concentrated. The residue was dissolved in tetrahydrofuran (5 mL) and the mixture was treated with 2 N hydrochloric acid (2 mL). The mixture was stirred at room temperature for 1 hour. The crude material was purified using an SCX cartridge and triturated with diethyl ether. 20 mg of 123 mg was purified by FCC (silica, 0-5% ethyl acetate in dichloromethane) to give the title compound 14 mg (8% yield) as a yellow solid. $\delta_H$ NMR (500 MHz, DMSO) 8.04-7.89 (m, 2H), 7.72 (d, J=2.5 Hz, 1H), 7.56-7.42 (m, 2H), 7.31 (d, J=2.5 Hz, 1H), 5.36 (s, 2H), 2.43 (s, 3H). Tr(MET-uHPLC-AB-101)=2.54 min, (ES+) (M+H)+ 226.

Step 4, Method 4: 4-Methoxy-N-[2-(3-methylphenyl)-[1,3]oxazolo[5,4-b]pyridin-6-yl]benzamide To a stirred solution of 2-(3-methylphenyl)-[1,3]oxazolo[5,4-b]pyridin-6-amine (0.249 mmol) in pyridine (1 mL) was added 4-methoxybenzoyl chloride (41 μL, 0.293 mmol) and the mixture stirred at room temperature for 16 hours. Water (10 mL) was added and the mixture was extracted with ethyl acetate (3×10 mL). The combined organic extracts were dried over sodium sulfate, filtered and concentrated. Purification by FCC (silica, 0-20% ethyl acetate in dichloromethane) gave the title compound 55 mg (52% yield) as a white powder.

Example 1, Method 4: 4-Methoxy-N-[2-(3-methylphenyl)-[1,3]oxazolo[5,4-b]pyridin-6-yl]benzamide $\delta_H$ NMR (500 MHz, DMSO) 10.47 (s, 1H), 8.67 (d, J=2.3 Hz, 1H), 8.62 (d, J=2.3 Hz, 1H), 8.10-7.94 (m, 4H), 7.58-7.44 (m, 2H), 7.15-7.05 (m, 2H), 3.86 (s, 3H), 2.45 (s, 3H). Tr(MET-uHPLC-AB-101)=3.64 min, (ES+) (M+H)+ 360.

The following example was prepared using Method 4 described above:

TABLE 5

| Ex. | Structure | Mol. Weight | IUPAC Name | LCMS data |
|---|---|---|---|---|
| 1 | 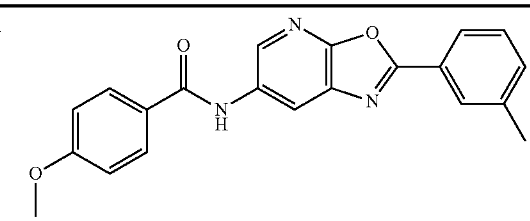 | 359.38 | 4-Methoxy-N-[2-(3-methylphenyl)-[1,3]oxazolo[5,4-b]pyridin-6-yl]benzamide | Tr(MET-uHPLC-AB-101) = 3.64 min, (ES⁺)(M + H)⁺ 360 |

Method 5
Scheme for Method 5

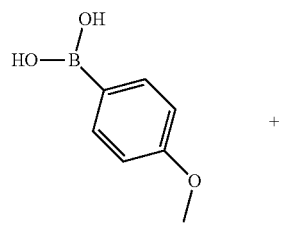

+ ethyl acetate (2×15 mL). The combined organic extracts were dried over sodium sulfate, filtered and concentrated. Purification by FCC (silica, 0-70% ethyl acetate in heptane) gave the title compound 74 mg (67% yield) as a white solid.

Example 1, Method 5: 5-(4-Methoxyphenyl)-2-(pyridin-3-yl)-1,3-benzoxazole $\delta_H$ NMR (500 MHz, chloroform) 9.50 (s, 1H), 8.78 (d, J=4.0 Hz, 1H), 8.54 (dt, J=8.0, 1.9 Hz, 1H), 7.94 (d, J=1.3 Hz, 1H), 7.64 (d, J=8.4 Hz, 1H), 7.62-7.54 (m, 3H), 7.50 (dd, J=7.9, 4.9 Hz, 1H), 7.05-6.98 (m, 2H), 3.87 (s, 3H). Tr(MET-uHPLC-AB-101)=3.58 min, (ES⁺) (M+H)⁺ 303.

The following example was prepared using Method 5 described above:

TABLE 6

| Ex. | Structure | Mol. Weight | IUPAC Name | LCMS data |
|---|---|---|---|---|
| 1 | 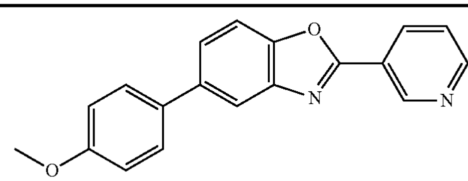 | 302.33 | 5-(4-Methoxyphenyl)-2-(pyridin-3-yl)-1,3-benzoxazole | Tr(MET-uHPLC-AB-101) = 3.58 min, (ES⁺)(M + H)⁺ 303 |

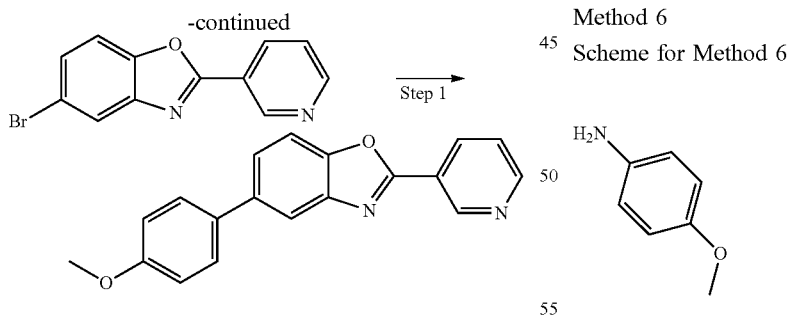

-continued

Step 1, Method 5: 5-(4-Methoxyphenyl)-2-(pyridin-3-yl)-1,3-benzoxazole

4-Methoxyphenylboronic acid (61 mg, 0.4 mmol) and 5-bromo-2-(3-pyridinyl)-1,3-benzoxazole (100 mg, 0.36 mmol) were dissolved in 1,4-dioxane (2 mL) under nitrogen in a sealed tube. 2 M sodium carbonate (0.36 mL, 0.73 mmol) was added followed by tetrakis(triphenylphosphine)palladium(0) (21 mg, 0.018 mmol) and the mixture was stirred at 110° C. overnight. The mixture was cooled to room temperature, diluted with water (15 mL) and extracted with Method 6
Scheme for Method 6

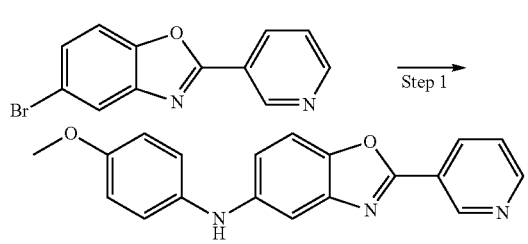

Step 1, Method 6: N-(4-Methoxyphenyl)-2-(pyridin-3-yl)-1,3-benzoxazol-5-amine A pressure tube was charged with 9,9-dimethyl-9H-xanthene-4,5-diyl)bis(diphenylphosphane) (32 mg, 0.055 mmol), tris(dibenzylideneacetone)dipalladium(0) (17 mg, 0.018 mmol) and 1,4-dioxane (2 mL). The mixture was degassed using a flow of nitrogen for 10 minutes. The mixture was then heated at 110° C. for 1 minute and cooled to room temperature. p-Anisidine (25 mg, 0.2 mmol), 2-(pyridin-3-yl)-1,3-benzoxazol-5-amine (50 mg, 0.18 mmol) and caesium carbonate (178 mg, 0.55 mmol) were added under nitrogen and the mixture was stirred at 110° C. overnight. The mixture was diluted with water (10 mL) and extracted with ethyl acetate (2×10 mL). The combined organic extracts were dried over sodium sulfate, filtered and concentrated. Purification by preparative HPLC (acetonitrile/water) gave the title compound 18 mg (31% yield) as a yellow powder.

Example 1, Method 6: N-(4-Methoxyphenyl)-2-(pyridin-3-yl)-1,3-benzoxazol-5-amine $\delta_H$ NMR (500 MHz, DMSO) 9.31 (d, J=1.6 Hz, 1H), 8.78 (dd, J=4.8, 1.6 Hz, 1H), 8.48 (dt, J=8.0, 1.9 Hz, 1H), 7.98 (s, 1H), 7.67-7.59 (m, 2H), 7.27 (d, J=2.2 Hz, 1H), 7.12-7.05 (m, 2H), 7.03 (dd, J=8.8, 2.3 Hz, 1H), 6.93-6.86 (m, 2H), 3.73 (s, 3H). Tr(MET-uHPLC-AB-101)=3.17 min, (ES$^+$) (M+H)$^+$ 318.

The following examples were prepared using Method 6 described above:

Method 7
Scheme for Method 7

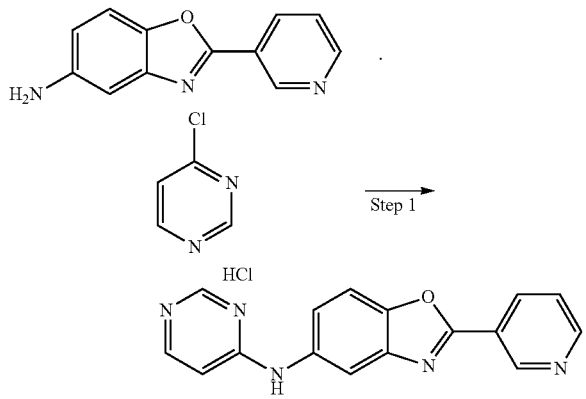

Step 1, Method 7: 2-(Pyridin-3-yl)-N-(pyrimidin-4-yl)-1,3-benzoxazol-5-amine 4-Chloropyrimidine hydrochloride (71 mg, 0.47 mmol), 2-(pyridin-3-yl)-1,3-benzoxazol-5-amine (50 mg, 0.24 mmol), diisopropylethylamine (0.12 mL, 0.71 mmol) and 2-propanol (1 mL) were heated in a microwave at 120° C. for 3 hours. The reaction mixture was filtered and the filtrate was concentrated in vacuo. Purification by preparative HPLC (acetonitrile/water) gave the title compound 7.2 mg (11% yield) as an off-white solid.

Example 1 Method 7: 2-(Pyridin-3-yl)-N-(pyrimidin-4-yl)-1,3-benzoxazol-5-amine $\delta_H$ NMR (500 MHz, DMSO) 9.79 (s, 1H), 9.35 (d, J=2.1 Hz, 1H), 8.81 (dd, J=4.8, 1.6 Hz, 1H), 8.66 (s, 1H), 8.53 (dt, J=8.0, 1.9 Hz, 1H), 8.33 (d, J=2.0 Hz, 1H), 8.29 (d, J=5.9 Hz, 1H), 7.79 (d, J=8.8 Hz, 1H), 7.66 (dd, J=8.0, 4.8 Hz, 1H), 7.60 (dd, J=8.8, 2.1 Hz, 1H), 6.82 (dd, J=5.9, 1.1 Hz, 1H). Tr(MET-uHPLC-AB-101)=1.23 min, (ES$^+$) (M+H)$^+$ 290.

The following examples were prepared using Method 7 described above:

TABLE 7

| Ex. | Structure | Mol. Weight | IUPAC Name | LCMS data |
|---|---|---|---|---|
| 1 | 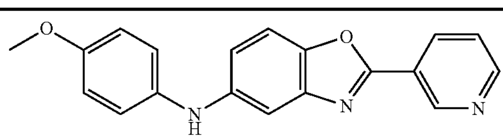 | 317.34 | N-(4-Methoxyphenyl)-2-(pyridin-3-yl)-1,3-benzoxazol-5-amine | Tr(MET-uHPLC-AB-101) = 3.17 min, (ES$^+$)(M + H)$^+$ 318 |
| 2 | 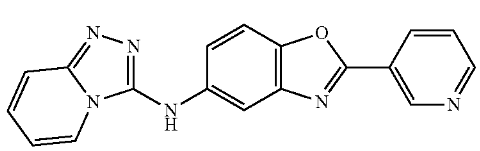 [SMILES: c1cncc(-c2nc3cc(Nc4nnc5ccccn45)ccc3o2)c1] | 328.33 | 2-(Pyridin-3-yl)-N-{[1,2,4]triazolo[4,3-a]pyridin-3-yl}-1,3-benzoxazol-5-amine | Tr(MET-uHPLC-AB-101) = 1.6 min, (ES$^+$)(M + H)$^+$ 329 |

TABLE 8

| Ex. | Structure | Mol. Weight | IUPAC Name | LCMS data |
|---|---|---|---|---|
| 1 | 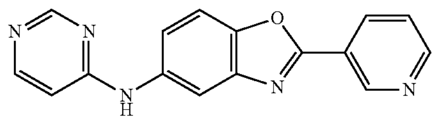 | 289.29 | 2-(Pyridin-3-yl)-N-(pyrimidin-4-yl)-1,3-benzoxazol-5-amine | Tr(MET-uHPLC-AB-101) = 1.23 min, (ES+)(M + H)+ 290 |
| 2 | 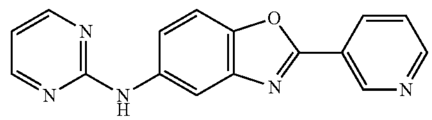 [SMILES: c1cnc(Nc2ccc3oc(-c4cccnc4)nc3c2)nc1] | 289.29 | 2-(Pyridin-3-yl)-N-(pyrimidin-2-yl)-1,3-benzoxazol-5-amine | Tr(METCR1416 Hi res 7 min) = 2.25 min, (ES+) (M + H)+ 290 |

Method 8
Scheme for Method 8

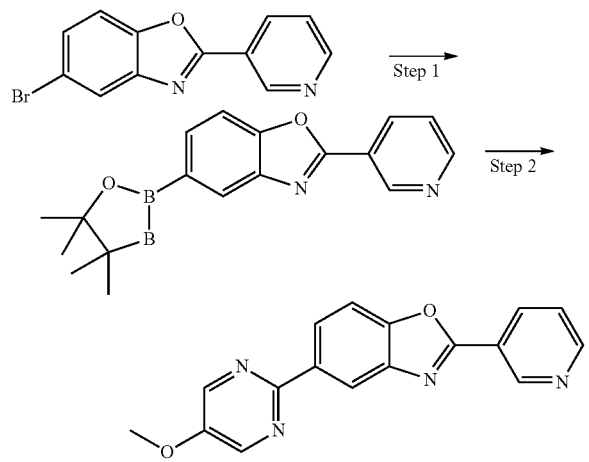

Step 1, Method 8: 2-(Pyridin-3-yl)-5-(tetramethyl-1,3,2-dioxaborolan-2-yl)-1,3-benzoxazole A suspension of 5-bromo-2-(3-pyridinyl)-1,3-benzoxazole (200 mg, 0.73 mmol), bis(pinacolato)diboron (221 mg, 0.87 mmol) and potassium acetate (214 mg, 2.18 mmol) in DMSO (4 mL) was degassed with nitrogen for 5 minutes. [1,1'-Bis(diphenylphosphino)ferrocene]dichloropalladium (II) (27 mg, 0.036 mmol) was added and the reaction was stirred at 80° C. under nitrogen for 16 hours. The reaction mixture was then cooled to room temperature, diluted with water (20 mL) and extracted with ethyl acetate (2×20 mL). The combined organic extracts were dried over sodium sulfate, filtered and concentrated. Purification by FCC (silica, 0-40% ethyl acetate in heptane) gave the title compound 143 mg (61% yield) as a white solid. Tr(METCR1278)=2.25 mins, (ES+) (M+H)+ 323.

Step 2, Method 8: 5-(5-Methoxypyrimidin-2-yl)-2-(pyridin-3-yl)-1,3-benzoxazole

2-Chloro-5-methoxypyrimidine (69 mg, 0.48 mmol) and 2-(pyridin-3-yl)-5-(tetramethyl-1,3,2-dioxaborolan-2-yl)-1,3-benzoxazole (140 mg, 0.43 mmol) were dissolved in 1,4-dioxane (3 mL) under nitrogen in a sealed tube. 2 M sodium carbonate (0.43 mL, 0.87 mmol) was added followed by tetrakis(triphenylphosphine)palladium(0) (25 mg, 0.022 mmol). The reaction mixture was stirred at 110° C. overnight. The reaction mixture was cooled to room temperature, diluted with water (20 mL) and extracted with ethyl acetate (2×20 mL). The combined organic layers were dried over sodium sulfate, filtered and concentrated. Purification by FCC (silica, 0-2% methanol in dichloromethane) gave the title compound 24 mg (18% yield) as a white solid.

Example 1, Method 8: (125-1) 5-(5-Methoxypyrimidin-2-yl)-2-(pyridin-3-yl)-1,3-benzoxazole $\delta_H$ NMR (500 MHz, DMSO) 9.38 (d, J=2.0 Hz, 1H), 8.83 (dd, J=4.8, 1.6 Hz, 1H), 8.69 (s, 2H), 8.66 (d, J=1.5 Hz, 1H), 8.57 (dt, J=8.0, 1.9 Hz, 1H), 8.46 (dd, J=8.6, 1.7 Hz, 1H), 7.93 (d, J=8.6 Hz, 1H), 7.67 (dd, J=7.9, 4.8 Hz, 1H), 3.98 (s, 3H). Tr(MET-uHPLC-AB-101)=2.87 min, (ES+) (M+H)+ 305.

The following examples were prepared using Method 8 described above:

TABLE 9

| Ex. | Structure | Mol. Weight | IUPAC Name | LCMS data |
|---|---|---|---|---|
| 1 | 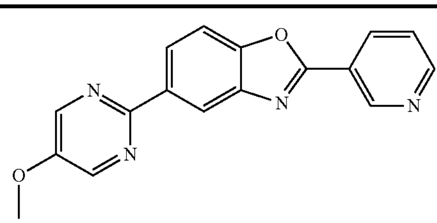 | 304.30 | 5-(5-Methoxypyrimidin-2-yl)-2-(pyridin-3-yl)-1,3-benzoxazole | Tr(MET-uHPLC-AB-101) = 2.87 min, (ES+)(M + H)+ 305 |

TABLE 9-continued

| Ex. | Structure | Mol. Weight | IUPAC Name | LCMS data |
|---|---|---|---|---|
| 2 | 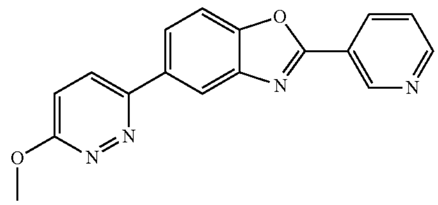 | 304.30 | 5-(6-Methoxypyridazin-3-yl)-2-(pyridin-3-yl)-1,3-benzoxazole | Tr(MET-uHPLC-AB-101) = 2.53 min, (ES⁺)(M + H)⁺ 305 |
| 3 | 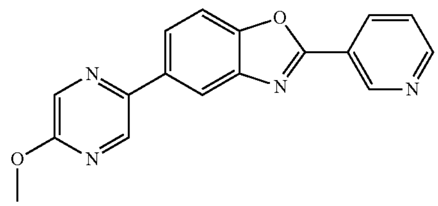 [SMILES: COc1ccc(-c2ccc3oc(-c4cccnc4)nc3c2)nc1] | 304.30 | 5-(5-Methoxypyrazin-2-yl)-2-(pyridin-3-yl)-1,3-benzoxazole | Tr(MET-uHPLC-AB-101) = 3.11 min, (ES⁺)(M + H)⁺ 305 |
| 4 | 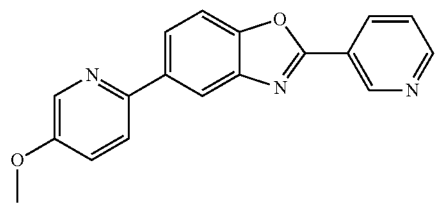 | 303.31 | 5-(5-Methoxypyridin-2-yl)-2-(pyridin-3-yl)-1,3-benzoxazole | Tr(MET-uHPLC-AB-101) = 2.02 min, (ES⁺)(M + H)⁺ 304 |
| 5 | 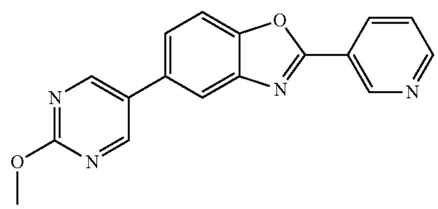 [SMILES: COc1ncc(-c2ccc3oc(-c4cccnc4)nc3c2)cn1] | 304.30 | 5-(2-Methoxypyrimidin-5-yl)-2-(pyridin-3-yl)-1,3-benzoxazole | Tr(MET-uHPLC-AB-101) = 2.57 min, (ES⁺)(M + H)⁺ 305 |

Method 9
Scheme for Method 9

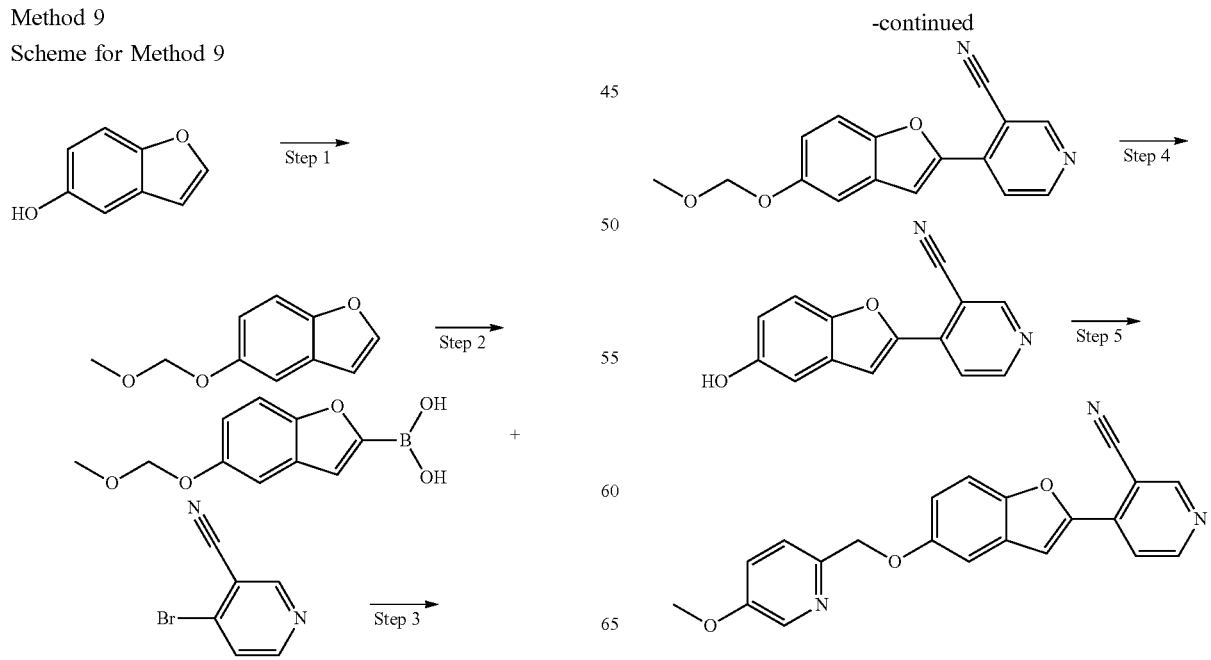

Step 1, Method 9: 5-(Methoxymethoxy)-1-benzofuran

Sodium hydride (60% in mineral oil, 579 mg, 14.48 mmol) was suspended in anhydrous N,N-dimethylformamide (25 mL) and cooled to 0° C. 5-Hydroxybenzofuran (1.85 g, 13.79 mmol) dissolved in N,N-dimethylformamide (10 mL) was added slowly. The mixture was stirred under nitrogen and warmed to room temperature over 1.5 hours. The mixture was cooled to 0° C. and chloro(methoxy)methane (1.1 mL, 14.48 mmol) was added drop-wise over 30 minutes. The reaction was warmed to room temperature and stirred for 3 hours. Water (5 mL) was added and the mixture was extracted with ethyl acetate (3×50 mL). The combined organic extracts were washed with water (5×50 mL), brine (10 mL), dried over magnesium sulfate, filtered and concentrated to give the title compound 2.3 g (89% yield) as a pale yellow oil. Tr(METCR1278)=1.95 min, no ionization.

Step 2, Method 9: [5-(Methoxymethoxy)-1-benzofuran-2-yl]boronic acid 5-(Methoxymethoxy)-1-benzofuran (1.00 g, 5.35 mmol) was dissolved in anhydrous tetrahydrofuran (15 mL) and cooled to −78° C. under nitrogen. 1.6 M n-butyllithium in hexanes (3.51 mL, 5.62 mmol) was added drop-wise and stirred for 1 hour at −78° C. Triisopropylborate (2.47 mL, 10.7 mmol) was added drop-wise and the reaction mixture was stirred for 2 hours. The reaction mixture was warmed to room temperature and stirred for 1 hour. 2 M hydrochloric acid (16 mL) was added and the reaction was stirred for 1 hour. The reaction mixture was diluted with water (10 mL) and extracted with tert-butyl methyl ether (3×40 mL). The combined organic extracts were washed with brine (10 mL), dried over magnesium sulfate, filtered and concentrated. Purification by FCC (silica, 20-80% ethyl acetate in heptane) gave the crude title compound 374 mg (31% yield) as a beige solid which was used in the next step without further purification.

Step 3, Method 9: 4-[5-(Methoxymethoxy)-1-benzofuran-2-yl]pyridine-3-carbonitrile

[5-(Methoxymethoxy)-1-benzofuran-2-yl]boronic acid (374 mg, 1.68 mmol), 4-bromopyridine-3-carbonitrile (339 mg, 1.85 mmol) and 2 M tripotassium phosphate (1.7 mL) were suspended in N,N-dimethylformamide (20 mL) and sonicated under a flow of nitrogen for 5 minutes. (1R,4S)-Bicyclo[2.2.1]hept-2-yl[(1S,4R)-bicyclo[2.2.1]hept-2-yl]phosphane-chloro[2'-(dimethylamino)biphenyl-2-yl]palladium (1:1) (47 mg, 0.08 mmol) was added and the reaction was heated to 75° C. for 1.5 hours. The reaction was cooled to room temperature and the solvents were removed in vacuo. The residue was partitioned between ethyl acetate (50 mL) and water (20 mL), the phases were separated and the aqueous was extracted with ethyl acetate (2×50 mL). The combined organic extracts were washed with brine (10 mL), dried over sodium sulfate, filtered and concentrated. Purification by FCC (silica, 0-50% ethyl acetate in heptane) gave the title compound 254 mg (52% yield) as a pale yellow solid. Tr(MET-uHPLC-AB-101)=3.20 min, (ES$^+$) (M+H)$^+$ 281.

Step 4, Method 9: 4-(5-Hydroxy-1-benzofuran-2-yl)pyridine-3-carbonitrile

To a solution of 4-[5-(methoxymethoxy)-1-benzofuran-2-yl]pyridine-3-carbonitrile (240 mg, 0.86 mmol) in tetrahydrofuran (10 mL) was added 3 M hydrochloric acid (2.8 mL) and the mixture was stirred at 60° C. for 2 hours. The reaction mixture was cooled to room temperature and saturated aqueous sodium bicarbonate (50 mL) and ethyl acetate (100 mL) were added. The mixture was filtered (glass fibre filterpaper) and dried under vacuum for 2 hours to give the title compound 207 mg (quantitative yield) as a yellow solid. Tr(MET-uHPLC-AB-101)=2.41 min, (ES$^+$) (M+H)$^+$ 237.

Step 5, Method 9: 4-{5-[(5-Methoxypyridin-2-yl)methoxy]-1-benzofuran-2-yl}pyridine-3-carbonitrile 4-(5-Hydroxy-1-benzofuran-2-yl)pyridine-3-carbonitrile (98%, 50 mg, 0.21 mmol), 2-(chloromethyl)-5-methoxypyridine hydrochloride (44 mg, 0.23 mmol) and potassium iodide (34 mg, 0.21 mmol) were dissolved in anhydrous N,N-dimethylformamide (2 mL) and stirred for 5 minutes at room temperature. Sodium hydride (60% in mineral oil, 25 mg, 0.62 mmol) was added and the reaction mixture was stirred under nitrogen for 15 hours. The solvents were removed in vacuo and the residue was partitioned between ethyl acetate (50 m) and water (20 m), the aqueous layer was extracted with ethyl acetate (2×30 m), the combined organics were washed with water (10 mL), brine (10 mL), dried over sodium sulfate, filtered, and concentrated. Purification by FCC (silica, 0-100% ethyl acetate in heptane) gave the title compound 34.8 mg (47% yield) as a white powder.

Example 1, Method 9: 4-{5-[(5-Methoxypyridin-2-yl)methoxy]-1-benzofuran-2-yl}pyridine-3-carbonitrile $\delta_H$ NMR (500 MHz, DMSO) 9.12 (s, 1H), 8.92 (d, J=5.4 Hz, 1H), 8.30 (d, J=2.9 Hz, 1H), 8.07 (d, J=5.4 Hz, 1H), 7.99-7.88 (m, 1H), 7.65 (d, J=9.0 Hz, 1H), 7.52 (d, J=8.6 Hz, 1H), 7.48-7.39 (m, 2H), 7.18 (dd, J=9.0, 2.6 Hz, 1H), 5.16 (s, 2H), 3.84 (s, 3H). Tr(MET-uHPLC-AB-101)=3.15 min, (ES+(M+H)$^+$ 358.

The following examples were prepared using Method 9 described above:

TABLE 10

| Ex. | Structure | Mol. Weight | IUPAC Name | LCMS data |
|---|---|---|---|---|
| 1 | 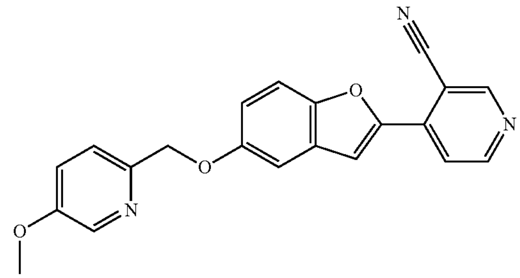 [SMILES: COc1ccc(COc2ccc3oc(-c4ccncc4C#N)cc3c2)nc1] | 357.36 | 4-{5-[(5-Methoxypyridin-2-yl)methoxy]-1-benzofuran-2-yl}pyridine-3-carbonitrile | Tr(MET-uHPLC-AB-101) = 3.15 min. $(ES^+)(M+H)^+$ 358 |
| 2 | 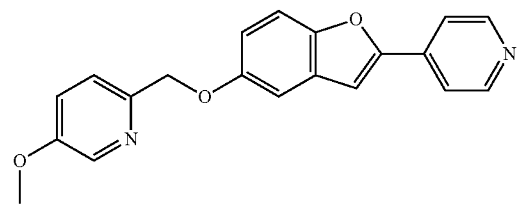 [SMILES: COc1ccc(COc2ccc3oc(-c4ccncc4)cc3c2)nc1] | 332.35 | 4-{5-[(5-Methoxypyridin-2-yl)methoxy]-1-benzofuran-2-yl}pyridine | Tr(MET-uHPLC-AB-101) = 1.92 min, $(ES^+)(M+H)^+$ 333 |
| 3 | 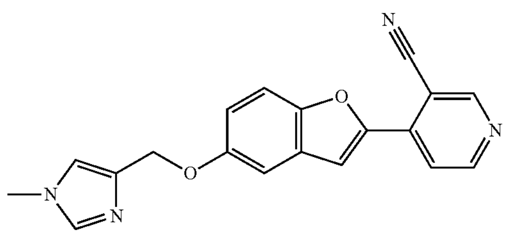 [SMILES: Cn1cnc(COc2ccc3oc(-c4ccncc4C#N)cc3c2)c1] | 330.34 | 4-{5-[(1-Methyl-1H-imidazol-4-yl)methoxy]-1-benzofuran-2-yl}pyridine-3-carbonitrile | Tr(MET-uHPLC-AB-101) = 1.67 min, $(ES^+)(M+H)^+$ 331 |
| 4 | 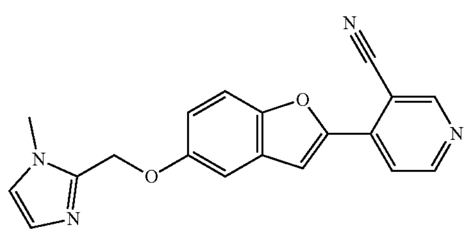 [SMILES: Cn1ccnc1COc1ccc2oc(-c3ccncc3C#N)cc2c1] | 330.34 | 4-{5-[(1-Methyl-1H-imidazol-2-yl)methoxy]-1-benzofuran-2-yl}pyridine-3-carbonitrile | Tr(MET-uHPLC-AB-101) = 1.66 min, $(ES^+)(M+H)^+$ 331.1 |
| 5 | 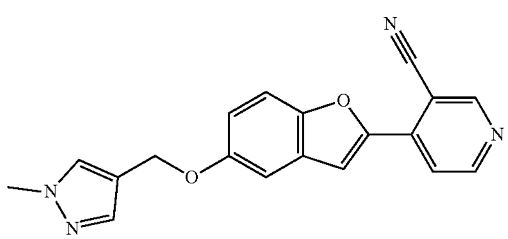 [SMILES: Cn1cc(COc2ccc3oc(-c4ccncc4C#N)cc3c2)cn1] | 330.34 | 4-{5-[(1-Methyl-1H-pyrazol-4-yl)methoxy]-1-benzofuran-2-yl}pyridine-3-carbonitrile | Tr(MET-uHPLC-AB-101) = 2.94 min, $(ES^+)(M+H)^+$ 331 |
| 6 | 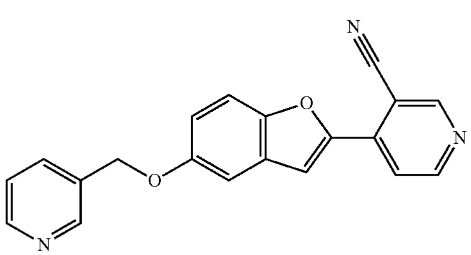 [SMILES: N#Cc1cnccc1-c1cc2cc(OCc3cccnc3)ccc2o1] | 327.34 | 3-[5-(Pyridin-3-ylmethoxy)-1-benzofuran-2-yl]pyridine-4-carbonitrile | Tr(MET-uHPLC-AB-101) = 2.24 min, $(ES^+)(M+H)^+$ 328 |

TABLE 10-continued

| Ex. | Structure | Mol. Weight | IUPAC Name | LCMS data |
|---|---|---|---|---|
| 7 | 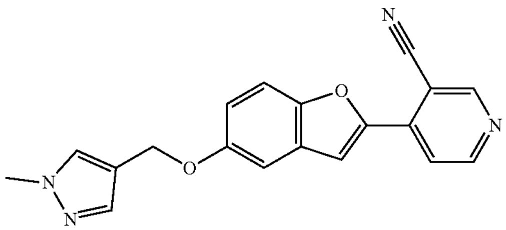 [SMILES: Cn1cc(COc2ccc3oc(-c4ccncc4C#N)cc3c2)cn1] | 330.34 | 3-{5-[(1-Methyl-1H-pyrazol-4-yl)methoxy]-1-benzofuran-2-yl}pyridine-4-carbonitrile | Tr(MET-uHPLC-AB-101) = 2.95 min, (ES⁺)(M + H)⁺ 331 |
| 8 | 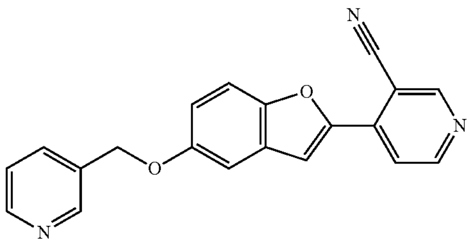 [SMILES: N#Cc1cnccc1-c1cc2cc(OCc3cccnc3)ccc2o1] | 327.34 | 4-[5-(Pyridin-3-ylmethoxy)-1-benzofuran-2-yl]pyridine-3-carbonitrile | Tr( ) = 2.22 min, (ES⁺)(M + H)⁺ 328 |
| 9 | 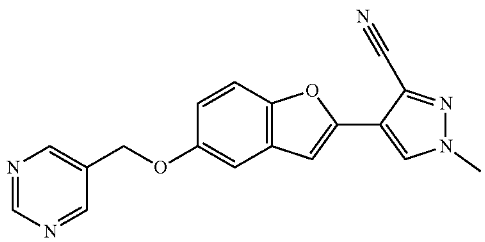 [SMILES: Cn1cc(-c2cc3cc(OCc4cncnc4)ccc3o2)c(C#N)n1] | 331.33 | 1-Methyl-4-[5-(pyrimidin-5-ylmethoxy)-1-benzofuran-2-yl]-1H-pyrazole-3-carbonitrile | Tr(MET-uHPLC-AB-101) = 2.91 min, (ES⁺)(M + H)⁺ 332 |

Method 10
Scheme for Method 10

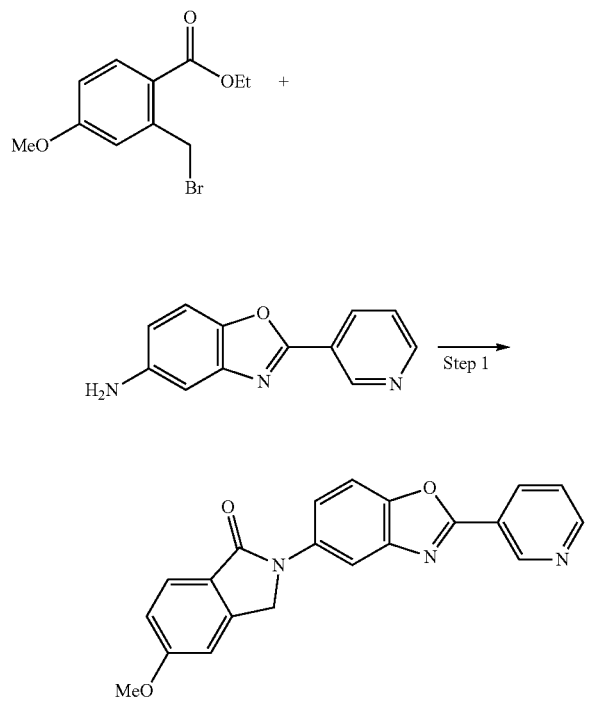

Step 1, Method 10: 5-Methoxy-2-[2-(pyridin-3-yl)-1,3-benzoxazol-5-yl]-2,3-dihydro-1H-isoindol-1-one Ethyl 2-(bromomethyl)-4-methoxybenzoate (100 mg, 0.37 mmol described in WO2009042907), 2-(pyridin-3-yl)-1,3-benzoxazol-5-amine (93 mg, 0.44 mmol) and diisopropylethylamine (77 µL, 0.44 mmol) were dissolved in ethanol (4 mL) and heated to 110° C. in a pressure tube for 18 hours. The reaction mixture was cooled to room temperature and treated with a solution of lithium hydroxide monohydrate (46 mg, 1.10 mmol) in water (0.5 mL). The reaction mixture was stirred at room temperature for 1.5 hours then concentrated. Trituration in boiling ethyl acetate-ethanol (1:1 v/v) followed by recrystallisation from DMSO gave the title compound 5 mg (5% yield) as a yellow powder.

Example 1, Method 10: 5-Methoxy-2-[2-(pyridin-3-yl)-1,3-benzoxazol-5-yl]-2,3-dihydro-1H-isoindol-1-one $\delta_H$ NMR (500 MHz, DMSO+5% DCl/D$_2$O) 9.56 (d, J=1.76 Hz, 1H), 9.18 (dt, J=1.53, 8.20 Hz, 1H), 9.10-9.04 (m, 1H), 8.35 (d, J=2.08 Hz, 1H), 8.24 (dd, J=5.70, 8.09 Hz, 1H), 8.03 (dd, J=2.17, 9.00 Hz, 1H), 7.92 (d, J=9.00 Hz, 1H), 7.70 (d, J=8.43 Hz, 1H), 7.22 (d, J=1.76 Hz, 1H), 7.08 (dd, J=2.16, 8.44 Hz, 1H), 5.05 (s, 2H), 3.85 (s, 3H). Tr(MET-uHPLC-AB-101)=2.88 min, (ES⁺) (M+H)⁺ 358.

The following example was prepared using Method 10 described above:

TABLE 11

| Ex. | Structure | Mol. Weight | IUPAC Name | LCMS data |
|---|---|---|---|---|
| 1 | 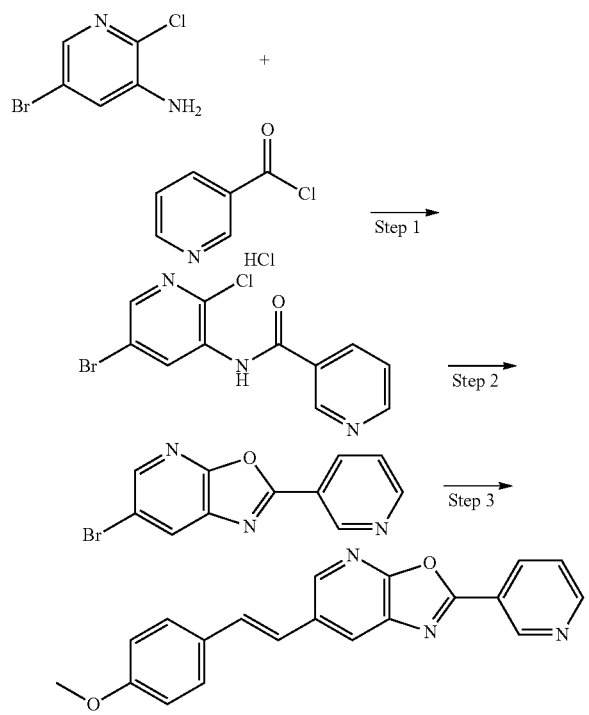 | 357.36 | 5-Methoxy-2-[2-(pyridin-3-yl)-1,3-benzoxazol-5-yl]-2,3-dihydro-1H-isoindol-1-one | Tr(MET-uHPLC-AB-101) = 2.88 min, (ES⁺)(M + H)⁺ 358 |

Method 11
Scheme for Method 11

Step 1, Method 11: N-(5-Bromo-2-chloropyridin-3-yl)pyridine-3-carboxamide

To a stirred solution of 5-bromo-2-chloropyridin-3-amine (1.00 g, 4.82 mmol) in pyridine (10 mL) with ice cooling, was added nicotinoyl chloride hydrochloride (0.94 g, 5.30 mmol). The mixture was stirred at room temperature for 1 hour. The mixture was concentrated, diluted with water (60 mL) and extracted with ethyl acetate (3×60 mL). The combined organic extracts were dried over sodium sulfate, filtered and concentrated to give the title compound 1.1 g as a grey solid. Filtration of the aqueous extract gave another 0.18 g of title compound, adding to 1.28 g (85% yield) as a grey powder. Tr(METCR1278)=1.57 min, (ES⁺) (M+H)⁺ 312, 314.

Step 2, Method 11: 3-{6-Bromo-[1,3]oxazolo[5,4-b]pyridin-2-yl}pyridine

A pressure tube was charged with N-(5-bromo-2-chloropyridin-3-yl)pyridine-3-carboxamide (318 mg, 0.68 mmol), copper(I) iodide (6.5 mg, 0.034 mmol), N,N-dimethylethane-1,2-diamine (6.0 mg, 0.068 mmol) and potassium carbonate (0.19 g, 1.36 mmol) in 1,4-dioxane (4 mL). The mixture was degassed using a flow of nitrogen for 10 minutes and heated at 110° C. for 16 hours. The mixture was then diluted with water (30 mL) and extracted with ethyl acetate (3×30 mL). The combined organic extracts were dried over sodium sulfate, filtered and concentrated. The residue was triturated with methanol (4 mL) to give the title compound 95 mg (50% yield) as a light brown powder. Tr(METCR1278)=1.85 min, (ES⁺) (M+H)⁺ 276/278.

Step 3, Method 11: 3-{6-[(E)-2-(4-Methoxyphenyl)ethenyl]-[1,3]oxazolo[5,4-b]pyridin-2-yl}pyridine A pressure tube was charged with 3-{6-bromo-[1,3]oxazolo[5,4-b]pyridin-2-yl}pyridine (95 mg, 0.18 mmol), 4-methoxystyrene (78 mg, 0.58 mmol), triphenylphosphine (15 mg, 0.058 mmol) and potassium carbonate (120 mg, 0.87 mmol) in N,N-dimethylformamide (1 mL). The mixture was degassed using a flow of nitrogen for 5 minutes then heated at 90° C. for 2 hours. The mixture was cooled to room temperature, diluted with water (10 mL) and filtered to give a brown solid which was dried under vacuum (80 mg). The solid was then charged in a pressure tube with 4-methoxystyrene (78 mg, 0.58 mmol), triphenylphosphine (15 mg, 0.058 mmol) and potassium carbonate (120 mg, 0.87 mmol) in N,N-dimethylformamide (1 mL). The mixture was degassed using a flow of nitrogen for 5 minutes then heated at 90° C. for 2 hours. The mixture was then cooled to room temperature, diluted with water (10 mL) and filtered to give a black solid, which was washed with ethyl acetate (2 mL). The solid was then dissolved in DMSO (2 mL), filtered and the filtrate was concentrated under reduced pressure. Purification by FCC (silica, 0-2% methanol in dichloromethane) and recrystallisation in DMSO:acetonitrile (1:1) gave the title compound 2 mg (2% yield) as a white powder.

Example 3, Method 11: 3-{6-[(E)-2-(4-Methoxyphenyl)ethenyl]-[1,3]oxazolo[5,4-b]pyridin-2-yl}pyridine $\delta_H$ NMR (500 MHz, DMSO) 9.38 (d, J=1.7 Hz, 1H), 8.85 (dd, J=4.8, 1.6 Hz, 1H), 8.65-8.52 (m, 3H), 7.69 (dd, J=8.0, 4.8 Hz, 1H), 7.58 (d, J=8.7 Hz, 2H), 7.44 (d, J=16.5 Hz, 1H), 7.29 (d, J=16.5 Hz, 1H), 6.99 (d, J=8.7 Hz, 2H), 3.79 (s, 3H). Tr(MET-uHPLC-AB-101)=3.54 min, (ES⁺) (M+H)⁺ 330.

The following example was prepared using Method 11 described above:

TABLE 12

| Ex. | Structure | Mol. Weight | IUPAC Name | LCMS data |
|---|---|---|---|---|
| 1 | 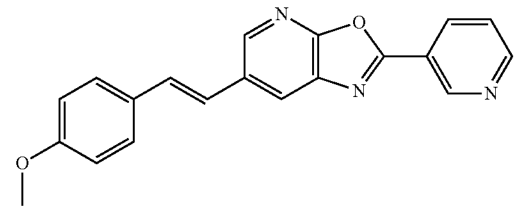 [SMILES: COc1ccc(/C=C/c2cnc3oc(-c4cccnc4)nc3c2)cc1] | 329.35 | 3-{6-[(E)-2-(4-Methoxyphenyl)ethenyl]-[1,3]oxazolo[5,4-b]pyridin-2-yl}pyridine | Tr(MET-uHPLC-AB-101) = 3.54 min, (ES⁺)(M + H)⁺ 330 |

Method 12
Scheme for Method 12:

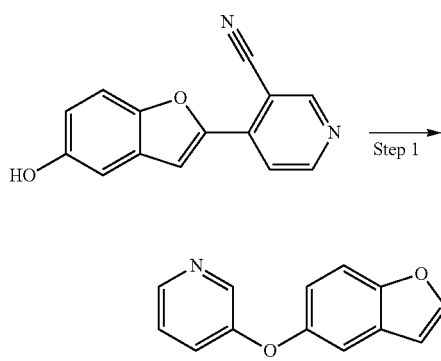

Step 1, Method 12: (4-[5-(Pyridin-3-yloxy)-1-benzofuran-2-yl]pyridine-3-carbonitrile Caesium carbonate (138 mg, 0.42 mmol), 2,2,6,6-tetramethylheptane-3,5-dione (47 μL, 0.21 mmol) and copper(I) iodide (4 mg, 0.02 mmol) were dissolved in N,N-dimethylformamide (1 mL) and stirred in a screw-cap vial for 5 minutes at room temperature. 4-(5-Hydroxy-1-benzofuran-2-yl)pyridine-3-carbonitrile (50 mg, 0.21 mmol, prepared by Method 9) and 3-iodopyridine (46 mg, 0.22 mmol) were added and the reaction was sealed and heated to 60° C. for 16 hours, then to 90° C. for 24 hours. The reaction mixture was cooled to room temperature and the solvents removed in vacuo. The residue was sonicated in ethyl acetate (20 mL) and passed through a pad of celite. The pad was washed with ethyl acetate (2×20 mL). The combined organics were washed with water (10 mL), brine (10 mL), dried over sodium sulfate, filtered and concentrated. Purification by preparative HPLC (acetonitrile/water+0.2% ammonium hydroxide) gave the title compound 12.5 mg (18% yield) as a tan powder.

Example 1, Method 12: 4-[5-(Pyridin-3-yloxy)-1-benzofuran-2-yl]pyridine-3-carbonitrile δ$_H$ NMR (500 MHz, DMSO) 9.14 (s, 1H), 8.95 (d, J=5.4 Hz, 1H), 8.41 (s, 1H), 8.37 (dd, J=3.9, 2.1 Hz, 1H), 8.10 (d, J=5.4 Hz, 1H), 7.99 (s, 1H), 7.80 (d, J=8.9 Hz, 1H), 7.59 (d, J=2.5 Hz, 1H), 7.47-7.39 (m, 2H), 7.28 (dd, J=8.9, 2.6 Hz, 1H). Tr(MET-uHPLC-AB-101)=2.65 min, (ES⁺) (M+H)⁺ 314.

The following example was prepared using Method 12 described above:

TABLE 13

| Ex. | Structure | Mol. Weight | IUPAC Name | LCMS data |
|---|---|---|---|---|
| 1 | 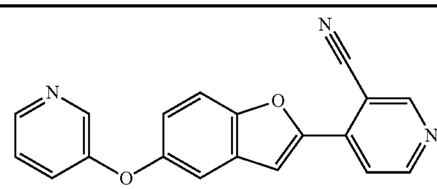 | 313.31 | 4-[5-(Pyridin-3-yloxy)-1-benzofuran-2-yl]pyridine-3-carbonitrile | Tr(MET-uHPLC-AB-101) = 2.65 min, (ES⁺) (M + H)⁺ 314 |

Method 13
Scheme for Method 13

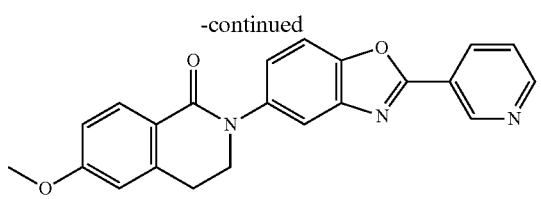
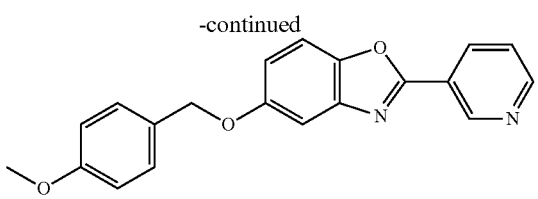

Step 1, Method 13: 6-Methoxy-2-[2-(pyridin-3-yl)-1,3-benzoxazol-5-yl]-1,2,3,4-tetrahydroisoquinolin-1-one 2-(2-Chloroethyl)-4-methoxybenzoyl chloride (226 mg, 0.97 mmol, described in WO2007093366) and 2-(pyridin-3-yl)-1,3-benzoxazol-5-amine (205 mg, 0.97 mmol) were dissolved in anhydrous tetrahydrofuran (10 mL) under nitrogen. Sodium hydride (60% in mineral oil, 78 mg, 1.9 mmol) was added and the mixture heated to 60° C. for 2 hours. The reaction mixture was cooled to room temperature, quenched with water (10 mL) and extracted with ethyl acetate (4×15 mL). The combined organic extracts were washed with water (15 mL) and brine (15 mL) then dried over magnesium sulfate, filtered and concentrated. Preparative HPLC (acetonitrile/water+0.1% formic acid) gave the title compound 23 mg (5% yield) as a white powder.

Example 1, Method 13: 6-Methoxy-2-[2-(pyridin-3-yl)-1,3-benzoxazol-5-yl]-1,2,3,4-tetrahydroisoquinolin-1-one $\delta_H$ NMR (500 MHz, DMSO) 9.37 (d, J=1.63 Hz, 1H), 8.82 (dd, J=1.59, 4.81 Hz, 1H), 8.56 (dt, J=1.87, 7.99 Hz, 1H), 7.93-7.82 (m, 3H), 7.67 (dd, J=4.82, 7.96 Hz, 1H), 7.50 (dd, J=2.08, 8.70 Hz, 1H), 6.97-6.91 (m, 2H), 4.01 (t, J=6.46 Hz, 2H), 3.85 (s, 3H), 3.15 (t, J=6.41 Hz, 2H). Tr(MET-uHPLC-AB-101)=2.83 min, (ES$^+$) (M+H)$^+$ 372.

The following example was prepared using Method 13 described above:

Step 1, Method 14: 2-(Pyridin-3-yl)-1,3-benzoxazol-5-ol 2-(Pyridin-3-yl)-1,3-benzoxazol-5-amine (350 mg, 1.66 mmol) was added portion-wise to a stirred solution of sulphuric acid (1.76 mL, 33.14 mmol) in water (5.25 mL) at room temperature. The solution was cooled to 0-5° C. and a solution of sodium nitrite (126 mg, 1.82 mmol) in water (3.5 mL) was added drop-wise. The mixture was stirred for 30 minutes at 0-5° C. A solution of copper(II) nitrate (20.5 g, 109.4 mmol) in water (35 mL) was added to the reaction mixture followed by copper(I) oxide (237 mg, 1.66 mmol). The mixture was shaken vigorously for 10 minutes. The mixture was then basified using saturated a solution of saturated sodium hydrogen carbonate until pH reached 8-9. 10% Aqueous ammonia (30 mL) was added and the resulting aqueous solution was extracted using ethyl acetate (2×150 mL). The combined organic extracts were dried over sodium sulfate, filtered and concentrated. Purification by FCC (silica, 0-5% methanol in dichloromethane) gave the title compound 127 mg (36% yield) as a yellow powder. Tr(MET-uHPLC-AB-101)=1.77 min, (ES$^+$) (M+H)$^+$ 213.

Step 2, Method 14: 5-[(4-Methoxyphenyl)methoxy]-2-(pyridin-3-yl)-1,3-benzoxazole To sodium hydride (60% in mineral oil, 5.7 mg, 0.14 mmol) under nitrogen was added a solution of 2-(pyridin-

TABLE 14

| Ex. | Structure | Mol. Weight | IUPAC Name | LCMS data |
| --- | --- | --- | --- | --- |
| 1 | 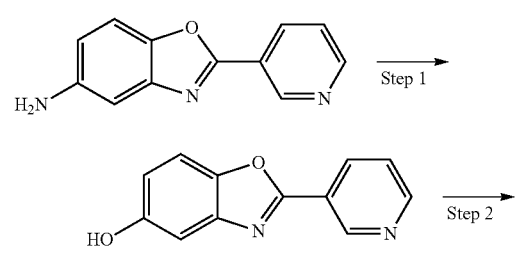 | 371.39 | 6-Methoxy-2-[2-(pyridin-3-yl)-1,3-benzoxazol-5-yl]-1,2,3,4-tetrahydroisoquinolin-1-one | Tr(MET-uHPLC-AB-101) = 2.83 min, (ES$^+$) (M + H)$^+$ 372 |

Method 14
Scheme for Method 14

3-yl)-1,3-benzoxazol-5-ol (30 mg, 0.14 mmol) in N,N-dimethylformamide (1 mL) and the mixture was stirred at room temperature for 30 minutes. A solution of 4-methoxybenzyl bromide (28 mg, 0.14 mmol) in N,N-dimethylformamide (0.5 mL) was added and the mixture was stirred at room temperature for 1 hour. The mixture was quenched with water (0.5 mL), diluted with water (15 mL) and extracted with ethyl acetate (2×15 mL). The combined organic extracts were dried over sodium sulfate, filtered and concentrated. Purification by FCC (silica, 20-100% ethyl acetate in heptane), trituration in acetonitrile (2 mL) and drying under vacuum gave the title compound 12 mg (26% yield) as a white powder.

Example 1, Method 14: 5-[(4-Methoxyphenyl)methoxy]-2-(pyridin-3-yl)-1,3-benzoxazole $\delta_H$ NMR (500 MHz, DMSO) 9.32 (d, J=1.8 Hz, 1H), 8.80 (dd, J=4.8, 1.6 Hz, 1H), 8.50 (dt, J=8.0, 1.9 Hz, 1H), 7.72 (d, J=8.9 Hz, 1H), 7.65 (dd, J=7.9, 4.8 Hz, 1H), 7.47 (d, J=2.5 Hz, 1H), 7.42 (d, J=8.6 Hz, 2H), 7.10 (dd, J=8.9, 2.5 Hz, 1H), 6.96 (d, J=8.6 Hz, 2H), 5.11 (s, 2H), 3.76 (s, 3H). Tr(MET-uHPLC-AB-101)=3.56 min, (ES$^+$) (M+H)$^+$ 333.

The following examples were prepared using Method 14 described above:

TABLE 15

| Ex. | Structure | Mol. Weight | IUPAC Name | LCMS data |
|---|---|---|---|---|
| 1 | 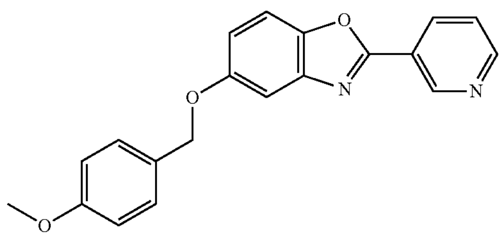 [SMILES: COc1ccc(COc2ccc3oc(-c4cccnc4)nc3c2)cc1] | 332.35 | 5-[(4-Methoxyphenyl)methoxy]-2-(pyridin-3-yl)-1,3-benzoxazole | Tr(MET-uHPLC-AB-101) = 3.56 min, (ES$^+$) (M + H)$^+$ 333 |
| 2 | 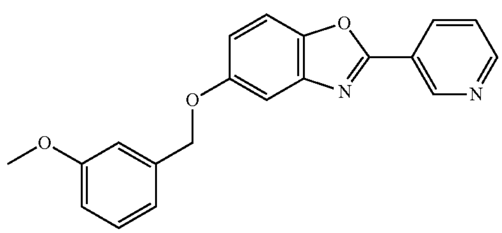 [SMILES: COc1cccc(COc2ccc3oc(-c4cccnc4)nc3c2)c1] | 332.35 | 5-[(3-Methoxyphenyl)methoxy]-2-(pyridin-3-yl)-1,3-benzoxazole | Tr(MET-uHPLC-AB-101) = 3.58 min, (ES$^+$) (M + H)$^+$ 333 |
| 3 | 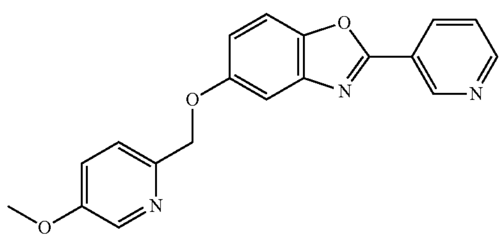 | 333.34 | 5-[(5-Methoxypyridin-2-yl)methoxy]-2-(pyridin-3-yl)-1,3-benzoxazole | Tr(MET-uHPLC-AB-101) = 2.61 min, (ES$^+$) (M + H)$^+$ 334 |
| 4 | 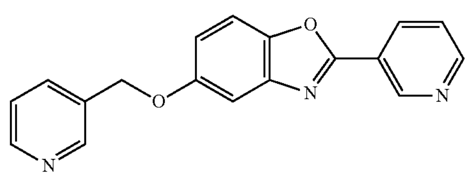 [SMILES: c1cncc(COc2ccc3oc(-c4cccnc4)nc3c2)c1] | 303.31 | 2-(Pyridin-3-yl)-5-(pyridin-3-ylmethoxy)-1,3-benzoxazole | Tr(MET-uHPLC-AB-101) = 1.73 min, (ES$^+$) (M + H)$^+$ 304 |
| 5 | 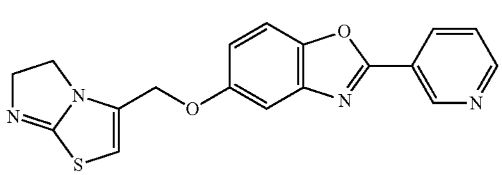 [SMILES: C1=C(COc2ccc3oc(-c4cccnc4)nc3c2)N2CCN=C2S1] | 350.39 | 5-{5H,6H-Imidazo[2,1-b][1,3]thiazol-3-ylmethoxy}-2-(pyridin-3-yl)-1,3-benzoxazole | Tr(MET-uHPLC-AB-101) = 1.47 min, (ES$^+$) (M + H)$^+$ 351 |
| 6 | 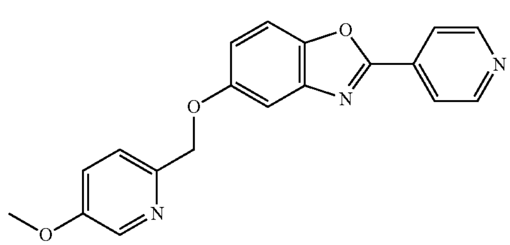 [SMILES: COc1ccc(COc2ccc3oc(-c4ccncc4)nc3c2)nc1] | 333.34 | 5-[(5-Methoxypyridin-2-yl)methoxy]-2-(pyridin-4-yl)-1,3-benzoxazole | Tr(MET-uHPLC-AB-101) = 2.45 min, (ES$^+$) (M + H)$^+$ 334 |

TABLE 15-continued

| Ex. | Structure | Mol. Weight | IUPAC Name | LCMS data |
|---|---|---|---|---|
| 7 | 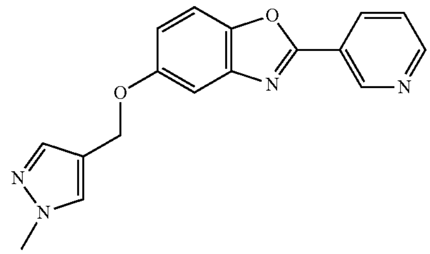 [SMILES: Cn1cc(COc2ccc3oc(-c4cccnc4)nc3c2)cn1] | 306.32 | 5-[(1-Methyl-1H-pyrazol-4-yl)methoxy]-2-(pyridin-3-yl)-1,3-benzoxazole | Tr(MET-uHPLC-AB-101) = 2.4 min, (ES$^+$) (M + H)$^+$ 307 |
| 8 | 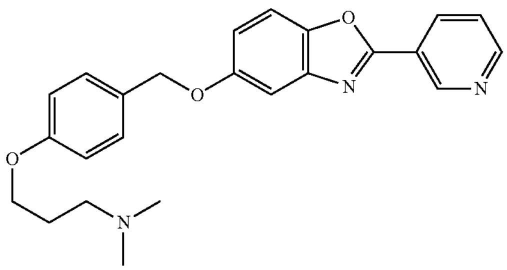 [SMILES: CN(C)CCCOc1ccc(COc2ccc3oc(-c4cccnc4)nc3c2)cc1] | 403.47 | Dimethyl({3-[4-({[2-(pyridin-3-yl)-1,3-benzoxazol-5-yl]oxy}methyl)phenoxy]propyl})amine | Tr(MET-uHPLC-AB-101) = 2.01 min, (ES$^+$) (M + H)$^+$ 404 |

Method 15
Scheme for Method 15

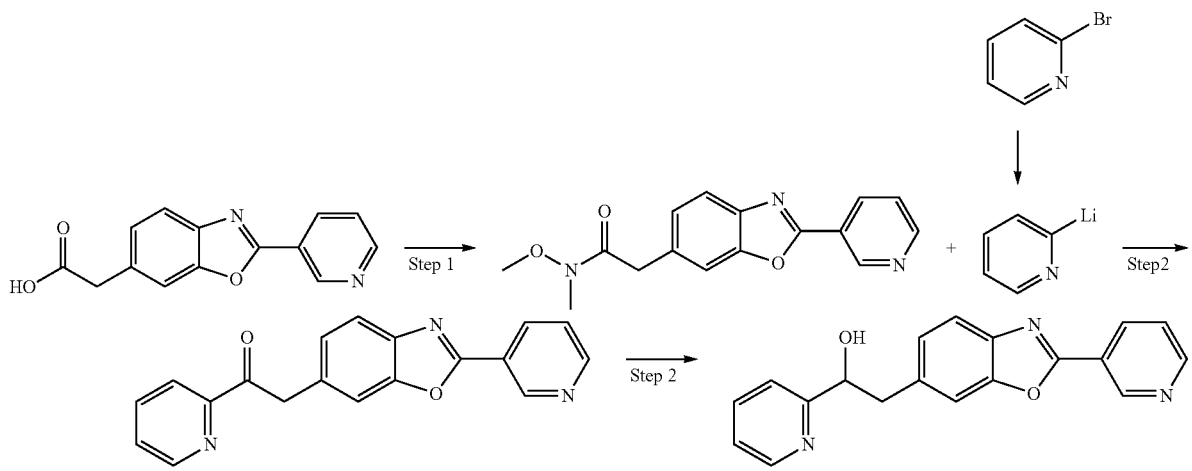

Step 1, Method 15: N-Methoxy-N-methyl-2-[2-(pyridin-3-yl)-1,3-benzoxazol-6-yl]acetamide To a stirred solution of 2-(pyridin-3-yl)-1,3-benzoxazol-5-yl]acetic acid (200 mg, 0.79 mmol) in N,N-dimethylformamide (2 mL), was added N-methoxymethanamine hydrochloride (92 mg, 0.94 mmol), 1-[bis(dimethylamino)methylene]-1H-1,2,3-triazolo[4,5-b]pyridinium 3-oxide hexafluorophosphate (329 mg, 0.86 mmol) and diisopropylethylamine (0.41 mL, 2.36 mmol). The mixture was stirred at room temperature for 2 hours then partitioned between ethyl acetate (20 mL) and water (20 mL). The organic extract was dried over sodium sulfate, filtered and concentrated. Purification by FCC (silica, 50-100% ethyl acetate in heptane) to give a white solid, which was dissolved in ethyl acetate (20 mL) and washed with water (2×15 mL). The organic extract was dried over sodium sulfate, filtered and concentrated to give the title compound 162 mg (69% yield) as a white solid. Tr(METCR1278)=1.54 min, (ES$^+$) (M+H)$^+$ 298.

Step 2, Method 15: 1-(Pyridin-2-yl)-2-[2-(pyridin-3-yl)-1,3-benzoxazol-5-yl]ethan-1-one To a solution of 2-bromopyridine (94 mg, 0.59 mmol) in tetrahydrofuran (4 mL) at −78° C. was added drop-wise n-butyllithium (1.6 M solution in hexanes, 0.40 mL, 0.64 mmol). After stirring for 30 minutes at −78° C., a solution of N-methoxy-N-methyl-2-[2-(pyridin-3-yl)-1,3-benzoxazol-6-yl]acetamide (160 mg, 0.54 mmol) in tetrahydrofuran (2 mL) was added drop-wise. The reaction was then stirred at −78° C. for 1 hour, then allowed to warm to room temperature and stirred for 1 hour. The mixture was cooled to −78° C. and quenched using saturated ammonium chloride (1 mL). The mixture was then diluted with water (30 mL) and extracted with ethyl acetate (2×30 mL). The combined organic extracts were dried over sodium sulfate, filtered and concentrated. Purification by FCC (silica, 0-100% ethyl acetate in heptane) gave the title compound 44 mg (26% yield) as a white solid. δ$_H$ NMR (500 MHz, chloroform) 9.46 (d, J=1.6 Hz, 1H), 8.79-8.73 (m, 2H), 8.51 (dt, J=8.0, 1.9 Hz, 1H), 8.07 (d, J=7.8 Hz, 1H), 7.84 (td, J=7.7, 1.7 Hz, 1H), 7.78 (d, J=1.3 Hz, 1H), 7.56 (d, J=8.4 Hz, 1H), 7.53-7.45 (m, 2H), 7.38 (dd, J=8.4, 1.6 Hz, 1H), 4.70 (s, 2H). Tr(MET-uHPLC-AB-101)=2.82 min, (ES$^+$) (M+H)$^+$ 316.

Step 3, Method 15: 1-(Pyridin-2-yl)-2-[2-(pyridin-3-yl)-1,3-benzoxazol-5-yl]ethan-1-ol Sodium borohydride (5 mg, 0.13 mmol) was added to a stirred solution of 1-(pyridin-2-yl)-2-[2-(pyridin-3-yl)-1,3-benzoxazol-5-yl]ethan-1-one (34 mg, 0.11 mmol) in anhydrous tetrahydrofuran (1 mL) and methanol (0.044 mL, 1.08 mmol) under nitrogen at room temperature. The reaction was stirred at this temperature for 2 hours. The mixture was quenched using water (0.5 mL), diluted with water (15 mL) and extracted with ethyl acetate (2×15 mL). The combined organic extract were dried over sodium sulfate, filtered and concentrated. Purification by FCC (silica, 20-100% ethyl acetate in heptane) gave the title compound 7 mg (20% yield) as a white solid.

Example 1, Method 15: 1-(Pyridin-2-yl)-2-[2-(pyridin-3-yl)-1,3-benzoxazol-5-yl]ethan-1-ol δ$_H$ NMR (500 MHz, DMSO) 9.33 (s, 1H), 8.80 (d, J=4.2 Hz, 1H), 8.60-8.47 (m, 2H), 7.78 (t, J=7.6 Hz, 1H), 7.70-7.62 (m, 2H), 7.59 (s, 1H), 7.46 (d, J=7.8 Hz, 1H), 7.31-7.23 (m, 2H), 5.55 (br. s, 1H), 4.89 (dd, J=7.6, 4.5 Hz, 1H), 3.27 (dd, J=13.8, 4.4 Hz, 1H), 3.04 (dd, J=13.6, 8.0 Hz, 1H). Tr(MET-uHPLC-AB-101)=1.43 min, (ES$^+$) (M+H)$^+$ 318.

The following examples were prepared using Method 15 described above:

Method 16

Scheme for Method 16

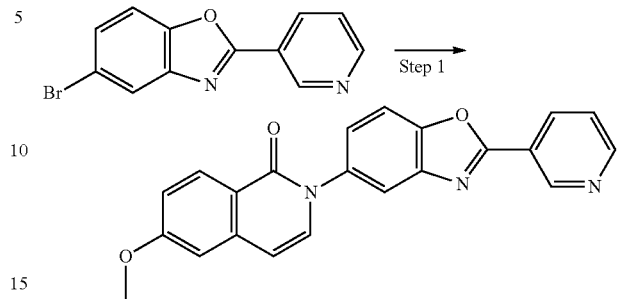

Step 1, Method 16: 6-Methoxy-2-[2-(pyridin-3-yl)-1,3-benzoxazol-5-yl]-1,2-dihydroisoquinolin-1-one 6-Methoxyisoquinolin-1(2H)-one (64 mg, 0.36 mmol), 5-bromo-2-(pyridin-3-yl)-1,3-benzoxazole (150 mg, 0.55 mmol), copper(I) iodide (14 mg, 0.07 mmol), L-proline (17 mg, 0.15 mmol) and anhydrous potassium carbonate (100 mg, 0.73 mmol) were placed in a round bottom flask under nitrogen. DMSO (5 mL) was added and the mixture heated to 120° C. overnight. Water (6 mL) and ethyl acetate (10 mL) were added and the mixture filtered. The solid was washed with ethyl acetate (2×5 mL) and water (2×2 mL) and recrystallised from a mixture of methanol (40 mL) and DMSO (3 mL) with hot filtration to give the title compound 23 mg (17% yield) as an off white powder.

Example 1, Method 16: 6-Methoxy-2-[2-(pyridin-3-yl)-1,3-benzoxazol-5-yl]-1,2-dihydroisoquinolin-1-one δ$_H$ NMR (500 MHz, DMSO) 9.41 (br. s, 1H), 8.85 (br. s, 1H), 8.59 (d, J=8.0 Hz, 1H), 8.18 (d, J=8.8 Hz, 1H), 8.00-7.94 (m, 2H), 7.69 (dd, J=7.9, 4.8 Hz, 1H), 7.55 (dd, J=8.6, 2.1 Hz, 1H), 7.51 (d, J=7.4 Hz, 1H), 7.23 (d, J=2.5 Hz, 1H), 7.14 (dd, J=8.9, 2.5 Hz, 1H), 6.69 (d, J=7.4 Hz, 1H), 3.91 (s, 3H). Tr(MET-uHPLC-AB-101)=2.86 min, (ES$^+$) (M+H)$^+$ 370.

The following example was prepared using Method 16 described above:

TABLE 16

| Ex. | Structure | Mol. Weight | IUPAC Name | LCMS data |
|---|---|---|---|---|
| 1 | 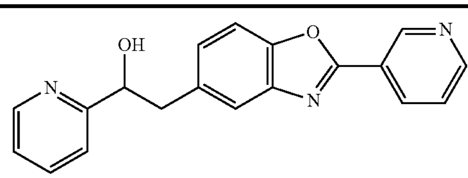 | 317.34 | 1-(Pyridin-2-yl)-2-[2-(pyridin-3-yl)-1,3-benzoxazol-5-yl]ethan-1-ol | Tr(MET-uHPLC-AB-101) = 1.43 min, (ES$^+$) (M + H)$^+$ 318 |
| 2 | 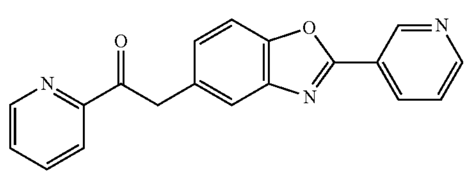 [SMILES: O=C(Cc1ccc2oc(-c3cccnc3)nc2c1)c1ccccn1] | 315.33 | 1-(Pyridin-2-yl)-2-[2-(pyridin-3-yl)-1,3-benzoxazol-5-yl]ethan-1-ol | Tr(MET-uHPLC-AB-101) = 2.82 min, (ES$^+$) (M + H)$^+$ 316 |

TABLE 17

| Ex. | Structure | Mol. Weight | IUPAC Name | LCMS data |
|---|---|---|---|---|
| 1 | 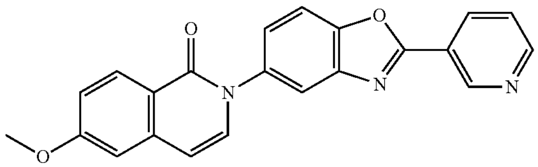 [SMILES: COc1ccc2c(=O)n(-c3ccc4oc(-c5cccnc5)nc4c3)ccc2c1] | 369.37 | 6-Methoxy-2-[2-(pyridin-3-yl)-1,3-benzoxazol-5-yl]-1,2-dihydroisoquinolin-1-one | Tr(MET-uHPLC-AB-101) = 2.86 min, (ES+) (M + H)+ 370 |

Method 17

Scheme for Method 17

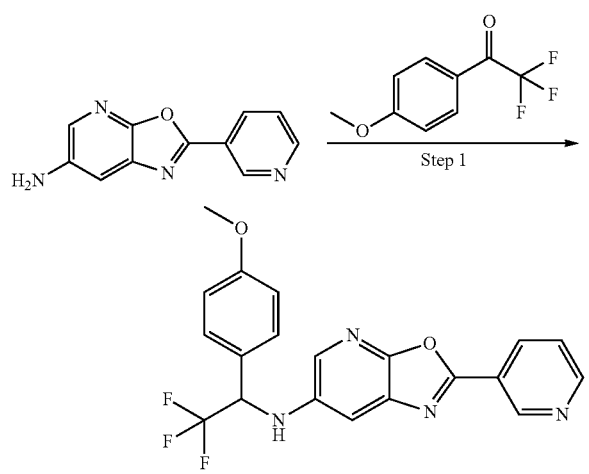

Step 1, Method 17: 2-(Pyridin-3-yl)-N-[2,2,2-trifluoro-1-(4-methoxyphenyl)ethyl]-[1,3]oxazolo[5,4-b]pyridin-6-amine To a stirred solution of 2,2,2-trifluoro-1-(4-methoxyphenyl)ethanone (51 mg, 0.25 mmol) in tetrahydrofuran (2.5 mL) at −78° C., was added 1 M titanium(IV) chloride in dichloromethane (0.25 mL, 0.25 mmol). The mixture was then left stirring for 10 minutes at −78° C., then 2-(pyridin-3-yl)-[1,3]oxazolo[5,4-b]pyridin-6-amine (53 mg, 0.25 mmol, prepared by Method 19) was added and the mixture was allowed to warm to room temperature. Triethyamine (0.1 mL, 0.75 mmol) was added and the mixture stirred at room temperature for 3 hours. Methanol (0.2 mL) followed by sodium borohydride (28 mg, 0.75 mmol) were added to the mixture and the mixture was stirred at room temperature overnight. The mixture was treated with sodium borohydride (28 mg, 0.75 mmol) and stirred at room temperature overnight. The mixture was diluted with water (15 mL) and extracted with ethyl acetate (2×15 mL). The combined organic extracts were dried over sodium sulfate, filtered and concentrated. Purification by preparative HPLC (acetonitrile/water) gave the title compound 1.7 mg (yield 2%) as a brown solid.

Example 1, Method 17: 2-(Pyridin-3-yl)-N-[2,2,2-trifluoro-1-(4-methoxyphenyl)ethyl]-[1,3]oxazolo[5,4-b]pyridin-6-am in e $\delta_H$ NMR (500 MHz, DMSO) 9.29 (d, J=1.7 Hz, 1H), 8.80 (dd, J=4.8, 1.6 Hz, 1H), 8.48 (dt, J=8.0, 1.9 Hz, 1H), 8.06 (d, J=2.6 Hz, 1H), 7.66 (d, J=2.6 Hz, 1H), 7.64 (dd, J=8.0, 4.9 Hz, 1H), 7.56 (d, J=8.7 Hz, 2H), 7.08 (d, J=10.3 Hz, 1H), 6.97 (d, J=8.8 Hz, 2H), 5.64 (p, J=8.4, 7.9 Hz, 1H), 3.74 (s, 3H). Tr(MET-uHPLC-AB-101)=3.23 min, (ES+) (M+H)+ 401.

The following example was prepared using Method 17 described above:

TABLE 18

| Ex. | Structure | Mol. Weight | IUPAC Name | LCMS data |
|---|---|---|---|---|
| 1 | 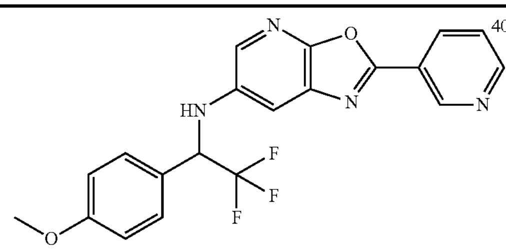 | 400.35 | 2-(Pyridin-3-yl)-N-[2,2,2-trifluoro-1-(4-methoxyphenyl)ethyl]-[1,3]oxazolo[5,4-b]pyridin-6-amine | Tr(MET-uHPLC-AB-101) = 3.23 min, (ES+) (M + H)+ 401 |

Method 18

Scheme for Method 18

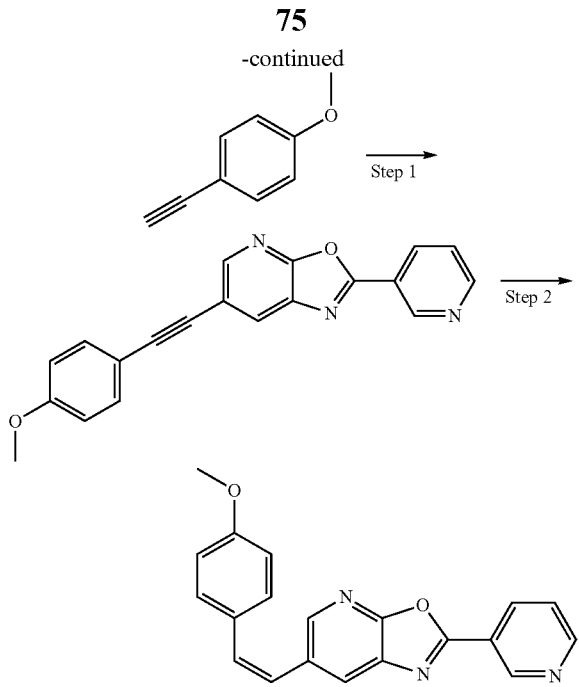

Step 1, Method 18: 3-{6-[2-(4-Methoxyphenyl)ethynyl]-[1,3]oxazolo[5,4-b]pyridin-2-yl}pyridine A mixture of 3-{6-bromo-[1,3]oxazolo[5,4-b]pyridin-2-yl}pyridine (50 mg, 0.18 mmol, prepared by Method 11), 1-ethynyl-4-methoxybenzene (72 mg, 0.54 mmol) and copper(I) iodide (3 mg, 0.013 mmol) in 1,4-dioxane (1.5 mL) and triethylamine (0.13 mL, 0.90 mmol) was degassed under a stream of nitrogen for 10 minutes. Palladium(II) chloride-triphenylphosphine (1:2:2) (9 mg, 0.013 mmol) was added and the mixture was stirred at 80° C. for 2 hours. The reaction was then scaled-up following the same procedure with 3-{6-bromo-[1,3]oxazolo[5,4-b]pyridin-2-yl}pyridine (200 mg, 0.72 mmol), 1-ethynyl-4-methoxybenzene (287 mg, 2.17 mmol), copper(I) iodide (10 mg, 0.053 mmol), triethylamine (0.50 mL, 3.61 mmol) and palladium(II) chloride-triphenylphosphine (1:2:2) (37 mg, 0.052 mmol) in 1,4-dioxane (6 mL) and stirred at 80° C. for 2.5 hours. Both reaction mixtures were then combined, diluted with water (35 mL) and extracted with ethyl acetate (2×35 mL). The combined organic extracts were dried over sodium sulfate, filtered and concentrated. Purification by FCC (silica, 0-100% ethyl acetate in heptane followed by 0-10% methanol in dichloromethane) gave the title compound 188 mg (63% yield) as a brown solid. Tr(METCR1278)=2.24 min, (ES$^+$) (M+H)$^+$ 328.

Step 2, Method 18: 3-{6-[(Z)-2-(4-Methoxyphenyl)ethenyl]-[1,3]oxazolo[5,4-b]pyridin-2-yl}pyridine To a stirred solution of 3-{6-[2-(4-methoxyphenyl)ethynyl]-[1,3]oxazolo[5,4-b]pyridin-2-yl}pyridine (88 mg, 0.27 mmol) and quinoline (0.032 mL, 0.27 mmol) in tetrahydrofuran (4 mL) and ethanol (4 mL) under nitrogen in a pressure vessel, was added Lindlar's catalyst (9 mg, 0.032 mmol). The mixture was placed under a hydrogen atmosphere (1 bar), heated to 80° C. and stirred at this temperature overnight. The mixture was filtered and rinsed with tetrahydrofuran (10 mL) then the filtrate was concentrated. The mixture was then treated with Lindlar's catalyst (8.6 mg, 0.032 mmol), placed under a hydrogen atmosphere (3.5 bars), heated to 80° C. and stirred at this temperature overnight. The mixture was filtered and rinsed with tetrahydrofuran (10 mL). The filtrate was concentrated and purified by FCC (silica, 0-3% methanol in dichloromethane) and preparative HPLC (acetonitrile/water) to give the title compound 6.2 mg (7% yield) as a white powder.

Example 1, Method 18: 3-{6-[(Z)-2-(4-Methoxyphenyl)ethenyl]-[1,3]oxazolo[5,4-b]pyridin-2-yl}pyridine $\delta_H$ NMR (500 MHz, DMSO) 9.35 (d, J=1.9 Hz, 1H), 8.84 (dd, J=4.8, 1.6 Hz, 1H), 8.54 (dt, J=8.0, 1.9 Hz, 1H), 8.25 (d, J=1.8 Hz, 1H), 8.05 (d, J=1.8 Hz, 1H), 7.67 (dd, J=8.0, 4.8 Hz, 1H), 7.17 (d, J=8.7 Hz, 2H), 6.85 (d, J=8.7 Hz, 2H), 6.79 (d, J=12.1 Hz, 1H), 6.69 (d, J=12.1 Hz, 1H), 3.74 (s, 3H). Tr(MET-uHPLC-AB-101)=3.53 min, (ES$^+$) (M+H)$^+$ 330.

The following examples were prepared using Method 18 described above:

TABLE 19

| Ex. | Structure | Mol. Weight | IUPAC Name | LCMS data |
|---|---|---|---|---|
| 1 | 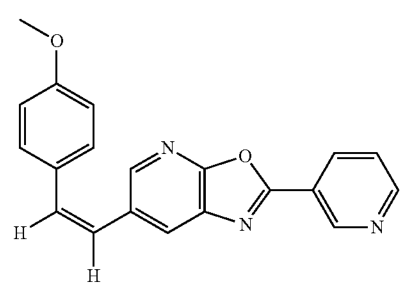 [SMILES: COc1ccc(/C=C\c2cnc3oc(-c4cccnc4)nc3c2)cc1] | 329.35 | 3-{6-[(Z)-2-(4-Methoxyphenyl)ethenyl]-[1,3]oxazolo[5,4-b]pyridin-2-yl}pyridine | Tr(MET-uHPLC-AB-101) = 3.53 min, (ES$^+$) (M + H)$^+$ 330 |

TABLE 19-continued

| Ex. | Structure | Mol. Weight | IUPAC Name | LCMS data |
|---|---|---|---|---|
| 2 | 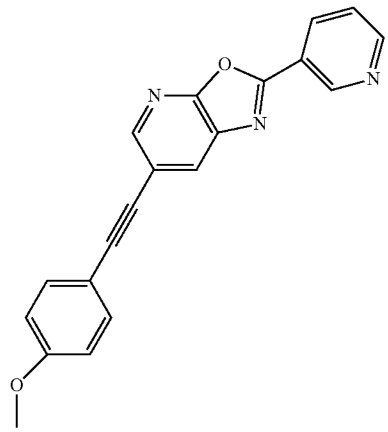 [SMILES: COc1ccc(C#Cc2cnc3oc(-c4cccnc4)nc3c2)cc1] | 327.34 | 3-{6-[2-(4-Methoxyphenyl)ethynyl]-[1,3]oxazolo[5,4-b]pyridin-2-yl}pyridine | Tr(MET-uHPLC-AB-101) = 3.73 min, (ES⁺) (M + H)⁺ 328 |
| 3 | 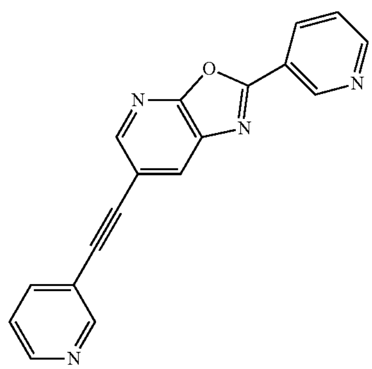 [SMILES: C(#Cc1cnc2oc(-c3cccnc3)nc2c1)c1cccnc1] | 298.30 | 3-{6-[2-(Pyridin-3-yl)ethynyl]-[1,3]oxazolo[5,4-b]pyridin-2-yl}pyridine | Tr(MET-uHPLC-AB-101) = 2.55 min, (ES⁺) (M + H)⁺ 299 |

Method 19

Scheme for Method 19

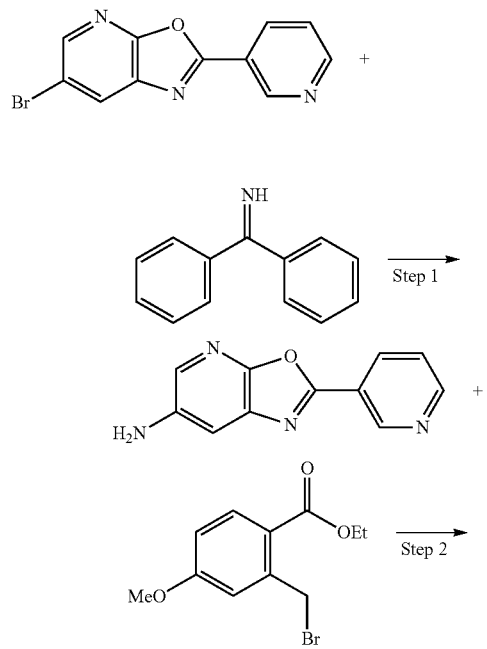

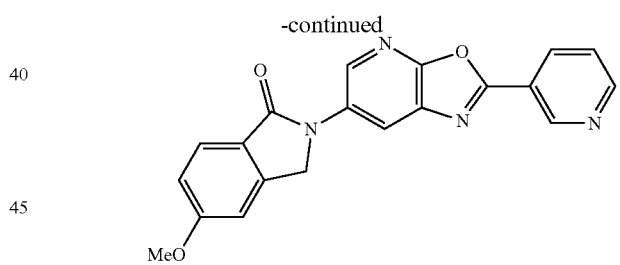

Step 1, Method 19: 2-(Pyridin-3-yl)-[1,3]oxazolo[5,4-b]pyridin-6-amine

A pressure tube was charged with 9,9-dimethyl-9H-xanthene-4,5-diyl)bis(diphenylphosphane) (189 mg, 0.33 mmol), tris(dibenzylideneacetone)dipalladium(0) (100 mg, 0.11 mmol), 3-{6-bromo-[1,3]oxazolo[5,4-b]pyridin-2-yl}pyridine (300 mg, 1.09 mmol, prepared by Method 11), diphenylmethanimine (236 mg, 1.30 mmol) and caesium carbonate (1.06 g, 3.26 mmol) in N,N-dimethylacetamide (6 mL). The mixture was degassed using a flow of nitrogen for 10 minutes. The mixture was then heated to 110° C. and stirred at this temperature overnight. The mixture was then diluted with water (70 mL) and extracted with ethyl acetate (2×70 mL). The combined organic extracts were dried over sodium sulfate, filtered and concentrated. The residue was diluted with tetrahydrofuran (15 mL), 2 M hydrochloric acid was added (6 mL) and the mixture was left standing at room temperature for 1 hour. The mixture was diluted with water (30 mL) and extracted with ethyl acetate (30 mL). The aqueous extract was then basified using saturated sodium bicarbonate solution to pH 8-9 and extracted with ethyl acetate (2×50 mL). The organic extracts were dried over sodium sulfate, filtered and concentrated. The solid was triturated with dichloromethane to give the title compound 94 mg as a light brown solid. The filtrate was concentrated then purified by FCC (silica, 0-100% heptane in ethyl acetate followed by 10% methanol in dichloromethane) to give the title compound 18 mg (total 112 mg, 40% yield) as a light brown solid. Tr(METCR1278)=1.17 min, (ES$^+$) (M+H)$^+$ 213.

Step 2, Method 19: 5-Methoxy-2-[2-(pyridin-3-yl)-[1,3]oxazolo[5,4-b]pyridin-6-yl]-2,3-dihydro-1H-isoindol-1-one To sodium hydride (60% in mineral oil, 15 mg, 0.37 mmol) under nitrogen was added a solution of 2-(pyridin-3-yl)-[1,3]oxazolo[5,4-b]pyridin-6-amine (50 mg, 0.18 mmol) in tetrahydrofuran (2 mL). The suspension was stirred at room temperature for 10 minutes. Ethyl 2-(bromomethyl)-4-methoxybenzoate (50 mg, 0.18 mmol, described in WO2009042907) in tetrahydrofuran (1 mL) was added and the mixture stirred at room temperature for 1 hour. The mixture was heated to 60° C. and stirred for 2 hours, then stood at room temperature overnight. The mixture was diluted with water (6 mL) and filtered to give a brown solid (22 mg). Recrystallization from DMSO (1 mL) and acetonitrile (1 mL) and recrystallisation from DMSO (2 mL) gave the title compound 1.5 mg (2% yield) as an off-white powder.

Example 1, Method 19: 5-Methoxy-2-[2-(pyridin-3-yl)-[1,3]oxazolo[5,4-b]pyridin-6-yl]-2,3-dihydro-1H-isoindol-1-one $\delta_H$ NMR (250 MHz, DMSO) 9.40 (s, 1H), 8.90 (d, J=2.4 Hz, 1H), 8.85 (d, J=5.5 Hz, 1H), 8.74 (d, J=2.4 Hz, 1H), 8.57 (dt, J=8.0, 1.9 Hz, 1H), 7.76 (d, J=8.5 Hz, 1H), 7.67 (dd, J=8.3, 4.6 Hz, 1H), 7.28-7.20 (m, 1H), 7.13 (dd, J=8.4, 2.2 Hz, 1H), 5.10 (s, 2H), 3.93 (s, 3H). Tr(MET-uHPLC-AB-101)=2.67 min, (ES$^+$) (M+H)$^+$ 359.

The following example was prepared using Method 19 described above:

Method 20
Scheme for Method 20

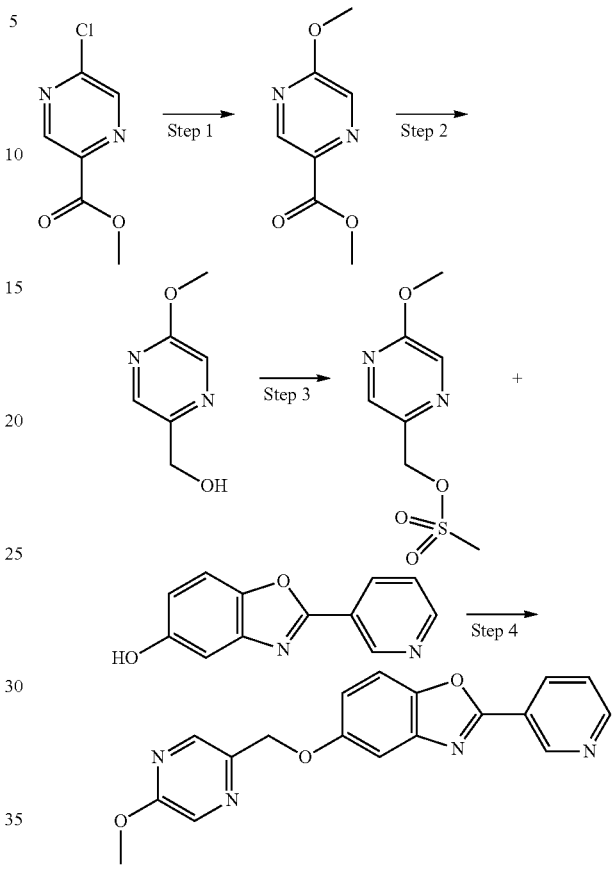

Step 1, Method 20: Methyl 5-methoxypyrazine-2-carboxylate

To methyl 5-chloropyrazine-2-carboxylate (2.00 g, 11.6 mmol) under nitrogen, was added a 0.5 M solution of sodium methoxide in methanol (27.8 mL, 13.9 mmol). The mixture was refluxed at 90° C. for 15 minutes. Water (80 mL) was added and the mixture extracted with ethyl acetate (2×100 mL). The combined organic extracts were dried over sodium sulfate, filtered and concentrated to give the title compound 1.68 g (79% yield) as a white powder. $\delta_H$ NMR

TABLE 20

| Ex. | Structure | Mol. Weight | IUPAC Name | LCMS data |
|---|---|---|---|---|
| 1 | 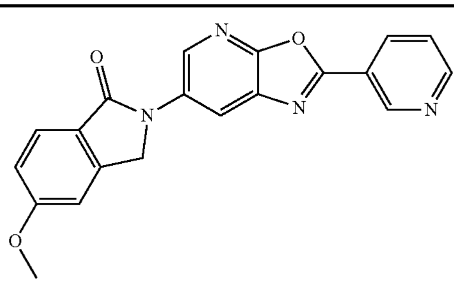 | 358.35 | 5-Methoxy-2-[2-(pyridin-3-yl)-[1,3]oxazolo[5,4-b]pyridin-6-yl]-2,3-dihydro-1H-isoindol-1-one | Tr(MET-uHPLC-AB-101) = 2.67 min, (ES$^+$) (M + H)$^+$ 359 |

(500 MHz, chloroform) 8.88 (d, J=1.2 Hz, 1H), 8.28 (d, J=1.2 Hz, 1H), 4.05 (s, 3H), 4.00 (s, 3H). Tr(METCR1278)= 1.23 min, (ES⁺) (M+H)⁺ 169.

Step 2, Method 20: (5-Methoxypyrazin-2-yl)methanol

Sodium borohydride (270 mg, 7.14 mmol) was added to a stirred solution of methyl 5-methoxypyrazine-2-carboxylate (200 mg, 1.19 mmol) in anhydrous tetrahydrofuran (8 mL) under nitrogen. The mixture was refluxed at 65° C. for 15 minutes, after which methanol (1.59 mL, 39.2 mmol) was added slowly. The reaction was refluxed at 65° C. for 1.5 hours. The mixture was quenched with water (0.5 mL), then diluted with water (15 mL), extracted with ethyl acetate (2×25 mL) then 20% 2-propanol in dichloromethane (25 mL). The combined organic extracts were dried over sodium sulfate, filtered and concentrated to give the title compound 115 mg (69% yield) as a white crystalline solid. δ$_H$ NMR (500 MHz, DMSO) 8.28-8.16 (m, 2H), 5.41 (t, J=5.8 Hz, 1H), 4.54 (d, J=5.6 Hz, 2H), 3.90 (s, 3H). Tr(METCR1278)= 0.74 min, (ES⁺) (M+H)⁺ 141.

Step 3, Method 20: (5-Methoxypyrazin-2-yl)methyl methanesulfonate

To a stirred solution of (5-methoxypyrazin-2-yl)methanol (73 mg, 0.52 mmol) in dichloromethane (1 mL) under nitrogen, was added triethylamine (0.08 mL, 0.73 mmol) followed by methanesulfonyl chloride (0.042 mL, 0.55 mmol). The mixture was stirred at room temperature for 1 hour. The mixture was then partitioned between dichloromethane (10 mL) and water (10 mL). The organic extract was dried over sodium sulfate, filtered and concentrated to give the title compound 59 mg (52% yield) as a yellow oil. Tr(METCR1278)=1.25 min, (ES⁺) (M+H)⁺ 219.

Step 4, Method 20: 5-[(5-Methoxypyrazin-2-yl)methoxy]-2-(pyridin-3-yl)-1,3-benzoxazole To sodium hydride (60% in mineral oil, 11.8 mg, 0.29 mmol) under nitrogen, was added a solution of 2-(pyridin-3-yl)-1,3-benzoxazol-5-ol (57 mg, 0.27 mmol, prepared by Method 14) in N,N-dimethylformamide (1 mL) and the mixture was stirred at room temperature for 30 minutes. A solution of (5-methoxypyrazin-2-yl)methyl methanesulfonate (59 mg, 0.27 mmol) in N,N-dimethylformamide (0.5 mL) was added and the mixture was stirred at room temperature overnight. The mixture was quenched with water (2 mL) and filtered to give a solid, which was purified by FCC (silica, 0-3% methanol in dichloromethane) to give the title compound 20.8 mg (23% yield) as an off-white powder.

Example 1, Method 20: 5-[(5-Methoxypyrazin-2-yl)methoxy]-2-(pyridin-3-yl)-1,3-benzoxazole δ$_H$ NMR (500 MHz, DMSO) 9.32 (s, 1H), 8.86-8.75 (m, 1H), 8.56-8.47 (m, 1H), 8.42 (s, 1H), 8.35 (s, 1H), 7.74 (d, J=8.9 Hz, 1H), 7.68-7.61 (m, 1H), 7.54 (s, 1H), 7.14 (d, J=8.9 Hz, 1H), 5.23 (s, 2H), 3.92 (s, 3H). Tr(MET-uHPLC-AB-101)=2.94 min, (ES⁺) (M+H)⁺ 335.

The following example was prepared using Method 20 described above:

TABLE 21

| Ex. | Structure | Mol. Weight | IUPAC Name | LCMS data |
|---|---|---|---|---|
| 1 | 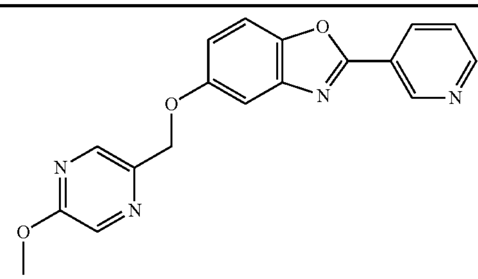 | 334.33 | 5-[(5-methoxypyrazin-2-yl)methoxy]-2-(pyridin-3-yl)-1,3-benzoxazole | Tr(MET-uHPLC-AB-101) = 2.94 min, (ES⁺) (M + H)⁺ 335 |

Method 21
Scheme for Method 21

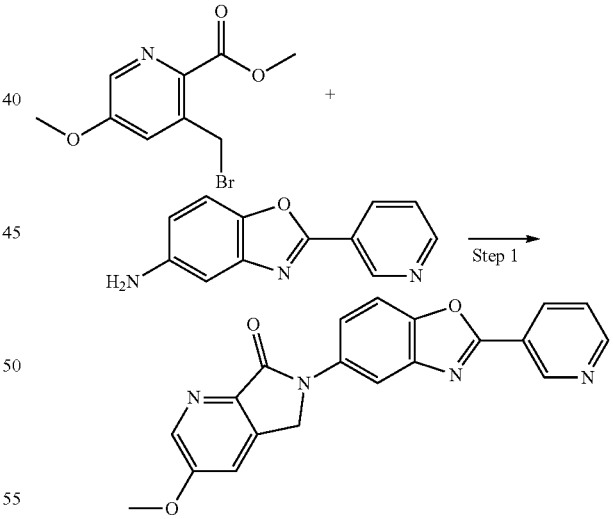

Step 1, Method 21: 3-Methoxy-6-[2-(pyridin-3-yl)-1,3-benzoxazol-5-yl]-5H,6H,7H-pyrrolo[3,4-b]pyridin-7-one To sodium hydride (60% in mineral oil, 15 mg, 0.38 mmol) and 2-(pyridin-3-yl)-1,3-benzoxazol-5-amine (41 mg, 0.19 mmol) under nitrogen was added tetrahydrofuran (2 mL). The suspension was stirred at room temperature for 10 minutes. Methyl 3-(bromomethyl)-5-methoxypyridine-2- carboxylate (50 mg, 0.19 mmol, described in Heterocycles (2013), 87(10), 2071-2079) in tetrahydrofuran (1 mL) was then added and the mixture was stirred at 60° C. for 2 hours, then at 70° C. for 2 hours, then at 80° C. for 2 hours, followed by stirring at room temperature for 2 days. The mixture was diluted with water (2 mL) and filtered to give a solid, which was triturated in ethyl acetate (2 mL) to give the title compound 18 mg (26% yield) as a brown powder.

Example 1, Method 21: 3-Methoxy-6-[2-(pyridin-3-yl)-1,3-benzoxazol-5-yl]-5H,6H,7H-pyrrolo[3,4-b]pyridin-7-one $\delta_H$ NMR (250 MHz, DMSO) 9.38 (d, J=1.5 Hz, 1H), 8.81 (dd, J=4.8, 1.7 Hz, 1H), 8.54 (dt, J=8.0, 2.1 Hz, 1H), 8.48 (d, J=2.7 Hz, 1H), 8.31 (d, J=1.9 Hz, 1H), 8.02 (dd, J=8.9, 2.2 Hz, 1H), 7.86 (d, J=9.0 Hz, 1H), 7.73-7.58 (m, 2H), 5.06 (s, 2H), 3.99 (s, 3H). Tr(MET-uHPLC-AB-101)=2.26 min, (ES$^+$) (M+H)$^+$ 359.

The following example was prepared using Method 21 described above:

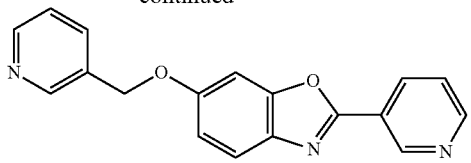

Step 1, Method 22:
N-(2,4-Dihydroxyphenyl)pyridine-3-carboxamide

To a stirred solution of 4-aminobenzene-1,3-diol hydrochloride (0.50 g, 3.09 mmol) in pyridine (6 mL) with ice cooling, was added nicotinoyl chloride hydrochloride (0.55 g, 3.09 mmol) portion-wise. The mixture was stirred at room temperature for 16 hours. The mixture was concentrated in vacuo and the residue was diluted with water (50 mL) and extracted with ethyl acetate (2×60 mL). The combined organic extracts were dried over sodium sulfate, filtered and concentrated. Purification by FCC (silica, 30-100% ethyl

TABLE 22

| Ex. | Structure | Mol. Weight | IUPAC Name | LCMS data |
|---|---|---|---|---|
| 1 | 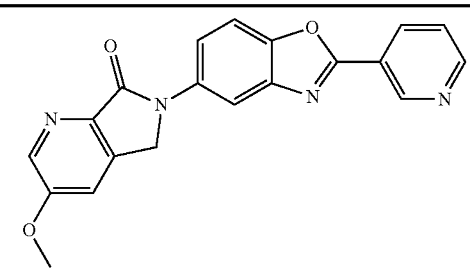 | 358.35 | 3-Methoxy-6-[2-(pyridin-3-yl)-1,3-benzoxazol-5-yl]-5H,6H,7H-pyrrolo[3,4-b]pyridin-7-one | Tr(MET-uHPLC-AB-101) = 2.26 min, (ES$^+$) (M + H)$^+$ 359 |

Method 22
Scheme for Method 22

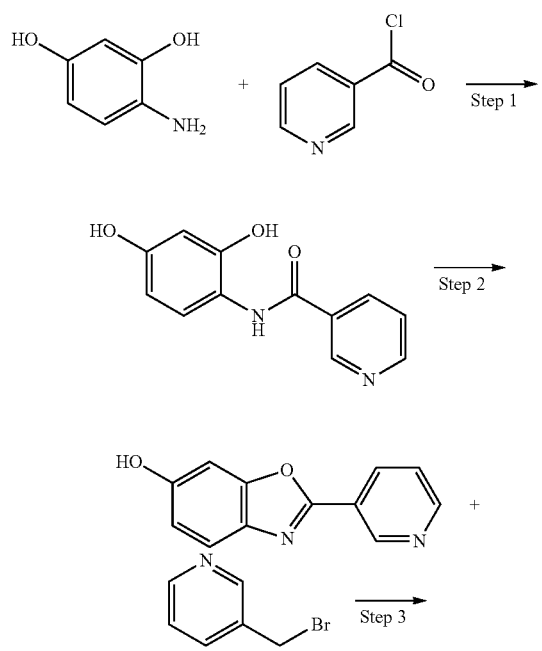

acetate in heptane) gave the title compound 148 mg (21% yield) as a light brown solid. $\delta_H$ NMR (250 MHz, DMSO) 9.47 (d, J=88.0 Hz, 3H), 9.10 (d, J=1.7 Hz, 1H), 8.73 (dd, J=4.8, 1.5 Hz, 1H), 8.28 (dt, J=7.9, 1.9 Hz, 1H), 7.53 (dd, J=7.7, 5.1 Hz, 1H), 7.20 (d, J=8.6 Hz, 1H), 6.36 (d, J=2.6 Hz, 1H), 6.24 (dd, J=8.6, 2.6 Hz, 1H). Tr(METCR1278)= 0.79 min, (ES$^+$) (M+H)$^+$ 231.

Step 2, Method 22:
2-(Pyridin-3-yl)-1,3-benzoxazol-6-ol

N-(2,4-dihydroxyphenyl)pyridine-3-carboxamide (150 mg, 0.65 mmol) and acetic acid (3 mL) were heated at 200° C. for 30 minutes in a microwave. The mixture was then concentrated in vacuo and the residue was triturated in ethyl acetate (10 mL) to give the title compound 55 mg (40% yield) as a light brown powder. $\delta_H$ NMR (500 MHz, DMSO) 9.96 (s, 1H), 9.28 (d, J=1.7 Hz, 1H), 8.76 (dd, J=4.8, 1.5 Hz, 1H), 8.45 (dt, J=8.0, 1.9 Hz, 1H), 7.67-7.59 (m, 2H), 7.12 (d, J=2.2 Hz, 1H), 6.89 (dd, J=8.6, 2.3 Hz, 1H). Tr(METCR1278)=1.38 min, (ES$^+$) (M+H)$^+$ 213.

Step 3, Method 22: 2-(Pyridin-3-yl)-6-(pyridin-3-ylmethoxy)-1,3-benzoxazole

To sodium hydride (60% in mineral oil, 10 mg, 0.25 mmol) under nitrogen, was added a solution of 2-(pyridin-3-yl)-1,3-benzoxazol-6-ol (50 mg, 0.24 mmol) in N,N-dimethylformamide (1 mL) and the mixture was stirred at room temperature for 30 minutes. Sodium hydride (60% in mineral oil, 10 mg, 0.25 mmol) and 3-(bromomethyl)pyridine hydrobromide (66 mg, 0.26 mmol) were dissolved in N,N-dimethylformamide (1 mL) and stirred at room temperature for 10 minutes. This suspension was then added to reaction mixture and the mixture was stirred at room temperature for 1 hour. The mixture was quenched with water (0.5 mL), then diluted with water (15 mL) and extracted with ethyl acetate (2×15 mL). The combined organic extracts were dried over sodium sulfate, filtered and concentrated. Purification by FCC (silica, 0 to 3% methanol in dichloromethane) gave the title compound 39 mg (55% yield) as an off-white powder.

Example 1, Method 22: 2-(Pyridin-3-yl)-6-(pyridin-3-ylmethoxy)-1,3-benzoxazole $\delta_H$ NMR (500 MHz, DMSO) 9.30 (d, J=1.8 Hz, 1H), 8.78 (dd, J=4.8, 1.6 Hz, 1H), 8.72 (d, J=1.9 Hz, 1H), 8.57 (dd, J=4.8, 1.6 Hz, 1H), 8.48 (dt, J=8.0, 1.9 Hz, 1H), 7.92 (dt, J=7.8, 1.9 Hz, 1H), 7.76 (d, J=8.7 Hz, 1H), 7.64 (dd, J=8.0, 4.8 Hz, 1H), 7.58 (d, J=2.4 Hz, 1H), 7.45 (dd, J=7.8, 4.8 Hz, 1H), 7.14 (dd, J=8.7, 2.4 Hz, 1H), 5.27 (s, 2H). Tr(MET-uHPLC-AB-101)=1.68 min, (ES+) (M+H)+ 304.

The following example was prepared using Method 22 described above:

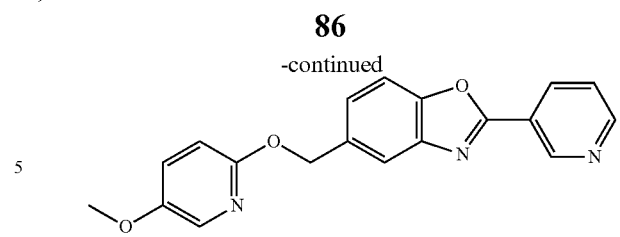

Step 1, Method 23: Methyl 2-(pyridin-3-yl)-1,3-benzoxazole-5-carboxylate

Methyl 3-amino-4-hydroxybenzoate (200 mg, 1.2 mmol) was suspended in 1,4-dioxane (3 mL) and pyridine-3-carbonyl chloride hydrochloride (234 mg, 1.32 mmol) was added and the mixture heated to 200° C. for 15 min in a microwave. This procedure was performed 5 times. All reaction mixtures were combined then partitioned between ethyl acetate (100 mL) and saturated aqueous sodium bicarbonate (80 mL). The organic extract was dried over sodium sulfate, filtered and concentrated. Purification by FCC (silica, 20-100% ethyl acetate in heptane) gave the title compound 560 mg (37% yield) as a light brown solid. $\delta_H$ NMR (500 MHz, DMSO) 9.37 (d, J=1.7 Hz, 1H), 8.84 (dd, J=4.8, 1.6 Hz, 1H), 8.56 (dt, J=8.0, 1.9 Hz, 1H), 8.37 (d,

TABLE 23

| Ex. | Structure | Mol. Weight | IUPAC Name | LCMS data |
|---|---|---|---|---|
| 1 | 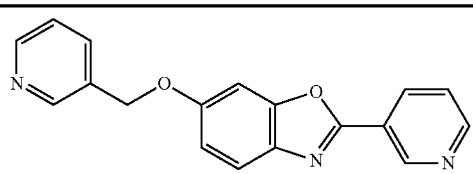 | 303.31 | 2-(Pyridin-3-yl)-6-(pyridin-3-ylmethoxy)-1,3-benzoxazole | Tr(MET-uHPLC-AB-101) = 1.68 min, (ES+) (M + H)+ 304 |

Method 23

Scheme for Method 23

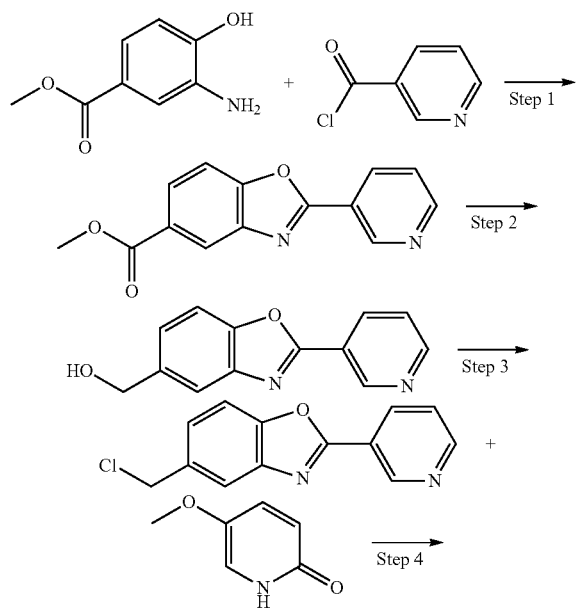

J=1.4 Hz, 1H), 8.09 (dd, J=8.6, 1.7 Hz, 1H), 7.97 (d, J=8.6 Hz, 1H), 7.68 (ddd, J=8.0, 4.8, 0.7 Hz, 1H), 3.91 (s, 3H). Tr(METCR1278)=1.74 min, (ES+) (M+H)+ 255.

Step 2, Method 23: [2-(Pyridin-3-yl)-1,3-benzoxazol-5-yl]methanol

4 M lithium aluminum hydride in tetrahydrofuran (0.25 mL, 1.00 mmol) was added to a stirred solution of methyl 2-(pyridin-3-yl)-1,3-benzoxazole-5-carboxylate (340 mg, 1.34 mmol) in anhydrous tetrahydrofuran (12 mL) under nitrogen. The mixture was stirred at 0° C. for 30 minutes. The mixture was quenched by cautious addition of water (1 mL) followed by saturated ammonium chloride solution (0.5 mL). The mixture was stirred at 0° C. for 20 minutes. The mixture was diluted with water (15 mL) and extracted with ethyl acetate (2×15 mL). The organic extracts were dried over sodium sulfate, filtered and concentrated. Purification by FCC (silica, 0-15% methanol in dichloromethane) gave the title compound 197 mg (65% yield) as an off-white solid. Tr(MET-uHPLC-AB-101)=1.7 min, (ES+) (M+H)+ 227.

Step 3, Method 23: 5-(Chloromethyl)-2-(pyridin-3-yl)-1,3-benzoxazole

To a stirred solution of [2-(pyridin-3-yl)-1,3-benzoxazol-5-yl]methanol (50 mg, 0.22 mmol) in dichloromethane (1 mL) under nitrogen with ice cooling, was added triethylamine (0.068 mL, 0.48 mmol) followed by methansulfonyl chloride (0.036 mL, 0.46 mmol). The mixture was then allowed to warm to room temperature and stirred for 48 hours. The mixture was retreated with triethylamine (0.068 mL, 0.48 mmol) and methanesulfonyl chloride (0.036 mL, 0.46 mmol) and stirred at room temperature for 2 hours. The mixture was partitioned between dichloromethane (10 mL) and water (10 mL). The organic extract was dried over sodium sulfate, filtered and concentrated to give the title compound 75 mg (91% yield) as an orange solid. Tr(METCR1278)=1.86 min, (ES+) (M+H)+ 245.

Step 4, Method 23: 5-{[(5-Methoxypyridin-2-yl)oxy]methyl}-2-(pyridin-3-yl)-1,3-benzoxazole A suspension of 5-(chloromethyl)-2-(pyridin-3-yl)-1,3-benzoxazole (50 mg, 0.20 mmol), 5-methoxy-1,2-dihydropyridin-2-one (28 mg, 0.22 mmol) and silver carbonate (38 mg, 0.14 mmol) in toluene (2 mL) was stirred at 80° C. for 24 hours. The mixture was diluted with water (20 mL) and extracted with ethyl acetate (2×20 mL). The combined organic extracts were dried over sodium sulfate, filtered and concentrated. Purification by preparative HPLC (acetonitrile/water) gave the title compound 2.4 mg (4% yield) as an off-white powder.

Example 1, Method 23: 5-{[(5-Methoxypyridin-2-yl)oxy]methyl}-2-(pyridin-3-yl)-1,3-benzoxazole δ$_H$ NMR (500 MHz, DMSO) 9.35 (d, J=2.0 Hz, 1H), 8.81 (dd, J=4.8, 1.5 Hz, 1H), 8.54 (dt, J=8.0, 1.9 Hz, 1H), 7.91 (s, 1H), 7.87 (d, J=3.1 Hz, 1H), 7.82 (d, J=8.4 Hz, 1H), 7.66 (dd, J=8.0, 4.8 Hz, 1H), 7.55 (dd, J=8.4, 1.5 Hz, 1H), 7.42 (dd, J=8.9, 3.1 Hz, 1H), 6.87 (d, J=8.9 Hz, 1H), 5.42 (s, 2H), 3.77 (s, 3H). Tr(MET-uHPLC-AB-101)=3.22 min, (ES+) (M+H)+ 334.

The following examples were prepared using Method 23 described above:

TABLE 24

| Ex. | Structure | Mol. Weight | IUPAC Name | LCMS data |
|---|---|---|---|---|
| 1 | 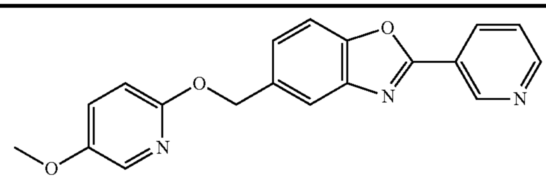 | 333.34 | 5-{[(5-Methoxypyridin-2-yl)oxy]methyl}-2-(pyridin-3-yl)-1,3-benzoxazole | Tr(MET-uHPLC-AB-101) = 3.22 min, (ES+) (M + H)+ 334 |

Method 24

Scheme for Method 24

Step 1, Method 24: 5-(Chloromethyl)pyrimidine hydrochloride

To a solution of pyrimidin-5-ylmethanol (48 mg, 0.43 mmol) in dichloromethane (3 mL), thionyl dichloride (0.26 mL, 3.6 mmol) was added dropwise slowly at 0° C. The mixture was heated to reflux (50° C.) for 2 hours and then the mixture was concentrated. Dichloromethane (5 mL) was added and the mixture was concentrated (×3) to give the title compound as a yellow oil which was used directly in the next step. Tr(METCR1278)=0.90 min, (ES+) (M+H)+ 129/131.

Step 2, Method 24: 4-[5-(Pyrimidin-5-ylmethoxy)-1-benzofuran-2-yl]pyridine-3-carbonitrile 4-(5-Hydroxy-1-benzofuran-2-yl)pyridine-3-carbonitrile (90%, 80 mg, 0.3 mmol, prepared by Method 9), 5-(chloromethyl)pyrimidine hydrochloride (0.43 mmol) and potassium iodide (56 mg, 0.34 mmol) were dissolved in anhydrous N,N-dimethylformamide (6 mL) and stirred for 5 minutes at room temperature. Sodium hydride (60% in mineral oil, 37 mg, 0.91 mmol) was added and the reaction mixture was stirred at room temperature for 3 hours. Water (0.1 mL) was added and the solvents were removed in vacuo. The residue was partitioned between ethyl acetate (50 mL) and water (50 mL) and the aqueous was extracted with ethyl acetate (2×50 mL). The combined organic extracts were washed with water (20 mL), brine (20 mL), dried over sodium sulfate, filtered and concentrated. Purification by FCC (silica, 0-80% ethyl acetate in heptane) gave the title compound 30.3 mg (30% yield) as an off-white solid.

Example 1, Method 24: 4-[5-(Pyrimidin-5-ylmethoxy)-1-benzofuran-2-yl]pyridine-3-carbonitrile δ$_H$ NMR (500 MHz, DMSO) 9.19 (s, 1H), 9.12 (s, 1H), 8.96 (s, 2H), 8.92 (d, J=5.4 Hz, 1H), 8.08 (d, J=5.5 Hz, 1H), 7.96 (s, 1H), 7.67 (d, J=9.0 Hz, 1H), 7.53 (d, J=2.6 Hz, 1H), 7.21 (dd, J=9.0, 2.6 Hz, 1H), 5.26 (s, 2H). Tr(MET-uHPLC-AB-101)=2.8 min, (ES+) (M+H)+ 329.

The following example was prepared using Method 24 described above:

TABLE 25

| Ex. | Structure | Mol. Weight | IUPAC Name | LCMS data |
|---|---|---|---|---|
| 1 | 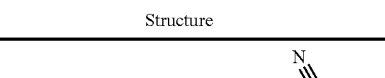 | 328.32 | 4-[5-(Pyrimidin-5-ylmethoxy)-1-benzofuran-2-yl]pyridine-3-carbonitrile | Tr(MET-uHPLC-AB-101) = 2.8 min, (ES⁺) (M + H)⁺ 329 |

Method 25
Scheme for Method 25

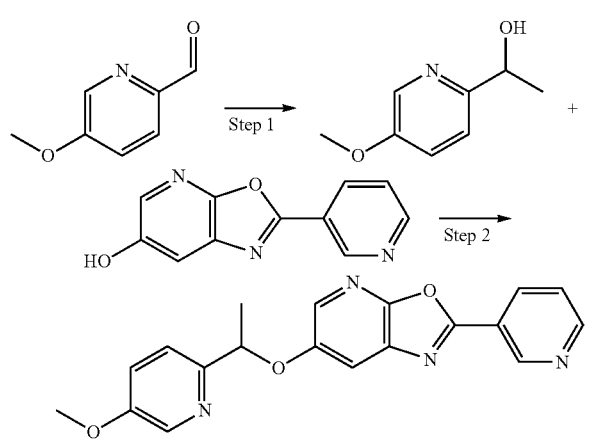

Step 1, Method 25:
1-(5-Methoxypyridin-2-yl)ethan-1-ol

To a stirred solution of 5-methoxypyridine-2-carbaldehyde (220 mg, 1.60 mmol) in tetrahydrofuran (3 mL) with ice cooling was added 1.4 M methyl magnesium bromide in tetrahydrofuran (1.15 mL, 1.60 mmol). The mixture was stirred for 30 minutes with ice cooling. The mixture was quenched with saturated aqueous ammonium chloride solution (0.5 mL), diluted with water (15 mL) and extracted with ethyl acetate (2×15 mL). The combined organic extracts were dried over sodium sulfate, filtered and concentrated to give the title compound 218 mg (89% yield) as a yellow oil.

$\delta_H$ NMR (500 MHz, DMSO) 8.17 (d, J=2.9 Hz, 1H), 7.42 (d, J=8.6 Hz, 1H), 7.36 (dd, J=8.7, 2.9 Hz, 1H), 5.23 (d, J=4.6 Hz, 1H), 4.72-4.64 (m, 1H), 3.80 (s, 3H), 1.32 (d, J=6.5 Hz, 3H).

Step 2, Method 25: 3-{6-[1-(5-Methoxypyridin-2-yl)ethoxy]-[1,3]oxazolo[5,4-b]pyridin-2-yl}pyridine To a stirred solution of 1-(5-methoxypyridin-2-yl)ethan-1-ol (20 mg, 0.13 mmol), 2-(pyridin-3-yl)-[1,3]oxazolo[5,4-b]pyridin-6-ol (22 mg, 0.10 mmol, prepared by Method 30) and triphenylphosphine (41 mg, 0.16 mmol) in anhydrous tetrahydrofuran (1 mL) at 0° C. was added diisopropyl azodicarboxylate (0.031 mL, 0.16 mmol). The mixture was allowed to warm to room temperature and stirred overnight. The mixture was diluted with water (15 mL) and extracted with ethyl acetate (2×15 mL). The combined organic extracts were dried over magnesium sulfate, filtered and concentrated. Purification by FCC (silica, 50-100% ethyl acetate in heptane) and preparative HPLC (acetonitrile/water) gave the title compound 7.4 mg (21% yield) as a colourless, crystalline solid.

Example 2, Method 25: 3-{6-[1-(5-Methoxypyridin-2-yl)ethoxy]-[1,3]oxazolo[5,4-b]pyridin-2-yl}pyridine $\delta_H$ NMR (500 MHz, DMSO) 9.31 (d, J=1.9 Hz, 1H), 8.81 (dd, J=4.8, 1.6 Hz, 1H), 8.50 (dt, J=8.0, 1.9 Hz, 1H), 8.28 (d, J=2.9 Hz, 1H), 8.12 (d, J=2.7 Hz, 1H), 7.87 (d, J=2.7 Hz, 1H), 7.65 (dd, J=7.9, 4.8 Hz, 1H), 7.49 (d, J=8.7 Hz, 1H), 7.38 (dd, J=8.7, 3.0 Hz, 1H), 5.63 (q, J=6.4 Hz, 1H), 3.80 (s, 3H), 1.64 (d, J=6.4 Hz, 3H). Tr(MET-uHPLC-AB-101)=2.6 min, (ES⁺) (M+H)⁺ 349.

The following example was prepared using Method 25 described above:

TABLE 26

| Ex. | Structure | Mol. Weight | IUPAC Name | LCMS data |
|---|---|---|---|---|
| 1 | 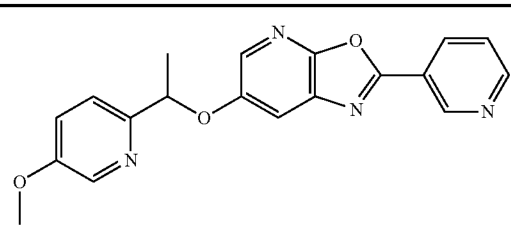 | 348.36 | 3-{6-[1-(5-Methoxypyridin-2-yl)ethoxy]-[1,3]oxazolo[5,4-b]pyridin-2-yl}pyridine | Tr(MET-uHPLC-AB-101) = 2.6 min, (ES⁺) (M + H)⁺ 349 |

Method 26
Scheme for Method 26

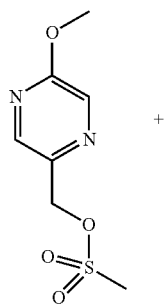

+

Method 20) in N,N-dimethylformamide (0.5 mL) was added and the mixture was stirred at room temperature overnight. The mixture was then quenched with water (3 mL) and allowed to cool to room temperature. The resulting suspension was filtered, washed with water (3 mL), methanol (2 mL) and heptane (5 mL) to give the title compound 63 mg (65% yield) as a tan powder.

Example 1, Method 26: 4-{5-[(5-Methoxypyrazin-2-yl)methoxy]-1-benzofuran-2-yl}pyridine-3-carbonitrile $\delta_H$ NMR (500 MHz, DMSO) 9.12 (s, 1H), 8.92 (d, J=5.4 Hz, 1H), 8.42 (d, J=1.0 Hz, 1H), 8.35 (d, J=1.3 Hz, 1H), 8.08 (d, J=5.4 Hz, 1H), 7.95 (s, 1H), 7.66 (d, J=9.0 Hz, 1H), 7.52 (d, J=2.6 Hz, 1H), 7.19 (dd, J=9.0, 2.6 Hz, 1H), 5.22 (s, 2H), 3.93 (s, 3H). Tr(MET-uHPLC-AB-101)=3.5 min, (ES⁺) (M+H)⁺ 359.

The following example was prepared using Method 26 described above:

TABLE 27

| Ex. | Structure | Mol. Weight | IUPAC Name | LCMS data |
|---|---|---|---|---|
| 1 | 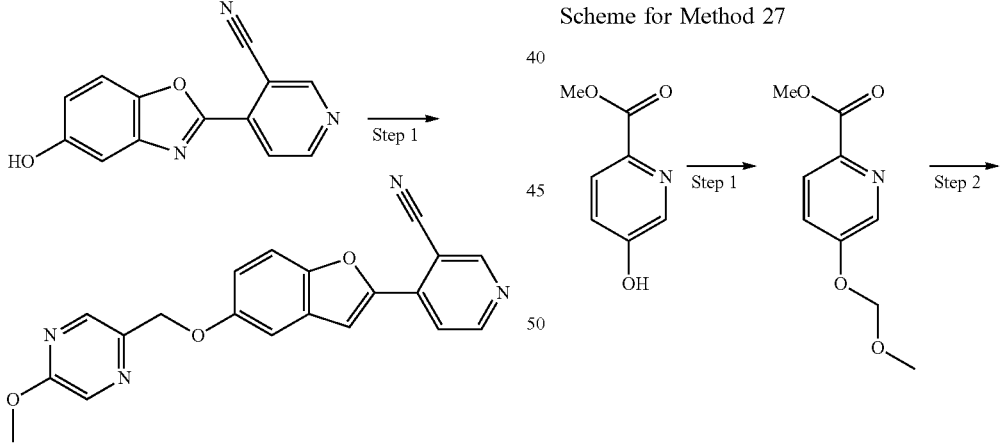 | 358.35 | 4-{5-[(5-Methoxypyrazin-2-yl)methoxy]-1-benzofuran-2-yl}pyridine-3-carbonitrile | Tr(MET-uHPLC-AB-101) = 3.5 min, (ES⁺) (M + H)⁺ 359 |

Step 1, Method 26: 4-{5-[(5-Methoxypyrazin-2-yl)methoxy]-1-benzofuran-2-yl}pyridine-3-carbonitrile To sodium hydride (60% in mineral oil, 11.8 mg, 0.29 mmol) under nitrogen, was added a solution of 4-(5-hydroxy-1-benzofuran-2-yl)pyridine-3-carbonitrile (57 mg, 0.27 mmol, prepared by Method 9) in N,N-dimethylformamide (1 mL) and the mixture was stirred at room temperature for 30 minutes. A solution of (5-methoxypyrazin-2-yl)methyl methanesulfonate (64 mg, 0.3 mmol, prepared by Method 27
Scheme for Method 27

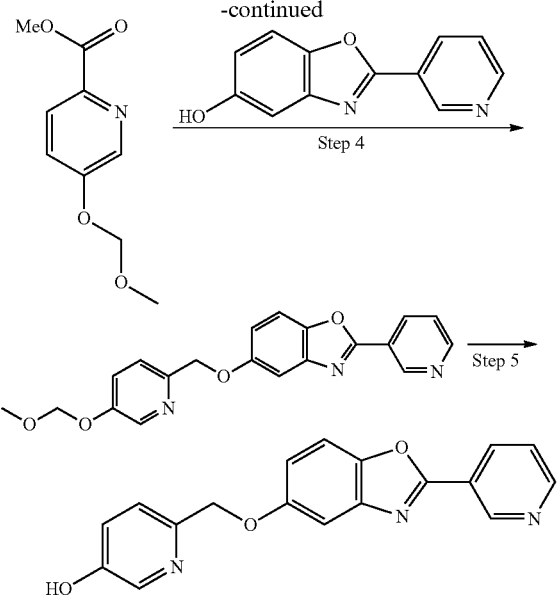

Step 1, Method 27: Methyl 5-(methoxymethoxy)pyridine-2-carboxylate

Sodium hydride (60% in mineral oil, 144 mg, 3.59 mmol) was suspended in anhydrous N,N-dimethylformamide (5 mL) and cooled to 0° C. Methyl 5-hydroxypyridine-2-carboxylate (500 mg, 3.27 mmol) dissolved in N,N-dimethylformamide (5 mL) was added slowly to the suspension. The reaction mixture was stirred under nitrogen and warmed to room temperature over 30 minutes. The reaction was cooled to 0° C. and chloro(methoxy)methane (0.26 mL, 3.43 mmol) was added drop-wise over 15 minutes. The reaction was warmed to room temperature and stirred for 16 hours. Water (20 mL) was added and the solvents were removed in vacuo. The mixture was partitioned between ethyl acetate and water (1:1; 100 mL) and extracted with ethyl acetate (3×60 mL). The combined organics were washed with water (3×80 mL), brine (50 mL), dried over magnesium sulfate, filtered and concentrated in vacuo to give the title compound 0.6 g (89% yield) as an orange oil which solidified upon standing. Tr(METCR1278)=1.33 min, (ES$^+$) (M+H)$^+$ 198.

Step 2, Method 27: [5-(Methoxymethoxy)pyridin-2-yl]methanol

Methyl 5-(methoxymethoxy)pyridine-2-carboxylate (0.39 g, 1.9 mmol) was dissolved in anhydrous tetrahydrofuran (15 mL) and cooled to 0° C. in a nitrogen atmosphere. 2.4 M lithium aluminium hydride in tetrahydrofuran (0.87 mL, 2.09 mmol) was added drop-wise over a period of 5 minutes, and the reaction was stirred at 0° C. for 1.5 hours. Rochelle's salt solution (1 mL) was added drop-wise with vigorous stirring over 10 minutes and the reaction mixture was warmed to room temperature over 1 hour. An emulsion formed which was filtered through paper. The filter paper was washed with saturated sodium bicarbonate solution (10 mL) followed by ethyl acetate (3×10 mL). The phases were separated and the aqueous was extracted with ethyl acetate (3×10 mL). The combined organics were washed with brine (10 mL) and dried over sodium sulfate, filtered and concentrated to give the title compound 276 mg (86% yield) as an orange oil. Tr(METCR1278)=1.09 min, (ES$^+$) (M+H)$^+$ 170.

Step 3, Method 27: [5-(Methoxymethoxy)pyridin-2-yl]methyl methanesulfonate

[5-(Methoxymethoxy)pyridin-2-yl]methanol (276 mg, 1.63 mmol) was dissolved in dichloromethane (5 mL), cooled to 0° C. and stirred in a nitrogen atmosphere. Triethylamine (250 μL, 1.79 mmol) was added, followed by drop-wise addition of methanesulfonyl chloride (133 μL, 1.71 mmol). The reaction was stirred for 45 minutes and warmed room temperature. Water (5 mL) was added and the phases separated. The aqueous layer was extracted with dichloromethane (3×15 mL); the combined organic extracts were washed with brine (10 mL), dried over sodium sulfate, filtered and was concentrated in vacuo to give the title compound 275 mg (59% yield) as a dark red oil which was used in the next step without further purification. Tr(METCR1278)=1.35 min, (ES$^+$) (M+H)$^+$ 248.

Step 4, Method 27: 5-{[5-(Methoxymethoxy)pyridin-2-yl]methoxy}-2-(pyridin-3-yl)-1,3-benzoxazole

[5-(Methoxymethoxy)pyridin-2-yl]methyl methanesulfonate (276 mg, 1.11 mmol) and 2-(pyridin-3-yl)-1,3-benzoxazol-5-ol (215 mg, 1.01 mmol, prepared by Method 14) were dissolved in anhydrous N,N-dimethylformamide (8 mL) and stirred for 10 minutes in a nitrogen atmosphere at 0° C. Sodium hydride (60% in mineral oil, 122 mg, 3.04 mmol) was added and the reaction mixture stirred for 16 hours. Water (1 mL) was added and the reaction stirred for 10 minutes. The solvents were removed in vacuo and the residue was partitioned between ethyl acetate (50 mL) and water (20 mL). The aqueous was extracted with ethyl acetate (3×50 mL). The combined organic extracts were washed with brine (10 mL), dried over sodium sulfate, filtered and concentrated. Purification by FCC (silica, 10-100% ethyl acetate in heptane) gave the title compound, 135 mg (36% yield) as a white solid. Tr(METCR1278)=1.78 min, (ES$^+$) (M+H)$^+$ 364.

Step 5, Method 27: 6-({[2-(Pyridin-3-yl)-1,3-benzoxazol-5-yl]oxy}methyl)pyridin-3-ol To a solution of 5-{[5-(methoxymethoxy)pyridin-2-yl]methoxy}-2-(pyridin-3-yl)-1,3-benzoxazole (135 mg, 0.37 mmol) in tetrahydrofuran (20 mL) was added 3 M aqueous hydrochloric acid (1.3 mL) and the mixture was stirred at 60° C. for 1 hour. The reaction was cooled to room temperature and the solvents removed in vacuo. The residue was diluted with water (10 mL), solid sodium bicarbonate was added until pH 8. The mixture was diluted with water. The mixture was filtered through paper and collected under suction to give the title compound 101 mg (85% yield) as a beige solid.

Example 1, Method 27: 6-({[2-(Pyridin-3-yl)-1,3-benzoxazol-5-yl]oxy}methyl)pyridin-3-ol $\delta_H$ NMR (500 MHz, DMSO) 9.33 (d, J=2.0 Hz, 1H), 8.80 (dd, J=4.8, 1.5 Hz, 1H), 8.51 (dt, J=8.0, 1.9 Hz, 1H), 8.13 (d, J=2.8 Hz, 1H), 7.73 (d, J=8.9 Hz, 1H), 7.65 (dd, J=8.0, 4.8 Hz, 1H), 7.47 (d, J=2.5 Hz, 1H), 7.40 (d, J=8.4 Hz, 1H), 7.19 (dd, J=8.4, 2.8 Hz, 1H), 7.12 (dd, J=8.9, 2.5 Hz, 1H), 5.12 (s, 2H). Tr(MET-uHPLC-AB-101)=1.91 min, (ES$^+$) (M+H)$^+$ 320.

The following example was prepared using Method 27 described above:

TABLE 28

| Ex. | Structure | Mol. Weight | IUPAC Name | LCMS data |
|---|---|---|---|---|
| 1 | 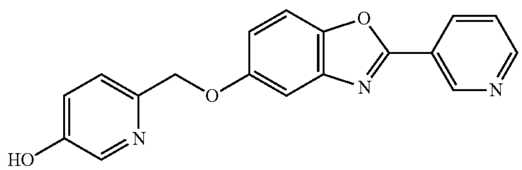 [SMILES: Oc1ccc(COc2ccc3oc(-c4cccnc4)nc3c2)nc1] | 319.31 | 6-({[2-(Pyridin-3-yl)-1,3-benzoxazol-5-yl]oxy}methyl)pyridin-3-ol | Tr(MET-uHPLC-AB-101) = 1.91 min, (ES+) (M + H)+ 320 |

Method 28

Scheme for Method 28

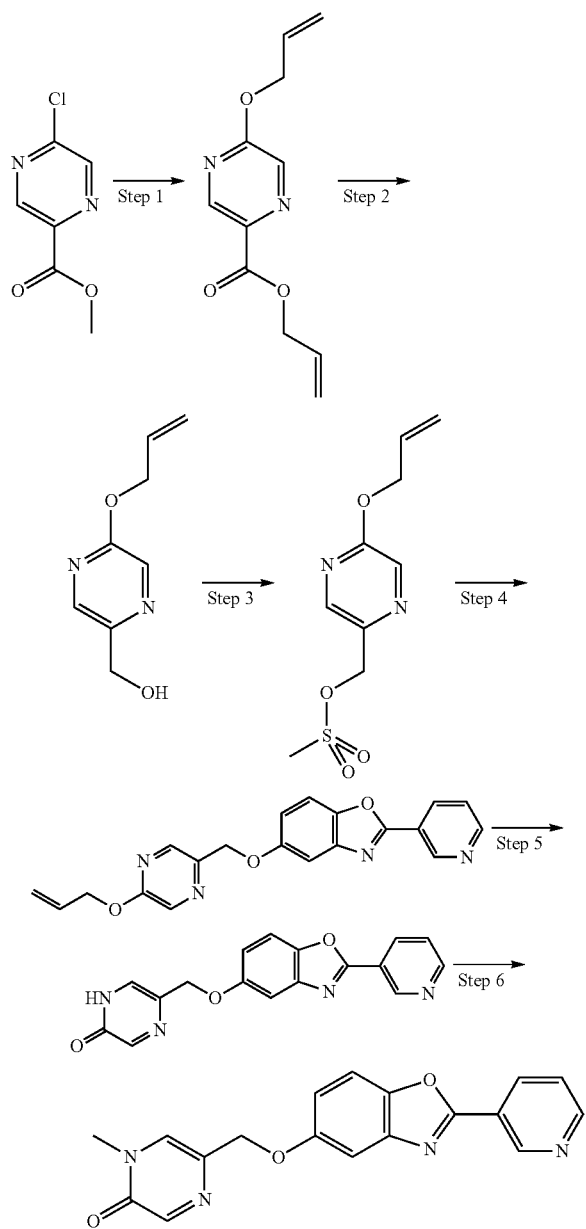

Step 1, Method 28: Prop-2-en-1-yl 5-(prop-2-en-1-yloxy)pyrazine-2-carboxylate

To sodium hydride (60% in mineral oil, 1.16 g, 29.0 mmol) in N,N-dimethylformamide (25 mL) under nitrogen, was added allyl alcohol (9.90 mL, 144.9 mmol) drop-wise and the mixture stirred at room temperature for 20 minutes. A solution of methyl 5-chloropyrazine-2-carboxylate (5 g, 29.0 mmol) in N,N-dimethylformamide (25 mL) was added and the mixture stirred at 90° C. for 20 minutes. The mixture was quenched with water (5 mL), diluted with water (200 mL) and extracted with ethyl acetate (2×200 mL). The combined organic extracts were dried over sodium sulfate, filtered and concentrated. Purification by FCC (silica, 0-30% ethyl acetate in heptane) gave the title compound 2.31 g (27% yield) as a light yellow oil. $\delta_H$ NMR (500 MHz, DMSO) 8.85 (s, 1H), 8.45 (s, 1H), 6.07 (dddd, J=25.3, 22.6, 10.7, 5.5 Hz, 2H), 5.43 (ddd, J=17.2, 9.2, 1.5 Hz, 2H), 5.34-5.25 (m, 2H), 4.94 (d, J=5.5 Hz, 2H), 4.83 (d, J=5.5 Hz, 2H). Tr(METCR1278)=1.83 min, (ES+) (M+H)+ 221.

Step 2, Method 28: [5-(Prop-2-en-1-yloxy)pyrazin-2-yl]methanol

Sodium borohydride (2.17 g, 57.4 mmol) was added to a stirred solution of prop-2-en-1-yl 5-(prop-2-en-1-yloxy)pyrazine-2-carboxylate (2.3 g, 10.4 mmol) in anhydrous tetrahydrofuran (150 mL) under nitrogen. The mixture was refluxed at 55° C. for 15 minutes then methanol (14 mL, 344.6 mmol) was added slowly. The reaction was refluxed at 65° C. for 30 minutes then quenched with water (10 mL). The mixture was diluted with water (200 mL) and extracted with ethyl acetate (2×200 mL). The combined organic extracts were dried over sodium sulfate, filtered and concentrated. Purification by FCC (silica, 20-60% ethyl acetate in heptane) gave the title compound 1.09 g (63% yield) as a colourless oil. $\delta_H$ NMR (500 MHz, DMSO) 8.25 (s, 1H), 8.19 (s, 1H), 6.07 (ddt, J=16.1, 10.6, 5.4 Hz, 1H), 5.44-5.36 (m, 2H), 5.28-5.23 (m, 1H), 4.84 (d, J=5.4 Hz, 2H), 4.54 (d, J=5.6 Hz, 2H). Tr(METCR1278)=1.23 min, (ES+) (M+H)+ 167.

Step 3, Method 28: [5-(Prop-2-en-1-yloxy)pyrazin-2-yl]methyl methanesulfonate

To a stirred suspension of [5-(prop-2-en-1-yloxy)pyrazin-2-yl]methanol (200 mg, 1.20 mmol) in dichloromethane (10 mL) under nitrogen was added triethylamine (0.18 mL, 1.32 mmol). The mixture was cooled to 0° C. and methanesulfonyl chloride (0.098 mL, 1.26 mmol) was added. The mixture was warmed to room temperature and stirred for 20 minutes. The mixture was partitioned between dichloromethane (30 mL) and water (30 mL). The organic extract was dried over sodium sulfate, filtered and concentrated to give the title compound 309 mg (quantitative yield) as a yellow oil which was used directly in the next step. Tr(METCR1278)=1.61 min, (ES⁺) (M+H)⁺ 245.

Step 4, Method 28: 5-{[5-(Prop-2-en-1-yloxy) pyrazin-2-yl]methoxy}-2-(pyridin-3-yl)-1,3-benzoxazole To [5-(prop-2-en-1-yloxy)pyrazin-2-yl]methyl methanesulfonate (291 mg, 1.19 mmol) and 2-(pyridin-3-yl)-1,3-benzoxazol-5-ol (230 mg, 1.08 mmol, prepared by Method 14) in N,N-dimethylformamide (6 mL) under nitrogen, was added sodium hydride (60% in mineral oil, 48 mg, 1.19 mmol). The mixture was stirred at room temperature overnight. The mixture was quenched with water (1 mL), diluted with water (30 mL) and extracted with ethyl acetate (2×30 mL). The combined organic extracts were dried over sodium sulfate, filtered and concentrated. Purification by FCC (silica, 0-2% methanol in dichloromethane) gave the title compound 262 mg (67% yield) as an off-white solid. Tr(MET-uHPLC-AB-101)=3.46 min, (ES⁺) (M+H)⁺ 361.

Step 5, Method 28: 5-({[2-(Pyridin-3-yl)-1,3-benzoxazol-5-yl]oxy}methyl)-1,2-dihydropyrazin-2-one A solution of 5-{[5-(prop-2-en-1-yloxy)pyrazin-2-yl]methoxy}-2-(pyridin-3-yl)-1,3-benzoxazole (250 mg, 0.69 mmol) and N,N-dimethyl barbituric acid (108 mg, 0.69 mmol) in N,N-dimethylformamide (10 mL) was degassed with a flow of nitrogen for 10 minutes. Tetrakis(triphenylphosphine)palladium(0) (16 mg, 0.014 mmol) was then added and the mixture was stirred under a nitrogen atmosphere for 1 hour. The mixture was diluted with water (20 mL) and the precipitate was filtered and dried under vacuum to give the crude product, 186 mg. 50 mg of the crude product was stirred at room temperature in dichloromethane (2 mL) for 2 hours. The solid was filtered and dried under vacuum to give the title compound 44 mg (20% yield) as an off white powder. Tr(MET-uHPLC-AB-101)=1.86 min, (ES⁺) (M+H)⁺ 321.

Step 6, Method 28: 1-Methyl-5-({[2-(pyridin-3-yl)-1,3-benzoxazol-5-yl]oxy}methyl)-1,2-dihydropyrazin-2-one To a stirred suspension of 5-({[2-(pyridin-3-yl)-1,3-benzoxazol-5-yl]oxy}methyl)-1,2-dihydropyrazin-2-one (30 mg, 0.094 mmol) and silver carbonate (65 mg, 0.23 mmol) in anhydrous toluene (2 mL) in a pressure tube was added methyl iodide (0.014 mL, 0.22 mmol). The mixture was heated at 100° C. for 2 hours, then at 140° C. for 1 hour. The mixture was diluted with ethyl acetate (10 mL), filtered through glass fibre filter GFF paper and washed with ethyl acetate (2×5 mL). The filtrate was concentrated in vacuo and purified by preparative HPLC (acetonitrile/water) to give the title compound 3.2 mg (10% yield) as an off-white solid.

Example 1, Method 28: 1-Methyl-5-({[2-(pyridin-3-yl)-1,3-benzoxazol-5-yl]oxy}methyl)-1,2-dihydropyrazin-2-one $\delta_H$ NMR (500 MHz, DMSO) 9.33 (d, J=2.0 Hz, 1H), 8.80 (dd, J=4.8, 1.6 Hz, 1H), 8.51 (dt, J=8.0, 1.9 Hz, 1H), 8.06-8.02 (m, 1H), 7.96 (s, 1H), 7.74 (d, J=8.9 Hz, 1H), 7.66 (dd, J=8.0, 4.8 Hz, 1H), 7.55 (d, J=2.5 Hz, 1H), 7.12 (dd, J=8.9, 2.5 Hz, 1H), 4.97 (s, 2H), 3.46 (s, 3H). Tr(MET-uHPLC-AB-101)=2.03 min, (ES⁺) (M+H)⁺ 335.

The following examples were prepared using Method 28 described above:

TABLE 29

| Ex. | Structure | Mol. Weight | IUPAC Name | LCMS data |
| --- | --- | --- | --- | --- |
| 1 | 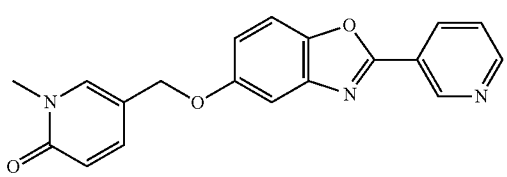 | 334.33 | 1-methyl-5-({[2-(pyridin-3-yl)-1,3-benzoxazol-5-yl]oxy}methyl)-1,2-dihydro-pyrazin-2-one | Tr(MET-uHPLC-AB-101) = 2.03 min, (ES⁺) (M + H)⁺ 335 |
| 2 | 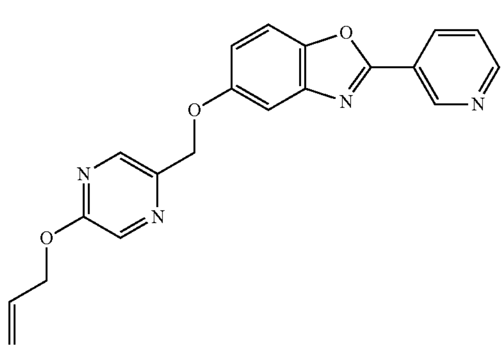 [SMILES: C=CCOc1cnc(COc2ccc3oc(-c4cccnc4)nc3c2)cn1] | 360.37 | 5-{[5-(Prop-2-en-1-yloxy)pyrazin-2-yl]methoxy}-2-(pyridin-3-yl)-1,3-benzoxazole | Tr(MET-uHPLC-AB-101) = 1.73 min, (ES⁺) (M + H)⁺ 361 |

TABLE 29-continued

| Ex. | Structure | Mol. Weight | IUPAC Name | LCMS data |
|---|---|---|---|---|
| 3 | 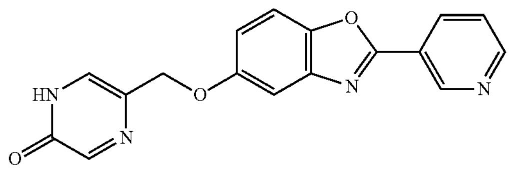 [SMILES: O=c1cnc(COc2ccc3oc(-c4cccnc4)nc3c2)c[nH]1] | 320.30 | 5-({[2-(Pyridin-3-yl)-1,3-benzoxazol-5-yl]oxy}methyl)-1,2-dihydropyrazin-2-one | Tr(MET-uHPLC-AB-101) = 1.86 min, (ES+) (M + H)+ 321 |

Method 29
Scheme for Method 29

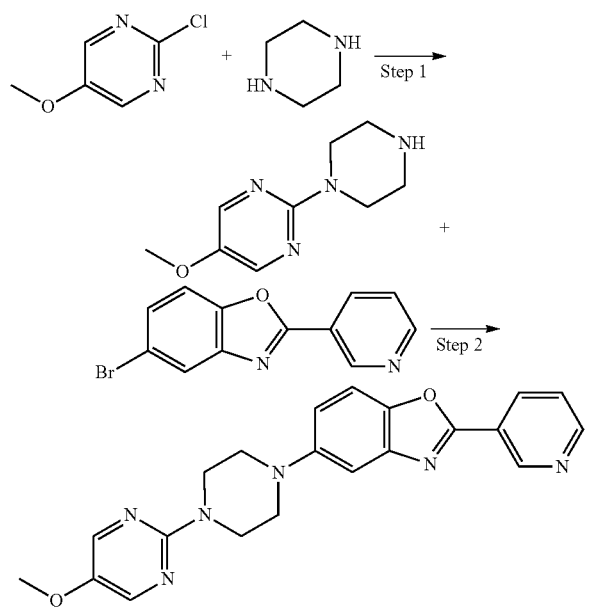

Step 1, Method 29:
5-Methoxy-2-(piperazin-1-yl)pyrimidine

Two microwave tubes were charged with 2-chloro-5-methoxypyrimidine (2×250 mg, 3.46 mmol) and piperazine (2×1.49 g, 34.6 mmol). Isopropanol (2×2.5 mL) was added to each and the reaction mixtures were stirred at 140° C. in a microwave for 1 hour. The reaction mixtures were combined, diluted with diethyl ether (50 mL), filtered, the filtrate concentrated and partitioned between water (50 mL) and diethyl ether (50 mL). The aqueous layer was extracted with diethyl ether (2×50 mL). The combined organic extracts were washed with brine (50 mL), dried over magnesium sulfate, filtered and concentrated to give the title compound 277 mg (32% yield) as a white solid. $\delta_H$ NMR (500 MHz, chloroform) 8.10 (s, 2H), 3.80 (s, 3H), 3.78-3.73 (m, 4H), 3.03-2.93 (m, 4H).

Step 2, Method 29: 5-[4-(5-Methoxypyrimidin-2-yl)piperazin-1-yl]-2-(pyridin-3-yl)-1,3-benzoxazole 5-Bromo-2-(pyridin-3-yl)-1,3-benzoxazole (200 mg, 0.73 mmol), 5-methoxy-2-(piperazin-1-yl)pyrimidine (180 mg, 0.87 mmol), sodium tert-butoxide (84 mg, 0.87 mmol) and tetrahydrofuran (5 mL) were degassed with nitrogen for 20 minutes. Palladium(II) acetate (8 mg, 0.04 mmol) and [2',6'-bis(propan-2-yloxy)biphenyl-2-yl](dicyclohexyl)phosphane (17 mg, 0.04 mmol) were added and the reaction mixture was stirred at 70° C. for 20 hours. The reaction mixture was cooled to room temperature and partitioned between ethyl acetate (20 mL) and water (20 mL). The aqueous layer was extracted with ethyl acetate (2×20 mL). The combined organic extracts were washed with brine (20 mL), dried over magnesium sulfate, filtered and concentrated. Purification by FCC (silica, 25-100% ethyl acetate in heptane) and trituration with diethyl ether (5 mL) gave the title compound 43 mg (15% yield) as a pale yellow solid.

Example 1, Method 29: 5-[4-(5-Methoxypyrimidin-2-yl)piperazin-1-yl]-2-(pyridin-3-yl)-1,3-benzoxazole $\delta_H$ NMR (500 MHz, DMSO) 9.32 (d, J=2.1 Hz, 1H), 8.79 (dd, J=4.8, 1.5 Hz, 1H), 8.50 (dt, J=8.0, 1.9 Hz, 1H), 8.25 (s, 2H), 7.69 (d, J=9.0 Hz, 1H), 7.65 (dd, J=8.0, 4.8 Hz, 1H), 7.38 (d, J=2.3 Hz, 1H), 7.22 (dd, J=9.0, 2.4 Hz, 1H), 3.86-3.80 (m, 4H), 3.79 (s, 3H), 3.27-3.21 (m, 4H). Tr(MET-uHPLC-AB-101)=3.13 min, (ES+) (M+H)+ 389.

The following example was prepared using Method 29 described above:

TABLE 30

| Ex. | Structure | Mol. Weight | IUPAC Name | LCMS data |
|---|---|---|---|---|
| 1 | 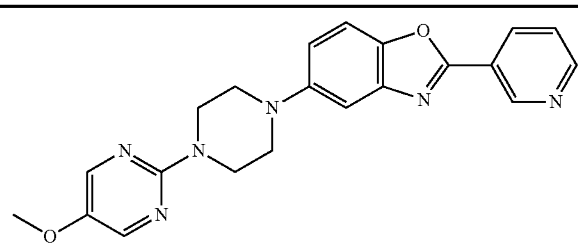 | 388.42 | 5-[4-(5-Methoxypyrimidin-2-yl)piperazin-1-yl]-2-(pyridin-3-yl)-1,3-benzoxazole | Tr(MET-uHPLC-AB-101) = 3.13 min, (ES+) (M + H)+ 389 |

Method 30
Scheme for Method 30

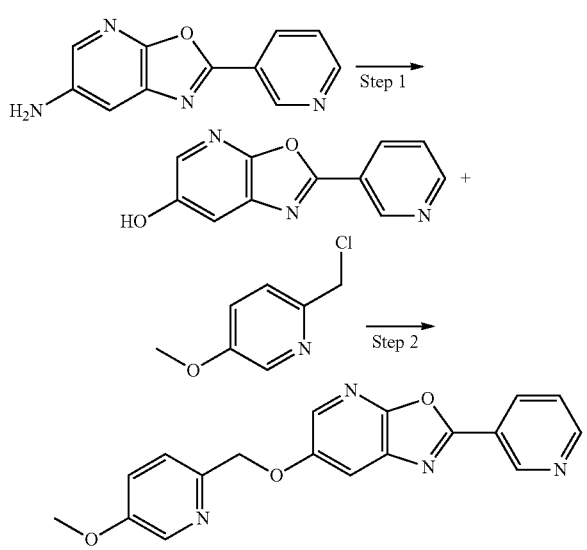

Step 1, Method 30: 2-(Pyridin-3-yl)-[1,3]oxazolo[5,4-b]pyridin-6-ol 2-(Pyridin-3-yl)-[1,3]oxazolo[5,4-b]pyridin-6-amine (960 mg, 4.52 mmol, prepared by Method 19) was added portion-wise to a stirred solution of sulphuric acid (4.82 mL, 90.5 mmol) in water (15 mL) at room temperature. The solution was cooled to 0-5° C. and a solution of sodium nitrite (343 mg, 4.98 mmol) in water (10 mL) was added drop-wise. The mixture was stirred for 10 minutes at 0-5° C. A solution of copper(II) nitrate trihydrate (55.1 g, 226.2 mmol) in water (100 mL) was added, followed by copper(I) oxide (647 mg, 4.52 mmol). The mixture was shaken vigorously for 10 minutes. The mixture was basified using saturated sodium bicarbonate until pH 8-9. 33% Aqueous ammonia (20 mL) was added and the aqueous solution was extracted with ethyl acetate (2×500 mL). The combined organic extracts were dried over sodium sulfate, filtered and concentrated. Trituration in dichloromethane (10 mL) gave the title compound 390 mg (40% yield) as a yellow solid. $\delta_H$ NMR (500 MHz, DMSO) 9.34 (s, 1H), 8.82 (d, J=4.6 Hz, 1H), 8.53 (dt, J=7.9, 1.9 Hz, 1H), 7.96 (d, J=2.5 Hz, 1H), 7.66 (dd, J=7.7, 4.7 Hz, 1H), 7.62 (d, J=2.5 Hz, 1H). Tr(METCR1278)=1.25 min, (ES$^+$) (M+H)$^+$ 214.

Step 2, Method 30: 3-{6-[(5-Methoxypyridin-2-yl)methoxy]-[1,3]oxazolo[5,4-b]pyridin-2-yl}pyridine To a solution of 2-(pyridin-3-yl)-[1,3]oxazolo[5,4-b]pyridin-6-ol (50 mg, 0.24 mmol) and 2-(chloromethyl)-5-methoxypyridine hydrochloride (46 mg, 0.24 mmol) in N,N-dimethylformamide (2 mL) under nitrogen, was added sodium hydride (60% in mineral oil, 21 mg, 0.52 mmol) and the mixture was stirred at room temperature overnight. The mixture was quenched with water (1 mL), diluted with water (15 mL) and extracted with ethyl acetate (2×15 mL). The combined organic extracts were dried over sodium sulfate, filtered and concentrated. Purification by FCC (silica, 0-3% methanol in dichloromethane) followed by preparative HPLC (acetonitrile/water) gave the title compound 29.3 mg (37% yield) as an off-white powder.

Example 1, Method 30: 3-{6-[(5-Methoxypyridin-2-yl)methoxy]-[1,3]oxazolo[5,4-b]pyridin-2-yl}pyridine $\delta_H$ NMR (500 MHz, DMSO) 9.35 (d, J=2.1 Hz, 1H), 8.83 (dd, J=4.8, 1.5 Hz, 1H), 8.55 (dt, J=8.0, 1.9 Hz, 1H), 8.31 (d, J=2.9 Hz, 1H), 8.22 (d, J=2.7 Hz, 1H), 8.08 (d, J=2.7 Hz, 1H), 7.67 (dd, J=8.0, 4.8 Hz, 1H), 7.57 (d, J=8.6 Hz, 1H), 7.45 (dd, J=8.6, 3.0 Hz, 1H), 5.27 (s, 2H), 3.84 (s, 3H). Tr(MET-uHPLC-AB-101)=2.36 min, (ES$^+$) (M+H)$^+$ 335.

The following example was prepared using Method 30 described above:

TABLE 31

| Ex. | Structure | Mol. Weight | IUPAC Name | LCMS data |
|---|---|---|---|---|
| 1 | 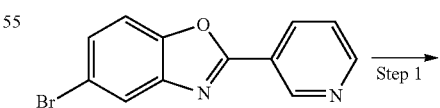 | 334.33 | 3-{6-[(5-methoxypyridin-2-yl)methoxy]-[1,3]oxazolo[5,4-b]pyridin-2-yl}pyridine | Tr(MET-uHPLC-AB-101) = 2.36 min, (ES$^+$) (M + H)$^+$ 335 |

Method 31
Scheme for Method 31

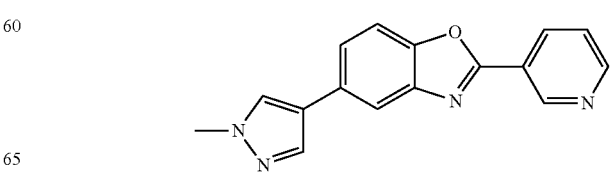

Step 1, Method 31: 5-(1-Methyl-1H-pyrazol-4-yl)-2-(pyridin-3-yl)-1,3-benzoxazole 5-Bromo-2-(pyridin-3-yl)-1,3-benzoxazole (300 mg, 1.09 mmol), 1-methyl-4-(4,4,5,5-tetramethyl-1,3,2-dioxaborolan-2-yl)-1H-pyrazole (250 mg, 1.2 mmol) and 2 M sodium carbonate (1 mL) were suspended in anhydrous N,N-dimethylformamide (10 mL) and sonicated under a flow of nitrogen for 5 minutes. Tetrakis(triphenylphosphine)palladium(0) (63 mg, 0.05 mmol) was added and the reaction mixture was heated to 80° C. for 16 hours. The reaction mixture was cooled to room temperature and the solvents were removed in vacuo. The residue was partitioned between ethyl acetate (50 mL) and water (30 mL) and the phases separated. The aqueous was extracted with ethyl acetate (2×30 mL), the combined organics were washed with brine solution (5 mL), dried over sodium sulfate, filtered and concentrated. Purification by FCC (silica, 0-60% ethyl acetate in heptane) gave the title compound, 160 mg (53% yield) as a white solid.

Example 1, Method 31: 5-(1-Methyl-1H-pyrazol-4-yl)-2-(pyridin-3-yl)-1,3-benzoxazole $\delta_H$ NMR (500 MHz, DMSO) 9.36 (d, J=2.1 Hz, 1H), 8.81 (dd, J=4.8, 1.5 Hz, 1H), 8.54 (dt, J=8.0, 1.9 Hz, 1H), 8.22 (s, 1H), 8.04 (d, J=1.5 Hz, 1H), 7.96 (s, 1H), 7.80 (d, J=8.5 Hz, 1H), 7.74-7.56 (m, 2H), 3.88 (s, 3H). Tr(MET-uHPLC-AB-101)=2.39 min, (ES$^+$) (M+H)$^+$ 277.

The following example was prepared using Method 31 described above:

TABLE 32

| Ex. | Structure | Mol. Weight | IUPAC Name | LCMS data |
|---|---|---|---|---|
| 1 | 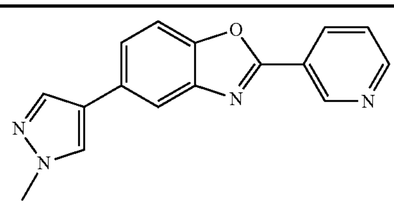 | 276.29 | 5-(1-Methyl-1H-pyrazol-4-yl)-2-(pyridin-3-yl)-1,3-benzoxazole | Tr(MET-uHPLC-AB-101) = 2.39 min, (ES$^+$) (M + H)$^+$ 277 |

Method 32
Scheme for Method 32

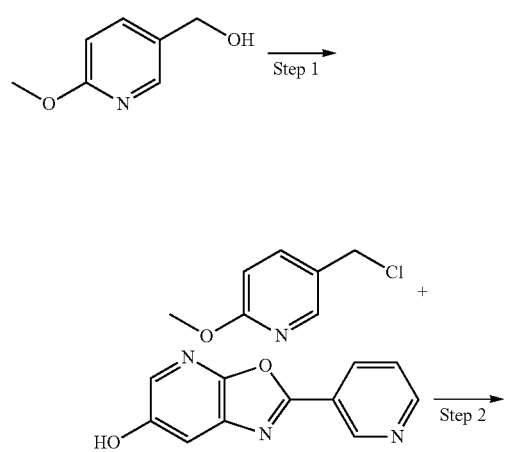

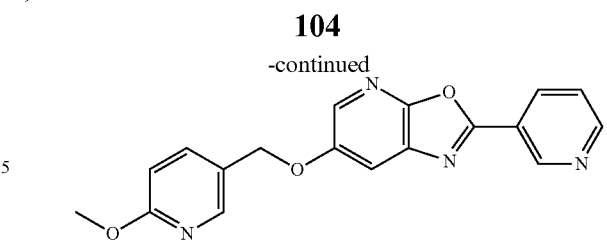

Step 1, Method 32: 5-(Chloromethyl)-2-methoxypyridine

To a stirred solution of (6-methoxypyridin-3-yl)methanol (75 mg, 0.54 mmol) in dichloromethane (2 mL) under nitrogen was added triethylamine (0.083 mL, 0.59 mmol) followed by methanesulfonyl chloride (0.044 mL, 0.57 mmol). The mixture was stirred at room temperature for 1 hour. The mixture was partitioned between dichloromethane (10 mL) and water (10 mL). The organic extract was dried over sodium sulfate, filtered and concentrated to give the title compound 88 mg (quantitative yield) as a yellow oil. Tr(METCR1278)=1.63 min, (ES$^+$) (M+H)$^+$ 158/160.

Step 2, Method 32: 3-{6-[(6-Methoxypyridin-3-yl)methoxy]-[1,3]oxazolo[5,4-b]pyridin-2-yl}pyridine To a solution of 2-(pyridin-3-yl)-[1,3]oxazolo[5,4-b]pyridin-6-ol (90 mg, 0.42 mmol, prepared by Method 30) and 5-(chloromethyl)-2-methoxypyridine (73 mg, 0.46 mmol) in N,N-dimethylformamide (4 mL) under nitrogen, was added sodium hydride (60% in mineral oil, 19 mg, 0.46 mmol) and the mixture was stirred at room temperature overnight. The mixture was quenched with water (1 mL), diluted with water (30 mL) and extracted with ethyl acetate (2×30 mL). The combined organic extracts were dried over sodium sulfate, filtered and concentrated. Purification by FCC (silica, 0-3% methanol in dichloromethane) and recrystallization from DMSO:acetonitrile (1:1, 10 mL) gave the title compound 25.2 mg (18% yield) as an off-white powder.

Example 1, Method 32: 3-{6-[(6-Methoxypyridin-3-yl)methoxy]-[1,3]oxazolo[5,4-b]pyridin-2-yl}pyridine $\delta_H$ NMR (500 MHz, DMSO) 9.35 (d, J=2.0 Hz, 1H), 8.83 (dd, J=4.8, 1.6 Hz, 1H), 8.55 (dt, J=8.0, 1.9 Hz, 1H), 8.32 (d, J=2.2 Hz, 1H), 8.19 (d, J=2.7 Hz, 1H), 8.10 (d, J=2.7 Hz, 1H), 7.86 (dd, J=8.5, 2.4 Hz, 1H), 7.67 (dd, J=8.0, 4.8 Hz, 1H), 6.87 (d, J=8.5 Hz, 1H), 5.22 (s, 2H), 3.86 (s, 3H). Tr(MET-uHPLC-AB-101)=2.78 min, (ES$^+$) (M+H)$^+$ 335.

The following example was prepared using Method 32 described above:

TABLE 33

| Ex. | Structure | Mol. Weight | IUPAC Name | LCMS data |
|---|---|---|---|---|
| 1 | 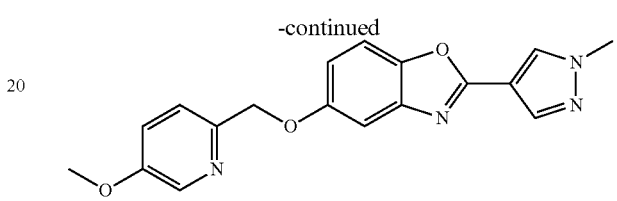 | 334.33 | 3-{6-[(6-methoxypyridin-3-yl)methoxy]-[1,3]oxazolo[5,4-b]pyridin-2-yl}pyridine | Tr(MET-uHPLC-AB-101) = 2.78 min, (ES⁺) (M + H)⁺ 335 |

Method 33
Scheme for Method 33

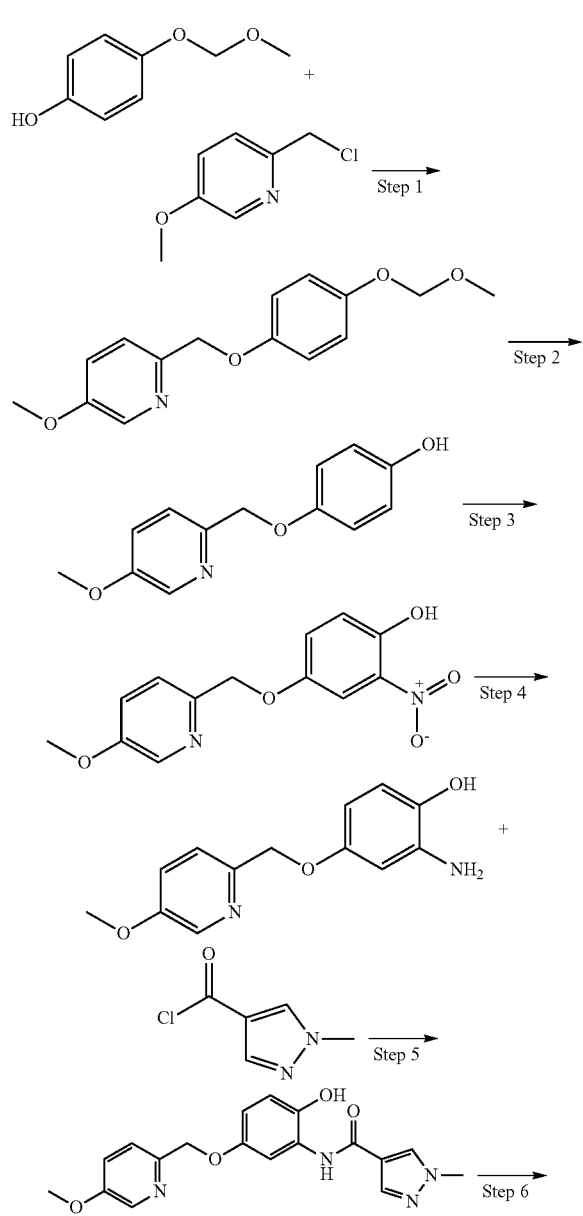

Step 1, Method 33: 5-Methoxy-2-[4-(methoxymethoxy)phenoxymethyl]pyridine

To a stirred solution of 4-(methoxymethoxy)phenol (1.1 g, 7.13 mmol, described in Journal of Organic Chemistry, 71(22), 2006, 8614) and 2-(chloromethyl)-5-methoxypyridine hydrochloride (1.39 g, 7.13 mmol) in N,N-dimethylformamide (40 mL) under nitrogen, was added sodium hydride (60% in mineral oil, 599 mg, 15.0 mmol) and the mixture stirred at room temperature for 16 hours. The mixture was then quenched with water (4 mL), diluted with water (150 mL) and extracted with ethyl acetate (2×150 mL). The combined organic extracts were dried over sodium sulfate, filtered and concentrated to give the title compound 2.2 g (quantitative yield) as a light brown oil. $\delta_H$ NMR (500 MHz, DMSO) 8.27 (d, J=2.8 Hz, 1H), 7.53-7.34 (m, 2H), 6.94 (s, 4H), 5.09 (s, 2H), 5.04 (s, 2H), 3.83 (s, 3H), 3.35 (s, 3H). Tr(METCR1278)=1.71 min, (ES⁺) (M+H)⁺ 276.

Step 2, Method 33: 4-[(5-Methoxypyridin-2-yl]methoxyphenol

To a solution of 5-methoxy-2-[4-(methoxymethoxy)phenoxymethyl]pyridine (1.96 g, 7.12 mmol) in tetrahydrofuran (100 mL) was added aqueous 3 M hydrochloric acid (23.4 mL) and the mixture was stirred at room temperature overnight. The mixture was then stirred at 40° C. for 5 hours. The mixture was diluted with saturated aqueous sodium bicarbonate (200 mL) and extracted with ethyl acetate (2×250 mL). The combined organic extracts were dried over sodium sulfate, filtered and concentrated to give the title compound 1.46 g (87% yield) as a light pink powder. $\delta_H$ NMR (500 MHz, DMSO) 8.92 (s, 1H), 8.26 (d, J=2.7 Hz, 1H), 7.47-7.37 (m, 2H), 6.86-6.78 (m, 2H), 6.69-6.62 (m, 2H), 4.98 (s, 2H), 3.83 (s, 3H). Tr(METCR1278)=1.32 min, (ES⁺) (M+H)⁺ 232.

Step 3, Method 33: 4-[(5-Methoxypyridin-2-yl)methoxy]-2-nitrophenol

To a stirred suspension of 4-[(5-methoxypyridin-2-yl)methoxy]phenol (1.46 g, 6.31 mmol) in 1,2-dimethoxyethane (30 mL) and sulpholane (15 mL) at −50° C. under nitrogen was added a suspension of nitronium tetrafluoroborate (845 mg, 6.31 mmol). The mixture was stirred for 30 minutes at −50° C., then slowly warmed to room temperature. The mixture was concentrated in vacuo and the residue was purified by FCC (silica, 20-50% ethyl acetate in heptane then 10% methanol in dichloromethane) to give the title compound 659 mg (33% yield) as a yellow powder. $\delta_H$ NMR (500 MHz, DMSO) 10.49 (s, 1H), 8.28 (d, J=2.8 Hz, 1H), 7.51 (d, J=3.1 Hz, 1H), 7.48 (d, J=8.6 Hz, 1H), 7.42 (dd, J=8.6, 2.9 Hz, 1H), 7.28 (dd, J=9.1, 3.1 Hz, 1H), 7.07 (d, J=9.1 Hz, 1H), 5.09 (s, 2H), 3.83 (s, 3H). Tr(METCR1278)=1.75 min, (ES$^+$) (M+H)$^+$ 277.

Step 4, Method 33: 2-Amino-4-[(5-methoxypyridin-2-yl)methoxy]phenol

To 4-[(5-methoxypyridin-2-yl)methoxy]-2-nitrophenol (460 mg, 1.66 mmol) and sodium dithionite (1.16 g, 6.66 mmol), was added ethanol (25 mL) and water (25 mL) and the mixture was stirred at 75° C. for 2.5 hours. The mixture was then treated with sodium dithionite (0.58 g, 3.33 mmol) and the mixture was stirred at 75° C. for 30 minutes. The mixture was diluted with water (150 mL) and extracted with ethyl acetate (2×150 mL). The combined organic extracts were dried over sodium sulfate, filtered and concentrated to give the title compound 292 mg (71% yield) as a light brown solid. $\delta_H$ NMR (500 MHz, DMSO) 8.49 (s, 1H), 8.25 (t, J=1.8 Hz, 1H), 7.40 (d, J=1.8 Hz, 2H), 6.50 (d, J=8.5 Hz, 1H), 6.27 (d, J=2.9 Hz, 1H), 6.02 (dd, J=8.5, 2.9 Hz, 1H), 4.91 (s, 2H), 4.55 (s, 2H), 3.82 (s, 3H). Tr(METCR1278)=1.23 min, (ES$^+$) (M+H)$^+$ 247.

Step 5, Method 33: N-{2-Hydroxy-5-[(5-methoxypyridin-2-yl)methoxy]phenyl}-1-methyl-1H-pyrazole-4-carboxamide To a stirred solution of 2-amino-4-[(5-methoxypyridin-2-yl)methoxy]phenol (95 mg, 0.39 mmol) and diisopropylethylamine (0.077 mL, 0.46 mmol) in tetrahydrofuran (2 mL) under nitrogen, was added 1-methyl-1H-pyrazole-4-carbonyl chloride (60 mg, 0.46 mmol) in one portion. The mixture was stirred at room temperature for 30 minutes. The mixture was diluted with water (15 mL) and extracted with ethyl acetate (2×15 mL). The combined organic extracts were dried over sodium sulfate, filtered and concentrated to give the title compound 131 mg (96% yield) as a light brown solid. Tr(METCR1278)=1.36 min, (ES$^+$) (M+H)$^+$ 355.

Step 6, Method 33: 5-[(5-Methoxypyridin-2-yl)methoxy]-2-(1-methyl-1H-pyrazol-4-yl)-1,3-benzoxazole N-{2-Hydroxy-5-[(5-methoxypyridin-2-yl)methoxy]phenyl}-1-methyl-1H-pyrazole-4-carboxamide (65 mg, 0.18 mmol) and acetic acid (1 mL) were heated at 200° C. for 30 minutes in a microwave. The mixture was concentrated in vacuo and the residue was diluted with saturated aqueous sodium bicarbonate solution (20 mL) and extracted with ethyl acetate (2×20 mL). The combined organic extracts were dried over sodium sulfate, filtered and concentrated. Purification by FCC (silica, 20-80% ethyl acetate in heptane) and preparative HPLC (acetonitrile/water) gave the title compound 36 mg (58% yield) as a white solid.

Example 1, Method 33: 5-[(5-Methoxypyridin-2-yl)methoxy]-2-(1-methyl-1H-pyrazol-4-yl)-1,3-benzoxazole $\delta_H$ NMR (500 MHz, DMSO) 8.52 (s, 1H), 8.30 (d, J=2.9 Hz, 1H), 8.08 (s, 1H), 7.59 (d, J=8.8 Hz, 1H), 7.51 (d, J=8.6 Hz, 1H), 7.43 (dd, J=8.6, 3.0 Hz, 1H), 7.33 (d, J=2.5 Hz, 1H), 7.01 (dd, J=8.8, 2.5 Hz, 1H), 5.15 (s, 2H), 3.95 (s, 3H), 3.84 (s, 3H). Tr(MET-uHPLC-AB-101)=2.46 min, (ES$^+$) (M+H)$^+$ 337.

The following examples were prepared using Method 33 described above:

TABLE 34

| Ex. | Structure | Mol. Weight | IUPAC Name | LCMS data |
|---|---|---|---|---|
| 1 | 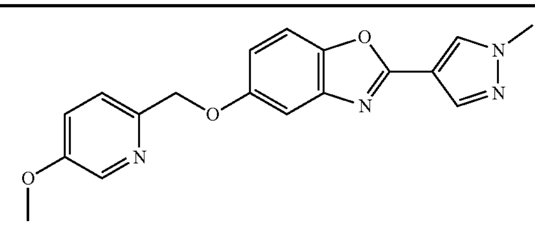 | 336.34 | 5-[(5-Methoxypyridin-2-yl)methoxy]-2-(1-methyl-1H-pyrazol-4-yl)-1,3-benzoxazole | Tr(MET-uHPLC-AB-101) = 2.46 min, (ES$^+$) (M + H)$^+$ 337 |
| 2 | 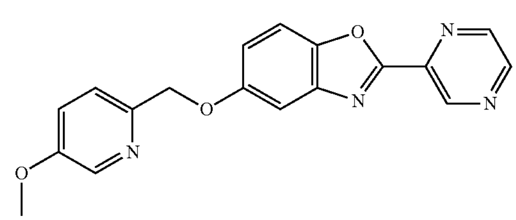 [SMILES: COc1ccc(COc2ccc3oc(-c4cnccn4)nc3c2)nc1] | 334.33 | 5-[(5-Methoxypyridin-2-yl)methoxy]-2-(pyrazin-2-yl)-1,3-benzoxazole | Tr(MET-uHPLC-AB-101) = 2.42 min, (ES$^+$) (M + H)$^+$ 335 |

TABLE 34-continued

| Ex. | Structure | Mol. Weight | IUPAC Name | LCMS data |
|---|---|---|---|---|
| 3 | 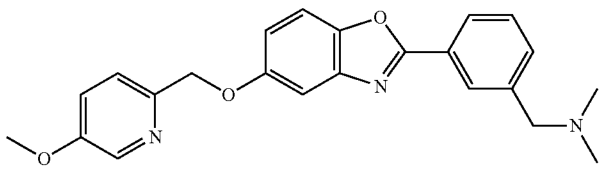 | 389.45 | [(3-{5-[(5-Methoxypyridin-2-yl)methoxy]-1,3-benzoxazol-2-yl}phenyl)methyl]dimethylamine | Tr(MET-uHPLC-AB-101) = 1.86 min, (ES⁺) (M + H)⁺ 390 |

Method 34
Scheme for Method 34

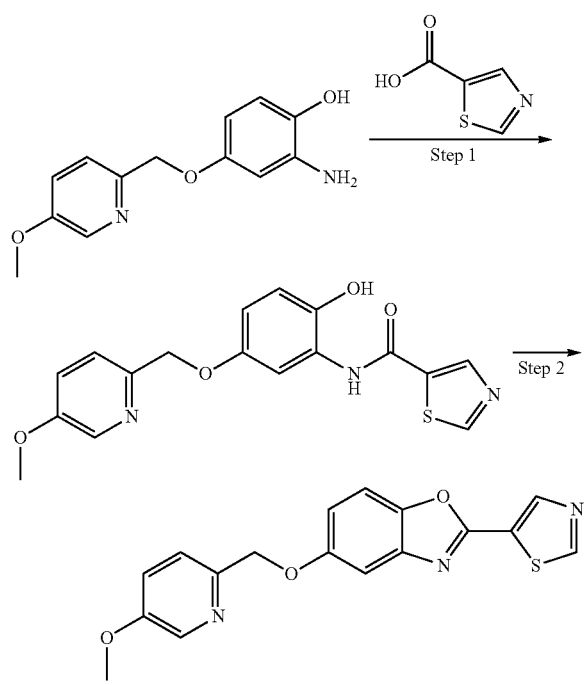

Step 1, Method 34: N-{2-Hydroxy-5-[(5-methoxypyridin-2-yl)methoxy]phenyl}-1,3-thiazole-5-carboxamide A stirred solution of 2-amino-4-[(5-methoxypyridin-2-yl)methoxy]phenol (150 mg, 50% purity, 0.30 mmol, prepared by Method 33), 1,3-thiazole-5-carboxylic acid (43 mg, 0.33 mmol) and ethylcarbodiimide hydrochloride (76 mg, 0.40 mmol) in pyridine (1 mL) under nitrogen was stirred at room temperature for 16 hours. The mixture was diluted with water (10 mL) and extracted with ethyl acetate (2×10 mL). The combined organic extracts were dried over sodium sulfate, filtered and concentrated to give the crude title compound 220 mg as a brown solid which was used without further purification. Tr(METCR1278)=1.44 min, (ES⁺) (M+H)⁺ 358.

Step 2, Method 34: 5-[(5-Methoxypyridin-2-yl)methoxy]-2-(1,3-thiazol-5-yl)-1,3-benzoxazole N-{2-Hydroxy-5-[(5-methoxypyridin-2-yl)methoxy]phenyl}-1,3-thiazole-5-carboxamide (109 mg, 0.30 mmol) and acetic acid (2 mL) were heated at 200° C. for 40 minutes in a microwave. The mixture was concentrated and the residue diluted with saturated aqueous sodium bicarbonate solution (10 mL) and extracted with ethyl acetate (2×10 mL). The combined organic extracts were dried over sodium sulfate, filtered and concentrated. Purification by FCC (silica, 25-80% ethyl acetate in heptane) and preparative HPLC (acetonitrile/water) gave the title compound 32 mg (31% yield) as a white powder.

Example 1, Method 34: 5-[(5-Methoxypyridin-2-yl)methoxy]-2-(1,3-thiazol-5-yl)-1,3-benzoxazole $\delta_H$ NMR (500 MHz, DMSO) 9.39 (s, 1H), 8.70 (s, 1H), 8.30 (d, J=2.9 Hz, 1H), 7.70 (d, J=8.9 Hz, 1H), 7.52 (d, J=8.6 Hz, 1H), 7.46-7.40 (m, 2H), 7.12 (dd, J=8.9, 2.6 Hz, 1H), 5.17 (s, 2H), 3.84 (s, 3H). Tr(MET-uHPLC-AB-101)=2.71 min, (ES⁺) (M+H)⁺ 340.

The following examples were prepared using Method 34 described above:

TABLE 35

| Ex. | Structure | Mol. Weight | IUPAC Name | LCMS data |
|---|---|---|---|---|
| 1 | 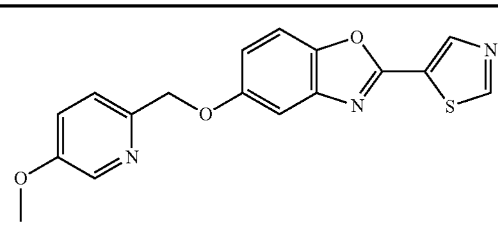 | 339.37 | 5-[(5-Methoxypyridin-2-yl)methoxy]-2-(1,3-thiazol-5-yl)-1,3-benzoxazole | Tr(MET-uHPLC-AB-101) = 2.71 min, (ES⁺) (M + H)⁺ 340 |

TABLE 35-continued

| Ex. | Structure | Mol. Weight | IUPAC Name | LCMS data |
|---|---|---|---|---|
| 2 | 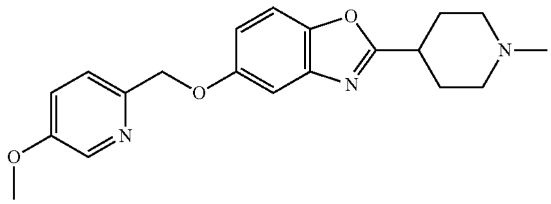 [SMILES: COc1ccc(COc2ccc3oc(C4CCN(C)CC4)nc3c2)nc1] | 353.41 | 5-[(5-Methoxypyridin-2-yl)methoxy]-2-(1-methylpiperidin-4-yl)-1,3-benzoxazole | Tr(MET-uHPLC-AB-101) = 1.44 min, (ES⁺) (M + H)⁺ 354 |
| 3 | 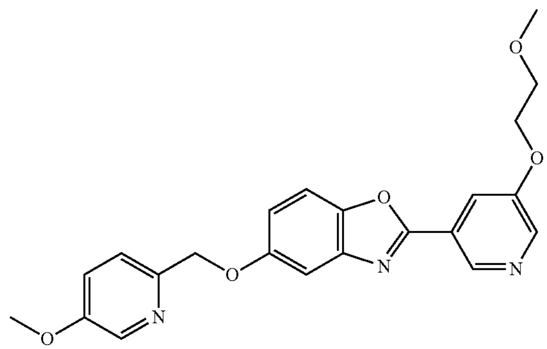 | 407.42 | 2-[5-(2-Methoxyethoxy)pyridin-3-yl]-5-[(5-methoxypyridin-2-yl)methoxy]-1,3-benzoxazole | Tr(MET-uHPLC-AB-101) = 2.85 min, (ES⁺) (M + H)⁺ 408 |
| 4 | 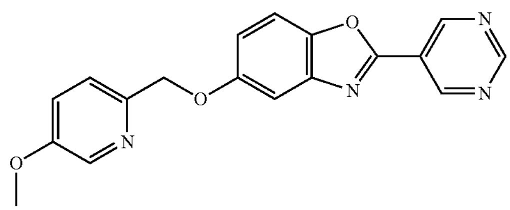 [SMILES: COc1ccc(COc2ccc3oc(-c4cncnc4)nc3c2)nc1] | 334.34 | 5-[(5-Methoxypyridin-2-yl)methoxy]-2-(pyrimidin-5-yl)-1,3-benzoxazole | Tr(MET-uHPLC-AB-101) = 2.46 min, (ES⁺) (M + H)⁺ 335 |
| 5 | 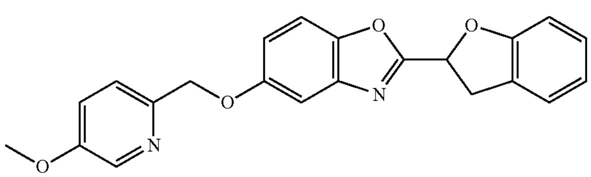 [SMILES: COc1ccc(COc2ccc3oc(C4Cc5ccccc5O4)nc3c2)nc1] | 374.40 | 2-(2,3-Dihydro-1-benzofuran-2-yl)-5-[(5-methoxypyridin-2-yl)methoxy]-1,3-benzoxazole | Tr(MET-uHPLC-AB-101) = 3.5 min, (ES⁺) (M + H)⁺ 375 |
| 6 | 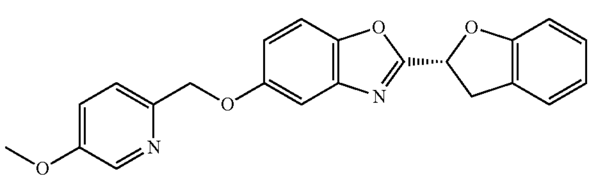 [SMILES: COc1ccc(COc2ccc3oc([C@H]4Cc5ccccc5O4)nc3c2)nc1] | 374.40 | 2-[(2R)-2,3-Dihydro-1-benzofuran-2-yl]-5-[(5-methoxypyridin-2-yl)methoxy]-1,3-benzoxazole | Tr(MET-uHPLC-AB-101) = 3.54 min, (ES⁺) (M + H)⁺ 375 |
| 7 | 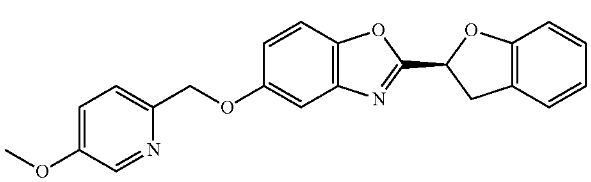 [SMILES: COc1ccc(COc2ccc3oc([C@@H]4Cc5ccccc5O4)nc3c2)nc1] | 374.40 | 2-[(2S)-2,3-Dihydro-1-benzofuran-2-yl]-5-[(5-methoxypyridin-2-yl)methoxy]-1,3-benzoxazole | Tr(MET-uHPLC-AB-101) = 3.55 min, (ES⁺) (M + H)⁺ 375 |
| 8 | 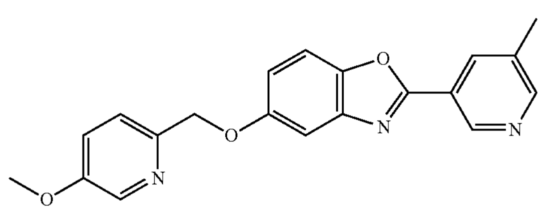 | 347.37 | 5-[(5-Methoxypyridin-2-yl)methoxy]-2-(5-methylpyridin-3-yl)-1,3-benzoxazole | Tr(MET-uHPLC-AB-101) = 2.89 min, (ES⁺) (M + H)⁺ 348 |

TABLE 35-continued

| Ex. | Structure | Mol. Weight | IUPAC Name | LCMS data |
|---|---|---|---|---|
| 9 | 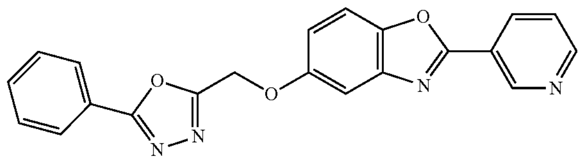 [SMILES: c1ccc(-c2nnc(COc3ccc4oc(-c5cccnc5)nc4c3)o2)cc1] | 383.37 | 5-Phenyl-N-[2-(pyridin-3-yl)-1,3-benzoxazol-5-yl]-1,3,4-oxadiazole-2-carboxamide | Tr(MET-uHPLC-AB-101) = 3.04 min, (ES+) (M + H)+ 384 |
| 10 | 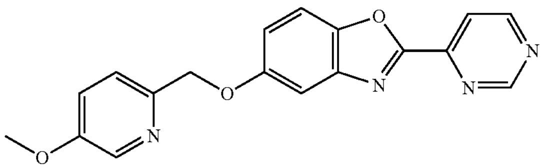 [SMILES: COc1ccc(COc2ccc3oc(-c4ccncn4)nc3c2)nc1] | 334.34 | 5-[(5-Methoxypyridin-2-yl)methoxy]-2-(pyrimidin-4-yl)-1,3-benzoxazole | Tr(MET-uHPLC-AB-101) = 2.37 min, (ES+) (M + H)+ 335 |

Method 35

Scheme for Method 35

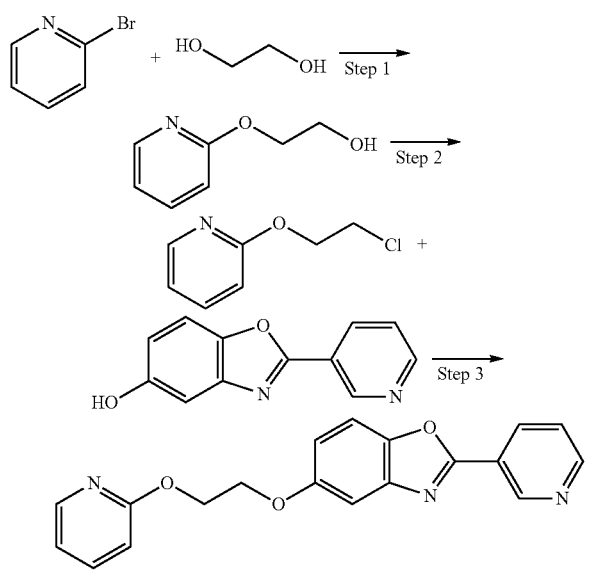

Step 1, Method 35: 2-(Pyridin-2-yloxy)ethan-1-ol

A mixture of sodium hydride (60% in mineral oil, 139 mg, 3.48 mmol) and 2-bromopyridine (500 mg, 3.16 mmol) was dissolved in N,N-dimethylformamide (5 mL). Ethane-1,2-diol (2.12 mL, 37.98 mmol) was added drop-wise and the mixture heated at 130° C. overnight. The mixture was cooled to room temperature, water (20 mL) added and the mixture extracted with ethyl acetate (3×10 mL). The combined organic layers were washed with water (2×10 mL), dried over sodium sulfate, filtered and concentrated. Purification by FCC (silica, 2-40% ethyl acetate in heptane) gave the title compound 135 mg (31% yield) as a colorless oil. $^5$H NMR (500 MHz, chloroform) 8.23-8.06 (m, 1H), 7.61 (ddd, J=9.0, 7.1, 2.0 Hz, 1H), 6.91 (ddd, J=7.0, 5.1, 0.8 Hz, 1H), 6.81 (d, J=8.4 Hz, 1H), 4.53-4.41 (m, 2H), 4.02-3.90 (m, 2H), 3.81 (br. s, 1H). Tr(METCR1278)=0.59 min, (ES+) (M+H)+ 140.

Step 2, Method 35: 2-(2-Chloroethoxy)pyridine

To a stirred solution of 2-(pyridin-2-yloxy)ethan-1-ol (56 mg, 0.4 mmol) in dichloromethane (2 mL) under nitrogen at 0° C. was added triethylamine (0.06 mL, 0.44 mmol) followed by methanesulfonyl chloride (0.03 mL, 0.42 mmol). The mixture was stirred at room temperature for 2 hours. The mixture was cooled to 0° C., triethylamine (0.06 mL, 0.44 mmol) and methanesulfonyl chloride (0.03 mL, 0.42 mmol) were added and the mixture was stirred at room temperature for 4 hours. The mixture was partitioned between dichloromethane (10 mL) and water (10 mL). The organic extract was dried over sodium sulfate, filtered and concentrated to give the crude title compound 58 mg (91% yield) as a yellow oil, which was used directly in the next step.

Step 3, Method 35: 5-[2-(Pyridin-2-yloxy)ethoxy]-2-(pyridin-3-yl)-1,3-benzoxazole To sodium hydride (60% in mineral oil, 12 mg, 0.3 mmol) under nitrogen was added a solution of 2-(pyridin-3-yl)-1,3-benzoxazol-5-ol (57 mg, 0.27 mmol, prepared by Method 14) in N,N-dimethylformamide (1 mL) and the mixture was stirred at room temperature for 30 minutes. A solution of 2-(2-chloroethoxy)pyridine (57 mg, 0.36 mmol) in N,N-dimethylformamide (0.5 mL) was added and the mixture was stirred at room temperature overnight. The mixture was heated to 60° C. for 3 hours, cooled to room temperature, sodium hydride (60% in mineral oil, 12 mg, 0.3 mmol) was added and the mixture stirred at room temperature overnight. The mixture was quenched with water (3 mL), extracted with ethyl acetate (3×5 mL), the combined organic layers washed with water (2×5 mL), dried over sodium sulfate, filtered and concentrated. Purification by FCC (silica, 1-10% methanol in dichloromethane) and recrystallisation from tert-butyl methyl ether:ethyl acetate (9:1, 10 mL) gave the title compound 15 mg (17% yield) as white crystals.

Example 1, Method 35: 5-[2-(Pyridin-2-yloxy)ethoxy]-2-(pyridin-3-yl)-1,3-benzoxazole $\delta_H$ NMR (500 MHz, DMSO) 9.32 (d, J=1.6 Hz, 1H), 8.80 (dd, J=4.8, 1.6 Hz, 1H), 8.51 (dt, J=8.0, 1.9 Hz, 1H), 7.74 (dd, J=6.8, 1.9 Hz, 1H), 7.71 (d, J=8.9 Hz, 1H), 7.65 (dd, J=8.0, 4.8 Hz, 1H), 7.47-7.40 (m, 2H), 7.03 (dd, J=8.9, 2.5

Hz, 1H), 6.41 (d, J=8.7 Hz, 1H), 6.24 (td, J=6.7, 1.3 Hz, 1H), 4.35-4.26 (m, 4H). Tr(MET-uHPLC-AB-101)=2.25 min, (ES⁺) (M+H)⁺ 334.

The following example was prepared using Method 35 described above:

TABLE 36

| Ex. | Structure | Mol. Weight | IUPAC Name | LCMS data |
|---|---|---|---|---|
| 1 | 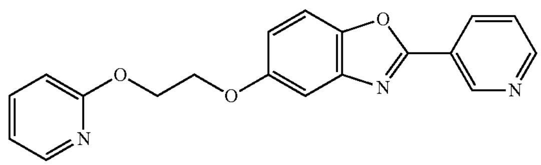 [SMILES: c1ccc(OCCOc2ccc3oc(-c4cccnc4)nc3c2)nc1] | 333.34 | 5-[2-(Pyridin-2-yloxy)ethoxy]-2-(pyridin-3-yl)-1,3-benzoxazole | Tr(MET-uHPLC-AB-101) = 2.25 min, (ES⁺) (M + H)⁺ 334 |

Method 36
Scheme for Method 36

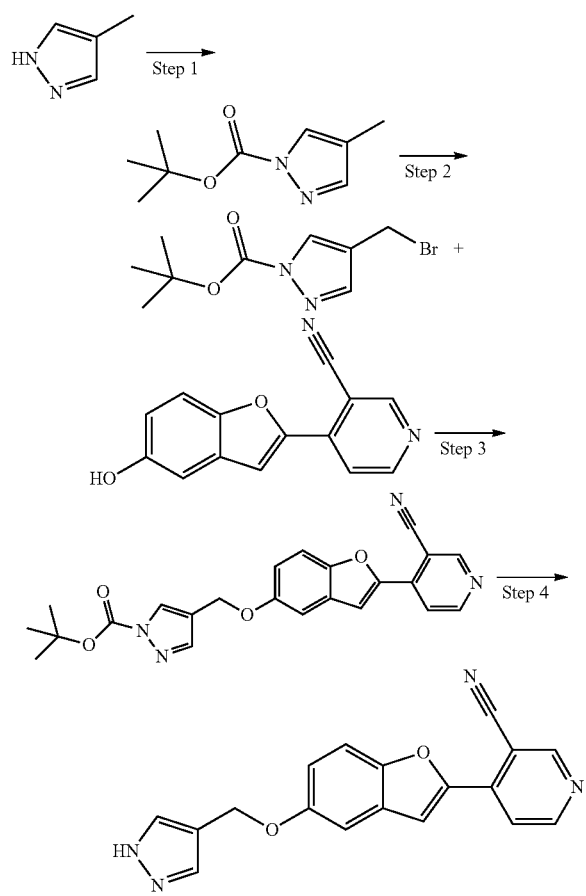

Step 1, Method 36: tert-Butyl 4-methyl-1H-pyrazole-1-carboxylate

To a solution of 4-methyl-1H-pyrazole (3.1 g, 37.8 mol) and N,N-diethylethanamine (10.5 mL, 75.3 mmol) in dichloromethane (100 mL) was added di-tert-butyl dicarbonate (9.1 g, 41.7 mmol) and the mixture was stirred at room temperature for 6 hours. The mixture was diluted with ethyl acetate (300 mL), washed with water (100 mL) and brine (100 mL), dried over magnesium sulfate, filtered and concentrated. Purification by FCC (silica, 0-30% ethyl acetate in heptane) gave the title compound 5.56 g (81% yield) as a yellow oil. δ$_H$ NMR (500 MHz, chloroform) 7.82 (s, 1H), 7.52 (s, 1H), 2.08 (s, 3H), 1.63 (s, 9H).

Step 2, Method 36: tert-Butyl 4-(bromomethyl)-1H-pyrazole-1-carboxylate

A mixture of tert-butyl 4-methyl-1H-pyrazole-1-carboxylate (4 g, 21.95 mmol) and N-bromosuccimide (4.3 g, 24.16 mmol) in carbon tetrachloride (50 mL) was heated to 70° C. After addition of 2,2'-diazene-1,2-diylbis(2-methylpropanenitrile) (0.5 g, 3.04 mmol) the mixture was refluxed for 18 hours. After cooling to room temperature, solids were removed by filtration and the filtrate was concentrated. Purification by FCC (silica, 0-20% ethyl acetate in heptane) gave the title compound 2.94 g (43% yield) as a colourless oil. ⁵H NMR (500 MHz, chloroform) 8.10 (s, 1H), 7.73 (s, 1H), 4.39 (s, 2H), 1.65 (s, 9H). Tr(METCR1278)=1.70 min, (ES⁺) (2M+Na)⁺ 545, 92%.

Step 3, Method 36: tert-Butyl 4-({[2-(3-cyanopyridin-4-yl)-4,5-dihydro-1-benzofuran-5-yl]oxy}methyl)-1H-pyrazole-1-carboxylate To a vigorously stirred solution of 4-(5-hydroxy-1-benzofuran-2-yl)pyridine-3-carbonitrile (275 mg, 1.16 mmol, prepared by Method 9) and tert-butyl 4-(bromomethyl)-1H-pyrazole-1-carboxylate (83%, 550 mg, 1.75 mmol) in N,N-dimethylformamide (15 mL) was added potassium iodide (20 mg, 0.12 mmol) and sodium hydride (60% in mineral oil, 60 mg, 1.5 mmol). After 2 hours the mixture was added to water (100 mL) and brine (100 mL) then extracted with ethyl acetate (3×100 mL). The combined organic extracts were washed with brine (50 mL), dried over magnesium sulfate, filtered and concentrated. Purification by FCC (silica, 0-80% ethyl acetate in heptane) gave the title compound 259 mg (53% yield). δ$_H$ NMR (500 MHz, chloroform) 8.93 (s, 1H), 8.83 (d, J=5.3 Hz, 1H), 8.17 (s, 1H), 7.96 (d, J=5.4 Hz, 1H), 7.91 (s, 1H), 7.80 (s, 1H), 7.48 (d, J=9.0 Hz, 1H), 7.17 (d, J=2.5 Hz, 1H), 7.08 (dd, J=9.0, 2.6 Hz, 1H), 5.03 (s, 2H), 1.66 (s, 9H). Tr(METCR1278)=2.12 min, (ES⁺) (M+Na)⁺ 439.

Step 4, Method 36: 4-[5-(1H-Pyrazol-4-ylmethoxy)-1-benzofuran-2-yl]pyridine-3-carbonitrile To a solution of tert-butyl 4-({[2-(3-cyanopyridin-4-yl)-4,5-dihydro-1-benzofuran-5-yl]oxy}methyl)-1H-pyrazole-1-carboxylate (255 mg, 0.61 mmol) in dichloromethane (10 mL) was added trifluoroacetic acid (2 mL) and the mixture was stirred for 3 hours at room temperature. The volatiles were removed in vacuo and the residue was partitioned between ethyl acetate (200 mL) and saturated aqueous sodium bicarbonate solution (100 mL). After separation the organic layer was washed with brine (50 mL), dried over magnesium sulfate, filtered and concentrated. The residue was triturated with ethyl acetate and heptane to give the title compound 132 mg (69% yield) as an off-white, crystalline solid.

Example 1, Method 36: 4-[5-(1H-Pyrazol-4-yl-methoxy)-1-benzofuran-2-yl]pyridine-3-carbonitrile $\delta_H$ NMR (500 MHz, DMSO) 12.84 (s, 1H), 9.12 (s, 1H), 8.92 (d, J=5.4 Hz, 1H), 8.07 (d, J=5.4 Hz, 1H), 7.99-7.91 (m, 1H), 7.88 (s, 1H), 7.69-7.56 (m, 2H), 7.47 (d, J=2.6 Hz, 1H), 7.10 (dd, J=9.0, 2.6 Hz, 1H), 5.04 (s, 2H). Tr(MET-uHPLC-AB-101)=2.68 min, (ES$^+$) (M+H)$^+$ 317.

The following example was prepared using Method 36 described above:

yl)ethan-1-one (500 mg, 2.84 mmol) and potassium iodide (50 g, 0.3 mmol) in N,N-dimethylformamide (25 mL) at 0° C. was added sodium hydride (60% in mineral oil, 270 mg, 6.75 mmol). The ice bath was removed and the mixture was stirred at room temperature for 16 hours before being added to brine (100 mL) and water (100 mL). The mixture was extracted with ethyl acetate (3×100 mL), the combined organic layers washed with brine (50 mL), dried over magnesium sulfate, filtered and concentrated. Purification by FCC (silica, 20-100% ethyl acetate in heptane) gave the title compound 626 mg (83% yield) as a colourless, crystalline solid. Tr(MET-uHPLC-AB-101)=1.7 min, (ES$^+$) (M+H)$^+$ 268.

TABLE 37

| Ex. | Structure | Mol. Weight | IUPAC Name | LCMS data |
|---|---|---|---|---|
| 1 | 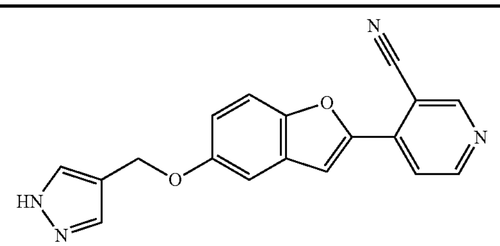 | 316.31 | 4-[5-(1H-Pyrazol-4-yl-methoxy)-1-benzofuran-2-yl]pyridine-3-carbonitrile | Tr(MET-uHPLC-AB-101) = 2.68 min, (ES$^+$) (M + H)$^+$ 317 |

Method 37
Scheme for Method 37

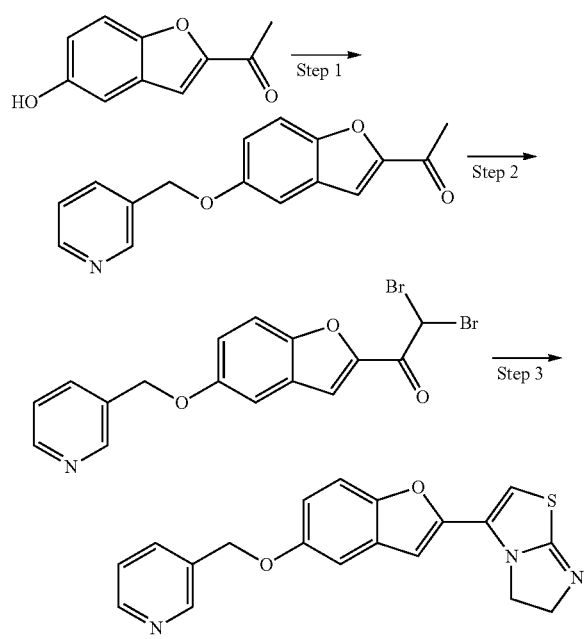

Step 1, Method 37: 1-[5-(Pyridin-3-ylmethoxy)-1-benzofuran-2-yl]ethan-1-one

To a suspension of 3-(bromomethyl)pyridine hydrobromide (861 mg, 3.40 mmol), 1-(5-hydroxy-1-benzofuran-2-

Step 2, Method 37: 2,2-Dibromo-1-[5-(pyridin-3-ylmethoxy)-1-benzofuran-2-yl]ethan-1-one To a suspension of 1-[5-(pyridin-3-ylmethoxy)-1-benzofuran-2-yl]ethan-1-one (1.5 g, 5.61 mmol) and pyridinium tribromide (2.2 g, 6.9 mmol) in acetic acid (30 mL) was added hydrobromic acid (30% in acetic acid, 1.1 mL) and the mixture was stirred at room temperature for 18 hours. After removal of the volatiles in vacuo, the residue was partitioned between ethyl acetate (300 mL) and saturated aqueous sodium bicarbonate (150 mL). The organic layer was separated, washed with brine (100 mL), dried over magnesium sulfate, filtered and concentrated. Purification by FCC (silica, 0-100% ethyl acetate in heptane) gave the title compound 472 mg (20% yield) as a colourless solid. $\delta_H$ NMR (500 MHz, chloroform) 8.72 (s, 1H), 8.61 (d, J=3.9 Hz, 1H), 7.81 (d, J=7.8 Hz, 1H), 7.76 (d, J=0.7 Hz, 1H), 7.53 (d, J=9.1 Hz, 1H), 7.36 (dd, J=7.8, 4.8 Hz, 1H), 7.24 (dd, J=9.1, 2.6 Hz, 1H), 7.19 (d, J=2.5 Hz, 1H), 6.70 (s, 1H), 5.14 (s, 2H).

Step 3, Method 37: 3-{[(2-{5H,6H-Imidazo[2,1-b][1,3]thiazol-3-yl}-1-benzofuran-5-yl)oxy]methyl}pyridine A mixture of 2,2-dibromo-1-[5-(pyridin-3-ylmethoxy)-1-benzofuran-2-yl]ethan-1-one (470 mg, 1.11 mmol) and imidazolidine-2-thione (114 mg, 1.12 mmol) in ethanol (20 mL) and acetic acid (10 mL) was stirred under reflux for 16 hours. The solvent was removed in vacuo and the residue was partitioned between ethyl acetate (200 mL) and saturated aqueous sodium bicarbonate solution (100 mL). The organic layer was washed with brine (50 mL), dried over magnesium sulfate, filtered and concentrated. Purification by SCX column and preparative HPLC (acetonitrile/water+ 0.2% ammonium hydroxide) gave the title compound 49 mg (15% yield) as a colourless, crystalline solid.

Example 1, Method 37: 3-{[(2-{5H,6H-Imidazo[2,1-b][1,3]thiazol-3-yl}-1-benzofuran-5-yl)oxy]methyl}pyridine $\delta_H$ NMR (500 MHz, DMSO) 8.69 (d, J=1.7 Hz, 1H), 8.55 (dd, J=4.8, 1.6 Hz, 1H), 7.89 (dd, J=7.8, 1.8 Hz, 1H), 7.52 (d, J=9.0 Hz, 1H), 7.43 (dd, J=7.8, 4.8 Hz, 1H), 7.27 (d, J=2.6 Hz, 1H), 7.17 (s, 1H), 7.05 (dd, J=8.9, 2.6 Hz, 1H), 6.52 (s, 1H), 5.19 (s, 2H), 4.27-3.97 (m, 4H). Tr(MET-uHPLC-AB-101)=1.15 min, (ES$^+$) (M+H)$^+$ 350.

The following example was prepared using Method 37 described above:

TABLE 38

| Ex. | Structure | Mol. Weight | IUPAC Name | LCMS data |
|---|---|---|---|---|
| 1 | 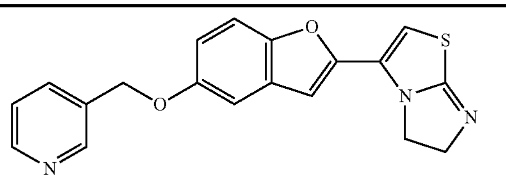 | 349.41 | 3-{[(2-{5H,6H-Imidazo[2,1-b][1,3]thiazol-3-yl}-1-benzofuran-5-yl)oxy]methyl}pyridine | Tr(MET-uHPLC-AB-101) = 1.15 min, (ES$^+$) (M + H)$^+$ 350 |

Method 38
Scheme for Method 38

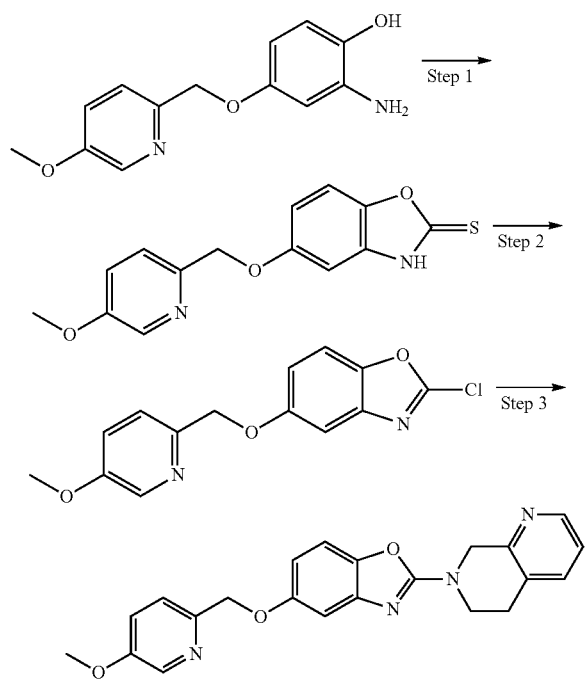

Step 1, Method 38: 5-[(5-Methoxypyridin-2-yl)methoxy]-2,3-dihydro-1,3-benzoxazole-2-thione 2-Amino-4-[(5-methoxypyridin-2-yl)methoxy]phenol (50% purity, 450 mg, 0.91 mmol, prepared by Method 33) and potassium ethyl xanthate (161 mg, 1.00 mmol) in ethanol (3 mL) were stirred in a sealed tube at 85° C. overnight. The mixture was concentrated in vacuo to give the title compound 263 mg (quantitative yield) as a brown solid. Tr(METCR1278)=1.59 min, (ES$^+$) (M+H)$^+$ 289.

Step 2, Method 38: 2-Chloro-5-[(5-methoxypyridin-2-yl)methoxy]-1,3-benzoxazole

To a stirred solution of 5-[(5-methoxypyridin-2-yl)methoxy]-2,3-dihydro-1,3-benzoxazole-2-thione (263 mg, 0.91 mmol) in thionyl chloride (1 mL) was added N,N-dimethylformamide (0.03 mL). The mixture was stirred at 65° C. for 1 hour. The mixture was concentrated in vacuo and purified by FCC (silica, 10-40% ethyl acetate in heptane) to give the title compound 117 mg (44% yield) as a white solid. $\delta_H$ NMR (500 MHz, DMSO) 8.29 (d, J=2.9 Hz, 1H), 7.67 (d, J=9.0 Hz, 1H), 7.50 (d, J=8.6 Hz, 1H), 7.46-7.38 (m, 2H), 7.11 (dd, J=9.0, 2.6 Hz, 1H), 5.16 (s, 2H), 3.83 (s, 3H). Tr(MET-uHPLC-AB-101)=2.92 min, (ES$^+$) (M+H)$^+$ 291/293.

Step 3, Method 38: 7-{5-[(5-Methoxypyridin-2-yl)methoxy]-1,3-benzoxazol-2-yl}-5,6,7,8-tetrahydro-1,7-naphthyridine 2-Chloro-5-[(5-methoxypyridin-2-yl)methoxy]-1,3-benzoxazole (9 mg, 0.031 mmol), 5,6,7,8-tetrahydro-1,7-naphthyridine dihydrochloride (14 mg, 0.068 mmol) and 2-propanol (0.4 mL) were heated at 150° C. for 20 minutes in a microwave. The mixture was diluted with water (10 mL) and extracted with ethyl acetate (2×10 mL). The combined organic extracts were dried over sodium sulfate, filtered and concentrated. Purification by FCC (silica, 20-100% ethyl acetate in heptane) gave the title compound 5.5 mg (46% yield) as an off-white powder.

Example 1, Method 38: 7-{5-[(5-Methoxypyridin-2-yl)methoxy]-1,3-benzoxazol-2-yl}-5,6,7,8-tetrahydro-1,7-naphthyridine $\delta_H$ NMR (500 MHz, DMSO) 8.42 (d, J=4.5 Hz, 1H), 8.28 (d, J=2.8 Hz, 1H), 7.64 (d, J=7.6 Hz, 1H), 7.47 (d, J=8.6 Hz, 1H), 7.41 (dd, J=8.6, 2.9 Hz, 1H), 7.32 (d, J=8.7 Hz, 1H), 7.26 (dd, J=7.6, 4.8 Hz, 1H), 6.99 (d, J=2.4 Hz, 1H), 6.67 (dd, J=8.7, 2.5 Hz, 1H), 5.08 (s, 2H), 4.78 (s, 2H), 3.91 (t, J=5.9 Hz, 2H), 3.83 (s, 3H), 2.98 (t, J=5.8 Hz, 2H). Tr(MET-uHPLC-AB-101)=2.28 min, (ES$^+$) (M+H)$^+$ 389.

The following examples were prepared using Method 38 described above:

TABLE 39

| Ex. | Structure | Mol. Weight | IUPAC Name | LCMS data |
|---|---|---|---|---|
| 1 | 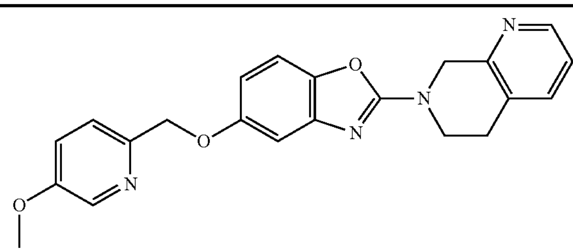 | 388.42 | 7-{5-[(5-Methoxypyridin-2-yl)methoxy]-1,3-benzoxazol-2-yl}-5,6,7,8-tetrahydro-1,7-naphthyridine | Tr(MET-uHPLC-AB-101) = 2.28 min, (ES+) (M + H)+ 389 |
| 2 | 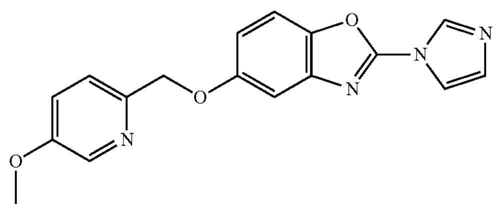 [SMILES: COc1ccc(COc2ccc3oc(-n4ccnc4)nc3c2)nc1] | 322.32 | 2-(1H-Imidazol-1-yl)-5-[(5-methoxypyridin-2-yl)methoxy]-1,3-benzoxazole | Tr(MET-uHPLC-AB-101) = 2.29 min, (ES+) (M + H)+ 323 |
| 3 | 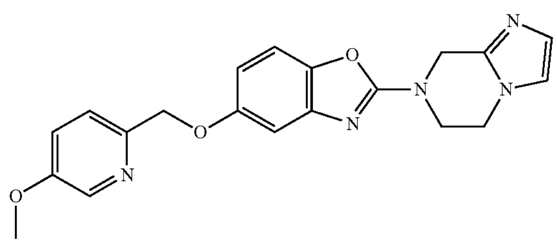 [SMILES: COc1ccc(COc2ccc3oc(N4CCn5ccnc5C4)nc3c2)nc1] | 377.40 | 2-{5H,6H,7H,8H-Imidazo[1,2-a]pyrazin-7-yl}-5-[(5-methoxypyridin-2-yl)methoxy]-1,3-benzoxazole | Tr(MET-uHPLC-AB-101) = 1.43 min, (ES+) (M + H)+ 378 |
| 4 | 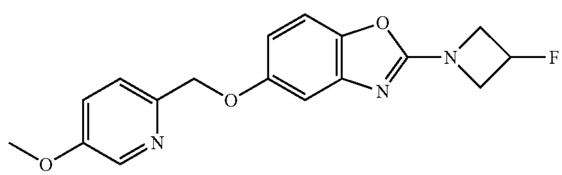 [SMILES: COc1ccc(COc2ccc3oc(N4CC(F)C4)nc3c2)nc1] | 329.33 | 2-(3-Fluoroazetidin-1-yl)-5-[(5-methoxypyridin-2-yl)methoxy]-1,3-benzoxazole | Tr(MET-uHPLC-AB-101) = 2.5 min, (ES+) (M + H)+ 330 |
| 6 | 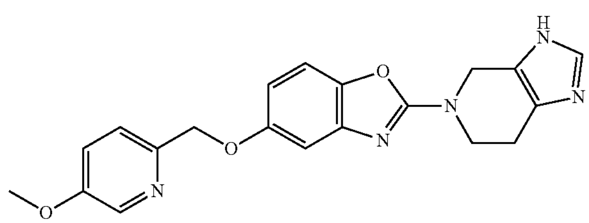 [SMILES: COc1ccc(COc2ccc3oc(N4CCc5nc[nH]c5C4)nc3c2)nc1] | 377.40 | 2-{3H,4H,5H,6H,7H-Imidazo[4,5-c]pyrazin-5-yl}-5-[(5-methoxypyridin-2-yl)methoxy]-1,3-benzoxazole | Tr(MET-uHPLC-AB-101) = 1.52 min, (ES+) (M + H)+ 378 |
| 8 | 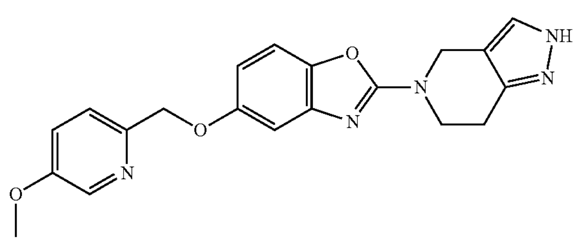 [SMILES: COc1ccc(COc2ccc3oc(N4CCc5n[nH]cc5C4)nc3c2)nc1] | 377.40 | 5-[(5-Methoxypyridin-2-yl)methoxy]-2-{5H,6H,7H-pyrrolo[3,4-b]pyridin-6-yl}-1,3-benzoxazole | Tr(MET-uHPLC-AB-101) = 2.18 min, (ES+) (M + H)+ 378 |
| 9 | 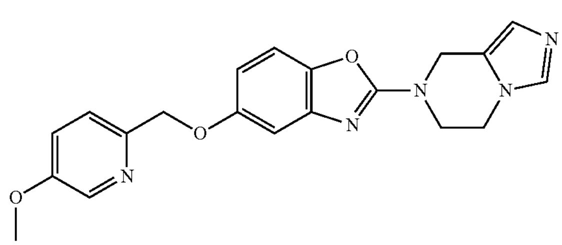 [SMILES: COc1ccc(COc2ccc3oc(N4CCn5cncc5C4)nc3c2)nc1] | 377.40 | 2-{5H,6H,7H,8H-Imidazo[1,5-a]pyrazin-7-yl}-5-[(5-methoxypyridin-2-yl)methoxy]-1,3-benzoxazole | Tr(MET-uHPLC-AB-101) = 1.45 min, (ES+) (M + H)+ 378 |

TABLE 39-continued

| Ex. | Structure | Mol. Weight | IUPAC Name | LCMS data |
|---|---|---|---|---|
| 10 | 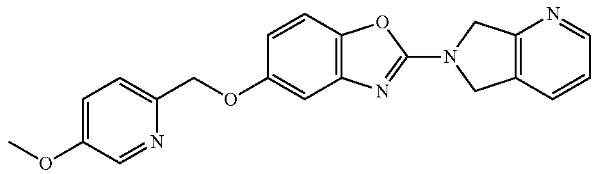 [SMILES: COc1ccc(COc2ccc3oc(N4Cc5cccnc5C4)nc3c2)nc1] | 374.39 | 5-[(5-Methoxypyridin-2-yl)methoxy]-2-{5H,6H,7H-pyrrolo[3,4-b]pyridin-6-yl}-1,3-benzoxazole | Tr(MET-uHPLC-AB-101) = 2.47 min, (ES⁺) (M + H)⁺ 375 |

Method 39
Scheme for Method 39

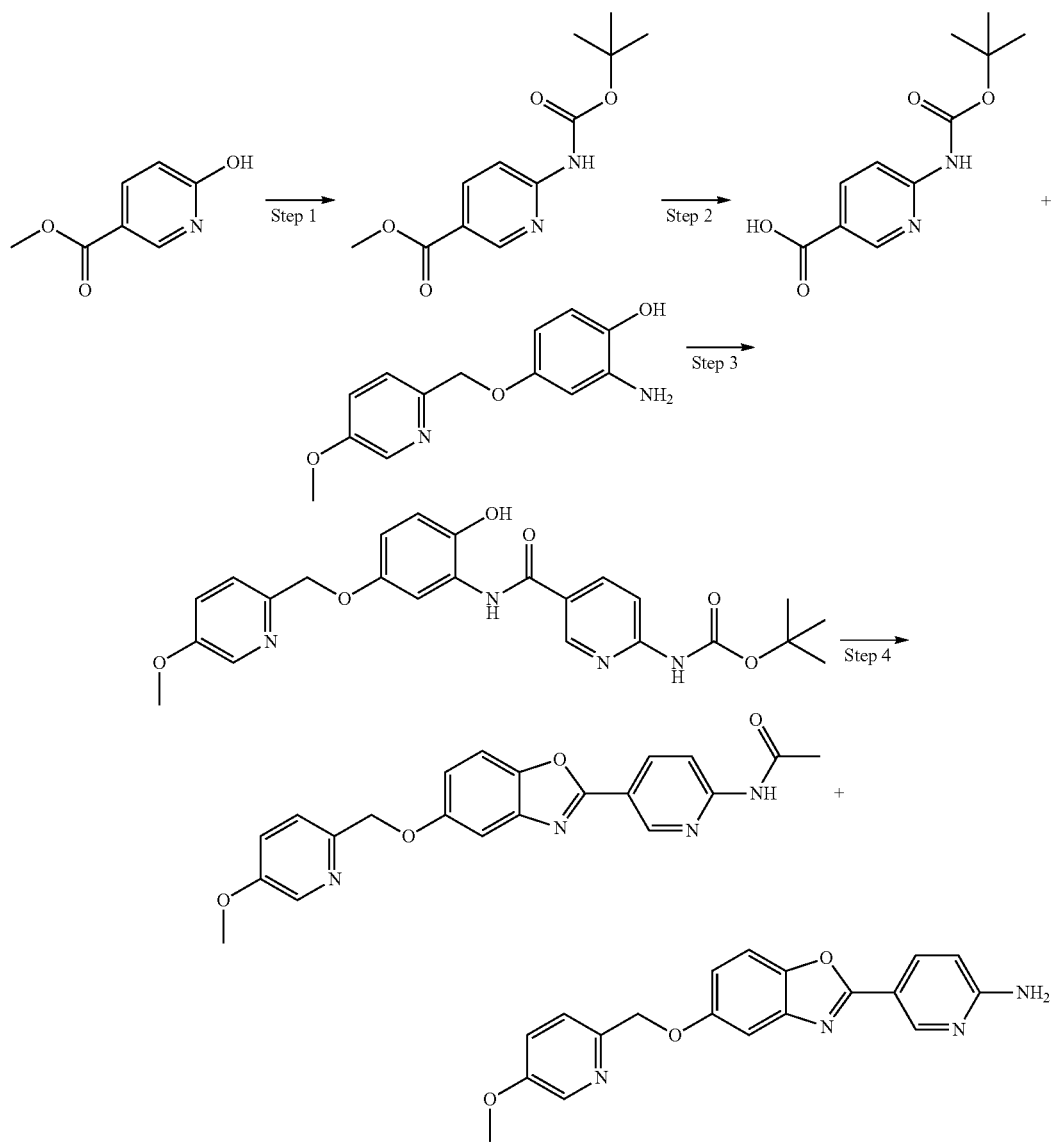

Step 1, Method 39: Methyl 6-{[(tert-butoxy)carbonyl]amino}pyridine-3-carboxylate A solution of methyl 6-aminopyridine-3-carboxylate (1 g, 6.57 mmol), di-tert butyl dicarbonate (1.72 g, 7.89 mmol) and N,N-dimethylaminopyridine (56 mg, 0.46 mmol) in tetrahydrofuran (60 mL) was stirred at room temperature overnight. The mixture was concentrated in vacuo to give the title compound 1.79 g (quantitative yield) as a light brown solid. Tr(METCR1278)=1.99 min, (ES⁺) (M+H)⁺ 253.

Step 2, Method 39: 6-{[(tert-Butoxy)carbonyl]amino}pyridine-3-carboxylic acid To a stirred solution of methyl 6-{[(tert-butoxy)carbonyl]amino}pyridine-3-carboxylate (1.66 g, 6.58 mmol) in ethanol (75 mL) and tetrahydrofuran (75 mL), was added 2 N sodium hydroxide (23.0 mL, 46.1 mmol). The mixture was stirred at 55° C. overnight. The mixture was then concentrated to remove ethanol and tetrahydrofuran and the resulting aqueous solution was neutralised using 1 N hydrochloric acid (46.1 mL). The resultant precipitate was filtered and dried under vacuum to give the title compound 729 mg (46% yield) as an off-white powder. $\delta_H$ NMR (500 MHz, DMSO) 13.04 (s, 1H), 10.25 (s, 1H), 8.75 (s, 1H), 8.40-8.06 (m, 1H), 7.91 (d, J=7.0 Hz, 1H), 1.48 (s, 9H). Tr(METCR1278)=1.57 min, (ES$^+$) (M+H)$^+$ 239.

Step 3, Method 39: tert-Butyl N-[5-({2-hydroxy-5-[(5-methoxypyridin-2-yl)methoxy]phenyl}carbamoyl)pyridin-2-yl]carbamate A stirred solution of 2-amino-4-[(5-methoxypyridin-2-yl)methoxy]phenol (50% purity, 150 mg, 0.30 mmol, prepared by Method 33), 6-{[(tert-butoxy)carbonyl]amino}pyridine-3-carboxylic acid (80 mg, 0.33 mmol) and ethylcarbodiimide hydrochloride (76 mg, 0.40 mmol) in pyridine (1 mL) under nitrogen was stirred at room temperature for 16 hours. The mixture was diluted with water (10 mL) and extracted with ethyl acetate (2×10 mL). The combined organic extracts were dried over sodium sulfate, filtered and concentrated to give the title compound 190 mg (quantitative yield) as a light brown solid. Tr(METCR1278)=1.78 min, (ES$^+$) (M+H)$^+$ 467.

Step 4, Method 39: N-(5-{5-[(5-Methoxypyridin-2-yl)methoxy]-1,3-benzoxazol-2-yl}pyridin-2-yl)acetamide and 5-{5-[(5-Methoxypyridin-2-yl)methoxy]-1,3-benzoxazol-2-yl}pyridin-2-amine tert-Butyl N-[5-({2-hydroxy-5-[(5-methoxypyridin-2-yl)methoxy]phenyl}carbamoyl)pyridin-2-yl]carbamate (142 mg, 0.30 mmol) and acetic acid (2 mL) were heated at 200° C. for 40 minutes in a microwave. The mixture was concentrated and the residue was diluted with saturated aqueous sodium bicarbonate solution (20 mL) and extracted with ethyl acetate (2×20 mL). The combined organic extracts were dried over sodium sulfate, filtered and concentrated. Purification by FCC (silica, 25-80% ethyl acetate in heptane) gave N-(5-{5-[(5-methoxypyridin-2-yl)methoxy]-1,3-benzoxazol-2-yl}pyridin-2-yl)acetamide 54 mg (45% yield) as a light pink powder. The fractions containing 5-{5-[(5-methoxypyridin-2-yl)methoxy]-1,3-benzoxazol-2-yl}pyridin-2-amine were concentrated and purified by preparative HPLC (acetonitrile/water) to give 5-{5-[(5-methoxypyridin-2-yl)methoxy]-1,3-benzoxazol-2-yl}pyridin-2-amine 2.7 mg (3% yield) as an off-white powder.

Example 1, Method 39: N-(5-{5-[(5-Methoxypyridin-2-yl)methoxy]-1,3-benzoxazol-2-yl}pyridin-2-yl)acetamide $\delta_H$ NMR (500 MHz, DMSO) 10.92 (s, 1H), 9.06 (d, J=2.3 Hz, 1H), 8.48 (dd, J=8.8, 2.4 Hz, 1H), 8.33-8.27 (m, 2H), 7.69 (d, J=8.9 Hz, 1H), 7.53 (d, J=8.6 Hz, 1H), 7.47-7.41 (m, 2H), 7.10 (dd, J=8.9, 2.5 Hz, 1H), 5.19 (s, 2H), 3.84 (s, 3H), 2.16 (s, 3H). Tr(MET-uHPLC-AB-101)=2.66 min, (ES$^+$) (M+H)$^+$ 391.

Example 2, Method 39: 5-{5-[(5-Methoxypyridin-2-yl)methoxy]-1,3-benzoxazol-2-yl}pyridin-2-amine $\delta_H$ NMR (500 MHz, DMSO) 8.70 (d, J=2.3 Hz, 1H), 8.30 (d, J=2.9 Hz, 1H), 8.04 (dd, J=8.8, 2.4 Hz, 1H), 7.59 (d, J=8.8 Hz, 1H), 7.51 (d, J=8.6 Hz, 1H), 7.43 (dd, J=8.6, 3.0 Hz, 1H), 7.33 (d, J=2.5 Hz, 1H), 6.99 (dd, J=8.8, 2.5 Hz, 1H), 6.81 (s, 2H), 6.58 (d, J=8.8 Hz, 1H), 5.15 (s, 2H), 3.83 (s, 3H). Tr(MET-uHPLC-AB-101)=1.76 min, (ES$^+$) (M+H)$^+$ 349.

The following examples were prepared using Method 39 described above:

TABLE 40

| Ex. | Structure | Mol. Weight | IUPAC Name | LCMS data |
|---|---|---|---|---|
| 1 | 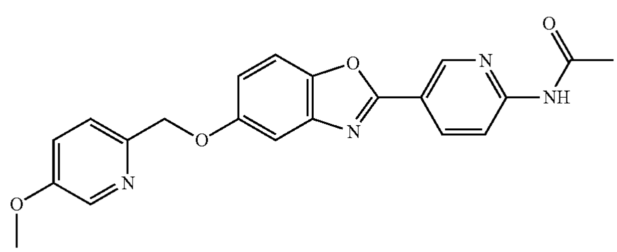 [SMILES: COc1ccc(COc2ccc3oc(-c4ccc(NC(C)=O)nc4)nc3c2)nc1] | 390.39 | N-(5-{5-[(5-methoxypyridin-2-yl)methoxy]-1,3-benzoxazol-2-yl}pyridin-2-yl)acetamide | Tr(MET-uHPLC-AB-101) = 2.66 min, (ES$^+$) (M + H)$^+$ 391 |
| 2 | 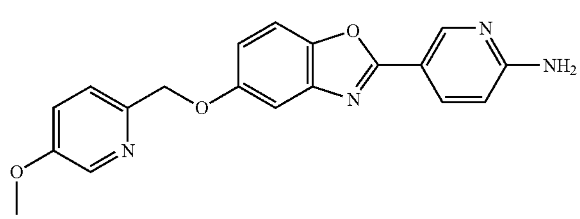 [SMILES: COc1ccc(COc2ccc3oc(-c4ccc(N)nc4)nc3c2)nc1] | 348.36 | 5-{5-[(5-Methoxypyridin-2-yl)methoxy]-1,3-benzoxazol-2-yl}pyridin-2-amine | Tr(MET-uHPLC-AB-101) = 1.76 min, (ES$^+$) (M + H)$^+$ 349 |

Method 40
Scheme for Method 40

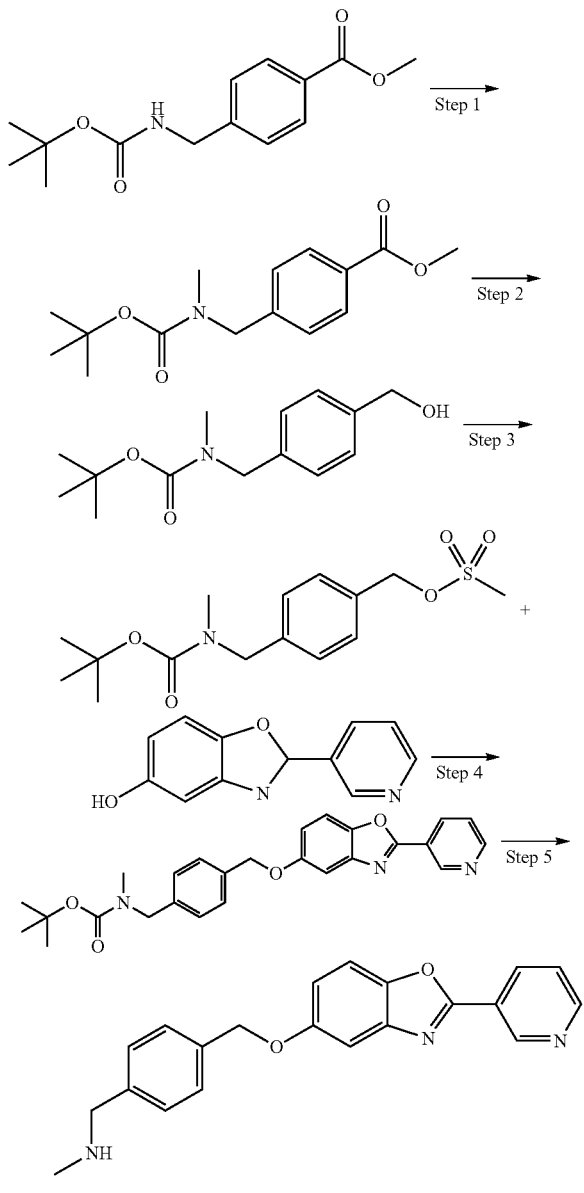

Step 1, Method 40: Methyl 4-({[(tert-butoxy)carbonyl](methyl)amino}methyl)benzoate To methyl 4-{[(tert-butoxycarbonyl)amino]methyl}benzoate (200 mg, 0.75 mmol) and sodium hydride (60% in mineral oil, 32 mg, 0.79 mmol) under nitrogen was added N,N-dimethylformamide (2 mL). The mixture was stirred at room temperature for 10 minutes. Iodomethane (49 µL, 0.79 mmol) was added and the mixture was stirred at room temperature for 1 hour. The mixture was diluted with water (20 mL) and extracted with ethyl acetate (2×20 mL). The organic extracts were dried over sodium sulfate, filtered and concentrated. Purification by FCC (silica, 0-40% ethyl acetate in heptane) gave the title compound 151 mg (72% yield) as a light yellow oil. $\delta_H$ NMR (500 MHz, DMSO) 7.95 (d, J=8.1 Hz, 2H), 7.34 (d, J=8.1 Hz, 2H), 4.44 (s, 2H), 3.84 (s, 3H), 2.79 (s, 3H), 1.39 (d, J=43.9 Hz, 9H). Tr(METCR1278)=2.03 min, (ES$^+$) (M-t-Bu+H)$^+$ 224, (M-t-Bu+acetonitrile)$^+$ 265.

Step 2, Method 40: tert-Butyl N-{[4-(hydroxymethyl)phenyl]methyl}-N-methylcarbamate 2.4 M lithium aluminium hydride in tetrahydrofuran (0.23 mL, 0.56 mmol) was added to a stirred solution of methyl 4-({[(tert-butoxy)carbonyl](methyl)amino}methyl)benzoate (148 mg, 0.53 mmol) in anhydrous tetrahydrofuran (7 mL) under nitrogen. The mixture was stirred at 0° C. for 30 minutes. The mixture was quenched by cautious addition of water (1 mL) followed by saturated ammonium chloride solution (0.5 mL). The mixture was stirred at 0° C. for 5 minutes. The mixture was diluted with water (20 mL) and extracted with ethyl acetate (2×20 mL). The combined organic extracts were dried over sodium sulfate, filtered and concentrated to give the title compound 124 mg (93% yield) as a light yellow oil. $\delta_H$ NMR (500 MHz, DMSO) 7.29 (d, J=7.7 Hz, 2H), 7.16 (d, J=7.8 Hz, 2H), 5.14 (t, J=5.7 Hz, 1H), 4.47 (d, J=5.6 Hz, 2H), 4.34 (s, 2H), 2.73 (s, 3H), 1.41 (d, J=12.9 Hz, 9H). Tr(METCR1278)=1.71 min, (ES$^+$) (M+Na)$^+$ 273 (M-t-Bu+H)$^+$ 196.

Step 3, Method 40: tert-Butyl N-({4-[(methanesulfonyloxy)methyl]phenyl}methyl)-N-methylcarbamate To a stirred solution of tert-butyl N-{[4-(hydroxymethyl)phenyl]methyl}-N-methylcarbamate (120 mg, 0.48 mmol) in dichloromethane (4 mL) under nitrogen with ice cooling was added triethylamine (0.073 mL, 0.52 mmol) followed by methanesulfonyl chloride (0.039 mL, 0.50 mmol). The mixture was warmed to room temperature and stirred for 2 hours. The mixture was treated with methanesulfonyl chloride (0.013 mL, 0.17 mmol) and stirred at room temperature for 1 hour. The mixture was partitioned between dichloromethane (20 mL) and water (20 mL). The organic extract was dried over sodium sulfate, filtered and concentrated to give the crude title compound 157 mg (57% yield) as a yellow oil which was taken on directly to the next step. Tr(METCR1278)=1.93 min, (ES$^+$) (M+Na)$^+$ 352, 57%.

Step 4, Method 40: tert-Butyl-N-methyl-N-{[4-({[2-(pyridin-3-yl)-1,3-benzoxazol-5-yl]oxy}methyl)phenyl]methyl}carbamate To tert-butyl N-({4-[(methanesulfonyloxy)methyl]phenyl}methyl)-N-methylcarbamate (92 mg, 0.43 mmol) and 2-(pyridin-3-yl)-1,3-benzoxazol-5-ol (157 mg, 0.48 mmol, prepared by Method 14) in N,N-dimethylformamide (3 mL) under nitrogen, was added sodium hydride (60% in mineral oil, 19 mg, 0.48 mmol). The mixture was stirred at room temperature overnight. The mixture was then quenched with water (1 mL), diluted with water (30 mL) and extracted with ethyl acetate (2×30 mL). The combined organic extracts were dried over sodium sulfate, filtered and concentrated. Purification by FCC (silica, 20-100% ethyl acetate in heptane) gave the title compound 42 mg (22% yield) as an off-white solid. $\delta_H$ NMR (500 MHz, DMSO) 9.33 (d, J=2.1 Hz, 1H), 8.80 (dd, J=4.8, 1.5 Hz, 1H), 8.51 (d, J=8.0 Hz, 1H), 7.73 (d, J=8.9 Hz, 1H), 7.65 (dd, J=8.0, 4.8 Hz, 1H), 7.51-7.44 (m, 3H), 7.25 (d, J=7.8 Hz, 2H), 7.13 (dd, J=8.9, 2.5 Hz, 1H), 5.18 (s, 2H), 4.38 (s, 2H), 2.76 (s, 3H), 1.40 (d, J=23.8 Hz, 9H). Tr(METCR1278)=2.47 min, (ES+) (M+H)+ 446 (M+Na)+ 468 (M-tBu+H)+ 390, 88%.

Step 5, Method 40: Methyl({[4-({[2-(pyridin-3-yl)-1,3-benzoxazol-5-yl]oxy}methyl)phenyl]methyl})amine To a solution of tert-butyl-N-methyl-N-{[4-({[2-(pyridin-3-yl)-1,3-benzoxazol-5-yl]oxy}methyl)phenyl]methyl}carbamate (40 mg, 0.09 mmol) in dichloromethane (2 mL), was added 4 M hydrogen chloride in 1,4-dioxane (3 mL) and the mixture was stood at room temperature for 1 hour. The mixture was concentrated in vacuo and purified by preparative HPLC (acetonitrile/water+0.2% ammonium hydroxide) to give the title compound 19.5 mg (63% yield) as an off-white solid.

Example 1, Method 40: Methyl({[4-({[2-(pyridin-3-yl)-1,3-benzoxazol-5-yl]oxy}methyl)phenyl]methyl})amine $\delta_H$ NMR (500 MHz, DMSO) 9.31 (s, 1H), 8.79 (d, J=3.6 Hz, 1H), 8.50 (t, J=7.5 Hz, 1H), 7.72 (t, J=7.8 Hz, 1H), 7.64 (dd, J=7.8, 5.0 Hz, 1H), 7.49-7.45 (m, 1H), 7.42 (d, J=7.9 Hz, 2H), 7.33 (d, J=7.8 Hz, 2H), 7.15-7.08 (m, 1H), 5.16 (d, J=4.2 Hz, 2H), 3.63 (s, 2H), 3.23 (br. s, 1H), 2.25 (s, 3H). Tr(MET-uHPLC-AB-101)=1.76 min, (ES+) (M+H)+ 346.

The following example was prepared using Method 40 described above:

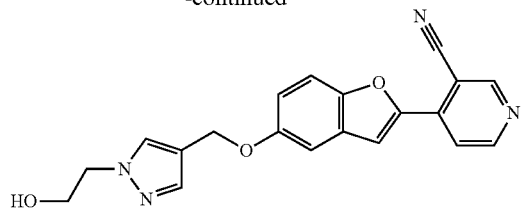

Step 1, Method 41: 4-{5-[(1-{2-[(tert-Butyldimethylsilyl)oxy]ethyl}-1H-pyrazol-4-yl)methoxy]-1-benzofuran-2-yl}pyridine-3-carbonitrile To a suspension of 4-[5-(1H-pyrazol-4-ylmethoxy)-1-benzofuran-2-yl]pyridine-3-carbonitrile (72 mg, 0.28 mmol, prepared by Method 36), (2-bromoethoxy)(tert-butyl)dimethylsilane (100 mg, 0.42 mmol) and potassium iodide (10 mg, 0.06 mmol) in N,N-dimethylformamide (5 mL) was added sodium hydride (60% in mineral oil, 15 mg, 0.38 mmol) and the mixture was stirred at room temperature for 2 hours. The mixture was added to water (50 mL) and brine (50 mL) then extracted with ethyl acetate (3×50 mL). The combined extracts were washed with brine (50 mL), dried over magnesium sulfate, filtered and concentrated. Purification by FCC (silica, 0-50% ethyl acetate in heptane) gave the title compound 79 mg (73% yield) as colourless oil. $\delta_H$

TABLE 41

| Ex. | Structure | Mol. Weight | IUPAC Name | LCMS data |
|---|---|---|---|---|
| 1 | 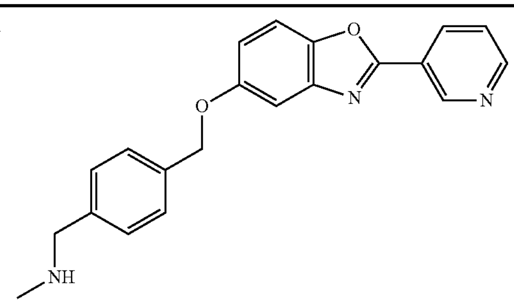 | 345.39 | Methyl({[4-({[2-(pyridin-3-yl)-1,3-benzoxazol-5-yl]oxy}methyl)phenyl]methyl})amine | Tr(MET-uHPLC-AB-101) = 1.76 min, (ES+) (M + H)+ 346 |

Method 41
Scheme for Method 41

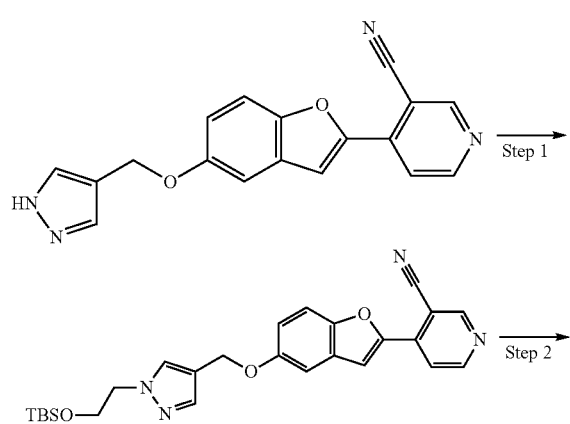

NMR (500 MHz, chloroform) 8.93 (s, 1H), 8.83 (d, J=5.1 Hz, 1H), 7.97 (d, J=5.4 Hz, 1H), 7.92 (s, 1H), 7.60 (s, 1H), 7.57 (s, 1H), 7.47 (d, J=9.0 Hz, 1H), 7.19 (d, J=2.5 Hz, 1H), 7.08 (dd, J=9.0, 2.6 Hz, 1H), 5.01 (s, 2H), 4.23 (t, J=5.2 Hz, 2H), 3.94 (t, J=5.2 Hz, 2H), 0.84 (s, 9H), −0.06 (s, 6H). Tr(METCR1278)=2.52 min, (ES+) (M+H)+ 475.

Step 2, Method 41: 4-(5-{[1-(2-Hydroxyethyl)-1H-pyrazol-4-yl]methoxy}-1-benzofuran-2-yl)pyridine-3-carbonitrile To a solution of 4-{5-[(1-{2-[(tert-butyldimethylsilyl)oxy]ethyl}-1H-pyrazol-4-yl)methoxy]-1-benzofuran-2-yl}pyridine-3-carbonitrile (79 mg, 0.17 mmol) in dry tetrahydrofuran (10 mL) at 0° C. was added 1 M tetrabutylammonium fluoride in tetrahydrofuran (200 μL, 0.2 mmol). The ice bath was removed and the mixture stirred for 3 hours at room temperature before being partitioned between ethyl acetate (200 mL) and water (50 mL). The organic layer was washed with brine (50 mL), dried over magnesium sulfate, filtered and concentrated. Purification by FCC (silica, 0-10% methanol in dichloromethane) gave the title compound 59 mg (98% yield) as a colourless crystalline solid.

Example 1, Method 41: 4-(5-{[1-(2-Hydroxyethyl)-1H-pyrazol-4-yl]methoxy}-1-benzofuran-2-yl)pyridine-3-carbonitrile $\delta_H$ NMR (500 MHz, DMSO) 9.12 (s, 1H), 8.92 (d, J=5.4 Hz, 1H), 8.07 (d, J=5.4 Hz, 1H), 7.95 (s, 1H), 7.84 (s, 1H), 7.62 (d, J=9.0 Hz, 1H), 7.55 (s, 1H), 7.47 (d, J=2.6 Hz, 1H), 7.11 (dd, J=9.0, 2.6 Hz, 1H), 5.00 (s, 2H), 4.89 (t, J=5.2 Hz, 1H), 4.13 (t, J=5.7 Hz, 2H), 3.80-3.63 (m, 2H). Tr(MET-uHPLC-AB-101)=2.58 min, (ES⁺) (M+H)⁺ 361.

The following examples were prepared using Method 41 described above:

Step 1, Method 42: Dimethyl({2-[4-({[2-(pyridin-3-yl)-1,3-benzoxazol-5-yl]oxy}methyl)phenoxy]ethyl})amine {2-[4-(Chloromethyl)phenoxy]ethyl}dimethylamine hydrochloride (95 mg, 0.38 mmol, described in Bioorg. Med. Chem. Lett. 15 (2005) 2891-2893) and 2-(pyridin-3-yl)-1,3-benzoxazol-5-ol (98 mg, 0.38 mmol, prepared by Method 14) were dissolved in anhydrous N,N-dimethylformamide (5 mL) under nitrogen. Sodium hydride (60% in mineral oil, 46 mg, 1.14 mmol) was added and the mixture stirred at room temperature for 20 hours. Additional sodium hydride (circa 30 mg) was added and the reaction mixture stirred at room temperature for 16 hours. The reaction mixture was then quenched with water (5 mL) and 2 M sodium hydroxide (5 mL) and then extracted with ethyl acetate (3×10 mL). The combined organic extracts were

TABLE 42

| Ex. | Structure | Mol. Weight | IUPAC Name | LCMS data |
|---|---|---|---|---|
| 1 | 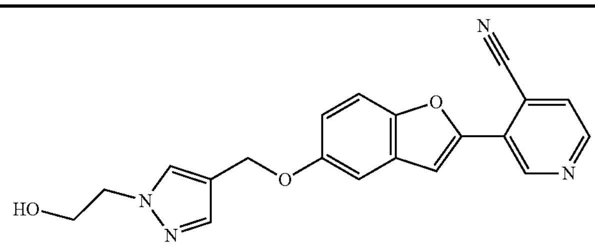 | 360.37 | 4-(5-{[1-(2-Hydroxyethyl)-1H-pyrazol-4-yl]methoxy}-1-benzofuran-2-yl)pyridine-3-carbonitrile | Tr(MET-uHPLC-AB-101) = 2.58 min, (ES⁺) (M + H)⁺ 361 |
| 2 | 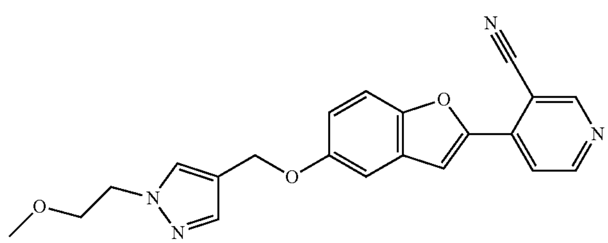 [SMILES: COCCn1cc(COc2ccc3oc(-c4ccncc4C#N)cc3c2)cn1] | 374.39 | 4-(5-{[1-(2-Methoxyethyl)-1H-pyrazol-4-yl]methoxy}-1-benzofuran-2-yl)pyridine-3-carbonitrile | Tr(MET-uHPLC-AB-101) = 3.04 min, (ES⁺) (M + H)⁺ 375 |

Method 42

Scheme for Method 42

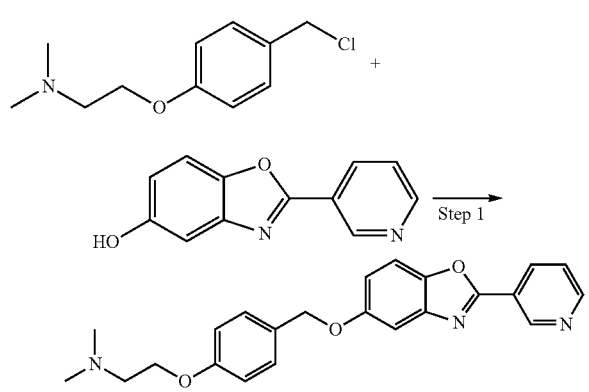

washed with brine (10 mL), dried, filtered and concentrated. Purification by preparative HPLC (acetonitrile/water+0.2% ammonium hydroxide) gave the title compound 9.2 mg (6% yield) as a white powder.

Example 1 Method 42: Dimethyl({2-[4-({[2-(pyridin-3-yl)-1,3-benzoxazol-5-yl]oxy}methyl)phenoxy]ethyl})amine $\delta_H$ NMR (500 MHz, DMSO) 9.33 (d, J=2.0 Hz, 1H), 8.80 (dd, J=4.8, 1.6 Hz, 1H), 8.51 (dt, J=8.0, 1.9 Hz, 1H), 7.72 (d, J=8.9 Hz, 1H), 7.65 (dd, J=8.0, 4.8 Hz, 1H), 7.47 (d, J=2.5 Hz, 1H), 7.41 (d, J=8.6 Hz, 2H), 7.10 (dd, J=8.9, 2.5 Hz, 1H), 6.96 (d, J=8.6 Hz, 2H), 5.10 (s, 2H), 4.04 (t, J=5.8 Hz, 2H), 2.61 (t, J=5.8 Hz, 2H), 2.20 (s, 6H). Tr(MET-uHPLC-AB-101)=1.91 min, (ES⁺) (M+H)⁺ 390.

The following example was prepared using Method 42 described above:

TABLE 43

| Ex. | Structure | Mol. Weight | IUPAC Name | LCMS data |
|---|---|---|---|---|
| 1 | 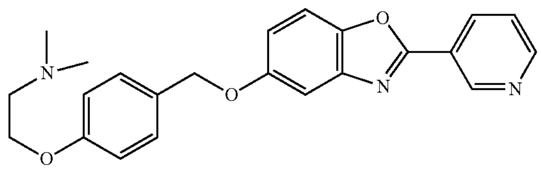 [SMILES: CN(C)CCOc1ccc(COc2ccc3oc(-c4cccnc4)nc3c2)cc1] | 389.45 | Dimethyl({2-[4-({[2-(pyridin-3-yl)-1,3-benzoxazol-5-yl]oxy}methyl)phenoxy]ethyl})amine | Tr(MET-uHPLC-AB-101) = 1.91 min, (ES⁺) (M + H)⁺ 390 |

Method 43

Scheme for Method 43

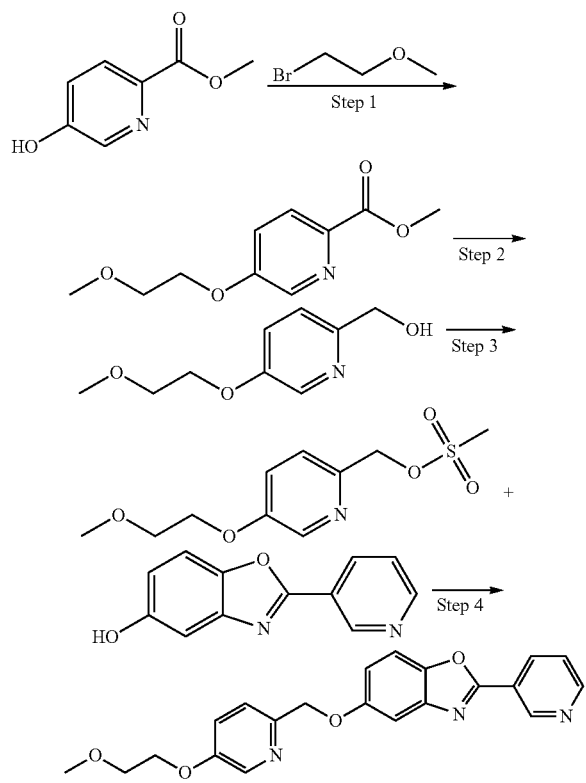

Step 1, Method 43: Methyl 5-(2-methoxyethoxy)pyridine-2-carboxylate

To sodium hydride (60% in mineral oil, 131 mg, 3.26 mmol) and methyl 5-hydroxypyridine-2-carboxylate (500 mg, 3.27 mmol) under nitrogen was added anhydrous N,N-dimethylformamide (5 mL) and the mixture stirred at room temperature for 15 minutes. A solution of 1-bromo-2-methoxyethane (477 mg, 3.43 mmol) in N,N-dimethylformamide (5 mL) was added slowly. The mixture was stirred at room temperature overnight and then heated at 65° C. for 3.5 hours. The mixture was diluted with water (50 mL) and extracted with ethyl acetate (2×50 mL). The combined organic extracts were dried over sodium sulfate, filtered and concentrated to give the title compound 688 mg (quantitative yield) as a light brown oil. $\delta_H$ NMR (500 MHz, DMSO) 8.39 (d, J=2.9 Hz, 1H), 8.03 (d, J=8.7 Hz, 1H), 7.53 (dd, J=8.7, 2.9 Hz, 1H), 4.31-4.23 (m, 2H), 3.84 (s, 3H), 3.72-3.66 (m, 2H), 3.31 (s, 3H). Tr(METCR1278)=1.25 min, (ES⁺) (M+H)⁺ 212.

Step 2, Method 43: [5-(2-Methoxyethoxy)pyridin-2-yl]methanol

Lithium aluminium hydride (2.4 M in tetrahydrofuran, 0.93 mL, 2.22 mmol) was added to a stirred solution of methyl 5-(2-methoxyethoxy)pyridine-2-carboxylate (148 mg, 0.53 mmol) in anhydrous tetrahydrofuran (35 mL) under nitrogen. The mixture was stirred at 0° C. for 30 minutes. The mixture was then quenched by cautious addition of water (2 mL) followed by saturated ammonium chloride solution (1 mL). The mixture was stirred at 0° C. for 5 minutes then diluted with water (100 mL), extracted with ethyl acetate (2×100 mL). The combined organic extracts were dried over sodium sulfate, filtered and concentrated to give the title compound 243 mg (63% yield) as a transparent oil. $\delta_H$ NMR (500 MHz, DMSO) 8.18 (d, J=2.7 Hz, 1H), 7.41-7.34 (m, 2H), 5.28 (t, J=5.7 Hz, 1H), 4.48 (d, J=5.1 Hz, 2H), 4.15 (dd, J=5.3, 3.7 Hz, 2H), 3.69-3.61 (m, 2H), 3.30 (s, 3H). Tr(METCR1278)=solvent front, (ES⁺) (M+H)⁺ 184.

Step 3, Method 43: [5-(2-Methoxyethoxy)pyridin-2-yl]methyl methanesulfonate

To a stirred solution of [5-(2-methoxyethoxy)pyridin-2-yl]methanol (88 mg, 0.48 mmol) in dichloromethane (3 mL) under nitrogen at 0° C., was added triethylamine (0.07 mL, 0.53 mmol) followed by methanesulfonyl chloride (0.04 mL, 0.5 mmol) and the mixture stirred at room temperature for 2 hours. The mixture was then partitioned between dichloromethane (10 mL) and water (10 mL). The organic extract was dried over sodium sulfate, filtered and concentrated to give the title compound 119 mg (95% yield) as a brown oil which was used in the next step.

Step 4, Method 43: 5-{[5-(2-Methoxyethoxy)pyridin-2-yl]methoxy}-2-(pyridin-3-yl)-1,3-benzoxazole To sodium hydride (60% in mineral oil, 21 mg, 0.53 mmol) under nitrogen, was added a solution of 2-(pyridin-3-yl)-1,3-benzoxazol-5-ol (102 mg, 0.48 mmol prepared by Method 14) in N,N-dimethylformamide (2 mL) and the mixture was stirred at room temperature for 30 minutes. After that, a solution of [5-(2-methoxyethoxy)pyridin-2-yl]methyl methanesulfonate (125 mg, 0.48 mmol) in N,N-dimethylformamide (1 mL) was added and the mixture was left stirring at room temperature overnight. Sodium hydride (60% in mineral oil, 21 mg, 0.53 mmol) and potassium iodide (8 mg, 0.05 mmol) were added and the mixture was stirred at room temperature for 2 hours. The mixture was then quenched with water (8 mL) extracted with ethyl acetate (2×5 mL) and the combined organic extracts washed with water (4×5 mL), dried over sodium sulfate, filtered and evaporated. Purification by FCC (silica, 0-10% methanol in dichloromethane) and recrystallisation from tert-butyl methyl ether (9 mL) gave the title compound 31 mg (17% yield) as a white powder.

Example 1, Method 43: 5-{[5-(2-Methoxyethoxy)pyridin-2-yl]methoxy}-2-(pyridin-3-yl)-1,3-benzoxazole $\delta_H$ NMR (500 MHz, DMSO) 9.33 (d, J=2.1 Hz, 1H), 8.80 (dd, J=4.8, 1.6 Hz, 1H), 8.51 (dt, J=8.0, 1.9 Hz, 1H), 8.31 (d, J=2.9 Hz, 1H), 7.74 (d, J=8.9 Hz, 1H), 7.65 (dd, J=8.0, 4.8 Hz, 1H), 7.55-7.42 (m, 3H), 7.14 (dd, J=8.9, 2.5 Hz, 1H), 5.19 (s, 2H), 4.23-4.15 (m, 2H), 3.70-3.63 (m, 2H), 3.31 (s, 3H). Tr(MET-uHPLC-AB-101)=2.61 min, (ES$^+$) (M+H)$^+$ 378.

The following example was prepared using Method 43 described above:

Step 1, Method 44: 4-(5-{[1-(2-Oxoethyl)-1H-pyrazol-4-yl]methoxy}-1-benzofuran-2-yl)pyridine-3-carbonitrile To a solution of 4-(5-{[1-(2-hydroxyethyl)-1H-pyrazol-4-yl]methoxy}-1-benzofuran-2-yl)pyridine-3-carbonitrile (48 mg, 0.13 mmol, prepared by Method 41) in dichloromethane (10 mL) was added 1,1,1-triacetoxy-1,1-dihydro-1,2-benziodoxol-3(1H)-one (57 mg, 0.13 mmol) and the mixture was stirred for 4 hours at room temperature. 1,1,1-Triacetoxy-1,1-dihydro-1,2-benziodoxol-3(1H)-one (57 mg, 0.13 mmol) was added and stirring was continued for 12 hours. 1,1,1-Triacetoxy-1,1-dihydro-1,2-benziodoxol-3 (1H)-one (57 mg, 0.13 mmol) was added and the mixture was stirred for 2 hours. The mixture was diluted with ethyl acetate (200 mL) then washed with saturated aqueous sodium bicarbonate solution, 10% aqueous sodium thiosulfate solution (50 mL, 1:1) and brine (50 mL). The organic phase was dried over magnesium sulfate, filtered and concentrated. Purification by FCC (silica, 0-10% methanol in dichloromethane)

TABLE 44

| Ex | Structure | Mol. Weight | IUPAC Name | LCMS data |
|---|---|---|---|---|
| 1 | 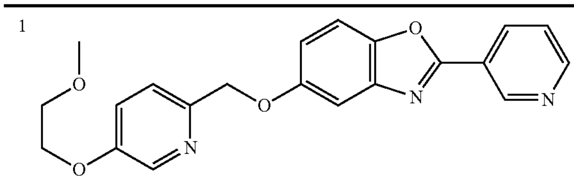 | 377.39 | 5-{[5-(2-Methoxyethoxy)pyridin-2-yl]methoxy}-2-(pyridin-3-yl)-1,3-benzoxazole | Tr(MET-uHPLC-AB-101) = 2.61 min, (ES$^+$) (M + H)$^+$ 378 |

Method 44
Scheme for Method 44

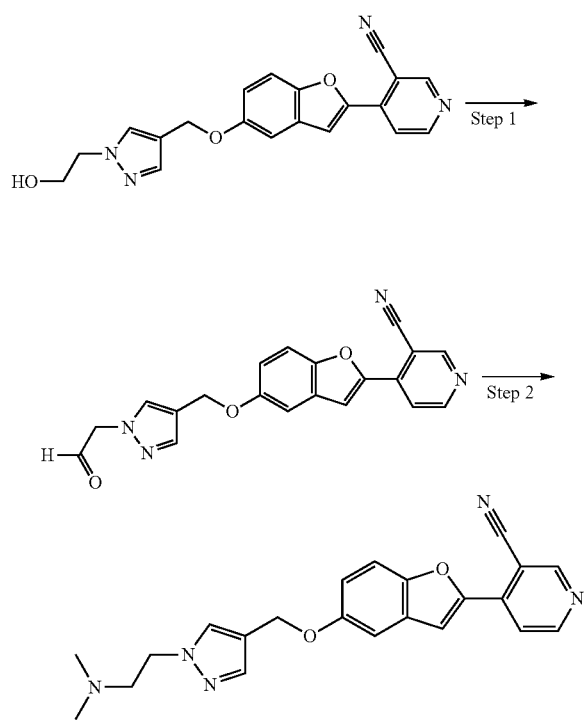

gave the title compound 43 mg (90% yield) as a colourless resin. Tr(METCR1278)=1.62 min, (ES$^+$) (M+H)$^+$ 377.

Step 2, Method 44: 4-[5-({1-[2-(Dimethylamino)ethyl]-1H-pyrazol-4-yl}methoxy)-1-benzofuran-2-yl]pyridine-3-carbonitrile To a solution of 4-(5-{[1-(2-oxoethyl)-1H-pyrazol-4-yl]methoxy}-1-benzofuran-2-yl)pyridine-3-carbonitrile (40 mg, 0.11 mmol), 2 M dimethylamine in methanol (0.170 mL, 0.34 mmol) and acetic acid (50 μL, 0.87 mmol) in dichloromethane was added sodium triacetoxyborohydride (80 mg, 0.38 mmol) and the mixture was stirred at room temperature for 18 hours. The mixture was partitioned between ethyl acetate (150 mL) and saturated aqueous sodium bicarbonate solution (50 mL). After separation the organic layer was washed with brine (50 mL), dried over magnesium sulfate, filtered and concentrated. Purification by preparative HPLC (acetonitrile/water+0.2% ammonium hydroxide) gave the title compound 15.8 mg (37% yield) as a yellow gum.

Example 1, Method 44: 4-[5-({1-[2-(Dimethylamino)ethyl]-1H-pyrazol-4-yl}methoxy)-1-benzofuran-2-yl]pyridine-3-carbonitrile $\delta_H$ NMR (500 MHz, DMSO) 9.12 (s, 1H), 8.92 (d, J=5.4 Hz, 1H), 8.07 (d, J=5.4 Hz, 1H), 7.95 (s, 1H), 7.87 (s, 1H), 7.62 (d, J=9.0 Hz, 1H), 7.53 (s, 1H), 7.46 (d, J=2.6 Hz, 1H), 7.11 (dd, J=9.0, 2.6 Hz, 1H), 5.00 (s, 2H), 4.17 (t, J=6.5 Hz, 2H), 2.62 (t, J=6.5 Hz, 2H), 2.15 (s, 6H). Tr(MET-uHPLC-AB-101)=1.85 min, (ES$^+$) (M+H)$^+$ 388.

The following example was prepared using Method 44 described above:

TABLE 45

| Ex. | Structure | Mol. Weight | IUPAC Name | LCMS data |
|---|---|---|---|---|
| 1 | 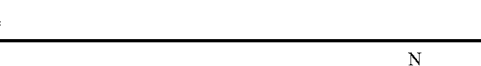 | 387.43 | 4-[5-({1-[2-(Dimethylamino)ethyl]-1H-pyrazol-4-yl}methoxy)-1-benzofuran-2-yl]pyridine-3-carbonitrile | Tr(MET-uHPLC-AB-101) = 1.85 min, (ES⁺) (M + H)⁺ 388 |

Method 45

Scheme for Method 45

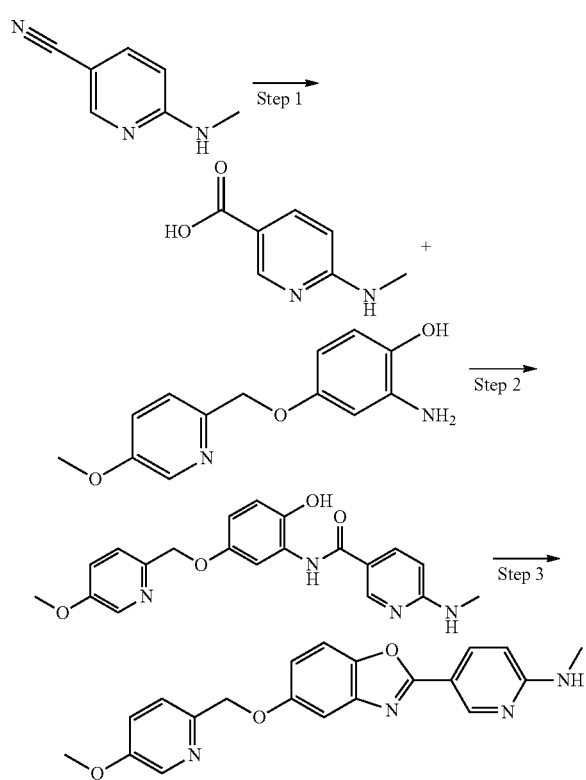

Step 1, Method 45: 6-(Methylamino)pyridine-3-carboxylic acid

To a solution of 6-(methylamino)pyridine-3-carbonitrile (1.0 g, 7.51 mmol) in ethanol (20 mL) and tetrahydrofuran (20 mL) was added sodium hydroxide (2.4 g, 60.0 mmol) and the mixture was stirred under reflux for 16 hours. After cooling the solid was collected, washed with ethyl acetate (50 mL) and dried under vacuum. The solid was taken up in water (30 mL) and then acidified with 1 N hydrochloric acid to pH 3. After dilution with tetrahydrofuran (300 mL) and washing with brine (50 mL), the solution was dried over magnesium sulfate, filtered and concentrated to give the title compound 1.2 g (84% yield, 80% NMR purity) as an off-white solid. $\delta_H$ NMR (500 MHz, DMSO) 12.80 (s, 1H), 8.44 (s, 2H), 7.93 (d, J=8.7 Hz, 1H), 6.77 (d, J=8.6 Hz, 1H), 2.92 (s, 3H).

Steps 2 and 3, Method 45: 5-{5-[(5-Methoxypyridin-2-yl)methoxy]-1,3-benzoxazol-2-yl}-N-methyl-pyridin-2-amine To a solution of 2-amino-4-[(5-methoxypyridin-2-yl)methoxy]phenol (50% pure, 125 mg, 0.25 mmol, prepared by Method 33) and 6-(methylamino)pyridine-3-carboxylic acid (80% pure, 63 mg, 0.33 mmol) in pyridine (2 mL) was added 1-(3-(dimethylamino)-propyl)-3-ethylcarbodiimide hydrochloride (70 mg, 0.37 mmol) and the mixture was stirred at room temperature for 18 hours. The solvent was removed in vacuo and the residue was taken up in ethyl acetate (200 mL). The solution was washed with water (50 mL) and brine (50 mL). The organic extract was dried over magnesium sulfate, filtered and concentrated. This was taken up in acetic acid (3 mL) and heated in a microwave at 200° C. for 40 minutes. After cooling the volatiles were removed in vacuo and the residue was partitioned between ethyl acetate (200 mL) and saturated aqueous sodium bicarbonate solution (100 mL). The organic layer was washed with brine (50 mL), dried over magnesium sulfate, filtered and then pre-absorbed onto a small amount of silica. Purification by FCC (silica, 0-10% methanol in dichloromethane) and preparative HPLC (acetonitrile/water) gave the title compound 9.9 mg (17% yield) as an off-white solid.

Example 1, Method 45: 5-{5-[(5-Methoxypyridin-2-yl)methoxy]-1,3-benzoxazol-2-yl}-N-methylpyridin-2-amine $\delta_H$ NMR (500 MHz, DMSO) 8.77 (d, J=2.2 Hz, 1H), 8.30 (d, J=2.9 Hz, 1H), 8.03 (d, J=7.6 Hz, 1H), 7.59 (d, J=8.8 Hz, 1H), 7.51 (d, J=8.6 Hz, 1H), 7.42 (dd, J=8.6, 2.9 Hz, 1H), 7.39-7.34 (m, 1H), 7.33 (d, J=2.5 Hz, 1H), 6.99 (dd, J=8.8, 2.5 Hz, 1H), 6.60 (d, J=8.9 Hz, 1H), 5.15 (s, 2H), 3.83 (s, 3H), 2.86 (d, J=4.8 Hz, 3H). Tr(MET-uHPLC-AB-101)= 1.98 min, (ES⁺) (M+H)⁺ 363.

The following examples were prepared using Method 45 described above:

TABLE 46

| Ex. | Structure | Mol. Weight | IUPAC Name | LCMS data |
|---|---|---|---|---|
| 1 | 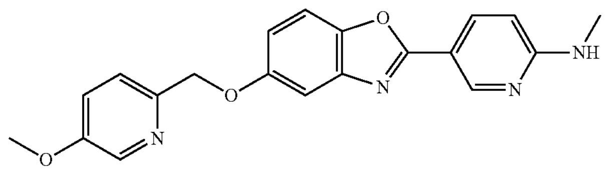 | 362.38 | 5-{5-[(5-Methoxypyridin-2-yl)methoxy]-1,3-benzoxazol-2-yl}-N-methylpyridin-2-amine | Tr(MET-uHPLC-AB-101) = 1.98 min, (ES+) (M + H)+ 363 |
| 2 | 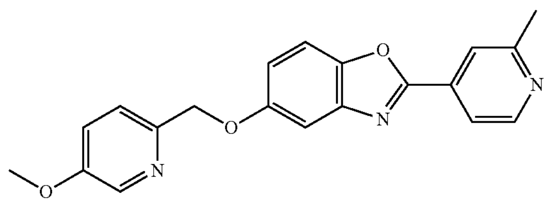 | 347.37 | 5-[(5-Methoxypyridin-2-yl)methoxy]-2-(2-methylpyridin-4-yl)-1,3-benzoxazole | Tr(MET-uHPLC-AB-101) = 2.4 min, (ES+) (M + H)+ 348 |
| 3 | 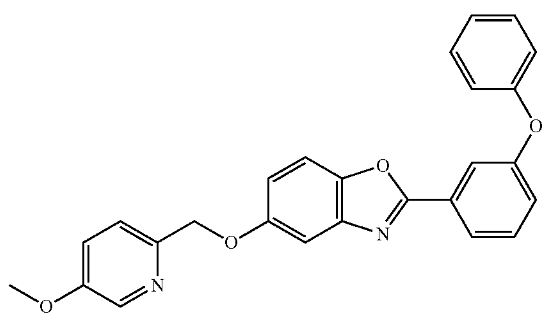 [SMILES: COc1ccc(COc2ccc3oc(-c4cccc(Oc5ccccc5)c4)nc3c2)nc1] | 424.46 | 5-[(5-Methoxypyridin-2-yl)methoxy]-2-(3-phenoxyphenyl)-1,3-benzoxazole | Tr(MET-uHPLC-AB-101) = 4.47 min, (ES+) (M + H)+ 425 |
| 4 | 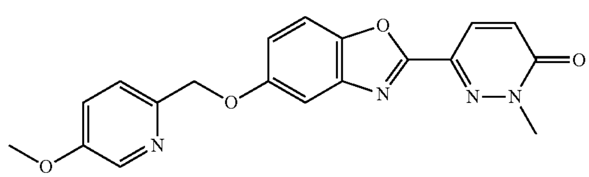 | 364.36 | 6-{5-[(5-Methoxypyridin-2-yl)methoxy]-1,3-benzoxazol-2-yl}-2-methyl-2,3-dihydropyridazin-3-one | Tr(MET-uHPLC-AB-101) = 2.58 min, (ES+) (M + H)+ 365 |
| 5 | 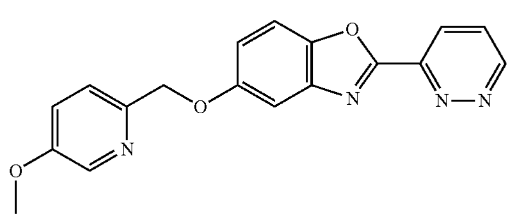 [SMILES: COc1ccc(COc2ccc3oc(-c4cccnn4)nc3c2)nc1] | 334.34 | 5-[(5-Methoxypyridin-2-yl)methoxy]-2-(pyridazin-3-yl)-1,3-benzoxazole | Tr(MET-uHPLC-AB-101) = 2.21 min, (ES+) (M + H)+ 335 |
| 6 | 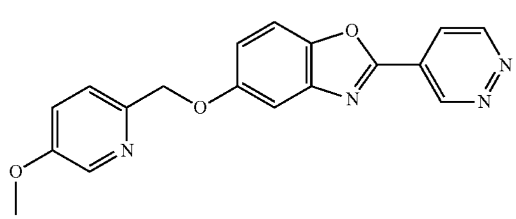 [SMILES: COc1ccc(COc2ccc3oc(-c4ccnnc4)nc3c2)nc1] | 334.34 | 5-[(5-Methoxypyridin-2-yl)methoxy]-2-(pyridazin-4-yl)-1,3-benzoxazole | Tr(MET-uHPLC-AB-101) = 2.33 min, (ES+) (M + H)+ 335 |

Method 46
Scheme for Method 46

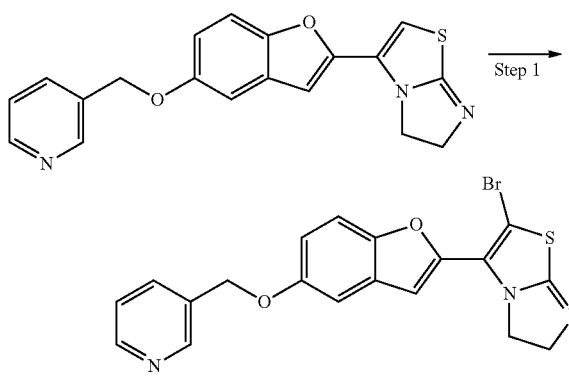

Method 47
Scheme for Method 47

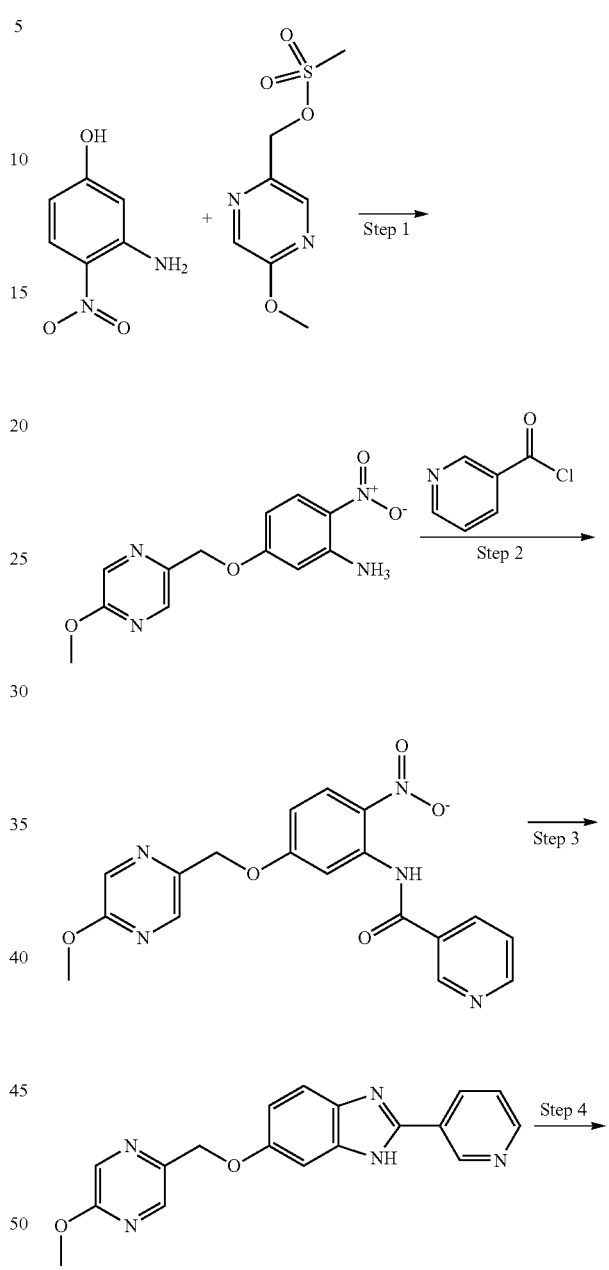

Step 1, Method 46: 3-{[(2-{5H,6H-Imidazo[2,1-b][1,3]thiazol-3-yl}-1-benzofuran-5-yl)oxy]methyl}pyridine To a solution of 3-{[(2-{5H,6H-imidazo[2,1-b][1,3]thiazol-3-yl}-1-benzofuran-5-yl)oxy]methyl}pyridine (30 mg, 0.086 mmol, prepared by Method 37) in dichloromethane at 0° C. was added 0.43 M bromine in dichloromethane (0.2 mL, 0.086 mmol). After removal of the ice-bath the mixture was stirred for 1 hour at room temperature before being diluted with ethyl acetate. The solid was collected by filtration and then dried under vacuum. Purification by preparative HPLC (acetonitrile/water+0.2% ammonium hydroxide) gave the title compound 9.9 mg (27% yield) as an off-white solid.

Example 1, Method 46: 3-{[(2-{2-Bromo-5H,6H-imidazo[2,1-b][1,3]thiazol-3-yl}-1-benzofuran-5-yl)oxy]methyl}pyridine $\delta_H$ NMR (500 MHz, DMSO) 8.70 (d, J=1.8 Hz, 1H), 8.55 (dd, J=4.8, 1.6 Hz, 1H), 7.94-7.85 (m, 1H), 7.57 (d, J=9.0 Hz, 1H), 7.49-7.40 (m, 2H), 7.36 (d, J=2.6 Hz, 1H), 7.11 (dd, J=9.0, 2.6 Hz, 1H), 5.20 (s, 2H), 4.15-4.00 (m, 4H). Tr(MET-uHPLC-AB-101)=1.36 min, (ES$^+$) (M+H)$^+$ 428/430.

The following example was prepared using Method 46 described above:

TABLE 47

| Ex. | Structure | Mol. Weight | IUPAC Name | LCMS data |
|---|---|---|---|---|
| 1 | 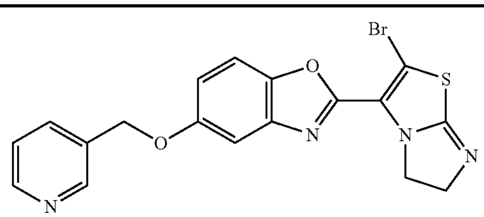 | 428.30 | 3-{[(2-{2-Bromo-5H,6H-imidazo[2,1-b][1,3]thiazol-3-yl}-1-benzofuran-5-yl)oxy]methyl}pyridine | Tr(MET-uHPLC-AB-101) = 1.36 min, (ES$^+$) (M + H)$^+$ 428/430 |

-continued

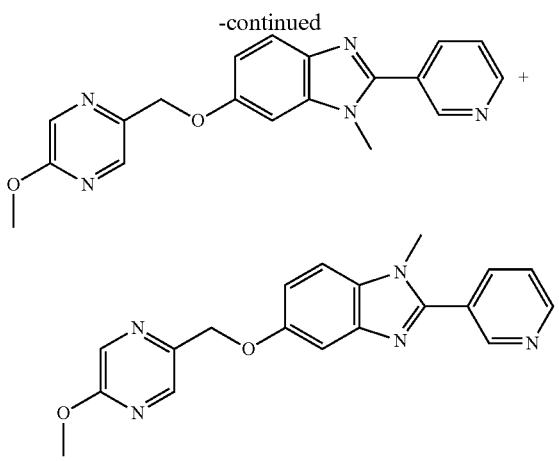

Step 1, Method 47: 5-[(5-Methoxypyrazin-2-yl)methoxy]-2-nitroaniline

To a stirred solution of 3-amino-4-nitrophenol (220 mg, 1.43 mmol) in N,N-dimethylformamide (5 mL) under nitrogen was added potassium tert-butoxide (160 mg, 1.42 mmol) and the mixture stirred for 5 minutes at room temperature. A solution of (5-methoxypyrazin-2-yl)methyl methanesulfonate (311 mg, 1.43 mmol, prepared by Method 20) in N,N-dimethylformamide (3 mL) was added and the mixture was stirred at room temperature for 16 hours. The mixture was diluted with water (100 mL) and extracted with ethyl acetate (2×100 mL). The combined organic extracts were washed with 0.2 M sodium hydroxide (3×50 mL), dried over sodium sulfate, filtered and concentrated to give the title compound 213 mg (54% yield) as a bright yellow solid. $\delta_H$ NMR (500 MHz, DMSO) 8.39-8.30 (m, 2H), 7.53 (d, J=3.0 Hz, 1H), 7.28 (s, 2H), 7.24 (dd, J=9.2, 3.0 Hz, 1H), 7.01 (d, J=9.2 Hz, 1H), 5.10 (s, 2H), 3.92 (s, 3H). Tr(METCR1278)=1.72 min, (ES$^+$) (M+H)$^+$ 277.

Step 2, Method 47: N-{5-[(5-Methoxypyrazin-2-yl)methoxy]-2-nitrophenyl}pyridine-3-carboxamide To a stirred solution of 5-[(5-methoxypyrazin-2-yl)methoxy]-2-nitroaniline (213 mg, 0.77 mmol) in tetrahydrofuran (8 mL), was added diisopropylethylamine (0.16 mL, 0.92 mmol) followed by pyridine-3-carbonyl chloride hydrochloride (144 mg, 0.81 mmol). The mixture was stirred at room temperature overnight. The mixture was diluted with water (30 mL) and saturated aqueous sodium bicarbonate solution (10 mL) and extracted with ethyl acetate (2×50 mL). The combined organic extracts were dried over sodium sulfate, filtered and concentrated to give the title compound 239 mg (81% yield) as a bright yellow solid. $\delta_H$ NMR (500 MHz, DMSO) 10.74 (s, 1H), 9.10 (d, J=2.1 Hz, 1H), 8.73 (d, J=4.6 Hz, 1H), 8.42 (d, J=1.2 Hz, 1H), 8.35 (d, J=1.4 Hz, 1H), 8.27 (dt, J=7.9, 1.9 Hz, 1H), 7.65 (d, J=8.9 Hz, 1H), 7.61 (s, 1H), 7.54 (dd, J=8.6, 4.0 Hz, 1H), 7.39 (d, J=8.7 Hz, 1H), 5.25 (s, 2H), 3.93 (s, 3H). Tr(METCR1278)=1.72 min, (ES$^+$) (M+H)$^+$ 382.

Step 3, Method 47: 5-[(5-Methoxypyrazin-2-yl)methoxy]-2-(pyridin-3-yl)-1H-1,3-benzodiazole To a stirred suspension of N-{5-[(5-methoxypyrazin-2-yl)methoxy]-2-nitrophenyl}pyridine-3-carboxamide (239 mg, 0.63 mmol) in acetic acid (4 mL) and ethanol (2 mL), was added iron powder (262 mg, 4.70 mmol). The mixture was stirred at 78° C. for 1.5 hours. The mixture was filtered through glass fibre filter paper and the filtrate was concentrated in vacuo. Purification by FCC (silica, 0-10% methanol in dichloromethane) and preparative HPLC (acetonitrile/water+0.2% ammonium hydroxide) gave the title compound 52 mg (25% yield) as an off-white crystalline solid. $\delta_H$ NMR (500 MHz, DMSO) 12.97 (s, 1H), 9.30 (d, J=1.9 Hz, 1H), 8.65 (d, J=4.8 Hz, 1H), 8.44 (d, J=8.0 Hz, 1H), 8.41 (s, 1H), 8.35 (s, 1H), 7.60-7.51 (m, 2H), 7.24 (s, 1H), 6.96 (dd, J=8.7, 2.3 Hz, 1H), 5.21 (s, 2H), 3.92 (s, 3H). Tr(MET-uHPLC-AB-101)=1.74 min, (ES$^+$) (M+H)$^+$ 334.

Step 4, Method 47: 6-[(5-Methoxypyrazin-2-yl)methoxy]-1-methyl-2-(pyridin-3-yl)-1H-1,3-benzodiazole and 5-[(5-Methoxypyrazin-2-yl)methoxy]-1-methyl-2-(pyridin-3-yl)-1H-1,3-benzodiazole 5-[(5-Methoxypyrazin-2-yl)methoxy]-2-(pyridin-3-yl)-1H-1,3-benzodiazole (40 mg, 0.12 mmol) was dissolved in acetone (1 mL) under nitrogen, and powdered potassium hydroxide (34 mg, 0.6 mmol) was added, followed by a solution of methyl iodide (0.007 mL, 0.12 mmol) in acetone (1 mL). The mixture was stirred at room temperature for 2 hours. The mixture was diluted with water (20 mL) and extracted with ethyl acetate (2×20 mL). The combined organic extracts were dried over sodium sulfate, filtered and concentrated. Purification by preparative HPLC (acetonitrile/water+0.1% formic acid) gave 5-[(5-methoxypyrazin-2-yl)methoxy]-1-methyl-2-(pyridin-3-yl)-1H-1,3-benzodiazole 5.8 mg (14% yield) and 6-[(5-methoxypyrazin-2-yl)methoxy]-1-methyl-2-(pyridin-3-yl)-1H-1,3-benzodiazole 10.1 mg (24% yield), as off-white powders.

Example 1, Method 47: 5-[(5-Methoxypyrazin-2-yl)methoxy]-1-methyl-2-(pyridin-3-yl)-1H-1,3-benzodiazole $\delta_H$ NMR (500 MHz, DMSO) 9.04 (s, 1H), 8.73 (d, J=3.8 Hz, 1H), 8.40 (d, J=1.0 Hz, 1H), 8.34 (d, J=1.3 Hz, 1H), 8.26 (dt, J=7.9, 1.7 Hz, 1H), 7.60 (dd, J=7.9, 4.6 Hz, 1H), 7.56 (d, J=8.8 Hz, 1H), 7.37 (d, J=2.3 Hz, 1H), 7.05 (dd, J=8.8, 2.3 Hz, 1H), 5.21 (s, 2H), 3.92 (s, 3H), 3.88 (s, 3H). Tr(MET-uHPLC-AB-101)=1.70 min, (ES$^+$) (M+H)$^+$ 348.

Example 2, Method 47: 6-[(5-Methoxypyrazin-2-yl)methoxy]-1-methyl-2-(pyridin-3-yl)-1H-1,3-benzodiazole $\delta_H$ NMR (500 MHz, DMSO) 9.04 (s, 1H), 8.73 (s, 1H), 8.45-8.41 (m, 1H), 8.35 (d, J=1.3 Hz, 1H), 8.25 (d, J=7.9 Hz, 1H), 7.64-7.58 (m, 2H), 7.38 (d, J=2.3 Hz, 1H), 6.98 (dd, J=8.7, 2.4 Hz, 1H), 5.25 (s, 2H), 3.93 (s, 3H), 3.88 (s, 3H). Tr(MET-uHPLC-AB-101)=1.74 min, (ES$^+$) (M+H)$^+$ 348.

The following examples were prepared using Method 47 described above:

TABLE 48

| Ex. | Structure | Mol. Weight | IUPAC Name | LCMS data |
|---|---|---|---|---|
| 1 | 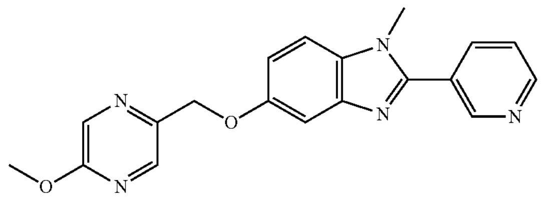 [SMILES: COc1cnc(COc2ccc3c(c2)nc(-c2cccnc2)n3C)cn1] | 347.37 | 5-[(5-Methoxypyrazin-2-yl)methoxy]-1-methyl-2-(pyridin-3-yl)-1H-1,3-benzodiazole | Tr(MET-uHPLC-AB-101) = 1.7 min, (ES+) (M + H)+ 348 |
| 2 | 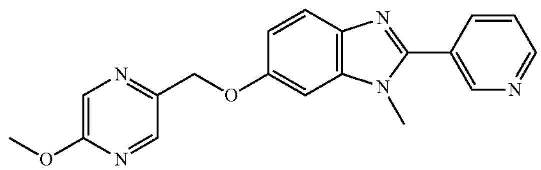 [SMILES: COc1cnc(COc2ccc3nc(-c4cccnc4)n(C)c3c2)cn1] | 347.37 | 6-[(5-Methoxypyrazin-2-yl)methoxy]-1-methyl-2-(pyridin-3-yl)-1H-1,3-benzodiazole | Tr(MET-uHPLC-AB-101) = 1.74 min, (ES+) (M + H)+ 348 |
| 3 | 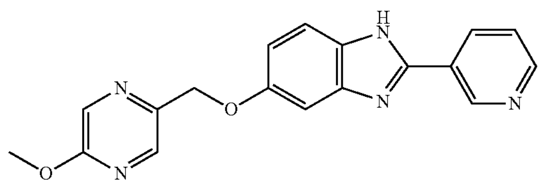 [SMILES: COc1cnc(COc2ccc3[nH]c(-c4cccnc4)nc3c2)cn1] | 333.34 | 5-[(5-Methoxypyazin-2-yl)methoxy]-2-methyl-2-(pyridin-3-yl)-1H-1,3-benzodiazole | Tr(MET-uHPLC-AB-101) = 1.74 min, (ES+) (M + H)+ 334 |

Method 48
Scheme for Method 48

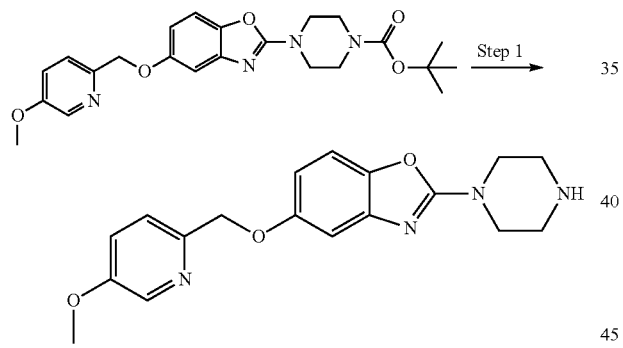

Step 1, Method 48: 5-[(5-Methoxypyridin-2-yl)methoxy]-2-(piperazin-1-yl)-1,3-benzoxazole tert-Butyl 4-{6[(5-methoxypyridin-2-yl)methoxy]-1,3-benzoxazol-2-yl}piperazine-1-carboxylate (50 mg, 0.11 mmol, prepared by Method 38) was stirred in 4 M hydrogen chloride in 1,4-dioxane (1 mL) for 2 hours. The reaction mixture was diluted with water (10 mL) and solid sodium bicarbonate was added portionwise (until pH 8). The solution was extracted with dichloromethane (3×10 mL), and the combined organic extracts were washed with brine (10 mL), dried over sodium sulfate, filtered and concentrated. Purification by preparative HPLC (acetonitrile/water+0.2% ammonium hydroxide) gave the title compound 11.3 mg (29% yield) as a white solid.

Example 1, Method 48: 5-[(5-Methoxypyridin-2-yl)methoxy]-2-(piperazin-1-yl)-1,3-benzoxazole $\delta_H$ NMR (500 MHz, DMSO) 8.28 (d, J=2.9 Hz, 1H), 7.47 (d, J=8.6 Hz, 1H), 7.42 (dd, J=8.6, 2.9 Hz, 1H), 7.26 (d, J=8.7 Hz, 1H), 6.93 (d, J=2.5 Hz, 1H), 6.64 (dd, J=8.7, 2.6 Hz, 1H), 5.08 (s, 2H), 3.84 (s, 3H), 3.53-3.46 (m, 4H), 2.82-2.73 (m, 4H). Tr(MET-uHPLC-AB-101)=1.33 min, (ES+) (M+H)+ 341.

The following example was prepared using Method 48 described above:

TABLE 49

| Ex. | Structure | Mol. Weight | IUPAC Name | LCMS data |
|---|---|---|---|---|
| 1 | 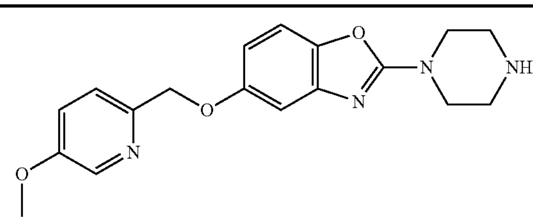 | 340.38 | 5-[(5-Methoxypyridin-2-yl)methoxy]-2-(piperazin-1-yl)-1,3-benzoxazole | Tr(MET-uHPLC-AB-101) = 1.33 min, (ES+) (M + H)+ 341 |

Method 49
Scheme for Method 49

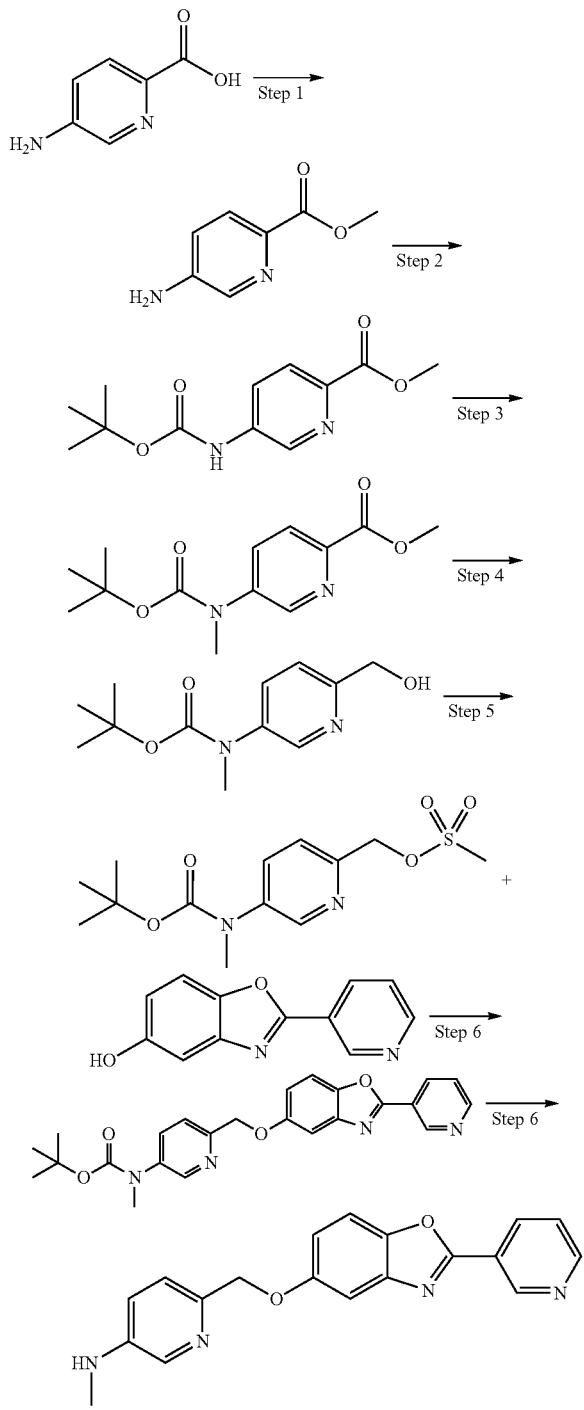

Step 1, Method 49: Methyl 5-aminopyridine-2-carboxylate

5-Aminopyridine-2-carboxylic acid (2.00 g, 14.5 mmol) was dissolved in anhydrous methanol (20 mL) and cooled to 0° C. Thionyl chloride (3.15 mL, 43.4 mmol) was added drop-wise over 5 minutes and the mixture allowed to warm to room temperature then heated to reflux for 24 hours. The reaction mixture was concentrated, partitioned between ethyl acetate (30 mL) and saturated aqueous sodium bicarbonate solution (30 mL). The mixture was sonicated, the layers separated and the aqueous layer extracted with ethyl acetate (2×15 mL). The combined organic extracts were washed with brine (20 mL), dried over magnesium sulfate, filtered and concentrated to give the title compound 850 mg (39% yield) as an off-white powder. $\delta_H$ NMR (500 MHz, DMSO) 7.97 (d, J=2.7 Hz, 1H), 7.74 (d, J=8.6 Hz, 1H), 6.91 (dd, J=8.6, 2.7 Hz, 1H), 6.18 (s, 2H), 3.76 (s, 3H).

Step 2, Method 49: Methyl 5-{[(tert-butoxy)carbonyl]amino}pyridine-2-carboxylate Methyl 5-aminopyridine-2-carboxylate (850 mg, 5.59 mmol), di-tert-butyl dicarbonate (1.34 g, 6.15 mmol) and 4-dimethylaminopyridine (68 mg, 0.56 mmol) were suspended in dichloromethane (10 mL) and stirred at room temperature for 20 hours. The reaction mixture was concentrated to give a white powder. The powder was suspended in ethyl acetate (20 mL), sonicated, heated to boiling and then filtered. The filtrate was diluted with additional ethyl acetate (20 mL) and loaded onto silica. Purification by FCC (silica, 18-100% ethyl acetate in heptane) gave the crude title compound 862 mg (51% yield) as a white powder which was used in the next step without further purification. $\delta_H$ NMR (500 MHz, DMSO) 10.01 (s, 1H), 8.71 (d, J=2.3 Hz, 1H), 8.06 (dd, J=8.7, 2.4 Hz, 1H), 8.00 (d, J=8.6 Hz, 1H), 3.83 (s, 3H), 1.49 (s, 9H). Tr(METCR1278)=1.64 min, (ES+) (M+H)+ 253, 83%.

Step 3, Method 49: Methyl 5-{[(tert-butoxy)carbonyl](methyl)amino}pyridine-2-carboxylate Methyl 5-{[(tert-butoxy)carbonyl]amino}pyridine-2-carboxylate (406 mg, 1.34 mmol) was dissolved in anhydrous N,N-dimethylformamide (5 mL) and cooled to 0° C. Sodium hydride (60% in mineral oil, 136 mg, 3.34 mmol) was added and the mixture stirred for 15 minutes. Iodomethane (100 µL, 1.60 mmol) was added and the mixture stirred at room temperature for 18 hours. The reaction mixture was quenched by the addition of water (5 mL) and extracted with ethyl acetate (2×15 mL). The combined organic extracts were washed with brine (3×10 mL), dried over magnesium sulfate, filtered and concentrated. Purification by FCC (silica, eluent: 50-75% ethyl acetate in heptane) gave the title compound 180 mg (51% yield) as a yellow oil. $\delta_H$ NMR (500 MHz, DMSO) 8.70 (d, J=2.5 Hz, 1H), 8.03 (d, J=8.5 Hz, 1H), 7.91 (dd, J=8.5, 2.6 Hz, 1H), 3.87 (s, 3H), 3.27 (s, 3H), 1.43 (s, 9H). Tr(METCR1278)=1.68 min, (ES+) (M+H)+ 267.

Step 4, Method 49: tert-Butyl N-[6-(hydroxymethyl)pyridin-3-yl]-N-methylcarbamate Methyl 5-{[(tert-butoxy)carbonyl](methyl)amino}pyridine-2-carboxylate (170 mg, 0.64 mmol) was dissolved in anhydrous tetrahydrofuran (10 mL) under nitrogen and cooled to 0° C. 1.2 M diisobutylaluminum hydride in toluene (1.06 mL, 1.28 mmol) was added and the mixture stirred for 1.5 hours. 1.2 M diisobutylaluminum hydride in toluene (0.13 mL) was added and the mixture stirred at room temperature for 16 hours. The reaction mixture was quenched with saturated aqueous Rochelle's salt solution (20 mL) and extracted with ethyl acetate (2×20 mL). The combined organic extracts were washed with brine (10 mL), dried over magnesium sulfate, filtered and concentrated to give the title compound 120 mg (63% yield) as a colourless gum. δ_H NMR (500 MHz, DMSO) 8.41 (d, J=2.5 Hz, 1H), 7.71 (dd, J=8.4, 2.6 Hz, 1H), 7.43 (d, J=8.4 Hz, 1H), 5.40 (t, J=5.7 Hz, 1H), 4.53 (d, J=5.2 Hz, 2H), 3.19 (s, 3H), 1.39 (s, 9H). Tr(METCR1278)=1.68 min, (ES+) (M+H)+ 239, 81%.

Step 5, Method 49: tert-Butyl N-{6-[(methanesulfonyloxy)methyl]pyridin-3-yl}-N-methylcarbamate tert-Butyl N-[6-(hydroxymethyl)pyridin-3-yl]-N-methylcarbamate (120 mg, 0.4 mmol) was dissolved in dichloromethane (3 mL) under nitrogen and cooled to 0° C. Triethylamine (84 μL, 0.60 mmol) and methanesulfonyl chloride (34 μL, 0.44 mmol) were added and the mixture stirred and warmed to room temperature over 18 hours. The reaction mixture was diluted with dichloromethane (5 mL) and washed with water (5 mL) and brine (5 mL). The organic layer was dried over magnesium sulfate, filtered and concentrated to give the crude title compound 124 mg (42% yield) as an orange oil. The product also contained 47% alkyl chloride. Tr(METCR1278)=1.69 min, (ES+) (M+H)+ 317, 43% (mesylate). Tr(METCR1278)=1.82 min, (ES+) (M+H)+ 257/259, 37% (chloride).

Step 6, Method 49: tert-Butyl N-methyl-N-[5-({[2-(pyridin-3-yl)-1,3-benzoxazol-5-yl]oxy}methyl)pyridin-2-yl]carbamate A mixture of tert-butyl N-{6-[(methanesulfonyloxy)methyl]pyridin-3-yl}-N-methylcarbamate and tert-butyl N-[6-(chloromethyl)pyridin-3-yl]-N-methylcarbamate (43%+37%, 120 mg, 0.34 mmol total alkylating agent) and 2-(pyridin-3-yl)-1,3-benzoxazol-5-ol (90 mg, 0.34 mmol, prepared by Method 14) were dissolved in anhydrous N,N-dimethylformamide (5 mL) under nitrogen and cooled to 0° C. Sodium hydride (60% in mineral oil, 41 mg, 1.04 mmol) was added and the mixture stirred and warmed to room temperature over 18 hours. The reaction mixture was quenched with water (5 mL) and extracted with ethyl acetate (3×15 mL). The combined ethyl acetate extracts were washed with brine (3×10 mL), dried over magnesium sulfate, filtered and concentrated. Purification by FCC (silica, 12-100% ethyl acetate in heptane) gave the title compound 52 mg (31% yield) as a tan powder. δ_H NMR (500 MHz, DMSO) 9.33 (d, J=1.6 Hz, 1H), 8.80 (dd, J=4.8, 1.6 Hz, 1H), 8.56 (d, J=2.5 Hz, 1H), 8.51 (dt, J=8.0, 1.9 Hz, 1H), 7.78 (dd, J=8.4, 2.6 Hz, 1H), 7.75 (d, J=8.9 Hz, 1H), 7.68-7.62 (m, 1H), 7.56 (d, J=8.4 Hz, 1H), 7.50 (d, J=2.5 Hz, 1H), 7.16 (dd, J=8.9, 2.6 Hz, 1H), 5.25 (s, 2H), 3.22 (s, 3H), 1.40 (s, 9H). Tr(METCR1278)=2.05 min, (ES+) (M+H)+ 433, 80%.

Step 7, Method 49: N-Methyl-6-({[2-(pyridin-3-yl)-1,3-benzoxazol-5-yl]oxy}methyl)pyridin-3-amine tert-Butyl N-methyl-N-[5-({[2-(pyridin-3-yl)-1,3-benzoxazol-5-yl]oxy}methyl)pyridin-2-yl]carbamate (52 mg, 0.12 mmol) was dissolved in 4 M hydrogen chloride in 1,4-dioxane (1 mL) and water (0.1 mL). The mixture was stirred at room temperature for 1.5 hours and concentrated. Purification by SCX and preparative HPLC (acetonitrile/water+0.1% formic acid) gave the title compound 12 mg (30% yield) as an off-white powder.

Example 1, Method 49: N-Methyl-6-({[2-(pyridin-3-yl)-1,3-benzoxazol-5-yl]oxy}methyl)pyridin-3-amine δ_H NMR (500 MHz, DMSO) 9.32 (d, J=1.5 Hz, 1H), 8.80 (dd, J=4.8, 1.6 Hz, 1H), 8.51 (dt, J=8.0, 1.9 Hz, 1H), 7.94 (d, J=2.7 Hz, 1H), 7.72 (d, J=8.9 Hz, 1H), 7.65 (ddd, J=8.0, 4.8, 0.7 Hz, 1H), 7.47 (d, J=2.5 Hz, 1H), 7.29 (d, J=8.4 Hz, 1H), 7.10 (dd, J=8.9, 2.5 Hz, 1H), 6.90 (dd, J=8.4, 2.9 Hz, 1H), 5.98 (d, J=5.0 Hz, 1H), 5.06 (s, 2H), 2.70 (d, J=5.0 Hz, 3H). Tr(MET-uHPLC-AB-101)=1.67 min, (ES+) (M+H)+ 333.

The following example was prepared using Method 49 described above:

TABLE 50

| Ex. | Structure | Mol. Weight | IUPAC Name | LCMS data |
|---|---|---|---|---|
| 1 | 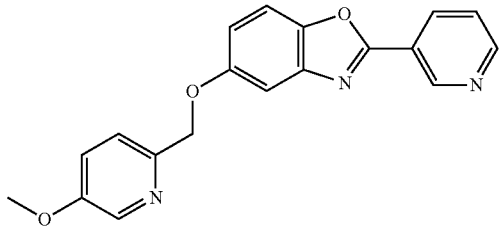 [SMILES: COc1ccc(COc2ccc3oc(-c4cccnc4)nc3c2)nc1] | 332.36 | N-Methyl-6-({[2-(pyridin-3-yl)-1,3-benzoxazol-5-yl]oxy}methyl)pyridin-3-amine | Tr(MET-uHPLC-AB-101) = 1.67 min, (ES+) (M + H)+ 333 |

Method 50

Scheme for Method 50

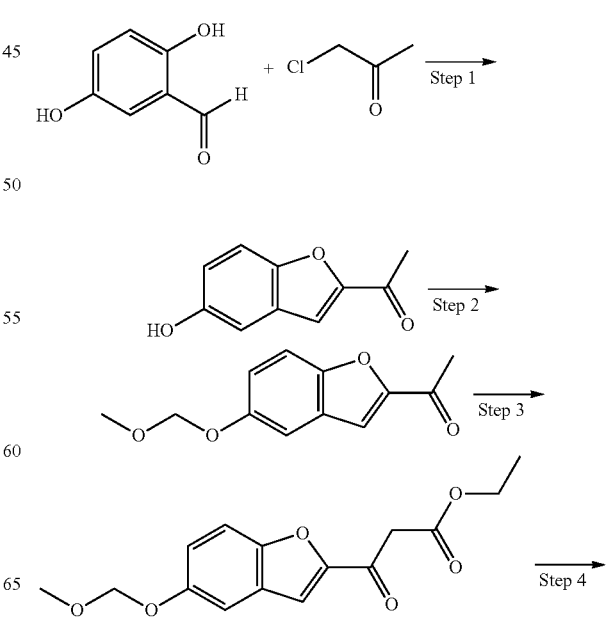

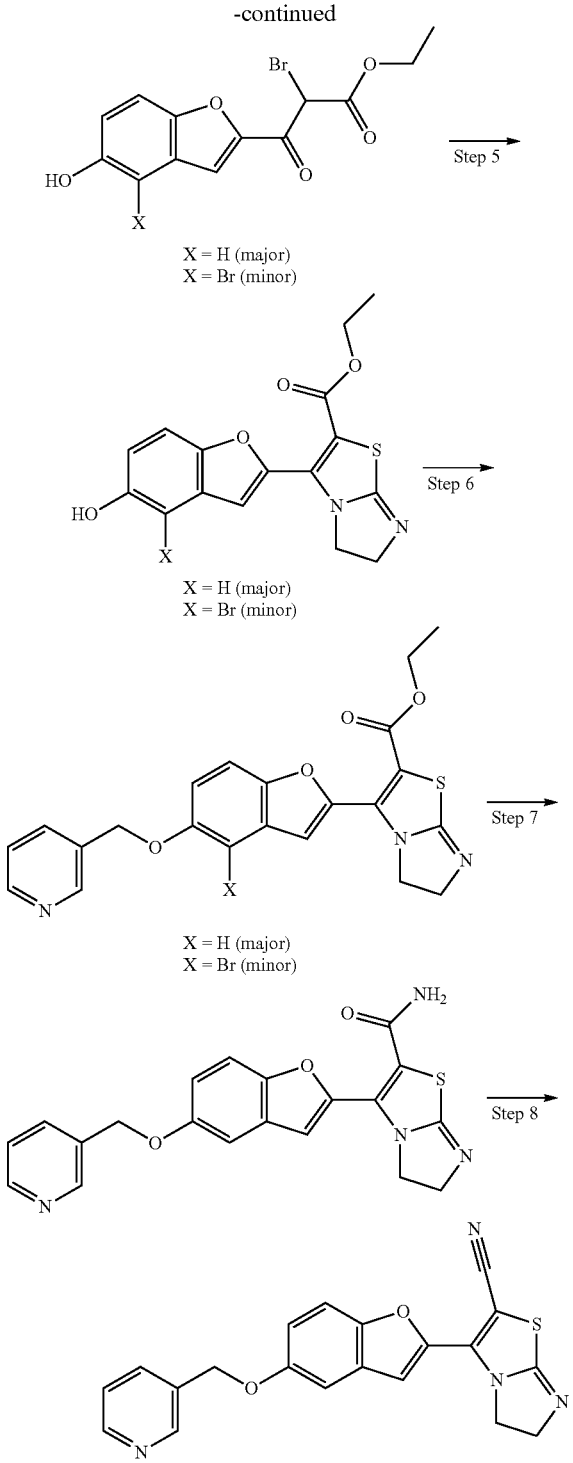

Step 1, Method 50: 1-(5-Hydroxy-1-benzofuran-2-yl)ethan-1-one

A mixture of 2,5-dihydroxybenzaldehyde (5.0 g, 36.2 mmol), 1-chloropropan-2-one (3.6 mL, 43.7 mmol) and potassium carbonate (6.0 g, 43.4 mmol) in acetone (100 mL) was heated to reflux for 18 hours. After cooling the suspension was diluted with acetone (100 mL) and filtered through a plug of celite. The filtrate was concentrated and the residue was taken up in ethyl acetate (300 mL), washed with water (50 mL) and brine (50 mL), dried over magnesium sulfate, filtered and absorbed onto a small amount of silica. Purification by FCC (silica, 0-60% ethyl acetate in heptane) gave the title compound 2.99 g (47% yield) as a colourless, crystalline solid. $\delta_H$ NMR (500 MHz, DMSO) 9.48 (s, 1H), 7.80-7.65 (m, 1H), 7.50 (d, J=8.9 Hz, 1H), 7.07 (d, J=2.4 Hz, 1H), 6.98 (dd, J=8.9, 2.5 Hz, 1H), 2.52 (s, 3H). Tr(METCR1278)=1.34 min, (ES$^+$) (M+H)$^+$ 177.

Step 2, Method 50: 1-[5-(Methoxymethoxy)-1-benzofuran-2-yl]ethan-1-one

To a solution of 1-(5-hydroxy-1-benzofuran-2-yl)ethan-1-one (2.84 g, 16.1 mmol) and chloro(methoxy)methane (3.0 mL, 39.5 mmol) in N,N-dimethylformamide (40 mL) at 0° C. was added sodium hydride (60% in mineral oil, 1.6 g, 40 mmol) in two portions. After 10 minutes the ice-bath was removed and the mixture was stirred at room temperature for 18 hours. After the addition of methanol (5 mL) stirring was continued for 30 minutes before the mixture was added to water (200 mL) and brine (200 mL). The mixture was extracted with ethyl acetate (4×150 mL), the combined organic layers were washed with brine (100 mL), dried over magnesium sulfate, filtered and concentrated. The residue was dissolved in tetrahydrofuran (100 mL) and absorbed onto a small amount of silica. Purification by FCC (silica, 0-50% ethyl acetate in heptane) gave the title compound 2.48 g (70% yield) as an off-white solid. $\delta_H$ NMR (500 MHz, DMSO) 7.84-7.79 (m, 1H), 7.64 (d, J=9.0 Hz, 1H), 7.42 (d, J=2.5 Hz, 1H), 7.22 (dd, J=9.0, 2.6 Hz, 1H), 5.23 (s, 2H), 3.40 (s, 3H), 2.55 (s, 3H). Tr(METCR1278)=1.70 min, (ES$^+$) (M+H)$^+$ 221.

Step 3, Method 50: Ethyl 3-[5-(methoxymethoxy)-1-benzofuran-2-yl]-3-oxopropanoate To a solution of 1-[5-(methoxymethoxy)-1-benzofuran-2-yl]ethan-1-one (2.45 g, 11.1 mmol) in diethyl carbonate (50 mL, 413 mmol) was added sodium hydride (60% in mineral oil, 890 mg, 22.3 mmol). After stirring for 10 minutes at room temperature the mixture was heated to 100° C. for 18 hours. The volatiles were removed in vacuo and the residue was partitioned between ethyl acetate (300 mL), water (100 mL) and acetic acid (2 mL). The organic layer was separated, washed with brine (50 mL), dried over magnesium sulfate, filtered and concentrated. Purification by FCC (silica, 0-20% ethyl acetate in heptane) gave the title compound 2.58 g (79% yield) as an off-white solid. $\delta_H$ NMR (500 MHz, DMSO) 7.91 (s, 1H), 7.66 (d, J=9.0 Hz, 1H), 7.44 (d, J=2.5 Hz, 1H), 7.25 (dd, J=9.0, 2.5 Hz, 1H), 5.24 (s, 2H), 4.24-3.96 (m, 4H), 3.40 (d, J=2.2 Hz, 3H), 1.18 (t, J=7.1 Hz, 3H). Tr(METCR1278)=1.86 min, (ES$^+$) (M+H)$^+$ 293.

Step 4, Method 50: Ethyl 2-bromo-3-[5-(methoxymethoxy)-1-benzofuran-2-yl]-3-oxopropanoate and 2-Bromo-3-(4-bromo-5-hydroxy-1-benzofuran-2-yl)-3-oxopropanoate To a solution of ethyl 3-[5-(methoxymethoxy)-1-benzofuran-2-yl]-3-oxopropanoate (2.5 g, 8.55 mmol) in tetrahydrofuran (100 mL) was added phenyltrimethylammonium tribromide (3.4 g, 9.04 mmol) and the mixture was stirred at room temperature for 18 hours. After dilution with ethyl acetate (100 mL) the mixture was filtered through celite and the filtrate was concentrated. The residue was taken up in ethyl acetate (300 mL), washed with 10% aqueous sodium thiosulfate (50 mL) and brine (50 mL), dried over magnesium sulfate, filtered and concentrated to give the title compounds 3.20 g (quantitative yield) (3.3/1 mixture by NMR) as a yellow oil. (X=H, major): $\delta_H$ NMR (500 MHz, DMSO) 9.62 (s, 1H), 8.03-7.92 (m, 1H), 7.54 (d, J=9.0 Hz, 1H), 7.12 (d, J=2.4 Hz, 1H), 7.06 (dd, J=9.0, 2.5 Hz, 1H), 6.39 (s, 1H), 4.22 (q, J=7.1 Hz, 2H), 1.16 (t, J=7.1 Hz, 3H). (X=H, major): Tr(METCR1278)=1.76 min, (ES$^+$) (M+H)$^+$ 327/329. (X=Br, minor): Tr(METCR1278)=1.91 min, (ES$^+$) (M+H)$^+$ 407.

Step 5, Method 50: Ethyl 3-(5-hydroxy-1-benzofuran-2-yl)-5H,6H-imidazo[2,1-b][1,3]thiazole-2-carboxylate and Ethyl 3-(4-bromo-5-hydroxy-1-benzofuran-2-yl)-5H,6H-imidazo[2,1-b][1,3]thiazole-2-carboxylate A mixture of crude ethyl 2-bromo-3-[5-(methoxymethoxy)-1-benzofuran-2-yl]-3-oxopropanoate and 2-bromo-3-(4-bromo-5-hydroxy-1-benzofuran-2-yl)-3-oxopropanoate (ratio: 3.3/1, max. 8.55 mmol in total) and imidazolidine-2-thione (880 mg, 8.61 mmol) in ethanol (20 mL) and acetic acid (20 mL) was stirred under reflux for 18 hours. The solvent was removed in vacuo and the residue was triturated with a mixture of ethyl acetate and acetonitrile (20 mL, 1/1), filtered and dried under vacuum to give the title compounds 2.58 g (70% yield) (hydrobromide salt, 3/1 mixture by LCMS) as a yellow solid. (X=H, major) Tr(MET-uHPLC-AB-101)=1.52 min, (ES$^+$) (M+H)$^+$ 331 and (X=Br, minor) Tr(MET-uHPLC-AB-101)=1.81 min, (ES$^+$) (M+H)$^+$ 409/411.

Step 5, Method 50: Ethyl 3-[5-(pyridin-3-ylmethoxy)-1-benzofuran-2-yl]-5H,6H-imidazo[2,1-b][1,3]thiazole-2-carboxylate and Ethyl 3-[4-bromo-5-(pyridin-3-ylmethoxy)-1-benzofuran-2-yl]-5H,6H-imidazo[2,1-b][1,3]thiazole-2-carboxylate To a suspension of ethyl 3-(5-hydroxy-1-benzofuran-2-yl)-5H,6H-imidazo[2,1-b][1,3]thiazole-2-carboxylate hydrobromide salt and ethyl 3-(4-bromo-5-hydroxy-1-benzofuran-2-yl)-5H,6H-imidazo[2,1-b][1,3]thiazole-2-carboxylate hydrobromide salt (3/1 mixture, 500 mg, 1.15 mmol), 3-(bromomethyl)pyridine hydrobromide (480 mg, 1.90 mmol) and potassium iodide (20 mg, 0.12 mmol) in N,N-dimethylformamide (20 mL) at 0° C. was added sodium hydride (60% in mineral oil, 170 mg, 4.26 mmol). The ice bath was removed and the mixture was stirred at 60° C. for 90 minutes before being partitioned between water (100 mL), brine (100 mL) and ethyl acetate (200 mL). The aqueous layer was extracted with ethyl acetate (2×100 mL). The combined organic extracts were washed with brine (100 mL), dried over magnesium sulfate, filtered and absorbed onto a small amount of silica. Purification by FCC (silica, 0-10% methanol in dichloromethane) followed by trituration with methanol (3 mL) provided a mixture 257 mg (51% yield) of the title compounds (4.3/1 mixture by LCMS) as a yellow solid. (X=H, major) Tr(MET-uHPLC-AB-101) =1.53 min, (ES$^+$) (M+H)$^+$ 422 and (X=Br, minor) Tr(MET-uHPLC-AB-101)=1.77 min, (ES$^+$) (M+H)$^+$ 500/502.

Step 6, Method 50: 3-[5-(Pyridin-3-ylmethoxy)-1-benzofuran-2-yl]-5H,6H-imidazo[2,1-b][1,3]thiazole-2-carboxamide A solution of ethyl 3-[5-(pyridin-3-ylmethoxy)-1-benzofuran-2-yl]-5H,6H-imidazo[2,1-b][1,3]thiazole-2-carboxylate (81%, 124 mg, 0.24 mmol) in 7 M ammonia in methanol (40 mL) in a pressure tube was heated to 80° C. for 24 hours and then stirred at room temperature for 3 days. The mixture was added to saturated aqueous ammonium chloride solution (300 mL) and then extracted with ethyl acetate (4×100 mL). The combined organic extracts were washed with brine (100 mL), dried over magnesium sulfate, filtered and then absorbed onto a small amount of silica. Purification by FCC (silica, 0-15% methanol in dichloromethane) gave the title compound 47 mg (37% yield) as a yellow solid. $\delta_H$ NMR (500 MHz, DMSO) 8.69 (d, J=1.8 Hz, 1H), 8.55 (dd, J=4.7, 1.7 Hz, 1H), 7.89 (d, J=7.9 Hz, 1H), 7.58 (d, J=9.0 Hz, 1H), 7.52 (s, 1H), 7.44 (dd, J=7.5, 4.7 Hz, 1H), 7.36 (d, J=2.6 Hz, 1H), 7.33 (bs, 2H), 7.12 (dd, J=9.0, 2.6 Hz, 1H), 5.22 (s, 2H), 4.16-3.94 (m, 4H). Tr(METCR1278)=1.03 min, (ES$^+$) (M+H)$^+$ 393, 74%.

Step 7, Method 50: 3-[5-(Pyridin-3-ylmethoxy)-1-benzofuran-2-yl]-5H,6H-imidazo[2,1-b][1,3]thiazole-2-carbonitrile To a solution of 3-[5-(pyridin-3-ylmethoxy)-1-benzofuran-2-yl]-5H,6H-imidazo[2,1-b][1,3]thiazole-2-carboxamide (74%, 44 mg, 0.083 mmol) and pyridine (0.02 mL, 0.248 mmol) in tetrahydrofuran (10 mL) at 0° C. was added trifluoroacetic anhydride (50 µL, 0.35 mmol). After stirring for 10 minutes the mixture was added to saturated aqueous sodium bicarbonate solution and extracted with ethyl acetate (3×50 mL). The combined organic extracts were washed with brine (50 mL), dried over magnesium sulfate, filtered and concentrated. Purification by preparative HPLC (acetonitrile/water+0.2% ammonium hydroxide) gave the title compound 12 mg (39% yield) as a yellow solid.

Example 1, Method 50: 3-[5-(Pyridin-3-ylmethoxy)-1-benzofuran-2-yl]-5H,6H-imidazo[2,1-b][1,3]thiazole-2-carbonitrile $\delta_H$ NMR (500 MHz, DMSO) 8.71 (d, J=1.9 Hz, 1H), 8.56 (dd, J=4.8, 1.5 Hz, 1H), 7.96-7.85 (m, 1H), 7.70-7.57 (m, 2H), 7.51-7.37 (m, 2H), 7.20 (dd, J=9.2, 2.6 Hz, 1H), 5.22 (s, 2H), 4.34-4.18 (m, J=5.1 Hz, 4H). Tr(MET-uHPLC-AB-101)=1.22 min, (ES$^+$) (M+H)$^+$ 375.

The following example was prepared using Method 50 described above:

TABLE 51

| Ex. | Structure | Mol. Weight | IUPAC Name | LCMS data |
|---|---|---|---|---|
| 1 | 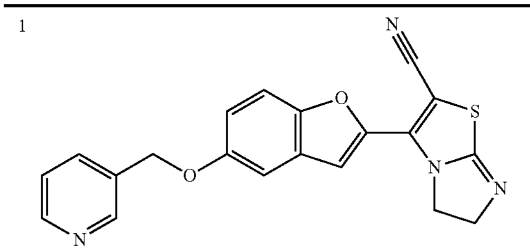 | 374.42 | 3-[5-(Pyridin-3-ylmethoxy)-1-benzofuran-2-yl]-5H,6H-imidazo[2,1-b][1,3]thiazole-2-carbonitrile | Tr(MET-uHPLC-AB-101) = 1.22 min, (ES⁺) (M + H)⁺ 375 |

Method 51
Scheme for Method 51

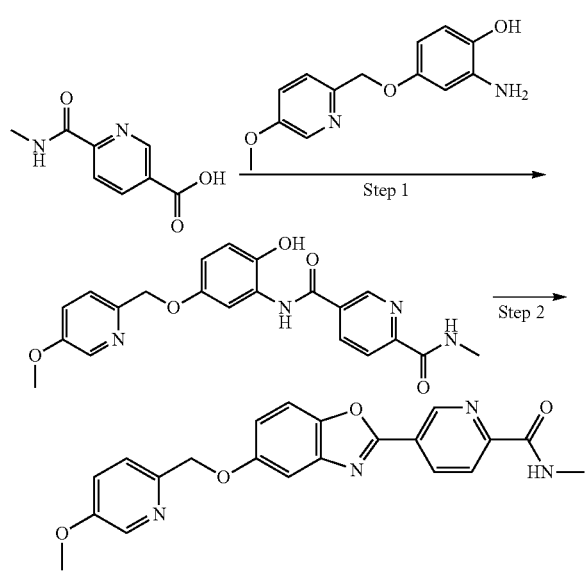

Step 1, Method 51: 5-N-{2-Hydroxy-5-[(5-methoxypyridin-2-yl)methoxy]phenyl}-2-N-methyl-pyridine-2,5-dicarboxamide To a solution of 2-amino-4-[(5-methoxypyridin-2-yl)methoxy]phenol (100 mg, 0.41 mmol, prepared by Method 33) in pyridine (2 mL) and 6-(methylcarbamoyl)pyridine-3-carboxylic acid (80 mg, 0.45 mmol, prepared as described in PCT Int. Appl 2006003378) in pyridine (2 mL) was added N-(3-dimethylaminopropyl)-N'-ethylcarbodiimide hydrochloride (101.2 mg, 0.53 mmol) and the mixture was stirred at room temperature for 18 hours. The solvent was removed in vacuo and the residue was taken up in ethyl acetate (50 mL), washed with water (2×10 mL) and dried over sodium sulfate. Filtration and concentration gave the title compound 164 mg (89% yield, 72% purity) as a yellow powder. The crude product was taken directly into the next step.

Step 2, Method 51: 5-{5-[(5-Methoxypyridin-2-yl)methoxy]-1,3-benzoxazol-2-yl}-N-methylpyridine-2-carboxamide Crude 5-N-{2-hydroxy-5-[(5-methoxypyridin-2-yl)methoxy]phenyl}-2-N-methylpyridine-2,5-dicarboxamide (164 mg, 2.91 mmol, 72% purity) was suspended in acetic acid (3 mL) and heated in a microwave at 200° C. for 40 minutes. After cooling the volatiles were removed in vacuo and the residue was distributed between ethyl acetate (2 mL) and saturated aqueous sodium bicarbonate solution (10 mL). The mixture was filtered, the solid was washed with warm methanol (30 mL) and the solution concentrated. Purification by FCC (silica, 12-100% ethyl acetate in heptane) gave the title compound 9 mg (8% yield) as a white powder.

Example 1, Method 51: 5-{5-[(5-Methoxypyridin-2-yl)methoxy]-1,3-benzoxazol-2-yl}-N-methylpyridine-2-carboxamide $\delta_H$ NMR (500 MHz, DMSO) 9.34 (d, J=2.0 Hz, 1H), 8.97 (q, J=4.8 Hz, 1H), 8.68 (dd, J=8.2, 2.1 Hz, 1H), 8.31 (d, J=2.9 Hz, 1H), 8.23 (d, J=8.2 Hz, 1H), 7.77 (d, J=8.9 Hz, 1H), 7.53 (d, J=8.6 Hz, 1H), 7.51 (d, J=2.5 Hz, 1H), 7.44 (dd, J=8.6, 3.0 Hz, 1H), 7.17 (dd, J=8.9, 2.5 Hz, 1H), 5.20 (s, 2H), 3.84 (s, 3H), 2.85 (d, J=4.8 Hz, 3H). Tr(MET-uHPLC-AB-101)=2.71 min, (ES⁺) (M+H)⁺ 391.

The following example was prepared using Method 51 described above:

TABLE 52

| Ex. | Structure | Mol. Weight | IUPAC Name | LCMS data |
|---|---|---|---|---|
| 1 | 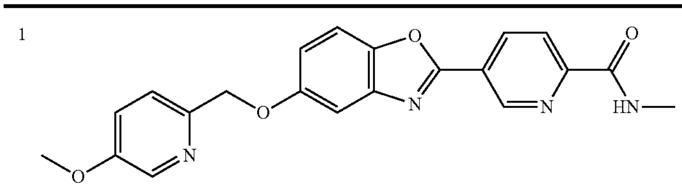 | 390.39 | 5-{5-[(5-Methoxypyridin-2-yl)methoxy]-1,3-benzoxazol-2-yl}-N-methylpyridine-2-carboxamide | Tr(MET-uHPLC-AB-101) = 2.71 min, (ES⁺) (M + H)⁺ 391 |

Method 52
Scheme for Method 52

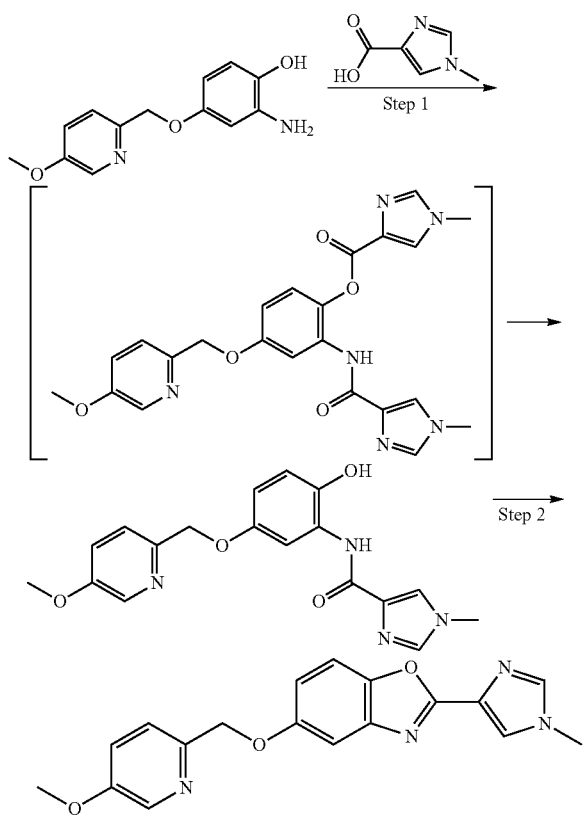

Step 1, Method 52: N-{2-Hydroxy-5-[(5-methoxy-pyridin-2-yl)methoxy]phenyl}-1-methyl-1H-imidazole-4-carboxamide To a solution of 2-amino-4-[(5-methoxypyridin-2-yl)methoxy]phenol (50%, 300 mg, 0.61 mmol, prepared by Method 33) and 1-methyl-1H-imidazole-4-carboxylic acid (85 mg, 0.67 mmol) in pyridine (3 mL) was added 1-(3-(dimethylamino)-propyl)-3-ethylcarbodiimide hydrochloride (150 mg, 0.78 mmol) and the mixture was stirred at room temperature for 18 hours. The solvent was removed in vacuo and the residue was taken up in ethyl acetate (200 mL), washed with water (50 mL) and brine (50 mL), dried over magnesium sulfate, filtered and concentrated. The residue was dissolved in methanol (50 mL) and stirred under reflux for 2 days. After cooling the crude product was pre-absorbed onto a small amount of silica and then purified by FCC (silica, 0-10% methanol in ethyl acetate) to give the title compound 25 mg (12% yield) as off-white solid. Tr(METCR1278)=1.35 min, (ES$^+$) (M+H)$^+$ 355.

Step 2, Method 52: 5-[(5-Methoxypyridin-2-yl)methoxy]-2-(1-methyl-1H-imidazol-4-yl)-1,3-benzoxazole formate salt N-{2-Hydroxy-5-[(5-methoxypyridin-2-yl)methoxy]phenyl}-1-methyl-1H-imidazole-4-carboxamide (25 mg, 0.07 mmol) was suspended in acetic acid (1 mL) and heated in a microwave at 200° C. for 40 minutes. After cooling the volatiles were removed in vacuo and the residue was partitioned between ethyl acetate (100 mL) and saturated aqueous sodium bicarbonate (50 mL). The organic layer was washed with brine (50 mL), dried over magnesium sulfate, filtered and concentrated. Purification by preparative HPLC (acetonitrile/water+0.1% formic acid) gave the title compound 8.6 mg (32% yield) as off-white solid.

Step 2, Method 52: 5-[(5-Methoxypyridin-2-yl)methoxy]-2-(1-methyl-1H-imidazol-4-yl)-1,3-benzoxazole formate salt $\delta_H$ NMR (500 MHz, DMSO) 8.33 (s, 1H), 8.30 (d, J=2.9 Hz, 1H), 8.04 (d, J=1.0 Hz, 1H), 7.83 (s, 1H), 7.60 (d, J=8.8 Hz, 1H), 7.51 (d, J=8.6 Hz, 1H), 7.43 (dd, J=8.6, 3.0 Hz, 1H), 7.33 (d, J=2.5 Hz, 1H), 7.00 (dd, J=8.8, 2.5 Hz, 1H), 5.15 (s, 2H), 3.83 (s, 3H), 3.76 (s, 3H). Tr(MET-uHPLC-AB-101)=1.96 min, (ES$^+$) (M+H)$^+$ 337.

The following example was prepared using Method 52 described above:

TABLE 53

| Ex. | Structure | Mol. Weight | IUPAC Name | LCMS data |
|---|---|---|---|---|
| 1 | 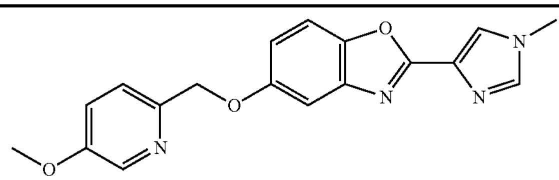 | 336.34 | 5-[(5-Methoxypyridin-2-yl)methoxy]-2-(1-methyl-1H-imidazol-4-yl)-1,3-benzoxazole | Tr(MET-uHPLC-AB-101) = 1.96 min, (ES$^+$)(M + H)$^+$ 337 |

Method 53
Scheme for Method 53

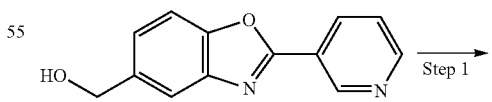

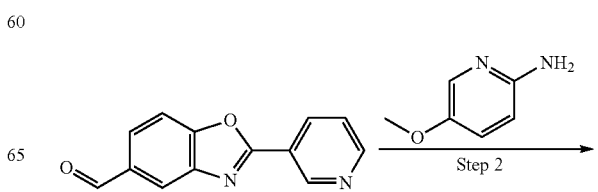

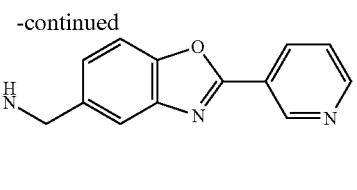

Step 1, Method 53: 2-(Pyridin-3-yl)-1,3-benzoxazole-5-carbaldehyde

To a stirred solution of [2-(pyridin-3-yl)-1,3-benzoxazol-5-yl]methanol (149 mg, 0.66 mmol, prepared by Method 23) in tetrahydrofuran (10 mL) under nitrogen, was added 1,1,1-triacetoxy-1,1-dihydro-1,2-benziodoxol-3(1H)-one (307 mg, 0.72 mmol). The mixture was stirred at room temperature for 1.5 hours. The mixture was filtered and concentrated. The residue was triturated in dichloromethane-methanol (9:1, 5 mL) and filtered. The filtrate was concentrated and purified by FCC (silica, 12-100% ethyl acetate in heptane) to give the title compound 152 mg (100% yield) as a white powder. $\delta_H$ NMR (500 MHz, DMSO) 10.13 (s, 1H), 9.39 (s, 1H), 8.85 (d, J=4.8 Hz, 1H), 8.59 (d, J=8.0 Hz, 1H), 8.41 (s, 1H), 8.06 (s, 2H), 7.69 (dd, J=8.0, 4.9 Hz, 1H). Tr(METCR1278)=1.57 min, (ES$^+$) (M+H)$^+$ 225.

Step 1, Method 53: 5-Methoxy-N-{[2-(pyridin-3-yl)-1,3-benzoxazol-5-yl]methyl}pyridin-2-amine A solution of 2-(pyridin-3-yl)-1,3-benzoxazole-5-carbaldehyde (50 mg, 0.22 mmol) and 5-methoxypyridin-2-amine (30 mg, 0.25 mmol) in toluene (5 mL) was treated with diethyl 2,6-dimethyl-1,4-dihydropyridine-3,5-dicarboxylate (68 mg, 0.27 mmol), thiourea (3 mg, 0.04 mmol) and molecular sieves (4 Å, 223 mg) and the mixture was stirred at 70° C. under nitrogen for 2 days. 2,6-Dimethyl-1,4-dihydropyridine-3,5-dicarboxylate (40 mg, 0.16 mmol) was added and the mixture stirred at 70° C. overnight. After filtration through celite, the filtrate was concentrated and the residue purified by FCC (silica, 20-100% ethyl acetate in heptane) to give the title compound 72 mg (97% yield) as an off white powder.

Example, 1 Method 53: 5-Methoxy-N-{[2-(pyridin-3-yl)-1,3-benzoxazol-5-yl]methyl}pyridin-2-amine $\delta_H$ NMR (500 MHz, DMSO) 9.34 (d, J=1.9 Hz, 1H), 8.80 (dd, J=4.8, 1.5 Hz, 1H), 8.52 (dt, J=8.0, 1.9 Hz, 1H), 7.77-7.70 (m, 3H), 7.65 (dd, J=8.0, 4.8 Hz, 1H), 7.44 (dd, J=8.4, 1.3 Hz, 1H), 7.14 (dd, J=9.0, 3.0 Hz, 1H), 6.79 (t, J=6.1 Hz, 1H), 6.52 (d, J=9.0 Hz, 1H), 4.55 (d, J=6.1 Hz, 2H), 3.67 (s, 3H). Tr(MET-uHPLC-AB-101)=1.49 min, (ES$^+$) (M+H)$^+$ 333.

The following example was prepared using Method 53 described above:

TABLE 54

| Ex. | Structure | Mol. Weight | IUPAC Name | LCMS data |
|---|---|---|---|---|
| 1 | 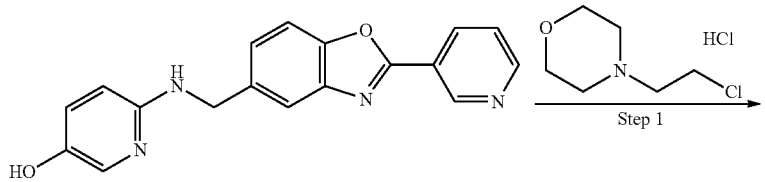 | 332.36 | 5-Methoxy-N-{[2-(pyridin-3-yl)-1,3-benzoxazol-5-yl]methyl}pyridin-2-amine | Tr(MET-uHPLC-AB-101) = 1.49 min, (ES$^+$) (M + H)$^+$ 333 |

Method 54
Scheme for Method 54

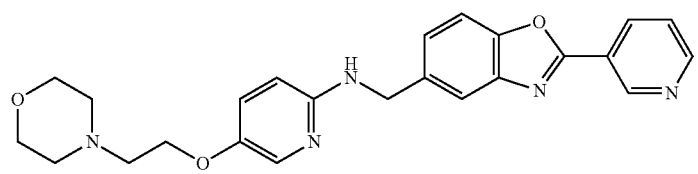

Step 1, Method 54: 5-({5-[2-(Morpholin-4-yl)ethoxy]pyridin-2-yl}methoxy)-2-(pyridin-3-yl)-1,3-benzoxazole 6-({[2-(Pyridin-3-yl)-1,3-benzoxazol-5-yl]oxy}methyl)pyridin-3-ol (50%, 59 mg, 0.09 mmol prepared by Method 27), 4-(2-chloroethyl)morpholine hydrochloride (20 mg, 0.11 mmol) and potassium iodide (15 mg, 0.09 mmol) were dissolved in anhydrous N,N-dimethylformamide (1 mL), sodium hydride (7 mg, 0.28 mmol) was added and the reaction was stirred at room temperature for 16 hours. The reaction was heated to 60° C. for 4 hours. The reaction mixture was cooled to room temperature and partitioned between ethyl acetate and water (1:1, 10 mL). The aqueous was extracted with ethyl acetate (2×10 mL). The combined organics were washed with water (2×1 mL), brine (2 mL), dried over sodium sulfate, filtered, and concentrated. Purification by preparative HPLC (acetonitrile/water+0.2% ammonium hydroxide) gave the title compound 2 mg (5% yield) as a white solid.

Example 1, Method 54: 5-({5-[2-(Morpholin-4-yl)ethoxy]pyridin-2-yl}methoxy)-2-(pyridin-3-yl)-1,3-benzoxazole $\delta_H$ NMR (500 MHz, DMSO) 9.32 (s, 1H), 8.80 (d, J=3.8 Hz, 1H), 8.50 (dt, J=8.0, 1.9 Hz, 1H), 8.30 (d, J=2.8 Hz, 1H), 7.73 (d, J=8.9 Hz, 1H), 7.65 (dd, J=8.0, 4.8 Hz, 1H), 7.59-7.33 (m, 3H), 7.13 (dd, J=8.9, 2.5 Hz, 1H), 5.18 (s, 2H), 4.17 (t, J=5.7 Hz, 2H), 3.64-3.45 (m, 4H), 2.70 (t, J=5.7 Hz, 2H), 2.49-2.41 (m, 4H). Tr(MET-uHPLC-AB-101)=1.59 min, (ES$^+$) (M+H)$^+$ 433.

The following example was prepared using Method 54 described above:

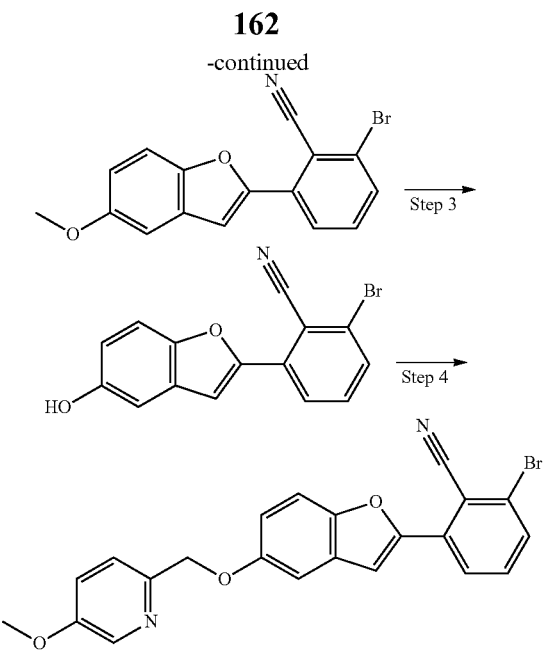

Step 1, Method 55:
(5-Methoxy-1-benzofuran-2-yl)boronic acid 2.5 M n-butyllithium in hexanes (2.8 mL, 7.00 mmol) was added slowly to a solution of 5-methoxy-1-benzofuran (1.0 g, 6.75 mmol) in dry tetrahydrofuran (15 mL) at −78° C. under a nitrogen atmosphere. After 1 hour stirring at −78° C., triisopropylborate (3.12 mL, 13.5 mmol) was added drop-wise and the mixture stirred for 30 minutes at −78° C.

TABLE 55

| Ex. | Structure | Mol. Weight | IUPAC Name | LCMS data |
|---|---|---|---|---|
| 1 | 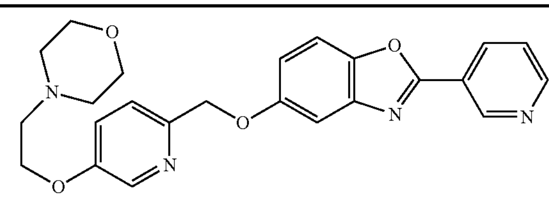 | 432.47 | 5-({5-[2-(Morpholin-4-yl)ethoxy]pyridin-2-yl}methoxy)-2-(pyridin-3-yl)-1,3-benzoxazole | Tr(MET-uHPLC-AB-101) = 1.59 min, (ES$^+$) (M + H)$^+$ 433 |

Method 55
Scheme for Method 55

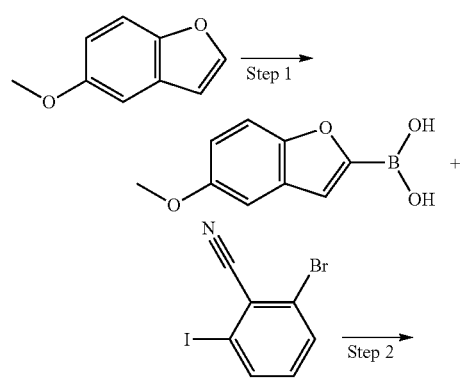

The dry ice bath was removed, 2 M aqueous hydrochloric acid (20 mL) was added and the mixture warmed to room temperature whilst stirring overnight. The reaction mixture was poured into water (25 mL) and extracted with diethyl ether (3×20 mL). The combined organics were washed with brine (20 mL), dried over magnesium sulfate, filtered and concentrated under reduced pressure. Dichloromethane (20 mL) was added and the mixture sonicated for 10 minutes. The minimum amount of methanol (ca. 1 mL) was added to fully dissolve the solids and the solution sonicated for 10 minutes. Heptane (20 mL) was added and the precipitated solids collected by vacuum filtration and allowed to dry under vacuum for 2 hours to give the title compound 476 mg (37% yield) as a white solid. $\delta_H$ NMR (500 MHz, DMSO) 8.53 (s, 2H), 7.46 (d, J=8.94 Hz, 1H), 7.39 (s, 1H), 7.19 (d, J=2.51 Hz, 1H), 6.93 (dd, J=2.60, 8.92 Hz, 1H), 3.78 (s, 3H).

Step 2, Method 55: 2-Bromo-6-(5-methoxy-1-benzofuran-2-yl)benzonitrile

A mixture of (5-methoxy-1-benzofuran-2-yl)boronic acid (156 mg, 0.813 mmol), 2-bromo-6-iodobenzonitrile (250 mg, 0.81 mmol) and 2 M sodium carbonate (0.82 mL, 1.64 mmol) in N,N-dimethylformamide (10 mL) was sonicated under a stream of nitrogen for 20 minutes. [1,1'-Bis(diphenylphosphino)ferrocene]dichloropalladium(II) complex with dichloromethane (50 mg, 0.14 mmol) was added and the mixture was stirred at 70° C. for 2 hours. After cooling the mixture was added to water (100 mL) and brine (100 mL). The mixture was extracted with ethyl acetate (3×100 mL), the combined extracts were washed with brine (50 mL), dried over magnesium sulfate, filtered and concentrated. Purification by FCC (silica, 0-50% ethyl acetate in heptane) gave the title compound 168 mg (37% yield, 82% pure by LCMS) as an off-white solid, which was taken on directly into the next step. A sample was purified by preparative HPLC (acetonitrile/water+0.1% formic acid) $\delta_H$ NMR (500 MHz, DMSO) 8.09 (d, J=8.0 Hz, 1H), 7.93 (d, J=8.0 Hz, 1H), 7.76 (t, J=8.1 Hz, 1H), 7.70 (s, 1H), 7.58 (d, J=9.0 Hz, 1H), 7.32 (d, J=2.6 Hz, 1H), 7.02 (dd, J=9.0, 2.6 Hz, 1H), 3.81 (s, 3H). Tr(MET-uHPLC-AB-101)=5.45 min, (ES$^+$) (M+H)$^+$ 328/330.

Step 3, Method 55: 2-Bromo-6-(5-hydroxy-1-benzofuran-2-yl)benzonitrile

1 M Boron tribromide in dichloromethane (2.0 mL, 2.0 mmol) was added drop-wise over 5 minutes to a stirred solution of 2-bromo-6-(5-methoxy-1-benzofuran-2-yl)benzonitrile (0.13 g, 0.39 mmol), in dichloromethane (15 mL) at room temperature and the resulting solution was stirred for 1 hour. The reaction was quenched by the addition of methanol (5 mL). The solvents were evaporated to give the title compound 0.12 g (77% yield) as a beige solid. $\delta_H$ NMR (500 MHz, chloroform) 8.05 (d, J=8.12 Hz, 1H), 7.70 (s, 1H), 7.66 (d, J=7.23 Hz, 1H), 7.53 (t, J=8.08 Hz, 1H), 7.40 (d, J=8.80 Hz, 1H), 7.06 (d, J=2.54 Hz, 1H), 6.91 (dd, J=2.57, 8.81 Hz, 1H).

Step 4, Method 55: 2-Bromo-6-{5-[(5-methoxypyridin-2-yl)methoxy]-1-benzofuran-2-yl}benzonitrile To a stirred solution of 2-bromo-6-(5-hydroxy-1-benzofuran-2-yl)benzonitrile (0.12 g, 0.38 mmol) and 2-(chloromethyl)-5-methoxypyridine hydrochloride (0.07 g, 0.38 mmol) in N,N-dimethylformamide (8 mL) under nitrogen, was added sodium hydride (60% in mineral oil, 0.03 g, 0.84 mmol) portion-wise at 0° C. The mixture was allowed to warm to room temperature and stirred for 48 hours. The mixture was quenched with water (4 mL) and the solvents removed in vacuo. The residue was partitioned between ethyl acetate (150 mL) and water (150 mL) and the aqueous layer was extracted with ethyl acetate (3×100 mL). The combined organic extracts were washed with brine (2×20 mL), dried over magnesium sulfate, filtered and concentrated. Purification by preparative HPLC (acetonitrile/water+0.2% ammonium hydroxide) gave the title compound 29 mg (17% yield) as a white, crystalline solid.

Example 1, Method 55: 2-Bromo-6-{5-[(5-methoxypyridin-2-yl)methoxy]-1-benzofuran-2-yl}benzonitrile $\delta_H$ NMR (500 MHz, DMSO) 8.31 (d, J=2.9 Hz, 1H), 8.10 (d, J=8.0 Hz, 1H), 7.94 (d, J=8.1 Hz, 1H), 7.77 (t, J=8.1 Hz, 1H), 7.70 (s, 1H), 7.61 (d, J=9.0 Hz, 1H), 7.52 (d, J=8.6 Hz, 1H), 7.48-7.36 (m, 2H), 7.12 (dd, J=9.0, 2.6 Hz, 1H), 5.16 (s, 2H), 3.84 (s, 3H). Tr(MET-uHPLC-AB-101)=4.12 min, (ES$^+$) (M+H)$^+$ 437/439.

The following example was prepared using Method 55 described above:

TABLE 56

| Ex. | Structure | Mol. Weight | IUPAC Name | LCMS data |
|---|---|---|---|---|
| 1 | 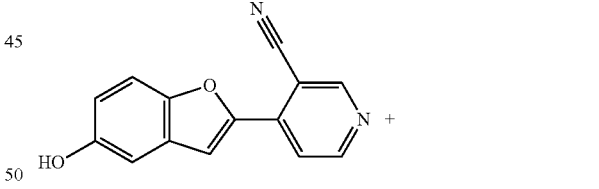 | 435.27 | 2-Bromo-6-{5-[(5-methoxypyridin-2-yl)methoxy]-1-benzofuran-2-yl}benzonitrile | Tr(MET-uHPLC-AB-101) = 4.12 min, (ES$^+$) (M + H)$^+$ 437/439 |

Method 56

Scheme for Method 56

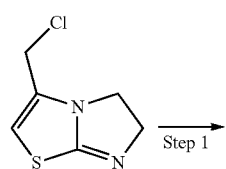

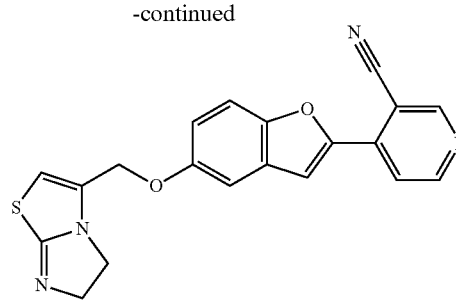

Step 1, Method 56: 4-(5-{5H,6H-Imidazo[2,1-b][1,3]thiazol-3-ylmethoxy}-1-benzofuran-2-yl)pyridine-3-carbonitrile hydrochloride To a mixture of 4-(5-hydroxy-1-benzofuran-2-yl)pyridine-3-carbonitrile (150 mg, 0.63 mmol, prepared by Method 9), 3-(chloromethyl)-5H,6H-imidazo[2,1-b][1,3]thiazole (170 mg, 0.97 mmol) and potassium iodide (10 mg, 0.06 mmol) in N,N-dimethylformamide (10 mL) was added sodium hydride (60% in mineral oil, 90 mg, 2.25 mmol). The mixture was stirred for 3 hours at room temperature then added to a mixture of water (150 mL) and brine (150 mL) and extracted with ethyl acetate (4×100 mL). The combined organic extracts were washed with brine (100 mL), dried over magnesium sulfate, filtered and concentrated. The residue was taken up in methanol (30 mL) and 1 M hydrochloric acid (3 mL) was added before the volatiles were removed in vacuo. The residue was triturated with DMSO:water (3 mL, 4:1 mixture) to give the title compound 19 mg (7% yield) as an off-white, crystalline solid.

Example 1, Method 56: 4-(5-{5H,6H-Imidazo[2,1-b][1,3]thiazol-3-ylmethoxy}-1-benzofuran-2-yl)pyridine-3-carbonitrile hydrochloride $\delta_H$ NMR (500 MHz, DMSO) 9.68 (s, 1H), 9.13 (s, 1H), 8.94 (d, J=5.4 Hz, 1H), 8.08 (d, J=5.4 Hz, 1H), 7.96 (s, 1H), 7.70 (d, J=9.0 Hz, 1H), 7.55 (d, J=2.6 Hz, 1H), 7.21 (dd, J=9.0, 2.6 Hz, 1H), 7.06 (s, 1H), 5.17 (s, 2H), 4.48 (dd, J=11.2, 8.2 Hz, 2H), 4.31 (dd, J=11.2, 8.2 Hz, 2H). Tr(METCR1416)=2.96 min, (ES$^+$) (M+H)$^+$ 375.

The following example was prepared using Method 56 described above:

Method 57
Scheme for Method 57

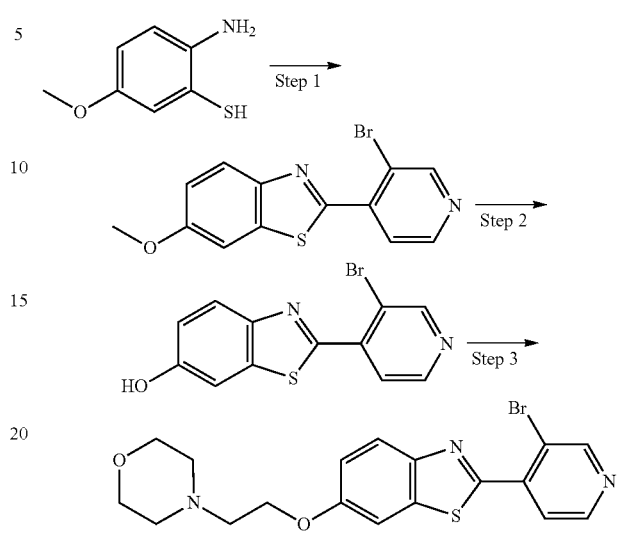

Step 1, Method 57: 2-(3-Bromopyridin-4-yl)-6-methoxy-1,3-benzothiazole

2-Amino-5-methoxybenzene-1-thiol (80%, 1 g, 5.15 mmol, described in J. Med. Chem., (2003) 46, 2740), 3-bromopyridine-4-carbaldehyde (0.98 g, 5.26 mmol) and sodium metabisulfite (1 g, 5.26 mmol) were dissolved in anhydrous dimethylsulfoxide (5 mL). The reaction mixture was stirred at 120° C. for 2 hours. The mixture was cooled to room temperature and water (100 mL) was added. The resulting black precipitate was filtered and washed with water. The precipitate was dissolved in dichloromethane. The suspension was passed through a pad of silica. The pad was washed with dichloromethane to give the title compound 1.123 g (68% yield) as a purple solid. $\delta_H$ NMR (500 MHz, DMSO) 8.99 (s, 1H), 8.71 (d, J=5.0 Hz, 1H), 8.13 (d, J=5.0 Hz, 1H), 8.07 (d, J=9.0 Hz, 1H), 7.83 (d, J=2.0 Hz, 1H), 7.23 (dd, J=8.9, 2.2 Hz, 1H), 3.88 (s, 3H). Tr(METuHPLC-AB-101)=3.57 min, (ES$^+$) (M+H)$^+$ 321/323.

Step 2, Method 57: 2-(3-Bromopyridin-4-yl)-1,3-benzothiazol-6-ol

To a suspension of 2-(3-bromopyridin-4-yl)-6-methoxy-1,3-benzothiazole (200 mg, 0.62 mmol) in dichloromethane

TABLE 57

| Ex. | Structure | Mol. Weight | IUPAC Name | LCMS data |
|---|---|---|---|---|
| 1 | 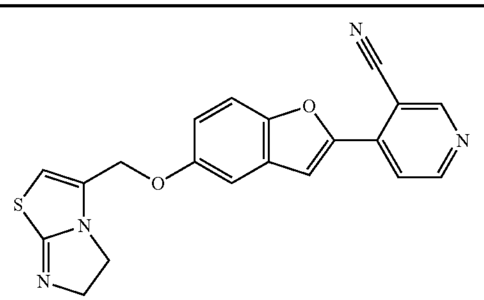 | 374.42 | 4-(5-{5H,6H-Imidazo[2,1-b][1,3]thiazol-3-ylmethoxy}-1-benzofuran-2-yl)pyridine-3-carbonitrile | Tr(METCR1416) = 2.96 min, (ES$^+$) (M + H)$^+$ 375 |

(6 mL) was added boron tribromide (1 M in dichloromethane, 2.80 mL, 2.80 mmol) and the mixture was stirred at room temperature for 24 hours. The reaction was quenched with water (10 mL), neutralized with solid sodium hydrogen carbonate (6 mmol) and extracted with a dichloromethane: ethanol 4:1 solution (3×20 mL). The organic layers were combined, washed with water (20 mL), dried over sodium sulfate, filtered and concentrated. The residue was purified by FCC (silica, 0-100% ethyl acetate in toluene, then 5-20% methanol in ethyl acetate, then 0-30% methanol in dichloromethane, then acetonitrile). The silica of the column was washed with a dichloromethane:isopropanol 4:1 solution (3×100 mL). The suspension was filtered. The filtrate was combined with the fractions containing the title compound and concentrated. The residue was dissolved in hot methanol and filtered. The filtrate was allowed to stand at room temperature for 18 hours. The precipitate was filtered. 50 mg were sonicated in 2 M aqueous sodium hydroxide (5 mL). The mixture was washed with ethyl acetate (5 mL). The aqueous phase was treated with a 2 M hydrochloric solution up to pH 7 and extracted with ethyl acetate (3×10 mL). The organic layers were combined, dried over sodium sulfate, filtered and concentrated. The residue was triturated in hot ethyl acetate and filtered to give the title compound 5.4 mg (3% yield) as an off white solid. $\delta_H$ NMR (500 MHz, DMSO) 8.97 (s, 1H), 8.69 (d, J=5.0 Hz, 1H), 8.11 (d, J=5.0 Hz, 1H), 7.98 (d, J=8.8 Hz, 1H), 7.50 (d, J=2.2 Hz, 1H), 7.08 (dd, J=8.9, 2.3 Hz, 1H). Tr(MET-uHPLC-AB-101)=2.67 min, (ES$^+$) (M+H)$^+$ 307/309.

Step 3, Method 57: 2-(3-Bromopyridin-4-yl)-6-[2-(morpholin-4-yl)ethoxy]-1,3-benzothiazole 2-(3-Bromopyridin-4-yl)-1,3-benzothiazol-6-ol (35 mg, 0.11 mmol), 4-(2-chloroethyl)morpholine hydrochloride (23 mg, 0.13 mmol) and potassium carbonate (55 mg, 0.4 mmol) were stirred at room temperature in N,N-dimethylformamide (1 mL) for 16 hours. The mixture was heated to 80° C. for 2 hours. The mixture was cooled to room temperature and water (10 mL) was added. The mixture was extracted with ethyl acetate (3×5 mL). The organic layers were combined, washed with brine (5 mL) and evaporated in vacuo. Purification by FCC (silica, 0-50% ethyl acetate in dichloromethane then 5% methanol in dichloromethane) gave the title compound 36 mg (75% yield) as a white solid.

Example 1, Method 57: 2-(3-Bromopyridin-4-yl)-6-[2-(morpholin-4-yl)ethoxy]-1,3-benzothiazole $\delta_H$ NMR (500 MHz, chloroform) 8.91 (s, 1H), 8.63 (d, J=5.1 Hz, 1H), 8.12 (d, J=5.1 Hz, 1H), 8.04 (d, J=9.0 Hz, 1H), 7.42 (d, J=2.3 Hz, 1H), 7.18 (dd, J=9.0, 2.5 Hz, 1H), 4.26 (s, 2H), 3.79 (s, 4H), 2.92 (s, 2H), 2.67 (s, 4H). Tr(MET-uHPLC-AB-101)=1.59 min, (ES$^+$) (M+H)$^+$ 420/422.

The following example was prepared using Method 57 described above:

Method 58
Scheme for Method 58

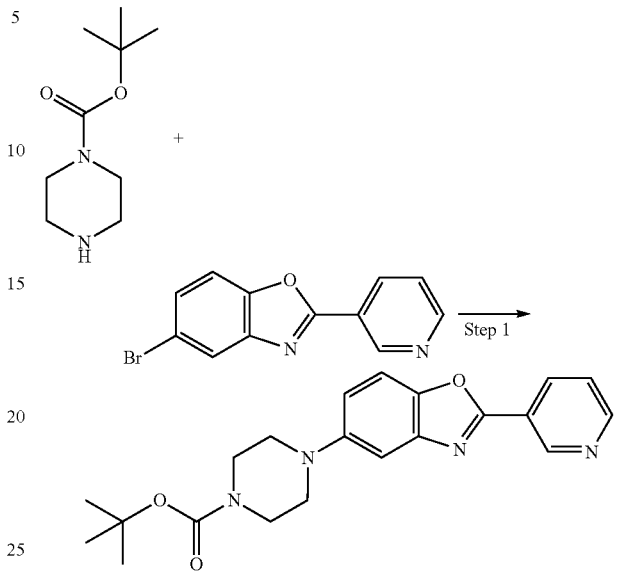

Step 1, Method 56: tert-Butyl 4-[2-(pyridin-3-yl)-1,3-benzoxazol-5-yl]piperazine-1-carboxylate A sealed tube was charged with 5-bromo-2-(pyridin-3-yl)-1,3-benzoxazole (200 mg, 0.73 mmol), tert-butyl piperazine-1-carboxylate (162 mg, 0.87 mmol), caesium carbonate (568 mg, 1.74 mmol), [2',6'-bis(propan-2-yloxy)biphenyl-2-yl](dicyclohexyl)phosphane (17 mg, 0.04 mmol) and tetrahydrofuran (5 mL). The reaction mixture was degassed by bubbling with nitrogen for 20 minutes. Palladium(II) acetate (8 mg, 0.04 mmol) was added and the reaction mixture was stirred overnight at 70° C. The reaction mixture was cooled to room temperature and partitioned between ethyl acetate (15 mL) and water (15 mL). The aqueous layer was separated and extracted with ethyl acetate (2×15 mL). The combined organic extracts were dried over sodium sulfate, filtered and concentrated. Purification by FCC (silica, 10-100% ethyl acetate in heptane) gave the title compound 235 mg (85% yield) as a yellow powder.

Example 1, Method 58: tert-butyl 4-[2-(pyridin-3-yl)-1,3-benzoxazol-5-yl]piperazine-1-carboxylate $\delta_H$ NMR (500 MHz, DMSO) 9.32 (d, J=2.1 Hz, 1H), 8.79 (dd, J=4.8, 1.6 Hz, 1H), 8.50 (dt, J=8.0, 1.9 Hz, 1H), 7.68 (d, J=9.0 Hz, 1H), 7.64 (dd, J=8.0, 4.8 Hz, 1H), 7.35 (d, J=2.4 Hz, 1H), 7.17 (dd, J=9.0, 2.4 Hz, 1H), 3.49 (d, J=4.9 Hz,

TABLE 58

| Ex. | Structure | Mol. Weight | IUPAC Name | LCMS data |
|---|---|---|---|---|
| 1 | 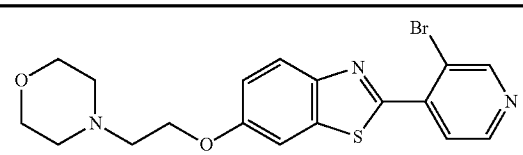 | 420.32 | 2-(3-Bromopyridin-4-yl)-6-[2-(morpholin-4-yl)ethoxy]-1,3-benzothiazole | Tr(MET-uHPLC-AB-101) = 1.59 min, (ES+) (M + H)+ 420/422 |

4H), 3.16-3.09 (m, 4H), 1.43 (s, 9H). Tr(MET-uHPLC-AB-101)=3.5 min, (ES⁺) (M+H)⁺ 381.

The following example was prepared using Method 58 described above:

TABLE 59

| Ex. | Structure | Mol. Weight | IUPAC Name | LCMS data |
|---|---|---|---|---|
| 1 | 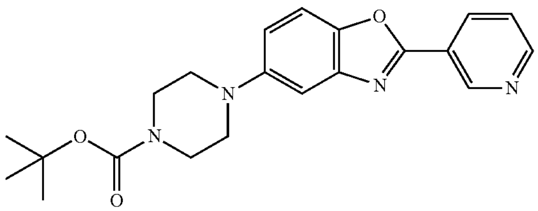 [SMILES: CC(C)(C)OC(=O)N1CCN(c2ccc3oc(-c4cccnc4)nc3c2)CC1] | 380.44 | tert-Butyl 4-[2-(pyridin-3-yl)-1,3-benzoxazol-5-yl]piperazine-1-carboxylate | Tr(MET-uHPLC-AB-101) = 3.5 min, (ES⁺) (M + H)⁺ 381 |

Method 59
Scheme for Method 59

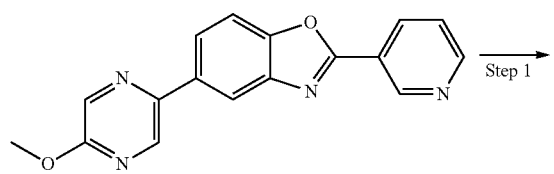

Step 1, Method 59: 5-[2-(Pyridin-3-yl)-1,3-benzoxazol-5-yl]pyrazin-2-ol 5-(5-Methoxypyrazin-2-yl)-2-(pyridin-3-yl)-1,3-benzoxazole (344 mg, 0.96 mmol, prepared using Method 8) and sodium iodide (216 mg, 1.44 mmol) were suspended in acetonitrile (30 mL), chloro(trimethyl)silane (182 μl, 1.44 mmol) was added and the reaction was sealed and stirred at room temperature for 60 hours. The reaction was heated to 70° C. for 8 hours. The reaction was stirred at room temperature for 15 hours. The reaction mixture was filtered through paper and the precipitate was washed with water (10 mL) and diethyl ether (2×10 mL). The solid was dried in vacuo to give the title compound, 220 mg (78% yield) as a brown solid.

Example 1, Method 59: 5-[2-(Pyridin-3-yl)-1,3-benzoxazol-5-yl]pyrazin-2-ol

δ$_H$ NMR (500 MHz, DMSO) 12.67 (br. s., 1H), 9.38 (d, J=2.1 Hz, 1H), 8.83 (dd, J=4.8, 1.6 Hz, 1H), 8.56 (dt, J=8.0, 1.9 Hz, 1H), 8.38-8.24 (m, 1H), 8.20 (br. s., 1H), 8.16 (d, J=1.1 Hz, 1H), 8.02 (dd, J=8.6, 1.5 Hz, 1H), 7.88 (d, J=8.6 Hz, 1H), 7.68 (dd, J=8.0, 4.8 Hz, 1H). Tr(MET-uHPLC-AB-101)=1.88 min, (ES⁺) (M+H)⁺ 291.

The following example was prepared using Method 59 described above:

TABLE 60

| Ex. | Structure | Mol. Weight | IUPAC Name | LCMS data |
|---|---|---|---|---|
| 1 | 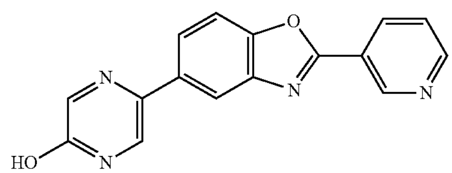 [SMILES: Oc1cnc(-c2ccc3oc(-c4cccnc4)nc3c2)cn1] | 290.28 | 5-[2-(Pyridin-3-yl)-1,3-benzoxazol-5-yl]pyrazin-2-ol | Tr(MET-uHPLC-AB-101) = 1.88 min, (ES⁺) (M + H)⁺ 291 |

Method 60
Scheme for Method 60

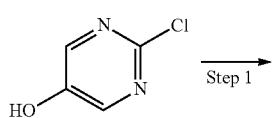

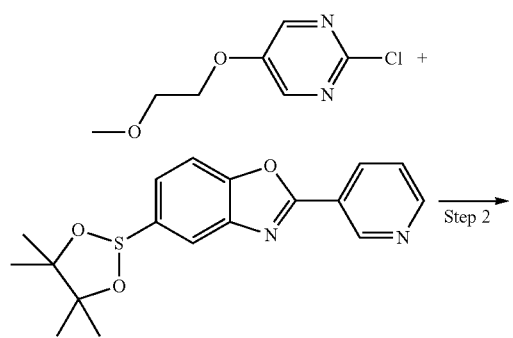

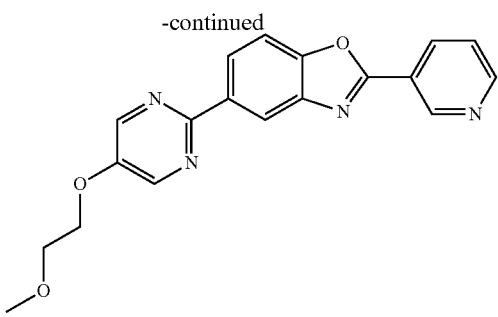

Step 1, Method 60: 2-Chloro-5-(2-methoxyethoxy)pyrimidine

2-Chloropyrimidin-5-ol (200 mg, 1.53 mmol), 1-bromo-2-methoxyethane (0.158 mL, 1.69 mmol) and potassium carbonate (423.5 mg, 3.06 mmol) were suspended in anhydrous N,N-dimethylformamide (5 mL) and heated to 50° C. in a nitrogen atmosphere for 16 hours. The solvents were removed in vacuo and the residue was partitioned between ethyl acetate (50 mL) and water (30 mL), the aqueous was extracted with ethyl acetate (2×30 mL) and the combined organics washed with brine (20 mL), dried over anhydrous sodium sulfate, filtered and concentrated to give the title compound 244 mg (yield 85%) as off-white translucent crystals. $\delta_H$ NMR (500 MHz, DMSO) 8.55 (s, 2H), 4.37-4.21 (m, 2H), 3.78-3.59 (m, 2H), 3.30 (s, 3H). Tr(METCR1278)=1.36 min, (ES$^+$) (M+Na)$^+$ 189.

Step 2, Method 60: 5-[5-(2-Methoxyethoxy)pyrimidin-2-yl]-2-(pyridin-3-yl)-1,3-benzoxazole 2-(Pyridin-3-yl)-5-(tetramethyl-1,3,2-dioxaborolan-2-yl)-1,3-benzoxazole (205 mg, 0.57 mmol, prepared using Method 8), 2-chloro-5-(2-methoxyethoxy)pyrimidine (119 mg, 0.63 mmol) and 2 M sodium carbonate (0.57 mL) were suspended in anhydrous 1,4-dioxane (4 mL) and sonicated under a flow of nitrogen for 5 minutes. Tetrakis(triphenylphosphine)palladium(0) (33 mg, 0.03 mmol) was added and the reaction mixture heated to 110° C. for 6 hours. The reaction mixture was cooled to room temperature and concentrated in vacuo. The residue was partitioned between ethyl acetate (50 mL) and water (50 mL). The aqueous was extracted with ethyl acetate (2×50 mL), the combined organics washed with brine solution (20 mL), dried over anhydrous sodium sulfate, filtered and concentrated. The residue was purified by FCC (silica, 20% tetrahydrofuran in dichloromethane) to give the title compound 33.5 mg (yield 17%) as a white solid.

Example 1, Method 60: 5-[5-(2-Methoxyethoxy)pyrimidin-2-yl]-2-(pyridin-3-yl)-1,3-benzoxazole $\delta_H$ NMR (500 MHz, DMSO) 9.39 (d, J=2.1 Hz, 1H), 8.83 (dd, J=4.8, 1.6 Hz, 1H), 8.71 (s, 2H), 8.68 (d, J=1.6 Hz, 1H), 8.64-8.52 (m, 1H), 8.47 (dd, J=8.6, 1.7 Hz, 1H), 7.94 (d, J=8.6 Hz, 1H), 7.68 (dd, J=7.9, 4.9 Hz, 1H), 4.69-4.11 (m, 2H), 3.85-3.58 (m, 2H), 3.33 (s, 3H). Tr(MET-uHPLC-AB-101)=2.85 min, (ES$^+$) (M+H)$^+$ 349.

The following example was prepared using Method 60 described above:

TABLE 61

| Ex. | Structure | Mol. Weight | IUPAC Name | LCMS data |
|---|---|---|---|---|
| 1 | 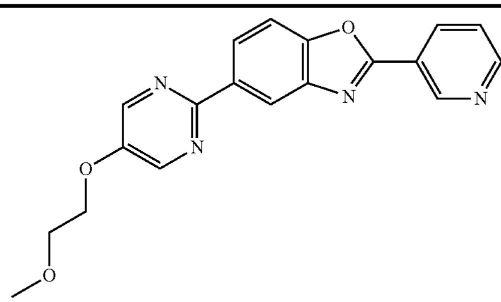 | 348.36 | 5-[5-(2-Methoxyethoxy)pyrimidin-2-yl]-2-(pyridin-3-yl)-1,3-benzoxazole | Tr(MET-uHPLC-AB-101) = 2.85 min, (ES$^+$) (M + H)$^+$ 349 |

Method 61
Scheme for Method 61

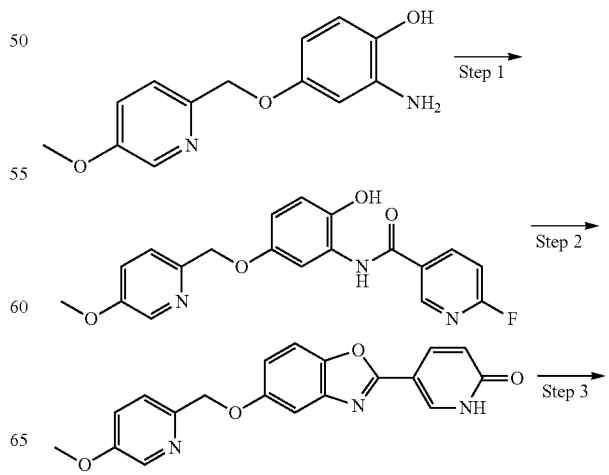

-continued

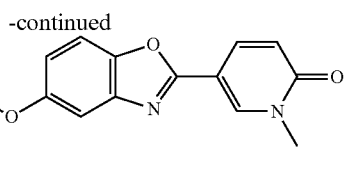

Step 1, Method 61: 6-Fluoro-N-{2-hydroxy-5-[(5-methoxypyridin-2-yl)methoxy]phenyl}pyridine-3-carboxamide 2-Amino-4-[(5-methoxypyridin-2-yl)methoxy]phenol (300 mg, 1.16 mmol, prepared using Method 33), 6-fluoropyridine-3-carboxylic acid (180 mg, 1.27 mmol) and 1-ethyl-3-(3-dimethylaminopropyl)carbodiimide hydrochloride (244 mg, 1.27 mmol) were suspended in pyridine (10 mL). The reaction was stirred at room temperature for 60 hours in a nitrogen atmosphere. The solvents were removed in vacuo and the residue partitioned between ethyl acetate (100 mL) and water (100 mL), the aqueous was extracted with ethyl acetate (2×50 mL), the combined organics were washed with brine (20 mL), dried over anhydrous sodium sulfate, filtered and concentrated. Purification by FCC (silica, 30-100% ethyl acetate in heptane) gave the title compound, 278 mg (61% yield) as a white powder. Tr(METCR1673)=1.02 min, (ES$^+$) (M+H)$^+$ 369.

Step 2, Method 61: 5-{5-[(5-Methoxypyridin-2-yl)methoxy]-1,3-benzoxazol-2-yl}-1,2-dihydropyridin-2-one 6-Fluoro-N-{2-hydroxy-5-[(5-methoxypyridin-2-yl)methoxy]phenyl}pyridine-3-carboxamide (278 mg, 0.72 mmol) was suspended in acetic acid (5 mL) the reaction was irradiated in the microwave (200 W power, 250 psi max) at 180° C. for 30 minutes. The reaction was retreated in the microwave at 200° C. for 3 hours. The reaction mixture was concentrated in vacuo and the residue partitioned between saturated sodium bicarbonate solution (50 mL) and ethyl acetate (100 mL), the aqueous extracted with ethyl acetate (2×100 mL), the combined organics washed with brine (20 mL), dried over anhydrous sodium sulfate, filtered and concentrated. Purification by FCC (silica, 0-15% methanol in dichloromethane) and recrystallisation from DMSO (3 mL) gave the title compound, 77.6 mg (30% yield) as a white solid. $\delta_H$ NMR (500 MHz, DMSO) 12.23 (br. s., 1H), 8.30 (d, J=2.9 Hz, 1H), 8.21 (d, J=2.4 Hz, 1H), 8.05 (dd, J=9.6, 2.6 Hz, 1H), 7.60 (d, J=8.9 Hz, 1H), 7.51 (d, J=8.6 Hz, 1H), 7.43 (dd, J=8.6, 3.0 Hz, 1H), 7.35 (d, J=2.5 Hz, 1H), 7.02 (dd, J=8.9, 2.5 Hz, 1H), 6.52 (d, J=9.6 Hz, 1H), 5.16 (s, 2H), 3.84 (s, 3H). Tr(MET-uHPLC-AB-101)=2.14 min, (ES$^+$) (M+H)$^+$ 350.

Step 3, Method 61: 5-{5-[(5-Methoxypyridin-2-yl)methoxy]-1,3-benzoxazol-2-yl}-1-methyl-1,2-dihydropyridin-2-one 5-{5-[(5-Methoxypyridin-2-yl)methoxy]-1,3-benzoxazol-2-yl}-1,2-dihydropyridin-2-one (42 mg, 0.12 mmol) and methyl 4-nitrobenzenesulfonate (28 mg, 0.13 mmol) were dissolved in anhydrous N,N-dimethylformamide (2 mL) and stirred at room temperature for 5 minutes. Sodium hydride in mineral oil (60%, 5 mg, 0.13 mmol) was added and the reaction stirred at room temperature for 2 hours. The reaction was diluted with water (15 mL) and extracted with ethyl acetate (3×20 mL). The combined organics were washed with brine (10 mL), dried over anhydrous magnesium sulfate, filtered and concentrated. The product was purified by FCC (silica, 20-80% premixed tetrahydrofuran: ethyl acetate (2:1) in heptane) and recrystallisation from ethanol to give the title compound 8 mg (19% yield) as an off white powder.

Example 1, Method 61: 5-{5-[(5-Methoxypyridin-2-yl)methoxy]-1,3-benzoxazol-2-yl}-1-methyl-1,2-dihydropyridin-2-one $\delta_H$ NMR NMR (500 MHz, DMSO) 8.70 (d, J=2.5 Hz, 1H), 8.30 (d, J=2.9 Hz, 1H), 8.04 (dd, J=9.5, 2.6 Hz, 1H), 7.59 (d, J=8.9 Hz, 1H), 7.51 (d, J=8.6 Hz, 1H), 7.42 (dd, J=8.6, 2.9 Hz, 1H), 7.34 (d, J=2.5 Hz, 1H), 7.03 (dd, J=8.9, 2.5 Hz, 1H), 6.56 (d, J=9.5 Hz, 1H), 5.16 (s, 2H), 3.83 (s, 3H), 3.57 (s, 3H). Tr(MET-uHPLC-AB-101)=2.41 min, (ES$^+$) (M+H)$^+$ 364.

The following examples were prepared using Method 61 described above:

TABLE 62

| Ex. | Structure | Mol. Weight | IUPAC Name | LCMS data |
|---|---|---|---|---|
| 1 | 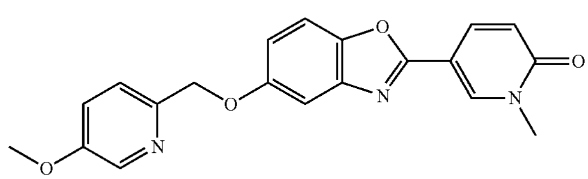 [SMILES: COc1ccc(COc2ccc3oc(-c4ccc(=O)n(C)c4)nc3c2)nc1] | 363.37 | 5-{5-[(5-methoxypyridin-2-yl)methoxy]-1,3-benzoxazol-2-yl}-1-methyl-1,2-dihydropyridin-2-one | Tr(MET-uHPLC-AB-101) = 2.41 min, (ES$^+$) (M + H)$^+$ 364 |
| 2 | 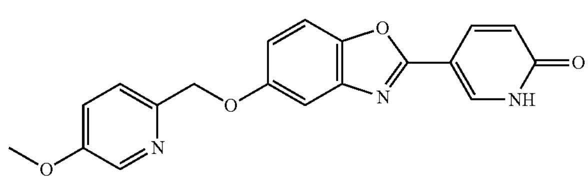 | 349.35 | 5-{5-[(5-methoxypyridin-2-yl)methoxy]-1,3-benzoxazol-2-yl}-1,2-dihydropyridin-2-one | Tr(MET-uHPLC-AB-101) = 2.14 min, (ES$^+$) (M + H)$^+$ 350 |

Method 62
Scheme for Method 62

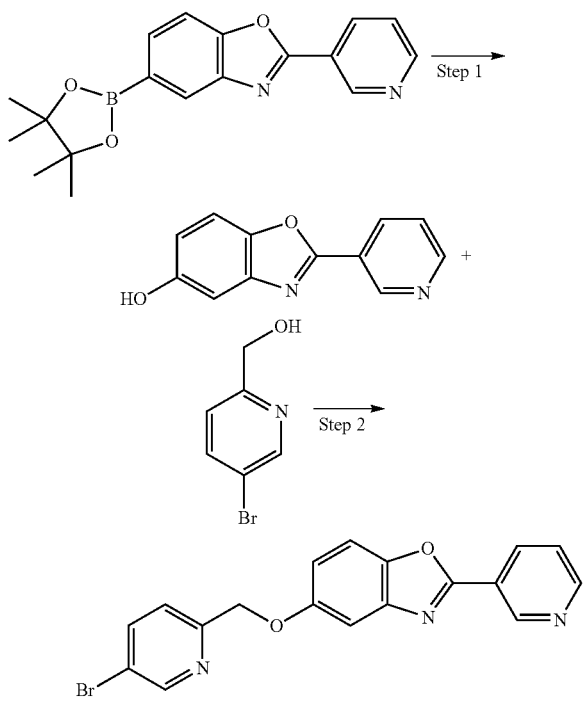

Step 1, Method 62:
2-(Pyridin-3-yl)-1,3-benzoxazol-5-ol 2-(Pyridin-3-yl)-5-(tetramethyl-1,3,2-dioxaborolan-2-yl)-1,3-benzoxazole (0.73 g, 1.58 mmol, prepared using Method 8) was dissolved in tetrahydrofuran (10 mL) and water (10 mL), sodium perborate tetrahydrate (0.61 g, 3.95 mmol) was added and the reaction was stirred at room temperature in a nitrogen atmosphere for 16 hours. Saturated ammonium chloride solution (30 mL) was added to the reaction mixture and the product was extracted with ethyl acetate (3×100 mL), the combined organic extracts were washed with brine (10 mL), dried over anhydrous magnesium sulfate, filtered and concentrated. Purification by FCC (silica, 20-60% ethyl acetate in heptane, followed by 10% methanol in dichloromethane) gave the title compound, 160 mg (48% yield) as a yellow powder. $\delta_H$ NMR (500 MHz, DMSO) 9.61 (s, 1H), 9.31 (d, J=2.1 Hz, 1H), 8.78 (dd, J=4.8, 1.6 Hz, 1H), 8.49 (dt, J=8.0, 1.9 Hz, 1H), 7.73-7.51 (m, 2H), 7.13 (d, J=2.4 Hz, 1H), 6.89 (dd, J=8.8, 2.4 Hz, 1H). Tr(METCR1410)=0.91 min, (ES$^+$) (M+H)$^+$ 213.

Step 2, Method 62: 5-[(5-Bromopyridin-2-yl)methoxy]-2-(pyridin-3-yl)-1,3-benzoxazole 2-(Pyridin-3-yl)-1,3-benzoxazol-5-ol (340 mg, 1.6 mmol) and (5-bromopyridin-2-yl)methanol (349 mg, 1.76 mmol) were suspended in anhydrous toluene (5 mL), cyanomethylenetributylphosphorane (0.63 mL, 2.4 mmol) was added and the reaction heated to 100° C. in a sealed tube for 3 hours. The reaction was cooled to room temperature and the solvents removed in vacuo. The residue was triturated with diethyl ether and heptane and filtered to give the title compound, 541 mg (87% yield) as a beige solid.

Example 1, Method 62: 5-[(5-Bromopyridin-2-yl)methoxy]-2-(pyridin-3-yl)-1,3-benzoxazole $\delta_H$ NMR (500 MHz, DMSO) 9.47-9.17 (m, 1H), 8.80 (dd, J=4.8, 1.6 Hz, 1H), 8.74 (d, J=2.2 Hz, 1H), 8.51 (dt, J=8.0, 1.9 Hz, 1H), 8.11 (dd, J=8.4, 2.4 Hz, 1H), 7.75 (d, J=8.9 Hz, 1H), 7.65 (ddd, J=8.0, 4.8, 0.7 Hz, 1H), 7.57 (d, J=8.4 Hz, 1H), 7.49 (d, J=2.5 Hz, 1H), 7.16 (dd, J=8.9, 2.6 Hz, 1H), 5.26 (s, 2H). Tr(MET-uHPLC-AB-101)=3.44 min, (ES$^+$) (M+H)$^+$ 382/384.

The following examples were prepared using Method 62 described above:

TABLE 63

| Ex. | Structure | Mol. Weight | IUPAC Name | LCMS data |
|---|---|---|---|---|
| 1 | ![structure] | 382.22 | 5-[(5-Bromopyridin-2-yl)methoxy]-2-(pyridin-3-yl)-1,3-benzoxazole | Tr(MET-uHPLC-AB-101) = 3.44 min, (ES$^+$) (M + H)$^+$ 382/384 |
| 2 | ![structure] | 303.32 | 5-(Pyridin-2-ylmethoxy)-2-(pyridin-3-yl)-1,3-benzoxazole | Tr(MET-uHPLC-AB-101) = 2.3 min, (ES$^+$) (M + H)$^+$ 304 |

Method 63
Scheme for Method 63

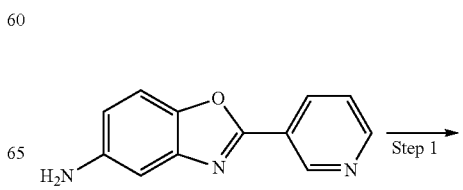

177

-continued

Step 1, Method 63: 2-Phenyl-N-[2-(pyridin-3-yl)-1,3-benzoxazol-5-yl]pyrimidine-5-carboxamide To a stirred solution of 2-(pyridin-3-yl)-1,3-benzoxazol-5-amine (100 mg, 0.47 mmol) in pyridine was added ethylcarbodiimide hydrochloride (91 mg, 0.47 mmol) and 2-phenylpyrimidine-5-carboxylic acid (95 mg, 0.47 mmol). The reaction mixture was stirred at room temperature for 16 hours. Water (10 mL) was added to the reaction mixture and a precipitate was produced. The precipitate was collected by filtration and dried in an oven for 16 hours to give the title compound 157 mg (84% yield) as a tan solid.

Example 1, Method 63: 2-Phenyl-N-[2-(pyridin-3-yl)-1,3-benzoxazol-5-yl]pyrimidine-5-carboxamide $\delta_H$ NMR (500 MHz, DMSO) 10.82 (s, 1H), 9.40 (s, 2H), 9.37 (s, 1H), 8.82 (d, J=4.6 Hz, 1H), 8.55 (d, J=7.8 Hz, 1H), 8.49 (d, J=6.5 Hz, 2H), 8.36 (s, 1H), 7.87 (d, J=8.8 Hz, 1H), 7.79 (d, J=8.8 Hz, 1H), 7.67 (dd, J=7.7, 5.0 Hz, 1H), 7.59 (d, J=6.9 Hz, 3H). Tr(MET-uHPLC-AB-101)=3.26 min, (ES$^+$) (M+H)$^+$ 394.

The following examples were prepared using Method 63 described above:

TABLE 64

| Ex. | Structure | Mol. Weight | IUPAC Name | LCMS data |
| --- | --- | --- | --- | --- |
| 1 | 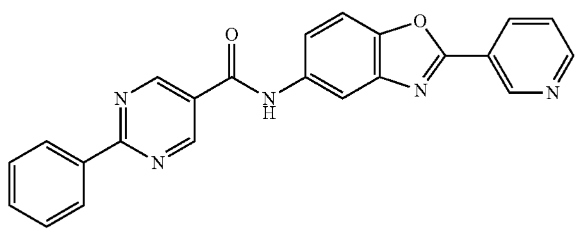 [SMILES: O=C(Nc1ccc2oc(-c3cccnc3)nc2c1)c1cnc(-c2ccccc2)nc1] | 393.41 | 2-Phenyl-N-[2-(pyridin-3-yl)-1,3-benzoxazol-5-yl]pyrimidine-5-carboxamide | Tr(MET-uHPLC-AB-101) = 3.26 min, (ES$^+$) (M + H)$^+$ 394 |
| 2 | 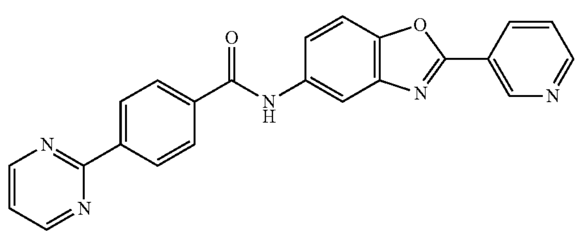 [SMILES: O=C(Nc1ccc2oc(-c3cccnc3)nc2c1)c1ccc(-c2ncccn2)cc1] | 393.41 | N-[2-(Pyridin-3-yl)-1,3-benzoxazol-5-yl]-4-(pyrimidin-2-yl)benzamide | Tr(MET-uHPLC-AB 101) = 2.77 min, (ES$^+$) (M + H)$^+$ 394 |
| 3 | 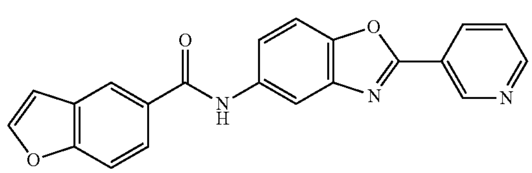 [SMILES: O=C(Nc1ccc2oc(-c3cccnc3)nc2c1)c1ccc2occc2c1] | 355.35 | N-[2-(Pyridin-3-yl)-1,3-benzoxazol-5-yl]-1-benzofuran-5-carboxamide | Tr(MET-uHPLC-AB-101) = 2.95 min, (ES$^+$) (M + H)$^+$ 356 |
| 4 | 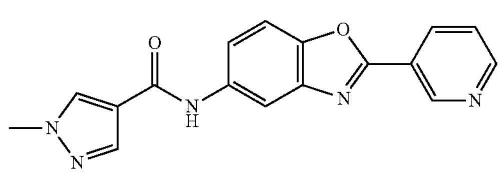 [SMILES: Cn1cc(C(=O)Nc2ccc3oc(-c4cccnc4)nc3c2)cn1] | 319.32 | 1-Methyl-N-[2-(pyridin-3-yl)-1,3-benzoxazol-5-yl]-1H-pyrazole-4-carboxamide | Tr(MET-uHPLC-AB-101) = 1.97 min, (ES$^+$) (M + H)$^+$ 320 |
| 5 | 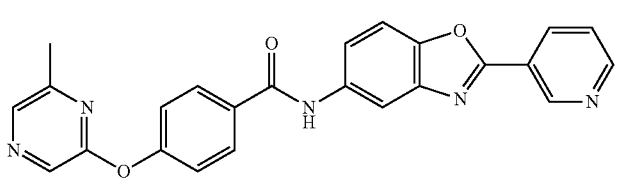 [SMILES: Cc1cncc(Oc2ccc(C(=O)Nc3ccc4oc(-c5cccnc5)nc4c3)cc2)n1] | 423.43 | 4-[(6-Methylpyrazin-2-yl)oxy]-N-[2-(pyridin-3-yl)-1,3-benzoxazol-5-yl]benzamide | Tr(MET-uHPLC-AB-101) = 2.92 min, (ES$^+$) (M + H)$^+$ 424 |

TABLE 64-continued

| Ex. | Structure | Mol. Weight | IUPAC Name | LCMS data |
|---|---|---|---|---|
| 6 | 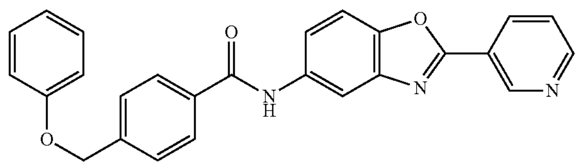 [SMILES: O=C(Nc1ccc2oc(-c3cccnc3)nc2c1)c1ccc(COc2ccccc2)cc1] | 421.46 | 4-(Phenoxymethyl)-N-[2-(pyridin-3-yl)-1,3-benzoxazol-5-yl]benzamide | Tr(MET-uHPLC-AB 101) = 3.65 min, (ES+) (M + H)+ 422 |
| 7 | 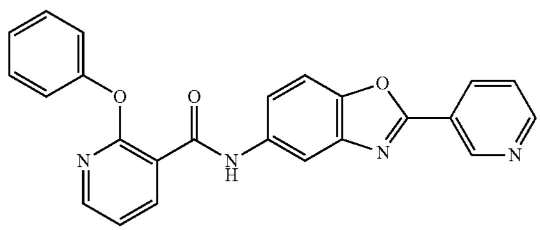 [SMILES: O=C(Nc1ccc2oc(-c3cccnc3)nc2c1)c1cccnc1Oc1ccccc1] | 408.42 | 2-Phenoxy-N-[2-(pyridin-3-yl)-1,3-benzoxazol-5-yl]pyridine-3-carboxamide | Tr(MET-uHPLC-AB-101) = 3.31 min, (ES+) (M + H)+ 409 |
| 8 | 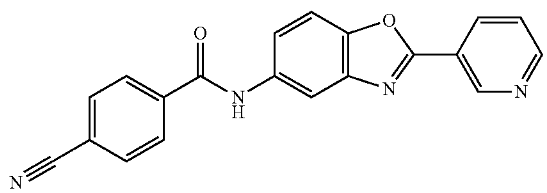 [SMILES: N#Cc1ccc(C(=O)Nc2ccc3oc(-c4cccnc4)nc3c2)cc1] | 340.34 | 4-Cyano-N-[2-(pyridin-3-yl)-1,3-benzoxazol-5-yl]benzamide | Tr(MET-uHPLC-AB-101) = 2.71 min, (ES+) (M + H)+ 341 |
| 9 | 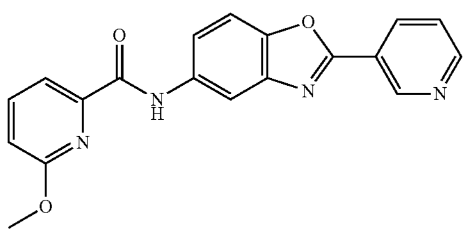 [SMILES: COc1cccc(C(=O)Nc2ccc3oc(-c4cccnc4)nc3c2)n1] | 346.35 | 6-Methoxy-N-[2-(pyridin-3-yl)-1,3-benzoxazol-5-yl]pyridine-2-carboxamide | Tr(MET-uHPLC-AB-101) = 3.24 min, (ES+) (M + H)+ 347 |
| 10 | 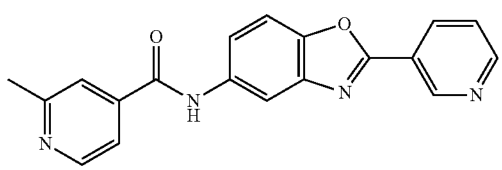 [SMILES: Cc1cc(C(=O)Nc2ccc3oc(-c4cccnc4)nc3c2)ccn1] | 330.35 | 2-Methyl-N-[2-(pyridin-3-yl)-1,3-benzoxazol-5-yl]pyridine-4-carboxamide | Tr(MET-uHPLC-AB-101) = 1.66 min, (ES+) (M + H)+ 331 |
| 11 | 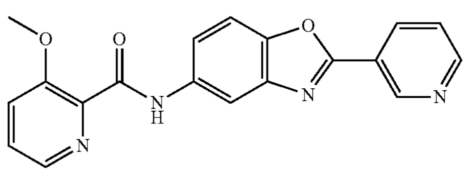 [SMILES: COc1cccnc1C(=O)Nc1ccc2oc(-c3cccnc3)nc2c1] | 346.35 | 3-Methoxy-N-[2-(pyridin-3-yl)-1,3-benzoxazol-5-yl]pyridine-2-carboxamide | Tr(MET-uHPLC-AB-101) = 2.36 min, (ES+) (M + H)+ 347 |
| 12 | 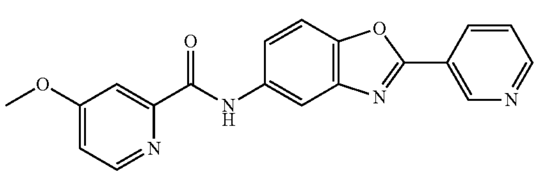 [SMILES: COc1ccnc(C(=O)Nc2ccc3oc(-c4cccnc4)nc3c2)c1] | 346.35 | 4-Methoxy-N-[2-(pyridin-3-yl)-1,3-benzoxazol-5-yl]pyridine-2-carboxamide | Tr(MET-uHPLC-AB-101) = 2.85 min, (ES+) (M + H)+ 347 |
| 13 | 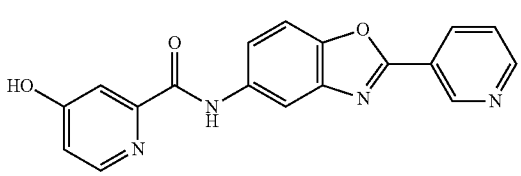 [SMILES: O=C(Nc1ccc2oc(-c3cccnc3)nc2c1)c1cc(O)ccn1] | 332.32 | 4-Hydroxy-N-[2-(pyridin-3-yl)-1,3-benzoxazol-5-yl]pyridine-2-carboxamide | Tr(MET-uHPLC-AB-101) = 1.91 min, (ES+) (M + H)+ 333 |

TABLE 64-continued

| Ex. | Structure | Mol. Weight | IUPAC Name | LCMS data |
|---|---|---|---|---|
| 14 | 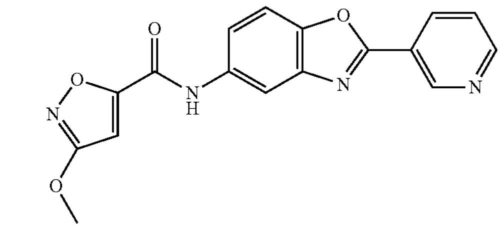 [SMILES: COc1cc(C(=O)Nc2ccc3oc(-c4cccnc4)nc3c2)on1] | 336.31 | 3-Methoxy-N-[2-(pyridin-3-yl)-1,3-benzoxazol-5-yl]-1,2-oxazole-5-carboxamide | Tr(MET-uHPLC-AB-101) = 2.53 min, (ES+) (M + H)+ 337 |
| 15 | 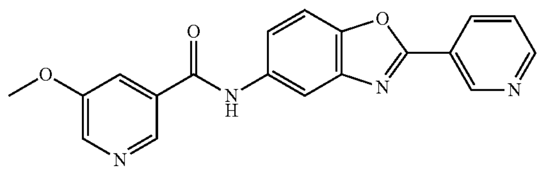 [SMILES: COc1cncc(C(=O)Nc2ccc3oc(-c4cccnc4)nc3c2)c1] | 346.35 | 5-Methoxy-N-[2-(pyridin-3-yl)-1,3-benzoxazol-5-yl]pyridine-3-carboxamide | Tr(MET-uHPLC-AB-101) = 2.17 min, (ES+) (M + H)+ 347 |

Method 64

Scheme for Method 64

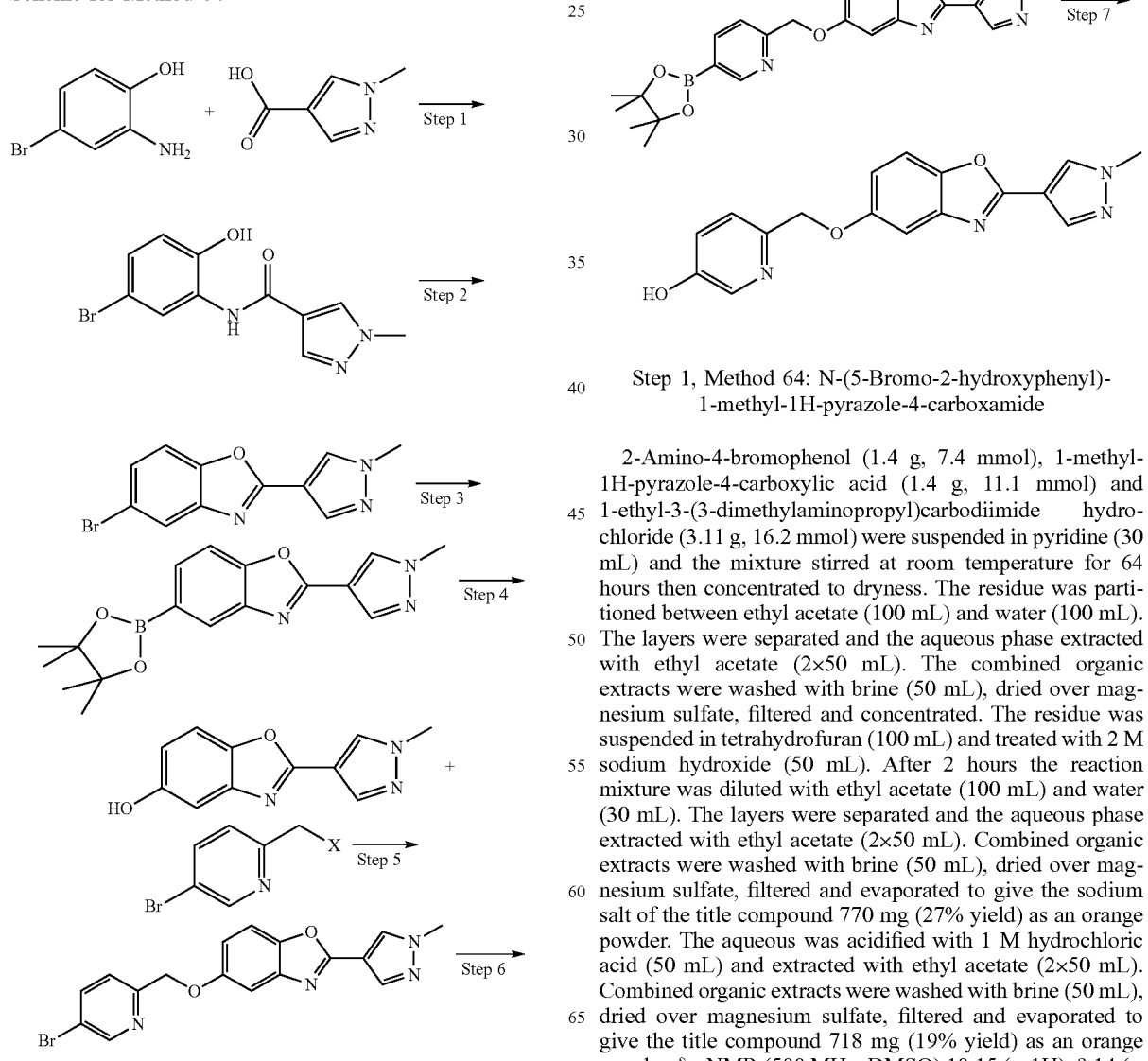

Step 1, Method 64: N-(5-Bromo-2-hydroxyphenyl)-1-methyl-1H-pyrazole-4-carboxamide 2-Amino-4-bromophenol (1.4 g, 7.4 mmol), 1-methyl-1H-pyrazole-4-carboxylic acid (1.4 g, 11.1 mmol) and 1-ethyl-3-(3-dimethylaminopropyl)carbodiimide hydrochloride (3.11 g, 16.2 mmol) were suspended in pyridine (30 mL) and the mixture stirred at room temperature for 64 hours then concentrated to dryness. The residue was partitioned between ethyl acetate (100 mL) and water (100 mL). The layers were separated and the aqueous phase extracted with ethyl acetate (2×50 mL). The combined organic extracts were washed with brine (50 mL), dried over magnesium sulfate, filtered and concentrated. The residue was suspended in tetrahydrofuran (100 mL) and treated with 2 M sodium hydroxide (50 mL). After 2 hours the reaction mixture was diluted with ethyl acetate (100 mL) and water (30 mL). The layers were separated and the aqueous phase extracted with ethyl acetate (2×50 mL). Combined organic extracts were washed with brine (50 mL), dried over magnesium sulfate, filtered and evaporated to give the sodium salt of the title compound 770 mg (27% yield) as an orange powder. The aqueous was acidified with 1 M hydrochloric acid (50 mL) and extracted with ethyl acetate (2×50 mL). Combined organic extracts were washed with brine (50 mL), dried over magnesium sulfate, filtered and evaporated to give the title compound 718 mg (19% yield) as an orange powder. $\delta_H$ NMR (500 MHz, DMSO) 10.15 (s, 1H), 9.14 (s, 1H), 8.35 (s, 1H), 7.99 (s, 1H), 7.89 (d, J=2.5 Hz, 1H), 7.15 (dd, J=8.6, 2.5 Hz, 1H), 6.86 (d, J=8.6 Hz, 1H), 3.89 (s, 3H). Tr(METCR1673)=1.03 min, (ES+) (M+H)+ 296/298, 58%.

Step 2 Method 64: 5-Bromo-2-(1-methyl-1H-pyrazol-4-yl)-1,3-benzoxazole

N-[5-Bromo-2-(sodiooxy)phenyl]-1-methyl-1H-pyrazole-4-carboxamide (82%, 770 mg, 2.13 mmol) was suspended in acetic acid (10 mL) in a pressure tube. N-(5-Bromo-2-hydroxyphenyl)-1-methyl-1H-pyrazole-4-carboxamide (58%, 718 mg, 2.43 mmol) was suspended in acetic acid (10 mL) in a pressure tube. Both tubes were sealed and the mixtures heated to 180° C. for 18 hours. Each solution was cooled to room temperature then concentrated to dryness. The residues were dissolved in ethyl acetate and combined, then washed with saturated aqueous sodium bicarbonate solution (20 mL) and brine (20 mL). The organic phase was dried over magnesium sulfate, filtered and concentrated onto silica. Purification by FCC (silica, 12-100% ethyl acetate in heptane) gave the title compound 572 mg (58% yield) as a light orange powder. $\delta_H$ NMR (500 MHz, DMSO) 8.58 (s, 1H), 8.18-8.07 (m, 1H), 7.92 (d, J=1.9 Hz, 1H), 7.69 (d, J=8.6 Hz, 1H), 7.51 (dd, J=8.6, 2.0 Hz, 1H), 3.96 (s, 3H). Tr(MET-uHPLC-AB-101)=2.99 min, (ES+) (M+H)+ 278/280.

Step 3 Method 64: 2-(1-Methyl-1H-pyrazol-4-yl)-5-(tetramethyl-1,3,2-dioxaborolan-2-yl)-1,3-benzoxazole A suspension of 5-bromo-2-(1-methyl-1H-pyrazol-4-yl)-1,3-benzoxazole (560 mg, 2.01 mmol), bis(pinacolato)diboron (562 mg, 2.21 mmol) and potassium acetate (0.54 g, 5.5 mmol) in anhydrous 1,4-dioxane (25 mL) was degassed with nitrogen for 5 minutes. [1,1'-Bis(diphenylphosphino)ferrocene]dichloropalladium(II) (147 mg, 0.20 mmol) was added and the reaction stirred at 100° C. under nitrogen for 1 hour. The reaction mixture was diluted with methyl tert-butyl ether (10 mL) and filtered through celite. The filtrate was evaporated to give a brown residue 1.57 g which was used in the next step without purification. Tr(METCR1673)=1.32 min, (ES+) (M+H)+ 326, 82%.

Step 4 Method 64: 2-(1-Methyl-1H-pyrazol-4-yl)-1,3-benzoxazol-5-ol 2-(1-Methyl-1H-pyrazol-4-yl)-5-(tetramethyl-1,3,2-dioxaborolan-2-yl)-1,3-benzoxazole (1.57 g, assumed 2.01 mmol) was dissolved in 1:1 tetrahydrofuran-water (20 mL). Sodium perborate tetrahydrate (1.54 g, 10.0 mmol) was added and the mixture stirred at room temperature for 1 hour. Saturated ammonium chloride solution (20 mL) was added to the reaction mixture and the product extracted with ethyl acetate (3×20 mL). The combined organic extracts were washed with brine (15 mL), dried over magnesium sulfate, filtered and evaporated to give a brown solid. Purification by FCC (silica, 25-100% ethyl acetate in heptane) gave the title compound 279 mg (32% yield) as an off-white powder. $\delta_H$ NMR (500 MHz, DMSO) 9.43 (s, 1H), 8.50 (s, 1H), 8.06 (s, 1H), 7.47 (d, J=8.7 Hz, 1H), 7.00 (d, J=2.4 Hz, 1H), 6.77 (dd, J=8.7, 2.4 Hz, 1H), 3.95 (s, 3H). Tr(METCR1673)=0.97 min, (ES+) (M+H)+ 216.

Step 5 Method 64: 5-[(5-Bromopyridin-2-yl) methoxy]-2-(1-methyl-1H-pyrazol-4-yl)-1,3-benzoxazole 2-(1-Methyl-1H-pyrazol-4-yl)-1,3-benzoxazol-5-ol (276 mg, 1.28 mmol) and (5-bromopyridin-2-yl)methanol (95%, 279 mg, 1.41 mmol) were suspended in anhydrous toluene (10 mL). Cyanomethylenetributylphosphorane (505 μl, 1.92 mmol) was added and the mixture heated to 100° C. under nitrogen for 2 hours. The reaction mixture was cooled to room temperature and concentrated. The residue was triturated with heptane-diethyl ether (1:1, 20 mL) and the solid collected by filtration and dried under suction to give the title compound 410 mg (79% yield) as a light brown powder. $\delta_H$ NMR (500 MHz, DMSO) 8.73 (d, J=2.2 Hz, 1H), 8.52 (s, 1H), 8.10 (dd, J=8.4, 2.4 Hz, 1H), 8.08 (s, 1H), 7.61 (d, J=8.8 Hz, 1H), 7.55 (d, J=8.4 Hz, 1H), 7.33 (d, J=2.5 Hz, 1H), 7.03 (dd, J=8.8, 2.5 Hz, 1H), 5.22 (s, 2H), 3.95 (s, 3H). Tr(METCR1673)=1.25 min, (ES+) (M+H)+ 385/387.

Step 6 Method 64: 2-(1-Methyl-1H-pyrazol-4-yl)-5-{[5-(tetramethyl-1,3,2-dioxaborolan-2-yl)pyridin-2-yl]methoxy}-1,3-benzoxazole A suspension of 5-[(5-bromopyridin-2-yl)methoxy]-2-(1-methyl-1H-pyrazol-4-yl)-1,3-benzoxazole (410 mg, 1.06 mmol), bis(pinacolato)diboron (297 mg, 1.17 mmol) and potassium acetate (261 mg, 2.66 mmol) in anhydrous 1,4-dioxane (15 mL) was degassed with nitrogen for 5 minutes. Bis(diphenylphosphino)ferrocene]dichloropalladium(II) (78 mg, 0.11 mmol) was added and the reaction stirred at 100° C. under nitrogen for 17 hours. The reaction mixture was diluted with tert-butyl methyl ether (20 mL), filtered and concentrated. The residue was triturated in 1:1 heptane: tert-butyl methyl ether and filtered to give the title compound 479 mg (100% yield) as a grey powder. $\delta_H$ NMR (500 MHz, DMSO) 8.77 (s, 1H), 8.52 (s, 1H), 8.08 (s, 1H), 8.05 (dd, J=7.8, 1.7 Hz, 1H), 7.60 (d, J=8.8 Hz, 1H), 7.57 (d, J=7.7 Hz, 1H), 7.31 (d, J=2.5 Hz, 1H), 7.03 (dd, J=8.9, 2.6 Hz, 1H), 5.27 (s, 2H), 3.95 (s, 3H), 1.31 (s, 12H). Tr(METCR1673)=0.91 min, (ES+) (M+H)+ 351 [corresponding boronic acid].

Step 7 Method 64: 6-({[2-(1-Methyl-1H-pyrazol-4-yl)-1,3-benzoxazol-5-yl]oxy}methyl)pyridin-3-ol 2-(1-Methyl-1H-pyrazol-4-yl)-5-{[5-(tetramethyl-1,3,2-dioxaborolan-2-yl)pyridin-2-yl]methoxy}-1,3-benzoxazole (479 mg, 1.11 mmol) was dissolved in 1:1 tetrahydrofuran-water (10 mL). Sodium perborate tetrahydrate (426 mg, 2.8 mmol) was added and the mixture stirred at room temperature for 1 hour. Saturated ammonium chloride solution (20 mL) was added to the reaction mixture and the mixture extracted with ethyl acetate (3×20 mL). The combined organic extracts were washed with brine (15 mL), dried over magnesium sulfate, filtered and concentrated. The residue was triturated in heptane-tert-butyl methyl ether/ethyl acetate and filtered. The filtrate stood at room temperature overnight, forming crystals. The mother liquor was decanted off and the crystals were suspended in heptane and collected by filtration. Drying under suction gave the title compound 114 mg (32% yield) as brown crystals.

Example 1, Method 64: 6-({[2-(1-Methyl-1H-pyrazol-4-yl)-1,3-benzoxazol-5-yl]oxy}methyl)pyridin-3-ol δH NMR (500 MHz, DMSO) 9.97 (s, 1H), 8.51 (s, 1H), 8.13 (d, J=2.7 Hz, 1H), 8.08 (s, 1H), 7.58 (d, J=8.8 Hz, 1H), 7.39 (d, J=8.4 Hz, 1H), 7.31 (d, J=2.5 Hz, 1H), 7.19 (dd, J=8.4, 2.8 Hz, 1H), 6.99 (dd, J=8.8, 2.5 Hz, 1H), 5.09 (s, 2H), 3.95 (s, 3H). Tr(MET-uHPLC-AB-101)=1.87 min, (ES+) (M+H)+ 323.

The following examples were prepared using Method 64 described above:

TABLE 65

| Ex. | Structure | Mol. Weight | IUPAC Name | LCMS data |
|---|---|---|---|---|
| 1 | 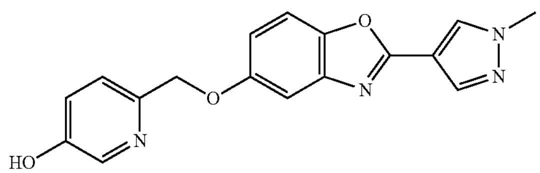 [SMILES: Cn1cc(-c2nc3cc(OCc4ccc(O)cn4)ccc3o2)cn1] | 322.32 | 6-({[2-(1-Methyl-1H-pyrazol-4-yl)-1,3-benzoxazol-5-yl]oxy}methyl)pyridin-3-ol | Tr(MET-uHPLC-AB-101) = 1.87 min, (ES$^+$) (M + H)$^+$ 323 |
| 2 | 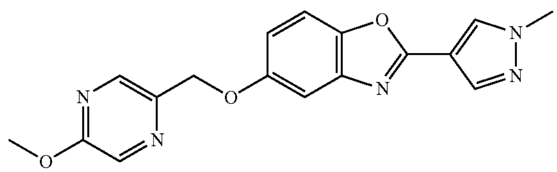 | 337.34 | 5-[(5-Methoxypyrazin-2-yl)methoxy]-2-(1-methyl-1H-pyrazol-4-yl)-1,3-benzoxazole | Tr(MET-uHPLC-AB-101) = 2.83 min, (ES$^+$) (M + H)$^+$ 338 |

Method 65
Scheme for Method 65

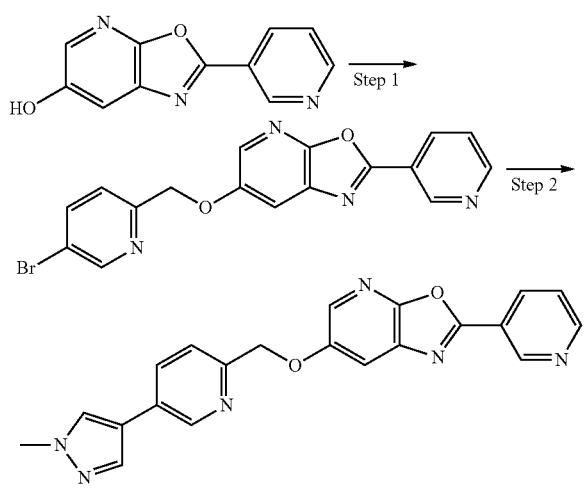

Step 1, Method 65: 3-{6-[(5-Bromopyridin-2-yl)methoxy]-[1,3]oxazolo[5,4-b]pyridin-2-yl}pyridine To a suspension of 2-(pyridin-3-yl)-[1,3]oxazolo[5,4-b]pyridin-6-ol (120 mg, 0.56 mmol, prepared using Method 30) and (5-bromopyridin-2-yl)methanol (95%, 123 mg, 0.62 mmol) in toluene (3 mL) was added cyanomethylenetributylphosphorane (0.25 mL, 0.95 mmol) and mixture heated at 100° C. for 3 hours in a sealed tube. After cooling the mixture was distributed between ethyl acetate (300 mL) and saturated sodium hydrogen carbonate solution (100 mL). The organic layer was washed with brine (50 mL), dried over magnesium sulfate, filtered and evaporated. The solid residue was triturated with ethyl acetate (~5 mL) and then re-crystallised from a hot mixture of tetrahydrofuran and acetonitrile (~5 mL, 1:1) to provide the title compound 74 mg (34% yield) as an off-white solid. $\delta_H$ NMR (500 MHz, DMSO) 9.40-9.26 (m, 1H), 8.83 (dd, J=4.8, 1.6 Hz, 1H), 8.74 (d, J=2.3 Hz, 1H), 8.54 (dt, J=8.0, 1.9 Hz, 1H), 8.25 (d, J=2.7 Hz, 1H), 8.13 (dd, J=8.4, 2.4 Hz, 1H), 8.08 (d, J=2.7 Hz, 1H), 7.73-7.64 (m, 1H), 7.60 (d, J=8.4 Hz, 1H), 5.33 (s, 2H). Tr(MET-uHPLC-AB-101)=3.08 min, (ES$^+$) (M+H)$^+$ 383, 385

Step 2, Method 65: 5-(1-Methyl-1H-pyrazol-4-yl)-2-({[2-(pyridin-3-yl)-[1,3]oxazolo[5,4-b]pyridin-6-yl]oxy}methyl)pyridine 3-{6-[(5-Bromopyridin-2-yl)methoxy]-[1,3]oxazolo[5,4-b]pyridin-2-yl}pyridine (69 mg, 0.16 mmol), (1-methyl-1H-pyrazol-4-yl)boronic acid (22 mg, 0.18 mmol) and 2 M sodium carbonate (0.16 mL) were suspended in anhydrous 1,2-dimethoxyethane (1 mL) and anhydrous ethanol (1 mL) and degassed under a flow of nitrogen for 5 minutes. Palladium tetrakis triphenylphosphine(0) (9 mg, 0.01 mmol) was added and the reaction was heated to 90° C. in a sealed tube for 2 hours. (1-Methyl-1H-pyrazol-4-yl)boronic acid (22 mg, 0.18 mmol) and palladium tetrakis triphenylphosphine(0) (9 mg, 0.01 mmol) were added and the reaction was heated to 90° C. for 2 hours. The reaction mixture was cooled to room temperature and partitioned between ethyl acetate (100 mL) and water (50 mL), a precipitate was filtered from the mixture and triturated with hot ethanol, filtered and washed with diethyl ether to give the title compound 39 mg (56% yield) as a grey solid.

Example 1, Method 65: 5-(1-Methyl-1H-pyrazol-4-yl)-2-({[2-(pyridin-3-yl)-[1,3]oxazolo[5,4-b]pyridin-6-yl]oxy}methyl)pyridine $\delta_H$ NMR (500 MHz, DMSO) 9.35 (d, J=1.7 Hz, 1H), 8.85 (d, J=2.0 Hz, 1H), 8.83 (dd, J=4.8, 1.6 Hz, 1H), 8.55 (dt, J=8.0, 1.9 Hz, 1H), 8.27 (s, 1H), 8.25 (d, J=2.7 Hz, 1H), 8.10 (d, J=2.7 Hz, 1H), 8.02 (dd, J=8.1, 2.3 Hz, 1H), 7.98 (s, 1H), 7.67 (dd, J=8.0, 4.8 Hz, 1H), 7.59 (d, J=8.1 Hz, 1H), 5.33 (s, 2H), 3.88 (s, 3H). Tr(MET-uHPLC-AB-101)=2.25 min, (ES$^+$) (M+H)$^+$ 385.

The following examples were prepared using Method 65 described above:

TABLE 66

| Ex. | Structure | Mol. Weight | IUPAC Name | LCMS data |
|---|---|---|---|---|
| 1 | 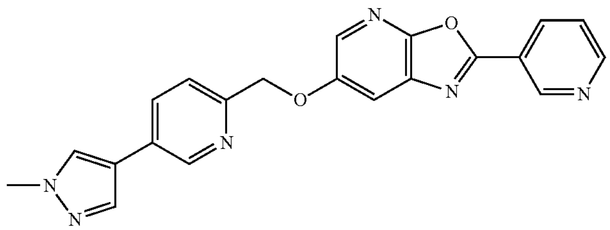 [SMILES: Cn1cc(-c2ccc(COc3cnc4oc(-c5cccnc5)nc4c3)nc2)cn1] | 384.40 | 5-(1-Methyl-1H-pyrazol-4-yl)-2-({[2-(pyridin-3-yl)-[1,3]oxazolo[5,4-b]pyridin-6-yl]oxy}methyl)pyridine | Tr(MET-uHPLC-AB-101) = 2.25 min, (ES$^+$) (M + H)$^+$ 385 |
| 2 | 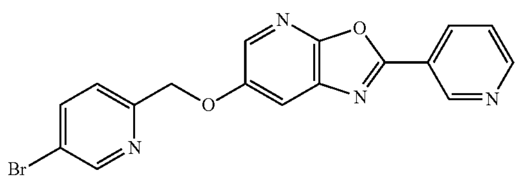 [SMILES: Brc1ccc(COc2cnc3oc(-c4cccnc4)nc3c2)nc1] | 383.21 | 3-{6-[(5-Bromopyridin-2-yl)methoxy]-[1,3]oxazolo[5,4-b]pyridin-2-yl}pyridine | Tr(MET-uHPLC-AB-101) = 3.08 min, (ES$^+$) (M + H)$^+$ 383/385 |
| 3 | 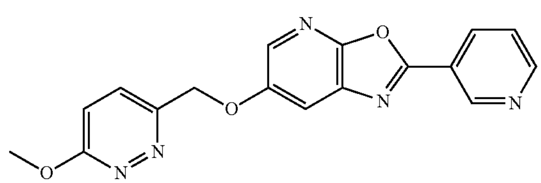 [SMILES: COc1ccc(COc2cnc3oc(-c4cccnc4)nc3c2)nn1] | 335.32 | 3-Methoxy-6-({[2-(pyridin-3-yl)-[1,3]oxazolo[5,4-b]pyridin-6-yl]oxy}methyl)pyridazine | Tr(MET-uHPLC-AB-101) = 2.31 min, (ES+) (M + H)+ 336 |

Method 66
Scheme for Method 66

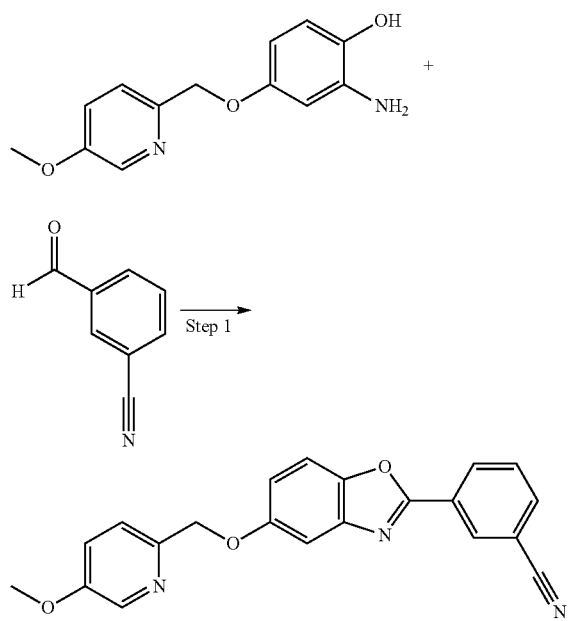

Step 1, Method 66: 3-{5-[(5-Methoxypyridin-2-yl)methoxy]-1,3-benzoxazol-2-yl}benzonitrile 2-Amino-4-[(5-methoxypyridin-2-yl)methoxy]phenol (190 mg, 0.77 mmol, prepared using Method 33) was dissolved in methanol (10 mL), 3-formylbenzonitrile (70 mg, 0.53 mmol) added and the reaction mixture stirred at room temperature for 90 minutes. The methanol was then removed in vacuo and the residue dissolved in dichloromethane (25 mL), cooled to 0° C. and 2,3-dichloro-5,6-dicyano-1,4-benzoquinone (205 mg, 0.9 mmol) added. The ice bath was removed and the mixture was stirred at room temperature for 2 hours, then diluted with dichloromethane (100 mL) and filtered. The solid was washed with dichloromethane (2×50 mL) and the washings and the filtrate combined, dried over magnesium sulfate, filtered and concentrated. Purification by FCC (silica, 0-80% ethyl acetate in heptane) and trituration with ethanol gave the title compound (65.2 mg, 34% yield) as an off-white solid.

Example 1, Method 66: 3-{5-[(5-Methoxypyridin-2-yl)methoxy]-1,3-benzoxazol-2-yl}benzonitrile $\delta_H$ NMR (500 MHz, DMSO) 8.53 (s, 1H), 8.47 (d, J=8.0 Hz, 1H), 8.31 (d, J=2.9 Hz, 1H), 8.09 (d, J=7.8 Hz, 1H), 7.83 (t, J=7.9 Hz, 1H), 7.73 (d, J=8.9 Hz, 1H), 7.53 (d, J=8.6 Hz, 1H), 7.48 (d, J=2.5 Hz, 1H), 7.43 (dd, J=8.6, 3.0 Hz, 1H), 7.15 (dd, J=8.9, 2.5 Hz, 1H), 5.19 (s, 2H), 3.84 (s, 3H). Tr(MET-uHPLC-AB-101)=3.49 min, (ES$^+$) (M+H)$^+$ 358.

The following examples were prepared using Method 66 described above:

TABLE 67

| Ex. | Structure | Mol. Weight | IUPAC Name | LCMS data |
|---|---|---|---|---|
| 1 | 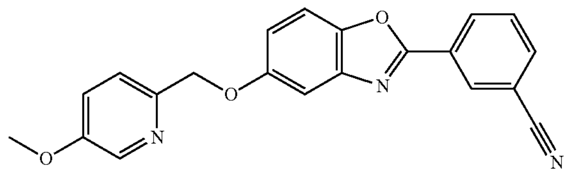 [SMILES: COc1ccc(COc2ccc3oc(-c4cccc(C#N)c4)nc3c2)nc1] | 357.37 | 3-{5-[(5-Methoxypyridin-2-yl)methoxy]-1,3-benzoxazol-2-yl}benzonitrile | Tr(MET-uHPLC-AB-101) = 3.49 min, (ES+) (M + H)+ 358 |
| 2 | 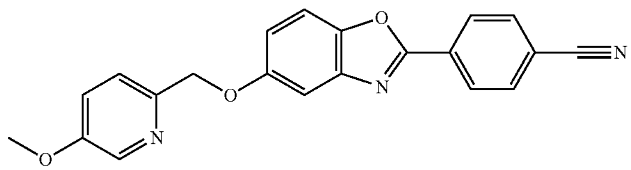 [SMILES: COc1ccc(COc2ccc3oc(-c4ccc(C#N)cc4)nc3c2)nc1] | 357.37 | 4-{5-[(5-Methoxypyridin-2-yl)methoxy]-1,3-benzoxazol-2-yl}benzonitrile | Tr(MET-uHPLC-AB-101) = 3.45 min, (ES+) (M + H)+ 358 |

Method 67
Scheme for Method 67

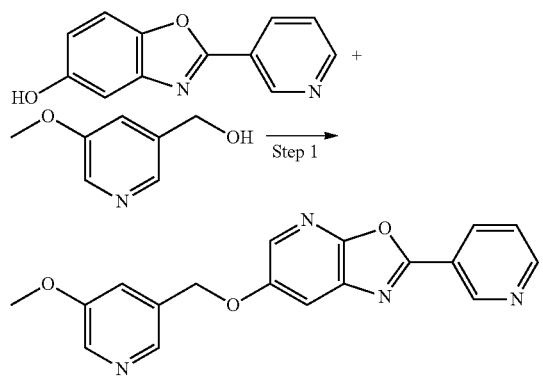

Step 1, Method 67: 3-Methoxy-5-({[2-(pyridin-3-yl)-[1,3]oxazolo[5,4-b]pyridin-6-yl]oxy}methyl)pyridine 2-(Pyridin-3-yl)-[1,3]oxazolo[5,4-b]pyridin-6-ol (86%, 100 mg, 0.4 mmol, prepared using Method 30) and (5-methoxypyridin-3-yl)methanol (65 mg, 0.44 mmol) were suspended in anhydrous toluene (3 mL). Cyanomethylenetributylphosphorane (0.16 mL, 0.61 mmol) was added and the reaction heated to 100° C. in a sealed tube for 18 hours. The reaction was cooled to room temperature and the solvents removed in vacuo. The residue was triturated with diethyl ether and heptane. Purification by FCC (silica, 0-10% methanol in dichloromethane) gave the title compound 45 mg (33% yield) as an off white solid.

Example 1, Method 67: 3-Methoxy-5-({[2-(pyridin-3-yl)-[1,3]oxazolo[5,4-b]pyridin-6-yl]oxy}methyl)pyridine $\delta_H$ NMR (500 MHz, DMSO) 9.35 (d, J=2.0 Hz, 1H), 8.83 (dd, J=4.8, 1.5 Hz, 1H), 8.55 (dt, J=8.0, 1.9 Hz, 1H), 8.32 (d, J=1.2 Hz, 1H), 8.29 (d, J=2.8 Hz, 1H), 8.24 (d, J=2.7 Hz, 1H), 8.11 (d, J=2.7 Hz, 1H), 7.67 (ddd, J=8.0, 4.8 Hz, 1H), 7.54 (s, 1H), 5.31 (s, 2H), 3.86 (s, 3H). Tr(MET-uHPLC-AB-101)=1.94 min, (ES+) (M+H)+ 335.

The following examples were prepared using Method 67 described above:

TABLE 68

| Ex. | Structure | Mol. Weight | IUPAC Name | LCMS data |
|---|---|---|---|---|
| 1 | 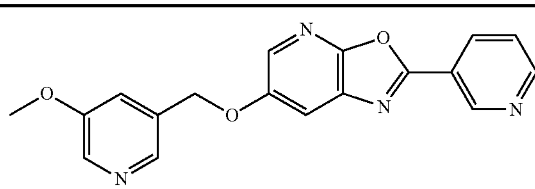 | 334.34 | 3-Methoxy-5-({[2-(pyridin-3-yl)-[1,3]oxazolo[5,4-b]pyridin-6-yl]oxy}methyl)pyridine | Tr(MET-uHPLC-AB-101) = 1.94 min, (ES+) (M + H)+ 335 |
| 2 | 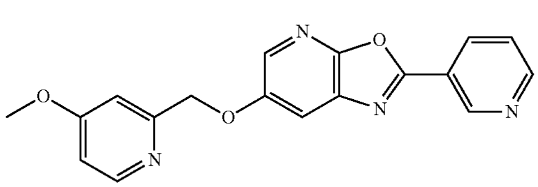 [SMILES: COc1ccnc(COc2cnc3oc(-c4cccnc4)nc3c2)c1] | 334.34 | 4-Methoxy-2-({[2-(pyridin-3-yl)-[1,3]oxazolo[5,4-b]pyridin-6-yl]oxy}methyl)pyridine | Tr(MET-uHPLC-AB-101) = 1.47 min, (ES+) (M + H)+ 335 |

TABLE 68-continued

| Ex. | Structure | Mol. Weight | IUPAC Name | LCMS data |
|---|---|---|---|---|
| 3 | 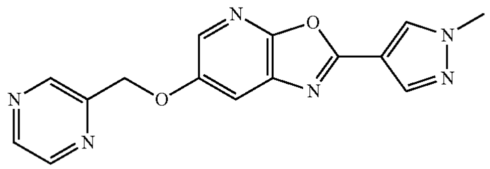 [SMILES: Cn1cc(-c2nc3cc(OCc4cnccn4)cnc3o2)cn1] | 308.30 | 2-({[2-(1-Methyl-1H-pyrazol-4-yl)-[1,3]oxazolo[5,4-b]pyridin-6-yl]oxy}methyl)pyrazine | Tr(MET-uHPLC-AB-101) = 1.99 min, (ES⁺) (M + H)⁺ 309 |

Method 68
Scheme for Method 68

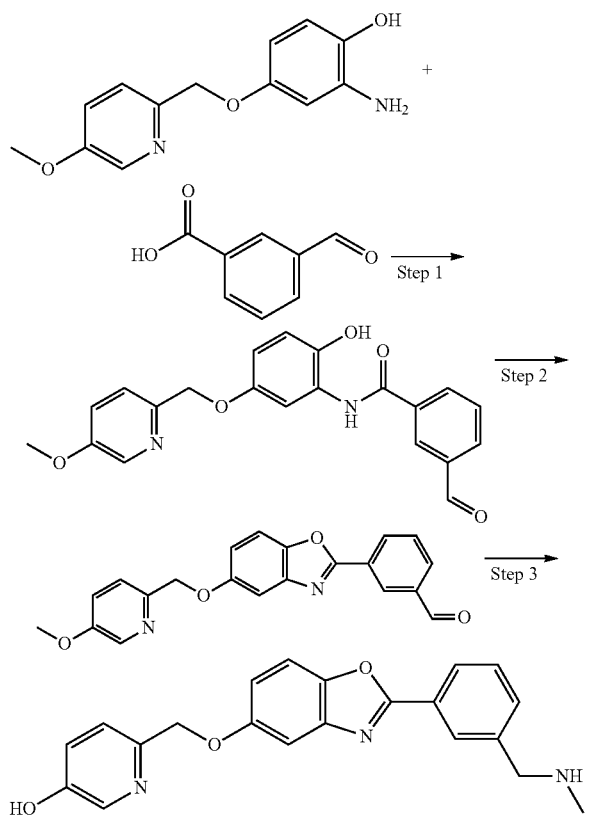

Step 1, Method 68: 3-Formyl-N-{2-hydroxy-5-[(5-methoxypyridin-2-yl)methoxy]phenyl}benzamide To a solution of 3-formylbenzoic acid (61 mg, 0.41 mmol), 2-amino-4-[(5-methoxypyridin-2-yl)methoxy] phenol (112 mg, 0.45 mmol) in pyridine (5 mL) was added ethylcarbodiimide hydrochloride (104 mg, 0.55 mmol) and the resulting mixture stirred overnight at room temperature. The solvent was evaporated and the residue portioned between dichloromethane and water, the dichloromethane layer separated, dried over sodium sulfate, filtered and concentrated to give the crude product, which was used in the next step without further purification.

Step 2, Method 68: 3-{5-[(5-Methoxypyridin-2-yl)methoxy]-1,3-benzoxazol-2-yl}benzaldehyde A solution of 3-formyl-N-{2-hydroxy-5-[(5-methoxypyridin-2-yl)methoxy]phenyl}benzamide (178 mg, 0.38 mmol, circa 80% purity) in acetic acid (4 mL) was heated to 180° C. in a microwave for 50 mins. The mixture was diluted with water and aqueous sodium hydrogen carbonate solution added to give pH 8, the aqueous layer extracted with dichloromethane (100 mL) and the combined organic layers dried over sodium sulfate, filtered and concentrated. Purification by preparative HPLC (acetonitrile/water+0.1% formic acid) gave the title compound 34 mg (25% yield over two steps) as an off-white solid. $\delta_H$ NMR (500 MHz, chloroform) 10.15 (s, 1H), 8.73 (s, 1H), 8.50 (d, J=7.8 Hz, 1H), 8.34 (d, J=2.8 Hz, 1H), 8.06 (d, J=7.7 Hz, 1H), 7.72 (t, J=7.7 Hz, 1H), 7.52 (d, J=8.9 Hz, 1H), 7.49 (d, J=8.6 Hz, 1H), 7.37 (d, J=2.5 Hz, 1H), 7.26 (dd, J=8.6, 2.9 Hz, 1H), 7.11 (dd, J=8.9, 2.5 Hz, 1H), 5.24 (s, 2H), 3.90 (s, 3H). Tr(METCR1678)=1.29 min (ES⁺) (M+H)⁺ 361.

Step 3, Method 68: [(3-{5-[(5-Methoxypyridin-2-yl)methoxy]-1,3-benzoxazol-2yl}phenyl)methyl](methyl)amine To a solution of 3-{5-[(5-methoxypyridin-2-yl)methoxy]-1,3-benzoxazol-2-yl}benzaldehyde (34 mg, 0.09 mmol) in toluene (5 mL) was added methylamine solution in ethanol (33 wt %, 0.5 mL) and the volatiles evaporated. The residue was dissolved in toluene and a further charge of methylamine solution in ethanol (33 wt %, 0.5 mL) added, along with magnesium sulfate. The mixture was stirred for 15 mins, filtered and concentrated to give the crude imine, which was redissolved in 1,2-dichloroethane (5 mL). Sodium triacetoxyborohydride (30 mg, 0.14 mmol) and one drop of acetic acid were added and the reaction mixture stirred overnight. The mixture was diluted with water, aqueous sodium hydrogen carbonate solution added and the organic layer separated, dried over sodium sulfate, filtered and concentrated. Purification by FCC (silica, dichloromethane:methanol:7 M methanolic ammonia (98:1.5:0.5)) gave the title compound 19 mg (54% yield) as an off-white solid.

Example 1, Method 68: [(3-{5-[(5-Methoxypyridin-2-yl)methoxy]-1,3-benzoxazol-2yl}phenyl)methyl](methyl)amine $\delta_H$ NMR (500 MHz, DMSO) 8.30 (d, J=2.7 Hz, 1H), 8.16 (s, 1H), 8.04 (d, J=6.6 Hz, 1H), 7.69 (d, J=8.9 Hz, 1H), 7.60-7.48 (m, 3H), 7.43 (m, 2H), 7.10 (dd, J=8.9, 2.4 Hz, 1H), 5.18 (s, 2H), 3.84 (s, 3H), 3.78 (s, 2H), 2.31 (s, 3H). Tr(METCR1600)=4.47 min (ES⁺) (M+H)⁺ 376.

The following example was prepared using Method 68 described above:

TABLE 69

| Ex. | Structure | Mol. Weight | IUPAC Name | LCMS data |
|---|---|---|---|---|
| 1 | 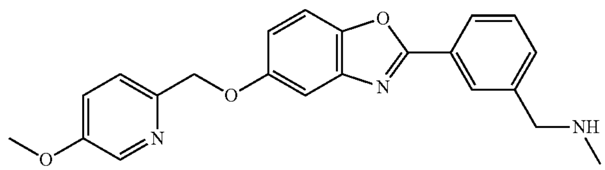 | 375.43 | [(3-{5-[(5-Methoxypyridin-2-yl)methoxy]-1,3-benzoxazol-2-yl}phenyl)methyl](methyl)amine | Tr(METCR1600) = 4.47 min, (ES+) (M + H)+ 376 |

Method 69
Scheme for Method 69

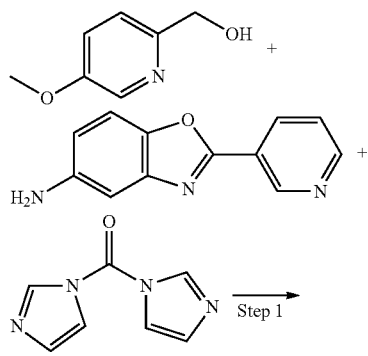

preparative HPLC (acetonitrile/water+0.1% formic acid) gave the title compound 12.3 mg (7% yield) as a pale pink solid Example 1, Method 69: (5-Methoxypyridin-2-yl)methyl N-[2-(pyridin-3-yl)-1,3-benzoxazol-5-yl]carbamate $\delta_H$ NMR (500 MHz, DMSO) 10.02 (s, 1H), 9.33 (d, J=1.6 Hz, 1H), 8.80 (dd, J=4.8, 1.6 Hz, 1H), 8.52 (dt, J=8.0, 1.9 Hz, 1H), 8.29 (dd, J=2.7, 0.8 Hz, 1H), 8.00 (s, 1H), 7.75 (d, J=8.8 Hz, 1H), 7.65 (ddd, J=8.0, 4.9, 0.8 Hz, 1H), 7.52-7.38 (m, 3H), 5.18 (s, 2H), 3.84 (s, 3H). Tr(MET-uHPLC-AB-101)=2.38 min, (ES+) (M+H)+ 377.

The following example was prepared using Method 69 described above:

TABLE 70

| Ex. | Structure | Mol. Weight | IUPAC Name | LCMS data |
|---|---|---|---|---|
| 1 | 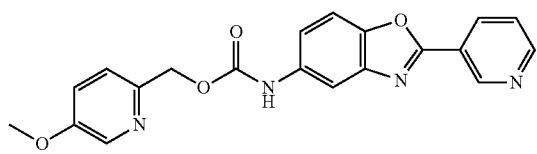 | 376.37 | (5-Methoxypyridin-2-yl)methyl N-[2-(pyridin-3-yl)-1,3-benzoxazol-5-yl]carbamate | Tr(MET-uHPLC-AB-101) = 2.38 min, (ES+) (M + H)+ 377 |

Method 70
Scheme for Method 70

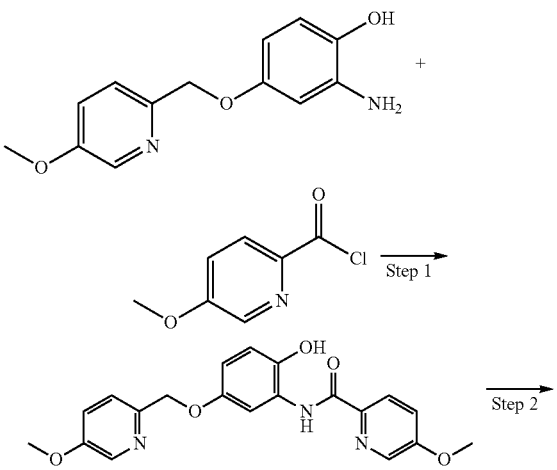

-continued

Step 1, Method 69: (5-Methoxypyridin-2-yl)methyl N-[2-(pyridin-3-yl)-1,3-benzoxazol-5-yl]carbamate (5-Methoxypyridin-2-yl)methanol (66 mg, 0.47 mmol) and carbonyldiimidazole (92 mg, 0.57 mmol) were dissolved in dichloromethane (2 mL) and stirred at room temperature for 4 hours. 2-(Pyridin-3-yl)-1,3-benzoxazol-5-amine (100 mg, 0.47 mmol) was added and the reaction mixture stirred at room temperature for 24 hours. The reaction mixture was diluted with ethyl acetate (25 mL), washed with water (3×20 mL), dried over anhydrous magnesium sulfate, filtered and concentrated. Purification by -continued

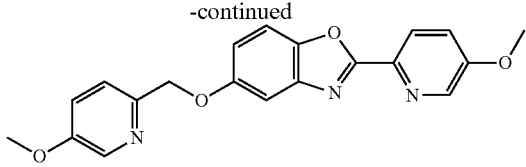

Step 1, Method 70: N-{2-Hydroxy-5-[(5-methoxypyridin-2-yl)methoxy]phenyl}-5-methoxypyridine-2-carboxamide To a solution of 2-Amino-4-[(5-methoxypyridin-2-yl)methoxy]phenol (80%, 100 mg, 0.32 mmol, prepared using Method 33) in pyridine was added 5-methoxypyridine-2-acid chloride (55 mg, 0.32 mmol). The reaction mixture was stirred at room temperature for two days. Pyridine was removed in vacuo and the residue taken up in dichloromethane (30 mL). This was washed with water (2×25 mL), brine (15 mL), dried over magnesium sulfate, filtered and concentrated to give the title compound 130 mg (67% yield) as a red solid. The crude material was taken directly into the next step.

Step 2, Method 70: 2-(5-Methoxypyridin-2-yl)-5-[(5-methoxypyridin-2-yl)methoxy]-1,3-benzoxazole N-{2-Hydroxy-5-[(5-methoxypyridin-2-yl)methoxy]phenyl}-5-methoxypyridine-2-carboxamide (130 mg, 0.27 mmol) was taken up in acetic acid (3 mL) and heated in a microwave at 200° C. for 1 hour. The acetic acid was removed in vacuo and the residue dissolved in dichloromethane (30 mL). The organic layer was washed with saturated sodium hydrogen carbonate solution (2×30 mL), brine (15 mL) and dried over magnesium sulfate. The magnesium sulfate was filtered off and dichloromethane removed in vacuo. Purification by FCC (silica, 0–10% methanol in dichloromethane) followed by recrystallisation from ethanol gave the title compound 6.6 mg, (7% yield) as an off white solid.

Example 1, Method 70: 2-(5-Methoxypyridin-2-yl)-5-[(5-methoxypyridin-2-yl)methoxy]-1,3-benzoxazole $\delta_H$ NMR (500 MHz, DMSO) 8.48 (d, J=2.8 Hz, 1H), 8.31 (d, J=2.8 Hz, 1H), 8.27 (d, J=8.8 Hz, 1H), 7.71 (d, J=8.9 Hz, 1H), 7.62 (dd, J=8.8, 2.9 Hz, 1H), 7.53 (d, J=8.6 Hz, 1H), 7.49–7.41 (m, 2H), 7.11 (dd, J=8.9, 2.5 Hz, 1H), 5.19 (s, 2H), 3.95 (s, 3H), 3.84 (s, 3H). Tr(MET-uHPLC-AB-101)=2.82 min, (ES$^+$) (M+H)$^+$ 364.

The following example was prepared using Method 70 described above:

TABLE 71

| Ex. | Structure | Mol. Weight | IUPAC Name | LCMS data |
|---|---|---|---|---|
| 1 | 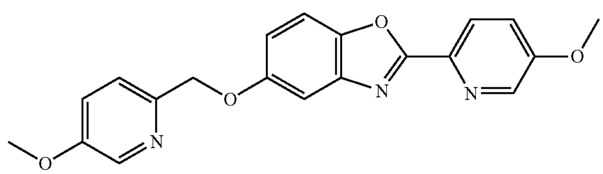 | 363.37 | 2-(5-Methoxypyridin-2-yl)-5-[(5-methoxypyridin-2-yl)methoxy]-1,3-benzoxazole | Tr(MET-uHPLC-AB-101) = 2.82 min, (ES$^+$) (M + H)$^+$ 364 |
| 2 | 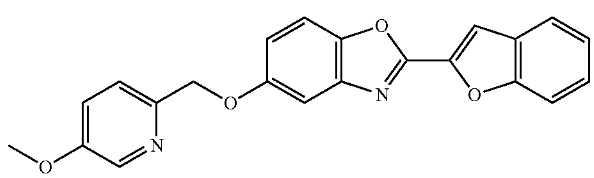 [SMILES: COc1ccc(COc2ccc3oc(-c4cc5ccccc5o4)nc3c2)nc1] | 372.38 | 2-(1-Benzofuran-2-yl)-5-[(5-methoxypyridin-2-yl)methoxy]-1,3-benzoxazole | Tr(MET-uHPLC-AB-101) = 4.04 min, (ES$^+$) (M + H)$^+$ 373 |
| 3 | 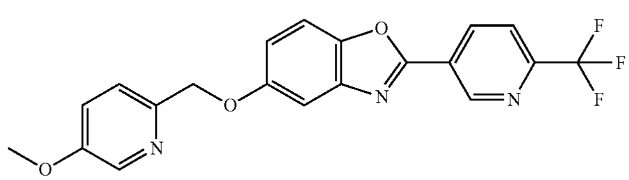 [SMILES: COc1ccc(COc2ccc3oc(-c4ccc(C(F)(F)F)nc4)nc3c2)nc1] | 401.35 | 5-[(5-Methoxypyridin-2-yl)methoxy]-2-[6-(trifluoromethyl)pyridin-3-yl]-1,3-benzoxazole | Tr(METCR1416 Hi res 7 min) = 4.36 min, (ES$^+$) (M + H)$^+$ 402 |
| 4 | 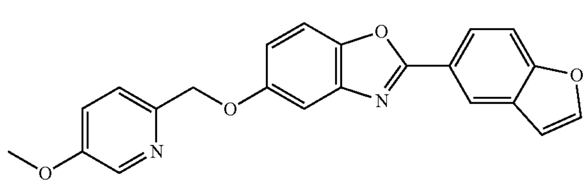 [SMILES: COc1ccc(COc2ccc3oc(-c4ccc5occc5c4)nc3c2)nc1] | 372.38 | 2-(1-Benzofuran-5-yl)-5-[(5-methoxypyridin-2-yl)methoxy]-1,3-benzoxazole | Tr(MET-uHPLC-AB-101) = 3.76 min, (ES$^+$) (M + H)$^+$ 373 |

TABLE 71-continued

| Ex. | Structure | Mol. Weight | IUPAC Name | LCMS data |
|---|---|---|---|---|
| 5 | 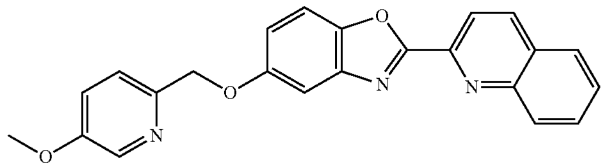 [SMILES: COc1ccc(COc2ccc3oc(-c4ccc5ccccc5n4)nc3c2)nc1] | 383.41 | 2-{5-[(5-Methoxypyridin-2-yl)methoxy]-1,3-benzoxazol-2-yl}quinoline | Tr(MET-uHPLC-AB-101) = 3.46 min, (ES+) (M + H)+ 384 |
| 6 | 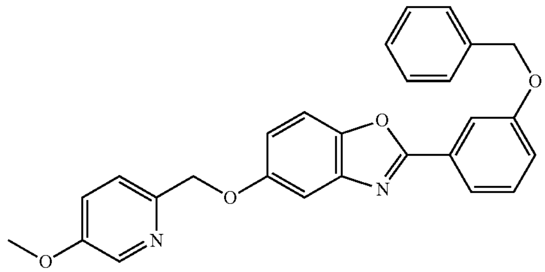 [SMILES: COc1ccc(COc2ccc3oc(-c4cccc(OCc5ccccc5)c4)nc3c2)nc1] | 438.48 | 2-[3-(Benzyloxy)phenyl]-5-[(5-methoxypyridin-2-yl)methoxy]-1,3-benzoxazole | Tr(MET-uHPLC-AB-101) = 4.44 min, (ES+) (M + H)+ 439 |
| 7 | 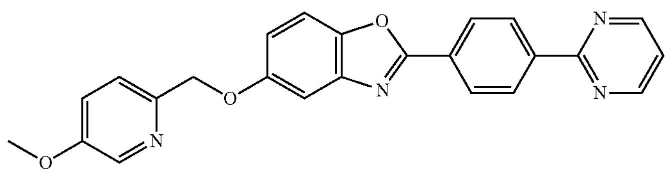 [SMILES: COc1ccc(COc2ccc3oc(-c4ccc(-c5ncccn5)cc4)nc3c2)nc1] | 410.43 | 5-[(5-Methoxypyridin-2-yl)methoxy]-2-[4-(pyrimidin-2-yl)phenyl]-1,3-benzoxazole | Tr(MET-uHPLC-AB-101) = 3.63 min, (ES+) (M + H)+ 411 |
| 8 | 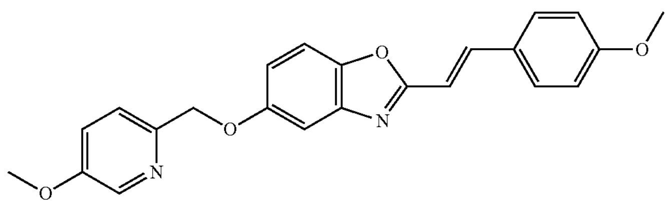 | 388.42 | 2-[(E)-2-(4-Methoxyphenyl)ethenyl]-5-[(5-methoxypyridin-2-yl)methoxy]-1,3-benzoxazole | Tr(MET-uHPLC-AB-101) = 3.81 min, (ES+) (M + H)+ 389 |

Method 71

Scheme for Method 71

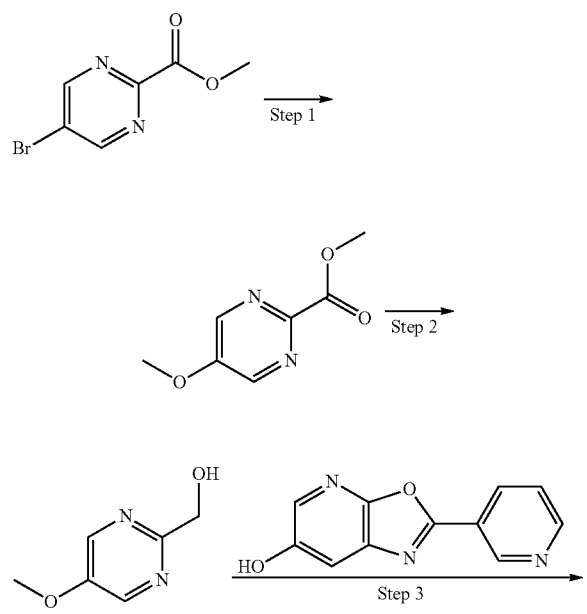

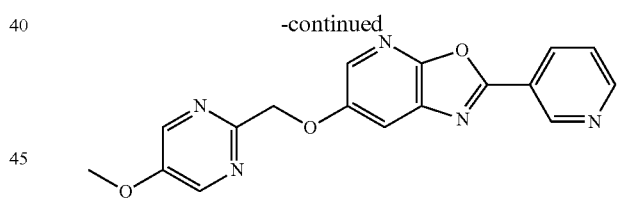

Step 1, Method 71: Methyl 5-methoxypyrimidine-2-carboxylate

To a round bottom flask were added sequentially methyl 5-bromopyrimidine-2-carboxylate (0.83 g, 3.82 mmol), di-tert-butyl({3,6-dimethoxy-2-[2,4,6-tris(propan-2-yl)phenyl]phenyl})phosphane (0.02 g, 0.04 mmol) and caesium carbonate (1.74 g, 5.35 mmol). These solids were mixed, then evacuated under vacuum and purged with nitrogen three times. Methanol (0.61 g, 19.12 mmol) was then added to this flask via a syringe. In a separate flask was weighed methanesulfonato(2-(di-tert-butylphosphino)-3,6-dimethoxy-2',4',6'-tri-i-propyl-1,1'-biphenyl)(2'-amino-1,1'-biphenyl-2-yl)palladium(II) (0.03 g, 0.04 mmol), which was evacuated and purged with nitrogen twice. Dioxane (3.8 mL) was added to this flask and the flask agitated until a greenish solution resulted; this solution was then transferred via syringe to the first flask. The resulting reaction mixture was heated to 50° C. for 4 hours. The reaction mixture was cooled, diluted with ethyl acetate and filtered. The volatiles were evaporated and the residue purified by FCC (silica, 50-100% ethyl acetate in heptane) to give the title compound 0.25 g (32% yield) as an off-white solid. $\delta_H$ NMR (500 MHz, Chloroform) 8.54 (s, 2H), 4.05 (s, 3H), 4.01 (s, 3H). Tr(METCR1673)=0.48 min, (ES$^+$) (M+H)$^+$ 169.

Step 2, Method 71: (5-Methoxypyrimidin-2-yl)methanol

To a solution of methyl 5-methoxypyrimidine-2-carboxylate (180 mg, 1.07 mmol) in ethanol (4 mL) was added sodium borohydride (81 mg, 2.14 mmol) and the resulting mixture stirred for 90 mins. The volatiles were evaporated, the residue diluted with ethyl acetate and filtered through a pad of silica. Evaporation gave the title compound 35 mg (23% yield) as a pale yellow solid. $\delta_H$ NMR (500 MHz, Chloroform) 8.40 (s, 2H), 4.79 (s, 2H), 3.93 (s, 3H).

Step 3, Method 71: 5-Methoxy-2-({[2-(pyridin-3-yl)-[1,3]oxazolo[5,4-b]pyridin-6-yl]oxy}methyl)pyrimidine A mixture of (5-methoxypyrimidin-2-yl)methanol (26 mg, 0.19 mmol), 2-(pyridin-3-yl)-[1,3]oxazolo[5,4-b]pyridin-6-ol (90%, 44 mg, 0.19 mmol, prepared using Method 30) and cyanomethylenetributylphosphorane (0.07 mL, 0.28 mmol) in toluene (1 mL) was heated to reflux for 6 hours. The reaction mixture was evaporated and purified by FCC (silica, 2-35% tetrahydrofuran in dichloromethane), triturated with ether (5 mL) and air-dried to give the title compound 13.1 mg (21% yield) as a light brown solid.

Example 1, Method 71: 5-Methoxy-2-({[2-(pyridin-3-yl)-[1,3]oxazolo[5,4-b]pyridin-6-yl]oxy}methyl)pyrimidine $\delta_H$ NMR (500 MHz, DMSO) 9.35 (dd, J=2.2, 0.7 Hz, 1H), 8.83 (dd, J=4.8, 1.6 Hz, 1H), 8.60 (s, 2H), 8.57-8.51 (m, 1H), 8.20 (d, J=2.7 Hz, 1H), 8.03 (d, J=2.7 Hz, 1H), 7.67 (ddd, J=8.0, 4.8, 0.8 Hz, 1H), 5.39 (s, 2H), 3.92 (s, 3H). Tr(MET-uHPLC-AB-101)=2.18 min, (ES$^+$) (M+H)$^+$ 336.

The following example was prepared using Method 71 described above:

Method 72
Scheme for Method 72

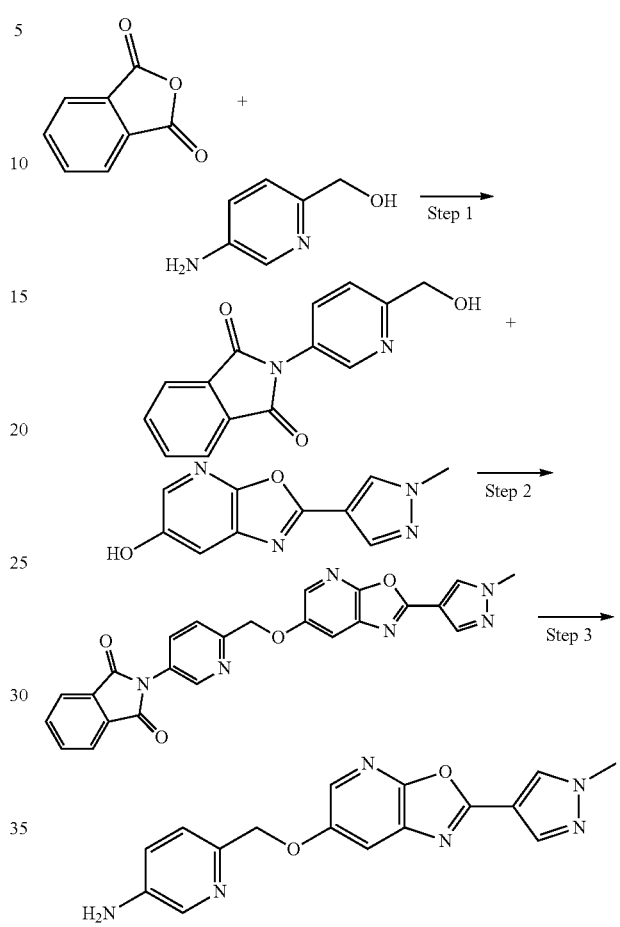

Step 1, Method 72: 2-[6-(Hydroxymethyl)pyridin-3-yl]-2,3-dihydro-1H-isoindole-1,3-dione 5-Aminopyridin-2-yl)methanol dihydrochloride (500 mg, 2.54 mmol) and 2-benzofuran-1,3-dione (376 mg, 2.54 mmol) were refluxed with stirring in pyridine (10 mL) for 4 hours under nitrogen. The mixture was evaporated and recrystallised from methanol (20 mL) to give the title compound 314 mg (48.7% yield) as an off white powder. $\delta_H$ NMR (500 MHz, DMSO) 8.57 (d, J=2.3 Hz, 1H), 8.03-7.96 (m, 2H), 7.96-7.92 (m, 2H), 7.90 (dd, J=8.3, 2.4 Hz, 1H), 7.64 (d, J=8.3 Hz, 1H), 5.53 (t, J=5.9 Hz, 1H), 4.63 (d, J=5.7 Hz, 2H). Tr(METCR1673 2 min method)=0.94 min, (ES$^+$) (M+H)$^+$ 255.

TABLE 72

| Ex. | Structure | Mol. Weight | IUPAC Name | LCMS data |
|---|---|---|---|---|
| 1 | 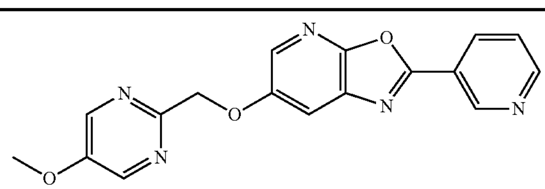 | 335.32 | 5-Methoxy-2-({[2-(pyridin-3-yl)-[1,3]oxazolo[5,4-b]pyridin-6-yl]oxy}methyl)pyrimidine | Tr(MET-uHPLC-AB-101) = 2.18 min, (ES$^+$) (M + H)$^+$ 336 |

Step 2, Method 72: 2-[6-({[2-(1-Methyl-1H-pyrazol-4-yl)-[1,3]oxazolo[5,4-b]pyridin-6-yl]oxy}methyl)pyridin-3-yl]-2,3-dihydro-1H-isoindole-1,3-dione 2-(1-Methyl-1H-pyrazol-4-yl)-[1,3]oxazolo[5,4-b]pyridin-6-ol (61 mg, 0.28 mmol, prepared using Method 30), 2-[6-(hydroxymethyl)pyridin-3-yl]-2,3-dihydro-1H-isoindole-1,3-dione (79 mg, 0.31 mmol) and cyanomethylenetributylphosphorane (111 μl, 0.42 mmol) in toluene (5 mL) were heated to 100° C. under nitrogen overnight. Cyanomethylenetributylphosphorane (111 μl, 0.42 mmol) in toluene (5 mL) was added and the mixture heated to 120° C. under nitrogen overnight. The reaction mixture was cooled to room temperature and concentrated. Trituration with diethyl ether (10 mL) gave a tan solid 62 mg 36% purity by LC-MS but ~90% by proton NMR and the crude material was taken on to the next step.

Step 3, Method 72: 6-({[2-(1-Methyl-1H-pyrazol-4-yl)-[1,3]oxazolo[5,4-b]pyridin-6-yl]oxy}methyl)pyridin-3-amine 2-[6-({[2-(1-Methyl-1H-pyrazol-4-yl)-[1,3]oxazolo[5,4-b]pyridin-6-yl]oxy}methyl)pyridin-3-yl]-2,3-dihydro-1H-isoindole-1,3-dione (90%, 62 mg, 0.12 mmol) was suspended in ethanol (2 mL) and hydrazine hydrate (1:1) (120.24 μl, 2.47 mmol) added and the mixture stirred at room temperature overnight. The mixture was filtered, and the solid washed with methanol (5 mL) and ethyl acetate (5 mL). The filtrate was concentrated and purified by preparative HPLC (acetonitrile/water+0.2% ammonium hydroxide) followed by recrystallisation from methanol (1 mL) gave the title compound 10 mg (24% yield) as an off white powder.

Example 1, Method 72: 6-({[2-(1-Methyl-1H-pyrazol-4-yl)-[1,3]oxazolo[5,4-b]pyridin-6-yl]oxy}methyl)pyridin-3-amine $\delta_H$ NMR (500 MHz, DMSO) 8.59 (s, 1H), 8.13 (s, 1H), 8.02 (d, J=2.7 Hz, 1H), 7.93 (d, J=2.6 Hz, 1H), 7.85 (d, J=2.7 Hz, 1H), 7.22 (d, J=8.3 Hz, 1H), 6.94 (dd, J=8.3, 2.7 Hz, 1H), 5.40 (s, 2H), 5.07 (s, 2H), 3.96 (s, 3H). Tr(MET-uHPLC-AB-101)=1.31 min, (ES$^+$) (M+H)$^+$ 323.

The following example was prepared using Method 72 described above:

Method 73
Scheme for Method 73

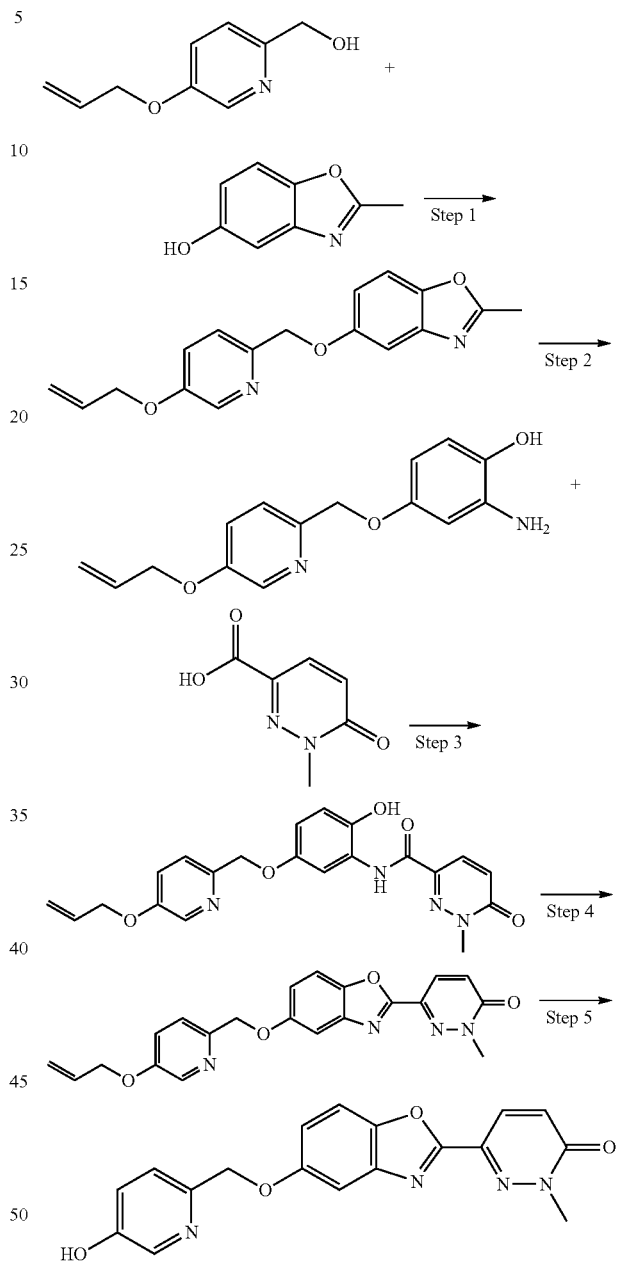

TABLE 73

| Ex. | Structure | Mol. Weight | IUPAC Name | LCMS data |
|---|---|---|---|---|
| 1 | 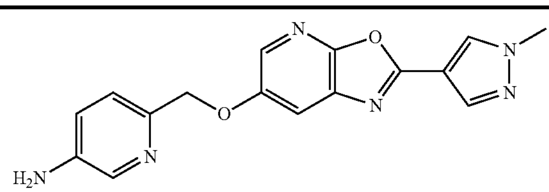 | 322.33 | 6-({[2-(1-Methyl-1H-pyrazol-4-yl)-[1,3]oxazolo[5,4-b]pyridin-6-yl]oxy}methyl)pyridin-3-amine | Tr(MET-uHPLC-AB-101) = 1.31 min, (ES$^+$) (M + H)$^+$ 323 |

Step 1, Method 73: 2-Methyl-5-{[5-(prop-2-en-1-yloxy)pyridin-2-yl]methoxy}-1,3-benzoxazole 2-Methyl-1,3-benzoxazol-5-ol (1.4 g, 9.39 mmol) and [5-(prop-2-en-1-yloxy)pyridin-2-yl]methanol (1.8 g, 10.33 mmol, described in U.S. Pat. No. 4,198,416 (1978) reference example 3) were suspended in anhydrous toluene (20 mL), cyanomethylenetributylphosphorane (3.69 mL, 14.08 mmol) added and the reaction heated to 100° C. for 4 hours under nitrogen. The reaction was cooled to room temperature and the solvent removed in vacuo. Trituration with diethyl ether and heptane (1:1, 10 mL) gave the title compound 1.449 g (52% yield) as a purple solid. $\delta_H$ NMR (250 MHz, DMSO) 8.31 (d, J=2.3 Hz, 1H), 7.55 (d, J=8.9 Hz, 1H), 7.49 (d, J=8.4 Hz, 1H), 7.43 (dd, J=8.6, 2.8 Hz, 1H), 7.29 (d, J=2.5 Hz, 1H), 7.00 (dd, J=8.9, 2.6 Hz, 1H), 6.05 (ddt, J=17.2, 10.5, 5.2 Hz, 1H), 5.42 (dq, J=17.3, 1.7 Hz, 1H), 5.29 (dq, J=10.5, 1.4 Hz, 1H), 5.14 (s, 2H), 4.67 (dt, J=5.2, 1.4 Hz, 2H), 2.58 (s, 3H) Tr(METCR1673)=1.26 min, (ES⁺) (M+H)⁺ 297.

Step 2, Method 73: 2-Amino-4-{[5-(prop-2-en-1-yloxy)pyridin-2-yl]methoxy}phenol 2-Methyl-5-{[5-(prop-2-en-1-yloxy)pyridin-2-yl]methoxy}-1,3-benzoxazole (98%, 1.7 g, 5.61 mmol) was dissolved in ethanol (30 mL) and 2 M hydrochloric acid (15 mL) added and the reaction heated to 105° C. for 40 hours. The reaction mixture was cooled to room temperature and the solvent removed in vacuo. The residue was sonicated with saturated sodium bicarbonate solution, adjusting the pH to 8 and then partitioned with dichloromethane (100 mL) and the layers separated. The aqueous layer was extracted with dichloromethane (2×75 mL). The combined organics were washed with brine (20 mL), dried over anhydrous sodium sulfate, and concentrated in vacuo to give the title compound 1.17 g (76% yield) as a bronze solid. $\delta_H$ NMR (500 MHz, DMSO) 8.48 (s, 1H), 8.26 (d, J=2.2 Hz, 1H), 7.46-7.34 (m, 2H), 6.50 (d, J=8.5 Hz, 1H), 6.27 (d, J=2.9 Hz, 1H), 6.12-5.96 (m, 2H), 5.41 (dd, J=17.3, 1.7 Hz, 1H), 5.28 (dd, J=10.5, 1.5 Hz, 1H), 4.90 (s, 2H), 4.65 (dt, J=5.2, 1.4 Hz, 2H), 4.53 (s, 2H). Tr(METCR1673)=0.87 min, (ES⁺) (M+H)⁺ 273, 93%.

Step 3, Method 73: N-(2-Hydroxy-5-{[5-(prop-2-en-1-yloxy)pyridin-2-yl]methoxy}phenyl)-1-methyl-6-oxo-1,6-dihydropyridazine-3-carboxamide To a solution of 2-amino-4-{[5-(prop-2-en-1-yloxy)pyridin-2-yl]methoxy}phenol (835 mg, 3.07 mmol) in pyridine (12 mL) was added 1-ethyl-3-(3-dimethylaminopropyl)carbodiimide hydrochloride (735 mg, 3.84 mmol) and 1-methyl-6-oxo-1,6-dihydropyridazine-3-carboxylic acid (591 mg, 3.84 mmol) and the reaction mixture stirred at room temperature for 22 hours. Water (25 mL) was added and the resulting precipitate collected by filtration. The solid was dried in a vacuum oven for 1 hour and then re-dissolved in 7 N ammonia in methanol and stirred at room temperature for 1 hour. The solvent was then removed in vacuo to give the title compound 702 mg (42% yield) as a yellow solid. $\delta_H$ NMR (500 MHz, DMSO) 9.56 (s, 1H), 8.28 (d, J=2.0 Hz, 1H), 7.98 (d, J=9.7 Hz, 1H), 7.92 (d, J=3.0 Hz, 1H), 7.51-7.33 (m, 2H), 7.09 (d, J=9.7 Hz, 1H), 6.84 (d, J=8.8 Hz, 1H), 6.66 (dd, J=8.8, 3.0 Hz, 1H), 6.04 (ddt, J=17.2, 10.5, 5.3 Hz, 1H), 5.41 (dd, J=17.3, 1.6 Hz, 1H), 5.29 (dd, J=10.5, 1.5 Hz, 1H), 5.01 (s, 2H), 4.77-4.55 (m, 2H), 3.76 (s, 3H), 3.71 (s, 1H). Tr(METCR1673)=1.12 min, (ES⁺) (M+H)⁺ 409.

Step 4, Method 73: 2-Methyl-6-(5-{[5-(prop-2-en-1-yloxy)pyridin-2-yl]methoxy}-1,3-benzoxazol-2-yl)-2,3-dihydropyridazin-3-one N-(2-Hydroxy-5-{[5-(prop-2-en-1-yloxy)pyridin-2-yl]methoxy}phenyl)-1-methyl-6-oxo-1,6-dihydropyridazine-3-carboxamide (702 mg, 1.39 mmol) was suspended in acetic acid (12 mL) and heated to 180° C. for 28 hours. The reaction was cooled to room temperature and concentrated. The residue was partitioned between dichloromethane and saturated sodium hydrogen carbonate solution, filtered and separated. The organic layer was washed with saturated sodium hydrogen carbonate solution, dried over magnesium sulfate, and concentrated. Purification by double recrystallisation from acetonitrile:methanol (99:1) gave the title compound 93 mg (17% yield) as a beige solid. Tr(METCR1673)=1.23 min, (ES⁺) (M+H)⁺ 391, 83%.

Step 5, Method 73: 6-{5-[(5-Hydroxypyridin-2-yl)methoxy]-1,3-benzoxazol-2-yl}-2-methyl-2,3-dihydropyridazin-3-one 2-Methyl-6-(5-{[5-(prop-2-en-1-yloxy)pyridin-2-yl]methoxy}-1,3-benzoxazol-2-yl)-2,3-dihydropyridazin-3-one (93 mg, 0.2 mmol) and 1,3-dimethylpyrimidine-2,4,6(1H,3H,5H)-trione (62 mg, 0.4 mmol) were suspended in anhydrous N,N-dimethylformamide (3 mL) and degassed under a flow of nitrogen for 5 minutes. Tetrakis(triphenylphosphine)palladium(0) (11 mg, 0.01 mmol) was added and the reaction stirred at room temperature under a nitrogen atmosphere for 4 hours then concentrated. The residue was triturated with water (15 mL) and filtered. Purification by hot filtration from tetrahydrofuran (5 mL) gave the title compound 55 mg (79% yield) as an orange powder.

Example 1, Method 73: 6-{5-[(5-Hydroxypyridin-2-yl)methoxy]-1,3-benzoxazol-2-yl}-2-methyl-2,3-dihydropyridazin-3-one $\delta_H$ NMR (500 MHz, DMSO) 10.03 (s, 1H), 8.21-8.08 (m, 2H), 7.73 (d, J=8.9 Hz, 1H), 7.46 (d, J=2.5 Hz, 1H), 7.40 (d, J=8.4 Hz, 1H), 7.20 (dd, J=8.4, 2.8 Hz, 1H), 7.16-7.09 (m, 2H), 5.12 (s, 2H), 3.79 (s, 3H). Tr(MET-uHPLC-AB-101)=1.85 min, (ES⁺) (M+H)⁺ 351, 92%.

The following examples were prepared using Method 73 described above:

| Ex. | Structure | Mol. Weight | IUPAC Name | LCMSdata |
|---|---|---|---|---|
| 1 | 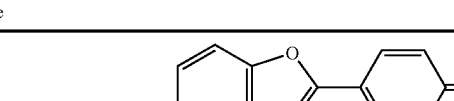 | 350.33 | 6-{5-[(5-Hydroxypyridin-2-yl)methoxy]-1,3-benzoxazol-2-yl}-2-methyl-2,3-dihydropyridazin-3-one | Tr(MET-uHPLC-AB-101) = 1.81 min, (ES$^+$) (M + H)$^+$ 351 |
| 2 | 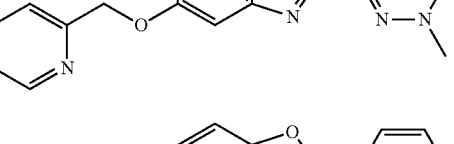 | 376.37 | 5-{5-[(5-Hydroxypyridin-2-yl)methoxy]-1,3-benzoxazol-2-yl}-N-methylpyridine-2-carboxamide | Tr(MET-uHPLC-AB-101) = 2.05 min, (ES$^+$) (M + H)$^+$ 377 |

Method 74

Scheme for Method 74

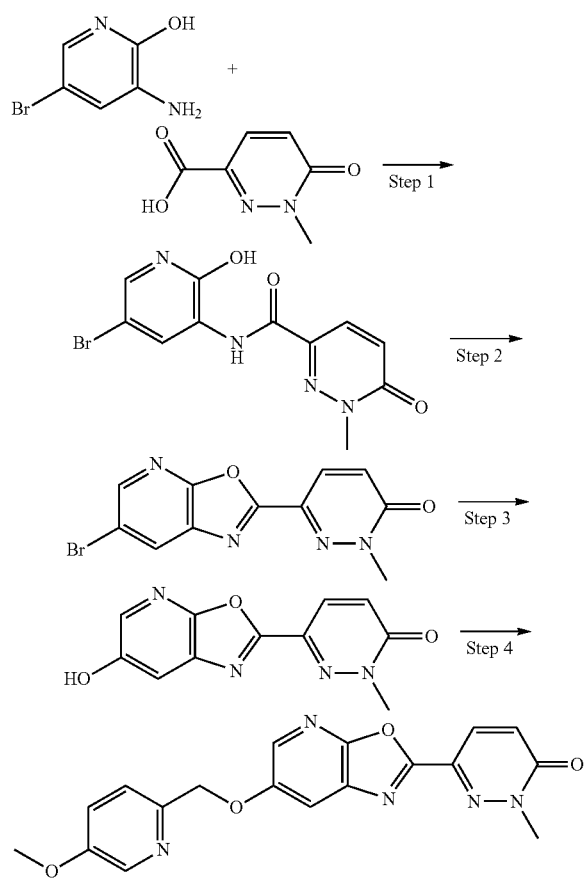

Step 1, Method 74: N-(5-bromo-2-hydroxypyridin-3-yl)-1-methyl-6-oxo-1,6-dihydropyridazine-3-carboxamide To a solution of 1-methyl-6-oxo-1,6-dihydropyridazine-3-carboxylic acid (0.82 g, 5.34 mmol) and 3-amino-5-bromopyridin-2-ol (1.01 g, 5.34 mmol) in pyridine (20 mL) was added 1-ethyl-3-(3-dimethylaminopropyl)carbodiimide hydrochloride (1.54 g, 8.02 mmol) and the resulting mixture stirred for 30 mins. The suspension was diluted with water and stood overnight.

The resulting solids were filtered, washed with water and heptane and air-dried. These solids were further azeotroped several times using heptane to give the title compound 1.53 g (88% yield) as a cream solid. δ$_H$ NMR (250 MHz, DMSO) 9.77 (s, 1H), 8.35 (d, J=2.6 Hz, 1H), 7.95 (d, J=9.7 Hz, 1H), 7.44 (d, J=2.6 Hz, 1H), 7.09 (d, J=9.7 Hz, 1H), 3.76 (s, 3H). Tr(MET1673)=0.98 min, (ES$^+$) (M+H)$^+$ 325/327.

Step 2, Method 74: 6-{6-Bromo-[1,3]oxazolo[5,4-b]pyridin-2-yl}-2-methyl-2,3-dihydropyridazin-3-one A mixture of triethylamine (2.74 g, 27.07 mmol), triphenylphosphine (3.55 g, 13.53 mmol) and hexachloroethane (2.0 g, 8.46 mmol) in dichloromethane (5 mL) was stirred for 10 minutes, then solid N-(5-bromo-2-hydroxypyridin-3-yl)-1-methyl-6-oxo-1,6-dihydropyridazine-3-carboxamide (1.1 g, 3.38 mmol) was added. The mixture was stirred at room temperature for 12 hours. The solids formed were removed by filtration and the volatiles evaporated. Purification by FCC (silica, 2-20% tetrahydrofuran in dichloromethane), suspension in hot ethanol (circa 30 mL), cooling and filtration gave the title compound 0.61 g (59% yield) as a white solid. δ$_H$ NMR (500 MHz, Chloroform) 8.49 (d, J=2.1 Hz, 1H), 8.24 (d, J=2.1 Hz, 1H), 8.11 (d, J=9.7 Hz, 1H), 7.09 (d, J=9.7 Hz, 1H), 3.98 (s, 3H). Tr(MET1673)= 1.62 min, (ES$^+$) (M+H)$^+$ 307/309.

Step 3, Method 74: 6-{6-Hydroxy-[1,3]oxazolo[5,4-b]pyridin-2-yl}-2-methyl-2,3-dihydropyridazin-3-one A mixture of potassium acetate (487 mg, 4.97 mmol), 6-{6-bromo-[1,3]oxazolo[5,4-b]pyridin-2-yl}-2-methyl-2,3-dihydro-pyridazin-3-one (610 mg, 1.99 mmol), bis(diphenylphosphino)ferrocene]dichloropalladium(II) (145 mg, 0.2 mmol) and bis(pinacolato)diboron (554 mg, 2.18 mmol) in degassed tetrahydrofuran (15 mL) was heated to reflux for 2 hours, then cooled overnight. Water (20 mL) and ethyl acetate (20 mL) were added and the insoluble material filtered off to give a silver grey solid. The ethyl acetate layer was separated, the aqueous layer extracted with ethyl acetate, the combined organic layers washed with brine (50 mL), dried over sodium sulfate and concentrated to give the boronic ester intermediate as a brown sticky solid, 0.79 g at circa 60% purity (as judged by 1H NMR). To a solution of the boronic ester intermediate isolated above (790 mg, 1.34 mmol, 60% purity) in tetrahydrofuran (10 mL) was added sodium perborate tetrahydrate (514.8 mg, 3.35 mmol) in water (5 mL) and the resulting suspension stirred at ambient temperature for 2 hours. Saturated ammonium chloride solution (20 mL) and ethyl acetate (20 mL) were added to the mixture and the solids removed by filtration to give the title compound 196 mg (60% yield) as a brown solid. $\delta_H$ NMR (250 MHz, DMSO) 8.13 (d, J=9.8 Hz, 1H), 7.99 (d, J=2.4 Hz, 1H), 7.62 (d, J=2.4 Hz, 1H), 7.14 (d, J=9.8 Hz, 1H), 3.81 (s, 3H). Tr(MET1673)=1.30 min, (ES$^+$) (M+H)$^+$ 245.

Step 4, Method 74: 6-{6-[(5-Methoxypyridin-2-yl)methoxy]-[1,3]oxazolo[5,4-b]pyridin-2-yl}-2-methyl-2,3-dihydropyridazin-3-one To a suspension of (5-methoxypyridin-2-yl)methanol (43 mg, 0.32 mmol) and 6-{6-hydroxy-[1,3]oxazolo[5,4-b]pyridin-2-yl}-2-methyl-2,3-dihydro-pyridazin-3-one (70 mg, 0.29 mmol) in toluene (5 mL) was added cyanomethylenetributylphosphorane (0.11 mL, 0.43 mmol) and the resulting mixture heated to reflux for 2 hours. After cooling the volatiles were evaporated, and the residue triturated with diethyl ether:heptane, filtered then triturated in acetonitrile:DMSO:water and filtered to give the title compound 34 mg (33% yield) as a light brown solid.

Example 1, Method 74: 6-{6-[(5-Methoxypyridin-2-yl)methoxy]-[1,3]oxazolo[5,4-b]pyridin-2-yl}-2-methyl-2,3-dihydropyridazin-3-one $\delta_H$ NMR (500 MHz, DMSO) 8.31 (d, J=2.9 Hz, 1H), 8.24 (d, J=2.7 Hz, 1H), 8.15 (d, J=9.7 Hz, 1H), 8.08 (d, J=2.7 Hz, 1H), 7.56 (d, J=8.6 Hz, 1H), 7.45 (dd, J=8.6, 3.0 Hz, 1H), 7.15 (d, J=9.7 Hz, 1H), 5.26 (s, 2H), 3.84 (s, 3H), 3.82 (s, 3H). Tr(MET-uHPLC-AB-101)=2.2 min, (ES$^+$) (M+H)$^+$ 366.

The following examples were prepared using Method 74 described above:

Method 75
Scheme for Method 75

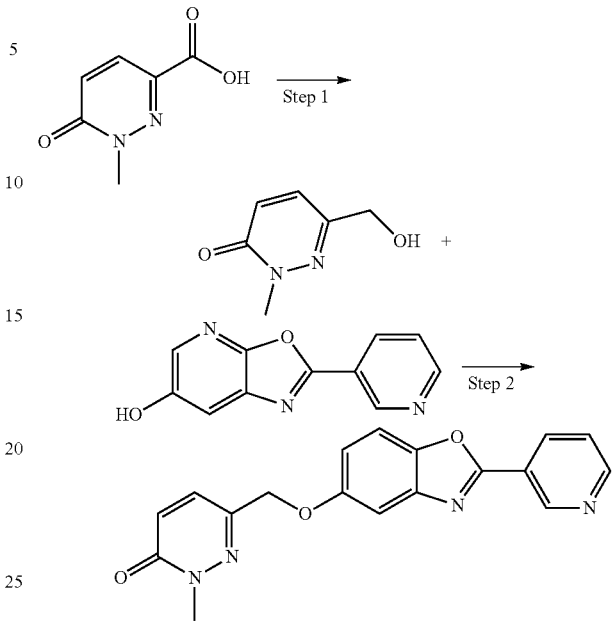

Step 1, Method 75: 6-(Hydroxymethyl)-2-methyl-2,3-dihydropyridazin-3-one isoButyl chloroformate (279.04 µl, 2.14 mmol) was added to a suspension of 1-methyl-6-oxo-1,6-dihydropyridazine-3-carboxylic acid (300 mg, 1.95 mmol) and triethylamine (298.43 µl, 2.14 mmol) in dry tetrahydrofuran (15 mL) at 0° C. The reaction was warmed to room temperature and stirred for 1 hour. The mixture was concentrated in vacuo and the residue dissolved in tetrahydrofuran (15 mL). Sodium borohydride (295 mg, 7.79 mmol) was added and the mixture stirred at room temperature for 1 hour then quenched by the addition of methanol (6 mL) and water (6 mL). The mixture was extracted with dichloromethane (3×25 mL) and the combined organic extracts dried over magnesium sulfate, filtered and concentrated. Purification by FCC (silica, ethyl acetate-heptane) gave the title compound 148 mg (51% yield) as a white solid. $\delta_H$ NMR (500 MHz, DMSO) 7.47 (d,

TABLE 75

| Ex. | Structure | Mol. Weight | IUPAC Name | LCMS data |
|---|---|---|---|---|
| 1 | 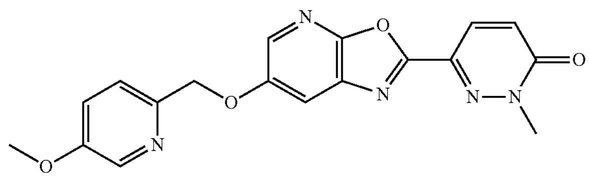 [SMILES: COc1ccc(COc2cnc3oc(-c4ccc(=O)n(C)n4)nc3c2)nc1] | 365.35 | 6-{6-[(5-Methoxypyridin-2-yl)methoxy]-[1,3]oxazolo[5,4-b]pyridin-2-yl}-2-methyl-2,3-dihydropyridazin-3-one | Tr(MET-uHPLC-AB-101) = 2.25 min, (ES$^+$) (M + H)$^+$ 366 |
| 2 | 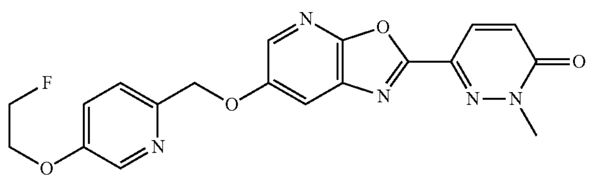 [SMILES: Cn1nc(-c2nc3cc(OCc4ccc(OCCF)cn4)cnc3o2)ccc1=O] | 397.37 | 6-(6-{[5-(2-Fluoroethoxy)pyridin-2-yl]methoxy}-[1,3]oxazolo[5,4-b]pyridin-2-yl)-2-methyl-2,3-dihydropyridazin-3-one | Tr(MET-uHPLC-AB-101) = 2.32 min, (ES$^+$) (M + H)$^+$ 398 |

J=9.5 Hz, 1H), 6.94 (d, J=9.5 Hz, 1H), 5.47 (t, J=6.0 Hz, 1H), 4.32 (d, J=6.0 Hz, 2H), 3.61 (s, 3H).

Step 2, Method 75: 2-Methyl-6-({[2-(pyridin-3-yl)-[1,3]oxazolo[5,4-b]pyridin-6-yl]oxy}methyl)-2,3-dihydropyridazin-3-one Cyanomethylenetributylphosphorane (0.18 mL, 0.7 mmol) was added to a stirred solution of 2-(pyridin-3-yl)-[1,3]oxazolo[5,4-b]pyridin-6-ol (100 mg, 0.47 mmol) and 6-(hydroxymethyl)-2-methyl-2,3-dihydropyridazin-3-one (72 mg, 0.52 mmol) in toluene (3 mL) and the reaction heated to 100° C. for 20 hours under nitrogen. Cyanomethylenetributylphosphorane (0.1 mL, 0.39 mmol) and 6-(hydroxymethyl)-2-methyl-2,3-dihydropyridazin-3-one (30.0 mg, 0.21 mmol) were added the the mixture and heated for a further 3 hours. The reaction was cooled to room temperature and the solid removed by filtration and washed with toluene. Purification by triturated with diethyl ether:heptane 1:1 (5 mL) followed by hot filtration from ethyl acetate (5 mL) give the title compound 14 mg (9% yield) as a beige sold.

Example 1, Method 75: 2-Methyl-6-({[2-(pyridin-3-yl)-[1,3]oxazolo[5,4-b]pyridin-6-yl]oxy}methyl)-2,3-dihydropyridazin-3-one $\delta_H$ NMR (500 MHz, DMSO) 9.36 (d, J=1.8 Hz, 1H), 8.84 (dd, J=4.8, 1.5 Hz, 1H), 8.55 (dt, J=8.0, 1.8 Hz, 1H), 8.23 (d, J=2.7 Hz, 1H), 8.11 (d, J=2.7 Hz, 1H), 7.70-7.63 (m, 2H), 7.02 (d, J=9.5 Hz, 1H), 5.15 (s, 2H), 3.67 (s, 3H). Tr(MET-uHPLC-AB-101)=2.04 min, (ES$^+$) (M+H)$^+$ 336.

The following example was prepared using Method 75 described above:

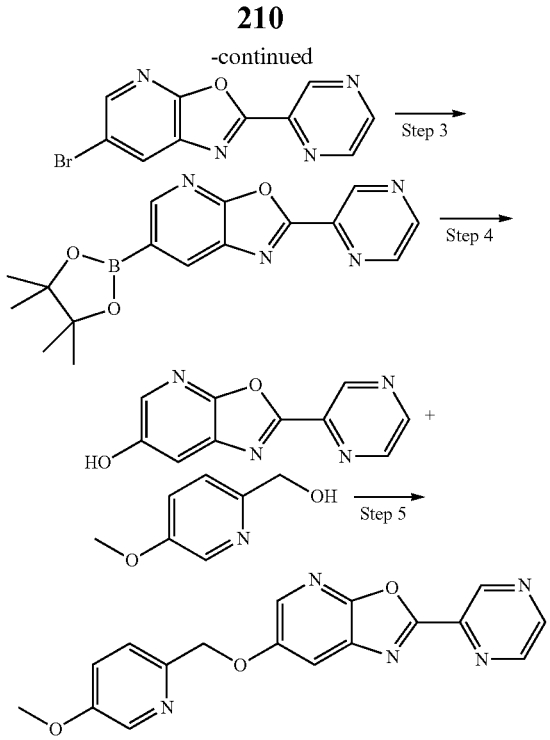

Step 1, Method 76: N-(5-Bromo-2-chloropyridin-3-yl)pyrazine-2-carboxamide

To a solution of 5-bromo-2-chloropyridin-3-amine (5.0 g, 24.1 mmol) in pyridine (50 mL) was added 1-ethyl-3-(3-

TABLE 76

| Ex. | Structure | Mol. Weight | IUPAC Name | LCMS data |
|---|---|---|---|---|
| 1 | 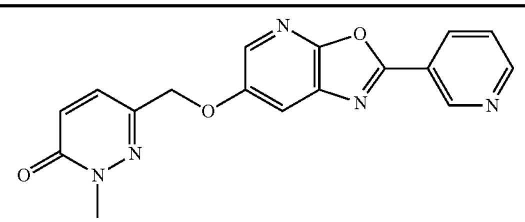 | 335.32 | 2-Methyl-6-({[2-(pyridin-3-yl)-[1,3]oxazolo[5,4-b]pyridin-6-yl]oxy}methyl)-2,3-dihydropyridazin-3-one | Tr(MET-uHPLC-AB-101) = 2.04 min, (ES$^+$) (M + H)$^+$ 336 |

Method 76

Scheme for Method 76

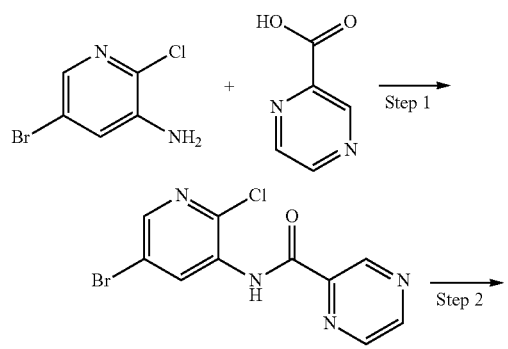

dimethylaminopropyl)carbodiimide hydrochloride (9.24 g, 48.2 mmol) and pyrazine-2-carboxylic acid (6.58 g, 53.02 mmol) and the reaction mixture stirred at room temperature for 48 hours. Water (50 mL) was added and the resultant precipitate collected by filtration to give the title compound 5.8 g (77% yield) as a beige solid. $\delta_H$ NMR (500 MHz, DMSO) 10.50 (s, 1H), 9.34 (d, J=1.1 Hz, 1H), 9.01 (d, J=2.5 Hz, 1H), 8.91-8.83 (m, 1H), 8.78 (d, J=2.3 Hz, 1H), 8.45 (d, J=2.1 Hz, 1H) Tr(METCR1673)=1.32 min, (ES$^+$) (M+H)$^+$ 313/315.

Step 2, Method 76: 2-{6-Bromo-[1,3]oxazolo[5,4-b]pyridin-2-yl}pyrazine

To a solution of N-(5-bromo-2-chloropyridin-3-yl)pyrazine-2-carboxamide (4.79 g, 15.28 mmol) in N,N-dimethylacetamide (100 mL) was added potassium phosphate (3.242 g, 15.28 mmol) and the resulting mixture was stirred at 180°

C. for 4.5 hours. The reaction mixture was cooled to room temperature and filtered. The filtrate was concentrated, the solid triturated with water. Purification by FCC (silica, 0-100% ethyl acetate in heptane) gave the title compound 1.72 g (35% yield) as an orange solid. $\delta_H$ NMR (500 MHz, DMSO) 9.51 (s, 1H), 8.92 (s, 2H), 8.74 (d, J=2.1 Hz, 1H), 8.62 (d, J=2.1 Hz, 1H)) Tr(METCR1673)=1.08 min, (ES$^+$) (M+H)$^+$ 277/279, 88%.

Step 3, Method 76: 2-[6-(Tetramethyl-1,3,2-dioxaborolan-2-yl)-[1,3]oxazolo[5,4-b]pyridin-2-yl]pyrazine A solution of 2-{6-bromo-[1,3]oxazolo[5,4-b]pyridin-2-yl}pyrazine (625 mg, 2.26 mmol), bis(pinacolato)diboron (630 mg, 2.48 mmol) and potassium acetate (0.55 g, 5.64 mmol) in tetrahydrofuran (31 mL) was degassed with nitrogen for 5 minutes. Bis(diphenylphosphino)ferrocene]dichloropalladium(II) (0.17 g, 0.23 mmol) was added and the reaction was stirred at 70° C. for 20 hours. The mixture was cooled to room temperature, diluted with water (100 mL) and filtered. The filtrate was extracted with ethyl acetate (3×100 mL), the organic layers combined, dried over magnesium sulfate, filtered and concentrated to give the title compound 1.11 g (88% yield) as a brown oil Tr(METCR1673)=0.78 min, (ES$^+$) (M+H)$^+$ 242 mass of boronic acid, 58%.

Step 4, Method 76: 2-(Pyrazin-2-yl)-[1,3]oxazolo[5,4-b]pyridin-6-ol

2-[6-(Tetramethyl-1,3,2-dioxaborolan-2-yl)-[1,3]oxazolo[5,4-b]pyridin-2-yl]pyrazine (1.11 g, 2.05 mmol) was dissolved in 1:1 tetrahydrofuran-water (30 mL). Sodium perborate tetrahydrate (790 mg, 5.14 mmol) was added and the mixture stirred at room temperature for 24 hours. Saturated ammonium chloride solution (60 mL) was added and the product extracted with ethyl acetate (3×100 mL). The organic layers were combined, dried over magnesium sulfate, filtered and concentrated. Trituration with diethyl ether gave the title compound 244 mg (52% yield) as a brown solid. $\delta_H$ NMR (500 MHz, DMSO) 10.28 (s, 1H), 9.47 (d, J=1.3 Hz, 1H), 9.02-8.76 (m, 2H), 8.03 (d, J=2.6 Hz, 1H), 7.68 (d, J=2.6 Hz, 1H) Tr(METCR1673)=0.80 min, (ES$^+$) (M+H)$^+$ 215, 94%.

Step 5, Method 76: 2-{6-[(5-Methoxypyridin-2-yl)methoxy]-[1,3]oxazolo[5,4-b]pyridin-2-yl}pyrazine 2-(Pyrazin-2-yl)-[1,3]oxazolo[5,4-b]pyridin-6-ol (150 mg, 0.66 mmol) and (5-methoxypyridin-2-yl) methanol (101 mg, 0.72 mmol) were suspended in anhydrous toluene (4 mL), cyanomethylenetributylphosphorane (0.26 mL, 0.99 mmol) added and the reaction heated to 100° C. in a sealed tube for 7 hours. The reaction mixture was cooled to room temperature and the solvents removed. The residue was triturated with 1:1 diethyl ether: heptane (10 mL). Purification by recrystallisation from tetrahydrofuran gave the title compound 41 mg (18% yield) as a beige solid.

Example 1, Method 76: 2-{6-[(5-Methoxypyridin-2-yl)methoxy]-[1,3]oxazolo[5,4-b]pyridin-2-yl}pyrazine $\delta_H$ NMR (500 MHz, DMSO) 9.49 (d, J=1.1 Hz, 1H), 8.99-8.79 (m, 2H), 8.31 (d, J=2.9 Hz, 1H), 8.28 (d, J=2.7 Hz, 1H), 8.13 (d, J=2.7 Hz, 1H), 7.57 (d, J=8.6 Hz, 1H), 7.45 (dd, J=8.6, 2.9 Hz, 1H), 5.28 (s, 2H), 3.84 (s, 3H). Tr(MET-uHPLC-AB-101)=2.21 min, (ES$^+$) (M+H)$^+$ 336.

The following examples were prepared using Method 76 described above:

TABLE 77

| Ex. | Structure | Mol. Weight | IUPAC Name | LCMS data |
|---|---|---|---|---|
| 1 | 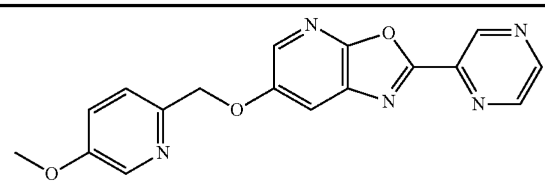 | 335.32 | 2-{6-[(5-Methoxypyridin-2-yl)methoxy]-[1,3]oxazolo[5,4-b]pyridin-2-yl}pyrazine | Tr(MET-uHPLC-AB-101) = 2.21 min, (ES$^+$) (M + H)$^+$ 336 |
| 2 | 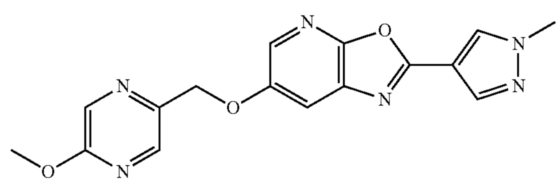 | 338.33 | 2-Methoxy-5-({[2-(1-methyl-1H-pyrazol-4-yl)-[1,3]oxazolo[5,4-b]pyridin-6-yl]oxy}methyl)pyrazine | Tr(MET-uHPLC-AB-101) = 2.51 min, (ES$^+$) (M + H)$^+$ 339 |

Method 77

Scheme for Method 77

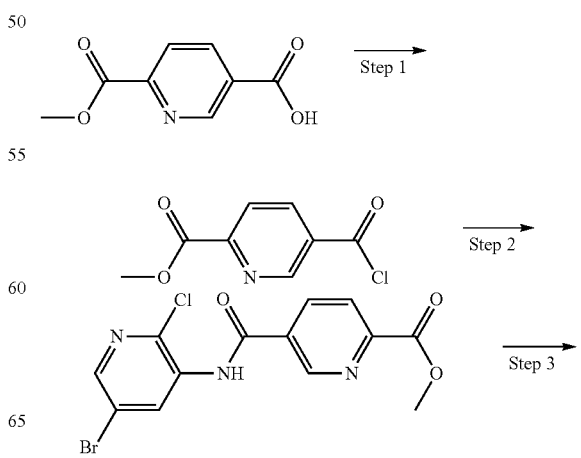

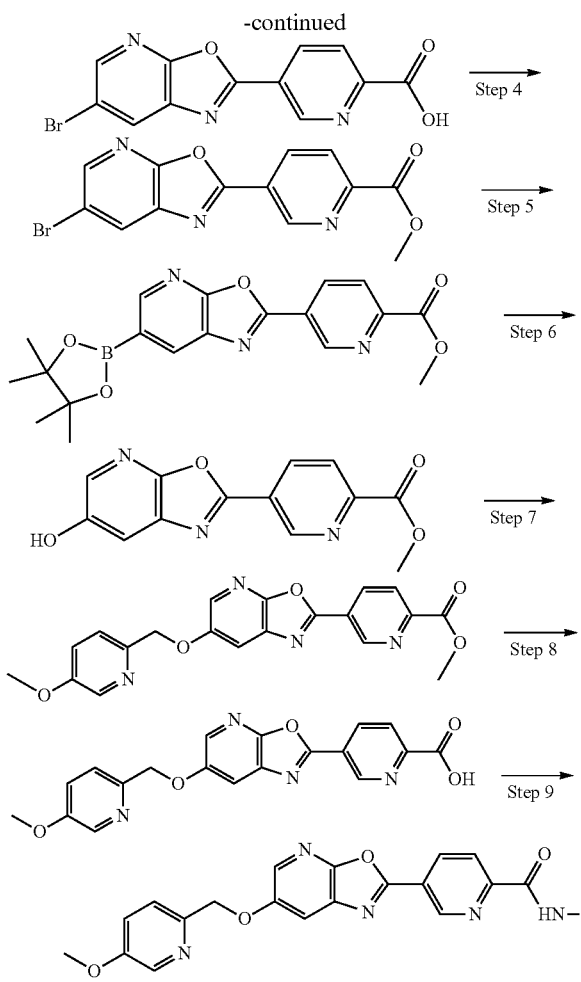

1H), 8.23 (dd, J=8.1, 0.6 Hz, 1H), 3.93 (s, 3H), Tr(METCR1410)=1.01 min, (ES+) (M+H)+ 370/372/374.

Step 3, Method 77: 5-{6-Bromo-[1,3]oxazolo[5,4-b]pyridin-2-yl}pyridine-2-carboxylic acid Potassium phosphate (207 mg, 0.98 mmol) was added to methyl 5-[(5-bromo-2-chloropyridin-3-yl)carbamoyl]pyridine-2-carboxylate (0.36 g, 0.98 mmol) in N,N-dimethylacetamide (12 mL) and the mixture stirred at 180° C. overnight. The reaction was cooled to room temperature and filtered. The solid was washed with water and dried in a vacuum oven to give the title compound 0.286 g (91% yield) as an off white solid. $\delta_H$ NMR (250 MHz, DMSO) 9.41 (d, J=1.6 Hz, 1H), 8.72 (dd, J=8.3, 2.2 Hz, 1H), 8.64 (d, J=2.1 Hz, 1H), 8.54 (d, J=2.1 Hz, 1H), 8.25 (d, J=8.2 Hz, 1H). Tr(METCR1673)=1.08 min, (ES+) (M+H)+ 320/322.

Step 4, Method 77: Methyl 5-{6-bromo-[1,3]oxazolo[5,4-b]pyridin-2-yl}pyridine-2-carboxylate Thionyl dichloride (170 µl, 0 mol) was added to 5-{6-bromo-[1,3]oxazolo[5,4-b]pyridin-2-yl}pyridine-2-carboxylic acid (1.5 g, 5.0 mmol) in methanol (25 mL) and the reaction heated to reflux under nitrogen for 17 hours. The reaction was cooled to room temperature and the solid filtered, washed with methanol (20 mL) and dried in a vacuum oven to give the title compound 0.81 g (43.4% yield) as an off white solid. Tr(METCR1410)=1.07 min, (ES+) (M+H)+ 334/336, 84%.

Step 5, Method 77: Methyl 5-[6-(tetramethyl-1,3,2-dioxaborolan-2-yl)-[1,3]oxazolo[5,4-b]pyridin-2-yl]pyridine-2-carboxylate Methyl 5-{6-bromo-[1,3]oxazolo[4,5-b]pyridin-2-yl}pyridine-2-carboxylate (800 mg, 2.39 mmol), bis(pinacolato)diboron (912 mg, 3.59 mmol) and potassium acetate (940 mg, 9.58 mmol) were dissolved in tetrahydrofuran (30 mL) and de-gassed with nitrogen. To this was added bis (diphenylphosphino)ferrocene]dichloropalladium(II) (175 mg, 0.24 mmol) and the reaction heated to 80° C. for 2 hours. The reaction was cooled to room temperature and filtered. The organic layer was concentrated in vacuo and the solid sonicated in diethyl ether:heptane (1:1). Filtration to give the title compound 0.793 g (74% yield) as a light brown solid. This material was used in the next step without further purification.

Step 6, Method 77: Methyl 5-{6-hydroxy-[1,3]oxazolo[5,4-b]pyridin-2-yl}pyridine-2-carboxylate Sodium perborate tetrahydrate (38 mg, 0.25 mmol) was added to methyl 5-[6-(tetramethyl-1,3,2-dioxaborolan-2-yl)-[1,3]oxazolo[5,4-b]pyridin-2-yl]pyridine-2-carboxylate (62%, 152 mg, 0.25 mmol) in tetrahydrofuran (5 mL) and water (2.5 mL) and the reaction stirred at room temperature for 1.5 hours. Saturated ammonium chloride solution (5 mL) was added and the aqueous layer extracted with ethyl acetate (3×25 mL). The combined organic layers were dried over sodium sulfate and concentrated. Purification by FCC (0-100% tetrahydrofuran in heptane) gave the title compound 44 mg (58% yield) as an off white solid. $\delta_H$ NMR (500 MHz, DMSO) 10.23 (s, 1H), 9.45 (dd, J=2.2, 0.7 Hz, 1H), 8.71 (dd, J=8.2, 2.2 Hz, 1H), 8.27 (dd, J=8.2, 0.7 Hz, Step 1, Method 77: Methyl 5-(carbonochloridoyl)pyridine-2-carboxylate Thionyl chloride (0.47 mL, 5.52 mmol) was added to 6-(methoxycarbonyl)pyridine-3-carboxylic acid (500 mg, 2.76 mmol) in toluene (5.0 mL) and dichloromethane (2.5 mL), followed by N,N-dimethylformamide (2 drops). After gas evolution had ceased the reaction was heated to 60° C. under nitrogen for 4 hours. The reaction was cooled to room temperature and concentrated in vacuo, dissolved in toluene (30 mL) and re-concentrated in vacuo. The solid was dried under vacuum for 1 hour to give the title compound 0.52 g (95% yield) as an off white solid. This material was used in the next step without further purification.

Step 2, Method 77: Methyl 5-[(5-bromo-2-chloro-pyridin-3-yl)carbamoyl]pyridine-2-carboxylate Methyl 5-(carbonochloridoyl)pyridine-2-carboxylate (3.86 g, 19.34 mmol) was added to 5-bromo-2-chloropyridin-3-amine (4.01 g, 19.34 mmol) in pyridine (80 mL) and the reaction mixture stirred at room temperature overnight. Water (80 mL) was added and the mixture stirred for a further 30 minutes. The precipitate was filtered, washed with water and dried in a vacuum oven to give the title compound 7.16 g (69% yield) as a white solid. $\delta_H$ NMR (500 MHz, DMSO) 10.78 (s, 1H), 9.21 (d, J=1.6 Hz, 1H), 8.53 (d, J=2.3 Hz, 1H), 8.49 (dd, J=8.1, 2.2 Hz, 1H), 8.44 (d, J=2.3 Hz, 1H), 8.01 (d, J=2.6 Hz, 1H), 7.67 (d, J=2.6 Hz, 1H), 3.95 (d, J=3.4 Hz, 3H), Tr(METCR1410)=0.89 min, (ES$^+$) (M+H)$^+$ 272, 89%.

Step 7, Method 77: Methyl 5-{6-[(5-methoxypyridin-2-yl)methoxyl-[1,3]oxazolo[5,4-b]pyridin-2-yl}pyridine-2-carboxylate Cyanomethylenetributylphosphorane (0.31 mL, 1.19 mmol) was added to a stirred solution of methyl 5-{6-hydroxy-[1,3]oxazolo[5,4-b]pyridin-2-yl}pyridine-2-carboxylate (215 mg, 0.79 mmol) and (5-methoxypyridin-2-yl)methanol (132 mg, 0.95 mmol) in toluene (5 mL) and the reaction heated to 100° C. for 3.5 hours under nitrogen. The reaction was cooled to room temperature and the solid filtered. The solid was washed with toluene (15 mL) and dried in a vac oven to give the title compound 216 mg (62% yield) as a beige solid. $\delta_H$ NMR (500 MHz, DMSO) 9.42 (d, J=1.6 Hz, 1H), 8.72 (dd, J=8.2, 2.2 Hz, 1H), 8.66 (d, J=2.8 Hz, 1H), 8.31 (d, J=2.7 Hz, 1H), 8.27 (d, J=7.9 Hz, 1H), 8.22 (dd, J=8.9, 2.8 Hz, 1H), 8.19 (d, J=2.7 Hz, 1H), 8.14 (d, J=9.0 Hz, 1H), 5.60 (s, 2H), 3.98 (s, 3H), 3.91 (s, 3H), Tr(METCR1410)=1.02 min, (ES$^+$) (M+H)$^+$ 393, 89%.

Step 8, Method 77: 5-{6-[(5-Methoxypyridin-2-yl)methoxy]-[1,3]oxazolo[5,4-b]pyridin-2-yl}pyridine-2-carboxylic acid 2 M sodium hydroxide (0.08 mL) was added to a solution of methyl 5-{6-[(5-methoxypyridin-2-yl)methoxy]-[1,3]oxazolo[5,4-b]pyridin-2-yl}pyridine-2-carboxylate (50 mg, 0.12 mmol) in tetrahydrofuran (1 mL) and the reaction stirred at room temperature overnight. Additional 2 M sodium hydroxide (0.05 mL) and tetrahydrofuran (1 mL) were added and the reaction stirred for a further 5 hours. The reaction was filtered under reduced pressure and the solid washed with water (5 mL) and dried under vacuum to give the sodium salt. The solid was suspended in water (2 mL) and 4 N hydrochloric acid in dioxane (0.2 mL) was added. The solid was sonicated until the solid became a fine powder and then concentrated in vacuo to give the title compound 52 mg (80% yield) as a light yellow solid. Tr(METCR1410) =0.94 min, (ES$^+$) (M+H)$^+$ 379, 80%.

Step 9, Method 77: 5-{6-[(5-Methoxypyridin-2-yl)methoxyl-[1,3]oxazolo[5,4-b]pyridin-2-yl}-N-methylpyridine-2-carboxamide Diisopropylethylamine (20 µl, 0.12 mmol) was added to 5-{6-[(5-Methoxypyridin-2-yl)methoxy]-[1,3]oxazolo[5,4-b]pyridin-2-yl}pyridine-2-carboxylic acid hydrochloride (80%, 52 mg, 0.1 mmol), 1-[bis(dimethylamino)methylene]-1H-1,2,3-triazolo[4,5-b]pyridinium 3-oxid hexafluorophosphate (46.9 mg, 0.12 mmol) and methanamine hydrochloride (1:1) (8 mg, 0.12 mmol) suspended in N,N-dimethylformamide (2 mL) and the reaction stirred at room temperature for 2 hours. The solid was filtered and washed with N,N-dimethylformamide (10 mL). The sample was triturated with methanol (3 mL) and then tetrahydrofuran (3 mL). The product was purified by re-crystallisation from DMSO (2 mL) followed by washing with DMSO (3 mL), water (5 mL) and methanol (5 mL). The solid was dried in a vacuum oven overnight to give the title compound 12 mg (29% yield) as an off white solid.

Example 1, Method 77: 5-{6-[(5-Methoxypyridin-2-yl)methoxy]-[1,3]oxazolo[5,4-b]pyridin-2-yl}-N-methylpyridine-2-carboxamide $\delta_H$ NMR (500 MHz, Pyridine) 9.51 (s, 1H), 9.30 (d, J=4.0 Hz, 1H), 8.64 (dd, J=8.1, 1.8 Hz, 1H), 8.58-8.49 (m, 3H), 8.15 (d, J=2.5 Hz, 1H), 7.64-7.61 (m, 1H), 7.35 (dd, J=8.6, 2.9 Hz, 1H), 5.47 (s, 2H), 3.73 (s, 3H), 3.13 (d, J=4.9 Hz, 3H), Tr(MET-uHPLC-AB-101)=2.51 min, (ES$^+$) (M+H)$^+$ 392.

The following example was prepared using Method 77 described above:

TABLE 78

| Ex. | Structure | Mol. Weight | IUPAC Name | LCMS data |
|---|---|---|---|---|
| 1 | 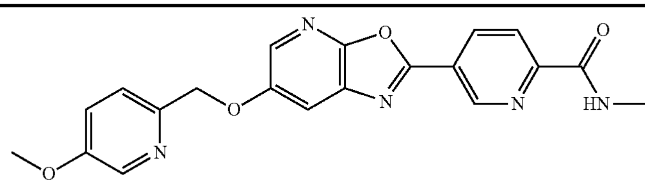 | 391.39 | 5-{6-[(5-Methoxypyridin-2-yl)methoxy]-[1,3]oxazolo[5,4-b]pyridin-2-yl}-N-methylpyridine-2-carboxamide | Tr(MET-uHPLC-AB-101) = 2.51 min, (ES$^+$) (M + H)$^+$ 392 |

Method 78

Scheme for Method 78

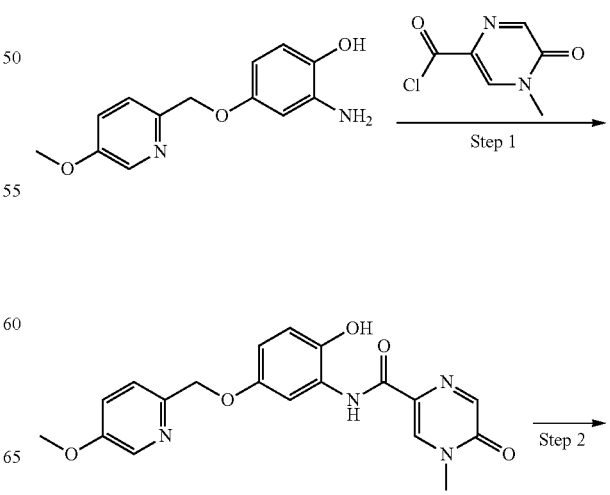

217

-continued

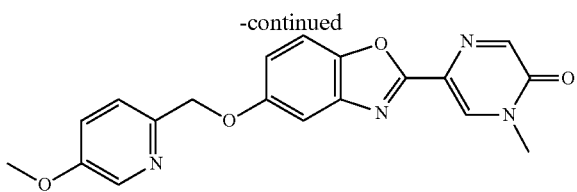

Step 1, Method 78: N-{2-Hydroxy-5-[(5-methoxy-pyridin-2-yl)methoxy]phenyl}-4-methyl-5-oxo-4,5-dihydropyrazine-2-carboxamide 2-Amino-4-[(5-methoxypyridin-2-yl)methoxy]phenol dihydrochloride (95%, 200 mg, 0.6 mmol, prepared using Method 33) and 4-methyl-5-oxo-4,5-dihydropyrazine-2-carbonyl chloride (50%, 226 mg, 0.65 mmol) were suspended in pyridine (5 mL) and the reaction stirred at room temperature in a nitrogen atmosphere for 2 hours. The reaction was concentrated in vacuo and triturated with water (20 mL). The mixture was filtered through glass fibre filter paper and dried in air overnight to give the title compound 203 mg (71% purity, 63% yield) as a yellow powder. $\delta_H$ NMR (500 MHz, DMSO) 9.82 (d, J=1.5 Hz, 1H), 8.55 (s, 1H), 8.28 (d, J=2.9 Hz, 1H), 8.08 (d, J=3.0 Hz, 1H), 8.06 (d, J=0.9 Hz, 1H), 7.47 (d, J=8.6 Hz, 1H), 7.43 (dd, J=8.6, 2.9 Hz, 1H), 6.83 (d, J=8.7 Hz, 1H), 6.62 (dd, J=8.8, 3.0 Hz, 1H), 5.02 (s, 2H), 3.84 (s, 4H), 3.55 (s, 3H). Tr(METCR1410)=0.88 min, (ES$^+$) (M+H)$^+$ 383, 71%.

Step 2, Method 78: 5-{5-[(5-Methoxypyridin-2-yl)methoxy]-1,3-benzoxazol-2-yl}-1-methyl-1,2-dihydropyrazin-2-one N-{2-Hydroxy-5-[(5-methoxypyridin-2-yl)methoxy]phenyl}-4-methyl-5-oxo-4,5-dihydropyrazine-2-carboxamide (71%, 203 mg, 0.38 mmol) was suspended in acetic acid (2 mL) and heated to 180° C. in a sealed tube for 16 hours. The solvents were removed in vacuo and the residue partitioned between ethyl acetate (30 mL) and saturated sodium bicarbonate solution (10 mL). The aqueous was extracted with ethyl acetate (2×30 mL), the combined organics washed with brine (10 mL), dried over anhydrous magnesium sulfate, filtered and concentrated. Purification by FCC (silica, 0-10% methanol in dichloromethane), trituration with diethyl ether, hot filtration from DMSO, preparative HPLC (acetonitrile/water and acetonitrile/water+0.2% ammonium hydroxide) gave the title compound, 4 mg (3% yield) as a white powder.

Example 1, Method 78: 5-{5-[(5-Methoxypyridin-2-yl)methoxy]-1,3-benzoxazol-2-yl}-1-methyl-1,2-dihydropyrazin-2-one $\delta_H$ NMR (500 MHz, DMSO) 8.78 (s, 1H), 8.30 (d, J=2.9 Hz, 1H), 8.13 (d, J=0.9 Hz, 1H), 7.65 (d, J=8.9 Hz, 1H), 7.52 (d, J=8.6 Hz, 1H), 7.43 (dd, J=8.6, 3.0 Hz, 1H), 7.37 (d, J=2.5 Hz, 1H), 7.07 (dd, J=8.9, 2.5 Hz, 1H), 5.17 (s, 2H), 3.84 (s, 3H), 3.57 (s, 3H). Tr(MET-uHPLC-AB-101)=2.11 min, (ES$^+$) (M+H)$^+$ 365.

The following example was prepared using Method 78 described above:

TABLE 79

| Ex. | Structure | Mol. Weight | IUPAC Name | LCMS data |
|---|---|---|---|---|
| 1 | 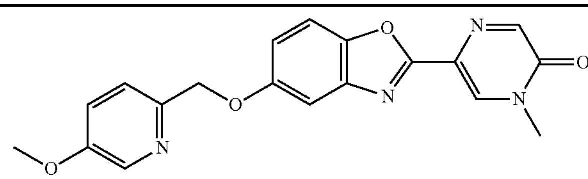 | 364.36 | 5-{5-[(5-Methoxypyridin-2-yl)methoxy]-1,3-benzoxazol-2-yl}-1-methyl-1,2-dihydropyrazin-2-one | Tr(MET-uHPLC-AB-101) = 2.11 min, (ES$^+$) (M + H)$^+$ 365 |

Method 79
Scheme for Method 79

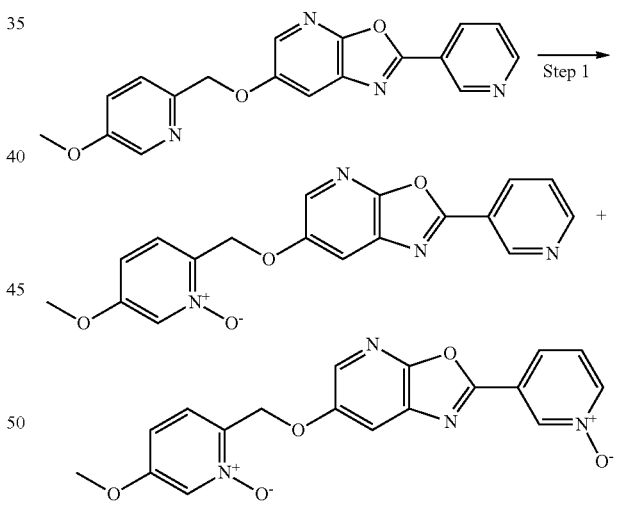

Step 1, Method 79: 5-Methoxy-2-({[2-(pyridin-3-yl)-[1,3]oxazolo[5,4-b]pyridin-6-yl]oxy}methyl)pyridin-1-ium-1-olate and 3-{6-[(5-methoxy-1-oxidopyridin-1-ium-2-yl)methoxy]-[1,3]oxazolo[5,4-b]pyridin-2-yl}pyridin-1-ium-1-olate 3-{6-[(5-Methoxypyridin-2-yl)methoxy]-[1,3]oxazolo[5,4-b]pyridin-2-yl}pyridine (93%, 78 mg, 0.22 mmol, prepared using Method 30) was dissolved in anhydrous dichloromethane (2 mL), 3-chlorobenzenecarboperoxoic acid (75%, 55 mg, 0.24 mmol) was added and the reaction stirred at room temperature for 2 hours. 3-Chlorobenzenecarboperoxoic acid (75%, 55 mg, 0.24 mmol) was added and the reaction stirred at room temperature for 16 hours. The reaction was diluted with dichloromethane (50 mL) and the organic layer washed with saturated sodium hydrogen carbonate solution (3×30 mL), saturated sodium sulfite solution (30 mL), dried over magnesium sulfate, filtered and concentrated. Purification by preparative HPLC (acetonitrile/water) gave the two title compounds 5-methoxy-2-({[2-(pyridin-3-yl)-[1,3]oxazolo[5,4-b]pyridin-6-yl]oxy}methyl)pyridin-1-ium-1-olate 8.1 mg (11% yield) as a white powder and 3-{6-[(5-methoxy-1-oxidopyridin-1-ium-2-yl)methoxy]-[1,3]oxazolo[5,4-b]pyridin-2-yl}pyridin-1-ium-1-olate 6.2 mg (8% yield) as a white powder.

Example 1, Method 79: 5-Methoxy-2-({[2-(pyridin-3-yl)-[1,3]oxazolo[5,4-b]pyridin-6-yl]oxy}methyl)pyridin-1-ium-1-olate $\delta_H$ NMR (500 MHz, DMSO) 9.36 (d, J=1.6 Hz, 1H), 8.84 (dd, J=4.8, 1.6 Hz, 1H), 8.55 (dt, J=8.0, 1.9 Hz, 1H), 8.25 (d, J=2.7 Hz, 1H), 8.22 (d, J=2.3 Hz, 1H), 8.12 (d, J=2.7 Hz, 1H), 7.71-7.64 (m, 1H), 7.62 (d, J=8.9 Hz, 1H), 7.12 (dd, J=8.9, 2.4 Hz, 1H), 5.36 (s, 2H), 3.84 (s, 3H). Tr(MET-uHPLC-AB-101)=1.99 min, (ES$^+$) (M+H)$^+$ 351.

Example 2, Method 79: 3-{6-[(5-Methoxy-1-oxidopyridin-1-ium-2-yl)methoxy]-[1,3] oxazolo[5,4-b]pyridin-2-yl}pyridin-1-ium-1-olate $\delta_H$ NMR (500 MHz, DMSO) 8.80 (s, 1H), 8.46 (d, J=7.2 Hz, 1H), 8.29 (d, J=2.7 Hz, 1H), 8.22 (d, J=2.3 Hz, 1H), 8.15 (d, J=2.7 Hz, 1H), 8.06 (d, J=8.1 Hz, 1H), 7.69-7.63 (m, 1H), 7.62 (d, J=8.9 Hz, 1H), 7.11 (dd, J=8.9, 2.3 Hz, 1H), 5.36 (s, 2H), 3.84 (s, 3H). Tr(MET-uHPLC-AB-101)=1.58 min, (ES$^+$) (M+H)$^+$ 367.

The following examples were prepared using Method 79 described above:

Method 80
Scheme for Method 80

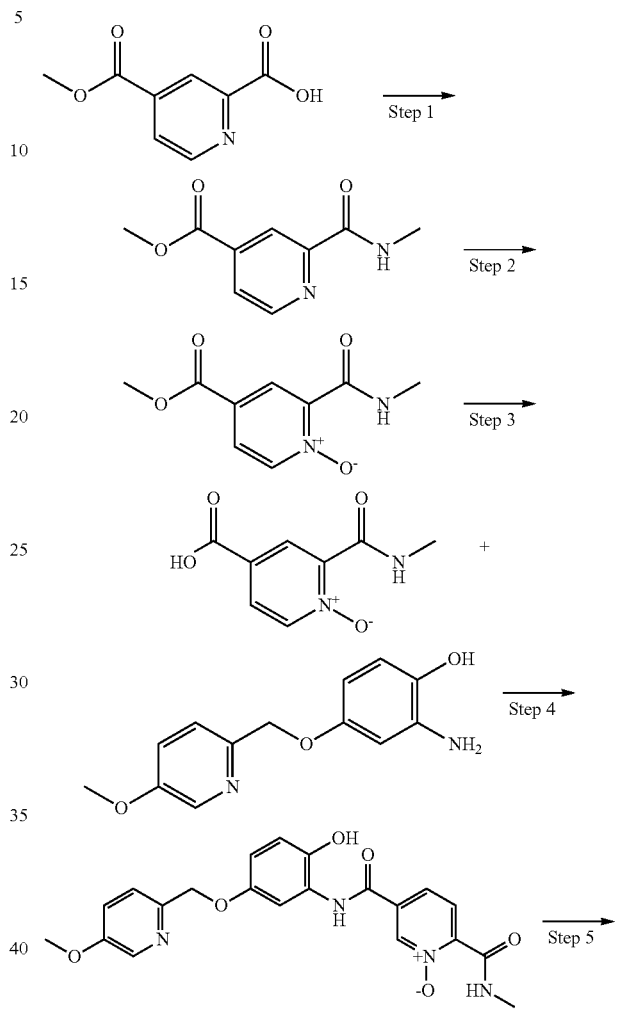

TABLE 80

| Ex. | Structure | Mol. Weight | IUPAC Name | LCMS data |
|---|---|---|---|---|
| 1 | 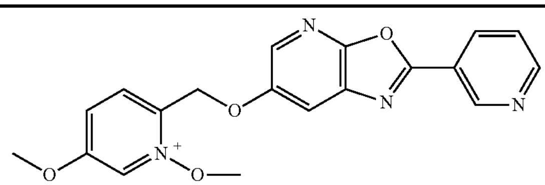 | 350.33 | 5-Methoxy-2-({[2-(pyridin-3-yl)-[1,3]oxazolo[5,4-b]pyridin-6-yl]oxy}methyl)pyridin-1-ium-1-olate | Tr(MET-uHPLC-AB-101) = 1.99 min, (ES$^+$) (M + H)$^+$ 351 |
| 2 | 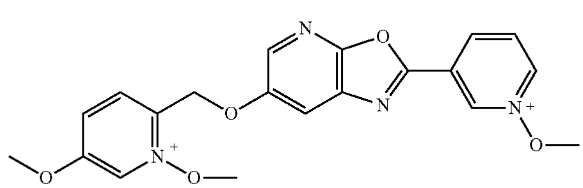 | 366.33 | 3-{6-[(5-Methoxy-1-oxidopyridin-1-ium-2-yl)methoxy]-[1,3]oxazolo[5,4-b]pyridin-2-yl}pyridin-1-ium-1-olate | Tr(MET-uHPLC-AB-101) = 1.58 min, (ES$^+$) (M + H)$^+$ 367 |

-continued

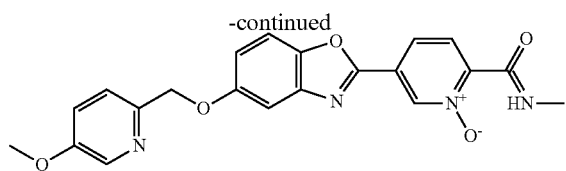

Step 1, Method 80: Methyl 6-(methylcarbamoyl)pyridine-3-carboxylate 5-(Methoxycarbonyl)pyridine-2-carboxylic acid (1 g, 5.52 mmol) was suspended in thionyl chloride (10 mL, 137.02 mmol), anhydrous N,N-dimethylformamide (0.01 mL) was added and the reaction heated to 80° C. under a nitrogen atmosphere for 1 hour. The reaction mixture was cooled to room temperature and the solvents removed in vacuo. The solid was dissolved in anhydrous tetrahydrofuran (25 mL) and stirred under a nitrogen atmosphere. 2 M methylamine in tetrahydrofuran (8.28 mL) was added dropwise and the reaction was stirred at 50° C. for 2 hours. The reaction was cooled to room temperature and the volatiles removed in vacuo. The residue was triturated with water and filtered to give the title compound 765 mg (71% yield) as a beige powder. Tr(METCR1410)=0.81 min, (ES$^+$) (M+H)$^+$ 195.

Step 2, Method 80: 5-(Methoxycarbonyl)-2-(methylcarbamoyl)pyridin-1-ium-1-olate Methyl 6-(methylcarbamoyl)pyridine-3-carboxylate (700 mg, 3.6 mmol) was suspended in anhydrous dichloromethane (20 mL), 3-chlorobenzenecarboperoxoic acid (1.74 g, 7.58 mmol) was added and the reaction was stirred at 45° C. for 3.5 days under a nitrogen atmosphere. The reaction was cooled to room temperature and diluted with dichloromethane (100 mL). The organic extract was washed with saturated sodium hydrogen carbonate solution (3×30 mL), saturated sodium sulfite solution solution (30 mL) then dried over anhydrous sodium sulfate, filtered and concentrated. The residue was dissolved in dichloromethane (30 mL) and washed with sodium hydrogen carbonate solution (3×15 mL). The organic layer was dried over magnesium sulfate, filtered and concentrated in vacuo. This solid was dissolved in dichloromethane (30 mL) and washed with sodium hydrogen carbonate solution (3×15 mL). The organic layer was dried over magnesium sulfate, filtered and concentrated in vacuo. Purification by FCC (silica, 0-10% methanol in dichloromethane) gave the title compound 425 mg (53% yield) as a white solid. Tr(METCR1410)=0.69 min, (ES$^+$) (M+H)$^+$ 211.

Step 3, Method 80: 5-Carboxy-2-(methylcarbamoyl)pyridin-1-ium-1-olate 5-(Methoxycarbonyl)-2-(methylcarbamoyl)pyridin-1-ium-1-olate (95%, 425 mg, 1.98 mmol) was suspended in tetrahydrofuran (10 mL), 2 M sodium hydroxide (0.96 mL) was added and the reaction mixture stirred at room temperature for 1.5 hours. The reaction mixture was acidified to pH 3 using 1 M hydrochloric acid and a gummy solid formed. Water was added to the mixture and the solid dissolved. The aqueous was extracted with ethyl acetate and the organic layer was concentrated. Purification by preparative HPLC (acetonitrile/water) gave the title compound 57 mg (15% yield) as a white solid. Tr(METCR1410)=0.30 min, (ES$^+$) (M+H)$^+$ 197.

Step 4, Method 80: 5-({2-Hydroxy-5-[(5-methoxypyridin-2-yl)methoxy]phenyl}carbamoyl)-2-(methylcarbamoyl)pyridin-1-ium-1-olate 2-Amino-4-[(5-methoxypyridin-2-yl)methoxy]phenol (41 mg, 0.13 mmol, prepared using Method 33) and 5-carboxy-2-(methylcarbamoyl)pyridin-1-ium-1-olate (25 mg, 0.13 mmol) were dissolved in pyridine (1 mL) and stirred at room temperature for 10 minutes. 1-Ethyl-3-(3-dimethylaminopropyl)carbodiimide hydrochloride (29 mg, 0.15 mmol) was added and the reaction mixture was left to stir at room temperature for 2 hours. Water was added to the reaction mixture and filtered. Purification by FCC (silica, 0-100% ethyl acetate in heptane followed by 0-20% methanol in dichloromethane) gave the title compound 12 mg (22% yield) as a yellow solid. $\delta_H$ NMR (500 MHz, DMSO) 10.89 (d, J=4.8 Hz, 1H), 9.97 (s, 1H), 9.26 (s, 1H), 8.89 (s, 1H), 8.32 (d, J=8.4 Hz, 1H), 8.27 (d, J=2.4 Hz, 1H), 8.00 (d, J=7.8 Hz, 1H), 7.46 (d, J=8.5 Hz, 1H), 7.41 (dd, J=8.6, 2.9 Hz, 1H), 7.33 (d, J=2.7 Hz, 1H), 6.83 (d, J=8.8 Hz, 1H), 6.76 (dd, J=8.9, 3.0 Hz, 1H), 5.01 (s, 2H), 3.83 (s, 3H), 2.92 (d, J=4.9 Hz, 3H). Tr(MET-uHPLC-AB-101)=1.75 min, (ES+) (M+H)+ 425.

Step 5, Method 80: 5-{5-[(5-Methoxypyridin-2-yl)methoxy]-1,3-benzoxazol-2-yl}-2-(methylcarbamoyl)pyridin-1-ium-1-olate 5-({2-Hydroxy-5-[(5-methoxypyridin-2-yl)methoxy]phenyl}carbamoyl)-2-(methylcarbamoyl)pyridin-1-ium-1-olate (102 mg, 0.24 mmol) was suspended in acetic acid (4 mL) and para-toluenesulfonic acid (457 mg, 2.4 mmol) added. The mixture was irradiated in the microwave at 120° C. for 2 hours. The mixture was cooled to room temperature and the pH adjusted to 7 by addition of saturated sodium bicarbonate solution. The product was extracted with ethyl acetate (3×50 mL), dried over magnesium sulfate and concentrated. Purification by FCC (Silica, 0-10% methanol in dichloromethane), and preparative HPLC (acetonitrile/water+0.2% ammonium hydroxide) gave the title compound 5.4 mg (6%) as a white powder.

Example 1, Method 80: 5-{5-[(5-Methoxypyridin-2-yl)methoxy]-1,3-benzoxazol-2-yl}-2-(methylcarbamoyl)pyridin-1-ium-1-olate $\delta_H$ NMR (500 MHz, DMSO) 10.78 (q, J=4.9 Hz, 1H), 8.95 (s, 1H), 8.39 (d, J=8.4 Hz, 1H), 8.30 (d, J=2.9 Hz, 1H), 8.22 (dd, J=8.4, 1.3 Hz, 1H), 7.77 (d, J=9.0 Hz, 1H), 7.56-7.50 (m, 2H), 7.43 (dd, J=8.6, 3.0 Hz, 1H), 7.20 (dd, J=9.0, 2.5 Hz, 1H), 5.20 (s, 2H), 3.84 (s, 3H), 2.92 (d, J=4.9 Hz, 3H). Tr(MET-uHPLC-AB-101)=2.4 min, (ES$^+$) (M+H)$^+$ 407.

The following example was prepared using Method 80 described above:

TABLE 81

| Ex. | Structure | Mol. Weight | IUPAC Name | LCMS data |
|---|---|---|---|---|
| 1 | 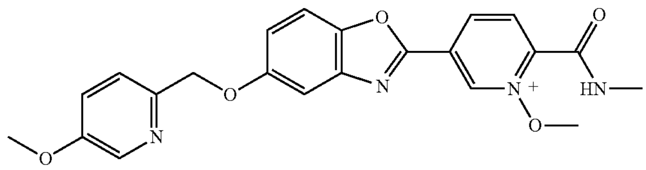 | 406.40 | 5-{5-[(5-Methoxypyridin-2-yl)methoxy]-1,3-benzoxazol-2-yl}-2-(methylcarbamoyl)pyridin-1-ium-1-olate | Tr(MET-uHPLC-AB-101) = 2.4 min, (ES⁺) (M + H)⁺ 407 |

Method 81
Scheme for Method 81

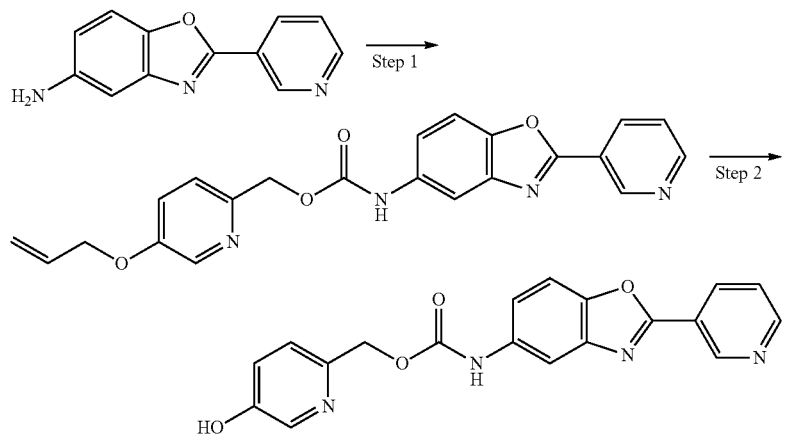

Step 1, Method 81: [5-(Prop-2-en-1-yloxy)pyridin-2-yl]methyl N-[2-(pyridin-3-yl)-1,3-benzoxazol-5-yl]carbamate 2-(Pyridin-3-yl)-1,3-benzoxazol-5-amine (500 mg, 2.37 mmol) was dissolved in tetrahydrofuran (40 mL) and triphosgene (232 mg, 0.78 mmol) added. The solution was stirred at room temperature for 10 minutes under a nitrogen flow attached to a 2 M sodium hydroxide scrubber. Triethylamine (0.51 mL, 3.55 mmol) was added and the reaction mixture left to stir for a further 30 minutes. [5-(Prop-2-en-1-yloxy)pyridin-2-yl]methanol (391 mg, 2.37 mmol, described in in U.S. Pat. No. 4,198,416 (1978) reference example 3) was dissolved in tetrahydrofuran (6 mL) and passed through magnesium sulfate under nitrogen into the top of a closed dropping funnel, the magnesium sulfate was washed with tetrahydrofuran into the dropping funnel under nitrogen. The dried allyl alcohol was added dropwise to the reaction mixture. The reaction mixture was stirred for 2 days at room temperature. The solvents were removed in vacuo, the residue triturated with water (50 mL) and filtered. The solid was suspended in 4:1 tetrahydrofuran:dichloromethane and heated to 50° C. The hot mixture was filtered and filtrate was concentrated in vacuo. The remaining residue was triturated in 1:1 diethyl ether:heptane to give the title compound 165 mg (15% yield) as a brown solid. $\delta_H$ NMR (500 MHz, DMSO) 10.02 (s, 1H), 9.33 (d, J=1.6 Hz, 1H), 8.80 (dd, J=4.8, 1.6 Hz, 1H), 8.52 (dt, J=8.0, 1.9 Hz, 1H), 8.30 (t, J=1.8 Hz, 1H), 8.00 (s, 1H), 7.75 (d, J=8.8 Hz, 1H), 7.65 (dd, J=8.6, 4.9 Hz, 1H), 7.49 (dd, J=8.8, 2.0 Hz, 1H), 7.45 (d, J=1.8 Hz, 2H), 6.04 (ddt, J=17.3, 10.5, 5.3 Hz, 1H), 5.41 (dq, J=17.3, 1.6 Hz, 1H), 5.35-5.24 (m, 1H), 5.18 (s, 2H), 4.67 (dt, J=5.2, 1.5 Hz, 2H); Tr(METCR1410)=1.08 min, (ES⁺) (M+H)⁺ 403, 84%.

Step 2, Method 81: (5-Hydroxypyridin-2-yl)methyl N-[2-(pyridin-3-yl)-1,3-benzoxazol-5-yl]carbamate 5[5-(Prop-2-en-1-yloxy)pyridin-2-yl]methyl N-[2-(pyridin-3-yl)-1,3-benzoxazol-5-yl]carbamate (84%, 145 mg, 0.3 mmol) and 1,3-dimethylpyrimidine-2,4,6(1H,3H,5H)-trione (95 mg, 0.61 mmol) were suspended in N,N-dimethylformamide (4 mL) and degassed under a flow of nitrogen. Tetrakis(triphenylphosphine)palladium(0) (17 mg, 0.02 mmol) was added and the reaction mixture stirred at room temperature for 1.5 hours. The reaction mixture was concentrated to ¼ of the original volume and water added. A precipitate formed which was collected by filtration. The collected solid was triturated with ethyl acetate and purified by a hot filtration from acetonitrile to give the title compound 57 mg (50% yield) as an orange solid.

Example 1, Method 81: (5-Hydroxypyridin-2-yl)methyl N-[2-(pyridin-3-yl)-1,3-benzoxazol-5-yl]carbamate $\delta_H$ NMR (500 MHz, DMSO) 10.08-9.92 (m, 2H), 9.33 (d, J=1.7 Hz, 1H), 8.80 (dd, J=4.8, 1.6 Hz, 1H), 8.52 (dt, J=8.0, 1.9 Hz, 1H), 8.12 (d, J=2.8 Hz, 1H), 8.00 (s, 1H), 7.74 (d, J=8.8 Hz, 1H), 7.65 (ddd, 1H), 7.49 (dd, J=8.9, 1.9 Hz, 1H), 7.34 (d, J=8.4 Hz, 1H), 7.20 (dd, J=8.4, 2.9 Hz, 1H), 5.13 (s, 2H). Tr(MET-uHPLC-AB-101)=1.82 min, (ES⁺) (M+H)⁺ 363.

The following example was prepared using Method 81 described above:

TABLE 82

| Ex. | Structure | Mol. Weight | IUPAC Name | LCMS data |
|---|---|---|---|---|
| 1 | 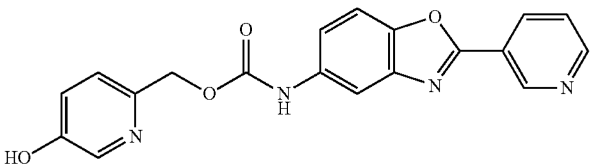 [SMILES: O=C(Nc1ccc2oc(-c3cccnc3)nc2c1)OCc1ccc(O)cn1] | 362.35 | (5-Hydroxypyridin-2-yl)methyl N-[2-(pyridin-3-yl)-1,3-benzoxazol-5-yl]carbamate | Tr(MET-uHPLC-AB-101) = 1.82 min, (ES$^+$) (M + H)$^+$ 363 |

Method 82
Scheme for Method 82

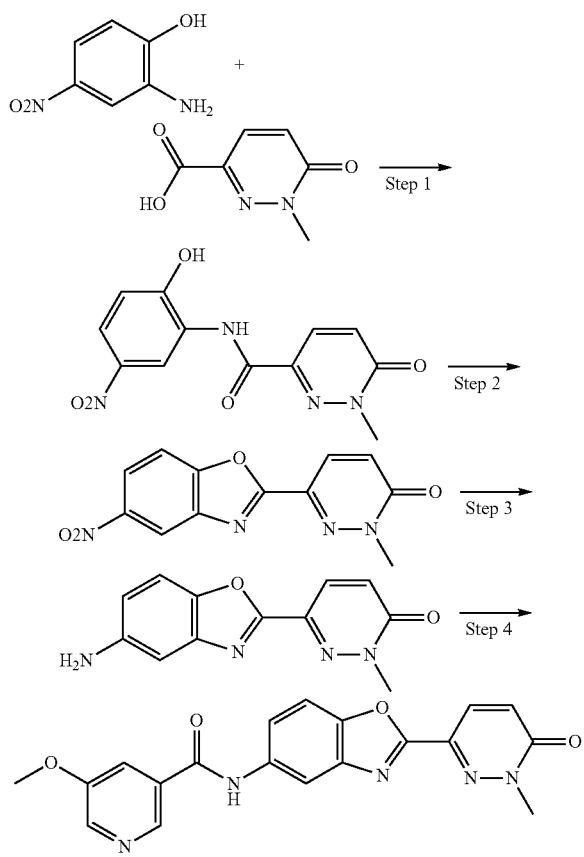

Step 1, Method 82: N-(2-Hydroxy-5-nitrophenyl)-1-methyl-6-oxo-1,6-dihydropyridazine-3-carboxamide To a suspension of 2-amino-4-nitrophenol (3.0 g, 19.46 mmol) and 1-methyl-6-oxo-1,6-dihydropyridazine-3-carboxylic acid (3.06 g, 19.85 mmol) in pyridine (30 mL) was added 1-ethyl-3-(3-dimethylaminopropyl)carbodiimide hydrochloride (4.85 g, 25.3 mmol) and the resulting suspension was stirred for 1 hour. The reaction mixture was slowly diluted with water (circa 70 mL) and the suspension stirred for 5 minutes. The solids were filtered off and air-dried to give the title compound 4.67 g (74% yield) as a tan solid. $\delta_H$ NMR (250 MHz, DMSO) 9.67 (s, 1H), 9.10 (d, J=2.8 Hz, 1H), 8.06-7.93 (m, 2H), 7.12 (dd, J=9.3, 3.8 Hz, 2H), 3.79 (s, 3H). Contains 14 wt % pyridine. Tr(METCR1410, 2 min)=1.03 min (ES$^+$) (M+H)$^+$ 291.

Step 2, Method 82: 2-Methyl-6-(5-nitro-1,3-benzoxazol-2-yl)-2,3-dihydropyridazin-3-one Polyphosphoric acid (approximately 20 mL) was poured onto N-(2-hydroxy-5-nitrophenyl)-1-methyl-6-oxo-1,6-dihydropyridazine-3-carboxamide (90%, 4.67 g, 14.48 mmol). The lumps were broken up and the resulting suspension heated to 110° C. for 3 hours. The mixture was cooled and the deep red solution added to ice-water (100 mL). The mixture was diluted with more water to give a total volume of circa 200 mL. A thick purple suspension resulted, to which ethyl acetate was added (circa 50 mL) and the suspension stirred rapidly for 15 mins. A tan solid formed which was removed by filtration. These solids were washed with water, heptane and air-dried under vacuum to give the title compound 2.95 g (75% yield) as a grey solid. $\delta_H$ NMR (250 MHz, DMSO) 8.74 (d, J=2.2 Hz, 1H), 8.41 (dd, J=9.0, 2.3 Hz, 1H), 8.19 (d, J=9.7 Hz, 1H), 8.13 (d, J=9.0 Hz, 1H), 7.18 (d, J=9.7 Hz, 1H), 3.83 (s, 3H). Tr(METCR0990)=1.48 min (ES$^+$) (M+H)$^+$ 273, 93%.

Step 3, Method 82: 6-(5-Amino-1,3-benzoxazol-2-yl)-2-methyl-2,3-dihydropyridazin-3-one A suspension of 2-methyl-6-(5-nitro-1,3-benzoxazol-2-yl)-2,3-dihydropyridazin-3-one (95%, 2.45 g, 8.55 mmol) in ethanol: N,N-dimethylformamide (1:1, 100 mL) and 10% palladium on carbon (0.45 g) was stirred under an atmosphere of hydrogen for 4 hours. The mixture was filtered, washed with N,N-dimethylformamide. The filtrates were evaporated to give the title compound (2.1 g, 92% yield) as a green to yellow solid. $\delta_H$ NMR (250 MHz, DMSO) 8.11 (d, J=9.7 Hz, 1H), 7.46 (d, J=8.7 Hz, 1H), 7.11 (d, J=9.7 Hz, 1H), 6.89 (d, J=1.9 Hz, 1H), 6.73 (dd, J=8.7, 2.2 Hz, 1H), 5.22 (s, 2H), 3.78 (s, 3H). Tr(METCR0990)=1.26 min (ES$^+$) (M+H)$^+$ 243.

Step 4, Method 82: 5-Methoxy-N-[2-(1-Methyl-6-oxo-1,6-dihydropyridazin-3-yl)-1,3-benzoxazol-5-yl]pyridine-3-carboxamide To a suspension of 6-(5-amino-1,3-benzoxazol-2-yl)-2-methyl-2,3-dihydropyridazin-3-one (90%, 42 mg, 0.16 mmol) and 5-methoxypyridine-3-carboxylic acid (25 mg, 0.16 mmol) in pyridine (2 mL) was added 1-ethyl-3-(3-dimethylaminopropyl)carbodiimide hydrochloride (39 mg, 0.2 mmol) and the resulting suspension stirred for 1 hour. The reaction mixture was slowly diluted with water (5 mL) and the resulting suspension stirred for 5 mins, before the solid was filtered off and air-dried. A hot ethanol trituration gave the title compound 27 mg (47% yield) as a red solid.

Example 1, Method 82: 5-Methoxy-N-[2-(1-Methyl-6-oxo-1,6-dihydropyridazin-3-yl)-1,3-benzoxazol-5-yl]pyridine-3-carboxamide $\delta_H$ NMR (500 MHz, DMSO) 10.61 (s, 1H), 8.76 (d, J=1.6 Hz, 1H), 8.50 (d, J=2.8 Hz, 1H), 8.34 (d, J=1.8 Hz, 1H), 8.19 (d, J=9.7 Hz, 1H), 7.90-7.83 (m, 2H), 7.79 (dd, J=8.8, 2.0 Hz, 1H), 7.15 (d, J=9.7 Hz, 1H), 3.94 (s, 3H), 3.81 (s, 3H). Tr(METCR1600)=3.6 min (ES$^+$) (M+H)$^+$ 378.

The following examples were prepared using Method 82 described above:

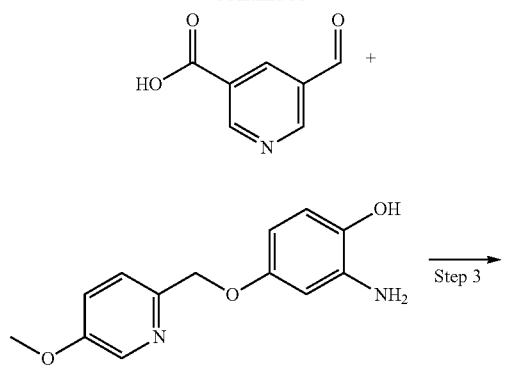

TABLE 83

| Ex. | Structure | Mol. Weight | IUPAC Name | LCMS data |
|---|---|---|---|---|
| 1 | 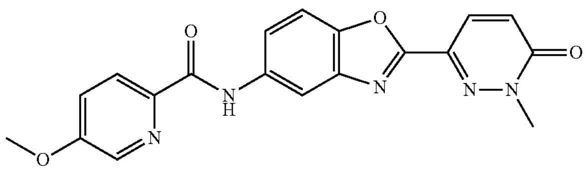 [SMILES: COc1ccc(C(=O)Nc2ccc3oc(-c4ccc(=O)n(C)n4)nc3c2)nc1] | 377.36 | 5-Methoxy-N-[2-(1-methyl-6-oxo-1,6-dihydropyridazin-3-yl)-1,3-benzoxazol-5-yl]pyridine-2-carboxamide | Tr(MET-uHPLC-AB-101) = 2.69 min, (ES$^+$) (M + H)$^+$ 378 |
| 2 | 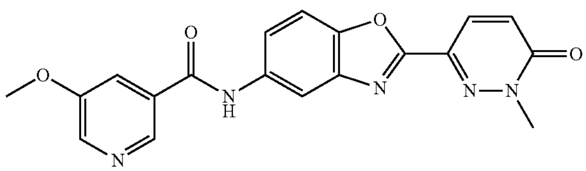 [SMILES: COc1cncc(C(=O)Nc2ccc3oc(-c4ccc(=O)n(C)n4)nc3c2)c1] | 377.36 | 5-Methoxy-N-[2-(1-methyl-6-oxo-1,6-dihydropyridazin-3-yl)-1,3-benzoxazol-5-yl]pyridine-3-carboxamide | Tr(METCR1600) = 3.6 min, (ES$^+$) (M + H)$^+$ 378 |
| 3 | 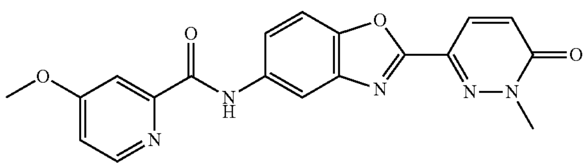 [SMILES: COc1ccnc(C(=O)Nc2ccc3oc(-c4ccc(=O)n(C)n4)nc3c2)c1] | 377.36 | 4-Methoxy-N-[2-(1-methyl-6-oxo-1,6-dihydropyridazin-3-yl)-1,3-benzoxazol-5-yl]pyridine-2-carboxamide | Tr(METCR1600) 4.14 min, (ES$^+$) (M + H)$^+$ 378 |
| 4 | 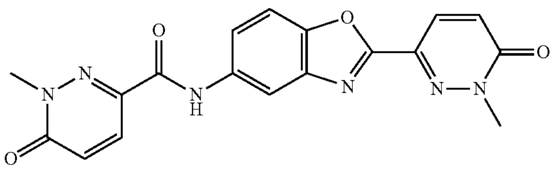 [SMILES: Cn1nc(C(=O)Nc2ccc3oc(-c4ccc(=O)n(C)n4)nc3c2)ccc1=O] | 378.35 | 1-Methyl-N-[2-(1-methyl-6-oxo-1,6-dihydropyridazin-3-yl)-1,3-benzoxazol-5-yl]-6-oxo-1,6-dihydropyridazine-3-carboxamide | Tr(METCR1600) = 3.46 min, (ES$^+$) (M + H)$^+$ 379 |

Method 83

Scheme for Method 83

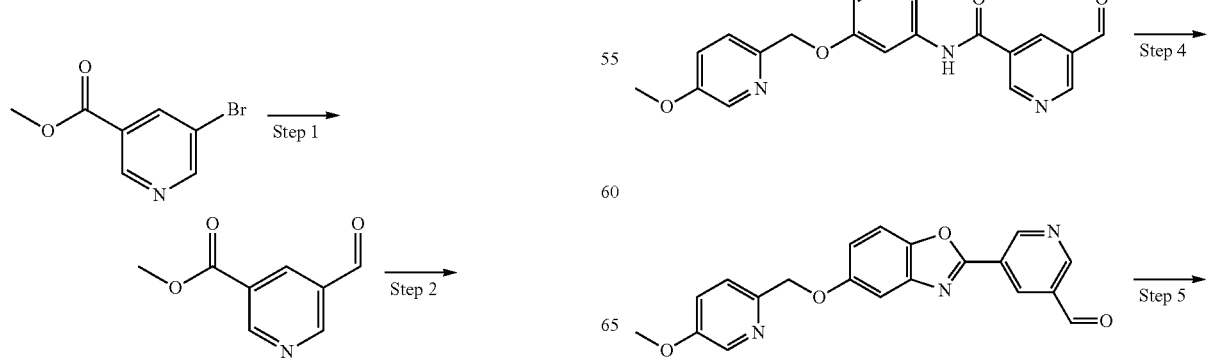

-continued

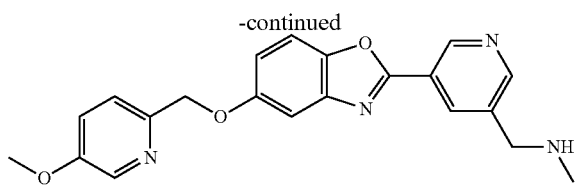

Step 1, Method 83: Methyl 5-formylpyridine-3-carboxylate

Methyl 5-bromopyridine-3-carboxylate (3.82 g, 17.66 mmol), tert-butyl isocyanide (2.4 mL, 21.2 mmol), triethylsilane (8.46 mL, 52.99 mmol), biphenyl-2-yl(dicyclohexyl)phosphane (0.28 g, 0.79 mmol) and disodium carbonate (1.87 g, 17.66 mmol) were suspended in N,N-dimethylformamide (40 mL) and the mixture degassed with nitrogen for 5 mins. Palladium(II) diacetate (0.12 g, 0.53 mmol) was added and the mixture heated at 65° C. overnight under nitrogen. The mixture was cooled to room temperature, diluted with water (200 mL) and ethyl acetate (40 mL), filtered, extracted with ethyl acetate (2×50 mL) then washed with water (5×25 mL), dried over sodium sulfate, filtered and concentrated. This material was stirred in 1 M hydrochloric acid (50 mL) for 2 hours, cooled to 0° C. and quenched with 1 M sodium carbonate to pH 9. The mixture was extracted with ethyl acetate (3×30 mL) dried over sodium sulfate filtered and concentrated to give the title compound 0.95 g (33% yield) as an off-white powder. $\delta_H$ (500 MHz, DMSO) 10.20 (s, 1H), 9.31 (d, J=2.1 Hz, 1H), 9.29 (d, J=2.0 Hz, 1H), 8.68 (t, J=2.1 Hz, 1H), 3.94 (s, 3H). Tr(METCR0990)=1.03 min, (ES$^+$) (M+H)$^+$ 166.

Step 2, Method 83: 5-Formylpyridine-3-carboxylic acid

Methyl 5-formylpyridine-3-carboxylate (0.95 g, 5.75 mmol) was dissolved in tetrahydrofuran (20 mL) and water (20 mL) and lithium hydroxide (0.14 g, 5.75 mmol) added and the mixture stirred at room temperature overnight. Lithium hydroxide (0.14 g, 5.75 mmol) was added and the mixture stirred for 2 hours. The organic solvent was evaporated and the aqueous layer washed with ethyl acetate (3×20 mL). The aqueous layer was neutralised with 1 M hydrochloric acid to pH 3 and extracted with ethyl acetate (3×20 mL) and 1:1 isopropanol:chloroform (3×10 mL). The combined organic fractions were dried over magnesium sulfate, filtered and concentrated. The mixture was azeotroped with toluene (15 mL) twice to give the title compound 0.63 g (72.6% yield) as a white powder. $\delta_H$ (500 MHz, DMSO) 13.74 (s, 1H), 10.19 (s, 1H), 9.29 (d, J=2.1 Hz, 1H), 9.26 (d, J=2.0 Hz, 1H), 8.66 (t, J=2.1 Hz, 1H).

Step 3, Method 83: 5-Formyl-N-{2-hydroxy-5-[(5-methoxypyridin-2-yl)methoxy]phenyl}pyridine-3-carboxamide 5-Formylpyridine-3-carboxylic acid (95%, 200 mg, 1.26 mmol) and 2-amino-4-[(5-methoxypyridin-2-yl)methoxy]phenol dihydrochloride (401.3 mg, 1.26 mmol, prepared using Method 33) were stirred in pyridine (10 mL) for 20 minutes. 1-Ethyl-3-(3-dimethylaminopropyl)carbodiimide hydrochloride (313 mg, 1.63 mmol) was added and the mixture stirred at room temperature under nitrogen overnight. Water (20 mL) was added and the mixture extracted with 1:1 isopropanol:chloroform (3×25 mL) and washed with water (2×10 mL). The combined organic layers were dried over sodium sulfate, filtered and concentrated to give a brown oil. Purification by FCC (silica, 0-10% methanol in dichloromethane) gave the title compound 0.07 g (13% yield) as a yellow solid. $\delta_H$ (500 MHz, DMSO) 10.20 (s, 1H), 9.90 (s, 1H), 9.33 (s, 1H), 9.23 (d, J=1.8 Hz, 1H), 8.73 (s, 1H), 8.27 (d, J=2.9 Hz, 1H), 7.55-7.31 (m, 3H), 6.84 (d, J=8.8 Hz, 1H), 6.75 (dd, J=8.8, 3.0 Hz, 1H), 5.02 (s, 2H), 3.83 (s, 3H), 3.17 (s, 1H). Tr(METCR1673)=0.89 min, (ES$^+$) (M+H)$^+$ 380, 86%.

Step 4, Method 83: 5-{5-[(5-Methoxypyridin-2-yl)methoxy]-1,3-benzoxazol-2-yl}pyridine-3-carbaldehyde 5-Formyl-N-{2-hydroxy-5-[(5-methoxypyridin-2-yl)methoxy]phenyl}pyridine-3-carboxamide (95%, 51 mg, 0.13 mmol) was suspended in acetic acid (2 mL) in a microwave tube and the mixture heated to 180° C. for 90 mins. The solution was cooled to room temperature then concentrated to dryness. Purification by FCC (silica, 0-10% methanol in dichloromethane) gave the title compound 20 mg (37% yield) of as an off white powder. $\delta_H$ NMR (500 MHz, chloroform) 10.20 (s, 1H), 9.63 (d, J=2.1 Hz, 1H), 9.18 (d, J=2.0 Hz, 1H), 8.89 (t, J=2.1 Hz, 1H), 8.31 (d, J=2.8 Hz, 1H), 7.51 (d, J=8.9 Hz, 1H), 7.45 (d, J=8.6 Hz, 1H), 7.35 (d, J=2.5 Hz, 1H), 7.23 (dd, J=8.6, 2.9 Hz, 1H), 7.11 (dd, J=8.9, 2.5 Hz, 1H), 5.20 (s, 2H), 3.86 (s, 3H). Tr(METCR1673)=1.04 min, (ES$^+$) (M+H)$^+$ 362, 86%.

Step 5, Method 83: [(5-{5-[(5-Methoxypyridin-2-yl)methoxy]-1,3-benzoxazol-2-yl}pyridin-3-yl)methyl](methyl)amine 5-{5-[(5-methoxypyridin-2-yl)methoxy]-1,3-benzoxazol-2-yl}pyridine-3-carbaldehyde (20 mg, 0.06 mmol) was dissolved in toluene (5 mL) and methanamine (33% wt in ethanol, 14 µl, 0.11 mmol) and magnesium sulfate (20 mg) added, and the mixture stirred for 10 minutes, filtered and concentrated. Toluene (5 mL), methanamine (33% wt in ethanol, 13.78 µl, 0.11 mmol) and magnesium sulfate (20 mg) were added and the mixture stirred for 10 minutes, filtered and concentrated. The residue was diluted with toluene, methanamine (33% wt in ethanol, 13.78 µl, 0.11 mmol) and magnesium sulfate were added and the mixture stirred overnight, filtered and evaporated. The mixture was dissolved in dichloromethane (50 mL), 2 M methylamine in tetrahydrofuran (110 µl, 0.22 mmol) and magnesium sulfate (246 mg) added and the mixture stirred overnight (the solvent evaporated). The mixture was dissolved in dichloromethane (50 mL), 2 M methylamine in tetrahydrofuran (220 µl, 0.44 mmol) and magnesium sulfate (1 g) added and the mixture stirred overnight. The mixture was filtered and evaporated then put in a freezer under nitrogen for 1 week. The mixture was dissolved in dichloromethane (50 mL), 2 M methylamine in tetrahydrofuran (220 µl, 0.44 mmol) and magnesium sulfate (1 g) added and the mixture stirred overnight. The mixture was filtered and evaporated. The mixture was diluted with 1,2-dichloroethane (2 mL) and sodium triacetoxyborohydride(18 mg, 0.08 mmol) and acetic acid (1 drop) were added and the mixture stirred overnight. Water (5 mL) and saturated sodium hydrogen carbonate solution (1 mL) were added and the mixture extracted with dichloromethane (4×5 mL). The combined organic layers were dried over sodium sulfate, filtered and concentrated. Purification by FCC (silica, 0-50% (25% 7 N ammonia in methanol in dichloromethane) in dichloromethane) and preparative HPLC (acetonitire/water+0.2% ammonium hydroxide) to give the title compound 10 mg (48% yield) as a white powder.

Example 1, Method 83: [(5-{5-[(5-Methoxypyridin-2-yl)methoxy]-1,3-benzoxazol-2-yl}pyridin-3-yl)methyl](methyl)amine $\delta_H$ NMR (500 MHz, Methanol) 9.27 (d, J=2.0 Hz, 1H), 8.72 (d, J=2.1 Hz, 1H), 8.59 (t, J=2.1 Hz, 1H), 8.25 (d, J=2.8 Hz, 1H), 7.63 (d, J=8.9 Hz, 1H), 7.57 (d, J=8.7 Hz, 1H), 7.45 (dd, J=8.6, 2.9 Hz, 1H), 7.38 (d, J=2.5 Hz, 1H), 7.16 (dd, J=8.9, 2.5 Hz, 1H), 5.20 (s, 2H), 3.91 (s, 2H), 3.90 (s, 3H), 2.46 (s, 3H). Tr(MET-uHPLC-AB-101)=1.56 min, (ES$^+$) (M+H)$^+$ 377.

The following example was prepared using Method 83 described above:

TABLE 84

| Ex. | Structure | Mol. Weight | IUPAC Name | LCMS data |
|---|---|---|---|---|
| 1 | 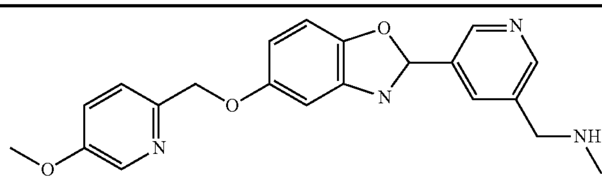 | 376.42 | [(5-{5-[(5-Methoxypyridin-2-yl)methoxy]-1,3-benzoxazol-2-yl}pyridin-3-yl)methyl](methyl)amine | Tr(MET-uHPLC-AB-101) = 1.56 min, (ES$^+$) (M + H)$^+$ 377 |

Method 84
Scheme for Method 84

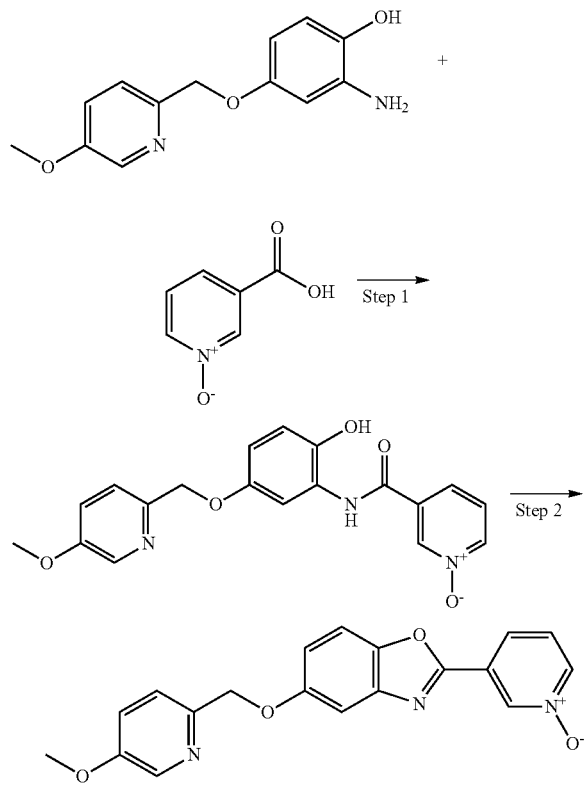

Step 1, Method 84: 3-({2-Hydroxy-5-[(5-methoxypyridin-2-yl)methoxy]phenyl}carbamoyl)pyridin-1-ium-1-olate 2-Ethoxy-1-ethoxycarbonyl-1,2-dihydroquinoline (0.090 g, 0.36 mmol) was added to a suspension of nicotinic acid N-oxide (0.051 g, 0.37 mmol) in dichloromethane (15 mL), and the mixture stirred at room temperature under nitrogen for 1 hour. 2-Amino-4-[(5-methoxypyridin-2-yl)methoxy]phenol (0.100 g, 0.406 mmol, prepared using Method 33) was added, and the mixture stirred overnight. The precipitate was collected by filtration and dried under reduced pressure. Purification by FCC (silica, 0-10% methanol in dichloromethane) gave the title compound 0.068 g (38% yield) as a light-brown solid: $\delta_H$ NMR (500 MHz, DMSO) 9.81 (br s, 1H), 9.23 (br s, 1H), 8.67 (s, 1H), 8.38 (d, J=6.0 Hz, 1H), 8.27 (d, J=2.5 Hz, 1H), 7.79 (d, J=7.5 Hz, 1H), 7.55 (dd, J=7.5, 6.5 Hz, 1H), 7.46 (d, J=8.5 Hz, 1H), 7.41 (dd, J=8.5, 3.0 Hz, 1H), 7.33 (d, J=3.0 Hz, 1H), 6.83 (d, J=8.5 Hz, 1H), 6.75 (dd, J=8.5, 3.0 Hz, 1H), 5.01 (s, 2H), 3.83 (s, 3H).

Step 2, Method 84: 3-{5-[(5-Methoxypyridin-2-yl)methoxy]-1,3-benzoxazol-2-yl}pyridin-1-ium-1-olate A mixture 3-({2-hydroxy-5-[(5-methoxypyridin-2-yl)methoxy]phenyl}carbamoyl)pyridin-1-ium-1-olate (0.100 g, 0.272 mmol) and para-toluenesulfonic acid monohydrate (0.518 g, 2.72 mmol) in glacial acetic acid (3 mL) was heated under microwave irradiation at 120° C. for 2.5 hours. The reaction was cooled to room temperature and added dropwise to ice cold saturated sodium bicarbonate solution. The pH of the resulting mixture was adjusted to 7 by adding saturated sodium bicarbonate solution, and the product extracted into ethyl acetate (3×50 mL). The combined organics were dried over sodium sulfate, filtered, and concentrated. Purification by FCC (silica, 0-10% methanol in dichloromethane) twice gave the title compound 0.055 g, (58% yield) as an off-white solid.

Example 1, Method 84: 3-{5-[(5-Methoxypyridin-2-yl)methoxy]-1,3-benzoxazol-2-yl}pyridin-1-ium-1-olate $\delta_H$ NMR (500 MHz, DMSO) 8.77-8.76 (m, 1H), 8.43-8.42 (m, 1H), 8.31 (d, J=3.0 Hz, 1H), 8.02-8.01 (m, 1H), 7.75 (d, J=9.0 Hz, 1H), 7.65-7.63 (m, 1H), 7.53-7.50 (m, 2H), 7.43 (dd, J=9.0, 3.0 Hz, 1H), 7.17 (dd, J=9.0, 2.5 Hz, 1H), 5.19 (s, 2H), 3.84 (s, 3H). Tr(METCR1416)=3.0 min, (ES$^+$) (M+H)$^+$ 350.

The following example was prepared using Method 84 described above:

TABLE 85

| Ex. | Structure | Mol. Weight | IUPAC Name | LCMS data |
|---|---|---|---|---|
| 1 | 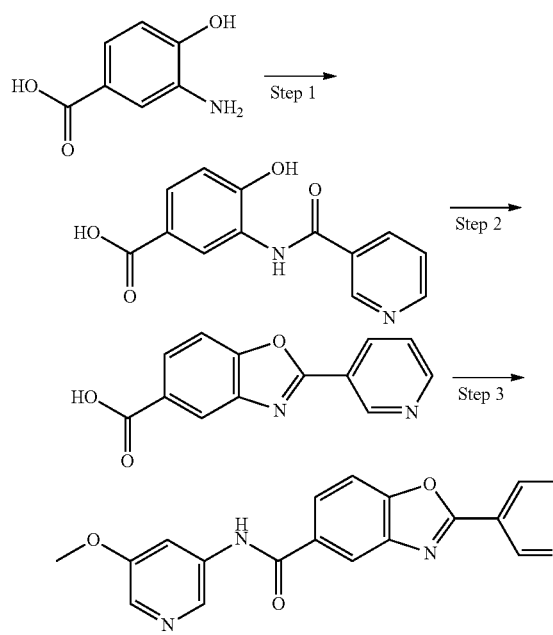 | 349.35 | 3-{5-[(5-Methoxypyridin-2-yl)methoxy]-1,3-benzoxazol-2-yl}pyridin-1-ium-1-olate | Tr(METCR1416) = 3.0 min, (ES⁺) (M + H)⁺ 350 |

Method 85
Scheme for Method 85

Step 1, Method 85:
4-Hydroxy-3-(pyridine-3-amido)benzoic acid

3-Amino-4-hydroxybenzoic acid (0.5 g, 3.27 mmol) was dissolved in pyridine (5 mL) and 2-chloronicotinoyl chloride hydrochloride (0.581 g, 3.27 mmol) added and the mixture stirred overnight. Pyridine was removed in vacuo and the resulting oil dissolved in ethyl acetate and washed with water twice. The organic layer was dried over magnesium sulfate, filtered and concentrated. Purification by FCC (silica, 30-70% ethyl acetate in dichloromethane) and FCC (silica, 1-5% methanol in dichloromethane) gave the tile compound 500 mg (59% yield) as an orange solid. $\delta_H$ NMR (500 MHz, DMSO) 12.55 (s, 1H), 10.63 (s, 1H), 9.84 (s, 1H), 9.13 (d, J=1.9 Hz, 1H), 8.83-8.73 (m, 1H), 8.33 (dt, J=7.9, 1.8 Hz, 1H), 8.26 (d, J=2.0 Hz, 1H), 7.69 (dd, J=8.5, 2.1 Hz, 1H), 7.62-7.51 (m, 1H), 7.00 (d, J=8.5 Hz, 1H). Tr(METCR1410)=1.15 min, (ES⁺) (M+H)⁺ 259, 75%.

Step 2, Method 85:
2-(Pyridin-3-yl)-1,3-benzoxazole-5-carboxylic acid

4-Hydroxy-3-(pyridine-3-amido)benzoic acid (150 mg, 0.517 mmol) was dissolved in acetic acid (3 mL) and heated in a microwave for 10 min at 200° C. The solvent was removed and preparative HPLC (acetonitrile/water+0.2% ammonium hydroxide) gave the title compound 55 mg (44% yield) as a white solid. $\delta_H$ NMR (500 MHz, DMSO) 9.38 (d, J=2.1 Hz, 1H), 8.82 (dd, J=4.8, 1.6 Hz, 1H), 8.57 (dt, J=8.0, 1.9 Hz, 1H), 8.29 (s, 1H), 8.06 (dd, J=8.5, 1.5 Hz, 1H), 7.80 (d, J=8.5 Hz, 1H), 7.67 (dd, J=8.0, 4.8 Hz, 1H). Tr(METCR1410)=0.96 min, (ES⁺) (M+H)⁺ 241.

Step 3, Method 85: N-(5-Methoxypyridin-3-yl)-2-(pyridin-3-yl)-1,3-benzoxazole-5-carboxamide 2-(Pyridin-3-yl)-1,3-benzoxazole-5-carboxylic acid (108 mg, 0.45 mmol) and 5-methoxypyridin-3-amine (56 mg, 0.45 mmol) were combined in pyridine (3 mL). 1-Ethyl-3-(3-dimethylaminopropyl)carbodiimide hydrochloride (70 mg, 0.45 mmol) was added and the solution stirred overnight. The reaction was diluted with water (10 mL) and then extracted with ethyl acetate (3×10 mL). The combined organics were washed with water (2×10 mL), dried over magnesium sulfate, filtered and concentrated. Purification by preparative HPLC (acetonitrile/water+0.1% formic acid) and preparative HPLC (acetonitrile/water+0.2% ammonium hydroxide) gave the title compound 12 mg (8% yield) as a white solid.

Example 1, Method 85: N-(5-Methoxypyridin-3-yl)-2-(pyridin-3-yl)-1,3-benzoxazole-5-carboxamide $\delta_H$ NMR (500 MHz, DMSO) 10.57 (s, 1H), 9.40 (d, J=1.4 Hz, 1H), 8.85 (dd, J=4.8, 1.5 Hz, 1H), 8.61 (d, J=1.9 Hz, 1H), 8.59 (dt, J=8.0, 1.8 Hz, 1H), 8.50 (d, J=1.2 Hz, 1H), 8.10 (dd, J=8.6, 1.7 Hz, 1H), 8.08 (d, J=2.6 Hz, 1H), 8.01 (d, J=8.6 Hz, 1H), 7.93 (t, J=2.3 Hz, 1H), 7.69 (dd, J=8.0, 4.8 Hz, 1H), 3.86 (s, 3H). Tr(METCR1600)=3.82 min, (ES⁺) (M+H)⁺ 347.

The following example was prepared using Method 85 described above:

TABLE 86

| Ex. | Structure | Mol. Weight | IUPAC Name | LCMS data |
|---|---|---|---|---|
| 1 | 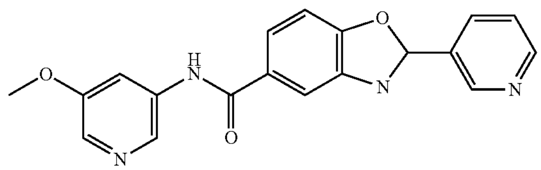 [SMILES: COc1cncc(NC(=O)c2ccc3c(c2)NC(c2cccnc2)O3)c1] | 346.35 | N-(5-Methoxypyridin-3-yl)-2-(pyridin-3-yl)-1,3-benzoxazole-5-carboxamide | Tr(METCR1600 High pH 7 min) = 3.82 min, (ES$^+$) (M + H)$^+$ 347 |

BIOLOGY EXAMPLES

Q46 Radioligand Binding Assay

For radioligand binding assays (RBA) GST-Q46 protein was generated based on a previous publication (Scherzinger et al. Cell, Vol. 90, 549-558, Aug. 8, 1997). For experiments 33 μM GST-Q46 was incubated with 150 μg/mL thrombin in assay buffer (150 mM NaCl, 50 mM Tris pH 8.0) and 2 mM CaCl$_2$ for 16 hours at 37° C. Aggregated Q46 was pelleted by centrifugation for 5 minutes at 13,000 rpm in a bench top centrifuge and re-dissolved in the same volume of assay buffer. Test compounds were prepared by titration in DMSO at 11 concentrations from 33 μM to 1 nM. For the RBA, Q46 protein aggregates and test compounds were pre-incubated in assay buffer for 20 minutes at room temperature, in 140 μL/well in a 96-well plate (pp, round bottom). Then, ligand was added in 10 μL/well and incubated for 60 minutes at 37° C. Final assay concentrations were 1 μM to 30 μM test compound, 5 μM Q46 protein (equivalent monomer concentration) and 10 nM ligand [$^3$H$_3$]MK-3328 (Harrision et al., ACS Med. Chem. Lett., 2 (2011), pp 498-502). Samples were transferred onto GF/B filter plates and washed 2× with 200 μL PBS using a Filtermate Harvester. After drying filter plates for 1 hour at 37° C., the back of the plates were sealed with foil and 30 μL/well scintillation fluid (Packard MicroScint 40) added, incubated for 15 minutes in the dark and counted in a TopCount reader. For analysis, replicate data from independent assay plates were normalized towards 0% and 100% inhibition using control wells of vehicle (0% inhibition) and 3 μM unlabelled MK-3328 (100% inhibition). IC$_{50}$ values were determined with a sigmoidal inhibition model with four variables (top, bottom, slope, IC$_{50}$) in a global fit using the normalized replicate data.

TABLE 87

| Structure | IUPAC Name | Activity |
|---|---|---|
| 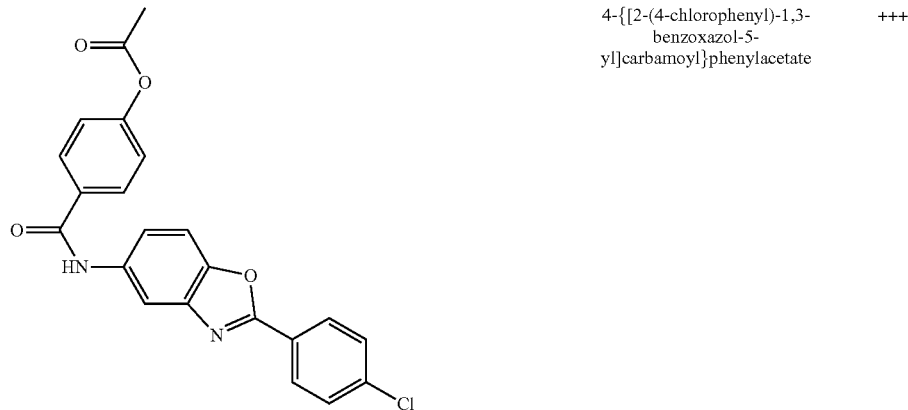 | 4-{[2-(4-chlorophenyl)-1,3-benzoxazol-5-yl]carbamoyl}phenylacetate | +++ |
| 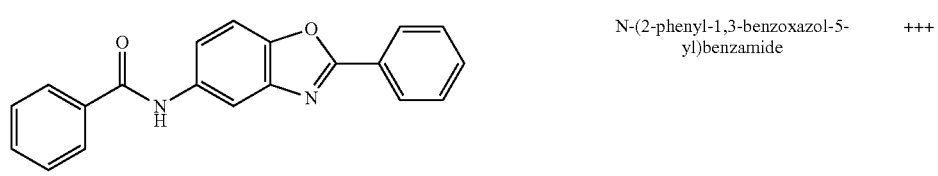 | N-(2-phenyl-1,3-benzoxazol-5-yl)benzamide | +++ |

TABLE 87-continued

| Structure | IUPAC Name | Activity |
|---|---|---|
| 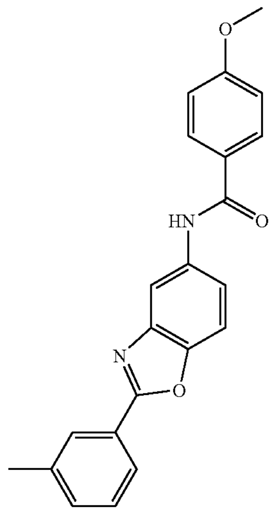 [SMILES: COc1ccc(C(=O)Nc2ccc3oc(-c4cccc(C)c4)nc3c2)cc1] | 4-methoxy-N-[2-(3-methylphenyl)-1,3-benzoxazol-5-yl]benzamide | +++ |
| 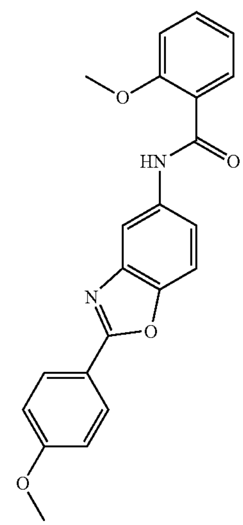 [SMILES: COc1ccc(-c2nc3cc(NC(=O)c4ccccc4OC)ccc3o2)cc1] | 2-methoxy-N-[2-(4-methoxyphenyl)-1,3-benzoxazol-5-yl]benzamide | +++ |
| 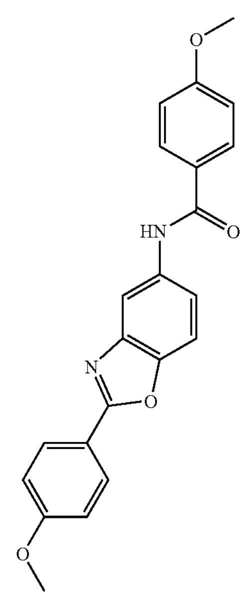 [SMILES: COc1ccc(C(=O)Nc2ccc3oc(-c4ccc(OC)cc4)nc3c2)cc1] | 4-methoxy-N-[2-(4-methoxyphenyl)-1,3-benzoxazol-5-yl]benzamide | +++ |

TABLE 87-continued

| Structure | IUPAC Name | Activity |
|---|---|---|
| 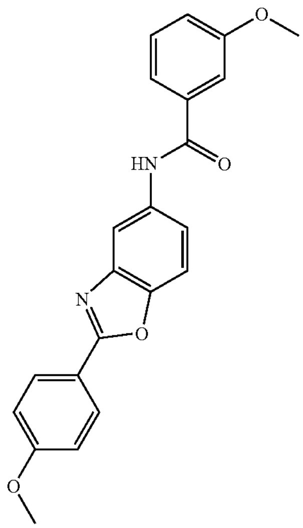 [SMILES: COc1ccc(-c2nc3cc(NC(=O)c4cccc(OC)c4)ccc3o2)cc1] | 3-methoxy-N-[2-(4-methoxyphenyl)-1,3-benzoxazol-5-yl]benzamide | +++ |
| 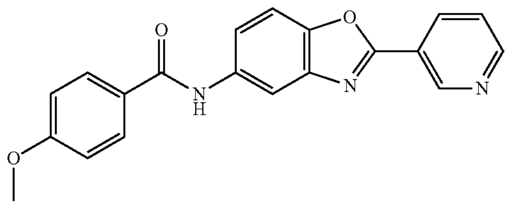 [SMILES: COc1ccc(C(=O)Nc2ccc3oc(-c4cccnc4)nc3c2)cc1] | 4-methoxy-N-[2-(pyridin-3-yl)-1,3-benzoxazol-5-yl]benzamide | +++ |
| 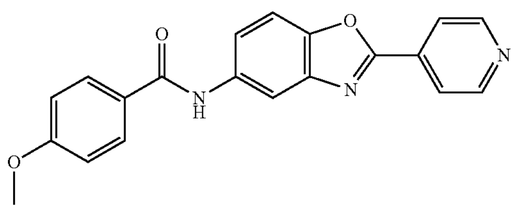 [SMILES: COc1ccc(C(=O)Nc2ccc3oc(-c4ccncc4)nc3c2)cc1] | 4-methoxy-N-[2-(pyridin-4-yl)-1,3-benzoxazol-5-yl]benzamide | +++ |
| 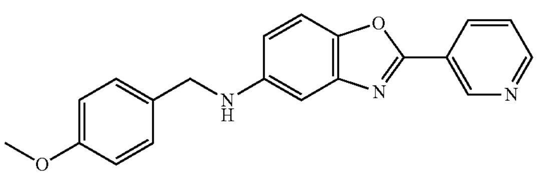 [SMILES: COc1ccc(CNc2ccc3oc(-c4cccnc4)nc3c2)cc1] | N-[(4-methoxyphenyl)methyl]-2-(pyridin-3-yl)-1,3-benzoxazol-5-amine | +++ |
| 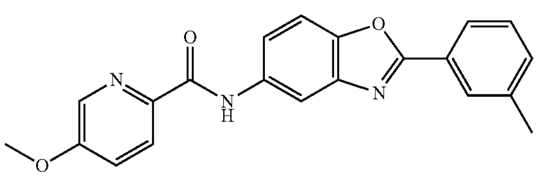 | 5-methoxy-N-[2-(3-methylphenyl)-1,3-benzoxazol-5-yl]pyridine-2-carboxamide | +++ |
| 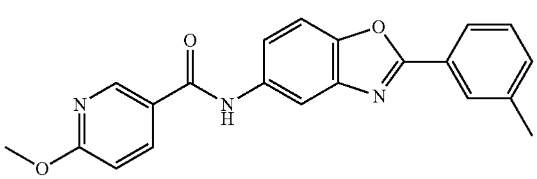 | 6-methoxy-N-[2-(3-methylphenyl)-1,3-benzoxazol-5-yl]pyridine-3-carboxamide | +++ |

TABLE 87-continued

| Structure | IUPAC Name | Activity |
|---|---|---|
| 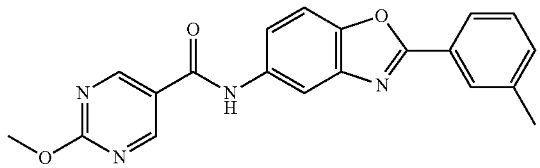 | 2-methoxy-N-[2-(3-methylphenyl)-1,3-benzoxazol-5-yl]pyrimidine-5-carboxamide | +++ |
| 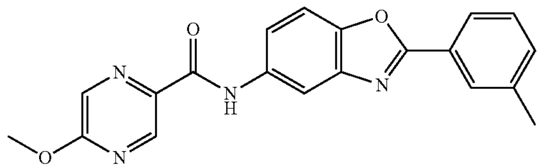 | 5-methoxy-N-[2-(3-methylphenyl)-1,3-benzoxazol-5-yl]pyrazine-2-carboxamide | +++ |
| 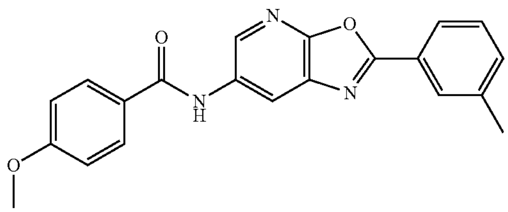 [SMILES: COc1ccc(C(=O)Nc2cnc3oc(-c4cccc(C)c4)nc3c2)cc1] | 4-methoxy-N-[2-(3-methylphenyl)-[1,3]oxazolo[5,4-b]pyridin-6-yl]benzamide | +++ |
| 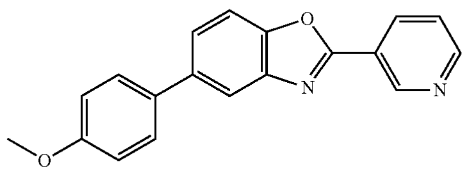 [SMILES: COc1ccc(-c2ccc3oc(-c4cccnc4)nc3c2)cc1] | 5-(4-methoxyphenyl)-2-(pyridin-3-yl)-1,3-benzoxazole | +++ |
| 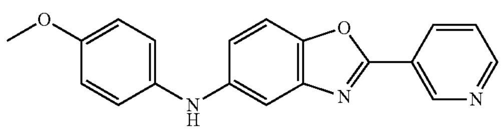 [SMILES: COc1ccc(Nc2ccc3oc(-c4cccnc4)nc3c2)cc1] | N-(4-methoxyphenyl)-2-(pyridin-3-yl)-1,3-benzoxazol-5-amine | ++ |
| 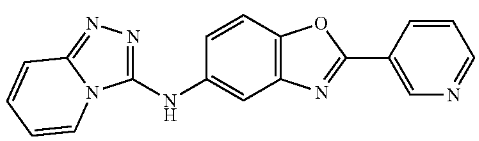 [SMILES: c1cncc(-c2nc3cc(Nc4nnc5ccccn45)ccc3o2)c1] | 2-(pyridin-3-yl)-N-{[1,2,4]triazolo[4,3-a]pyridin-3-yl}-1,3-benzoxazol-5-amine | +++ |
| 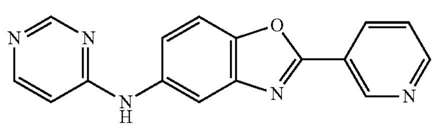 [SMILES: c1cncc(-c2nc3cc(Nc4ccncn4)ccc3o2)c1] | 2-(pyridin-3-yl)-N-(pyrimidin-4-yl)-1,3-benzoxazol-5-amine | +++ |
| 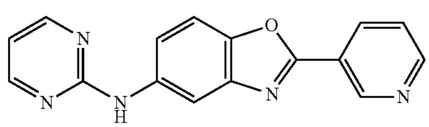 [SMILES: c1cnc(Nc2ccc3oc(-c4cccnc4)nc3c2)nc1] | 2-(pyridin-3-yl)-N-(pyrimidin-2-yl)-1,3-benzoxazol-5-amine | +++ |
| 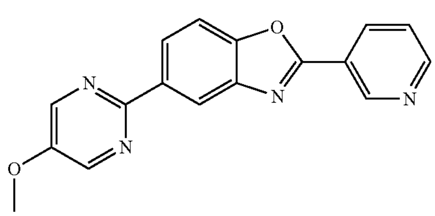 [SMILES: COc1cnc(-c2ccc3oc(-c4cccnc4)nc3c2)nc1] | 5-(5-methoxypyrimidin-2-yl)-2-(pyridin-3-yl)-1,3-benzoxazole | +++ |

TABLE 87-continued

| Structure | IUPAC Name | Activity |
|---|---|---|
| 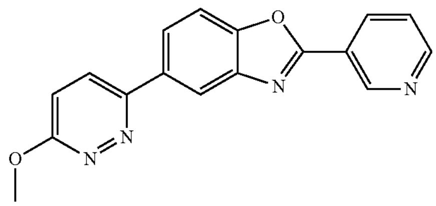 [SMILES: COc1ccc(-c2ccc3oc(-c4cccnc4)nc3c2)nn1] | 5-(6-methoxypyridazin-3-yl)-2-(pyridin-3-yl)-1,3-benzoxazole | +++ |
| 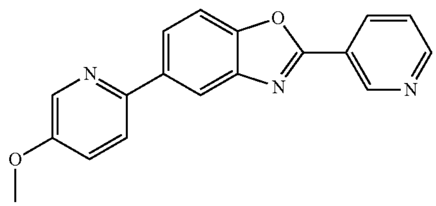 [SMILES: COc1ccc(-c2ccc3oc(-c4cccnc4)nc3c2)nc1] | 5-(5-methoxypyridin-2-yl)-2-(pyridin-3-yl)-1,3-benzoxazole | ++ |
| 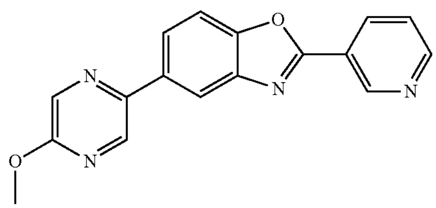 | 5-(5-methoxypyrazin-2-yl)-2-(pyridin-3-yl)-1,3-benzoxazole | +++ |
| 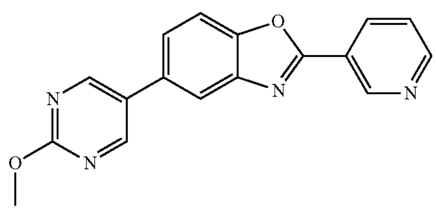 [SMILES: COc1ncc(-c2ccc3oc(-c4cccnc4)nc3c2)cn1] | 5-(2-methoxypyrimidin-5-yl)-2-(pyridin-3-yl)-1,3-benzoxazole | ++ |
| 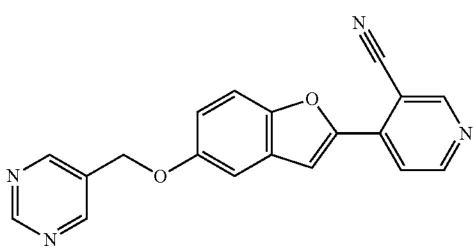 [SMILES: N#Cc1cnccc1-c1cc2cc(OCc3cncnc3)ccc2o1] | 4-[5-(pyrimidin-5-ylmethoxy)-1-benzofuran-2-yl]pyridine-3-carbonitrile | +++ |
| 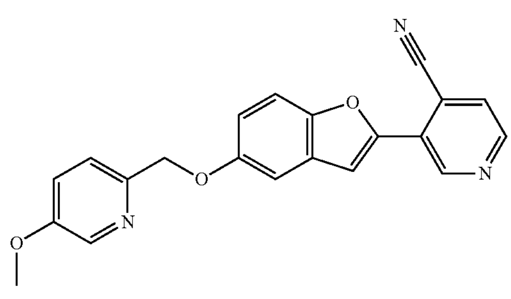 [SMILES: COc1ccc(COc2ccc3oc(-c4cnccc4C#N)cc3c2)nc1] | 4-{5-[(5-methoxypyridin-2-yl)methoxy]-1-benzofuran-2-yl}pyridine-3-carbonitrile | +++ |
| 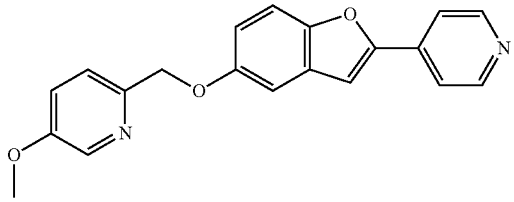 [SMILES: COc1ccc(COc2ccc3oc(-c4ccncc4)cc3c2)nc1] | 4-{5-[(5-methoxypyridin-2-yl)methoxy]-1-benzofuran-2-yl}pyridine | +++ |

TABLE 87-continued

| Structure | IUPAC Name | Activity |
|---|---|---|
| 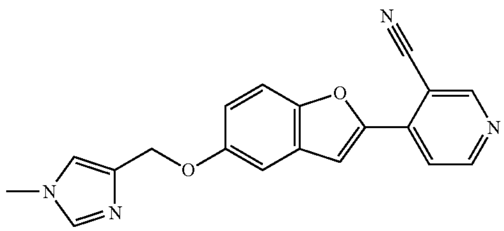 [SMILES: Cn1cnc(COc2ccc3oc(-c4ccncc4C#N)cc3c2)c1] | 4-{5-[(1-methyl-1H-imidazol-4-yl)methoxy]-1-benzofuran-2-yl}pyridine-3-carbonitrile | +++ |
| 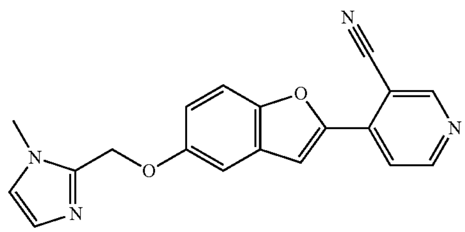 [SMILES: Cn1ccnc1COc1ccc2oc(-c3ccncc3C#N)cc2c1] | 4-{5-[(1-methyl-1H-imidazol-2-yl)methoxy]-1-benzofuran-2-yl}pyridine-3-carbonitrile | ++ |
| 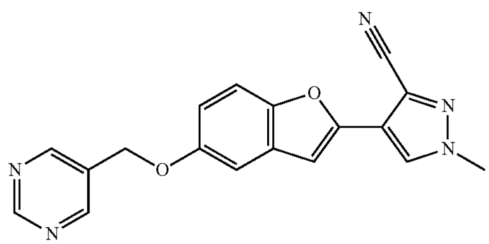 [SMILES: Cn1cc(-c2cc3cc(OCc4cncnc4)ccc3o2)c(C#N)n1] | 1-methyl-4-[5-(pyrimidin-5-ylmethoxy)-1-benzofuran-2-yl]-1H-pyrazole-3-carbonitrile | +++ |
| 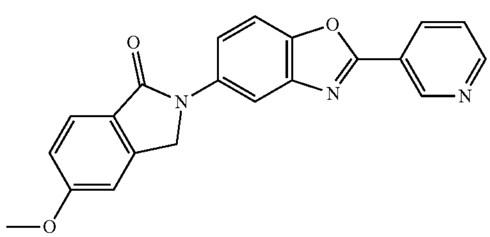 [SMILES: COc1ccc2c(c1)CN(c1ccc3oc(-c4cccnc4)nc3c1)C2=O] | 5-methoxy-2-[2-(pyridin-3-yl)-1,3-benzoxazol-5-yl]-2,3-dihydro-1H-isoindol-1-one | +++ |
| 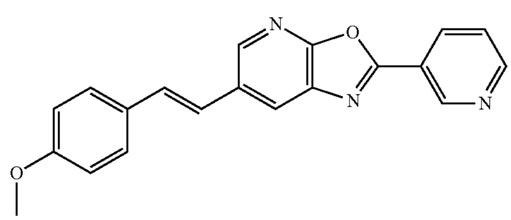 [SMILES: COc1ccc(/C=C/c2cnc3oc(-c4cccnc4)nc3c2)cc1] | 3-{6-[(E)-2-(4-methoxyphenyl)ethenyl]-[1,3]oxazolo[5,4-b]pyridin-2-yl}pyridine | +++ |
| 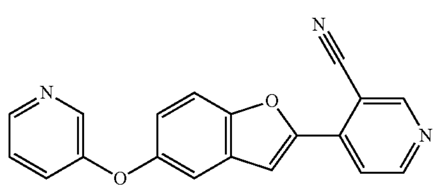 [SMILES: N#Cc1cnccc1-c1cc2cc(Oc3cccnc3)ccc2o1] | 4-[5-(pyridin-3-yloxy)-1-benzofuran-2-yl]pyridine-3-carbonitrile | +++ |
| 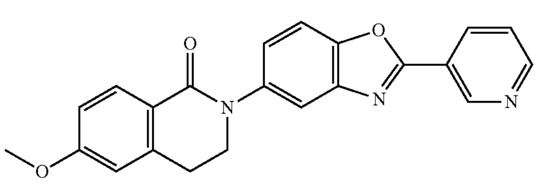 [SMILES: COc1ccc2c(c1)CCN(c1ccc3oc(-c4cccnc4)nc3c1)C2=O] | 6-methoxy-2-[2-(pyridin-3-yl)-1,3-benzoxazol-5-yl]-1,2,3,4-tetrahydroisoquinolin-1-one | ++ |

TABLE 87-continued

| Structure | IUPAC Name | Activity |
|---|---|---|
| 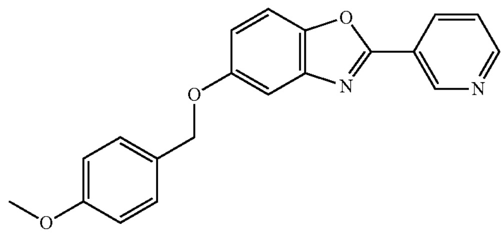 | 5-[(4-methoxyphenyl)methoxy]-2-(pyridin-3-yl)-1,3-benzoxazole | +++ |
| 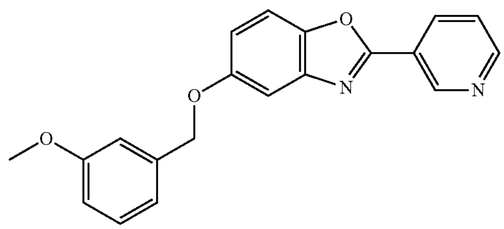 [SMILES: COc1cccc(COc2ccc3oc(-c4cccnc4)nc3c2)c1] | 5-[(3-methoxyphenyl)methoxy]-2-(pyridin-3-yl)-1,3-benzoxazole | +++ |
| 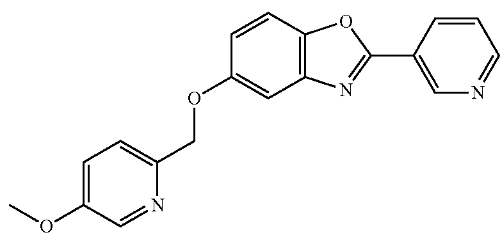 [SMILES: COc1ccc(COc2ccc3oc(-c4cccnc4)nc3c2)nc1] | 5-[(5-methoxypyridin-2-yl)methoxy]-2-(pyridin-3-yl)-1,3-benzoxazole | +++ |
| 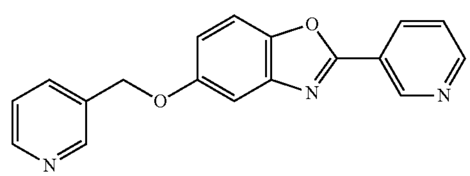 [SMILES: c1cncc(COc2ccc3oc(-c4cccnc4)nc3c2)c1] | 2-(pyridin-3-yl)-5-(pyridin-3-ylmethoxy)-1,3-benzoxazole | +++ |
| 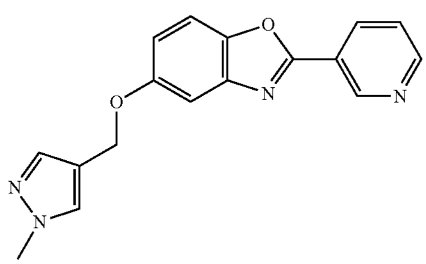 [SMILES: Cn1cc(COc2ccc3oc(-c4cccnc4)nc3c2)cn1] | 5-[(1-methyl-1H-pyrazol-4-yl)methoxy]-2-(pyridin-3-yl)-1,3-benzoxazole | ++ |
| 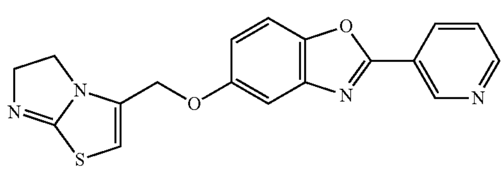 [SMILES: C1=C(COc2ccc3oc(-c4cccnc4)nc3c2)N2CCN=C2S1] | 5-{5H,6H-imidazo[2,1-b][1,3]thiazol-3-ylmethoxy}-2-(pyridin-3-yl)-1,3-benzoxazole | ++ |
| 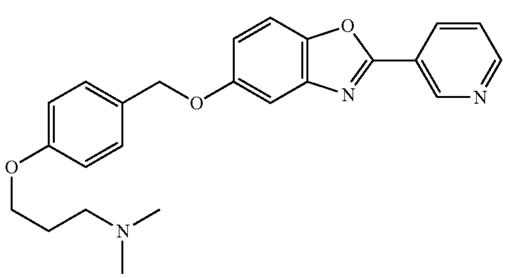 [SMILES: CN(C)CCCOc1ccc(COc2ccc3oc(-c4cccnc4)nc3c2)cc1] | dimethyl({3-[4-({[2-(pyridin-3-yl)-1,3-benzoxazol-5-yl]oxy}methyl)phenoxy]propyl})amine | +++ |

TABLE 87-continued

| Structure | IUPAC Name | Activity |
|---|---|---|
| 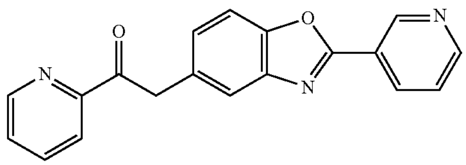 [SMILES: O=C(Cc1ccc2oc(-c3cccnc3)nc2c1)c1ccccn1] | 1-(pyridin-2-yl)-2-[2-(pyridin-3-yl)-1,3-benzoxazol-5-yl]ethan-1-one | ++ |
| 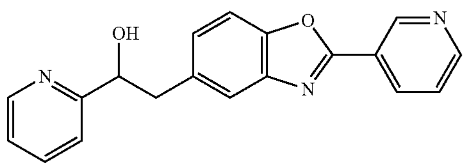 [SMILES: OC(Cc1ccc2oc(-c3cccnc3)nc2c1)c1ccccn1] | 1-(pyridin-2-yl)-2-[2-(pyridin-3-yl)-1,3-benzoxazol-5-yl]ethan-1-ol | ++ |
| 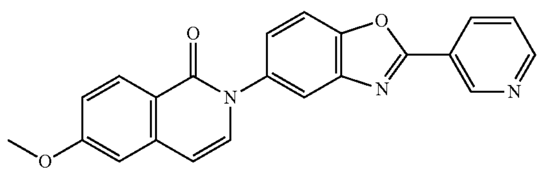 | 6-methoxy-2-[2-(pyridin-3-yl)-1,3-benzoxazol-5-yl]-1,2-dihydroisoquinolin-1-one | ++ |
| 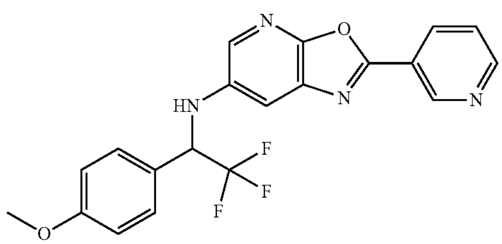 [SMILES: COc1ccc(C(Nc2cnc3oc(-c4cccnc4)nc3c2)C(F)(F)F)cc1] | 2-(pyridin-3-yl)-N-[2,2,2-trifluoro-1-(4-methoxyphenyl)ethyl]-[1,3]oxazolo[5,4-b]pyridin-6-amine | + |
| 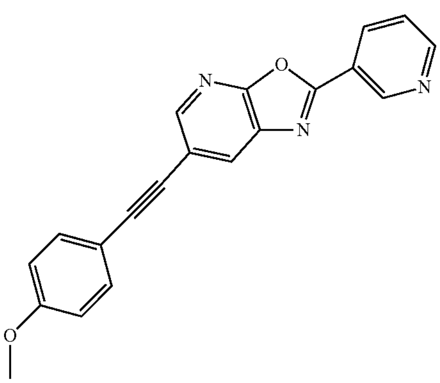 [SMILES: COc1ccc(C#Cc2cnc3oc(-c4cccnc4)nc3c2)cc1] | 3-{6-[2-(4-methoxyphenyl)ethynyl]-[1,3]oxazolo[5,4-b]pyridin-2-yl}pyridine | +++ |
| 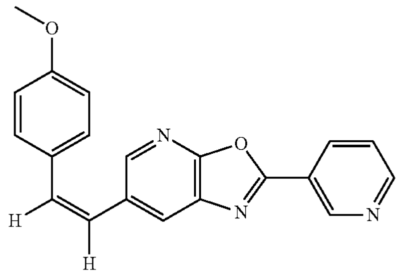 [SMILES: COc1ccc(/C=C\c2cnc3oc(-c4cccnc4)nc3c2)cc1] | 3-{6-[(Z)-2-(4-methoxyphenyl)ethenyl]-[1,3]oxazolo[5,4-b]pyridin-2-yl}pyridine | +++ |

TABLE 87-continued

| Structure | IUPAC Name | Activity |
|---|---|---|
| 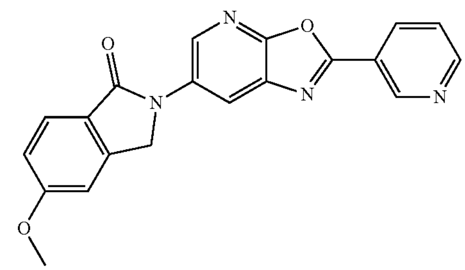 [SMILES: COc1ccc2c(c1)CN(c1cnc3oc(-c4cccnc4)nc3c1)C2=O] | 5-methoxy-2-[2-(pyridin-3-yl)-[1,3]oxazolo[5,4-b]pyridin-6-yl]-2,3-dihydro-1H-isoindol-1-one | +++ |
| 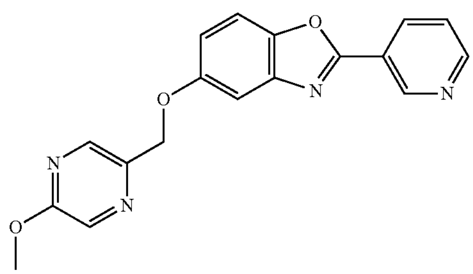 [SMILES: COc1cnc(COc2ccc3oc(-c4cccnc4)nc3c2)cn1] | 5-[(5-methoxypyrazin-2-yl)methoxy]-2-(pyridin-3-yl)-1,3-benzoxazole | +++ |
| 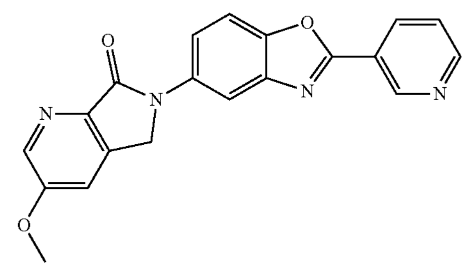 [SMILES: COc1cnc2c(c1)CN(c1ccc3oc(-c4cccnc4)nc3c1)C2=O] | 3-methoxy-6-[2-(pyridin-3-yl)-1,3-benzoxazol-5-yl]-5H,6H,7H-pyrrolo[3,4-b]pyridin-7-one | +++ |
| 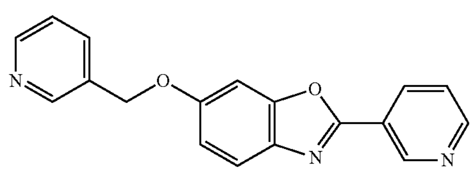 [SMILES: c1cncc(COc2ccc3nc(-c4cccnc4)oc3c2)c1] | 2-(pyridin-3-yl)-6-(pyridin-3-ylmethoxy)-1,3-benzoxazole | +++ |
| 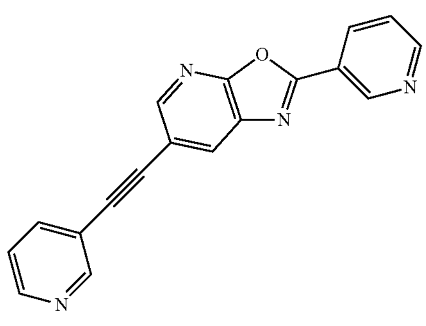 [SMILES: C(#Cc1cnc2oc(-c3cccnc3)nc2c1)c1cccnc1] | 3-{6-[2-(pyridin-3-yl)ethynyl]-[1,3]oxazolo[5,4-b]pyridin-2-yl}pyridine | +++ |
| 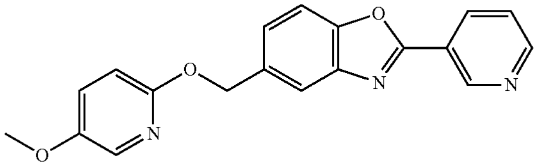 [SMILES: COc1ccc(OCc2ccc3oc(-c4cccnc4)nc3c2)nc1] | 5-{[(5-methoxypyridin-2-yl)oxy]methyl}-2-(pyridin-3-yl)-1,3-benzoxazole | +++ |

TABLE 87-continued

| Structure | IUPAC Name | Activity |
|---|---|---|
| 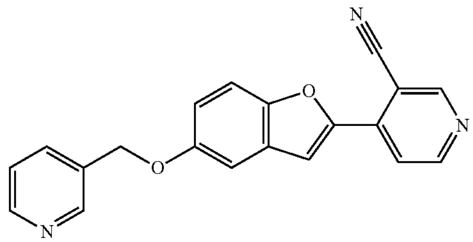 [SMILES: N#Cc1cnccc1-c1cc2cc(OCc3cccnc3)ccc2o1] | 4-[5-(pyridin-3-ylmethoxy)-1-benzofuran-2-yl]pyridine-3-carbonitrile | +++ |
| 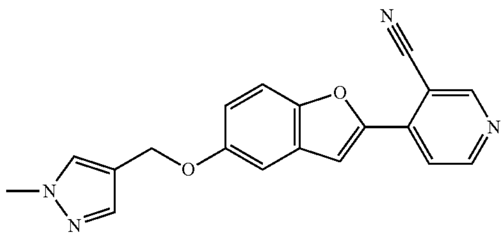 [SMILES: Cn1cc(COc2ccc3oc(-c4ccncc4C#N)cc3c2)cn1] | 4-{5-[(1-methyl-1H-pyrazol-4-yl)methoxy]-1-benzofuran-2-yl}pyridine-3-carbonitrile | +++ |
| 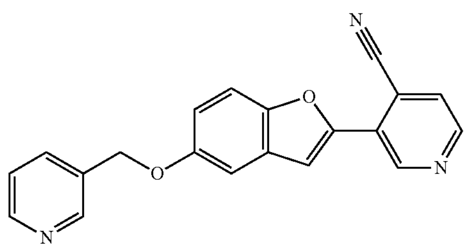 [SMILES: N#Cc1ccncc1-c1cc2cc(OCc3cccnc3)ccc2o1] | 3-[5-(pyridin-3-ylmethoxy)-1-benzofuran-2-yl]pyridine-4-carbonitrile | +++ |
| 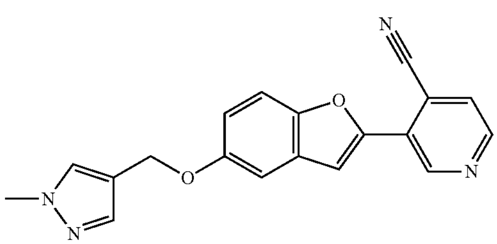 [SMILES: Cn1cc(COc2ccc3oc(-c4cnccc4C#N)cc3c2)cn1] | 3-{5-[(1-methyl-1H-pyrazol-4-yl)methoxy]-1-benzofuran-2-yl}pyridine-4-carbonitrile | +++ |
| 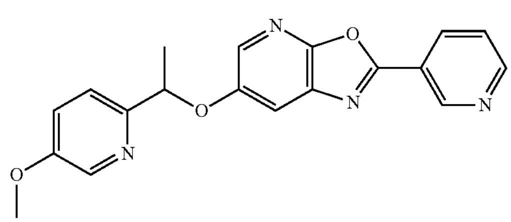 [SMILES: COc1ccc(C(C)Oc2cnc3oc(-c4cccnc4)nc3c2)nc1] | 3-{6-[1-(5-methoxypyridin-2-yl)ethoxy]-[1,3]oxazolo[5,4-b]pyridin-2-yl}pyridine | ++ |
| 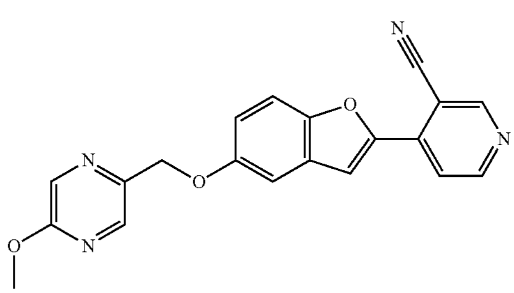 [SMILES: COc1cnc(COc2ccc3oc(-c4ccncc4C#N)cc3c2)cn1] | 4-{5-[(5-methoxypyrazin-2-yl)methoxy]-1-benzofuran-2-yl}pyridine-3-carbonitrile | +++ |

TABLE 87-continued

| Structure | IUPAC Name | Activity |
|---|---|---|
| 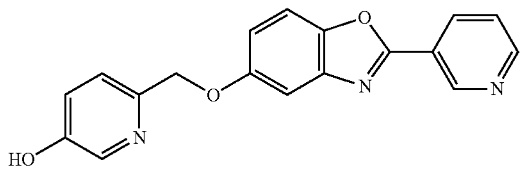 [SMILES: Oc1ccc(COc2ccc3oc(-c4cccnc4)nc3c2)nc1] | 6-({[2-(pyridin-3-yl)-1,3-benzoxazol-5-yl]oxy}methyl)pyridin-3-ol | +++ |
| 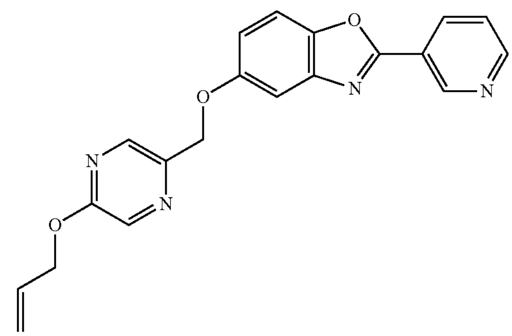 [SMILES: C=CCOc1cnc(COc2ccc3oc(-c4cccnc4)nc3c2)cn1] | 5-{[5-(prop-2-en-1-yloxy)pyrazin-2-yl]methoxy}-2-(pyridin-3-yl)-1,3-benzoxazole | +++ |
| 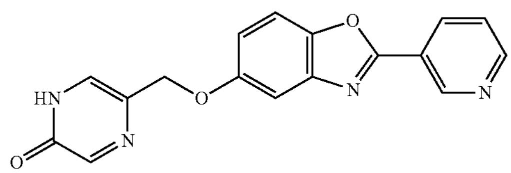 [SMILES: O=c1cnc(COc2ccc3oc(-c4cccnc4)nc3c2)c[nH]1] | 5-({[2-(pyridin-3-yl)-1,3-benzoxazol-5-yl]oxy}methyl)-1,2-dihydropyrazin-2-one | ++ |
| 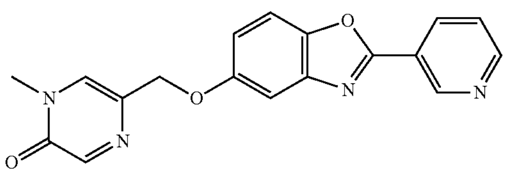 [SMILES: Cn1cc(COc2ccc3oc(-c4cccnc4)nc3c2)ncc1=O] | 1-methyl-5-({[2-(pyridin-3-yl)-1,3-benzoxazol-5-yl]oxy}methyl)-1,2-dihydropyrazin-2-one | ++ |
| 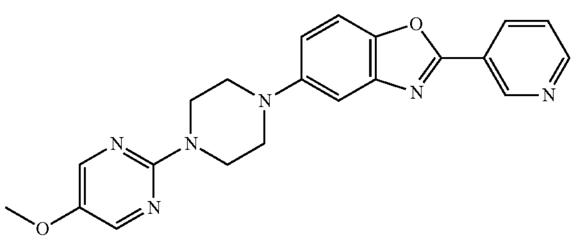 [SMILES: COc1cnc(N2CCN(c3ccc4oc(-c5cccnc5)nc4c3)CC2)nc1] | 5-[4-(5-methoxypyrimidin-2-yl)piperazin-1-yl]-2-(pyridin-3-yl)-1,3-benzoxazole | +++ |
| 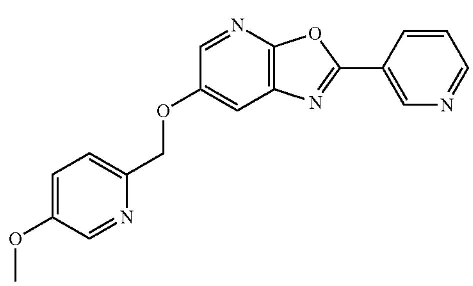 [SMILES: COc1ccc(COc2cnc3oc(-c4cccnc4)nc3c2)nc1] | 3-{6-[(5-methoxypyridin-2-yl)methoxy]-[1,3]oxazolo[5,4-b]pyridin-2-yl}pyridine | +++ |
| 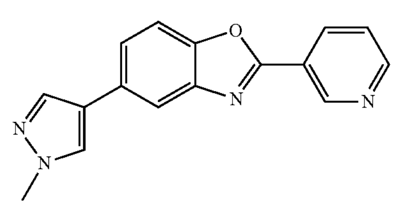 [SMILES: Cn1cc(-c2ccc3oc(-c4cccnc4)nc3c2)cn1] | 5-(1-methyl-1H-pyrazol-4-yl)-2-(pyridin-3-yl)-1,3-benzoxazole | ++ |

TABLE 87-continued

| Structure | IUPAC Name | Activity |
|---|---|---|
| 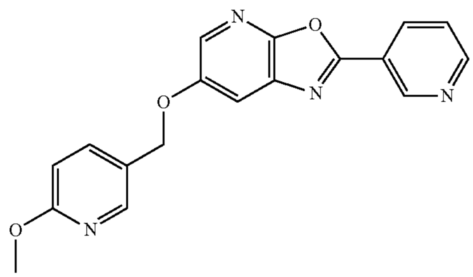 [SMILES: COc1ccc(COc2cnc3oc(-c4cccnc4)nc3c2)cn1] | 3-{6-[(6-methoxypyridin-3-yl)methoxy]-[1,3]oxazolo[5,4-b]pyridin-2-yl}pyridine | +++ |
| 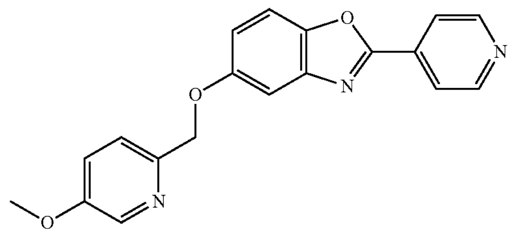 [SMILES: COc1ccc(COc2ccc3oc(-c4ccncc4)nc3c2)nc1] | 5-[(5-methoxypyridin-2-yl)methoxy]-2-(pyridin-4-yl)-1,3-benzoxazole | +++ |
| 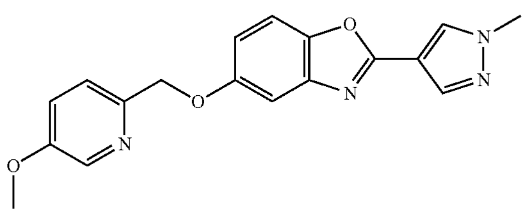 [SMILES: COc1ccc(COc2ccc3oc(-c4cnn(C)c4)nc3c2)nc1] | 5-[(5-methoxypyridin-2-yl)methoxy]-2-(1-methyl-1H-pyrazol-4-yl)-1,3-benzoxazole | +++ |
| 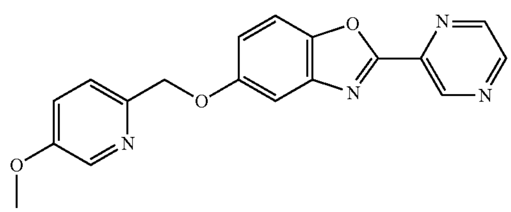 [SMILES: COc1ccc(COc2ccc3oc(-c4cnccn4)nc3c2)nc1] | 5-[(5-methoxypyridin-2-yl)methoxy]-2-(pyrazin-2-yl)-1,3-benzoxazole | +++ |
| 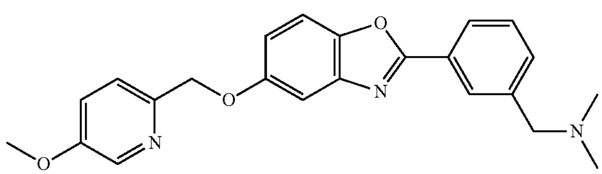 | [(3-{5-[(5-methoxypyridin-2-yl)methoxy]-1,3-benzoxazol-2-yl}phenyl)methyl]dimethylamine | +++ |
| 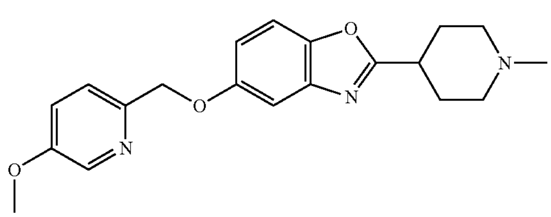 [SMILES: COc1ccc(COc2ccc3oc(C4CCN(C)CC4)nc3c2)nc1] | 5-[(5-methoxypyridin-2-yl)methoxy]-2-(1-methylpiperidin-4-yl)-1,3-benzoxazole | ++ |
| 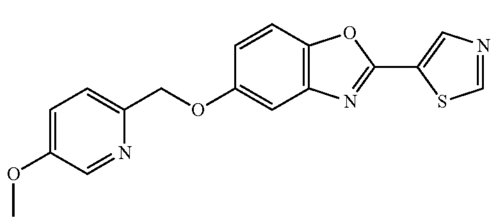 [SMILES: COc1ccc(COc2ccc3oc(-c4cncs4)nc3c2)nc1] | 5-[(5-methoxypyridin-2-yl)methoxy]-2-(1,3-thiazol-5-yl)-1,3-benzoxazole | +++ |

TABLE 87-continued

| Structure | IUPAC Name | Activity |
|---|---|---|
| 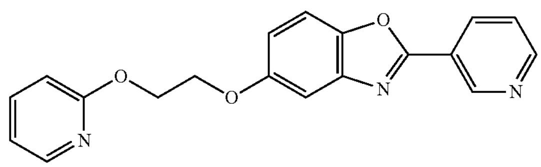 [SMILES: c1ccc(OCCOc2ccc3oc(-c4cccnc4)nc3c2)nc1] | 5-[2-(pyridin-2-yloxy)ethoxy]-2-(pyridin-3-yl)-1,3-benzoxazole | ++ |
| 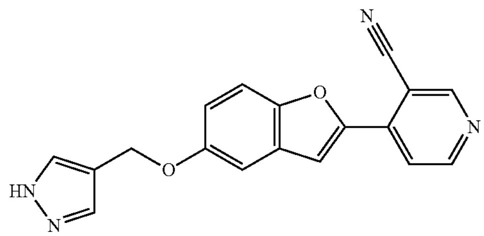 [SMILES: N#Cc1cnccc1-c1cc2cc(OCc3cn[nH]c3)ccc2o1] | 4-[5-(1H-pyrazol-4-ylmethoxy)-1-benzofuran-2-yl]pyridine-3-carbonitrile | +++ |
| 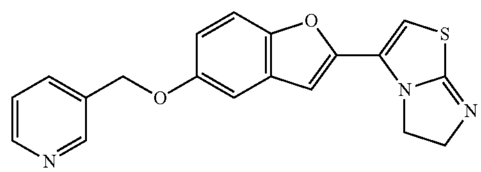 [SMILES: C1=C(c2cc3cc(OCc4cccnc4)ccc3o2)N2CCN=C2S1] | 3-{[(2-{5H,6H-imidazo[2,1-b][1,3]thiazol-3-yl}-1-benzofuran-5-yl)oxy]methyl}pyridine | +++ |
| 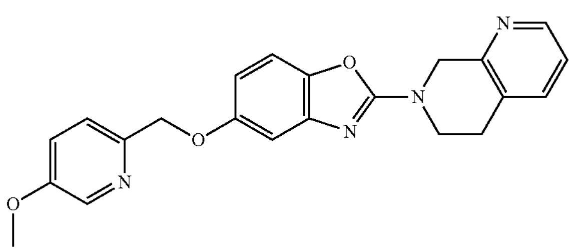 [SMILES: COc1ccc(COc2ccc3oc(N4CCc5cccnc5C4)nc3c2)nc1] | 7-{5-[(5-methoxypyridin-2-yl)methoxy]-1,3-benzoxazol-2-yl}-5,6,7,8-tetrahydro-1,7-naphthyridine | +++ |
| 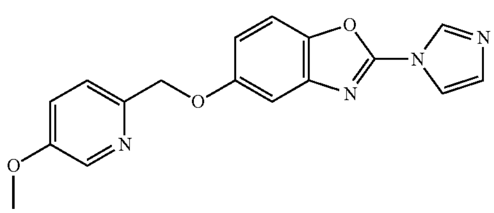 [SMILES: COc1ccc(COc2ccc3oc(-n4ccnc4)nc3c2)nc1] | 2-(1H-imidazol-1-yl)-5-[(5-methoxypyridin-2-yl)methoxy]-1,3-benzoxazole | +++ |
| 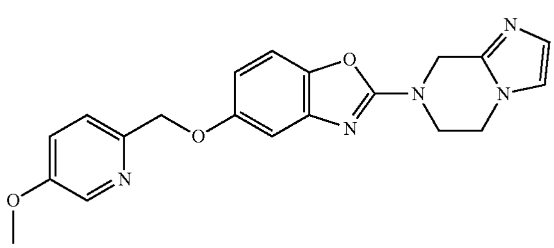 [SMILES: COc1ccc(COc2ccc3oc(N4CCn5ccnc5C4)nc3c2)nc1] | 2-{5H,6H,7H,8H-imidazo[1,2-a]pyrazin-7-yl}-5-[(5-methoxypyridin-2-yl)methoxy]-1,3-benzoxazole | +++ |
| 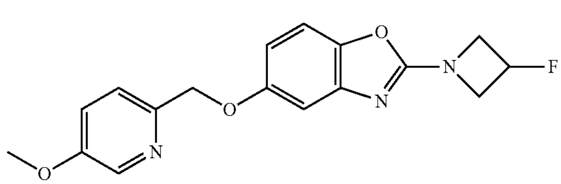 [SMILES: COc1ccc(COc2ccc3oc(N4CC(F)C4)nc3c2)nc1] | 2-(3-fluoroazetidin-1-yl)-5-[(5-methoxypyridin-2-yl)methoxy]-1,3-benzoxazole | ++ |

TABLE 87-continued

| Structure | IUPAC Name | Activity |
|---|---|---|
| 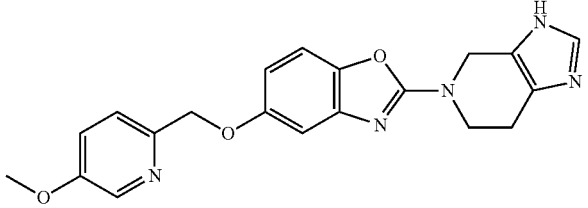 [SMILES: COc1ccc(COc2ccc3oc(N4CCc5nc[nH]c5C4)nc3c2)nc1] | 2-{3H,4H,5H,6H,7H-imidazo[4,5-c]pyridin-5-yl}-5-[(5-methoxypyridin-2-yl)methoxy]-1,3-benzoxazole | +++ |
| 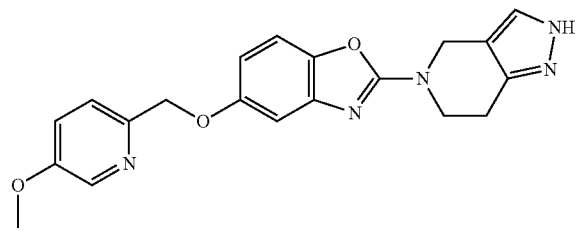 [SMILES: COc1ccc(COc2ccc3oc(N4CCc5n[nH]cc5C4)nc3c2)nc1] | 5-[(5-methoxypyridin-2-yl)methoxy]-2-{2H,4H,5H,6H,7H-pyrazolo[4,3-c]pyridin-5-yl}-1,3-benzoxazole | +++ |
| 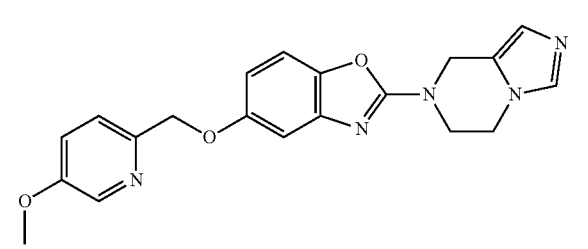 [SMILES: COc1ccc(COc2ccc3oc(N4CCn5cncc5C4)nc3c2)nc1] | 2-{5H,6H,7H,8H-imidazo[1,5-a]pyrazin-7-yl}-5-[(5-methoxypyridin-2-yl)methoxy]-1,3-benzoxazole | +++ |
| 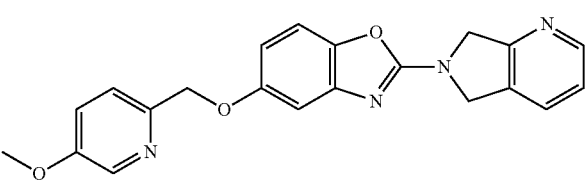 [SMILES: COc1ccc(COc2ccc3oc(N4Cc5cccnc5C4)nc3c2)nc1] | 5-[(5-methoxypyridin-2-yl)methoxy]-2-{5H,6H,7H-pyrrolo[3,4-b]pyridin-6-yl}-1,3-benzoxazole | +++ |
| 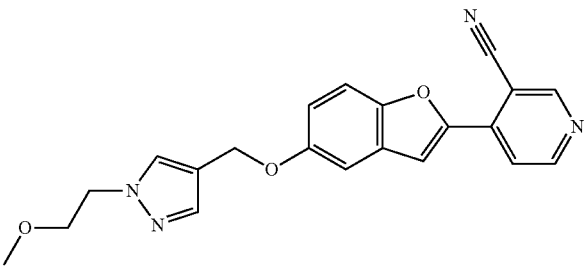 [SMILES: COCCn1cc(COc2ccc3oc(-c4ccncc4C#N)cc3c2)cn1] | 4-(5-{[1-(2-methoxyethyl)-1H-pyrazol-4-yl]methoxy}-1-benzofuran-2-yl)pyridine-3-carbonitrile | +++ |
| 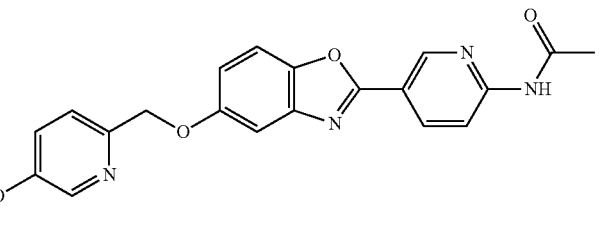 | N-(5-{5-[(5-methoxypyridin-2-yl)methoxy]-1,3-benzoxazol-2-yl}pyridin-2-yl)acetamide | +++ |
| 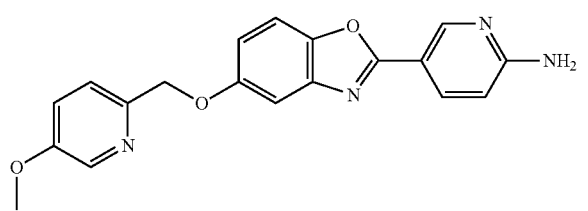 [SMILES: COc1ccc(COc2ccc3oc(-c4ccc(N)nc4)nc3c2)nc1] | 5-{5-[(5-methoxypyridin-2-yl)methoxy]-1,3-benzoxazol-2-yl}pyridin-2-amine | +++ |

TABLE 87-continued

| Structure | IUPAC Name | Activity |
|---|---|---|
| 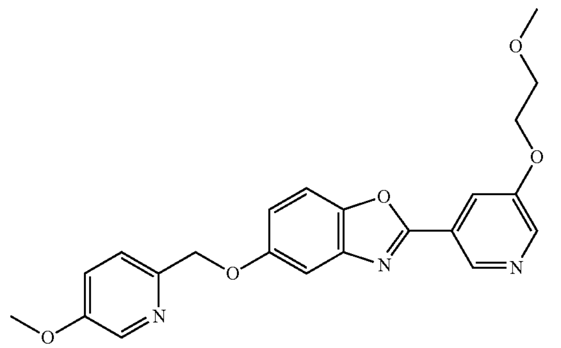 | 2-[5-(2-methoxyethoxy)pyridin-3-yl]-5-[(5-methoxypyridin-2-yl)methoxy]-1,3-benzoxazole | +++ |
| 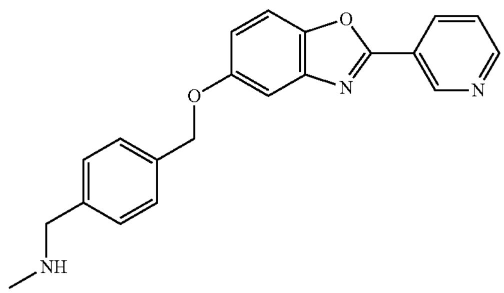 [SMILES: CNCc1ccc(COc2ccc3oc(-c4cccnc4)nc3c2)cc1] | methyl({[4-({[2-(pyridin-3-yl)-1,3-benzoxazol-5-yl]oxy}methyl)phenyl]methyl})amine | ++ |
| 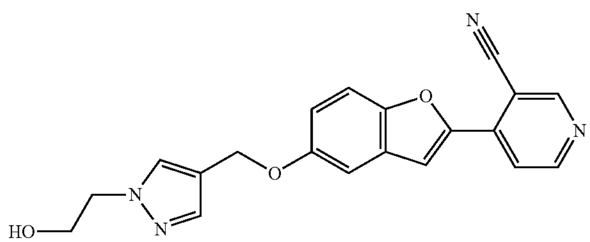 [SMILES: N#Cc1cnccc1-c1cc2cc(OCc3cnn(CCO)c3)ccc2o1] | 4-(5-{[1-(2-hydroxyethyl)-1H-pyrazol-4-yl]methoxy}-1-benzofuran-2-yl)pyridine-3-carbonitrile | +++ |
| 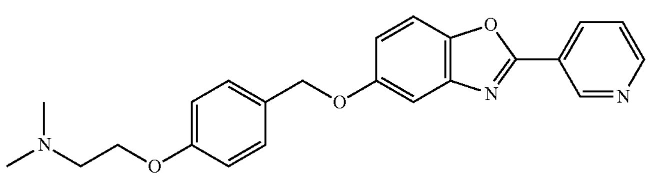 [SMILES: CN(C)CCOc1ccc(COc2ccc3oc(-c4cccnc4)nc3c2)cc1] | dimethyl({2-[4-({[2-(pyridin-3-yl)-1,3-benzoxazol-5-yl]oxy}methyl)phenoxy]ethyl})amine | ++ |
| 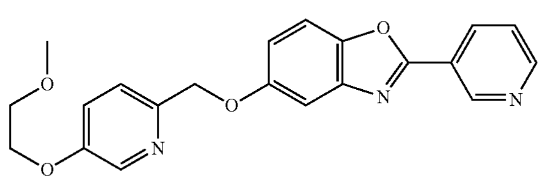 [SMILES: COCCOc1ccc(COc2ccc3oc(-c4cccnc4)nc3c2)nc1] | 5-{[5-(2-methoxyethoxy)pyridin-2-yl]methoxy}-2-(pyridin-3-yl)-1,3-benzoxazole | +++ |
| 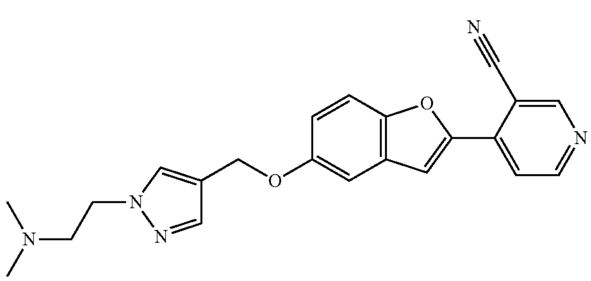 [SMILES: CN(C)CCn1cc(COc2ccc3oc(-c4ccncc4C#N)cc3c2)cn1] | 4-[5-({1-[2-(dimethylamino)ethyl]-1H-pyrazol-4-yl}methoxy)-1-benzofuran-2-yl]pyridine-3-carbonitrile | +++ |

TABLE 87-continued

| Structure | IUPAC Name | Activity |
|---|---|---|
| 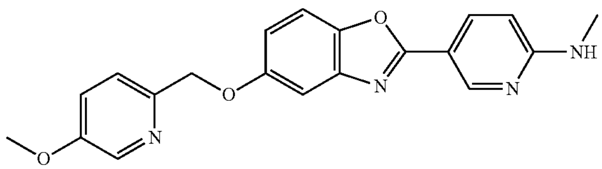 | 5-{5-[(5-methoxypyridin-2-yl)methoxy]-1,3-benzoxazol-2-yl}-N-methylpyridin-2-amine | +++ |
| 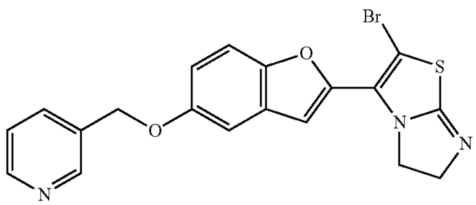 [SMILES: BrC1=C(c2cc3cc(OCc4cccnc4)ccc3o2)N2CCN=C2S1] | 3-{[(2-{2-bromo-5H,6H-imidazo[2,1-b][1,3]thiazol-3-yl}-1-benzofuran-5-yl)oxy]methyl}pyridine | +++ |
| 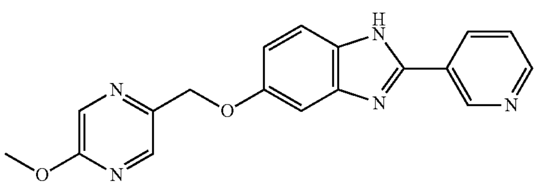 [SMILES: COc1cnc(COc2ccc3[nH]c(-c4cccnc4)nc3c2)cn1] | 5-[(5-methoxypyrazin-2-yl)methoxy]-2-(pyridin-3-yl)-1H-1,3-benzodiazole | +++ |
| 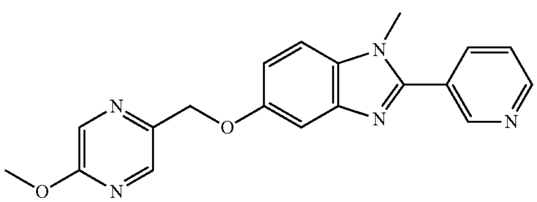 [SMILES: COc1cnc(COc2ccc3c(c2)nc(-c2cccnc2)n3C)cn1] | 5-[(5-methoxypyrazin-2-yl)methoxy]-1-methyl-2-(pyridin-3-yl)-1H-1,3-benzodiazole | ++ |
| 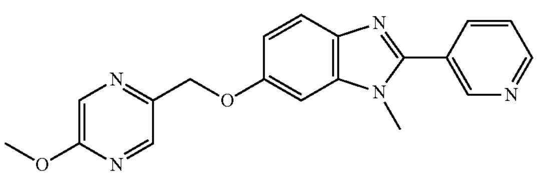 [SMILES: COc1cnc(COc2ccc3nc(-c4cccnc4)n(C)c3c2)cn1] | 6-[(5-methoxypyrazin-2-yl)methoxy]-1-methyl-2-(pyridin-3-yl)-1H-1,3-benzodiazole | ++ |
| 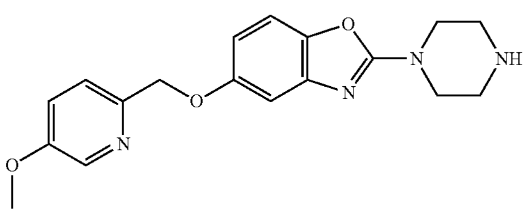 [SMILES: COc1ccc(COc2ccc3oc(N4CCNCC4)nc3c2)nc1] | 5-[(5-methoxypyridin-2-yl)methoxy]-2-(piperazin-1-yl)-1,3-benzoxazole | + |
| 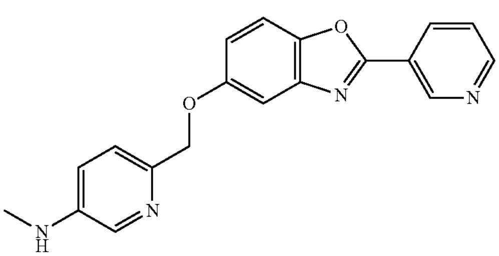 [SMILES: CNc1ccc(COc2ccc3oc(-c4cccnc4)nc3c2)nc1] | N-methyl-6-({[2-(pyridin-3-yl)-1,3-benzoxazol-5-yl]oxy}methyl)pyridin-3-amine | +++ |

TABLE 87-continued

| Structure | IUPAC Name | Activity |
|---|---|---|
| 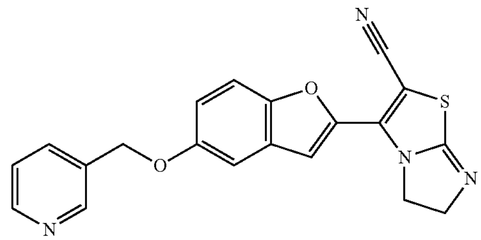 [SMILES: N#CC1=C(c2cc3cc(OCc4cccnc4)ccc3o2)N2CCN=C2S1] | 3-[5-(pyridin-3-ylmethoxy)-1-benzofuran-2-yl]-5H,6H-imidazo[2,1-b][1,3]thiazole-2-carbonitrile | +++ |
| 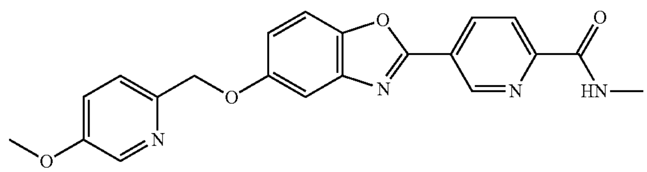 | 5-{5-[(5-methoxypyridin-2-yl)methoxy]-1,3-benzoxazol-2-yl}-N-methylpyridine-2-carboxamide | +++ |
| 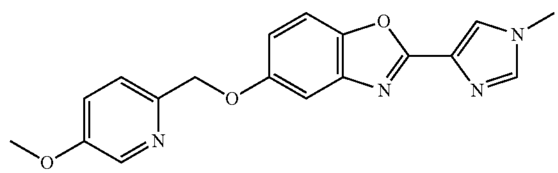 | 5-[(5-methoxypyridin-2-yl)methoxy]-2-(1-methyl-1H-imidazol-4-yl)-1,3-benzoxazole | ++ |
| 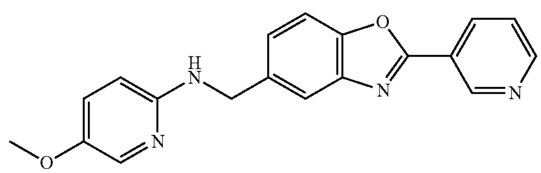 [SMILES: COc1ccc(NCc2ccc3oc(-c4cccnc4)nc3c2)nc1] | 5-methoxy-N-{[2-(pyridin-3-yl)-1,3-benzoxazol-5-yl]methyl}pyridin-2-amine | ++ |
| 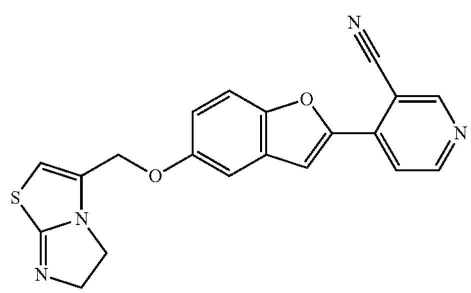 [SMILES: N#Cc1cnccc1-c1cc2cc(OCC3=CSC4=NCCN34)ccc2o1] | 4-(5-{5H,6H-imidazo[2,1-b][1,3]thiazol-3-ylmethoxy}-1-benzofuran-2-yl)pyridine-3-carbonitrile | +++ |
| 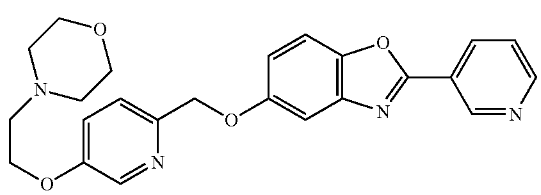 [SMILES: c1cncc(-c2nc3cc(OCc4ccc(OCCN5CCOCC5)cn4)ccc3o2)c1] | 5-({5-[2-(morpholin-4-yl)ethoxy]pyridin-2-yl}methoxy)-2-(pyridin-3-yl)-1,3-benzoxazole | +++ |
| 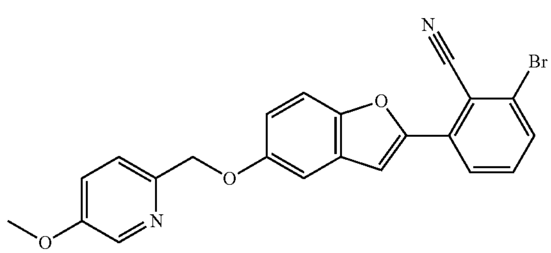 | 2-bromo-6-{5-[(5-methoxypyridin-2-yl)methoxy]-1-benzofuran-2-yl}benzonitrile | +++ |

TABLE 87-continued

| Structure | IUPAC Name | Activity |
|---|---|---|
| 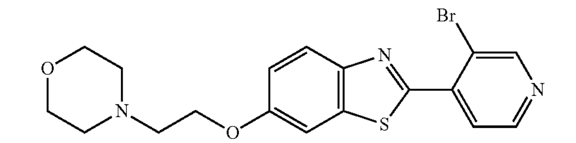 [SMILES: Brc1cnccc1-c1nc2ccc(OCCN3CCOCC3)cc2s1] | 2-(3-bromopyridin-4-yl)-6-[2-(morpholin-4-yl)ethoxy]-1,3-benzothiazole | +++ |
| 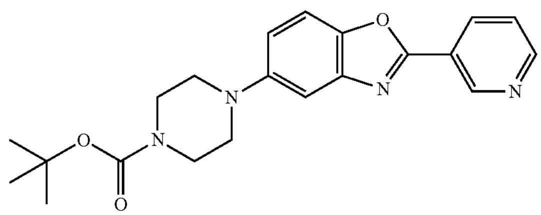 [SMILES: CC(C)(C)OC(=O)N1CCN(c2ccc3oc(-c4cccnc4)nc3c2)CC1] | tert-butyl 4-[2-(pyridin-3-yl)-1,3-benzoxazol-5-yl]piperazine-1-carboxylate | ++ |
| 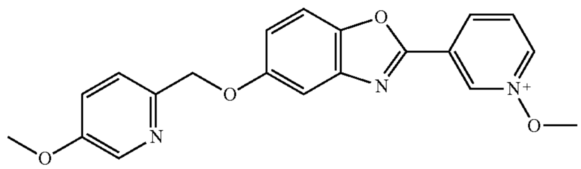 | 3-{5-[(5-methoxypyridin-2-yl)methoxy]-1,3-benzoxazol-2-yl}pyridin-1-ium-1-olate | +++ |
| 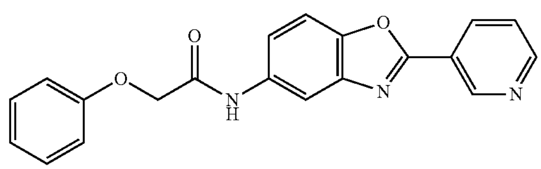 [SMILES: O=C(COc1ccccc1)Nc1ccc2oc(-c3cccnc3)nc2c1] | 2-phenoxy-N-[2-(pyridin-3-yl)-1,3-benzoxazol-5-yl]acetamide | +++ |
| 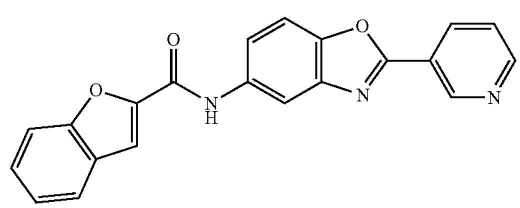 [SMILES: O=C(Nc1ccc2oc(-c3cccnc3)nc2c1)c1cc2ccccc2o1] | N-[2-(pyridin-3-yl)-1,3-benzoxazol-5-yl]-1-benzofuran-2-carboxamide | +++ |
| 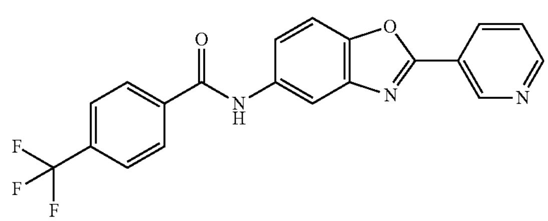 [SMILES: O=C(Nc1ccc2oc(-c3cccnc3)nc2c1)c1ccc(C(F)(F)F)cc1] | N-[2-(pyridin-3-yl)-1,3-benzoxazol-5-yl]-6-(trifluoromethyl)pyridine-3-carboxamide | +++ |
| 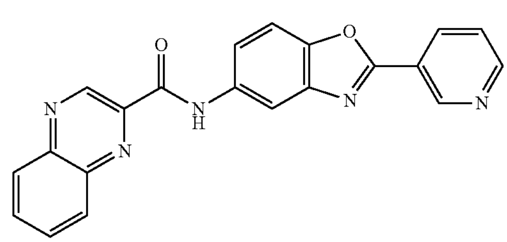 [SMILES: O=C(Nc1ccc2oc(-c3cccnc3)nc2c1)c1cnc2ccccc2n1] | N-[2-(pyridin-3-yl)-1,3-benzoxazol-5-yl]quinoxaline-2-carboxamide | +++ |
| 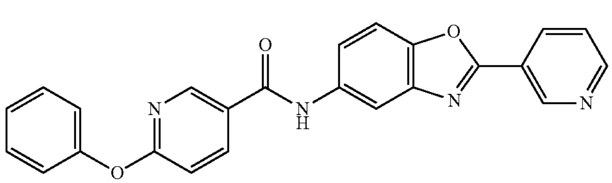 [SMILES: O=C(Nc1ccc2oc(-c3cccnc3)nc2c1)c1ccc(Oc2ccccc2)nc1] | 6-phenoxy-N-[2-(pyridin-3-yl)-1,3-benzoxazol-5-yl]pyridine-3-carboxamide | +++ |

TABLE 87-continued

| Structure | IUPAC Name | Activity |
|---|---|---|
| 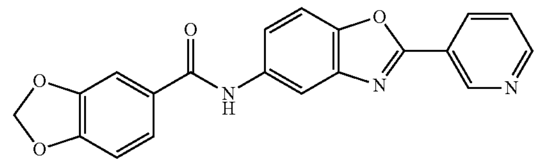 | N-[2-(pyridin-3-yl)-1,3-benzoxazol-5-yl]-2H-1,3-benzodioxole-5-carboxamide | +++ |
| 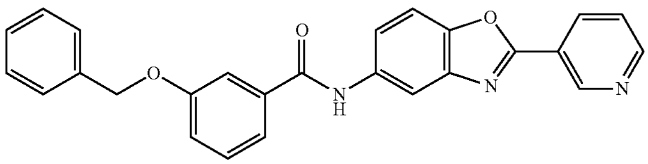 [SMILES: O=C(Nc1ccc2oc(-c3cccnc3)nc2c1)c1cccc(OCc2ccccc2)c1] | 3-(benzyloxy)-N-[2-(pyridin-3-yl)-1,3-benzoxazol-5-yl]benzamide | +++ |
| 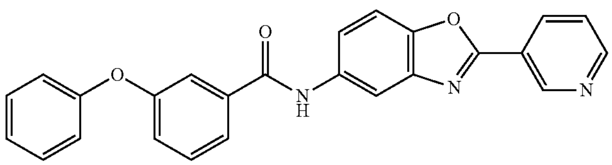 [SMILES: O=C(Nc1ccc2oc(-c3cccnc3)nc2c1)c1cccc(Oc2ccccc2)c1] | 3-phenoxy-N-[2-(pyridin-3-yl)-1,3-benzoxazol-5-yl]benzamide | +++ |
| 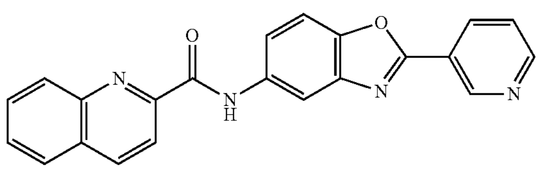 [SMILES: O=C(Nc1ccc2oc(-c3cccnc3)nc2c1)c1ccc2ccccc2n1] | N-[2-(pyridin-3-yl)-1,3-benzoxazol-5-yl]quinoline-2-carboxamide | +++ |
| 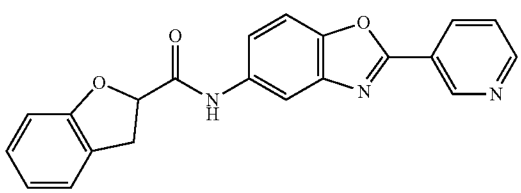 [SMILES: O=C(Nc1ccc2oc(-c3cccnc3)nc2c1)C1Cc2ccccc2O1] | N-[2-(pyridin-3-yl)-1,3-benzoxazol-5-yl]-2,3-dihydro-1-benzofuran-2-carboxamide | +++ |
| 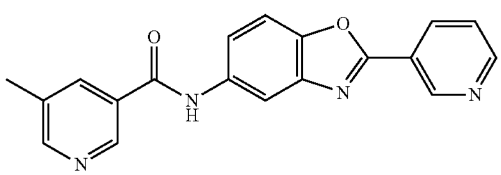 [SMILES: Cc1cncc(C(=O)Nc2ccc3oc(-c4cccnc4)nc3c2)c1] | 5-methyl-N-[2-(pyridin-3-yl)-1,3-benzoxazol-5-yl]pyridine-3-carboxamide | +++ |
| 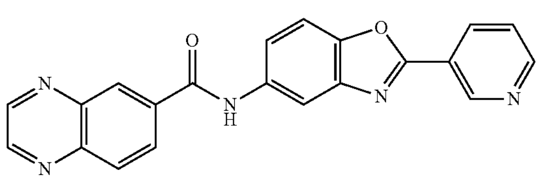 [SMILES: O=C(Nc1ccc2oc(-c3cccnc3)nc2c1)c1ccc2nccnc2c1] | N-[2-(pyridin-3-yl)-1,3-benzoxazol-5-yl]quinoxaline-6-carboxamide | +++ |
| 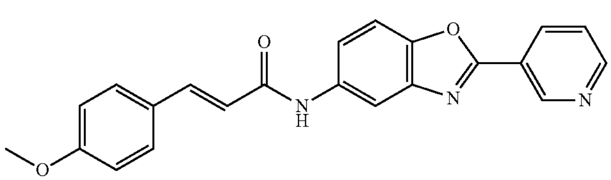 [SMILES: COc1ccc(/C=C/C(=O)Nc2ccc3oc(-c4cccnc4)nc3c2)cc1] | (2E)-3-(4-methoxyphenyl)-N-[2-(pyridin-3-yl)-1,3-benzoxazol-5-yl]prop-2-enamide | +++ |
| 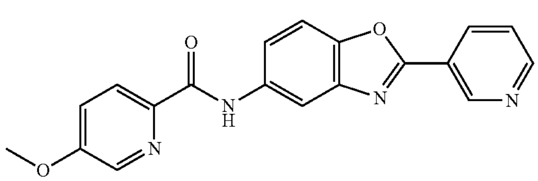 [SMILES: COc1ccc(C(=O)Nc2ccc3oc(-c4cccnc4)nc3c2)nc1] | 5-methoxy-N-[2-(pyridin-3-yl)-1,3-benzoxazol-5-yl]pyridine-2-carboxamide | +++ |

TABLE 87-continued

| Structure | IUPAC Name | Activity |
|---|---|---|
| 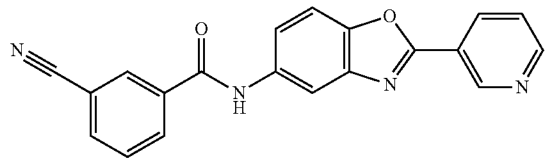 [SMILES: N#Cc1cccc(C(=O)Nc2ccc3oc(-c4cccnc4)nc3c2)c1] | 3-cyano-N-[2-(pyridin-3-yl)-1,3-benzoxazol-5-yl]benzamide | +++ |
| 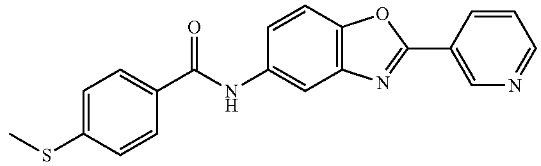 | 4-(methylsulfanyl)-N-[2-(pyridin-3-yl)-1,3-benzoxazol-5-yl]benzamide | +++ |
| 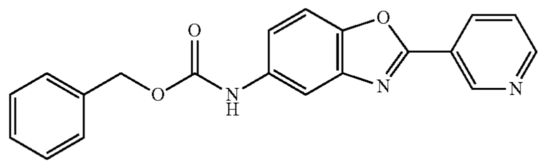 [SMILES: O=C(Nc1ccc2oc(-c3cccnc3)nc2c1)OCc1ccccc1] | benzyl N-[2-(pyridin-3-yl)-1,3-benzoxazol-5-yl]carbamate | +++ |
| 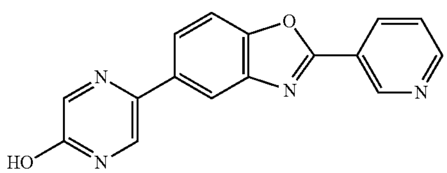 [SMILES: Oc1cnc(-c2ccc3oc(-c4cccnc4)nc3c2)cn1] | 5-[2-(pyridin-3-yl)-1,3-benzoxazol-5-yl]pyrazin-2-ol | ++ |
| 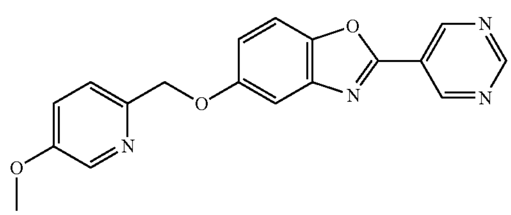 [SMILES: COc1ccc(COc2ccc3oc(-c4cncnc4)nc3c2)nc1] | 5-[(5-methoxypyridin-2-yl)methoxy]-2-(pyrimidin-5-yl)-1,3-benzoxazole | +++ |
| 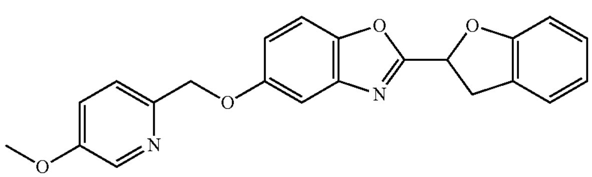 [SMILES: COc1ccc(COc2ccc3oc(C4Cc5ccccc5O4)nc3c2)nc1] | 2-(2,3-dihydro-1-benzofuran-2-yl)-5-[(5-methoxypyridin-2-yl)methoxy]-1,3-benzoxazole | +++ |
| 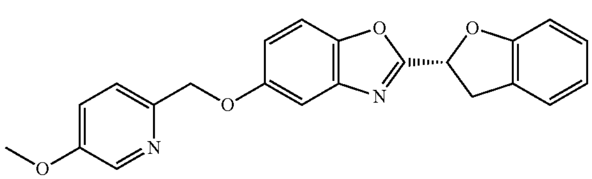 | 2-[(2R)-2,3-dihydro-1-benzofuran-2-yl]-5-[(5-methoxypyridin-2-yl)methoxy]-1,3-benzoxazole | +++ |
| 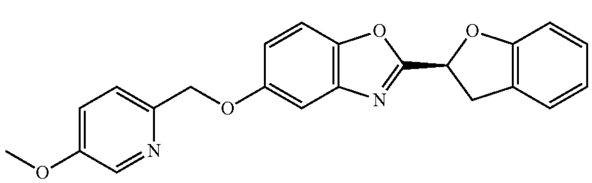 [SMILES: COc1ccc(COc2ccc3oc([C@@H]4Cc5ccccc5O4)nc3c2)nc1] | 2-[(2S)-2,3-dihydro-1-benzofuran-2-yl]-5-[(5-methoxypyridin-2-yl)methoxy]-1,3-benzoxazole | +++ |

TABLE 87-continued

| Structure | IUPAC Name | Activity |
|---|---|---|
| 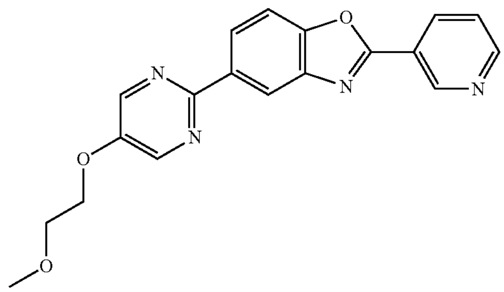 [SMILES: COCCOc1cnc(-c2ccc3oc(-c4cccnc4)nc3c2)nc1] | 5-[5-(2-methoxyethoxy)pyrimidin-2-yl]-2-(pyridin-3-yl)-1,3-benzoxazole | +++ |
| 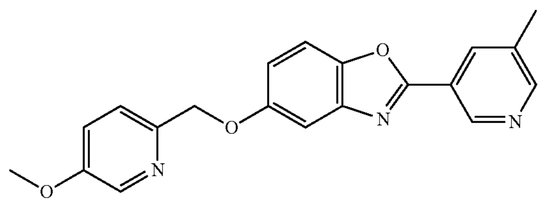 | 5-[(5-methoxypyridin-2-yl)methoxy]-2-(5-methylpyridin-3-yl)-1,3-benzoxazole | +++ |
| 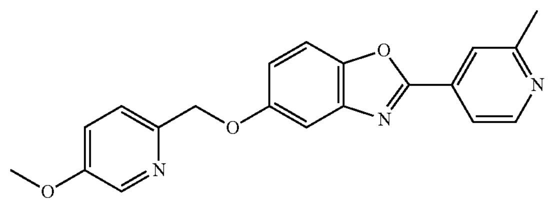 | 5-[(5-methoxypyridin-2-yl)methoxy]-2-(2-methylpyridin-4-yl)-1,3-benzoxazole | +++ |
| 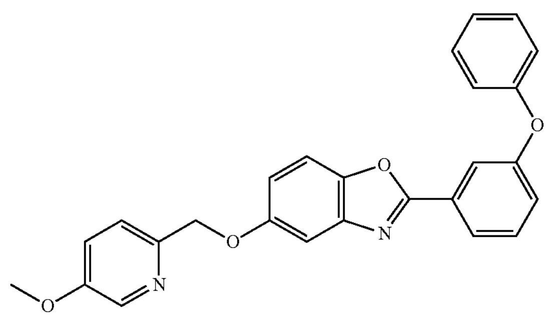 [SMILES: COc1ccc(COc2ccc3oc(-c4cccc(Oc5ccccc5)c4)nc3c2)nc1] | 5-[(5-methoxypyridin-2-yl)methoxy]-2-(3-phenoxyphenyl)-1,3-benzoxazole | +++ |
| 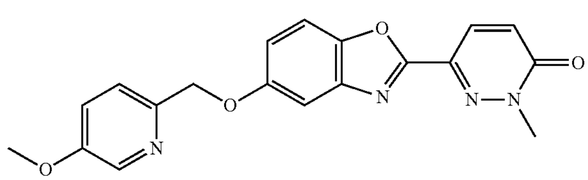 [SMILES: COc1ccc(COc2ccc3oc(-c4ccc(=O)n(C)n4)nc3c2)nc1] | 6-{5-[(5-methoxypyridin-2-yl)methoxy]-1,3-benzoxazol-2-yl}-2-methyl-2,3-dihydropyridazin-3-one | +++ |
| 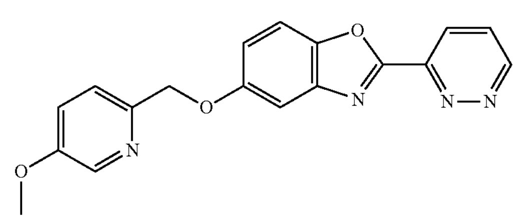 [SMILES: COc1ccc(COc2ccc3oc(-c4cccnn4)nc3c2)nc1] | 5-[(5-methoxypyridin-2-yl)methoxy]-2-(pyridazin-3-yl)-1,3-benzoxazole | +++ |

TABLE 87-continued

| Structure | IUPAC Name | Activity |
|---|---|---|
| 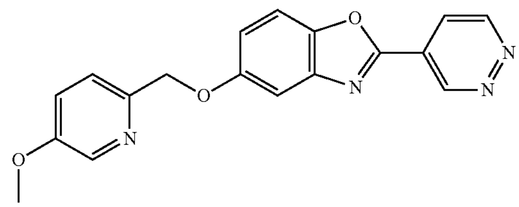 [SMILES: COc1ccc(COc2ccc3oc(-c4ccnnc4)nc3c2)nc1] | 5-[(5-methoxypyridin-2-yl)methoxy]-2-(pyridazin-4-yl)-1,3-benzoxazole | +++ |
| 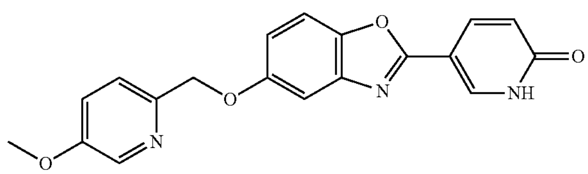 [SMILES: COc1ccc(COc2ccc3oc(-c4ccc(=O)[nH]c4)nc3c2)nc1] | 5-{5-[(5-methoxypyridin-2-yl)methoxy]-1,3-benzoxazol-2-yl}-1,2-dihydropyridin-2-one | +++ |
| 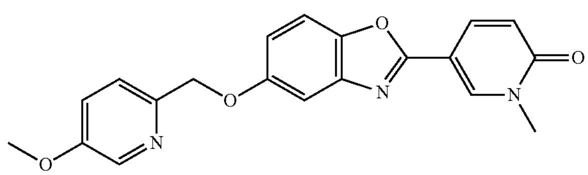 [SMILES: COc1ccc(COc2ccc3oc(-c4ccc(=O)n(C)c4)nc3c2)nc1] | 5-{5-[(5-methoxypyridin-2-yl)methoxy]-1,3-benzoxazol-2-yl}-1-methyl-1,2-dihydropyridin-2-one | +++ |
| 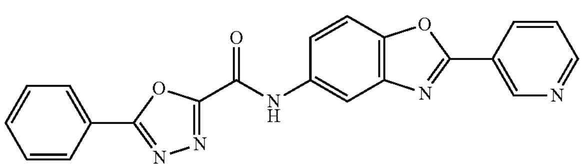 [SMILES: O=C(Nc1ccc2oc(-c3cccnc3)nc2c1)c1nnc(-c2ccccc2)o1] | 5-phenyl-N-[2-(pyridin-3-yl)-1,3-benzoxazol-5-yl]-1,3,4-oxadiazole-2-carboxamide | +++ |
| 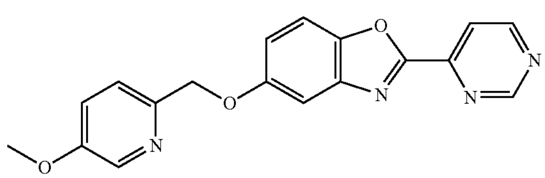 [SMILES: COc1ccc(COc2ccc3oc(-c4ccncn4)nc3c2)nc1] | 5-[(5-methoxypyridin-2-yl)methoxy]-2-(pyrimidin-4-yl)-1,3-benzoxazole | +++ |
| 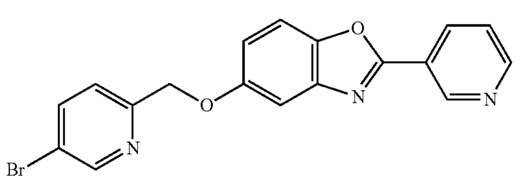 [SMILES: Brc1ccc(COc2ccc3oc(-c4cccnc4)nc3c2)nc1] | 5-[(5-bromopyridin-2-yl)methoxy]-2-(pyridin-3-yl)-1,3-benzoxazole | +++ |
| 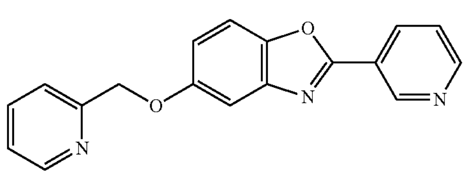 [SMILES: c1ccc(COc2ccc3oc(-c4cccnc4)nc3c2)nc1] | 5-(pyridin-2-ylmethoxy)-2-(pyridin-3-yl)-1,3-benzoxazole | ++ |
| 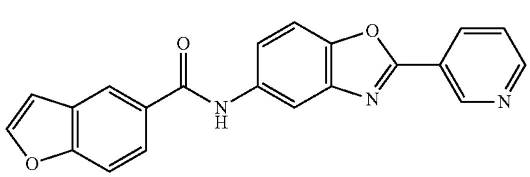 [SMILES: O=C(Nc1ccc2oc(-c3cccnc3)nc2c1)c1ccc2occc2c1] | N-[2-(pyridin-3-yl)-1,3-benzoxazol-5-yl]-1-benzofuran-5-carboxamide | +++ |

TABLE 87-continued

| Structure | IUPAC Name | Activity |
|---|---|---|
| 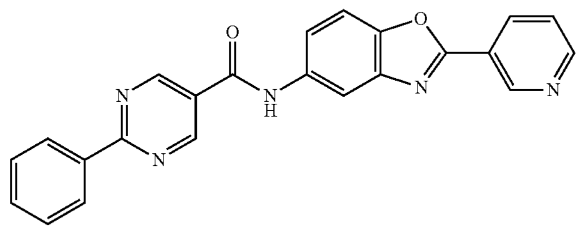 [SMILES: O=C(Nc1ccc2oc(-c3cccnc3)nc2c1)c1cnc(-c2ccccc2)nc1] | 2-phenyl-N-[2-(pyridin-3-yl)-1,3-benzoxazol-5-yl]pyrimidine-5-carboxamide | +++ |
| 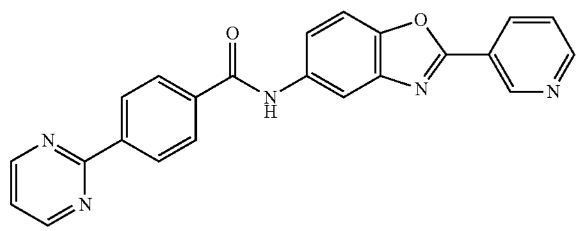 [SMILES: O=C(Nc1ccc2oc(-c3cccnc3)nc2c1)c1ccc(-c2ncccn2)cc1] | N-[2-(pyridin-3-yl)-1,3-benzoxazol-5-yl]-4-(pyrimidin-2-yl)benzamide | +++ |
| 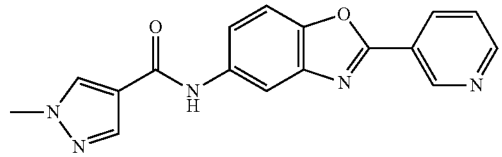 [SMILES: Cn1cc(C(=O)Nc2ccc3oc(-c4cccnc4)nc3c2)cn1] | 1-methyl-N-[2-(pyridin-3-yl)-1,3-benzoxazol-5-yl]-1H-pyrazole-4-carboxamide | +++ |
| 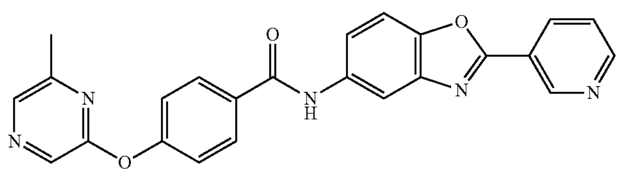 [SMILES: Cc1cncc(Oc2ccc(C(=O)Nc3ccc4oc(-c5cccnc5)nc4c3)cc2)n1] | 4-[(6-methylpyrazin-2-yl)oxy]-N-[2-(pyridin-3-yl)-1,3-benzoxazol-5-yl]benzamide | +++ |
| 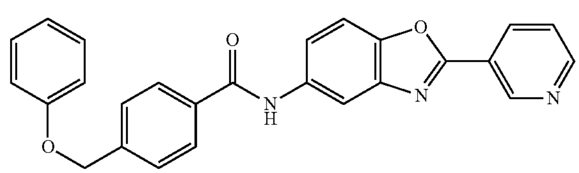 [SMILES: O=C(Nc1ccc2oc(-c3cccnc3)nc2c1)c1ccc(COc2ccccc2)cc1] | 4-(phenoxymethyl)-N-[2-(pyridin-3-yl)-1,3-benzoxazol-5-yl]benzamide | +++ |
| 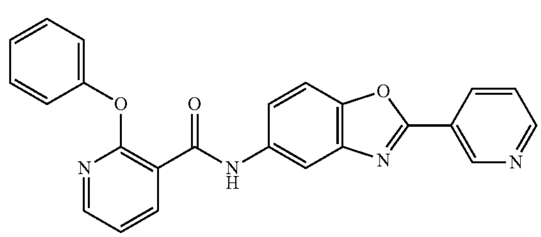 [SMILES: O=C(Nc1ccc2oc(-c3cccnc3)nc2c1)c1cccnc1Oc1ccccc1] | 2-phenoxy-N-[2-(pyridin-3-yl)-1,3-benzoxazol-5-yl]pyridine-3-carboxamide | +++ |
| 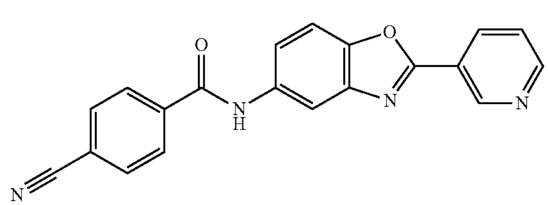 [SMILES: N#Cc1ccc(C(=O)Nc2ccc3oc(-c4cccnc4)nc3c2)cc1] | 4-cyano-N-[2-(pyridin-3-yl)-1,3-benzoxazol-5-yl]benzamide | +++ |

TABLE 87-continued

| Structure | IUPAC Name | Activity |
|---|---|---|
| 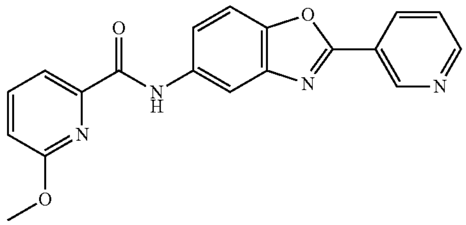 [SMILES: COc1cccc(C(=O)Nc2ccc3oc(-c4cccnc4)nc3c2)n1] | 6-methoxy-N-[2-(pyridin-3-yl)-1,3-benzoxazol-5-yl]pyridine-2-carboxamide | +++ |
| 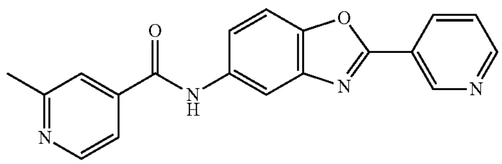 [SMILES: Cc1cc(C(=O)Nc2ccc3oc(-c4cccnc4)nc3c2)ccn1] | 2-methyl-N-[2-(pyridin-3-yl)-1,3-benzoxazol-5-yl]pyridine-4-carboxamide | +++ |
| 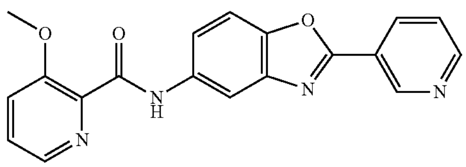 [SMILES: COc1cccnc1C(=O)Nc1ccc2oc(-c3cccnc3)nc2c1] | 3-methoxy-N-[2-(pyridin-3-yl)-1,3-benzoxazol-5-yl]pyridine-2-carboxamide | ++ |
| 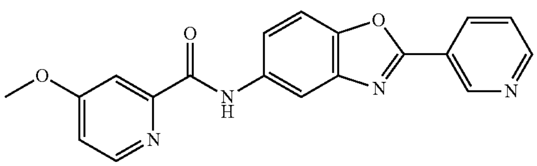 [SMILES: COc1ccnc(C(=O)Nc2ccc3oc(-c4cccnc4)nc3c2)c1] | 4-methoxy-N-[2-(pyridin-3-yl)-1,3-benzoxazol-5-yl]pyridine-2-carboxamide | +++ |
| 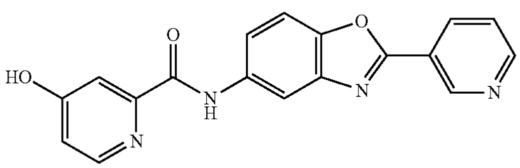 [SMILES: O=C(Nc1ccc2oc(-c3cccnc3)nc2c1)c1cc(O)ccn1] | 4-hydroxy-N-[2-(pyridin-3-yl)-1,3-benzoxazol-5-yl]pyridine-2-carboxamide | ++ |
| 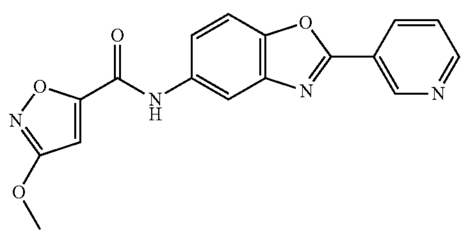 [SMILES: COc1cc(C(=O)Nc2ccc3oc(-c4cccnc4)nc3c2)on1] | 3-methoxy-N-[2-(pyridin-3-yl)-1,3-benzoxazol-5-yl]-1,2-oxazole-5-carboxamide | +++ |
| 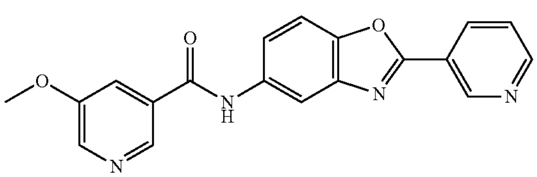 [SMILES: COc1cncc(C(=O)Nc2ccc3oc(-c4cccnc4)nc3c2)c1] | 5-methoxy-N-[2-(pyridin-3-yl)-1,3-benzoxazol-5-yl]pyridine-3-carboxamide | +++ |
| 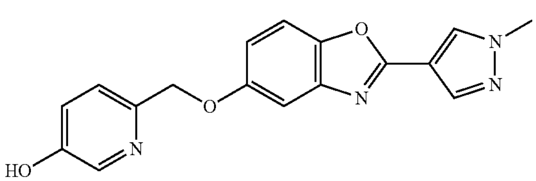 [SMILES: Cn1cc(-c2nc3cc(OCc4ccc(O)cn4)ccc3o2)cn1] | 6-({[2-(1-methyl-1H-pyrazol-4-yl)-1,3-benzoxazol-5-yl]oxy}methyl)pyridin-3-ol | ++ |

TABLE 87-continued

| Structure | IUPAC Name | Activity |
|---|---|---|
| 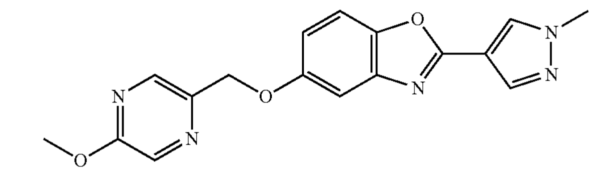 | 5-[(5-methoxypyrazin-2-yl)methoxy]-2-(1-methyl-1H-pyrazol-4-yl)-1,3-benzoxazole | +++ |
| 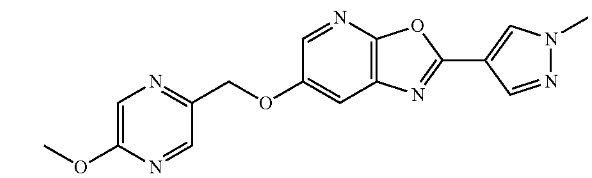 | 2-methoxy-5-({[2-(1-methyl-1H-pyrazol-4-yl)-[1,3]oxazolo[5,4-b]pyridin-6-yl]oxy}methyl)pyrazine | +++ |
| 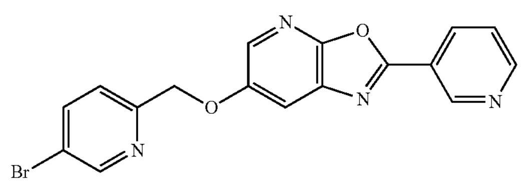 [SMILES: Brc1ccc(COc2cnc3oc(-c4cccnc4)nc3c2)nc1] | 3-{6-[(5-bromopyridin-2-yl)methoxy]-[1,3]oxazolo[5,4-b]pyridin-2-yl}pyridine | +++ |
| 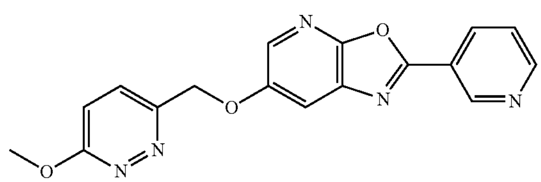 [SMILES: COc1ccc(COc2cnc3oc(-c4cccnc4)nc3c2)nn1] | 3-methoxy-6-({[2-(pyridin-3-yl)-[1,3]oxazolo[5,4-b]pyridin-6-yl]oxy}methyl)pyridazine | +++ |
| 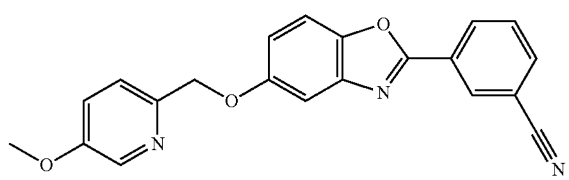 [SMILES: COc1ccc(COc2ccc3oc(-c4cccc(C#N)c4)nc3c2)nc1] | 3-{5-[(5-methoxypyridin-2-yl)methoxy]-1,3-benzoxazol-2-yl}benzonitrile | +++ |
| 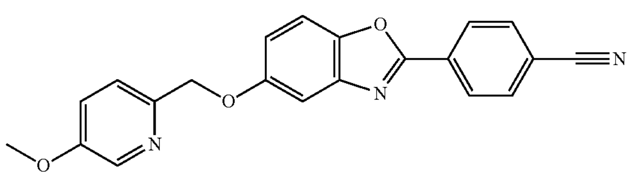 [SMILES: COc1ccc(COc2ccc3oc(-c4ccc(C#N)cc4)nc3c2)nc1] | 4-{5-[(5-methoxypyridin-2-yl)methoxy]-1,3-benzoxazol-2-yl}benzonitrile | +++ |
| 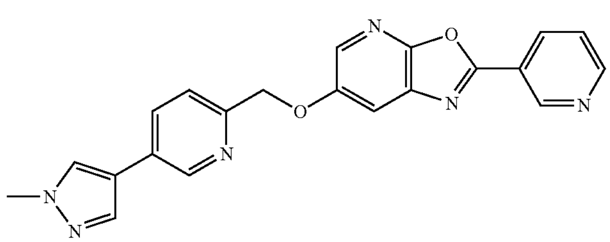 [SMILES: Cn1cc(-c2ccc(COc3cnc4oc(-c5cccnc5)nc4c3)nc2)cn1] | 5-(1-methyl-1H-pyrazol-4-yl)-2-({[2-(pyridin-3-yl)-[1,3]oxazolo[5,4-b]pyridin-6-yl]oxy}methyl)pyridine | +++ |
| 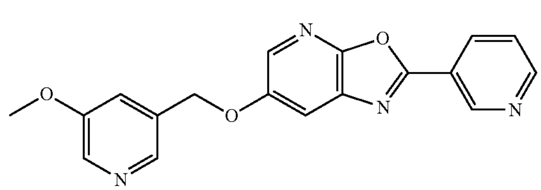 [SMILES: COc1cncc(COc2cnc3oc(-c4cccnc4)nc3c2)c1] | 3-methoxy-5-({[2-(pyridin-3-yl)-[1,3]oxazolo[5,4-b]pyridin-6-yl]oxy}methyl)pyridine | +++ |

TABLE 87-continued

| Structure | IUPAC Name | Activity |
|---|---|---|
| 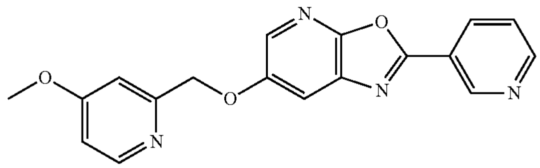 [SMILES: COc1ccnc(COc2cnc3oc(-c4cccnc4)nc3c2)c1] | 4-methoxy-2-({[2-(pyridin-3-yl)-[1,3]oxazolo[5,4-b]pyridin-6-yl]oxy}methyl)pyridine | +++ |
| 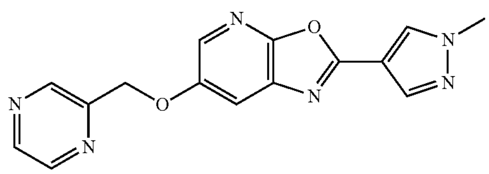 [SMILES: Cn1cc(-c2nc3cc(OCc4cnccn4)cnc3o2)cn1] | 2-({[2-(1-methyl-1H-pyrazol-4-yl)-[1,3]oxazolo[5,4-b]pyridin-6-yl]oxy}methyl)pyrazine | ++ |
| 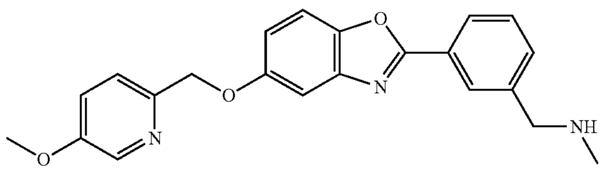 | [(3-{5-[(5-methoxypyridin-2-yl)methoxy]-1,3-benzoxazol-2-yl}phenyl)methyl](methyl)amine | +++ |
| 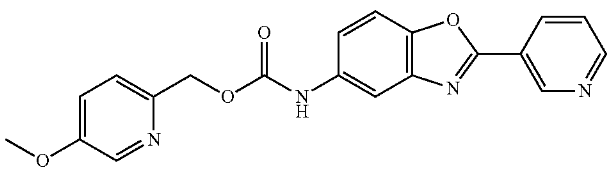 [SMILES: COc1ccc(COC(=O)Nc2ccc3oc(-c4cccnc4)nc3c2)nc1] | (5-methoxypyridin-2-yl)methyl N-[2-(pyridin-3-yl)-1,3-benzoxazol-5-yl]carbamate | +++ |
| 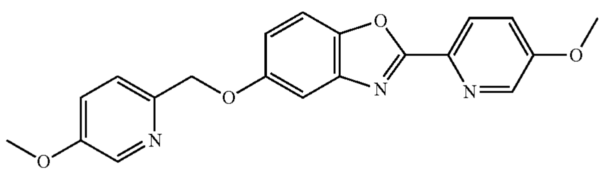 | 2-(5-methoxypyridin-2-yl)-5-[(5-methoxypyridin-2-yl)methoxy]-1,3-benzoxazole | +++ |
| 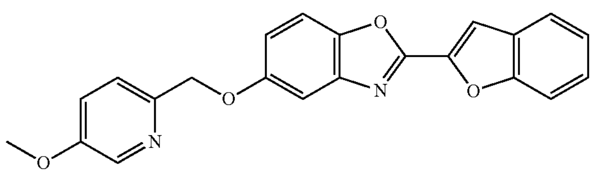 [SMILES: COc1ccc(COc2ccc3oc(-c4cc5ccccc5o4)nc3c2)nc1] | 2-(1-benzofuran-2-yl)-5-[(5-methoxypyridin-2-yl)methoxy]-1,3-benzoxazole | +++ |
| 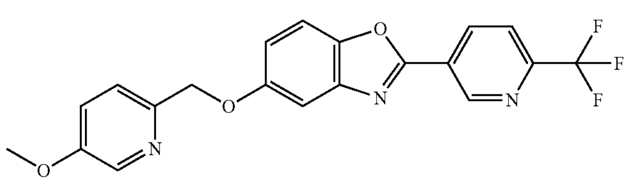 [SMILES: COc1ccc(COc2ccc3oc(-c4ccc(C(F)(F)F)nc4)nc3c2)nc1] | 5-[(5-methoxypyridin-2-yl)methoxy]-2-[6-(trifluoromethyl)pyridin-3-yl]-1,3-benzoxazole | +++ |
| 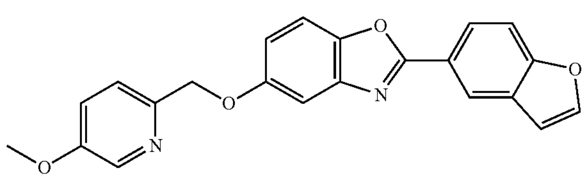 [SMILES: COc1ccc(COc2ccc3oc(-c4ccc5occc5c4)nc3c2)nc1] | 2-(1-benzofuran-5-yl)-5-[(5-methoxypyridin-2-yl)methoxy]-1,3-benzoxazole | +++ |
| 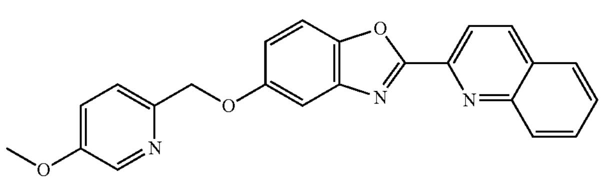 [SMILES: COc1ccc(COc2ccc3oc(-c4ccc5ccccc5n4)nc3c2)nc1] | 2-{5-[(5-methoxypyridin-2-yl)methoxy]-1,3-benzoxazol-2-yl}quinoline | +++ |

TABLE 87-continued

| Structure | IUPAC Name | Activity |
|---|---|---|
| 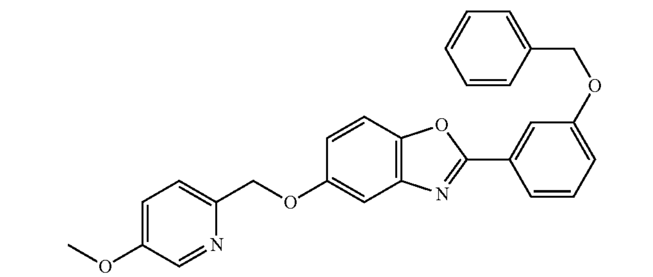 [SMILES: COc1ccc(COc2ccc3oc(-c4cccc(OCc5ccccc5)c4)nc3c2)nc1] | 2-[3-(benzyloxy)phenyl]-5-[(5-methoxypyridin-2-yl)methoxy]-1,3-benzoxazole | +++ |
| 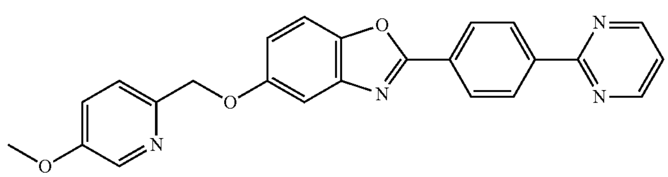 [SMILES: COc1ccc(COc2ccc3oc(-c4ccc(-c5ncccn5)cc4)nc3c2)nc1] | 5-[(5-methoxypyridin-2-yl)methoxy]-2-[4-(pyrimidin-2-yl)phenyl]-1,3-benzoxazole | +++ |
| 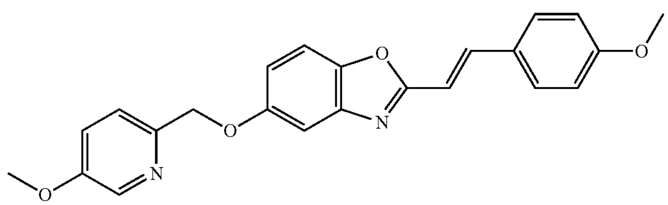 | 2-[(E)-2-(4-methoxyphenyl)ethenyl]-5-[(5-methoxypyridin-2-yl)methoxy]-1,3-benzoxazole | +++ |
| 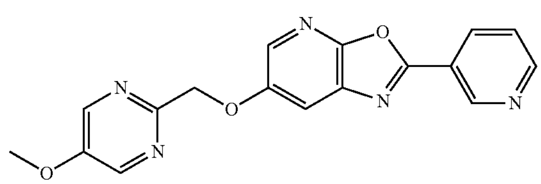 [SMILES: COc1cnc(COc2cnc3oc(-c4cccnc4)nc3c2)nc1] | 5-methoxy-2-({[2-(pyridin-3-yl)-[1,3]oxazolo[5,4-b]pyridin-6-yl]oxy}methyl)pyrimidine | +++ |
| 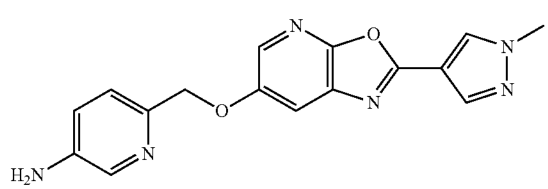 [SMILES: Cn1cc(-c2nc3cc(OCc4ccc(N)cn4)cnc3o2)cn1] | 6-({[2-(1-methyl-1H-pyrazol-4-yl)-[1,3]oxazolo[5,4-b]pyridin-6-yl]oxy}methyl)pyridin-3-amine | ++ |
| 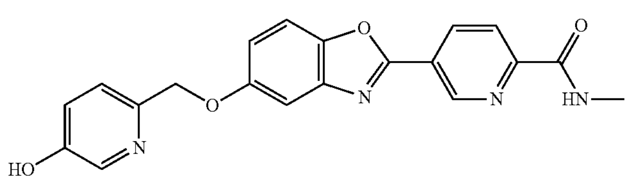 [SMILES: CNC(=O)c1ccc(-c2nc3cc(OCc4ccc(O)cn4)ccc3o2)cn1] | 5-{5-[(5-hydroxypyridin-2-yl)methoxy]-1,3-benzoxazol-2-yl}-N-methylpyridine-2-carboxamide | +++ |
| 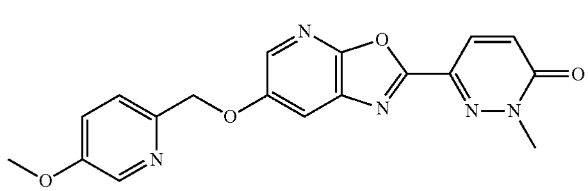 [SMILES: COc1ccc(COc2cnc3oc(-c4ccc(=O)n(C)n4)nc3c2)nc1] | 6-{6-[(5-methoxypyridin-2-yl)methoxy]-[1,3]oxazolo[5,4-b]pyridin-2-yl}-2-methyl-2,3-dihydropyridazin-3-one | +++ |

TABLE 87-continued

| Structure | IUPAC Name | Activity |
|---|---|---|
| 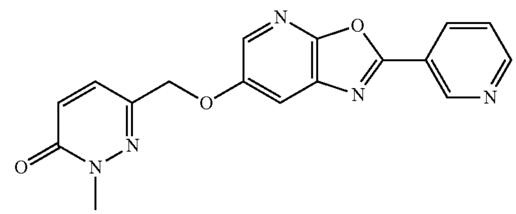 [SMILES: Cn1nc(COc2cnc3oc(-c4cccnc4)nc3c2)ccc1=O] | 2-methyl-6-({[2-(pyridin-3-yl)-[1,3]oxazolo[5,4-b]pyridin-6-yl]oxy}methyl)-2,3-dihydropyridazin-3-one | ++ |
| 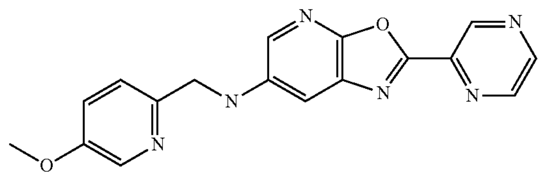 [SMILES: COc1ccc(CNc2cnc3oc(-c4cnccn4)nc3c2)nc1] | 2-{6-[(5-methoxypyridin-2-yl)methoxy]-[1,3]oxazolo[5,4-b]pyridin-2-yl}pyrazine | +++ |
| 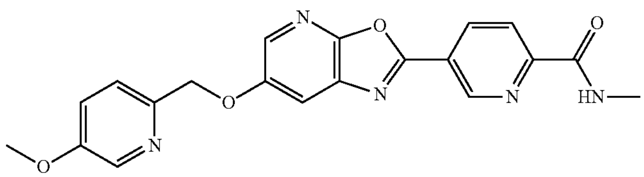 | 5-{6-[(5-methoxypyridin-2-yl)methoxy]-[1,3]oxazolo[5,4-b]pyridin-2-yl}-N-methylpyridine-2-carboxamide | +++ |
| 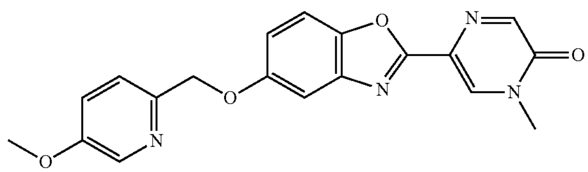 [SMILES: COc1ccc(COc2ccc3oc(-c4cn(C)c(=O)cn4)nc3c2)nc1] | 5-{5-[(5-methoxypyridin-2-yl)methoxy]-1,3-benzoxazol-2-yl}-1-methyl-1,2-dihydropyrazin-2-one | +++ |
| 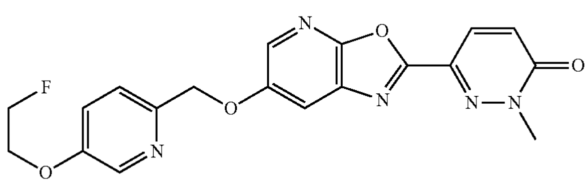 [SMILES: Cn1nc(-c2nc3cc(OCc4ccc(OCCF)cn4)cnc3o2)ccc1=O] | 6-(6-{[5-(2-fluoroethoxy)pyridin-2-yl]methoxy}-[1,3]oxazolo[5,4-b]pyridin-2-yl)-2-methyl-2,3-dihydropyridazin-3-one | +++ |
| 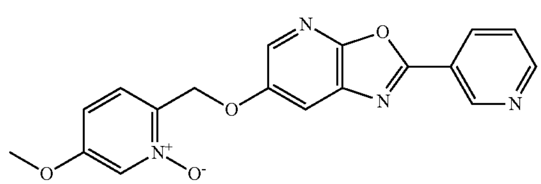 [SMILES: COc1ccc(COc2cnc3oc(-c4cccnc4)nc3c2)[n+]([O-])c1] | 5-methoxy-2-({[2-(pyridin-3-yl)-[1,3]oxazolo[5,4-b]pyridin-6-yl]oxy}methyl)pyridin-1-ium-1-olate | +++ |
| 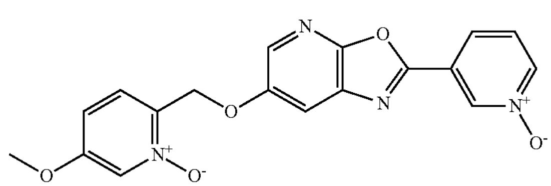 [SMILES: COc1ccc(COc2cnc3oc(-c4ccc[n+]([O-])c4)nc3c2)[n+]([O-])c1] | 3-{6-[(5-methoxy-1-oxidopyridin-1-ium-2-yl)methoxy]-[1,3]oxazolo[5,4-b]pyridin-2-yl}pyridin-1-ium-1-olate | ++ |
| 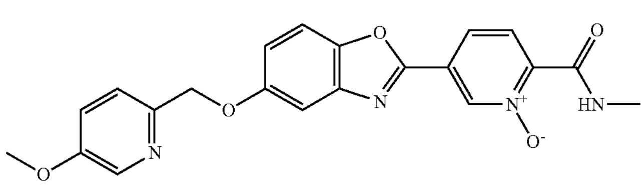 | 5-{5-[(5-methoxypyridin-2-yl)methoxy]-1,3-benzoxazol-2-yl}-2-(methylcarbamoyl)pyridin-1-ium-1-olate | +++ |

TABLE 87-continued

| Structure | IUPAC Name | Activity |
|---|---|---|
| 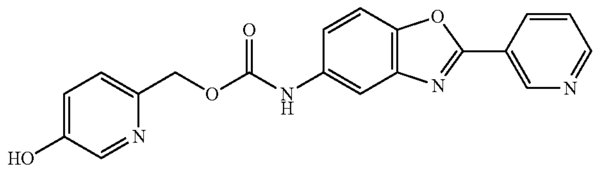 [SMILES: O=C(Nc1ccc2oc(-c3cccnc3)nc2c1)OCc1ccc(O)cn1] | (5-hydroxypyridin-2-yl)methyl N-[2-(pyridin-3-yl)-1,3-benzoxazol-5-yl]carbamate | +++ |
| 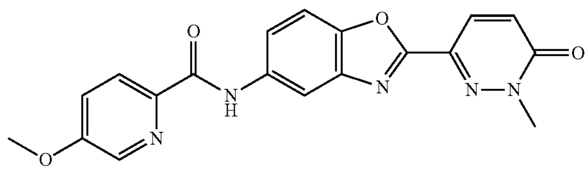 [SMILES: COc1ccc(C(=O)Nc2ccc3oc(-c4ccc(=O)n(C)n4)nc3c2)nc1] | 5-methoxy-N-[2-(1-methyl-6-oxo-1,6-dihydropyridazin-3-yl)-1,3-benzoxazol-5-yl]pyridine-2-carboxamide | +++ |
| 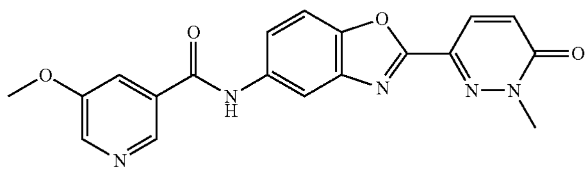 [SMILES: COc1cncc(C(=O)Nc2ccc3oc(-c4ccc(=O)n(C)n4)nc3c2)c1] | 5-methoxy-N-[2-(1-methyl-6-oxo-1,6-dihydropyridazin-3-yl)-1,3-benzoxazol-5-yl]pyridine-3-carboxamide | +++ |
| 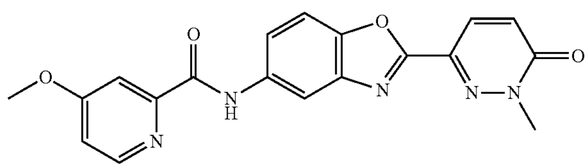 [SMILES: COc1ccnc(C(=O)Nc2ccc3oc(-c4ccc(=O)n(C)n4)nc3c2)c1] | 4-methoxy-N-[2-(1-methyl-6-oxo-1,6-dihydropyridazin-3-yl)-1,3-benzoxazol-5-yl]pyridine-2-carboxamide | +++ |
| 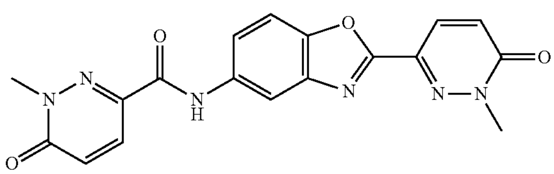 [SMILES: Cn1nc(C(=O)Nc2ccc3oc(-c4ccc(=O)n(C)n4)nc3c2)ccc1=O] | 1-methyl-N-[2-(1-methyl-6-oxo-1,6-dihydropyridazin-3-yl)-1,3-benzoxazol-5-yl]-6-oxo-1,6-dihydropyridazine-3-carboxamide | +++ |
| 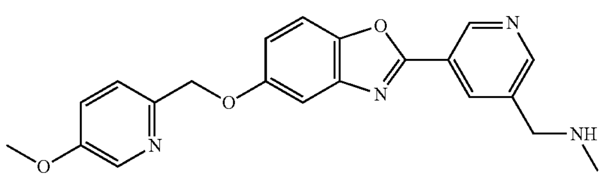 | [(5-{5-[(5-methoxypyridin-2-yl)methoxy]-1,3-benzoxazol-2-yl}pyridin-3-yl)methyl](methyl)amine | +++ |
| 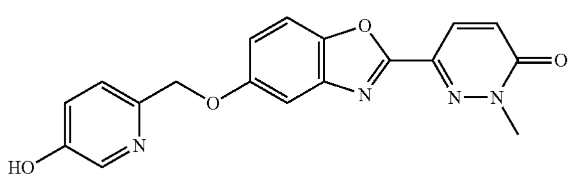 [SMILES: Cn1nc(-c2nc3cc(OCc4ccc(O)cn4)ccc3o2)ccc1=O] | 6-{5-[(5-hydroxypyridin-2-yl)methoxy]-1,3-benzoxazol-2-yl}-2-methyl-2,3-dihydropyridazin-3-one | +++ |
| 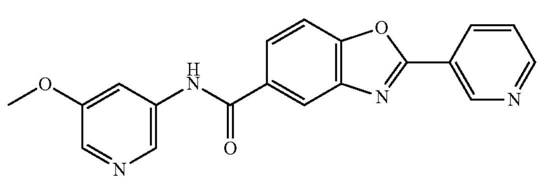 [SMILES: COc1cncc(NC(=O)c2ccc3oc(-c4cccnc4)nc3c2)c1] | N-(5-methoxypyridin-3-yl)-2-(pyridin-3-yl)-1,3-benzoxazole-5-carboxamide | +++ |

RBA IC$_{50}$ activity summary:
<100 nM +++,
100-500 nM ++,
>500 nM +

In Vivo Imaging with [¹¹C]-Compound 3 of Method 14 (5-[(5-[¹¹C-]-Methoxypyridin-2-yl)methoxy]-2-(pyridin-3-yl)-1,3-benzoxazole)) in a Knock-in Model of Huntington's Disease (5-[(5-[¹¹C-]-Methoxypyridin-2-yl)methoxy]-2-(pyridin-3-yl)-1,3-benzoxazole) was synthesized from 2-(pyridin-3-yl)-1,3-benzoxazol-5-ol (Method 14) via O-methylation, using [¹¹C]methyl triflate (obtained from cyclotron-produced [¹¹C]methane) as an alkylating agent in the presence of base according to the method of Chitneni, S. K. et al.: Synthesis and biological evaluation of carbon-11-labeled acyclic and furo[2,3-d]pyrimidine derivatives of bicyclic nucleoside analogues (BCNAs) for structure-brain uptake relationship study of BCNA tracers, Journal of Labelled Compounds and Radiopharmaceuticals 2008, 51, 159-166. The incorporation rate was >80% and the radiochemical purity was >99%. The labeled product was purified on semi-preparative HPLC column (Ascentis RP-Amide C18) using acetonitrile/aq. triethyl amine (0.1%) as eluent. The product was then concentrated using solid-phase extraction procedure (on Waters tC18 Vac 1 cc SPE cartridge) and formulated in sterile saline (0.9% NaCl) with >10% ethanol. The radiochemical purity of the product was analyzed on an HPLC system using Ascentis RP-Amide C18 analytical column and acetonitrile/aq. triethyl amine (0.1%) as eluent, with sequential UV absorbance and radioactivity detectors. The radiochemical purity of the formulated product was determined to be >99%.

¹¹C-labeled Compound 3 of Method 14 was evaluated for its ability to penetrate the central nervous system of mice following systemic administration, and its binding to the cerebellum, striatum, hippocampus, and cortex was quantitated. Three groups of animals were compared: wild-type, and mice that were heterozygous or homozygous for the zQ175 knock-in allele. (Menalled L. B. et al. Comprehensive behavioral and molecular characterization of a new knock-in mouse model of Huntington's disease: zQ175. PLoS One 2012, 7, e49838).

Forty-eight nine months old animals (16 WT, 16 heterozygous and 16 homozygous zQ175) were obtained from The Jackson Laboratory, USA. The animals were housed at the animal department of Karolinska University Hospital in a temperature (±21° C.) and humidity (±40%) controlled environment on a 12 h light/dark cycle (lights on 7:00 AM) with access to food and water ad libitum. Animals were allowed at least one week to habituate to the animal department before the start of the imaging sessions. All experiments were conducted during the light phase of the cycle.

Animals were anesthetized with inhalation of isoflurane (4-5% isoflurane in 100% oxygen). After induction of anesthesia, the isoflurane concentration was lowered to 1.5-2% (50/50 air/oxygen) and the animals were positioned in the scanner in a designated mouse bed. A cannula was inserted in the tail vein through which the radioligand was administered. A 63-minute dynamic PET scan was initiated immediately upon intravenous injection of the radioligand. Upon completion of the imaging sessions, each animal was returned to its cage.

Image and Statistical Analysis

The acquired list mode data, was reconstructed into 25 timeframes (63 min scan=4×10 s, 4×20 s, 4×60 s, 7×180 s, 6×360 s). The image reconstruction was made with a fully 3-dimensional maximum-likelihood expectation maximization algorithm (MLEM) with 20 iterations, without scatter and attenuation correction. The reconstructed dynamic PET images were co-registered to an inbuilt mouse MRI template available in PMOD, which also incorporates volumes of interest (VOI's) sets (PMOD Technologies Ltd., Zurich, Switzerland). With the help of these VOI sets, decay corrected time activity curves (TAC) were generated. The regional brain uptake values were expressed as percent standard uptake value (% SUV), which normalizes for injected radioactivity and body weight. In addition, the area under the curve (AUC) was calculated. The selected regions of interest (ROI) were: cortex, hippocampus, striatum and cerebellum.

The average % SUV and AUC values for the ¹¹C-labeled Compound 3 of Method 14 in the four brain regions, for the three groups of mice, are shown in Table 88. Increased binding of the radioligand, relative to wild type, was observed in all four brain regions in mice which were homozygous for the zQ 175 allele. FIG. 1 presents the AUC values for the three groups of animals in the four regions of the brain.

TABLE 88

Average % SUV and AUC values of ¹¹C-labeled Compound 3 of Method 14 in the cortex, hippocampus, striatum and cerebellum of WT, het zQ175 and hom zQ175 animals. Each value is expressed as Mean ± SD

| | % SUV | | | AUC | | |
|---|---|---|---|---|---|---|
| | WT (n = 7) | Het (n = 7) | Hom (n = 6) | WT (n = 7) | Het (n = 7) | Hom (n = 6) |
| Cortex | 69.1 ± 3.1 | 75.1 ± 4.3 | 93.9 ± 8.0 | 4965 ± 484 | 5685 ± 297 | 8233 ± 883 |
| Hippocampus | 72.0 ± 3.6 | 80.3 ± 5.5 | 104.6 ± 7.9 | 4840 ± 402 | 5824 ± 364 | 8983 ± 1078 |
| Striatum | 68.8 ± 2.7 | 79.7 ± 5.8 | 104.4 ± 9.1 | 4589 ± 311 | 5833 ± 431 | 9006 ± 1205 |
| Cerebellum | 74.2 ± 3.0 | 78.4 ± 5.9 | 88.2 ± 5.0 | 4934 ± 325 | 5570 ± 153 | 7118 ± 541 |

Various modifications, additions, substitutions, and variations to the illustrative examples set forth herein will be apparent to those skilled in the art from the foregoing description. Such modifications are also intended to fall within the scope of the appended claims.

What is claimed is:

1. A compound of Formula (I), or a pharmaceutically acceptable salt thereof,

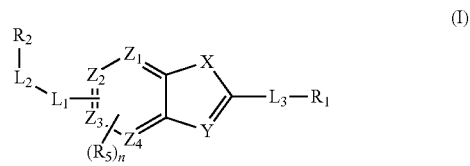

wherein
X is NR$_4$, O, or S;
Y is CR$_4$ or N;
Z$_1$, Z$_2$, Z$_3$, and Z$_4$ are independently chosen from CH and N, provided that at least two of Z$_1$, Z$_2$, Z$_3$, and Z$_4$ are CH;
R$_1$ is heteroaryl, heterocycloalkenyl, or heterocycloalkyl, each of which is optionally substituted with one or two groups independently chosen from cyano, halo, lower alkyl optionally substituted with amino, alkylamino, or di(alkyl)amino, lower alkoxy optionally substituted with lower alkoxy, optionally substituted amino, haloalkyl, di(alkyl)aminocarbonyl, alkylaminocarbonyl, and aminocarbonyl, or
R$_1$ is phenyl optionally substituted with one or two groups independently chosen from cyano, heteroaryl, halo, phenoxy, benzyloxy, heteroaryl, lower alkyl optionally substituted with amino, (alkyl)amino, or di(alkyl)amino, lower alkoxy, optionally substituted amino, di(alkyl)aminocarbonyl, alkylaminocarbonyl, and aminocarbonyl;
L$_1$ is —O—;
L$_2$ is —(CR$_7$R$_8$)$_m$—;
L$_3$ is —CH═CH— or is absent;
R$_2$ is phenyl, pyridin-2-yl, pyridin-3-yl, pyrazin-2-yl, pyrimidin-5-yl, 1H-imidazol-4-yl, 1H-imidazol-2-yl, or 1H-pyrazol-4-yl, each of which is optionally substituted with one or two groups independently chosen from halo; haloalkyl; hydroxyl; lower alkoxy; lower alkoxy substituted with lower alkoxy, amino, (alkyl)amino, (dialkyl)amino, heterocycloalkyl, heteroaryl, or halo; lower alkyl; and lower alkyl substituted with hydroxyl, lower alkoxy, amino, (alkyl)amino, or (dialkyl)amino;
R$_4$ is chosen from hydrogen, halo, cyano, and lower alkyl;
R$_5$ is chosen from lower alkyl, lower alkoxy, and halo;
R$_7$ is chosen from hydrogen, hydroxyl, trifluoromethyl, and lower alkyl;
R$_8$ is chosen from hydrogen and lower alkyl;
n is 0 or 1; and
m is 0, 1, or 2;
wherein the compound of Formula (I), or a pharmaceutically acceptable salt thereof, is labeled with one or more positron-emitting radionuclides.

2. The compound of claim 1, wherein R$_1$ is phenyl, pyridin-2-yl, pyridin-3-yl, pyridin-3-yl-1-oxide, pyridin-4-yl, 1H-pyrazol-4-yl, pyrazin-2-yl, pyridazin-3-yl, pyridazin-4-yl, pyrimidin-4-yl, pyrimidin-5-yl, 2,3-dihydropyridazin-3-one-6-yl, 1,2-dihydropyridin-2-one-5-yl, 1,2-dihydropyrazin-2-one-5-yl, 1,3-thiazol-5-yl, 5,6,7,8-tetrahydro-1,7-naphthyridine-7-yl, 1H-imidazol-1-yl, 1-benzofuran-2-yl, 1-benzofuran-5-yl, 2,3-dihydro-1-benzofuran-2-yl, quinolin-2-yl, or 5H,6H,7H,8H-imidazo[1,2-a]pyrazin-7-yl, each of which is optionally substituted with one or two groups independently chosen from halo, lower alkyl, lower alkoxy, and optionally substituted amino.

3. The compound of claim 1, wherein R$_1$ is

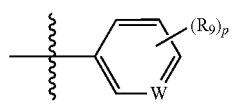

wherein
W is CH, N, or N(O);
p is 0, 1, or 2;

for each occurrence, R$_9$ is independently chosen from cyano, halo, lower alkyl, lower alkyl substituted with —NR$_{10}$R$_{11}$, lower alkoxy, —C(O)NR$_{10}$R$_{11}$, and —NR$_{10}$R$_{11}$;
R$_{10}$ is chosen from hydrogen and lower alkyl;
R$_{11}$ is chosen from hydrogen and lower alkyl.

4. The compound of claim 1, wherein R$_1$ is

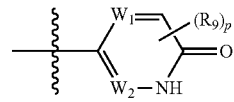

wherein
W$_1$ and W$_2$ are chosen from CH and N, provided that at least one of W$_1$ and W$_2$ is CH;
p is 0, 1, or 2; and
for each occurrence, R$_9$ is independently chosen from lower alkyl.

5. The compound of claim 1, wherein X is O.
6. The compound of claim 1, wherein X is S.
7. The compound of claim 1, wherein X is NR$_4$.
8. The compound of claim 1, wherein Y is CR$_4$.
9. The compound of claim 1, wherein Y is N.
10. The compound of claim 1, wherein Z$_1$, Z$_2$, Z$_3$, and Z$_4$ are CH.
11. The compound of claim 1, wherein Z$_1$ is N and Z$_2$, Z$_3$, and Z$_4$ are CH.
12. The compound of claim 1, wherein Z$_2$ is N and Z$_1$, Z$_3$, and Z$_4$ are CH.
13. The compound of claim 1, wherein Z$_2$ and Z$_4$ are N and Z$_1$ and Z$_3$ are CH.
14. A compound selected from:
tert-butyl 4-[2-(pyridin-3-yl)-1,3-benzoxazol-5-yl]piperazine-1-carboxylate;
4-methoxy-N-[2-(pyridin-3-yl)-1,3-benzoxazol-5-yl]benzamide;
4-methoxy-N-[2-(pyridin-4-yl)-1,3-benzoxazol-5-yl]benzamide;
N-[(4-methoxyphenyl)methyl]-2-(pyridin-3-yl)-1,3-benzoxazol-5-amine;
2-(3-bromopyridin-4-yl)-6-[2-(morpholin-4-yl)ethoxy]-1,3-benzothiazole;
5-methoxy-N-[2-(3-methylphenyl)-1,3-benzoxazol-5-yl]pyridine-2-carboxamide;
6-methoxy-N-[2-(3-methylphenyl)-1,3-benzoxazol-5-yl]pyridine-3-carboxamide;
2-methoxy-N-[2-(3-methylphenyl)-1,3-benzoxazol-5-yl]pyrimidine-5-carboxamide;
5-methoxy-N-[2-(3-methylphenyl)-1,3-benzoxazol-5-yl]pyrazine-2-carboxamide;
4-methoxy-N-[2-(3-methylphenyl)-[1,3]oxazolo[5,4-b]pyridin-6-yl]benzamide;
5-(4-methoxyphenyl)-2-(pyridin-3-yl)-1,3-benzoxazole;
N-(4-methoxyphenyl)-2-(pyridin-3-yl)-1,3-benzoxazol-5-amine;
2-(pyridin-3-yl)-N-{[1,2,4]triazolo[4,3-a]pyridin-3-yl}-1,3-benzoxazol-5-amine;
2-(pyridin-3-yl)-N-(pyrimidin-4-yl)-1,3-benzoxazol-5-amine;
2-(pyridin-3-yl)-N-(pyrimidin-2-yl)-1,3-benzoxazol-5-amine;
5-(5-methoxypyridin-2-yl)-2-(pyridin-3-yl)-1,3-benzoxazole;

5-(2-methoxypyrimidin-5-yl)-2-(pyridin-3-yl)-1,3-benzoxazole;
5-(5-methoxypyrimidin-2-yl)-2-(pyridin-3-yl)-1,3-benzoxazole;
5-(6-methoxypyridazin-3-yl)-2-(pyridin-3-yl)-1,3-benzoxazole;
5-(5-methoxypyrazin-2-yl)-2-(pyridin-3-yl)-1,3-benzoxazole;
1-methyl-4-[5-(pyrimidin-5-ylmethoxy)-1-benzofuran-2-yl]-1H-pyrazole-3-carbonitrile;
4-[5-(pyrimidin-5-ylmethoxy)-1-benzofuran-2-yl]pyridine-3-carbonitrile;
4-{5-[(5-methoxypyridin-2-yl)methoxy]-1-benzofuran-2-yl}pyridine-3-carbonitrile;
4-{5-[(5-methoxypyridin-2-yl)methoxy]-1-benzofuran-2-yl}pyridine;
4-{5-[(1-methyl-1H-imidazol-4-yl)methoxy]-1-benzofuran-2-yl)}pyridine-3-carbonitrile;
4-{5-[(1-methyl-1H-imidazol-2-yl)methoxy]-1-benzofuran-2-yl}pyridine-3-carbonitrile;
5-methoxy-2-[2-(pyridin-3-yl)-1,3-benzoxazol-5-yl]-2,3-dihydro-1H-isoindol-1-one;
3-{6-[(E)-2-(4-methoxyphenyl)ethenyl]-[1,3]oxazolo[5,4-b]pyridin-2-yl}pyridine;
4-[5-(pyridin-3-yloxy)-1-benzofuran-2-yl]pyridine-3-carbonitrile;
6-methoxy-2-[2-(pyridin-3-yl)-1,3-benzoxazol-5-yl]-1,2,3,4-tetrahydroisoquinolin-1-one;
dimethyl({3-[4-({[2-(pyridin-3-yl)-1,3-benzoxazol-5-yl]oxy}methyl)phenoxy]propyl})amine;
5-[(1-methyl-1H-pyrazol-4-yl)methoxy]-2-(pyridin-3-yl)-1,3-benzoxazole;
5-[(4-methoxyphenyl)methoxy]-2-(pyridin-3-yl)-1,3-benzoxazole;
5-[(3-methoxyphenyl)methoxy]-2-(pyridin-3-yl)-1,3-benzoxazole;
5-[(5-methoxypyridin-2-yl)methoxy]-2-(pyridin-3-yl)-1,3-benzoxazole;
2-(pyridin-3-yl)-5-(pyridin-3-ylmethoxy)-1,3-benzoxazole;
5-{5H,6H-imidazo[2,1-b][1,3]thiazol-3-ylmethoxy}-2-(pyridin-3-yl)-1,3-benzoxazole;
1-(pyridin-2-yl)-2-[2-(pyridin-3-yl)-1,3-benzoxazol-5-yl]ethan-1-ol;
1-(pyridin-2-yl)-2-[2-(pyridin-3-yl)-1,3-benzoxazol-5-yl]ethan-1-one;
6-methoxy-2-[2-(pyridin-3-yl)-1,3-benzoxazol-5-yl]-1,2-dihydroisoquinolin-1-one;
2-(pyridin-3-yl)-N-[2,2,2-trifluoro-1-(4-methoxyphenyl)ethyl]-[1,3]oxazolo[5,4-b]pyridin-6-amine;
3-{6-[2-(4-methoxyphenyl)ethynyl]-[1,3]oxazolo[5,4-b]pyridin-2-yl}pyridine;
3-{6-[(Z)-2-(4-methoxyphenyl)ethenyl]-[1,3]oxazolo[5,4-b]pyridin-2-yl}pyridine;
5-methoxy-2-[2-(pyridin-3-yl)-[1,3]oxazolo[5,4-b]pyridin-6-yl]-2,3-dihydro-1H-isoindol-1-one;
5-[(5-methoxypyrazin-2-yl)methoxy]-2-(pyridin-3-yl)-1,3-benzoxazole;
3-methoxy-6-[2-(pyridin-3-yl)-1,3-benzoxazol-5-yl]-5H,6H,7H-pyrrolo[3,4-b]pyridin-7-one;
2-(pyridin-3-yl)-6-(pyridin-3-ylmethoxy)-1,3-benzoxazole;
3-{6-[2-(pyridin-3-yl)ethynyl]-[1,3]oxazolo[5,4-b]pyridin-2-yl}pyridine;
5-{[(5-methoxypyridin-2-yl)oxy]methyl}-2-(pyridin-3-yl)-1,3-benzoxazole;
4-[5-(pyridin-3-ylmethoxy)-1-benzofuran-2-yl]pyridine-3-carbonitrile;
4-{5-[(1-methyl-1H-pyrazol-4-yl)methoxy]-1-benzofuran-2-yl}pyridine-3-carbonitrile;
3-[5-(pyridin-3-ylmethoxy)-1-benzofuran-2-yl]pyridine-4-carbonitrile;
3-{5-[(1-methyl-1H-pyrazol-4-yl)methoxy]-1-benzofuran-2-yl}pyridine-4-carbonitrile;
3-{6-[1-(5-methoxypyridin-2-yl)ethoxy]-[1,3]oxazolo[5,4-b]pyridin-2-yl}pyridine;
4-{5-[(5-methoxypyrazin-2-yl)methoxy]-1-benzofuran-2-yl}pyridine-3-carbonitrile;
6-({[2-(pyridin-3-yl)-1,3-benzoxazol-5-yl]oxy}methyl)pyridin-3-ol;
5-{[5-(prop-2-en-1-yloxy)pyrazin-2-yl]methoxy}-2-(pyridin-3-yl)-1,3-benzoxazole;
5-({[2-(pyridin-3-yl)-1,3-benzoxazol-5-yl]oxy}methyl)-1,2-dihydropyrazin-2-one;
1-methyl-5-({[2-(pyridin-3-yl)-1,3-benzoxazol-5-yl]oxy}methyl)-1,2-dihydropyrazin-2-one;
5-[4-(5-methoxypyrimidin-2-yl)piperazin-1-yl]-2-(pyridin-3-yl)-1,3-benzoxazole;
3-{6-[(5-methoxypyridin-2-yl)methoxy]-[1,3]oxazolo[5,4-b]pyridin-2-yl}pyridine;
5-(1-methyl-1H-pyrazol-4-yl)-2-(pyridin-3-yl)-1,3-benzoxazole;
3-{6-[(6-methoxypyridin-3-yl)methoxy]-[1,3]oxazolo[5,4-b]pyridin-2-yl}pyridine;
5-[(5-methoxypyridin-2-yl)methoxy]-2-(pyridin-4-yl)-1,3-benzoxazole;
[(3-{5-[(5-methoxypyridin-2-yl)methoxy]-1,3-benzoxazol-2-yl}phenyl)methyl]dimethylamine;
5-[(5-methoxypyridin-2-yl)methoxy]-2-(1-methyl-1H-pyrazol-4-yl)-1,3-benzoxazole;
5-[(5-methoxypyridin-2-yl)methoxy]-2-(pyrazin-2-yl)-1,3-benzoxazole;
5-[(5-methoxypyridin-2-yl)methoxy]-2-(1-methylpiperidin-4-yl)-1,3-benzoxazole;
5-[(5-methoxypyridin-2-yl)methoxy]-2-(1,3-thiazol-5-yl)-1,3-benzoxazole;
5-[2-(pyridin-2-yloxy)ethoxy]-2-(pyridin-3-yl)-1,3-benzoxazole;
4-[5-(1H-pyrazol-4-ylmethoxy)-1-benzofuran-2-yl]pyridine-3-carbonitrile;
3-{[(2-{5H,6H-imidazo[2,1-b][1,3]thiazol-3-yl}-1-benzofuran-5-yl)oxy]methyl}pyridine;
2-(3-fluoroazetidin-1-yl)-5-[(5-methoxypyridin-2-yl)methoxy]-1,3-benzoxazole;
2-{3H,4H,5H,6H,7H-imidazo[4,5-c]pyridin-5-yl}-5-[(5-methoxypyridin-2-yl)methoxy]-1,3-benzoxazole;
5-[(5-methoxypyridin-2-yl)methoxy]-2-{2H,4H,5H,6H,7H-pyrazolo[4,3-c]pyridin-5-yl}-1,3-benzoxazole;
2-{5H,6H,7H,8H-imidazo[1,5-a]pyrazin-7-yl}-5-[(5-methoxypyridin-2-yl)methoxy]-1,3-benzoxazole;
5-[(5-methoxypyridin-2-yl)methoxy]-2-{5H,6H,7H-pyrrolo[3,4-b]pyridin-6-yl})-1,3-benzoxazole;
7-{5-[(5-methoxypyridin-2-yl)methoxy]-1,3-benzoxazol-2-yl}-5,6,7,8-tetrahydro-1,7-naphthyridine;
2-(1H-imidazol-1-yl)-5-[(5-methoxypyridin-2-yl)methoxy]-1,3-benzoxazole;
2-{5H,6H,7H,8H-imidazo[1,2-a]pyrazin-7-yl}-5-[(5-methoxypyridin-2-yl)methoxy]-1,3-benzoxazole;
4-(5-{[1-(2-methoxyethyl)-1H-pyrazol-4-yl]methoxy}-1-benzofuran-2-yl)pyridine-3-carbonitrile;
2-[5-(2-methoxyethoxy)pyridin-3-yl]-5-[(5-methoxypyridin-2-yl)methoxy]-1,3-benzoxazole;

N-(5-{5-[(5-methoxypyridin-2-yl)methoxy]-1,3-benzoxazol-2-yl}pyridin-2-yl)acetamide;
5-{5-[(5-methoxypyridin-2-yl)methoxy]-1,3-benzoxazol-2-yl}pyridin-2-amine;
methyl({[4-({[2-(pyridin-3-yl)-1,3-benzoxazol-5-yl]oxy}methyl)phenyl]methyl})amine;
4-(5-{[1-(2-hydroxyethyl)-1H-pyrazol-4-yl]methoxy}-1-benzofuran-2-yl)pyridine-3-carbonitrile;
dimethyl({2-[4-({[2-(pyridin-3-yl)-1,3-benzoxazol-5-yl]oxy}methyl)phenoxy]ethyl})amine;
5-{[5-(2-methoxyethoxy)pyridin-2-yl]methoxy}-2-(pyridin-3-yl)-1,3-benzoxazole;
4-[5-({1-[2-(dimethylamino)ethyl]-1H-pyrazol-4-yl}methoxy)-1-benzofuran-2-yl]pyridine-3-carbonitrile;
5-{5-[(5-methoxypyridin-2-yl)methoxy]-1,3-benzoxazol-2-yl}-N-methylpyridin-2-amine;
3-{[(2-{2-bromo-5H,6H-imidazo[2,1-b][1,3]thiazol-3-yl}-1-benzofuran-5-yl)oxy]methyl}pyridine;
5-[(5-methoxypyrazin-2-yl)methoxy]-1-methyl-2-(pyridin-3-yl)-1H-1,3-benzodiazole;
6-[(5-methoxypyrazin-2-yl)methoxy]-1-methyl-2-(pyridin-3-yl)-1H-1,3-benzodiazole;
5-[(5-methoxypyrazin-2-yl)methoxy]-2-(pyridin-3-yl)-1H-1,3-benzodiazole;
5-[(5-methoxypyridin-2-yl)methoxy]-2-(piperazin-1-yl)-1,3-benzoxazole;
N-methyl-6-({[2-(pyridin-3-yl)-1,3-benzoxazol-5-yl]oxy}methyl)pyridin-3-amine;
3-[5-(pyridin-3-ylmethoxy)-1-benzofuran-2-yl]-5H,6H-imidazo[2,1-b]thiazole-2-carbonitrile;
5-{5-[(5-methoxypyridin-2-yl)methoxy]-1,3-benzoxazol-2-yl}-N-methylpyridine-2-carboxamide;
5-[(5-methoxypyridin-2-yl)methoxy]-2-(1-methyl-1H-imidazol-4-yl)-1,3-benzoxazole;
5-methoxy-N-{[2-(pyridin-3-yl)-1,3-benzoxazol-5-yl]methyl}pyridin-2-amine;
4-(5-{5H,6H-imidazo[2,1-b][1,3]thiazol-3-ylmethoxy}-1-benzofuran-2-yl)pyridine-3-carbonitrile;
5-({5-[2-(morpholin-4-yl)ethoxy]pyridin-2-yl}methoxy)-2-(pyridin-3-yl)-1,3-benzoxazole;
2-bromo-6-{5-[(5-methoxypyridin-2-yl)methoxy]-1-benzofuran-2-yl}benzonitrile;
4-{[2-(4-chlorophenyl)-1,3-benzoxazol-5-yl]carbamoyl}phenyl acetate;
N-(2-phenyl-1,3-benzoxazol-5-yl)benzamide;
4-methoxy-N-[2-(3-methylphenyl)-1,3-benzoxazol-5-yl]benzamide;
2-methoxy-N-[2-(4-methoxyphenyl)-1,3-benzoxazol-5-yl]benzamide;
4-methoxy-N-[2-(4-methoxyphenyl)-1,3-benzoxazol-5-yl]benzamide;
3-methoxy-N-[2-(4-methoxyphenyl)-1,3-benzoxazol-5-yl]benzamide;
3-{5-[(5-methoxypyridin-2-yl)methoxy]-1,3-benzoxazol-2-yl}pyridin-1-ium-1-olate;
2-phenoxy-N-[2-(pyridin-3-yl)-1,3-benzoxazol-5-yl]acetamide;
N-[2-(pyridin-3-yl)-1,3-benzoxazol-5-yl]-1-benzofuran-2-carboxamide;
N-[2-(pyridin-3-yl)-1,3-benzoxazol-5-yl]-6-(trifluoromethyl)pyridine-3-carboxamide;
N-[2-(pyridin-3-yl)-1,3-benzoxazol-5-yl]quinoxaline-2-carboxamide;
6-phenoxy-N-[2-(pyridin-3-yl)-1,3-benzoxazol-5-yl]pyridine-3-carboxamide;
N-[2-(pyridin-3-yl)-1,3-benzoxazol-5-yl]-2H-1,3-benzodioxole-5-carboxamide;
3-(benzyloxy)-N-[2-(pyridin-3-yl)-1,3-benzoxazol-5-yl]benzamide;
3-phenoxy-N-[2-(pyridin-3-yl)-1,3-benzoxazol-5-yl]benzamide;
N-[2-(pyridin-3-yl)-1,3-benzoxazol-5-yl]quinoline-2-carboxamide;
N-[2-(pyridin-3-yl)-1,3-benzoxazol-5-yl]-2,3-dihydro-1-benzofuran-2-carboxamide;
5-methyl-N-[2-(pyridin-3-yl)-1,3-benzoxazol-5-yl]pyridine-3-carboxamide;
N-[2-(pyridin-3-yl)-1,3-benzoxazol-5-yl]quinoxaline-6-carboxamide;
(2E)-3-(4-methoxyphenyl)-N-[2-(pyridin-3-yl)-1,3-benzoxazol-5-yl]prop-2-enamide;
5-methoxy-N-[2-(pyridin-3-yl)-1,3-benzoxazol-5-yl]pyridine-2-carboxamide;
3-cyano-N-[2-(pyridin-3-yl)-1,3-benzoxazol-5-yl]benzamide;
4-(methylsulfanyl)-N-[2-(pyridin-3-yl)-1,3-benzoxazol-5-yl]benzamide;
benzyl N-[2-(pyridin-3-yl)-1,3-benzoxazol-5-yl]carbamate;
5-[2-(pyridin-3-yl)-1,3-benzoxazol-5-yl]pyrazin-2-ol;
5-[(5-methoxypyridin-2-yl)methoxy]-2-(pyrimidin-5-yl)-1,3-benzoxazole;
2-(2,3-dihydro-1-benzofuran-2-yl)-5-[(5-methoxypyridin-2-yl)methoxy]-1,3-benzoxazole;
2-[(2R)-2,3-dihydro-1-benzofuran-2-yl]-5-[(5-methoxypyridin-2-yl)methoxy]-1,3-benzoxazole;
2-[(2S)-2,3-dihydro-1-benzofuran-2-yl]-5-[(5-methoxypyridin-2-yl)methoxy]-1,3-benzoxazole;
5-[5-(2-methoxyethoxy)pyrimidin-2-yl]-2-(pyridin-3-yl)-1,3-benzoxazole;
5-[(5-methoxypyridin-2-yl)methoxy]-2-(5-methylpyridin-3-yl)-1,3-benzoxazole;
5-[(5-methoxypyridin-2-yl)methoxy]-2-(2-methylpyridin-4-yl)-1,3-benzoxazole;
5-[(5-methoxypyridin-2-yl)methoxy]-2-(3-phenoxyphenyl)-1,3-benzoxazole;
6-{5-[(5-methoxypyridin-2-yl)methoxy]-1,3-benzoxazol-2-yl}-2-methyl-2,3-dihydropyridazin-3-one;
5-[(5-methoxypyridin-2-yl)methoxy]-2-(pyridazin-3-yl)-1,3-benzoxazole;
5-[(5-methoxypyridin-2-yl)methoxy]-2-(pyridazin-4-yl)-1,3-benzoxazole;
5-{5-[(5-methoxypyridin-2-yl)methoxy]-1,3-benzoxazol-2-yl}-1,2-dihydropyridin-2-one;
5-{5-[(5-methoxypyridin-2-yl)methoxy]-1,3-benzoxazol-2-yl}-1-methyl-1,2-dihydropyridin-2-one;
5-phenyl-N-[2-(pyridin-3-yl)-1,3-benzoxazol-5-yl]-1,3,4-oxadiazole-2-carboxamide;
5-[(5-methoxypyridin-2-yl)methoxy]-2-(pyrimidin-4-yl)-1,3-benzoxazole;
5-[(5-bromopyridin-2-yl)methoxy]-2-(pyridin-3-yl)-1,3-benzoxazole;
5-(pyridin-2-ylmethoxy)-2-(pyridin-3-yl)-1,3-benzoxazole;
N-[2-(pyridin-3-yl)-1,3-benzoxazol-5-yl]-1-benzofuran-5-carboxamide;
2-phenyl-N-[2-(pyridin-3-yl)-1,3-benzoxazol-5-yl]pyrimidine-5-carboxamide;
N-[2-(pyridin-3-yl)-1,3-benzoxazol-5-yl]-4-(pyrimidin-2-yl)benzamide;
1-methyl-N-[2-(pyridin-3-yl)-1,3-benzoxazol-5-yl]-1H-pyrazole-4-carboxamide;

4-[(6-methylpyrazin-2-yl)oxy]-N-[2-(pyridin-3-yl)-1,3-benzoxazol-5-yl]benzamide;
4-(phenoxymethyl)-N-[2-(pyridin-3-yl)-1,3-benzoxazol-5-yl]benzamide;
2-phenoxy-N-[2-(pyridin-3-yl)-1,3-benzoxazol-5-yl]pyridine-3-carboxamide;
4-cyano-N-[2-(pyridin-3-yl)-1,3-benzoxazol-5-yl]benzamide;
6-methoxy-N-[2-(pyridin-3-yl)-1,3-benzoxazol-5-yl]pyridine-2-carboxamide;
2-methyl-N-[2-(pyridin-3-yl)-1,3-benzoxazol-5-yl]pyridine-4-carboxamide;
3-methoxy-N-[2-(pyridin-3-yl)-1,3-benzoxazol-5-yl]pyridine-2-carboxamide;
4-methoxy-N-[2-(pyridin-3-yl)-1,3-benzoxazol-5-yl]pyridine-2-carboxamide;
4-hydroxy-N-[2-(pyridin-3-yl)-1,3-benzoxazol-5-yl]pyridine-2-carboxamide;
3-methoxy-N-[2-(pyridin-3-yl)-1,3-benzoxazol-5-yl]-1,2-oxazole-5-carboxamide;
5-methoxy-N-[2-(pyridin-3-yl)-1,3-benzoxazol-5-yl]pyridine-3-carboxamide;
6-({[2-(1-methyl-1H-pyrazol-4-yl)-1,3-benzoxazol-5-yl]oxy}methyl)pyridin-3-ol;
5-[(5-methoxypyrazin-2-yl)methoxy]-2-(1-methyl-1H-pyrazol-4-yl)-1,3-benzoxazole;
2-methoxy-5-({[2-(1-methyl-1H-pyrazol-4-yl)-[1,3]oxazolo[5,4-b]pyridin-6-yl]oxy}methyl)pyrazine;
3-{6-[(5-bromopyridin-2-yl)methoxy]-[1,3]oxazolo[5,4-b]pyridin-2-yl}pyridine;
3-methoxy-6-({[2-(pyridin-3-yl)-[1,3]oxazolo[5,4-b]pyridin-6-yl]oxy}methyl)pyridazine;
3-{5-[(5-methoxypyridin-2-yl)methoxy]-1,3-benzoxazol-2-yl}benzonitrile;
4-{5-[(5-methoxypyridin-2-yl)methoxy]-1,3-benzoxazol-2-yl}benzonitrile;
5-(1-methyl-1H-pyrazol-4-yl)-2-({[2-(pyridin-3-yl)-[1,3]oxazolo[5,4-b]pyridin-6-yl]oxy}methyl)pyridine;
3-methoxy-5-({[2-(pyridin-3-yl)-[1,3]oxazolo[5,4-b]pyridin-6-yl]oxy}methyl)pyridine;
4-methoxy-2-({[2-(pyridin-3-yl)-[1,3]oxazolo[5,4-b]pyridin-6-yl]oxy}methyl)pyridine;
2-({[2-(1-methyl-1H-pyrazol-4-yl)-[1,3]oxazolo[5,4-b]pyridin-6-yl]oxy}methyl)pyrazine;
[(3-{5-[(5-methoxypyridin-2-yl)methoxy]-1,3-benzoxazol-2-yl}phenyl)methyl](methyl)amine;
(5-methoxypyridin-2-yl)methyl N-[2-(pyridin-3-yl)-1,3-benzoxazol-5-yl]carbamate;
2-(5-methoxypyridin-2-yl)-5-[(5-methoxypyridin-2-yl)methoxy]-1,3-benzoxazole;
2-(1-benzofuran-2-yl)-5-[(5-methoxypyridin-2-yl)methoxy]-1,3-benzoxazole;
5-[(5-methoxypyridin-2-yl)methoxy]-2-[6-(trifluoromethyl)pyridin-3-yl]-1,3-benzoxazole;
2-(1-benzofuran-5-yl)-5-[(5-methoxypyridin-2-yl)methoxy]-1,3-benzoxazole;
2-{5-[(5-methoxypyridin-2-yl)methoxy]-1,3-benzoxazol-2-yl}quinoline;
2-[3-(benzyloxy)phenyl]-5-[(5-methoxypyridin-2-yl)methoxy]-1,3-benzoxazole;
5-[(5-methoxypyridin-2-yl)methoxy]-2-[4-(pyrimidin-2-yl)phenyl]-1,3-benzoxazole;
2-[(E)-2-(4-Methoxyphenyl)ethenyl]-5-[(5-methoxypyridin-2-yl)methoxy]-1,3-benzoxazole;
5-methoxy-2-({[2-(pyridin-3-yl)-[1,3]oxazolo[5,4-b]pyridin-6-yl]oxy}methyl)pyrimidine;
6-({[2-(1-methyl-1H-pyrazol-4-yl)-[1,3]oxazolo[5,4-b]pyridin-6-yl]oxy}methyl)pyridin-3-amine;
5-{5-[(5-hydroxypyridin-2-yl)methoxy]-1,3-benzoxazol-2-yl}-N-methylpyridine-2-carboxamide;
6-{6-[(5-methoxypyridin-2-yl)methoxy]-[1,3]oxazolo[5,4-b]pyridin-2-yl}-2-methyl-2,3-dihydropyridazin-3-one;
2-methyl-6-({[2-(pyridin-3-yl)-[1,3]oxazolo[5,4-b]pyridin-6-yl]oxy}methyl)-2,3-dihydropyridazin-3-one;
2-{6-[(5-methoxypyridin-2-yl)methoxy]-[1,3]oxazolo[5,4-b]pyridin-2-yl}pyrazine;
5-{6-[(5-methoxypyridin-2-yl)methoxy]-[1,3]oxazolo[5,4-b]pyridin-2-yl}-N-methylpyridine-2-carboxamide;
5-{5-[(5-methoxypyridin-2-yl)methoxy]-1,3-benzoxazol-2-yl}-1-methyl-1,2-dihydropyrazin-2-one;
6-(6-{[5-(2-fluoroethoxy)pyridin-2-yl]methoxy}-[1,3]oxazolo[5,4-b]pyridin-2-yl)-2-methyl-2,3-dihydropyridazin-3-one;
5-methoxy-2-({[2-(pyridin-3-yl)-[1,3]oxazolo[5,4-b]pyridin-6-yl]oxy}methyl)pyridin-1-ium-1-olate;
3-{6-[(5-methoxy-1-oxidopyridin-1-ium-2-yl)methoxy]-[1,3]oxazolo[5,4-b]pyridin-2-yl}pyridin-1-ium-1-olate;
5-{5-[(5-methoxypyridin-2-yl)methoxy]-1,3-benzoxazol-2-yl}-2-(methylcarbamoyl)pyridin-1-ium-1-olate;
(5-hydroxypyridin-2-yl)methyl N-[2-(pyridin-3-yl)-1,3-benzoxazol-5-yl]carbamate;
5-methoxy-N-[2-(1-methyl-6-oxo-1,6-dihydropyridazin-3-yl)-1,3-benzoxazol-5-yl]pyridine-2-carboxamide;
5-methoxy-N-[2-(1-methyl-6-oxo-1,6-dihydropyridazin-3-yl)-1,3-benzoxazol-5-yl]pyridine-3-carboxamide;
4-methoxy-N-[2-(1-methyl-6-oxo-1,6-dihydropyridazin-3-yl)-1,3-benzoxazol-5-yl]pyridine-2-carboxamide;
1-methyl-N-[2-(1-methyl-6-oxo-1,6-dihydropyridazin-3-yl)-1,3-benzoxazol-5-yl]-6-oxo-1,6-dihydropyridazine-3-carboxamide;
[(5-{5-[(5-methoxypyridin-2-yl)methoxy]-1,3-benzoxazol-2-yl}pyridin-3-yl)methyl](methyl)amine;
6-{5-[(5-hydroxypyridin-2-yl)methoxy]-1,3-benzoxazol-2-yl}-2-methyl-2,3-dihydropyridazin-3-one; and
N-(5-Methoxypyridin-3-yl)-2-(pyridin-3-yl)-1,3-benzoxazole-5-carboxamide, or a pharmaceutically acceptable salt thereof, and wherein the compound is labeled with one or more positron-emitting radionuclides.

15. The compound of claim 1, wherein said one or more positron-emitting radionuclides are selected from: $^{11}C$, $^{13}N$, $^{15}O$, and $^{18}F$.

16. A method of generating diagnostic images in an individual comprising administering an effective amount of a compound of claim 1 to an individual, and generating an image of at least a part of said individual.

17. The method of claim 16, wherein generating an image of at least a part of said individual comprises generating an image to detect a presence or absence of huntingtin protein (HTT protein) monomers or aggregates in a brain of said individual; and detecting a presence or absence of a pathologic process.

18. The method of claim 17, wherein said HTT protein monomers or aggregates are present in the basal ganglia of said brain of said individual.

19. The method of claim 17, wherein the pathologic process is a neurodegenerative disease.

20. The method of claim 19, wherein the neurodegenerative disease is chosen from Alzheimer's disease, amyotrophic lateral sclerosis, Huntington's disease, Parkinson's disease, Prion disease and spinocerebellar ataxias.

21. The method of claim 20, wherein the neurodegenerative disease is Huntington's disease (HD).

22. The method of claim 16, wherein said effective amount of said compound comprises from about 0.1 to about 20 mCi.

23. The method of claim 16, wherein said generating an image comprises positron emission tomography (PET) imaging, PET with concurrent computed tomography imaging (PET/CT), PET with concurrent magnetic resonance imaging (PET/MRI), or a combination thereof.

24. The method of claim 23, wherein said generating an image comprises PET imaging.

25. A compound selected from:
tert-butyl 4-[2-(pyridin-3-yl)-1,3-benzoxazol-5-yl]piperazine-1-carboxylate;
4-methoxy-N-[2-(pyridin-3-yl)-1,3-benzoxazol-5-yl]benzamide;
4-methoxy-N-[2-(pyridin-4-yl)-1,3-benzoxazol-5-yl]benzamide;
N-[(4-methoxyphenyl)methyl]-2-(pyridin-3-yl)-1,3-benzoxazol-5-amine;
2-(3-bromopyridin-4-yl)-6-[2-(morpholin-4-yl)ethoxy]-1,3-benzothiazole;
5-methoxy-N-[2-(3-methylphenyl)-1,3-benzoxazol-5-yl]pyridine-2-carboxamide;
6-methoxy-N-[2-(3-methylphenyl)-1,3-benzoxazol-5-yl]pyridine-3-carboxamide;
2-methoxy-N-[2-(3-methylphenyl)-1,3-benzoxazol-5-yl]pyrimidine-5-carboxamide;
5-methoxy-N-[2-(3-methylphenyl)-1,3-benzoxazol-5-yl]pyrazine-2-carboxamide;
4-methoxy-N-[2-(3-methylphenyl)-[1,3]oxazolo[5,4-b]pyridin-6-yl]benzamide;
5-(4-methoxyphenyl)-2-(pyridin-3-yl)-1,3-benzoxazole;
N-(4-methoxyphenyl)-2-(pyridin-3-yl)-1,3-benzoxazol-5-amine;
2-(pyridin-3-yl)-N-{[1,2,4]triazolo[4,3-a]pyridin-3-yl}-1,3-benzoxazol-5-amine;
2-(pyridin-3-yl)-N-(pyrimidin-4-yl)-1,3-benzoxazol-5-amine;
2-(pyridin-3-yl)-N-(pyrimidin-2-yl)-1,3-benzoxazol-5-amine;
5-(5-methoxypyridin-2-yl)-2-(pyridin-3-yl)-1,3-benzoxazole;
5-(2-methoxypyrimidin-5-yl)-2-(pyridin-3-yl)-1,3-benzoxazole;
5-(5-methoxypyrimidin-2-yl)-2-(pyridin-3-yl)-1,3-benzoxazole;
5-(6-methoxypyridazin-3-yl)-2-(pyridin-3-yl)-1,3-benzoxazole;
5-(5-methoxypyrazin-2-yl)-2-(pyridin-3-yl)-1,3-benzoxazole;
1-methyl-4-[5-(pyrimidin-5-ylmethoxy)-1-benzofuran-2-yl]-1H-pyrazole-3-carbonitrile;
4-[5-(pyrimidin-5-ylmethoxy)-1-benzofuran-2-yl]pyridine-3-carbonitrile;
4-{5-[(5-methoxypyridin-2-yl)methoxy]-1-benzofuran-2-yl}pyridine-3-carbonitrile;
4-{5-[(5-methoxypyridin-2-yl)methoxy]-1-benzofuran-2-yl}pyridine;
4-{5-[(1-methyl-1H-imidazol-4-yl)methoxy]-1-benzofuran-2-yl}pyridine-3-carbonitrile;
4-{5-[(1-methyl-1H-imidazol-2-yl)methoxy]-1-benzofuran-2-yl}pyridine-3-carbonitrile;
5-methoxy-2-[2-(pyridin-3-yl)-1,3-benzoxazol-5-yl]-2,3-dihydro-1H-isoindol-1-one;
3-{6-[(E)-2-(4-methoxyphenyl)ethenyl]-[1,3]oxazolo[5,4-b]pyridin-2-yl}pyridine;
4-[5-(pyridin-3-yloxy)-1-benzofuran-2-yl]pyridine-3-carbonitrile;
6-methoxy-2-[2-(pyridin-3-yl)-1,3-benzoxazol-5-yl]-1,2,3,4-tetrahydroisoquinolin-1-one;
dimethyl({3-[4-({[2-(pyridin-3-yl)-1,3-benzoxazol-5-yl]oxy}methyl)phenoxy]propyl})amine;
5-[(1-methyl-1H-pyrazol-4-yl)methoxy]-2-(pyridin-3-yl)-1,3-benzoxazole;
5-[(4-methoxyphenyl)methoxy]-2-(pyridin-3-yl)-1,3-benzoxazole;
5-[(3-methoxyphenyl)methoxy]-2-(pyridin-3-yl)-1,3-benzoxazole;
5-[(5-methoxypyridin-2-yl)methoxy]-2-(pyridin-3-yl)-1,3-benzoxazole;
2-(pyridin-3-yl)-5-(pyridin-3-ylmethoxy)-1,3-benzoxazole;
5-{5H,6H-imidazo[2,1-b][1,3]thiazol-3-ylmethoxy}-2-(pyridin-3-yl)-1,3-benzoxazole;
1-(pyridin-2-yl)-2-[2-(pyridin-3-yl)-1,3-benzoxazol-5-yl]ethan-1-ol;
1-(pyridin-2-yl)-2-[2-(pyridin-3-yl)-1,3-benzoxazol-5-yl]ethan-1-one;
6-methoxy-2-[2-(pyridin-3-yl)-1,3-benzoxazol-5-yl]-1,2-dihydroisoquinolin-1-one;
2-(pyridin-3-yl)-N-[2,2,2-trifluoro-1-(4-methoxyphenyl)ethyl]-[1,3]oxazolo[5,4-b]pyridin-6-amine;
3-{6-[2-(4-methoxyphenyl)ethynyl]-[1,3]oxazolo[5,4-b]pyridin-2-yl}pyridine;
3-{6-[(Z)-2-(4-methoxyphenyl)ethenyl]-[1,3]oxazolo[5,4-b]pyridin-2-yl}pyridine;
5-methoxy-2-[2-(pyridin-3-yl)-[1,3]oxazolo[5,4-b]pyridin-6-yl]-2,3-dihydro-1H-isoindol-1-one;
5-[(5-methoxypyrazin-2-yl)methoxy]-2-(pyridin-3-yl)-1,3-benzoxazole;
3-methoxy-6-[2-(pyridin-3-yl)-1,3-benzoxazol-5-yl]-5H,6H,7H-pyrrolo[3,4-b]pyridin-7-one;
2-(pyridin-3-yl)-6-(pyridin-3-ylmethoxy)-1,3-benzoxazole;
3-{6-[2-(pyridin-3-yl)ethynyl]-[1,3]oxazolo[5,4-b]pyridin-2-yl}pyridine;
5-{[(5-methoxypyridin-2-yl)oxy]methyl}-2-(pyridin-3-yl)-1,3-benzoxazole;
4-[5-(pyridin-3-ylmethoxy)-1-benzofuran-2-yl]pyridine-3-carbonitrile;
4-{5-[(1-methyl-1H-pyrazol-4-yl)methoxy]-1-benzofuran-2-yl}pyridine-3-carbonitrile;
3-[5-(pyridin-3-ylmethoxy)-1-benzofuran-2-yl]pyridine-4-carbonitrile;
3-{5-[(1-methyl-1H-pyrazol-4-yl)methoxy]-1-benzofuran-2-yl}pyridine-4-carbonitrile;
3-{6-[1-(5-methoxypyridin-2-yl)ethoxy]-[1,3]oxazolo[5,4-b]pyridin-2-yl}pyridine;
4-{5-[(5-methoxypyrazin-2-yl)methoxy]-1-benzofuran-2-yl}pyridine-3-carbonitrile;
6-({[2-(pyridin-3-yl)-1,3-benzoxazol-5-yl]oxy}methyl)pyridin-3-ol;
5-{[5-(prop-2-en-1-yloxy)pyrazin-2-yl]methoxy}-2-(pyridin-3-yl)-1,3-benzoxazole;
5-({[2-(pyridin-3-yl)-1,3-benzoxazol-5-yl]oxy}methyl)-1,2-dihydropyrazin-2-one;
1-methyl-5-({[2-(pyridin-3-yl)-1,3-benzoxazol-5-yl]oxy}methyl)-1,2-dihydropyrazin-2-one;
5-[4-(5-methoxypyrimidin-2-yl)piperazin-1-yl]-2-(pyridin-3-yl)-1,3-benzoxazole;

3-{6-[(5-methoxypyridin-2-yl)methoxy]-[1,3]oxazolo[5,4-b]pyridin-2-yl}pyridine;
5-(1-methyl-1H-pyrazol-4-yl)-2-(pyridin-3-yl)-1,3-benzoxazole;
3-{6-[(6-methoxypyridin-3-yl)methoxy]-[1,3]oxazolo[5,4-b]pyridin-2-yl}pyridine;
5-[(5-methoxypyridin-2-yl)methoxy]-2-(pyridin-4-yl)-1,3-benzoxazole;
[(3-{5-[(5-methoxypyridin-2-yl)methoxy]-1,3-benzoxazol-2-yl}phenyl)methyl]dimethylamine;
5-[(5-methoxypyridin-2-yl)methoxy]-2-(1-methyl-1H-pyrazol-4-yl)-1,3-benzoxazole;
5-[(5-methoxypyridin-2-yl)methoxy]-2-(pyrazin-2-yl)-1,3-benzoxazole;
5-[(5-methoxypyridin-2-yl)methoxy]-2-(1-methylpiperidin-4-yl)-1,3-benzoxazole;
5-[(5-methoxypyridin-2-yl)methoxy]-2-(1,3-thiazol-5-yl)-1,3-benzoxazole;
5-[2-(pyridin-2-yloxy)ethoxy]-2-(pyridin-3-yl)-1,3-benzoxazole;
4-[5-(1H-pyrazol-4-ylmethoxy)-1-benzofuran-2-yl]pyridine-3-carbonitrile;
3-{[(2-{5H,6H-imidazo[2,1-b][1,3]thiazol-3-yl}-1-benzofuran-5-yl)oxy]methyl}pyridine;
2-(3-fluoroazetidin-1-yl)-5-[(5-methoxypyridin-2-yl)methoxy]-1,3-benzoxazole;
2-{3H,4H,5H,6H,7H-imidazo[4,5-c]pyridin-5-yl}-5-[(5-methoxypyridin-2-yl)methoxy]-1,3-benzoxazole;
5-[(5-methoxypyridin-2-yl)methoxy]-2-{2H,4H,5H,6H,7H-pyrazolo[4,3-c]pyridin-5-yl}-1,3-benzoxazole;
2-{5H,6H,7H,8H-imidazo[1,5-a]pyrazin-7-yl}-5-[(5-methoxypyridin-2-yl)methoxy]-1,3-benzoxazole;
5-[(5-methoxypyridin-2-yl)methoxy]-2-{5H,6H,7H-pyrrolo[3,4-b]pyridin-6-yl}-1,3-benzoxazole;
7-{5-[(5-methoxypyridin-2-yl)methoxy]-1,3-benzoxazol-2-yl}-5,6,7,8-tetrahydro-1,7-naphthyridine;
2-(1H-imidazol-1-yl)-5-[(5-methoxypyridin-2-yl)methoxy]-1,3-benzoxazole;
2-{5H,6H,7H,8H-imidazo[1,2-a]pyrazin-7-yl}-5-[(5-methoxypyridin-2-yl)methoxy]-1,3-benzoxazole;
4-(5-{[1-(2-methoxyethyl)-1H-pyrazol-4-yl]methoxy}-1-benzofuran-2-yl)pyridine-3-carbonitrile;
2-[5-(2-methoxyethoxy)pyridin-3-yl]-5-[(5-methoxypyridin-2-yl)methoxy]-1,3-benzoxazole;
N-(5-{5-[(5-methoxypyridin-2-yl)methoxy]-1,3-benzoxazol-2-yl}pyridin-2-yl)acetamide;
5-{5-[(5-methoxypyridin-2-yl)methoxy]-1,3-benzoxazol-2-yl}pyridin-2-amine;
methyl({[4-({[2-(pyridin-3-yl)-1,3-benzoxazol-5-yl]oxy}methyl)phenyl]methyl})amine;
4-(5-{[1-(2-hydroxyethyl)-1H-pyrazol-4-yl]methoxy}-1-benzofuran-2-yl)pyridine-3-carbonitrile;
dimethyl({2-[4-({[2-(pyridin-3-yl)-1,3-benzoxazol-5-yl]oxy}methyl)phenoxy]ethyl})amine;
5-{[5-(2-methoxyethoxy)pyridin-2-yl]methoxy}-2-(pyridin-3-yl)-1,3-benzoxazole;
4-[5-({1-[2-(dimethylamino)ethyl]-1H-pyrazol-4-yl}methoxy)-1-benzofuran-2-yl]pyridine-3-carbonitrile;
5-{5-[(5-methoxypyridin-2-yl)methoxy]-1,3-benzoxazol-2-yl}-N-methylpyridin-2-amine;
3-{[(2-{2-bromo-5H,6H-imidazo[2,1-b][1,3]thiazol-3-yl}-1-benzofuran-5-yl)oxy]methyl}pyridine;
5-[(5-methoxypyrazin-2-yl)methoxy]-1-methyl-2-(pyridin-3-yl)-1H-1,3-benzodiazole;
6-[(5-methoxypyrazin-2-yl)methoxy]-1-methyl-2-(pyridin-3-yl)-1H-1,3-benzodiazole;
5-[(5-methoxypyrazin-2-yl)methoxy]-2-(pyridin-3-yl)-1H-1,3-benzodiazole;
5-[(5-methoxypyridin-2-yl)methoxy]-2-(piperazin-1-yl)-1,3-benzoxazole;
N-methyl-6-({[2-(pyridin-3-yl)-1,3-benzoxazol-5-yl]oxy}methyl)pyridin-3-amine;
3-[5-(pyridin-3-ylmethoxy)-1-benzofuran-2-yl]-5H,6H-imidazo[2,1-b][1,3]thiazole-2-carbonitrile;
5-{5-[(5-methoxypyridin-2-yl)methoxy]-1,3-benzoxazol-2-yl}-N-methylpyridine-2-carboxamide;
5-[(5-methoxypyridin-2-yl)methoxy]-2-(1-methyl-1H-imidazol-4-yl)-1,3-benzoxazole;
5-methoxy-N-{[2-(pyridin-3-yl)-1,3-benzoxazol-5-yl]methyl}pyridin-2-amine;
4-(5-{5H,6H-imidazo[2,1-b][1,3]thiazol-3-ylmethoxy}-1-benzofuran-2-yl)pyridine-3-carbonitrile;
5-({5-[2-(morpholin-4-yl)ethoxy]pyridin-2-yl}methoxy)-2-(pyridin-3-yl)-1,3-benzoxazole;
2-bromo-6-{5-[(5-methoxypyridin-2-yl)methoxy]-1-benzofuran-2-yl}benzonitrile;
4-{[2-(4-chlorophenyl)-1,3-benzoxazol-5-yl]carbamoyl}phenyl acetate;
N-(2-phenyl-1,3-benzoxazol-5-yl)benzamide;
4-methoxy-N-[2-(3-methylphenyl)-1,3-benzoxazol-5-yl]benzamide;
2-methoxy-N-[2-(4-methoxyphenyl)-1,3-benzoxazol-5-yl]benzamide;
4-methoxy-N-[2-(4-methoxyphenyl)-1,3-benzoxazol-5-yl]benzamide;
3-methoxy-N-[2-(4-methoxyphenyl)-1,3-benzoxazol-5-yl]benzamide;
3-{5-[(5-methoxypyridin-2-yl)methoxy]-1,3-benzoxazol-2-yl}pyridin-1-ium-1-olate;
2-phenoxy-N-[2-(pyridin-3-yl)-1,3-benzoxazol-5-yl]acetamide;
N-[2-(pyridin-3-yl)-1,3-benzoxazol-5-yl]-1-benzofuran-2-carboxamide;
N-[2-(pyridin-3-yl)-1,3-benzoxazol-5-yl]-6-(trifluoromethyl)pyridine-3-carboxamide;
N-[2-(pyridin-3-yl)-1,3-benzoxazol-5-yl]quinoxaline-2-carboxamide;
6-phenoxy-N-[2-(pyridin-3-yl)-1,3-benzoxazol-5-yl]pyridine-3-carboxamide;
N-[2-(pyridin-3-yl)-1,3-benzoxazol-5-yl]-2H-1,3-benzodioxole-5-carboxamide;
3-(benzyloxy)-N-[2-(pyridin-3-yl)-1,3-benzoxazol-5-yl]benzamide;
3-phenoxy-N-[2-(pyridin-3-yl)-1,3-benzoxazol-5-yl]benzamide;
N-[2-(pyridin-3-yl)-1,3-benzoxazol-5-yl]quinoline-2-carboxamide;
N-[2-(pyridin-3-yl)-1,3-benzoxazol-5-yl]-2,3-dihydro-1-benzofuran-2-carboxamide;
5-methyl-N-[2-(pyridin-3-yl)-1,3-benzoxazol-5-yl]pyridine-3-carboxamide;
N-[2-(pyridin-3-yl)-1,3-benzoxazol-5-yl]quinoxaline-6-carboxamide;
(2E)-3-(4-methoxyphenyl)-N-[2-(pyridin-3-yl)-1,3-benzoxazol-5-yl]prop-2-enamide;
5-methoxy-N-[2-(pyridin-3-yl)-1,3-benzoxazol-5-yl]pyridine-2-carboxamide;
3-cyano-N-[2-(pyridin-3-yl)-1,3-benzoxazol-5-yl]benzamide;
4-(methylsulfanyl)-N-[2-(pyridin-3-yl)-1,3-benzoxazol-5-yl]benzamide;
benzyl N-[2-(pyridin-3-yl)-1,3-benzoxazol-5-yl]carbamate;

5-[2-(pyridin-3-yl)-1,3-benzoxazol-5-yl]pyrazin-2-ol;
5-[(5-methoxypyridin-2-yl)methoxy]-2-(pyrimidin-5-yl)-1,3-benzoxazole;
2-(2,3-dihydro-1-benzofuran-2-yl)-5-[(5-methoxypyridin-2-yl)methoxy]-1,3-benzoxazole;
2-[(2R)-2,3-dihydro-1-benzofuran-2-yl]-5-[(5-methoxypyridin-2-yl)methoxy]-1,3-benzoxazole;
2-[(2S)-2,3-dihydro-1-benzofuran-2-yl]-5-[(5-methoxypyridin-2-yl)methoxy]-1,3-benzoxazole;
5-[5-(2-methoxyethoxy)pyrimidin-2-yl]-2-(pyridin-3-yl)-1,3-benzoxazole;
5-[(5-methoxypyridin-2-yl)methoxy]-2-(5-methylpyridin-3-yl)-1,3-benzoxazole;
5-[(5-methoxypyridin-2-yl)methoxy]-2-(2-methylpyridin-4-yl)-1,3-benzoxazole;
5-[(5-methoxypyridin-2-yl)methoxy]-2-(3-phenoxyphenyl)-1,3-benzoxazole;
6-{5-[(5-methoxypyridin-2-yl)methoxy]-1,3-benzoxazol-2-yl}-2-methyl-2,3-dihydropyridazin-3-one;
5-[(5-methoxypyridin-2-yl)methoxy]-2-(pyridazin-3-yl)-1,3-benzoxazole;
5-[(5-methoxypyridin-2-yl)methoxy]-2-(pyridazin-4-yl)-1,3-benzoxazole;
5-{5-[(5-methoxypyridin-2-yl)methoxy]-1,3-benzoxazol-2-yl}-1,2-dihydropyridin-2-one;
5-{5-[(5-methoxypyridin-2-yl)methoxy]-1,3-benzoxazol-2-yl}-1-methyl-1,2-dihydropyridin-2-one;
5-phenyl-N-[2-(pyridin-3-yl)-1,3-benzoxazol-5-yl]-1,3,4-oxadiazole-2-carboxamide;
5-[(5-methoxypyridin-2-yl)methoxy]-2-(pyrimidin-4-yl)-1,3-benzoxazole;
5-[(5-bromopyridin-2-yl)methoxy]-2-(pyridin-3-yl)-1,3-benzoxazole;
5-(pyridin-2-ylmethoxy)-2-(pyridin-3-yl)-1,3-benzoxazole;
N-[2-(pyridin-3-yl)-1,3-benzoxazol-5-yl]-1-benzofuran-5-carboxamide;
2-phenyl-N-[2-(pyridin-3-yl)-1,3-benzoxazol-5-yl]pyrimidine-5-carboxamide;
N-[2-(pyridin-3-yl)-1,3-benzoxazol-5-yl]-4-(pyrimidin-2-yl)benzamide;
1-methyl-N-[2-(pyridin-3-yl)-1,3-benzoxazol-5-yl]-1H-pyrazole-4-carboxamide;
4-[(6-methylpyrazin-2-yl)oxy]-N-[2-(pyridin-3-yl)-1,3-benzoxazol-5-yl]benzamide;
4-(phenoxymethyl)-N-[2-(pyridin-3-yl)-1,3-benzoxazol-5-yl]benzamide;
2-phenoxy-N-[2-(pyridin-3-yl)-1,3-benzoxazol-5-yl]pyridine-3-carboxamide;
4-cyano-N-[2-(pyridin-3-yl)-1,3-benzoxazol-5-yl]benzamide;
6-methoxy-N-[2-(pyridin-3-yl)-1,3-benzoxazol-5-yl]pyridine-2-carboxamide;
2-methyl-N-[2-(pyridin-3-yl)-1,3-benzoxazol-5-yl]pyridine-4-carboxamide;
3-methoxy-N-[2-(pyridin-3-yl)-1,3-benzoxazol-5-yl]pyridine-2-carboxamide;
4-methoxy-N-[2-(pyridin-3-yl)-1,3-benzoxazol-5-yl]pyridine-2-carboxamide;
4-hydroxy-N-[2-(pyridin-3-yl)-1,3-benzoxazol-5-yl]pyridine-2-carboxamide;
3-methoxy-N-[2-(pyridin-3-yl)-1,3-benzoxazol-5-yl]-1,2-oxazole-5-carboxamide;
5-methoxy-N-[2-(pyridin-3-yl)-1,3-benzoxazol-5-yl]pyridine-3-carboxamide;
6-({[2-(1-methyl-1H-pyrazol-4-yl)-1,3-benzoxazol-5-yl]oxy}methyl)pyridin-3-ol;
5-[(5-methoxypyrazin-2-yl)methoxy]-2-(1-methyl-1H-pyrazol-4-yl)-1,3-benzoxazole;
2-methoxy-5-({[2-(1-methyl-1H-pyrazol-4-yl)-[1,3]oxazolo[5,4-b]pyridin-6-yl]oxy}methyl)pyrazine;
3-{6-[(5-bromopyridin-2-yl)methoxy]-[1,3]oxazolo[5,4-b]pyridin-2-yl}pyridine;
3-methoxy-6-({[2-(pyridin-3-yl)-[1,3]oxazolo[5,4-b]pyridin-6-yl]oxy}methyl)pyridazine;
3-{5-[(5-methoxypyridin-2-yl)methoxy]-1,3-benzoxazol-2-yl}benzonitrile;
4-{5-[(5-methoxypyridin-2-yl)methoxy]-1,3-benzoxazol-2-yl}benzonitrile;
5-(1-methyl-1H-pyrazol-4-yl)-2-({[2-(pyridin-3-yl)-[1,3]oxazolo[5,4-b]pyridin-6-yl]oxy}methyl)pyridine;
3-methoxy-5-({[2-(pyridin-3-yl)-[1,3]oxazolo[5,4-b]pyridin-6-yl]oxy}methyl)pyridine;
4-methoxy-2-({[2-(pyridin-3-yl)-[1,3]oxazolo[5,4-b]pyridin-6-yl]oxy}methyl)pyridine;
2-({[2-(1-methyl-1H-pyrazol-4-yl)-[1,3]oxazolo[5,4-b]pyridin-6-yl]oxy}methyl)pyrazine;
[(3-{5-[(5-methoxypyridin-2-yl)methoxy]-1,3-benzoxazol-2-yl}phenyl)methyl](methyl)amine;
(5-methoxypyridin-2-yl)methyl N-[2-(pyridin-3-yl)-1,3-benzoxazol-5-yl]carbamate;
2-(5-methoxypyridin-2-yl)-5-[(5-methoxypyridin-2-yl)methoxy]-1,3-benzoxazole;
2-(1-benzofuran-2-yl)-5-[(5-methoxypyridin-2-yl)methoxy]-1,3-benzoxazole;
5-[(5-methoxypyridin-2-yl)methoxy]-2-[6-(trifluoromethyl)pyridin-3-yl]-1,3-benzoxazole;
2-(1-benzofuran-5-yl)-5-[(5-methoxypyridin-2-yl)methoxy]-1,3-benzoxazole;
2-{5-[(5-methoxypyridin-2-yl)methoxy]-1,3-benzoxazol-2-yl}quinoline;
2-[3-(benzyloxy)phenyl]-5-[(5-methoxypyridin-2-yl)methoxy]-1,3-benzoxazole;
5-[(5-methoxypyridin-2-yl)methoxy]-2-[4-(pyrimidin-2-yl)phenyl]-1,3-benzoxazole;
2-[(E)-2-(4-Methoxyphenyl)ethenyl]-5-[(5-methoxypyridin-2-yl)methoxy]-1,3-benzoxazole;
5-methoxy-2-({[2-(pyridin-3-yl)-[1,3]oxazolo[5,4-b]pyridin-6-yl]oxy}methyl)pyrimidine;
6-({[2-(1-methyl-1H-pyrazol-4-yl)-[1,3]oxazolo[5,4-b]pyridin-6-yl]oxy}methyl)pyridin-3-amine;
5-{5-[(5-hydroxypyridin-2-yl)methoxy]-1,3-benzoxazol-2-yl}-N-methylpyridine-2-carboxamide;
6-{6-[(5-methoxypyridin-2-yl)methoxy]-[1,3]oxazolo[5,4-b]pyridin-2-yl}-2-methyl-2,3-dihydropyridazin-3-one;
2-methyl-6-({[2-(pyridin-3-yl)-[1,3]oxazolo[5,4-b]pyridin-6-yl]oxy}methyl)-2,3-dihydropyridazin-3-one;
2-{6-[(5-methoxypyridin-2-yl)methoxy]-[1,3]oxazolo[5,4-b]pyridin-2-yl}pyrazine;
5-{6-[(5-methoxypyridin-2-yl)methoxy]-[1,3]oxazolo[5,4-b]pyridin-2-yl}-N-methylpyridine-2-carboxamide;
5-{5-[(5-methoxypyridin-2-yl)methoxy]-1,3-benzoxazol-2-yl}-1-methyl-1,2-dihydropyrazin-2-one;
6-(6-{[5-(2-fluoroethoxy)pyridin-2-yl]methoxy}-[1,3]oxazolo[5,4-b]pyridin-2-yl)-2-methyl-2,3-dihydropyridazin-3-one;
5-methoxy-2-({[2-(pyridin-3-yl)-[1,3]oxazolo[5,4-b]pyridin-6-yl]oxy}methyl)pyridin-1-ium-1-olate;
3-{6-[(5-methoxy-1-oxidopyridin-1-ium-2-yl)methoxy]-[1,3]oxazolo[5,4-b]pyridin-2-yl}pyridin-1-ium-1-olate;
5-{5-[(5-methoxypyridin-2-yl)methoxy]-1,3-benzoxazol-2-yl}-2-(methylcarbamoyl)pyridin-1-ium-1-olate;

(5-hydroxypyridin-2-yl)methyl N-[2-(pyridin-3-yl)-1,3-benzoxazol-5-yl]carbamate;
5-methoxy-N-[2-(1-methyl-6-oxo-1,6-dihydropyridazin-3-yl)-1,3-benzoxazol-5-yl]pyridine-2-carboxamide;
5-methoxy-N-[2-(1-methyl-6-oxo-1,6-dihydropyridazin-3-yl)-1,3-benzoxazol-5-yl]pyridine-3-carboxamide;
4-methoxy-N-[2-(1-methyl-6-oxo-1,6-dihydropyridazin-3-yl)-1,3-benzoxazol-5-yl]pyridine-2-carboxamide;
1-methyl-N-[2-(1-methyl-6-oxo-1,6-dihydropyridazin-3-yl)-1,3-benzoxazol-5-yl]-6-oxo-1,6-dihydropyridazine-3-carboxamide;
[(5-{5-[(5-methoxypyridin-2-yl)methoxy]-1,3-benzoxazol-2-yl}pyridin-3-yl)methyl](methyl)amine;
6-{5-[(5-hydroxypyridin-2-yl)methoxy]-1,3-benzoxazol-2-yl}-2-methyl-2,3-dihydropyridazin-3-one; and
N-(5-Methoxypyridin-3-yl)-2-(pyridin-3-yl)-1,3-benzoxazole-5-carboxamide,
or a pharmaceutically acceptable salt thereof.

* * * * *

UNITED STATES PATENT AND TRADEMARK OFFICE
CERTIFICATE OF CORRECTION

PATENT NO. : 10,479,802 B2
APPLICATION NO. : 15/507208
DATED : November 19, 2019
INVENTOR(S) : Celia Dominguez et al.

It is certified that error appears in the above-identified patent and that said Letters Patent is hereby corrected as shown below:

On the Title Page

Inventors (item (72)), please replace "Elise Luciennen Paulette Gadouleau" with --Elise Lucienne Paulette Gadouleau--.

Signed and Sealed this
Seventeenth Day of September, 2024

Katherine Kelly Vidal
*Director of the United States Patent and Trademark Office*